US008450306B2

(12) United States Patent
Hauel et al.

(10) Patent No.: US 8,450,306 B2
(45) **Date of Patent: *May 28, 2013**

(54) BRADYKININ B1-RECEPTOR ANTAGONISTS

(75) Inventors: Norbert Hauel, Schemmerhofen (DE); Angelo Ceci, Mittelbiberach (DE); Henri Doods, Warthausen (DE); Iris Kauffmann-Hefner, Attenweiler (DE); Ingo Konetzki, Warthausen (DE); Annette Schuler-Metz, Ulm (DE); Rainer Walter, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 439 days.

This patent is subject to a terminal disclaimer.

(21) Appl. No.: 12/672,650

(22) PCT Filed: Aug. 12, 2008

(86) PCT No.: PCT/EP2008/060564

§ 371 (c)(1),
(2), (4) Date: Apr. 15, 2010

(87) PCT Pub. No.: WO2009/021946

PCT Pub. Date: Feb. 19, 2009

(65) Prior Publication Data

US 2011/0294775 A1 Dec. 1, 2011

(30) Foreign Application Priority Data

Aug. 14, 2007 (WO) ................. PCT/EP2007/058408
Feb. 26, 2008 (EP) .................................... 08102047

(51) Int. Cl.
*A61K 31/551* (2006.01)
*A61K 31/4965* (2006.01)
*C07D 243/08* (2006.01)
*C07D 243/04* (2006.01)
*A61P 25/00* (2006.01)
*A61P 29/00* (2006.01)

(52) U.S. Cl.
USPC ....... 514/218; 514/255.03; 540/575; 544/400

(58) Field of Classification Search
None
See application file for complete search history.

(56) References Cited

U.S. PATENT DOCUMENTS

| | | | |
|---|---|---|---|
| 7,858,618 | B2 | 12/2010 | Kauffmann-Hefner et al. |
| 2004/0063725 | A1 | 4/2004 | Barth et al. |
| 2005/0175591 | A1 | 8/2005 | Stout et al. |
| 2006/0084699 | A1 | 4/2006 | Barth et al. |
| 2006/0100219 | A1 | 5/2006 | Kauffmann-Hefner et al. |
| 2006/0178360 | A1 | 8/2006 | Barth et al. |
| 2009/0137545 | A1 | 5/2009 | Kauffmann-Hefner et al. |
| 2010/0197664 | A1 | 8/2010 | Kauffmann-Hefner et al. |
| 2010/0210842 | A1 | 8/2010 | Duran et al. |
| 2010/0331544 | A1 | 12/2010 | Puder et al. |
| 2011/0021488 | A1 | 1/2011 | Kauffmann-Hefner et al. |
| 2011/0077231 | A1 | 3/2011 | Hauel et al. |
| 2011/0098282 | A1 | 4/2011 | Hauel et al. |
| 2011/0294775 | A1 | 12/2011 | Hauel et al. |
| 2011/0301350 | A1 | 12/2011 | Pfrengle et al. |

FOREIGN PATENT DOCUMENTS

| | | | |
|---|---|---|---|
| CA | 2585535 | A1 | 5/2006 |
| DE | 102006039003 | A1 | 2/2008 |
| EP | 0173552 | A1 | 3/1986 |
| JP | 2006516132 | A | 6/2006 |
| WO | 9610022 | A1 | 4/1996 |
| WO | 0137826 | A1 | 5/2001 |
| WO | 02053516 | A2 | 7/2002 |
| WO | 03106428 | A1 | 12/2003 |
| WO | 2006021544 | A1 | 3/2006 |
| WO | 2006035967 | A1 | 4/2006 |
| WO | 2006036664 | A1 | 4/2006 |
| WO | 2006048209 | A1 | 5/2006 |
| WO | 2006071775 | A2 | 7/2006 |
| WO | 2008022945 | A1 | 2/2008 |
| WO | 2008145681 | A2 | 12/2008 |
| WO | 2009021944 | A1 | 2/2009 |
| WO | 2010017850 | A1 | 2/2010 |

OTHER PUBLICATIONS

International Search Report, Form PCT/ISA/210, for corresponding PCT/EP2008/060564; date of mailing: Dec. 23, 2008.
Database EMBL: AL604045; Aug. 29, 2001 "Mouse DNA sequence from clone RP23-418011 on chromosome 11 contains the 3' end of the Eml gene for endoplasmic reticulum (ER) to nucleus signalling, the 3' end of the Ddx42 gene for DEAD (Asp-Glu-Ala-Asp) box polypeptide 42, the Cd79b gene for CD79B antigen, the Icam2 gene for intercellular adhesion" Database accession No. AL604045 sequences NT82216-82409.
Zarudnaya, Margarita I, et al. "Downstream elements of mammalian pre-mRNA polyadenylation signals: primary, secondary and higher-order structures" Nucleic Acids Research, Oxford University Presss, vol. 31, No. 5, Mar. 1, 2003. pp. 1375-1386.

(Continued)

*Primary Examiner* — Bong-Sook Baek
(74) *Attorney, Agent, or Firm* — Michael P. Morris; Alan R. Stempel

(57) ABSTRACT

Novel compounds which are useful for treating acute pain, visceral pain, neuropathic pain, inflammatory/pain receptor-mediated pain, tumor pain and headache diseases. The following is exemplary:

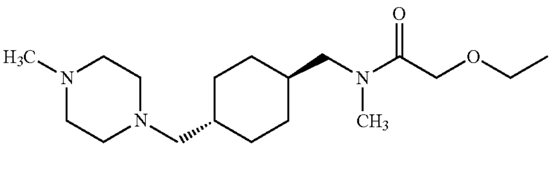

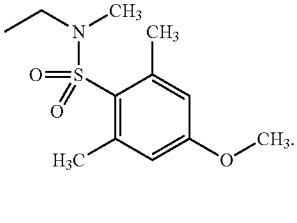

4 Claims, No Drawings

OTHER PUBLICATIONS

Molander et al.; Reduction of 2-Acylaziridines by Samarium(II) Iodide. An Efficient and Regioselective Route to Beta-Amino Carbonyl Compounds; Tetrahedron; 1997; vol. 53; No. 26; pp. 8887-8912.

Sartori et al.; Synthesis and activities of new arylsulfonamido thromboxane A2 receptor atagonists; European Journal of Medicinal Chemistry; 1993; vol. 28; pp. 6250-6632.

El-Naggar et al.; Beilstein Registry No. 6007541; Pol. J. Chem.; 1982; Bd. 56; Nr. 10-12; pp. 1279-1285; XP002466545.

El-Naggar et al.; Beilstein Registry No. 6009473; Pol. J. Chem.; 1982; Bd. 56; Nr. 10-12; pp. 1279-1285; XP002466834.

Braichenko et al.; Beilstein Registry No. 2905397; Pharm. Chem. J.; 1972; Bd. 6; Nr. 8; pp. 492-494; XP002466835.

Braichenko et al.; Beilstein Registry No. 2400317; Pharm. Chem. J.; 1972; Bd. 6; Nr. 8; pp. 492-494; XP002466836.

Mukherjee et al.; Beilstein Registry No. 9271162; J. Indian Chem. Soc.; 2002; Bd. 79; Nr. 2; pp. 137-141; XP002466837.

Selvamurugan et al.; Beilstein Registry No. 8906721; Indrapal Singh: Synthesis; 2001; Bd. 15; pp. 2239-2246; XP002466838.

Paul et al.; Beilstein Registry No. 2709200; Arch. Pharm. Ber. Dtsch. Pharm. Ges; 1968; Bd. 301; pp. 512-519; XP002466839.

El-Sharief et al.; Beilstein Registry No. 8789325; Molecules; 2001; Bd. 6; Nr. 3; pp. 267-278; XP002466840.

Shoeb et al.; Beilstein Registry No. 2664221; Indian J. Chem.; 1965; Bd. 3; pp. 507; XP002466841.

Sen et al.; Beilstein Registry No. 2674860; J. Indian Chem. Soc.; 1965; Bd. 42; pp. 145-146; XP002466842.

Sen et al.; Beilstein Registry No. 2709563; J. Indian Chem. Soc.; 1965; Bd. 42; pp. 145-146; XP002466843.

Sen et al.; Beilstein Registry No. 2709564; J. Indian Chem. Soc.; 1965; Bd. 42; pp. 145-146; XP002466844.

Sen et al.; Beilstein Registry No. 2710222; J. Indian Chem. Soc.; 1965; Bd. 42; pp. 145-146; XP002466845.

Sen et al.; Beilstein Registry No. 2956418; J. Indian Chem. Soc.; 1965; Bd. 42; pp. 145-146; XP002466846.

Sen et al.; Beilstein Registry No. 2955989; J. Indian Chem. Soc.; 1965; Bd. 42; pp. 145-146; XP002466847.

Morissette et al.; Dual antagonists of the bradykinin B1 and B2 receptors based on a postulated common pharmacophore from existing non-peptide antagonists; Biological Chemistry; 2006; vol. 387, No. 2; pp. 189-194.

Braichenko et al.; Investigations in the field of N-aryl-b-amino acids; Khimiko-Farmatsevicheskii Zhurnal; 1972; vol. 6, No. 8; pp. 6-8.

BRADYKININ B1-RECEPTOR ANTAGONISTS

This application is a national phase entry under 35 U.S.C. 371 of international application PCT/EP2008/060564, filed Aug. 12, 2008, which claims priority to PCT/EP2007/058408, filed Aug. 14, 2007, and EP08102047.1, filed Feb. 26, 2008, each of which is hereby incorporated by reference in its entirety.

The present invention relates to compounds of general formula I

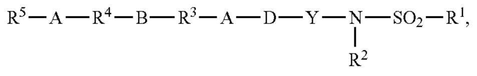

(I)

wherein A, B, D, Y, $R^1$, $R^2$, $R^3$, $R^4$ and $R^5$ are defined as in claim 1, the enantiomers, diastereomers, mixtures thereof and the salts thereof, particularly the physiologically acceptable salts thereof with organic or inorganic acids or bases, which have valuable properties, the preparation thereof, the pharmaceutical compositions containing the pharmacologically effective compounds, the preparation thereof and the use thereof.

DETAILED DESCRIPTION OF THE INVENTION

In the above general formula I in a first embodiment

A denotes a bond, $C_{1-4}$-alkylene or —$CH_2$—C(O),

B denotes a bond, $C_{1-3}$-alkylene, —O or —C(O),

D denotes a group of general formulae II

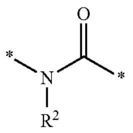 or 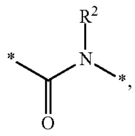,

Y denotes a $C_{1-6}$-alkylene group optionally substituted by the group $R^2$, wherein a methylene group may additionally be replaced by $Y^1$ and $Y^1$ denotes —O, —S, —S(O), —N($R^2$), —N($R^2$)—C(O), —C(O)—N($R^2$), —C(O), —CH(aryl), $C_{3-6}$-cycloalkylene or —$S(O)_2$—, $R^1$ denotes $C_{3-7}$-cycloalkyl or aryl, heteroaryl or aryl-$C_{1-3}$-alkyl, each of which may be substituted by one, two, three or four groups $R^{1.1}$, while the groups $R^{1.1}$ may be identical or different and $R^{1.1}$ denotes H, F, Cl, Br, I, $C_{1-3}$-alkyl, $F_3C$, HO, $C_{1-3}$-alkyl-O or $C_{1-3}$-alkyl-O—$C_{2-4}$-alkylene-O—, $R^2$ denotes H or $C_{1-3}$-alkyl, while each methylene group may be substituted by up to two and each methyl group may be substituted by up to three fluorine atoms, or also denotes $H_3C$—C(O), $R^3$ denotes a) $C_{1-6}$-alkylene, b) a $C_{3-6}$-cycloalkylene group mono-, di or trisubstituted by $R^{3.1}$, c) a $C_{5-7}$-cycloalkenylene group mono- or disubstituted by $R^{3.1}$ which is fused to a phenyl ring via the unsaturated bond, d) —N($R^2$), e) an arylene group mono- or disubstituted by $R^{3.1}$, f) a heteroarylene group mono- or disubstituted by $R^{3.1}$, g) a saturated 4- to 7-membered heterocyclic ring mono- or disubstituted by $R^{3.1}$, h) an unsaturated 5- to 7-membered heterocyclic ring mono- or disubstituted by $R^{3.1}$, which is fused to one or two phenyl rings via the unsaturated bonds, or i) a saturated 8- to 10-membered aza-heterobicyclic group mono- or disubstituted by $R^{3.1}$, while the groups $R^{3.1}$ may be identical or different in each case and $R^{3.1}$ denotes H, F, Cl, Br, I, $C_{1-3}$-alkyl, HO, $C_{1-3}$-alkyl-O or $C_{1-3}$-alkyl-O—$C_{2-4}$-alkylene-O—, or $R^3$ also denotes —O, if B does not denote the group —O—, $R^4$ denotes a) —O, b) —C(O)O, c) —C(O)N$R^2$, d) —N$R^2$, e) —N$R^2$—N$R^2$, f) $C_{3-7}$-cycloalkylene, g) $C_{1-6}$-alkylene, h) an arylene group mono- or disubstituted by $R^{4.1}$, i) a heteroarylene group mono- or disubstituted by $R^{4.1}$, j) a 4- to 7-membered saturated heterocyclic ring mono- or disubstituted by $R^{4.1}$, k) a saturated 8- to 10-membered diaza-heterobicyclic group mono- or disubstituted by $R^{4.1}$, l) a 5- to 7-membered unsaturated heterocyclic ring mono- or disubstituted by $R^{4.1}$, which is fused to one or two phenyl rings via the unsaturated bonds, or m) a saturated 9- to 11-membered diaza-spirocyclic group, while the groups $R^{4.1}$ may be identical or different in each case and $R^{4.1}$ denotes H, F, Cl, Br, I, $C_{1-3}$-alkyl, HO, $C_{1-3}$-alkyl-O or $C_{1-3}$-alkyl-O—$C_{2-4}$-alkylene-O—, $R^5$ denotes H, HO, $C_{1-8}$-alkyl, a $C_{3-7}$-cycloalkyl group optionally substituted by $C_{1-3}$-alkyl, $H_2N$, $C_{1-4}$-alkyl-NH, ($C_{3-6}$-cycloalkyl)-NH, $(C_{1-4}\text{-alkyl})_2N$, ($C_{1-4}$-alkyl)($C_{3-6}$-cycloalkyl)N, (cyclopropylmethyl)(methyl)N, $H_2N$—C(O), a phenyl group mono- or disubstituted by $R^{5.1}$, a heteroaryl group mono- or disubstituted by $R^{5.1}$ or a 4- to 7-membered saturated heterocyclic ring mono- or disubstituted by $R^{5.1}$, while the groups $R^{5.1}$ may be identical or different in each case and $R^{5.1}$ denotes H, F, Cl, Br, I, $C_{1-3}$-alkyl, HO, $C_{1-3}$-alkyl-O, $(C_{1-3}\text{-alkyl})_2N$ or $C_{1-3}$-alkyl-O—$C_{2-4}$-alkylene-O—, the enantiomers, the diastereomers, the mixtures and the salts thereof, particularly the physiologically acceptable salts thereof with organic or inorganic acids or bases.

A second embodiment of the present invention comprises the compounds of the above general formula I, wherein A denotes a bond, $C_{1-4}$-alkylene or —$CH_2$—C(O), B denotes a bond, $C_{1-2}$-alkylene, —O or —C(O), D denotes a group of general formula II

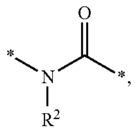,

Y denotes $C_{1-4}$-alkylene or a group selected from

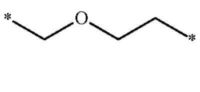 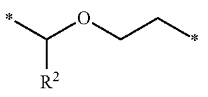 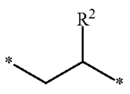

-continued

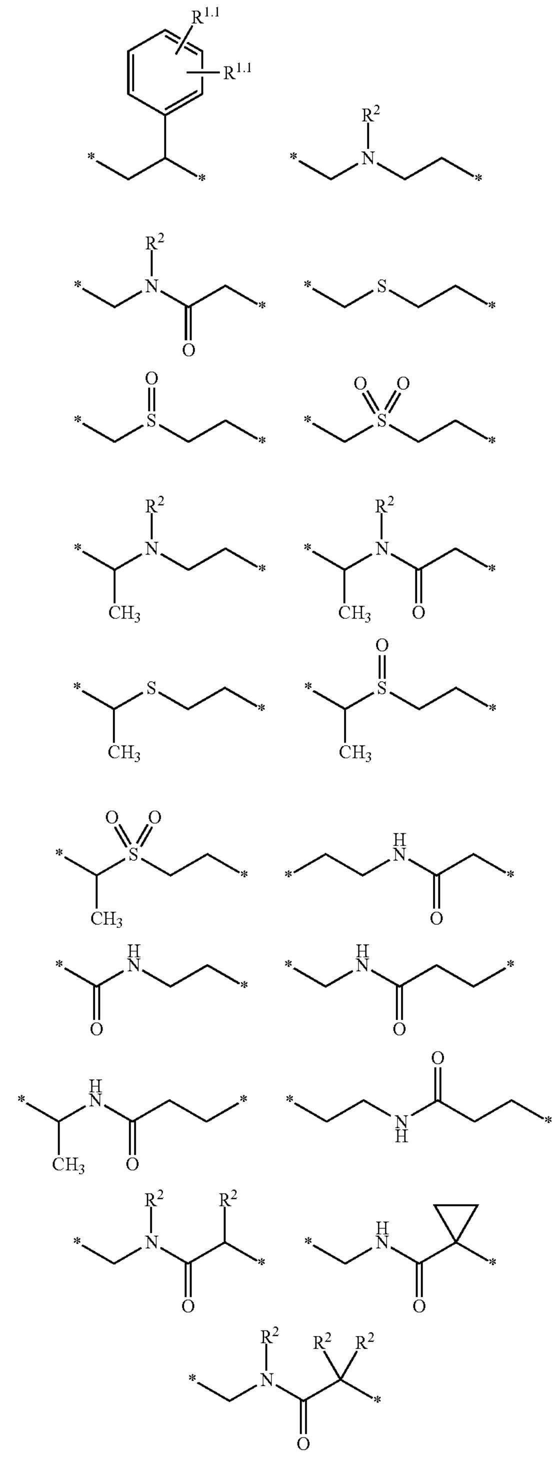

$R^1$ denotes aryl or heteroaryl, each of which may be substituted by one, two, three or four groups $R^{1.1}$, while the groups $R^{1.1}$ may be identical or different and $R^{1.1}$ denotes H, F, Cl, Br, I, $C_{1-3}$-alkyl, $F_3C$, HO, $C_{1-3}$-alkyl-O or $C_{1-3}$-alkyl-O—$C_{2-4}$-alkylene-O—, $R^2$ denotes H, $H_3C$, $H_5C_2$, isopropyl, $F_3C$—$CH_2$, $F_2CH$—$CH_2$ or $FH_2C$—$H_2C$, $R^3$ denotes $C_{1-4}$-alkylene, —N($R^2$) or a group selected from

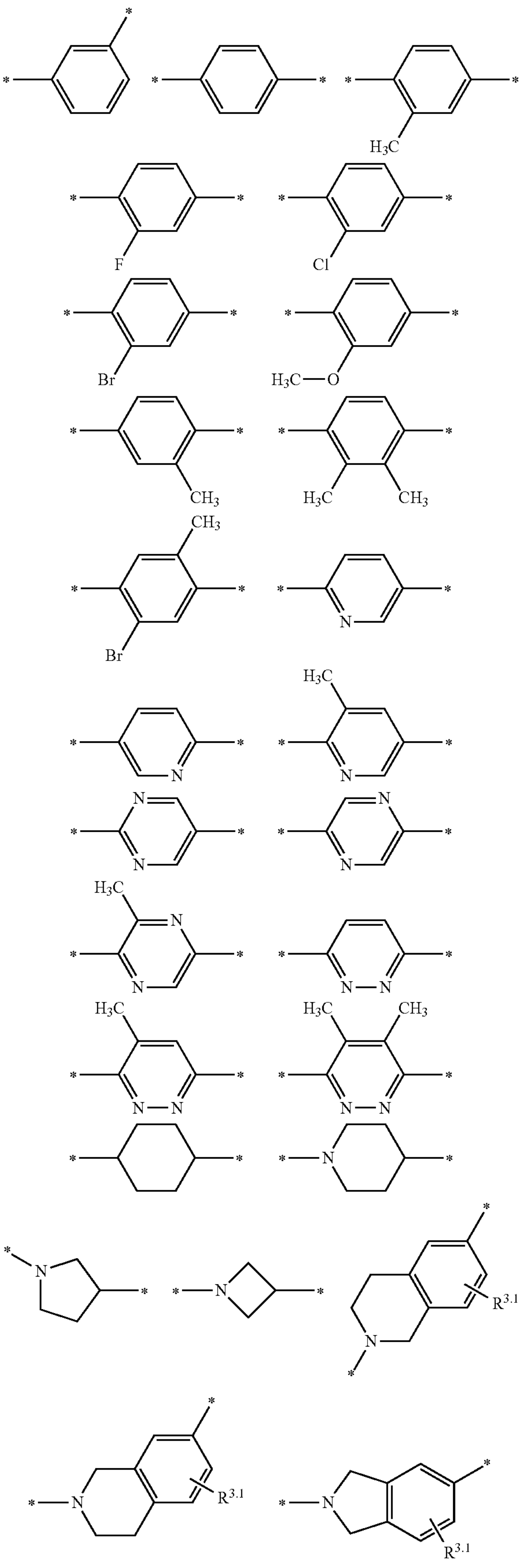

-continued
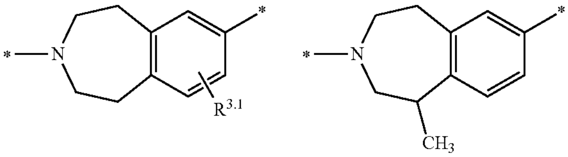
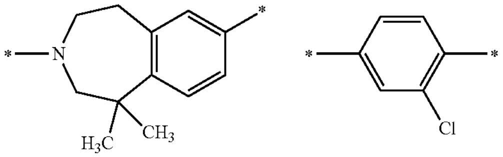
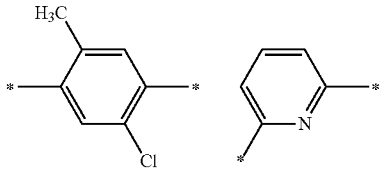
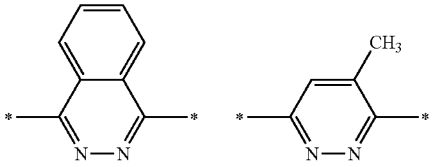
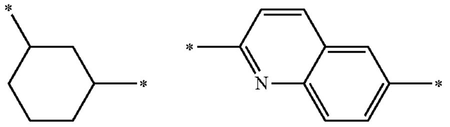
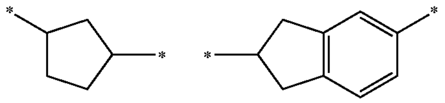
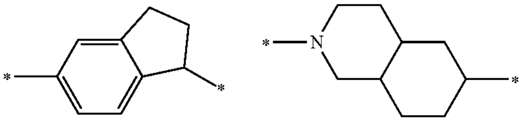
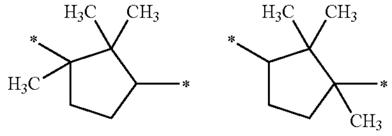
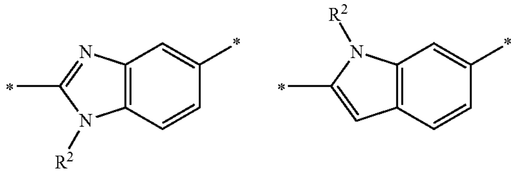
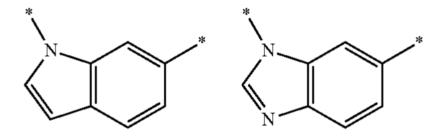
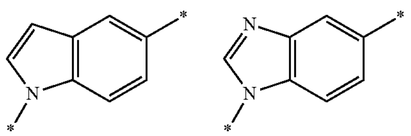
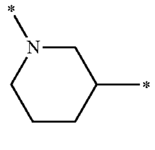
wherein
$R^{3.1}$ denotes H, F, Cl, Br, I, $C_{1-3}$-alkyl, HO, $C_{1-3}$-alkyl-O or $C_{1-3}$-alkyl-O—$C_{2-4}$-alkylene-O—, or
$R^3$ also denotes —O, if B does not denote the group —O—,
$R^4$ denotes $C_{1-4}$-alkylene, $C_{3-7}$-cycloalkylene, —O or a group selected from
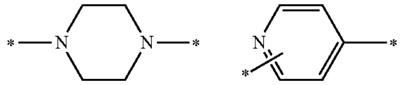
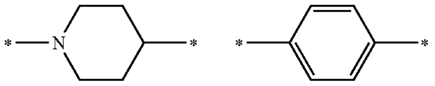
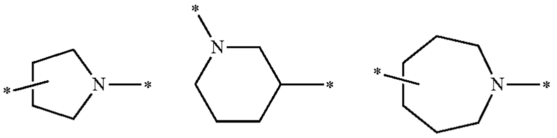
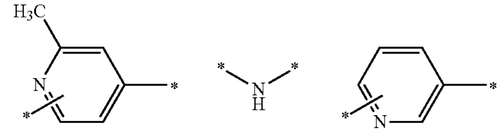
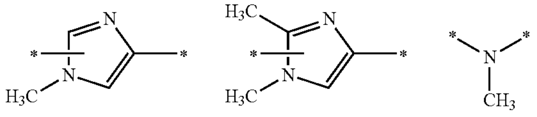
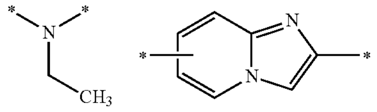
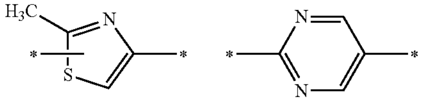
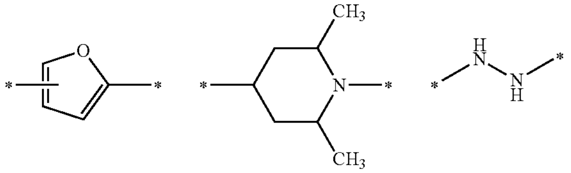
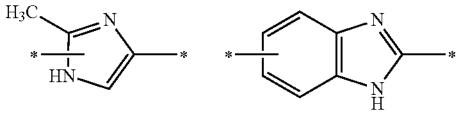
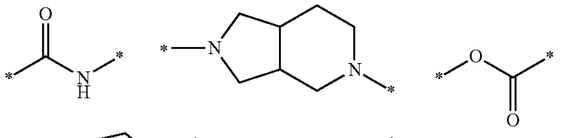
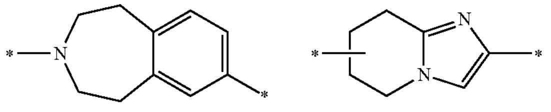
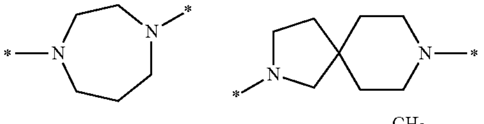
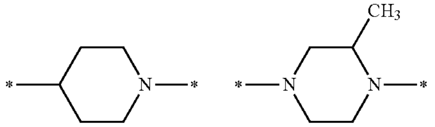

-continued

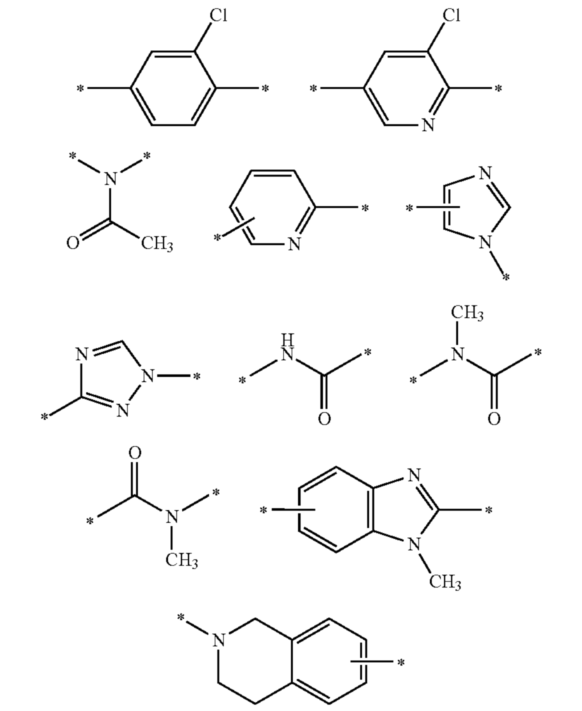

$R^5$ denotes H, $C_{1-8}$-alkyl, $C_{3-7}$-cycloalkyl, HO, ($C_{1-3}$-alkyl)-O, ($C_{1-4}$-alkyl)-NH, ($C_{3-6}$-cycloalkyl)-NH, ($C_{1-4}$-alkyl)$_2$N, ($C_{1-4}$-alkyl)($C_{3-6}$-cycloalkyl)N, (cyclopropylmethyl)(methyl)N, $H_2N$—C(O), or $R^5$ denotes a group selected from

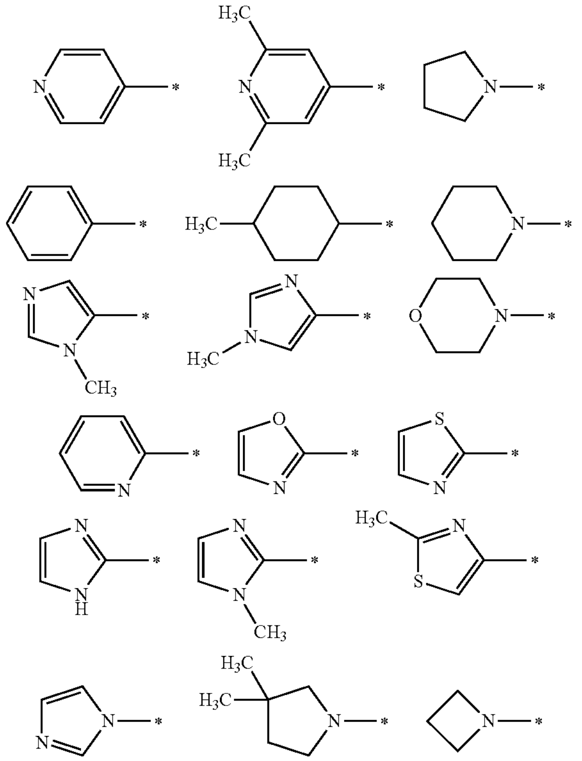

-continued

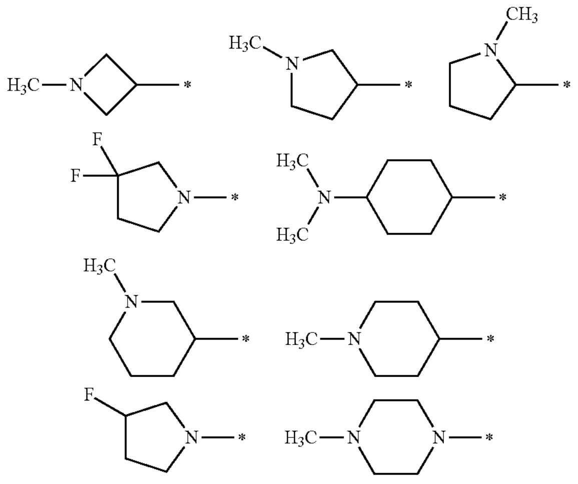

the enantiomers, the diastereomers, the mixtures and the salts thereof, particularly the physiologically acceptable salts thereof with organic or inorganic acids or bases.

A third embodiment of the present invention comprises the compounds of the above general formula I, wherein A denotes a bond, $C_{1-3}$-alkylene or —$CH_2$—C(O), B denotes a bond, $C_{1-2}$-alkylene, —O or —C(O), D denotes a group of general formula II

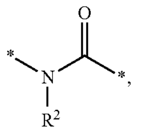

Y denotes a group selected from

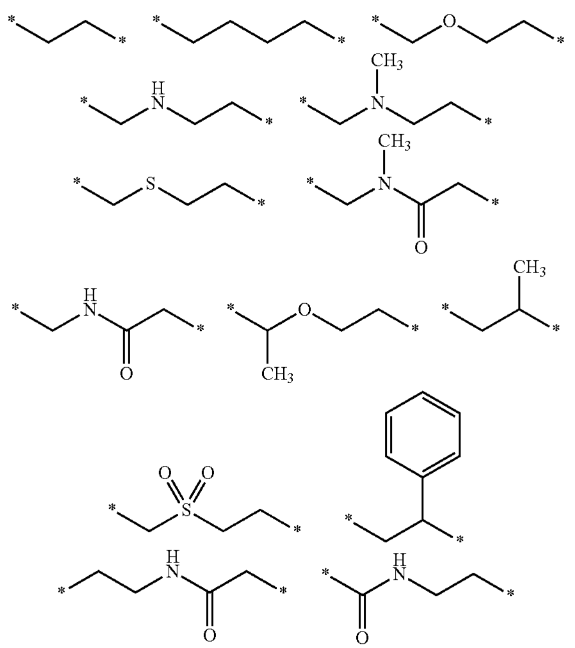

-continued
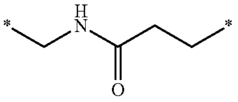
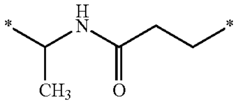
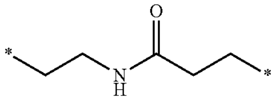
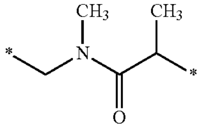
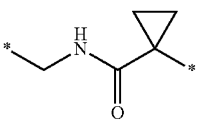
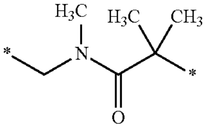
$R^1$ denotes a group selected from
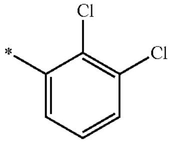
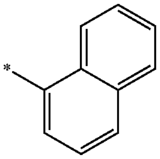
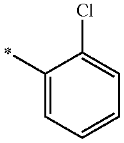
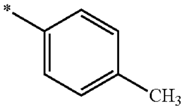
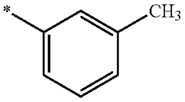
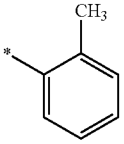
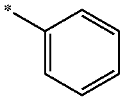
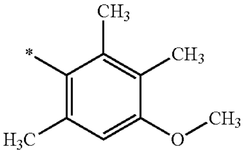
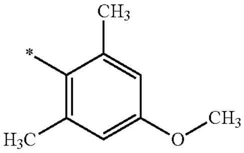
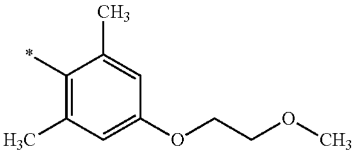
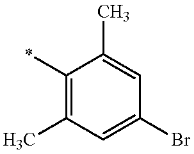
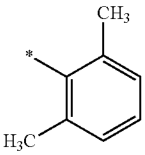
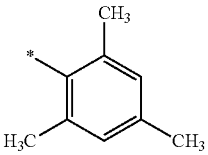
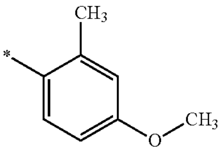
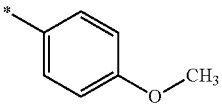
-continued
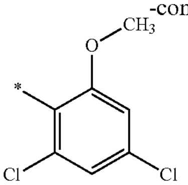
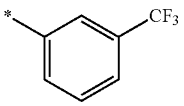
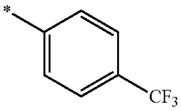
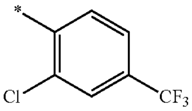
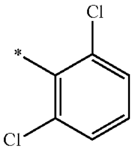
$R^2$ denotes H, $H_3C$, $H_5C_2$ or $FH_2C—H_2C$,
$R^3$ denotes $C_{1-4}$-alkylene, —NH, —$N(CH_3)$ or a group selected from
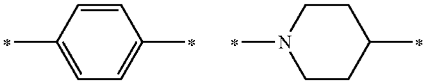
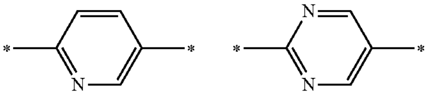
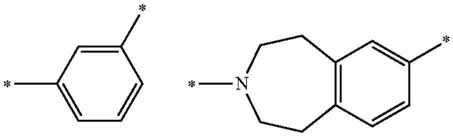
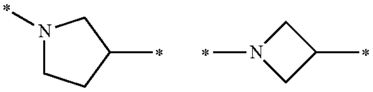
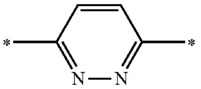
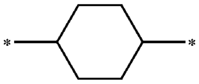
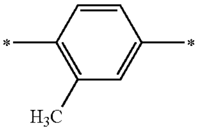
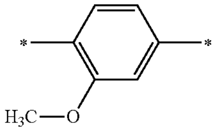
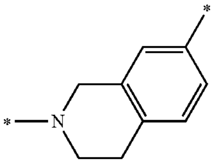
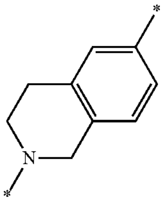
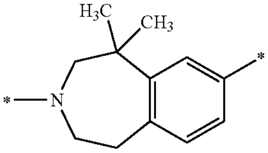
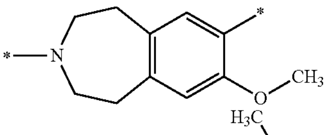
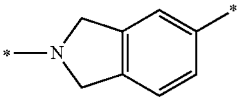
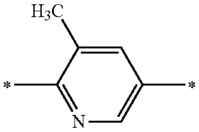

-continued
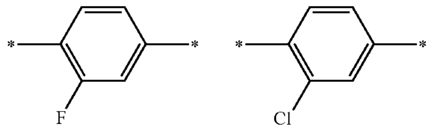
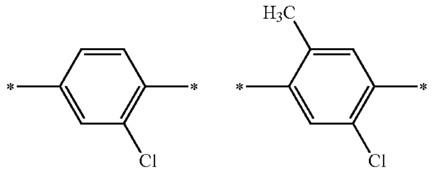
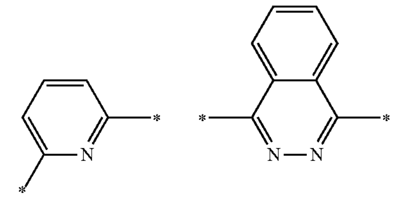
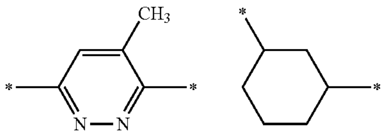
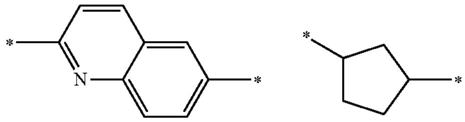
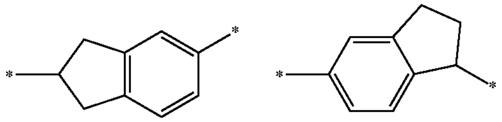
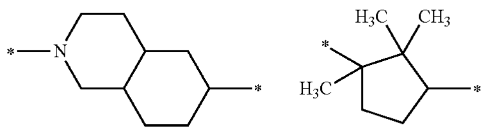
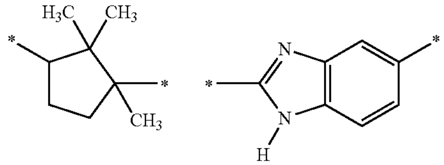
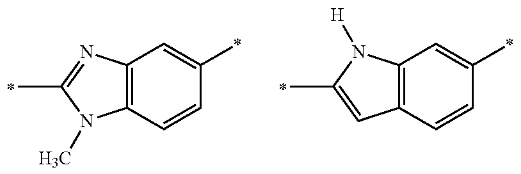
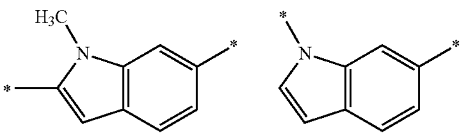
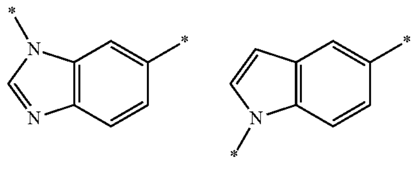
-continued
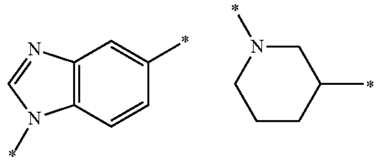
or
$R^3$ also denotes —O, if B does not denote the group —O—,
$R^4$ denotes $C_{1-4}$-alkylene, $C_{3-7}$-cycloalkylene, —O or a group selected from
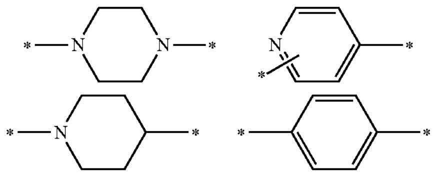
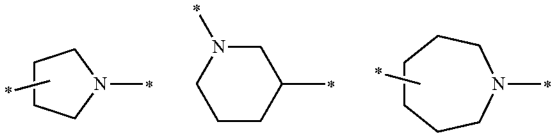
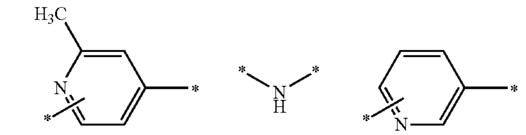
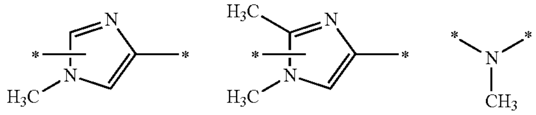
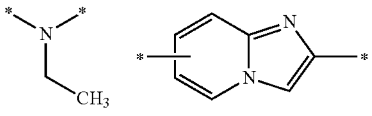
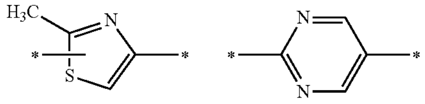
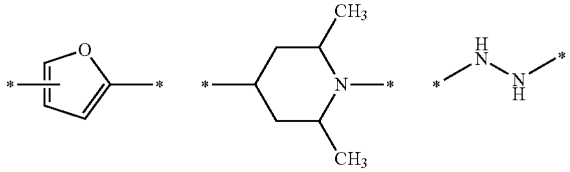
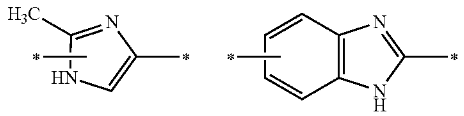
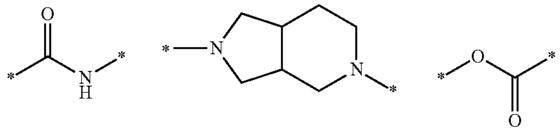
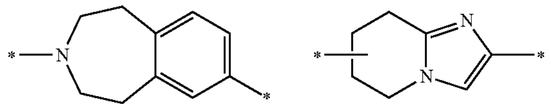

-continued

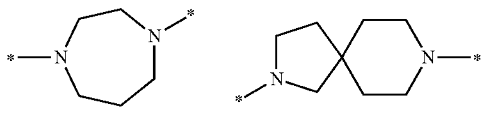

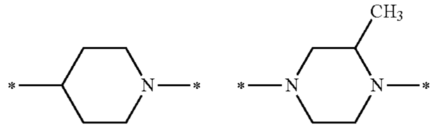

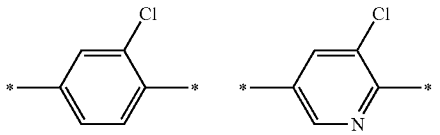

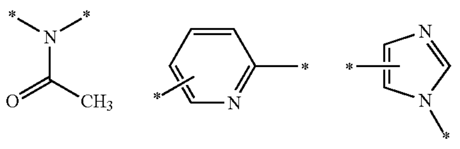

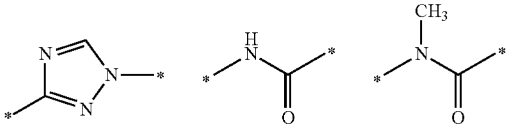

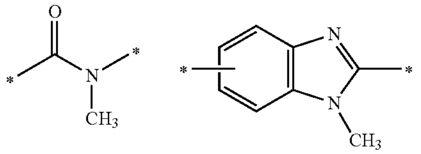

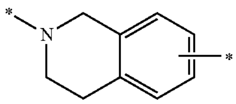

$R^5$ denotes H, HO, $C_{1-5}$-alkyl, $C_{3-5}$-cycloalkyl, $H_2N$, ($C_{1-2}$-alkyl)-NH, ($C_{3-6}$-cycloalkyl)-NH, ($C_{1-2}$-alkyl)$_2$N, ($C_{1-4}$-alkyl)($C_{3-6}$-cycloalkyl)N, (cyclopropylmethyl)(methyl)N, $H_2N$—C(O), or $R^5$ denotes a group selected from

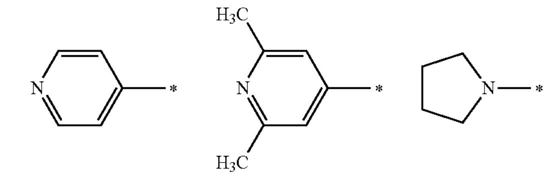

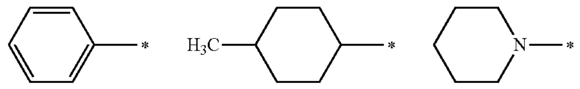

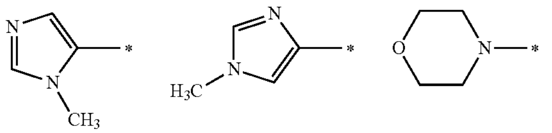

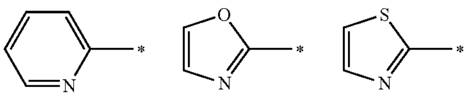

-continued

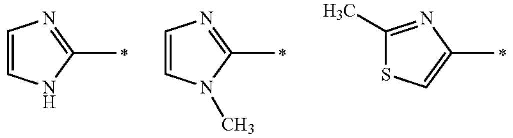

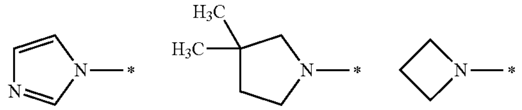

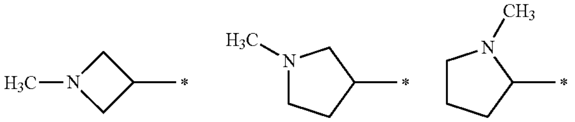

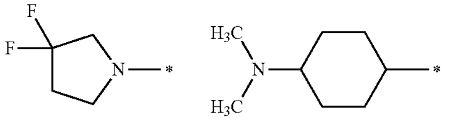

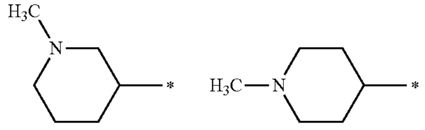

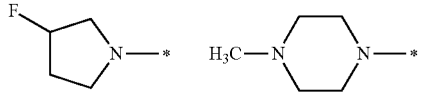

the enantiomers, the diastereomers, the mixtures and the salts thereof, particularly the physiologically acceptable salts thereof with organic or inorganic acids or bases.

A fourth embodiment of the present invention comprises the compounds of the above general formula I, wherein A, B, D, Y, $R^2$, $R^3$, $R^4$ and $R^5$ are defined as hereinbefore under the first to third embodiments and $R^1$ denotes the group

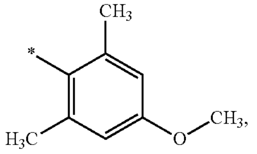

the enantiomers, the diastereomers, the mixtures and the salts thereof, particularly the physiologically acceptable salts thereof with organic or inorganic acids or bases.

A fifth embodiment of the present invention comprises the compounds of the above general formula I, wherein A, B, $R^1$, $R^3$, $R^4$ and $R^5$ are defined as hereinbefore under the first to fourth embodiments and -D-Y— together denote a group selected from

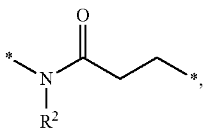

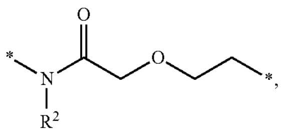

-continued
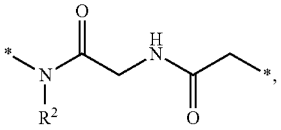
, and
$R^2$ denotes H or $C_{1-3}$-alkyl-,
the enantiomers, the diastereomers, the mixtures and the salts thereof, particularly the physiologically acceptable salts thereof with organic or inorganic acids or bases.
The following are mentioned as examples of most particularly preferred compounds of the above general formula I:
| Example | Structure |
|---|---|
| (1) | 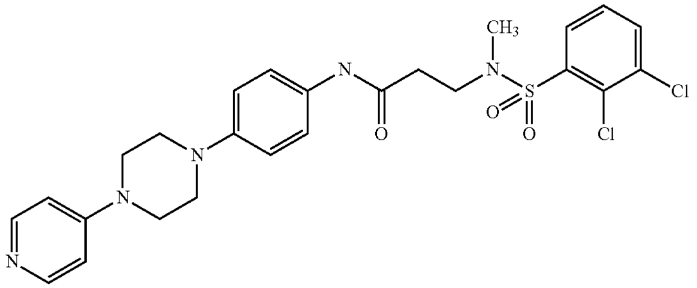 [SMILES: CN(CCC(=O)Nc1ccc(N2CCN(c3ccncc3)CC2)cc1)S(=O)(=O)c1cccc(Cl)c1Cl] |
| (2) | 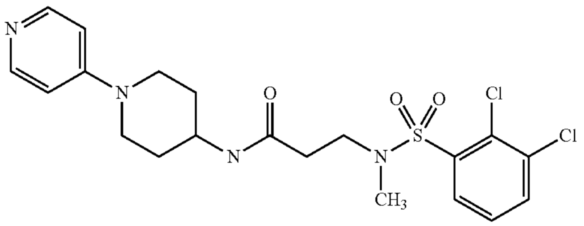 [SMILES: CN(CCC(=O)NC1CCN(c2ccncc2)CC1)S(=O)(=O)c1cccc(Cl)c1Cl] |
| (3) | 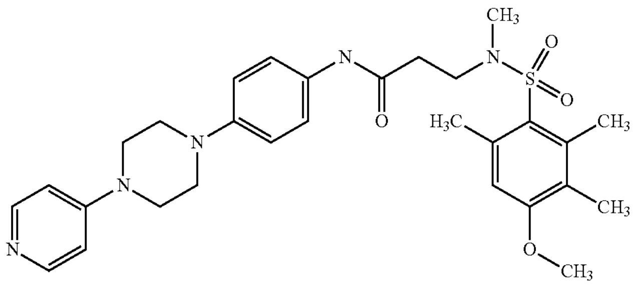 [SMILES: COc1cc(C)c(S(=O)(=O)N(C)CCC(=O)Nc2ccc(N3CCN(c4ccncc4)CC3)cc2)c(C)c1C] |
| (4) | 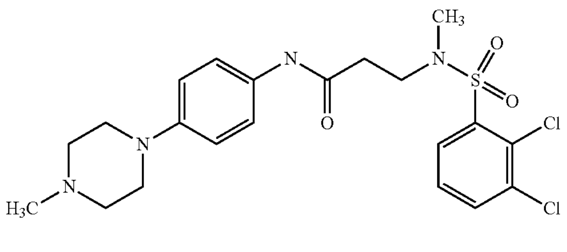 [SMILES: CN1CCN(c2ccc(NC(=O)CCN(C)S(=O)(=O)c3cccc(Cl)c3Cl)cc2)CC1] |
| (5) | 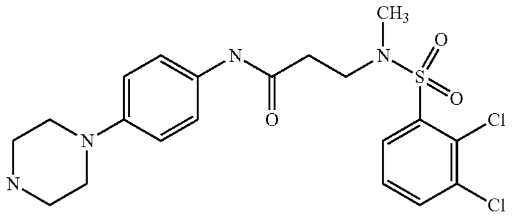 [SMILES: CN(CCC(=O)Nc1ccc(N2CCNCC2)cc1)S(=O)(=O)c1cccc(Cl)c1Cl] |

-continued
| Example | Structure |
|---|---|
| (6) | 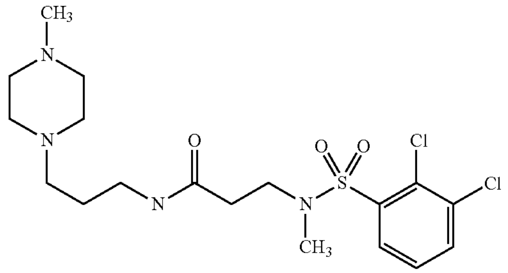 [SMILES: CN1CCN(CCCNC(=O)CCN(C)S(=O)(=O)c2cccc(Cl)c2Cl)CC1] |
| (7) | 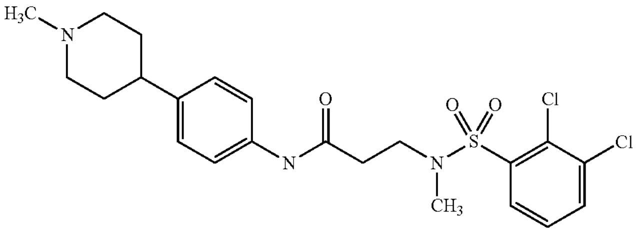 [SMILES: CN1CCC(c2ccc(NC(=O)CCN(C)S(=O)(=O)c3cccc(Cl)c3Cl)cc2)CC1] |
| (8) | 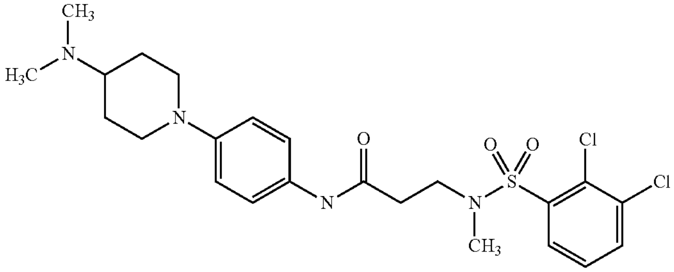 [SMILES: CN(C)C1CCN(c2ccc(NC(=O)CCN(C)S(=O)(=O)c3cccc(Cl)c3Cl)cc2)CC1] |
| (9) | 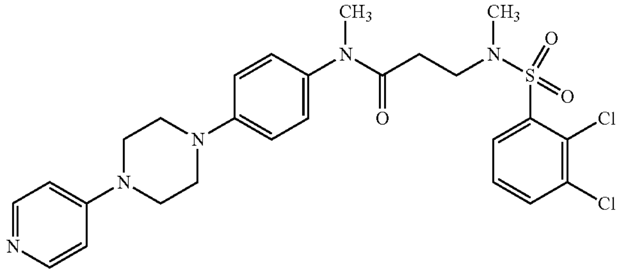 [SMILES: CN(C(=O)CCN(C)S(=O)(=O)c1cccc(Cl)c1Cl)c1ccc(N2CCN(c3ccncc3)CC2)cc1] |
| (10) | 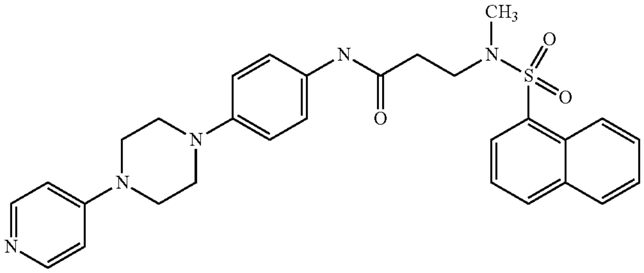 [SMILES: CN(CCC(=O)Nc1ccc(N2CCN(c3ccncc3)CC2)cc1)S(=O)(=O)c1cccc2ccccc12] |

-continued
| Example | Structure |
|---|---|
| (11) | 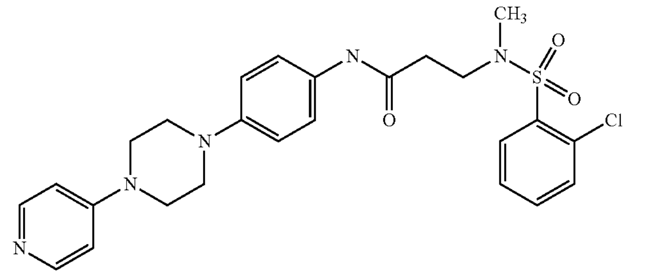 [SMILES: CN(CCC(=O)Nc1ccc(N2CCN(c3ccncc3)CC2)cc1)S(=O)(=O)c1ccccc1Cl] |
| (12) | 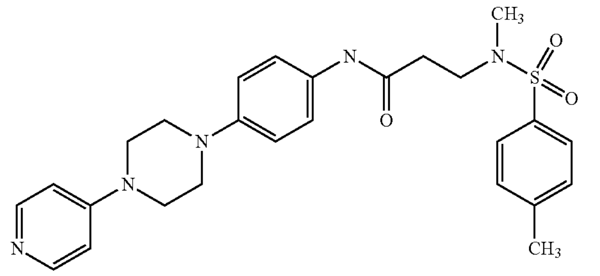 [SMILES: Cc1ccc(S(=O)(=O)N(C)CCC(=O)Nc2ccc(N3CCN(c4ccncc4)CC3)cc2)cc1] |
| (13) | 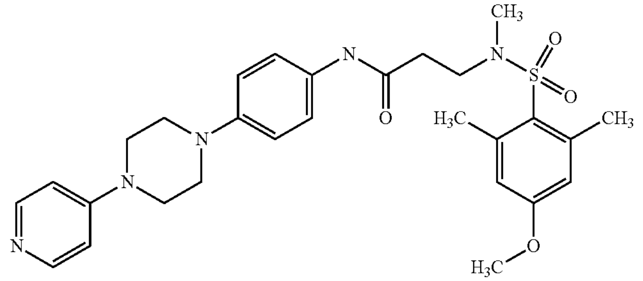 [SMILES: COc1cc(C)c(S(=O)(=O)N(C)CCC(=O)Nc2ccc(N3CCN(c4ccncc4)CC3)cc2)c(C)c1] |
| (14) | 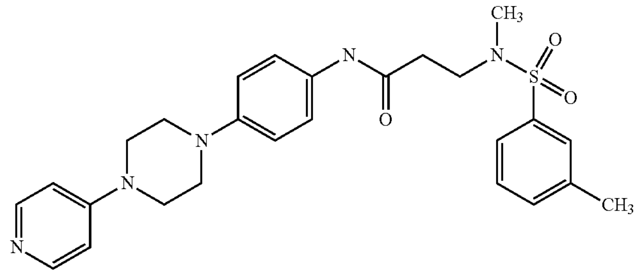 [SMILES: Cc1cccc(S(=O)(=O)N(C)CCC(=O)Nc2ccc(N3CCN(c4ccncc4)CC3)cc2)c1] |
| (15) | 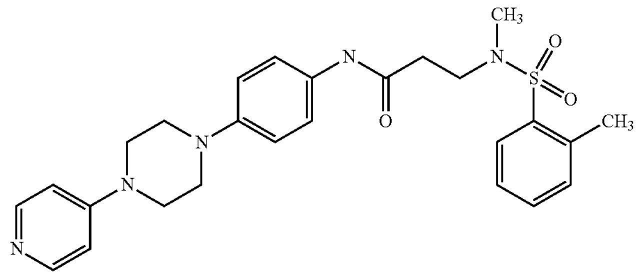 [SMILES: Cc1ccccc1S(=O)(=O)N(C)CCC(=O)Nc1ccc(N2CCN(c3ccncc3)CC2)cc1] |

-continued
| Example | Structure |
|---|---|
| (16) | 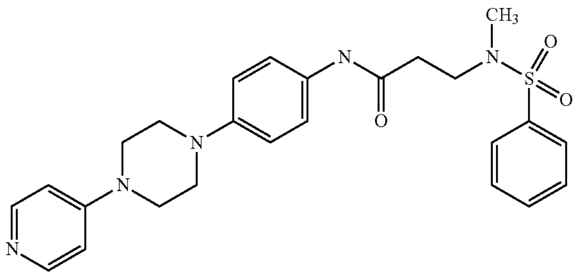 [SMILES: CN(CCC(=O)Nc1ccc(N2CCN(c3ccncc3)CC2)cc1)S(=O)(=O)c1ccccc1] |
| (17) | 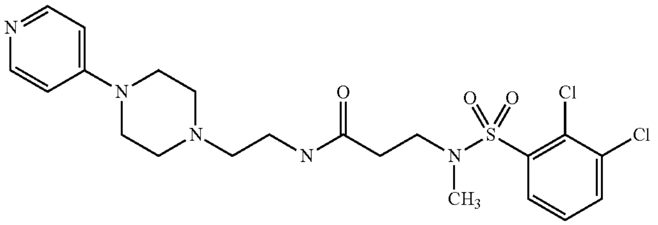 [SMILES: CN(CCC(=O)NCCN1CCN(c2ccncc2)CC1)S(=O)(=O)c1cccc(Cl)c1Cl] |
| (18) | 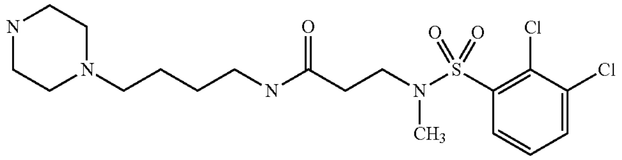 [SMILES: CN(CCC(=O)NCCCCN1CCNCC1)S(=O)(=O)c1cccc(Cl)c1Cl] |
| (19) | 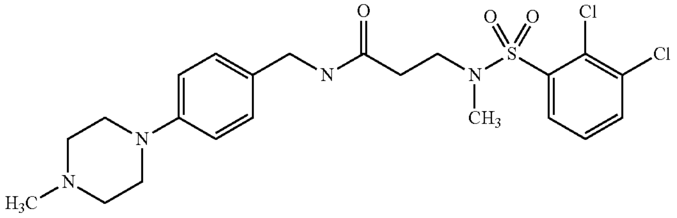 [SMILES: CN1CCN(c2ccc(CNC(=O)CCN(C)S(=O)(=O)c3cccc(Cl)c3Cl)cc2)CC1] |
| (20) | 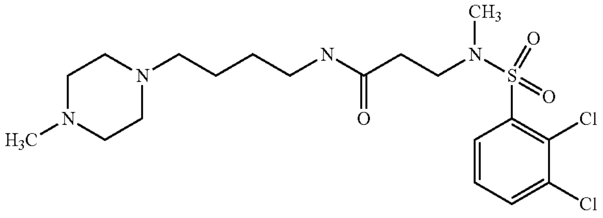 [SMILES: CN1CCN(CCCCNC(=O)CCN(C)S(=O)(=O)c2cccc(Cl)c2Cl)CC1] |
| (21) | 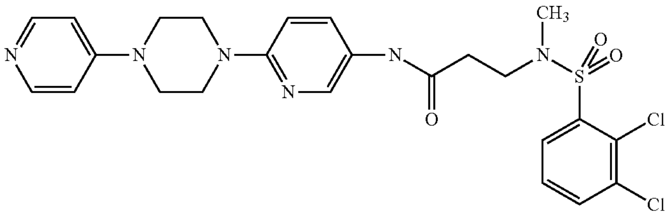 [SMILES: CN(CCC(=O)Nc1ccc(N2CCN(c3ccncc3)CC2)nc1)S(=O)(=O)c1cccc(Cl)c1Cl] |

-continued
| Example | Structure |
|---|---|
| (22) | 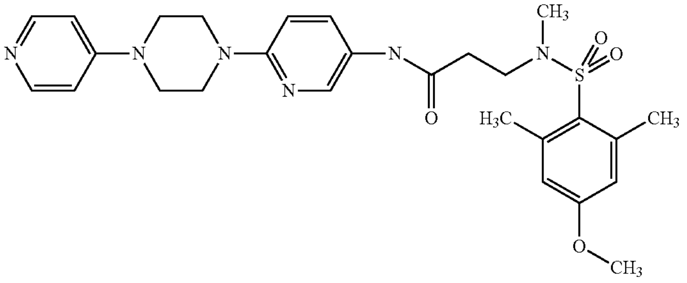 [SMILES: COc1cc(C)c(S(=O)(=O)N(C)CCC(=O)Nc2ccc(N3CCN(c4ccncc4)CC3)nc2)c(C)c1] |
| (23) | 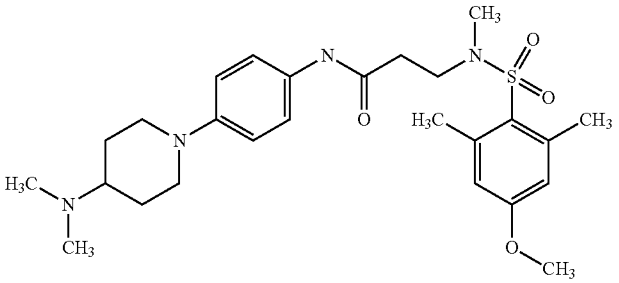 |
| (24) | 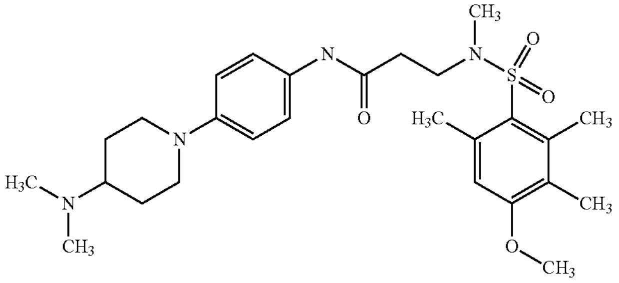 |
| (25) | 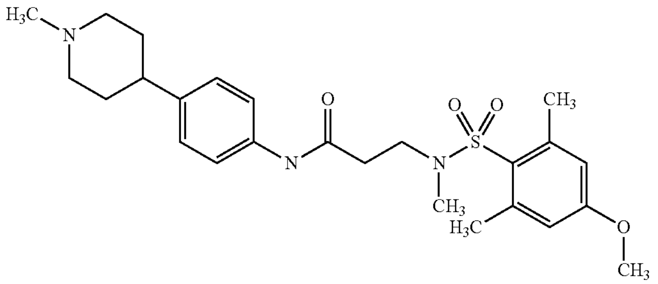 |
| (26) | 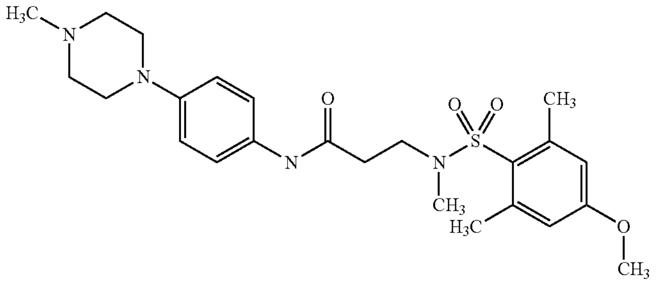 |

-continued
| Example | Structure |
|---|---|
| (27) | 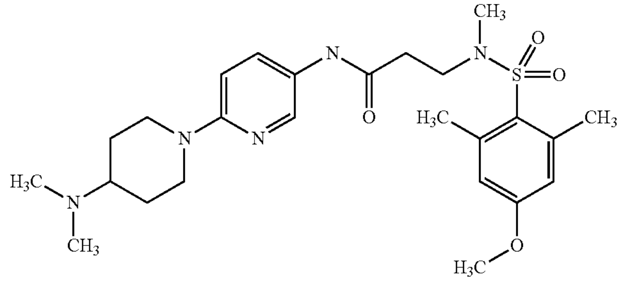 |
| (28) | 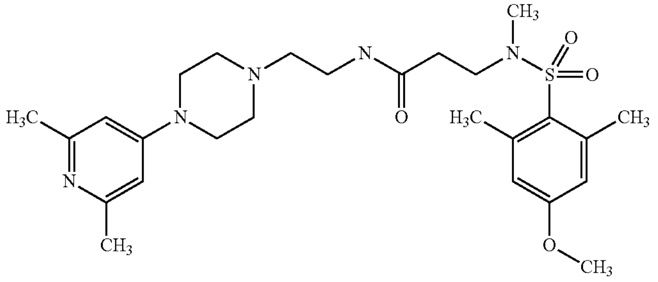 |
| (29) | 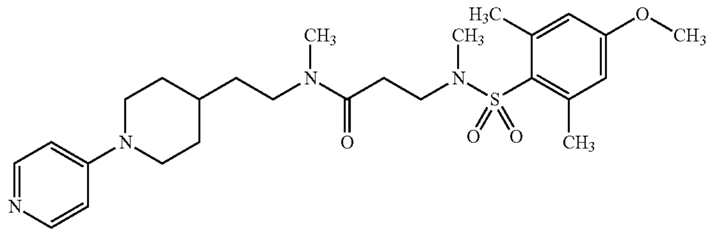 [SMILES: COc1cc(C)c(S(=O)(=O)N(C)CCC(=O)N(C)CCC2CCN(c3ccncc3)CC2)c(C)c1] |
| (30) | 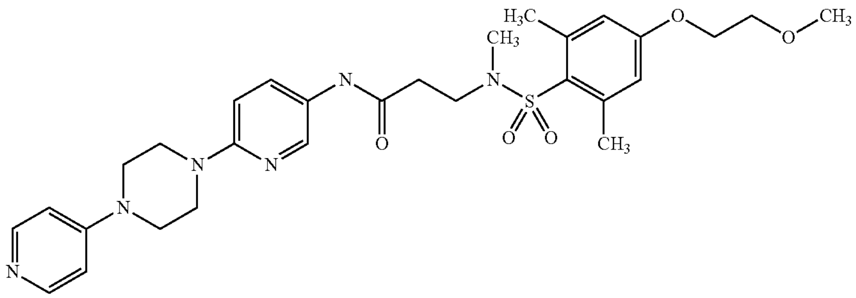 [SMILES: COCCOc1cc(C)c(S(=O)(=O)N(C)CCC(=O)Nc2ccc(N3CCN(c4ccncc4)CC3)nc2)c(C)c1] |
| (31) | 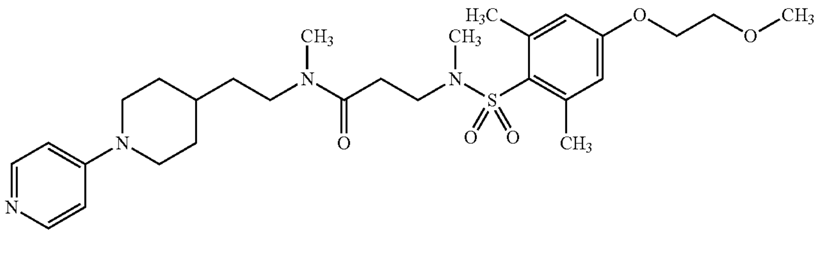 [SMILES: COCCOc1cc(C)c(S(=O)(=O)N(C)CCC(=O)N(C)CCC2CCN(c3ccncc3)CC2)c(C)c1] |

-continued
| Example | Structure |
| --- | --- |
| (32) | 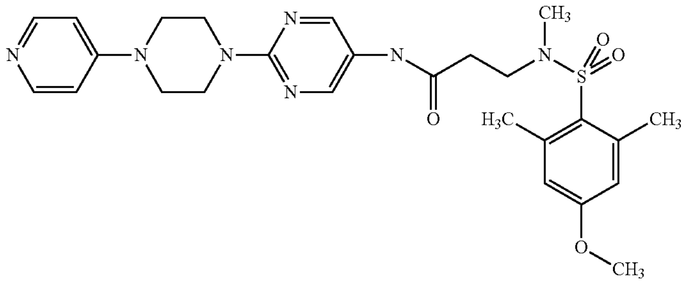 [SMILES: COc1cc(C)c(S(=O)(=O)N(C)CCC(=O)Nc2cnc(N3CCN(c4ccncc4)CC3)nc2)c(C)c1] |
| (33) | 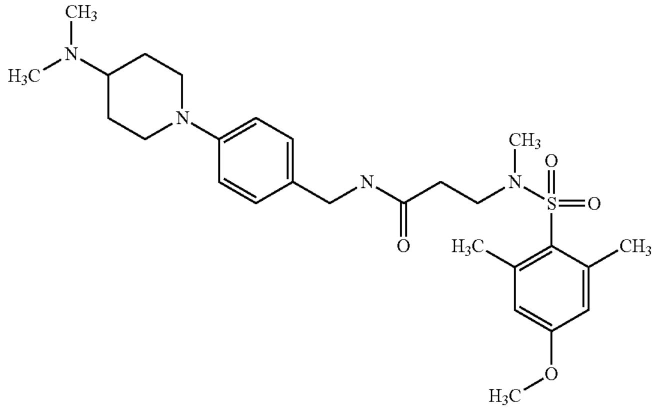 |
| (34) | 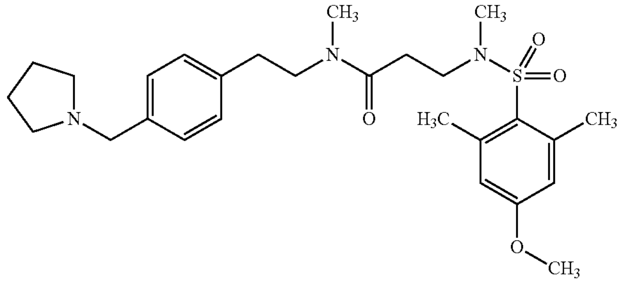 [SMILES: COc1cc(C)c(S(=O)(=O)N(C)CCC(=O)N(C)CCc2ccc(CN3CCCC3)cc2)c(C)c1] |
| (35) | 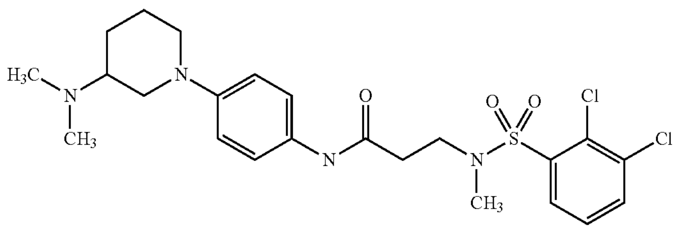 [SMILES: CN(C)C1CCCN(c2ccc(NC(=O)CCN(C)S(=O)(=O)c3cccc(Cl)c3Cl)cc2)C1] |
| (36) | 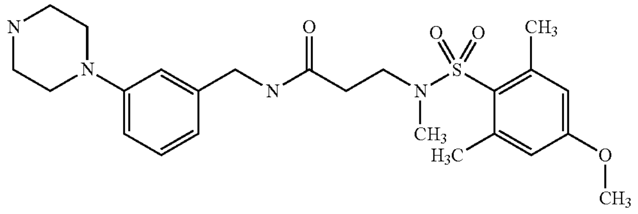 [SMILES: COc1cc(C)c(S(=O)(=O)N(C)CCC(=O)NCc2cccc(N3CCNCC3)c2)c(C)c1] |

-continued
| Example | Structure |
| --- | --- |
| (37) | 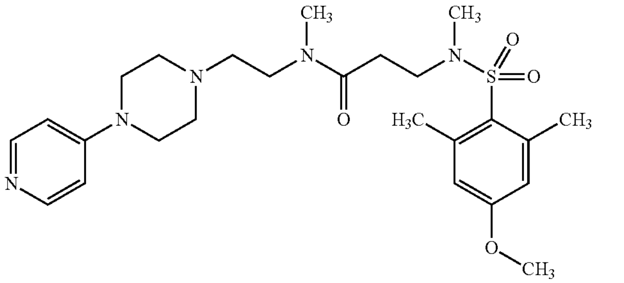 [SMILES: COc1cc(C)c(S(=O)(=O)N(C)CCC(=O)N(C)CCN2CCN(c3ccncc3)CC2)c(C)c1] |
| (38) | 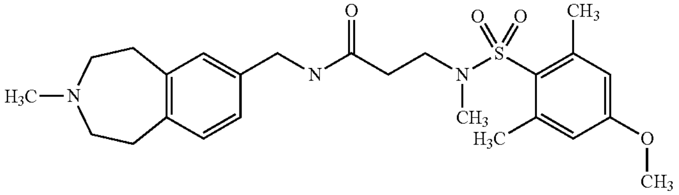 |
| (39) | 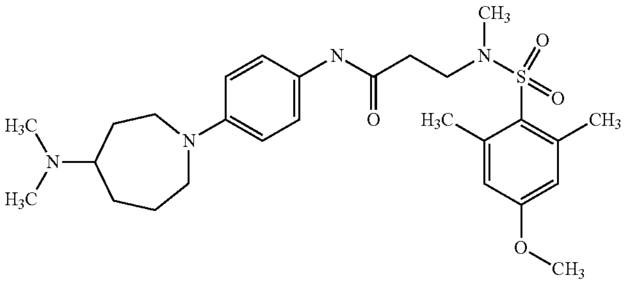 |
| (40) | 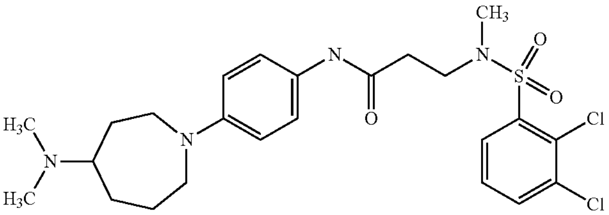 [SMILES: CN(C)C1CCCN(c2ccc(NC(=O)CCN(C)S(=O)(=O)c3cccc(Cl)c3Cl)cc2)CC1] |
| (41) | 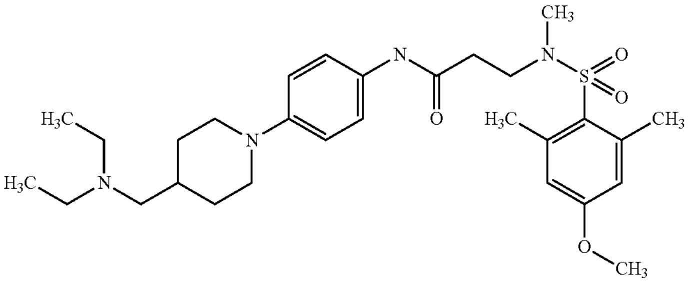 [SMILES: CCN(CC)CC1CCN(c2ccc(NC(=O)CCN(C)S(=O)(=O)c3c(C)cc(OC)cc3C)cc2)CC1] |
| (42) | 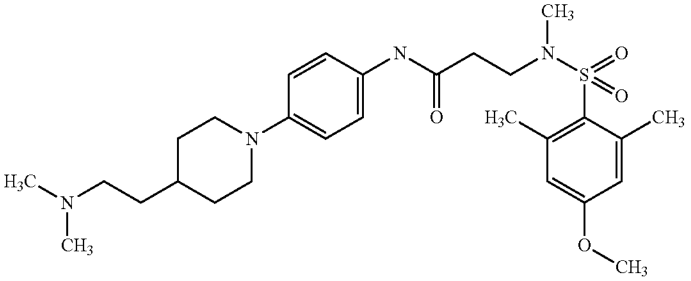 |

-continued
| Example | Structure |
| --- | --- |
| (43) | 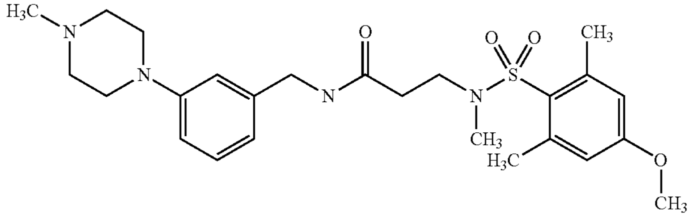 |
| (44) | 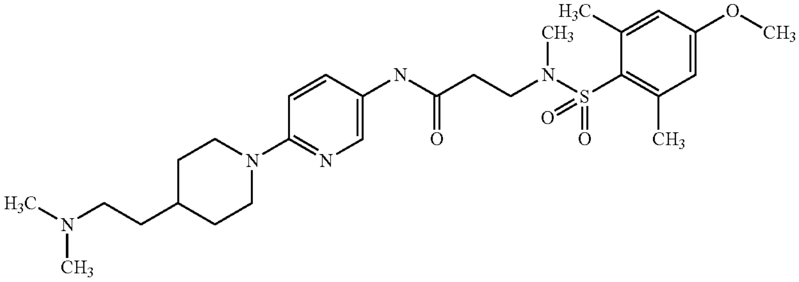 |
| (45) | 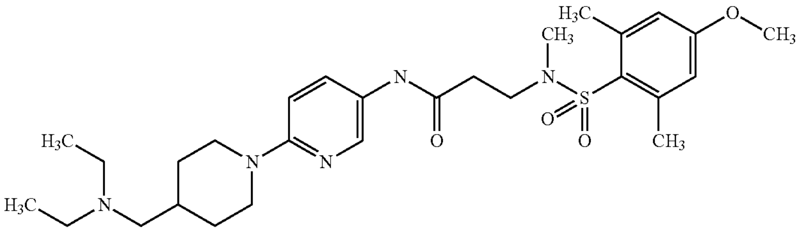 [SMILES: CCN(CC)CC1CCN(c2ccc(NC(=O)CCN(C)S(=O)(=O)c3c(C)cc(OC)cc3C)cn2)CC1] |
| (46) | 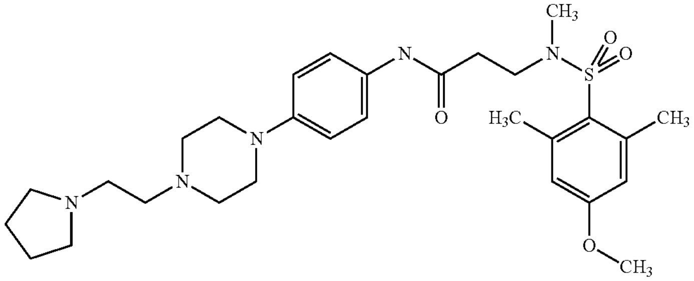 [SMILES: COc1cc(C)c(S(=O)(=O)N(C)CCC(=O)Nc2ccc(N3CCN(CCN4CCCC4)CC3)cc2)c(C)c1] |
| (47) | 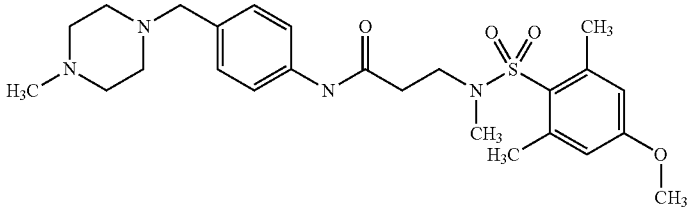 |
| (48) | 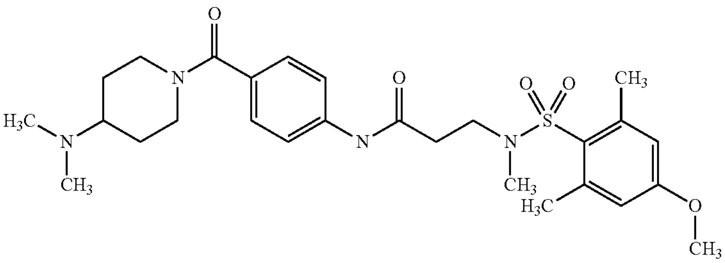 |

-continued
| Example | Structure |
| --- | --- |
| (49) | 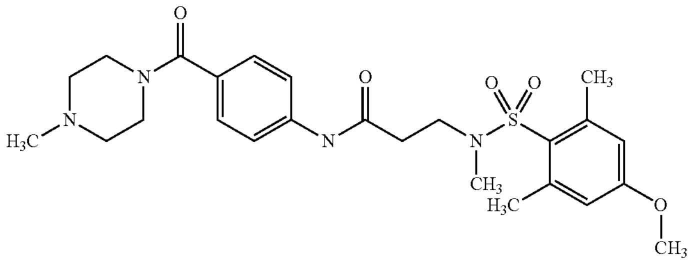 |
| (50) | 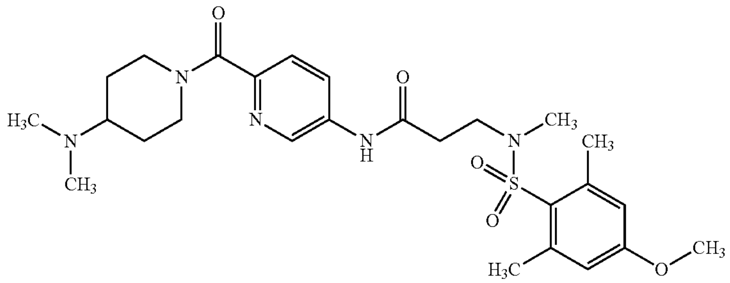 |
| (51) | 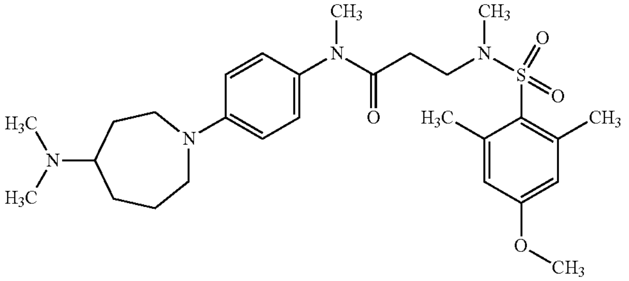 |
| (52) | 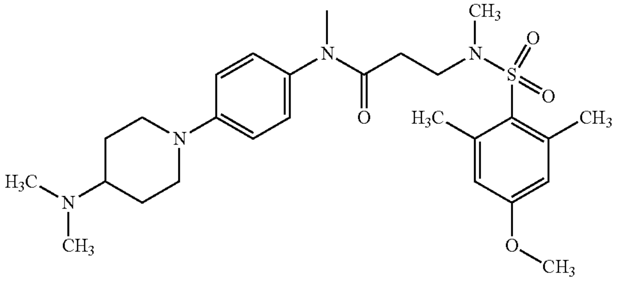 |
| (53) | 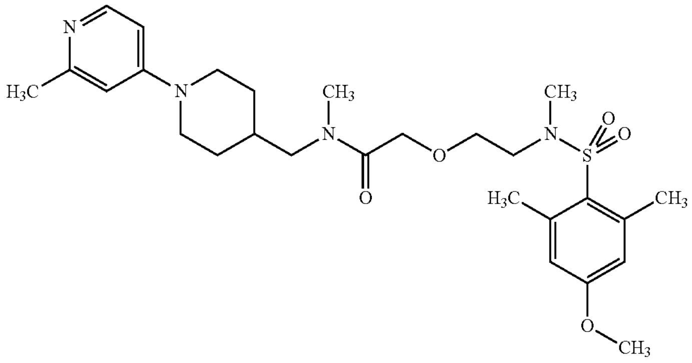 |

-continued
| Example | Structure |
| --- | --- |
| (54) | 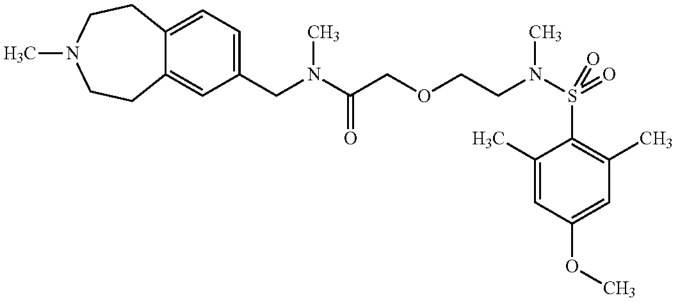 |
| (55) | 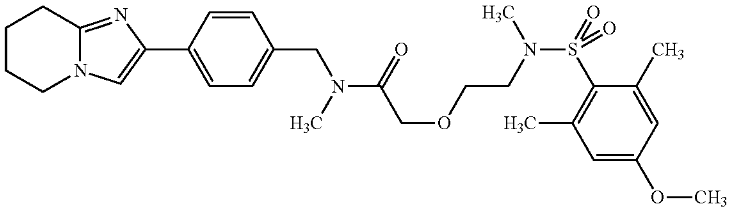 [SMILES: COc1cc(C)c(S(=O)(=O)N(C)CCOCC(=O)N(C)Cc2ccc(-c3cn4c(n3)CCCC4)cc2)c(C)c1] |
| (56) | 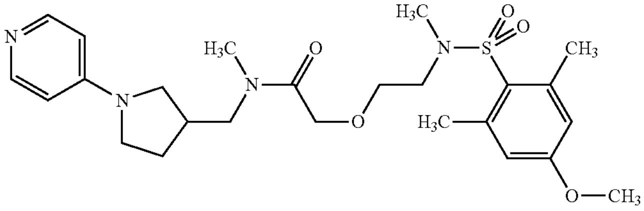 [SMILES: COc1cc(C)c(S(=O)(=O)N(C)CCOCC(=O)N(C)CC2CCN(c3ccncc3)C2)c(C)c1] |
| (57) | 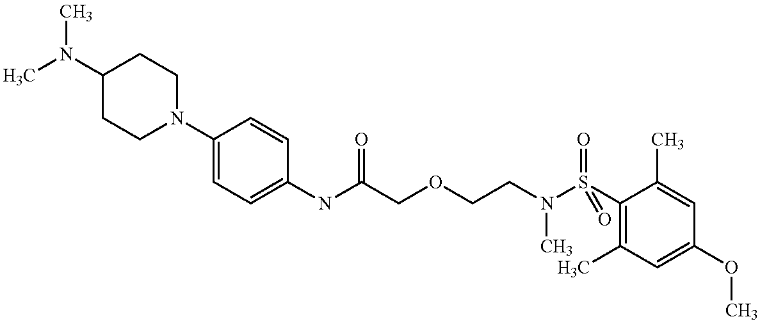 |
| (58) | 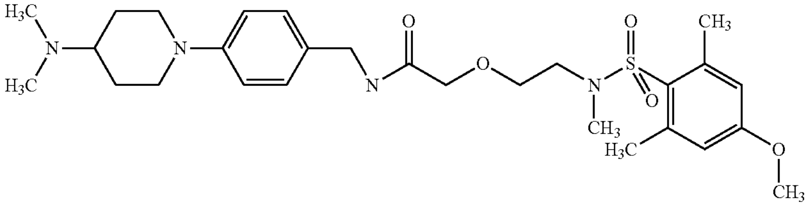 |
| (59) | 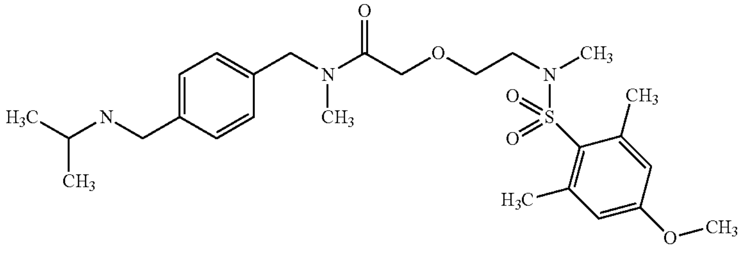 [SMILES: COc1cc(C)c(S(=O)(=O)N(C)CCOCC(=O)N(C)Cc2ccc(CNC(C)C)cc2)c(C)c1] |

-continued
| Example | Structure |
| --- | --- |
| (60) | 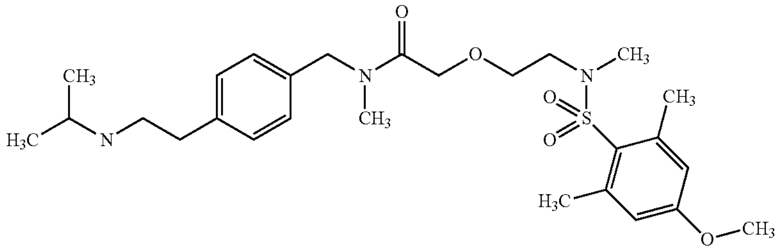 [SMILES: COc1cc(C)c(S(=O)(=O)N(C)CCOCC(=O)N(C)Cc2ccc(CCNC(C)C)cc2)c(C)c1] |
| (61) | 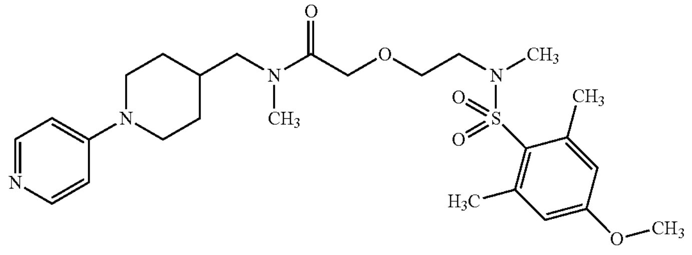 [SMILES: COc1cc(C)c(S(=O)(=O)N(C)CCOCC(=O)N(C)CC2CCN(c3ccncc3)CC2)c(C)c1] |
| (62) | 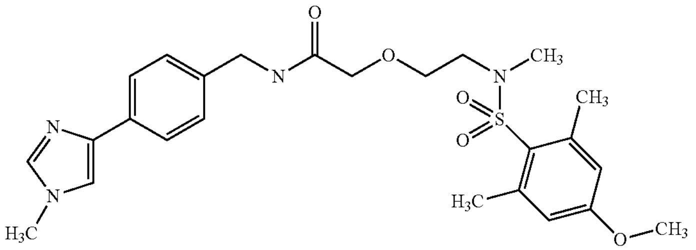 [SMILES: COc1cc(C)c(S(=O)(=O)N(C)CCOCC(=O)NCc2ccc(-c3cn(C)cn3)cc2)c(C)c1] |
| (63) | 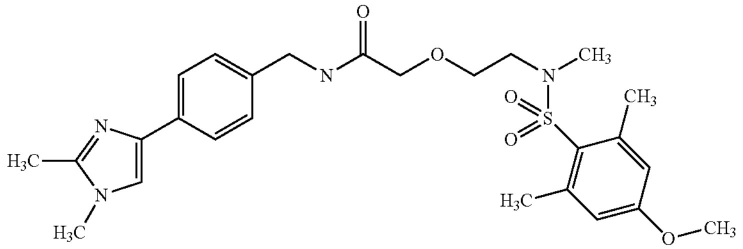 |
| (64) | 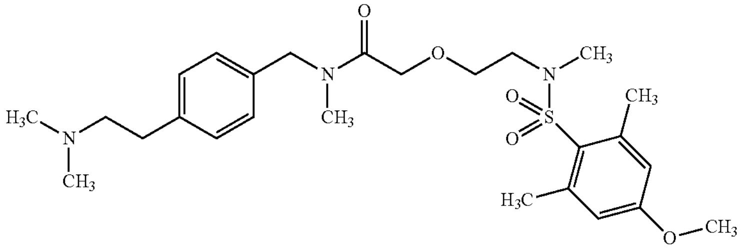 |
| (65) | 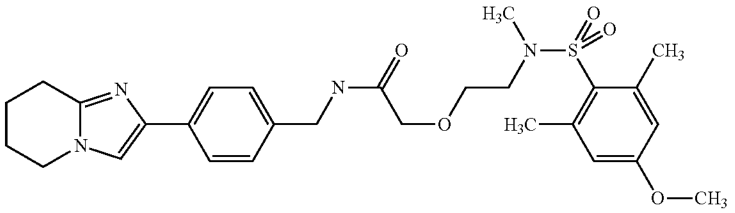 [SMILES: COc1cc(C)c(S(=O)(=O)N(C)CCOCC(=O)NCc2ccc(-c3cn4c(n3)CCCC4)cc2)c(C)c1] |

-continued
| Example | Structure |
| --- | --- |
| (66) | 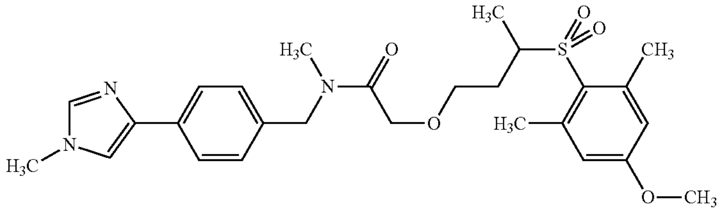 |
| (67) | 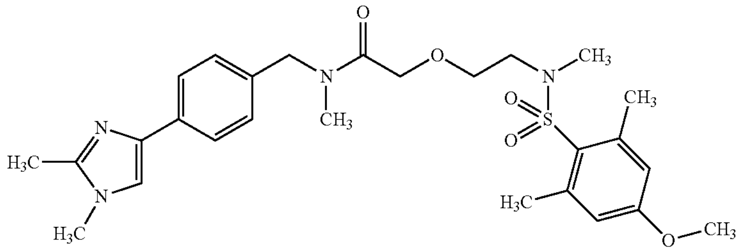 |
| (68) | 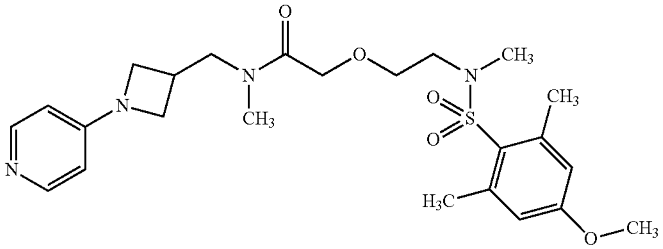 [SMILES: COc1cc(C)c(S(=O)(=O)N(C)CCOCC(=O)N(C)CC2CN(c3ccncc3)C2)c(C)c1] |
| (69) | 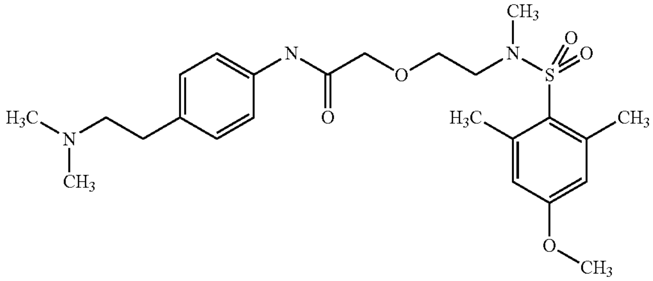 |
| (70) | 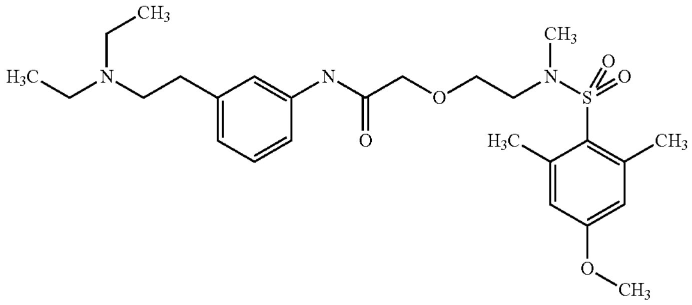 [SMILES: CCN(CC)CCc1cccc(NC(=O)COCCN(C)S(=O)(=O)c2c(C)cc(OC)cc2C)c1] |

-continued
| Example | Structure |
|---|---|
| (71) | 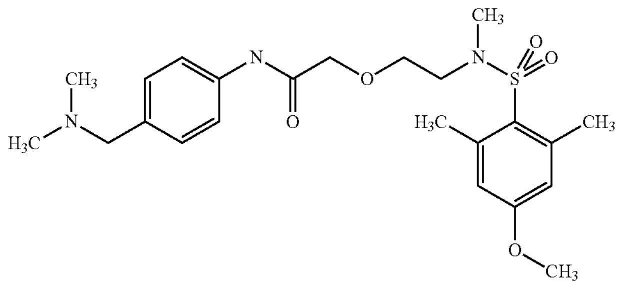 |
| (72) | 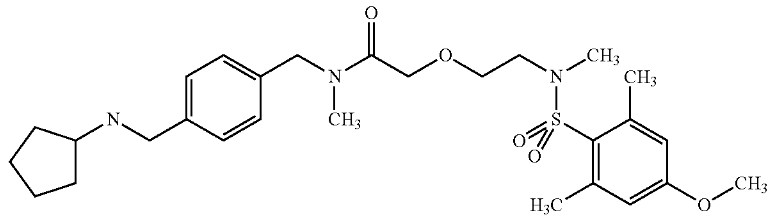 [SMILES: COc1cc(C)c(S(=O)(=O)N(C)CCOCC(=O)N(C)Cc2ccc(CNC3CCCC3)cc2)c(C)c1] |
| (73) | 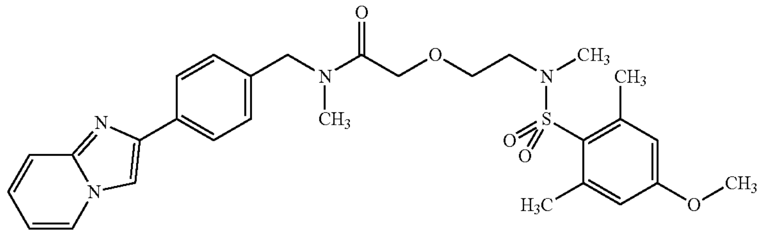 [SMILES: COc1cc(C)c(S(=O)(=O)N(C)CCOCC(=O)N(C)Cc2ccc(-c3cn4ccccc4n3)cc2)c(C)c1] |
| (74) | 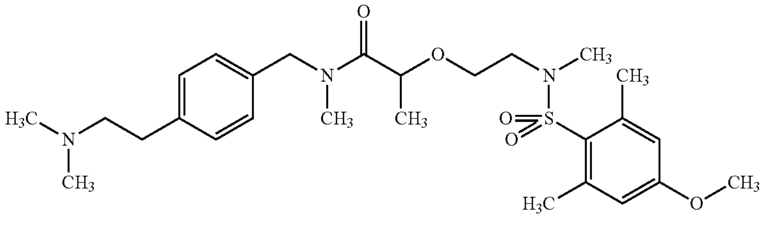 |
| (75) | 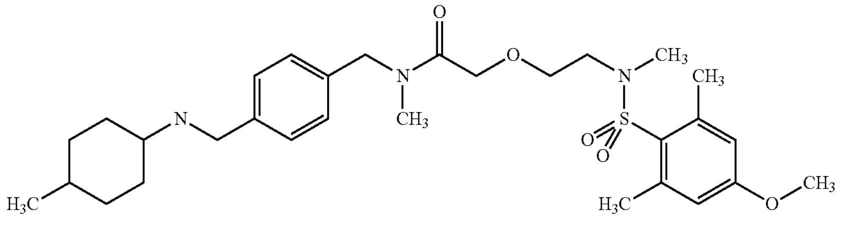 |
| (76) | 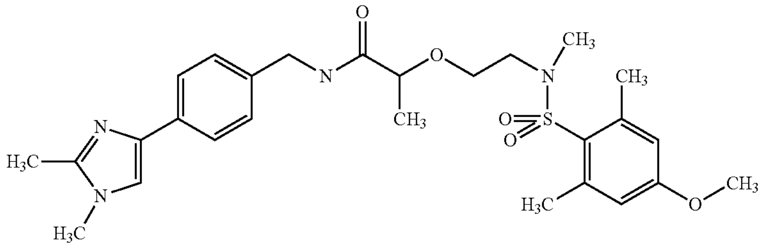 |

-continued
| Example | Structure |
| --- | --- |
| (77) | 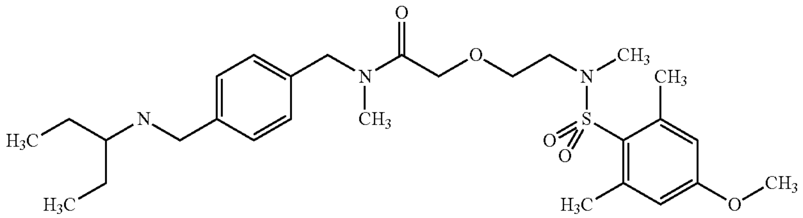 [SMILES: CCC(CC)NCc1ccc(CN(C)C(=O)COCCN(C)S(=O)(=O)c2c(C)cc(OC)cc2C)cc1] |
| (78) | 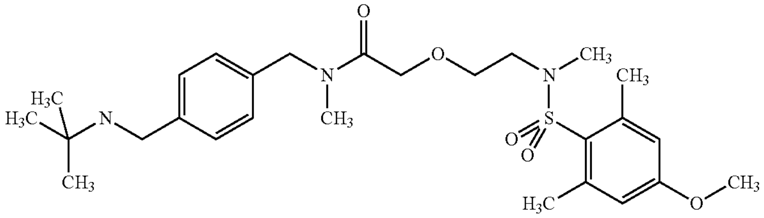 [SMILES: COc1cc(C)c(S(=O)(=O)N(C)CCOCC(=O)N(C)Cc2ccc(CNC(C)(C)C)cc2)c(C)c1] |
| (79) | 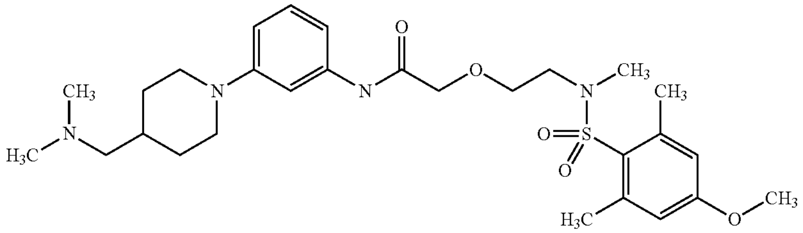 |
| (80) | 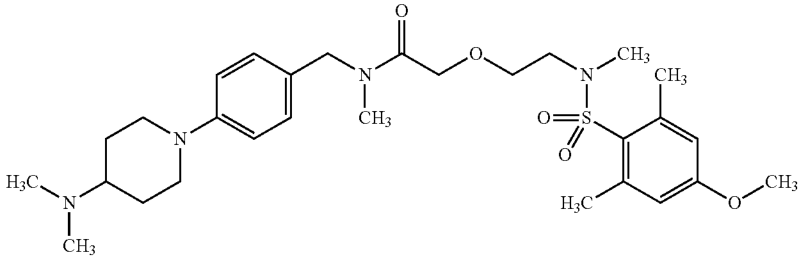 |
| (81) | 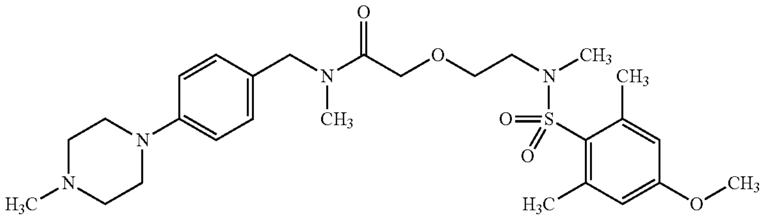 |
| (82) | 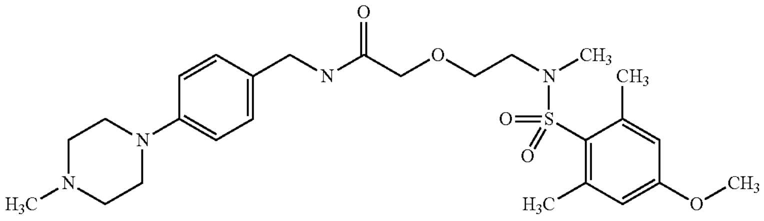 |

-continued
| Example | Structure |
| --- | --- |
| (83) | 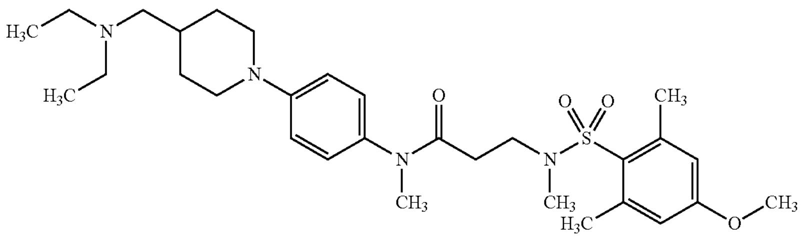 [SMILES: CCN(CC)CC1CCN(c2ccc(N(C)C(=O)CCN(C)S(=O)(=O)c3c(C)cc(OC)cc3C)cc2)CC1] |
| (84) | 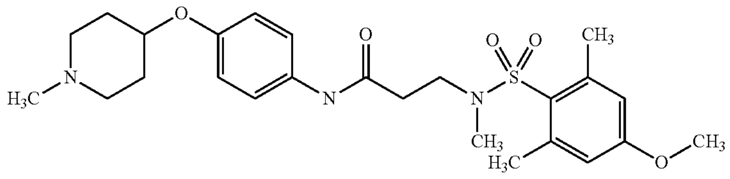 |
| (85) | 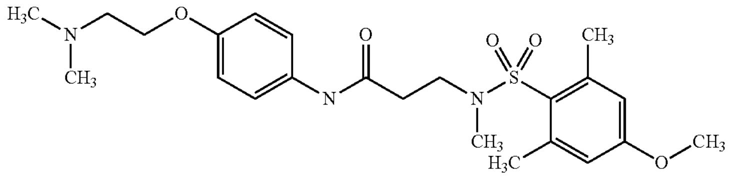 |
| (86) | 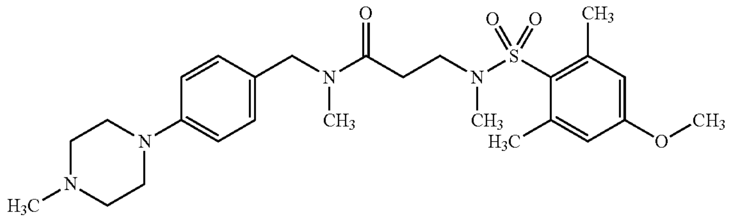 |
| (87) | 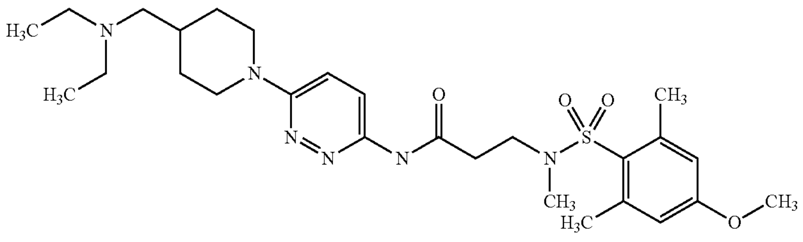 [SMILES: CCN(CC)CC1CCN(c2ccc(NC(=O)CCN(C)S(=O)(=O)c3c(C)cc(OC)cc3C)nn2)CC1] |
| (88) | 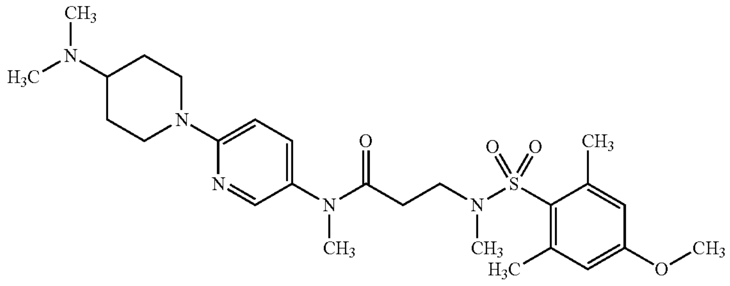 |

-continued
| Example | Structure |
| --- | --- |
| (89) | 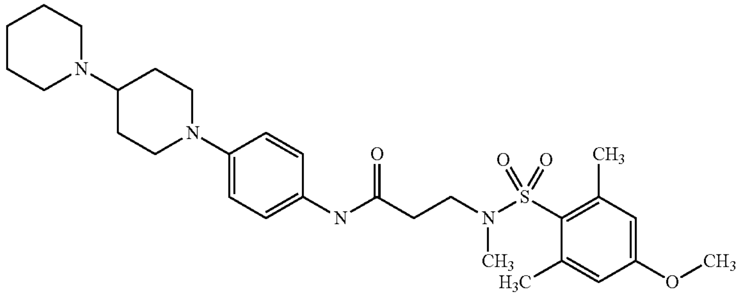 [SMILES: COc1cc(C)c(S(=O)(=O)N(C)CCC(=O)Nc2ccc(N3CCC(N4CCCCC4)CC3)cc2)c(C)c1] |
| (90) | 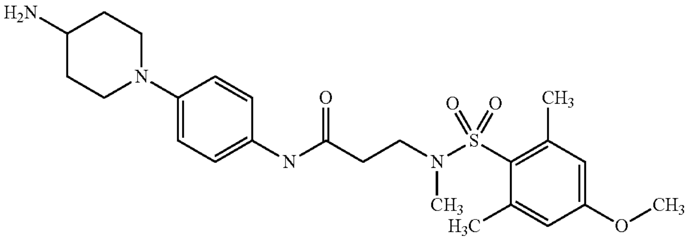 [SMILES: COc1cc(C)c(S(=O)(=O)N(C)CCC(=O)Nc2ccc(N3CCC(N)CC3)cc2)c(C)c1] |
| (91) | 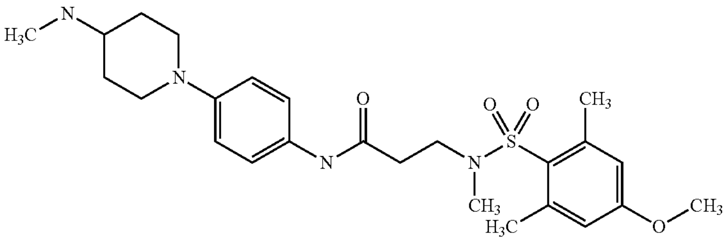 |
| (92) | 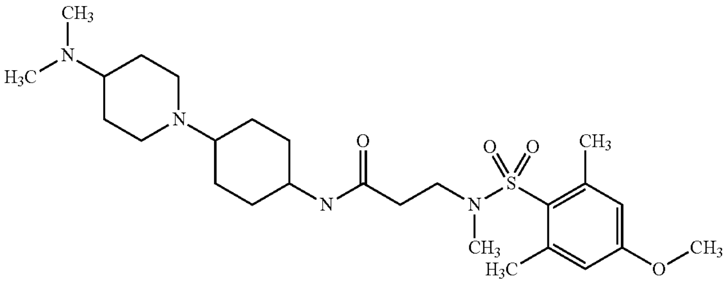 |
| (93) | 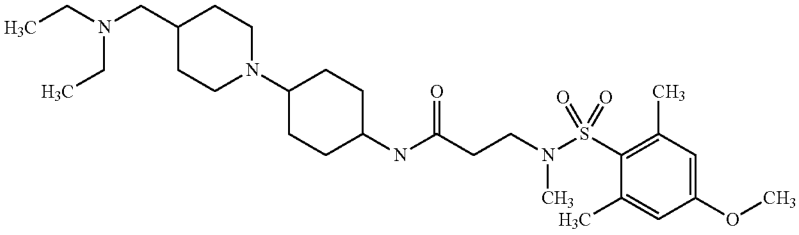 [SMILES: CCN(CC)CC1CCN(C2CCC(NC(=O)CCN(C)S(=O)(=O)c3c(C)cc(OC)cc3C)CC2)CC1] |

-continued
| Example | Structure |
| --- | --- |
| (94) | 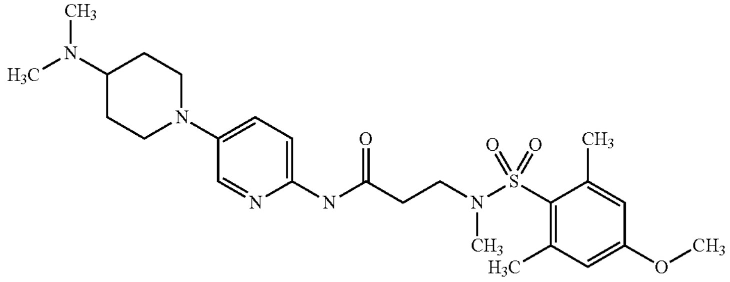 |
| (95) | 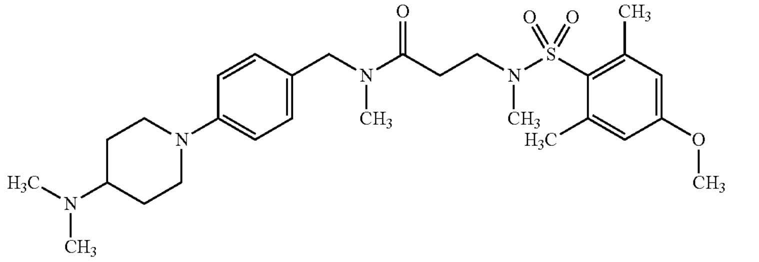 |
| (96) | 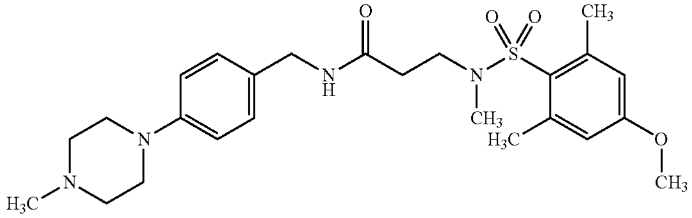 |
| (97) | 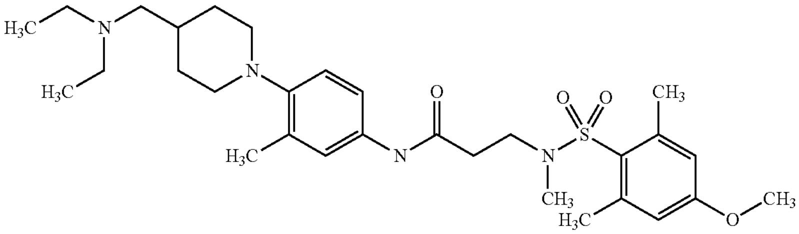 [SMILES: CCN(CC)CC1CCN(c2ccc(NC(=O)CCN(C)S(=O)(=O)c3c(C)cc(OC)cc3C)cc2C)CC1] |
| (98) | 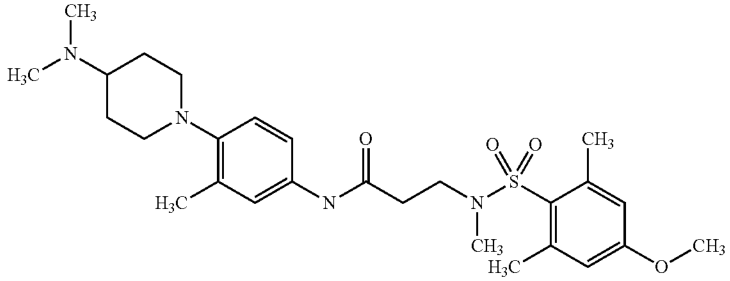 |

-continued
| Example | Structure |
|---|---|
| (99) | 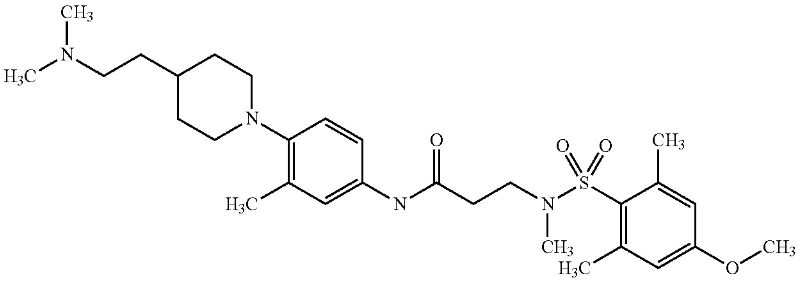 |
| (100) | 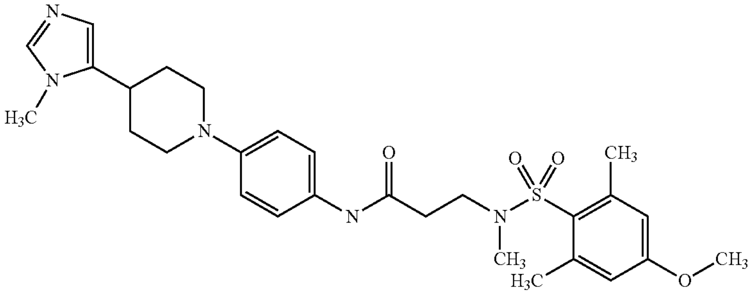 [SMILES: COc1cc(C)c(S(=O)(=O)N(C)CCC(=O)Nc2ccc(N3CCC(c4cncn4C)CC3)cc2)c(C)c1] |
| (101) | 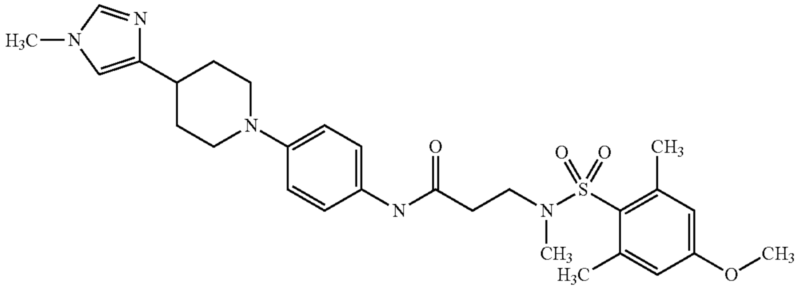 |
| (102) | 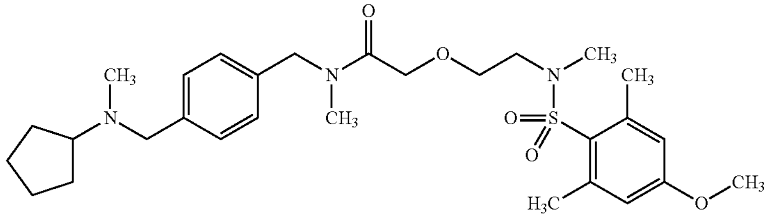 [SMILES: COc1cc(C)c(S(=O)(=O)N(C)CCOCC(=O)N(C)Cc2ccc(CN(C)C3CCCC3)cc2)c(C)c1] |
| (103) | 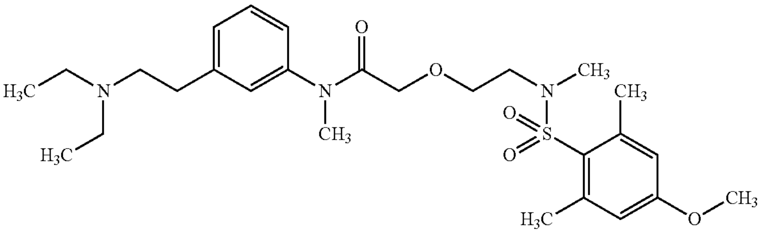 [SMILES: CCN(CC)CCc1cccc(N(C)C(=O)COCCN(C)S(=O)(=O)c2c(C)cc(OC)cc2C)c1] |
| (104) | 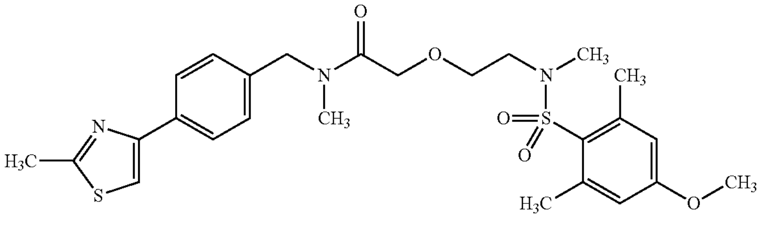 |

-continued
| Example | Structure |
| --- | --- |
| (105) | 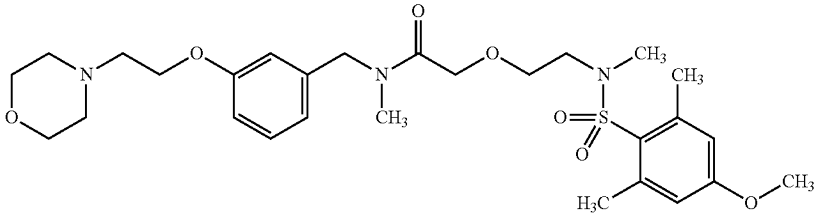 [SMILES: COc1cc(C)c(S(=O)(=O)N(C)CCOCC(=O)N(C)Cc2cccc(OCCN3CCOCC3)c2)c(C)c1] |
| (106) | 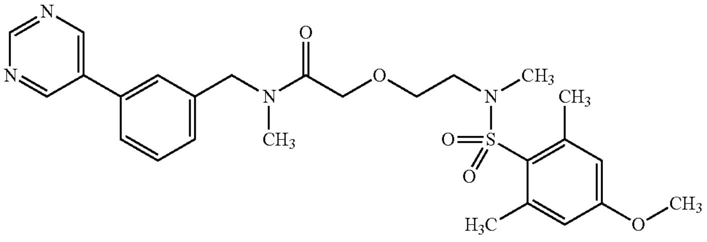 [SMILES: COc1cc(C)c(S(=O)(=O)N(C)CCOCC(=O)N(C)Cc2cccc(-c3cncnc3)c2)c(C)c1] |
| (107) | 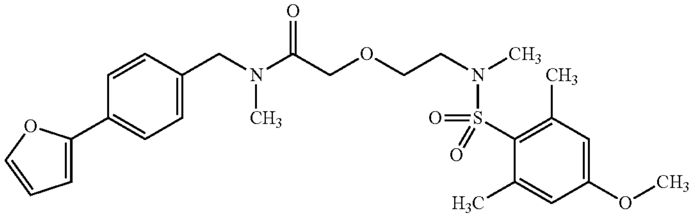 [SMILES: COc1cc(C)c(S(=O)(=O)N(C)CCOCC(=O)N(C)Cc2ccc(-c3ccco3)cc2)c(C)c1] |
| (108) | 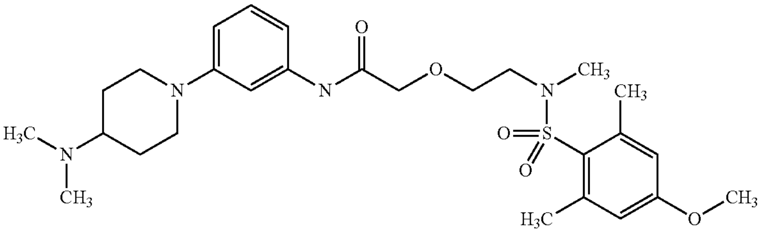 |
| (109) | 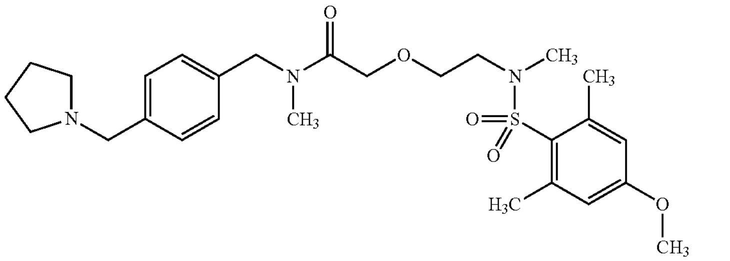 [SMILES: COc1cc(C)c(S(=O)(=O)N(C)CCOCC(=O)N(C)Cc2ccc(CN3CCCC3)cc2)c(C)c1] |
| (110) | 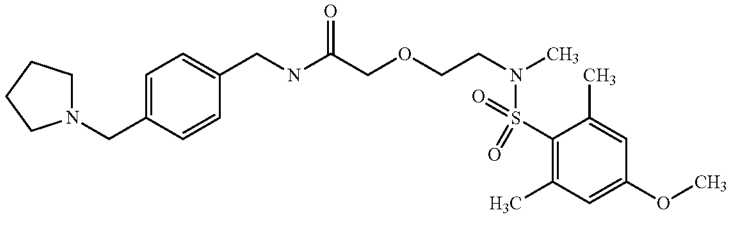 [SMILES: COc1cc(C)c(S(=O)(=O)N(C)CCOCC(=O)NCc2ccc(CN3CCCC3)cc2)c(C)c1] |

-continued
| Example | Structure |
|---|---|
| (111) | 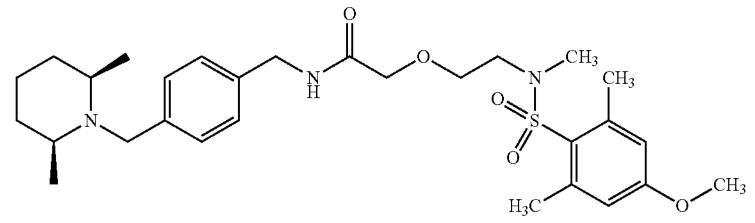 [SMILES: COc1cc(C)c(S(=O)(=O)N(C)CCOCC(=O)NCc2ccc(CN3[C@H](C)CCC[C@@H]3C)cc2)c(C)c1] |
| (112) | 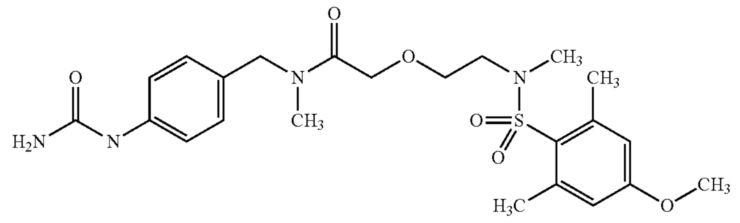 [SMILES: COc1cc(C)c(S(=O)(=O)N(C)CCOCC(=O)N(C)Cc2ccc(NC(N)=O)cc2)c(C)c1] |
| (113) | 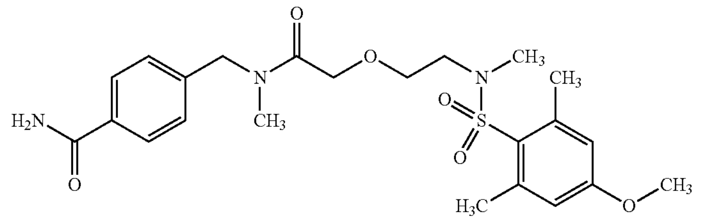 [SMILES: COc1cc(C)c(S(=O)(=O)N(C)CCOCC(=O)N(C)Cc2ccc(C(N)=O)cc2)c(C)c1] |
| (114) | 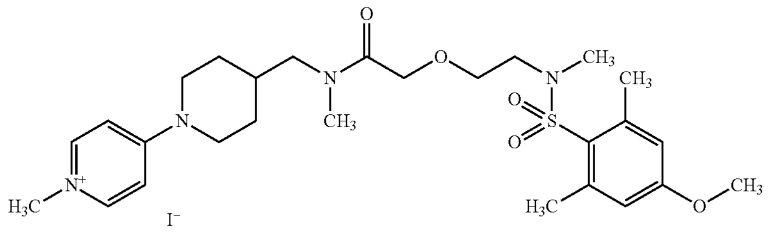 |
| (115) | 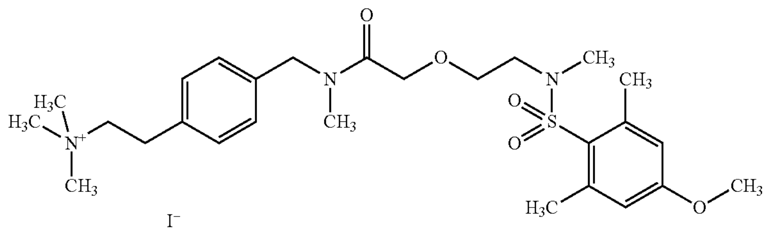 |
| (116) | 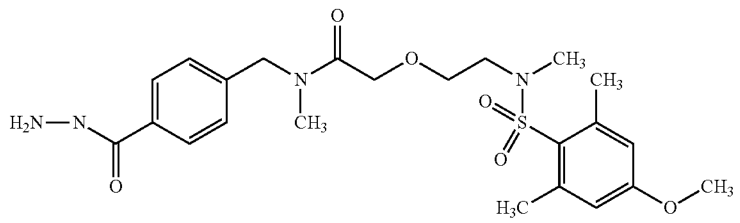 [SMILES: COc1cc(C)c(S(=O)(=O)N(C)CCOCC(=O)N(C)Cc2ccc(C(=O)NN)cc2)c(C)c1] |
| (117) | 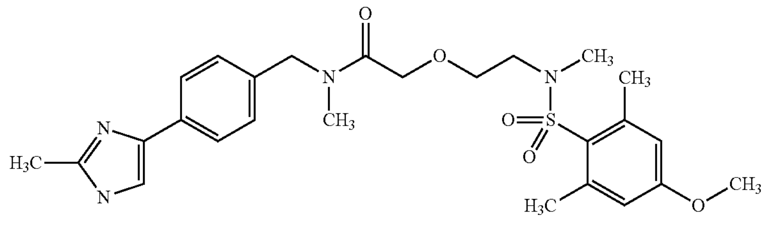 |

-continued
| Example | Structure |
| --- | --- |
| (118) | 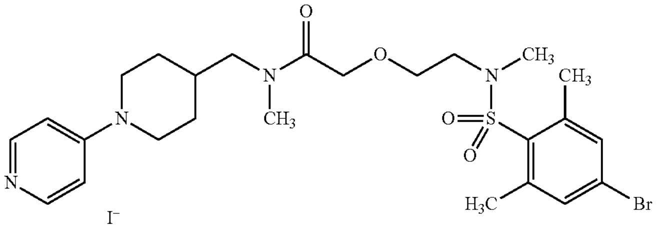 [SMILES: Cc1cc(Br)cc(C)c1S(=O)(=O)N(C)CCOCC(=O)N(C)CC1CCN(c2ccncc2)CC1 ; [I-]] |
| (119) | 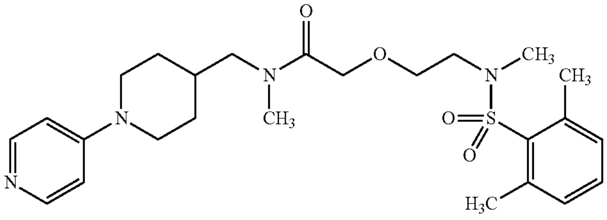 [SMILES: Cc1cccc(C)c1S(=O)(=O)N(C)CCOCC(=O)N(C)CC1CCN(c2ccncc2)CC1] |
| (120) | 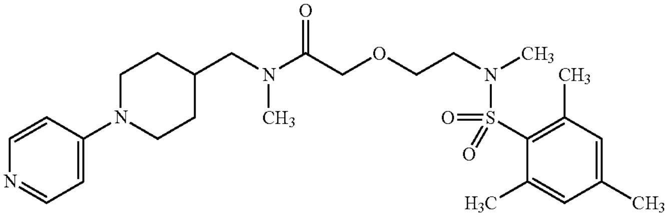 [SMILES: Cc1cc(C)c(S(=O)(=O)N(C)CCOCC(=O)N(C)CC2CCN(c3ccncc3)CC2)c(C)c1] |
| (121) | 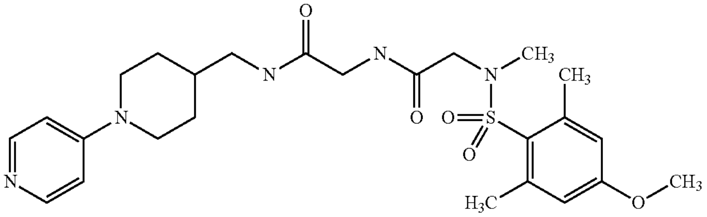 [SMILES: COc1cc(C)c(S(=O)(=O)N(C)CC(=O)NCC(=O)NCC2CCN(c3ccncc3)CC2)c(C)c1] |
| (122) | 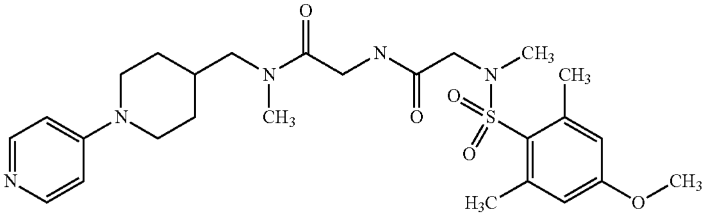 [SMILES: COc1cc(C)c(S(=O)(=O)N(C)CC(=O)NCC(=O)N(C)CC2CCN(c3ccncc3)CC2)c(C)c1] |
| (123) | 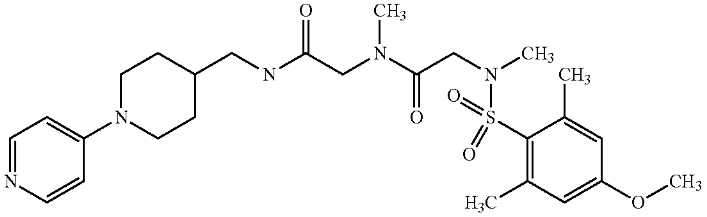 [SMILES: COc1cc(C)c(S(=O)(=O)N(C)CC(=O)N(C)CC(=O)NCC2CCN(c3ccncc3)CC2)c(C)c1] |

-continued
| Example | Structure |
| --- | --- |
| (124) | 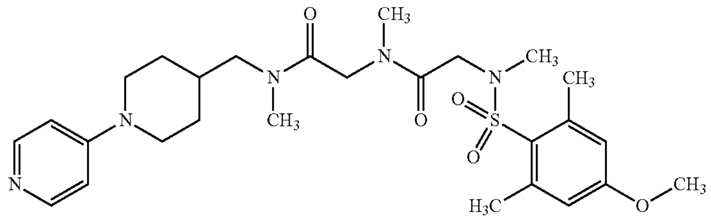 [SMILES: COc1cc(C)c(S(=O)(=O)N(C)CC(=O)N(C)CC(=O)N(C)CC2CCN(c3ccncc3)CC2)c(C)c1] |
| (125) | 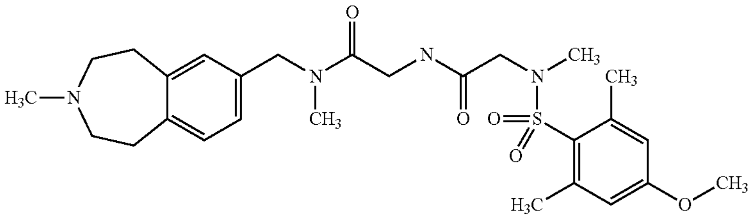 |
| (126) | 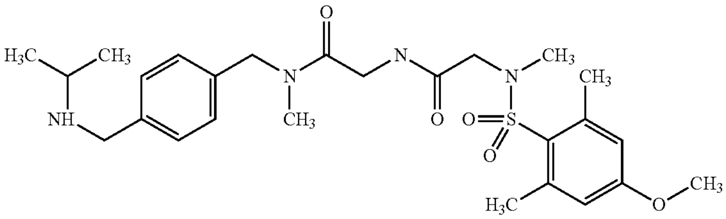 [SMILES: COc1cc(C)c(S(=O)(=O)N(C)CC(=O)NCC(=O)N(C)Cc2ccc(CNC(C)C)cc2)c(C)c1] |
| (127) | 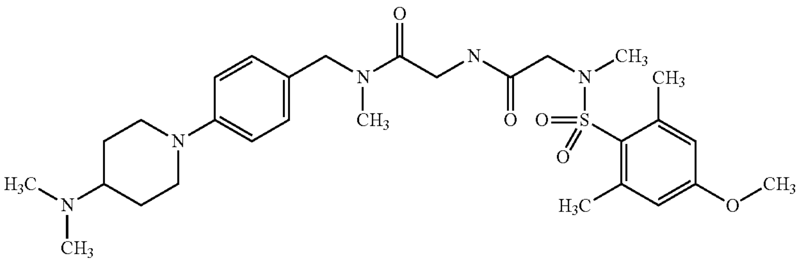 |
| (128) | 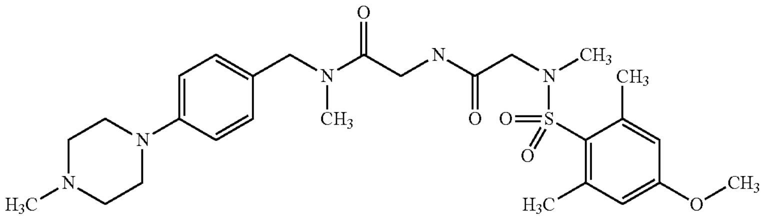 |
| (129) | 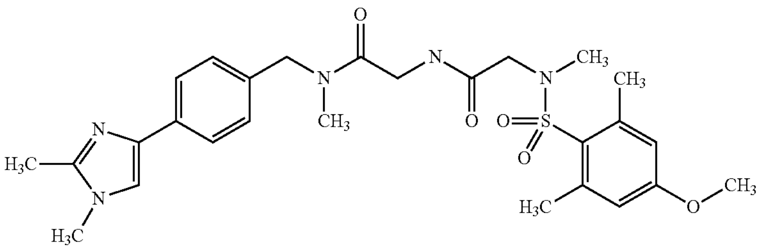 |

-continued
| Example | Structure |
|---|---|
| (130) | 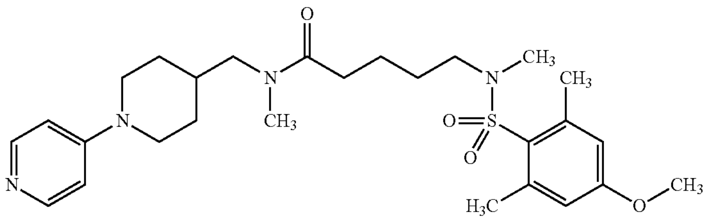 [SMILES: COc1cc(C)c(S(=O)(=O)N(C)CCCCC(=O)N(C)CC2CCN(c3ccncc3)CC2)c(C)c1] |
| (131) | 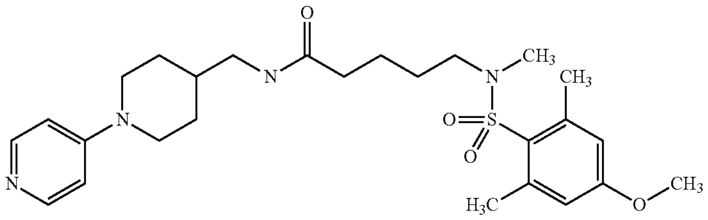 [SMILES: COc1cc(C)c(S(=O)(=O)N(C)CCCCC(=O)NCC2CCN(c3ccncc3)CC2)c(C)c1] |
| (132) | 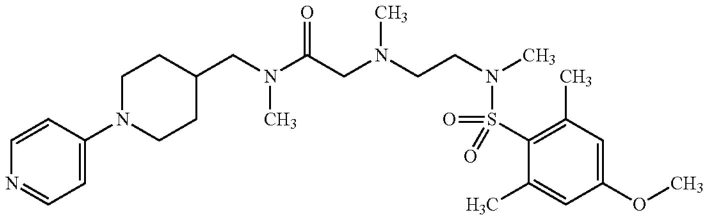 [SMILES: COc1cc(C)c(S(=O)(=O)N(C)CCN(C)CC(=O)N(C)CC2CCN(c3ccncc3)CC2)c(C)c1] |
| (133) | 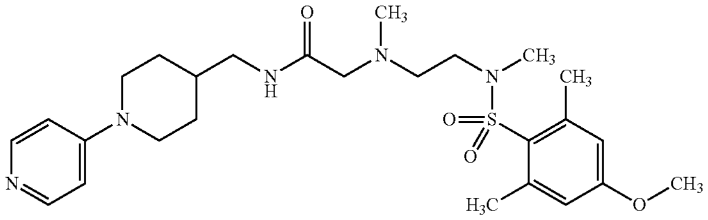 [SMILES: COc1cc(C)c(S(=O)(=O)N(C)CCN(C)CC(=O)NCC2CCN(c3ccncc3)CC2)c(C)c1] |
| (134) | 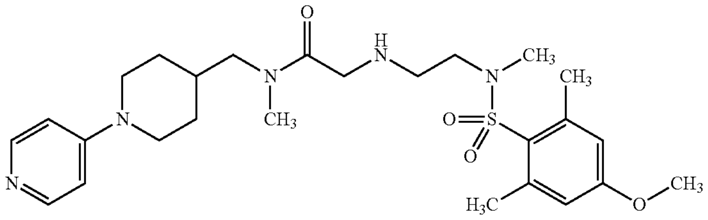 [SMILES: COc1cc(C)c(S(=O)(=O)N(C)CCNCC(=O)N(C)CC2CCN(c3ccncc3)CC2)c(C)c1] |
| (135) | 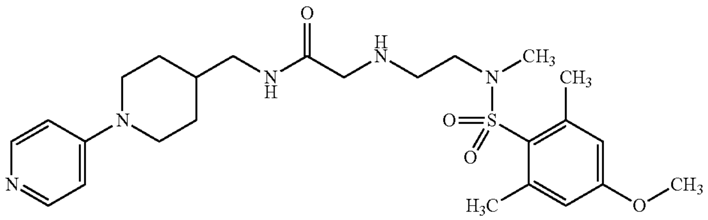 [SMILES: COc1cc(C)c(S(=O)(=O)N(C)CCNCC(=O)NCC2CCN(c3ccncc3)CC2)c(C)c1] |
| (136) | 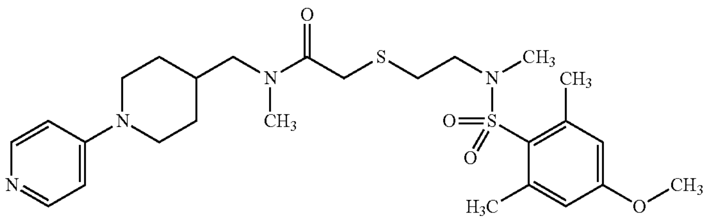 [SMILES: COc1cc(C)c(S(=O)(=O)N(C)CCSCC(=O)N(C)CC2CCN(c3ccncc3)CC2)c(C)c1] |

-continued
| Example | Structure |
| --- | --- |
| (137) | 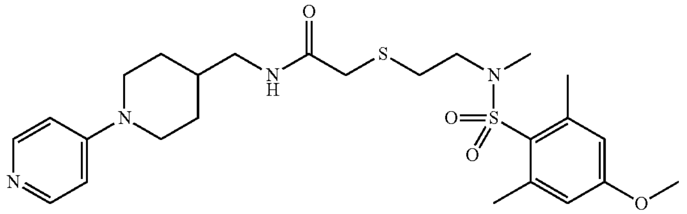 [SMILES: COc1cc(C)c(S(=O)(=O)N(C)CCSCC(=O)NCC2CCN(c3ccncc3)CC2)c(C)c1] |
| (138) | 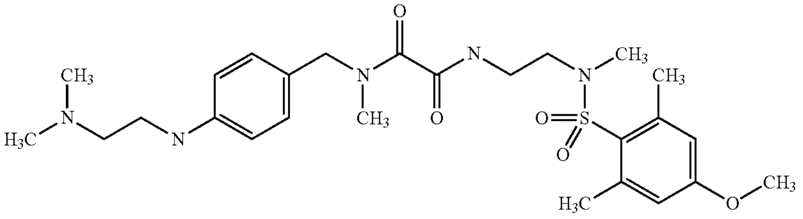 |
| (139) | 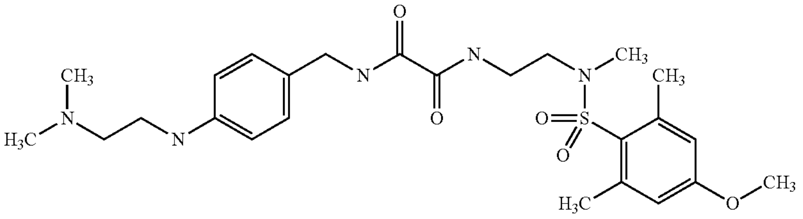 |
| (140) | 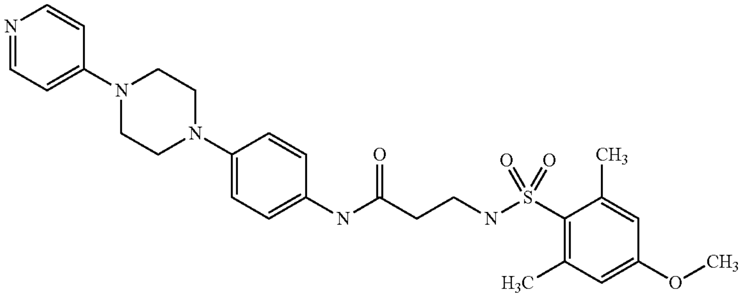 [SMILES: COc1cc(C)c(S(=O)(=O)NCCC(=O)Nc2ccc(N3CCN(c4ccncc4)CC3)cc2)c(C)c1] |
| (141) | 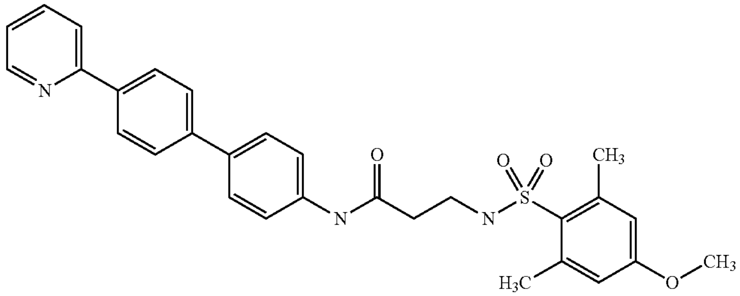 [SMILES: COc1cc(C)c(S(=O)(=O)NCCC(=O)Nc2ccc(-c3ccc(-c4ccccn4)cc3)cc2)c(C)c1] |
| (142) | 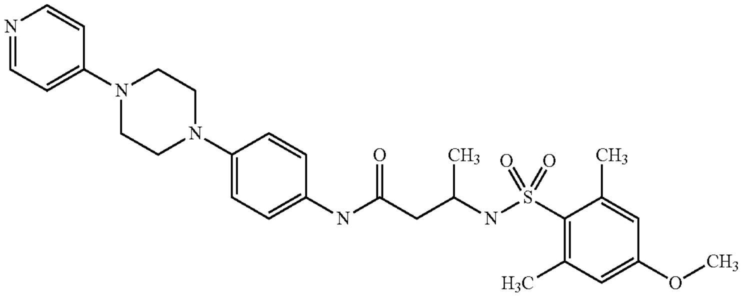 [SMILES: COc1cc(C)c(S(=O)(=O)NC(C)CC(=O)Nc2ccc(N3CCN(c4ccncc4)CC3)cc2)c(C)c1] |

-continued
| Example | Structure |
|---|---|
| (143) | 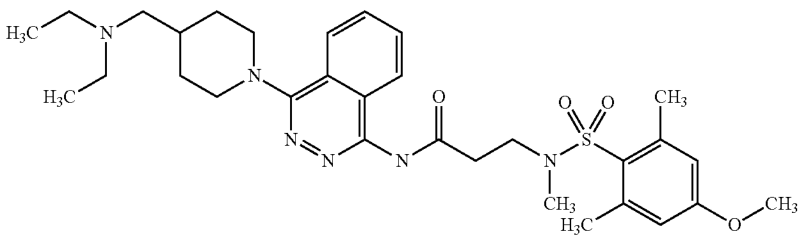 [SMILES: CCN(CC)CC1CCN(c2nnc(NC(=O)CCN(C)S(=O)(=O)c3c(C)cc(OC)cc3C)c3ccccc23)CC1] |
| (144) | 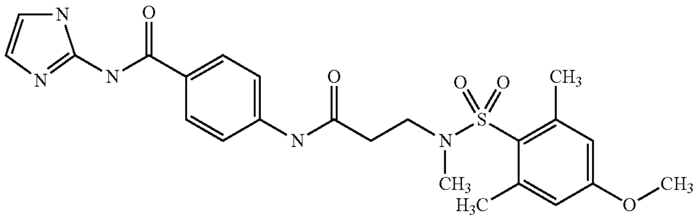 [SMILES: COc1cc(C)c(S(=O)(=O)N(C)CCC(=O)Nc2ccc(C(=O)Nc3ncc[nH]3)cc2)c(C)c1] |
| (145) | 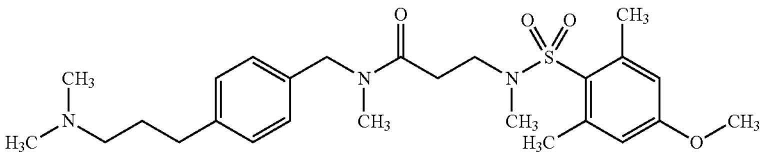 |
| (146) | 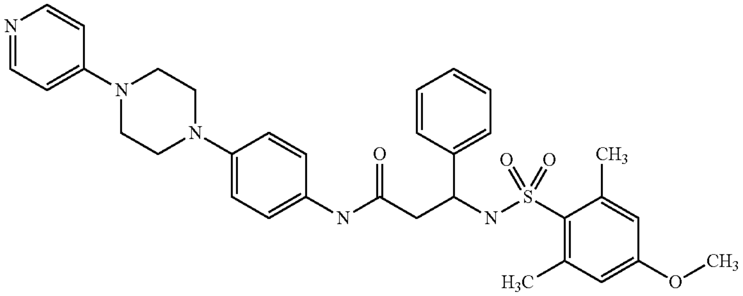 [SMILES: COc1cc(C)c(S(=O)(=O)NC(CC(=O)Nc2ccc(N3CCN(c4ccncc4)CC3)cc2)c2ccccc2)c(C)c1] |
| (147) | 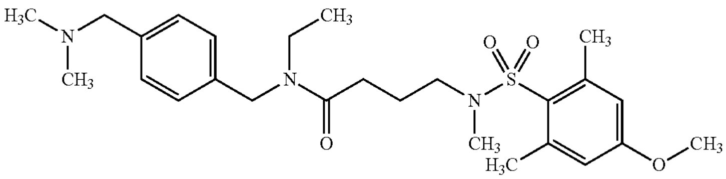 |
| (148) | 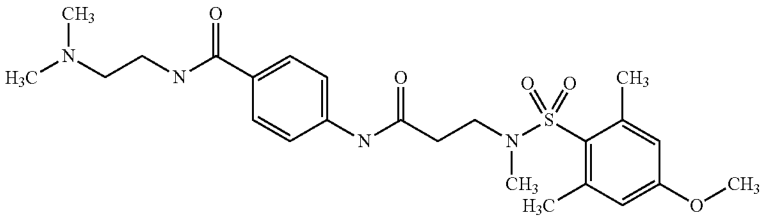 |
| (149) | 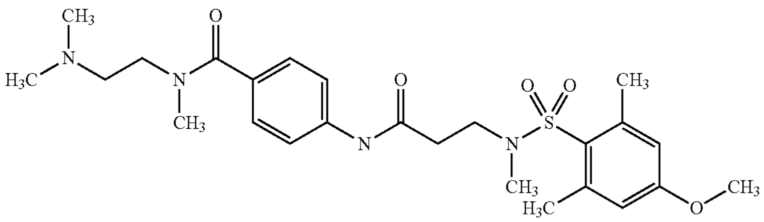 |

-continued
| Example | Structure |
| --- | --- |
| (150) | 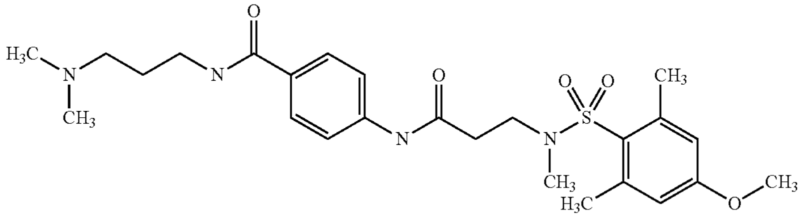 |
| (151) | 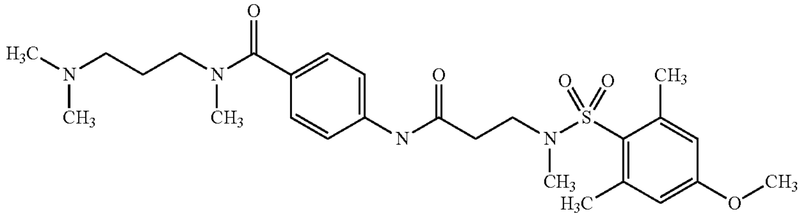 |
| (152) | 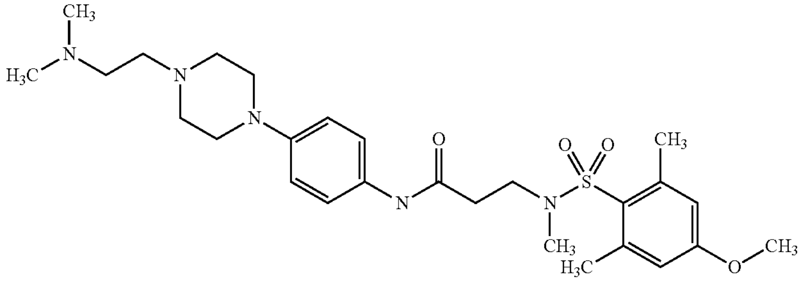 |
| (153) | 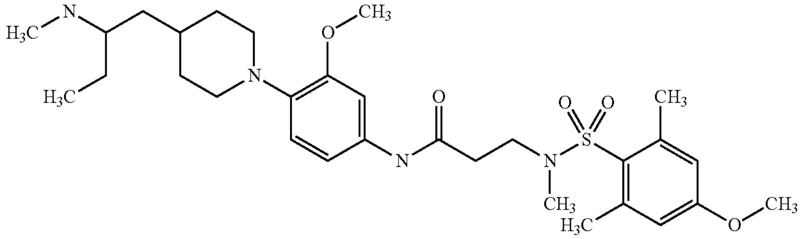 |
| (154) | 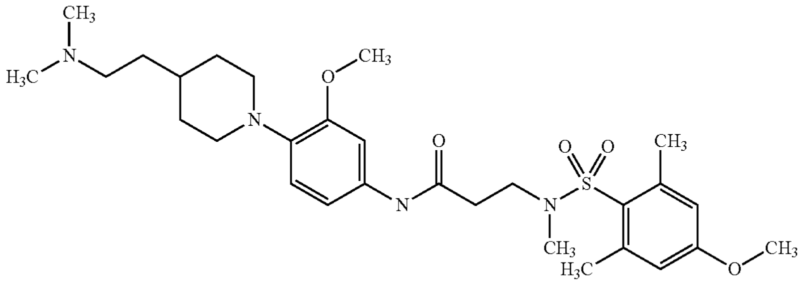 |
| (155) | 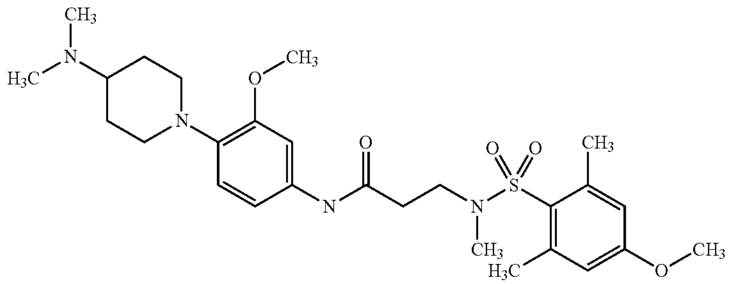 |

-continued
| Example | Structure |
| --- | --- |
| (156) | 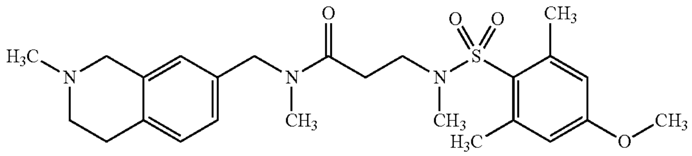 |
| (157) | 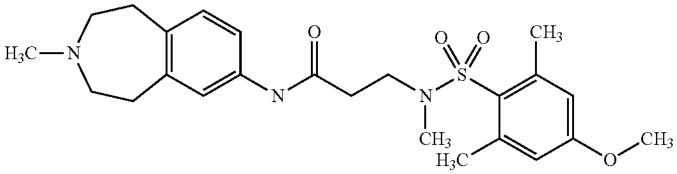 |
| (158) | 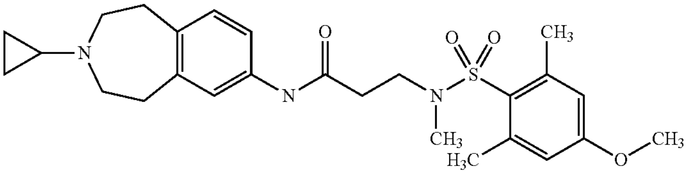 [SMILES: COc1cc(C)c(S(=O)(=O)N(C)CCC(=O)Nc2ccc3c(c2)CCN(C2CC2)CC3)c(C)c1] |
| (159) | 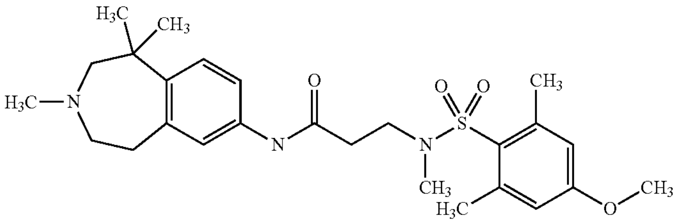 |
| (160) | 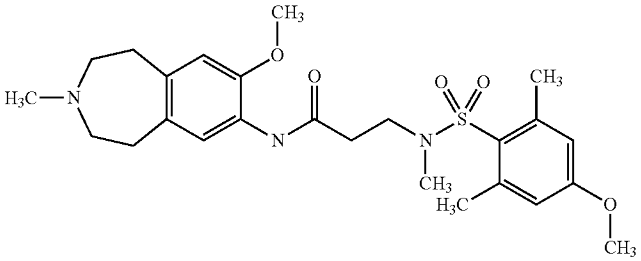 |
| (161) | 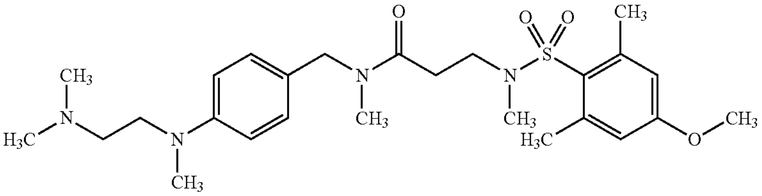 |
| (162) | 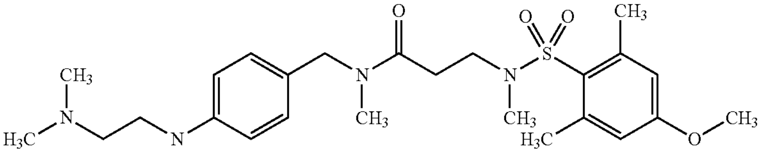 |
| (163) | 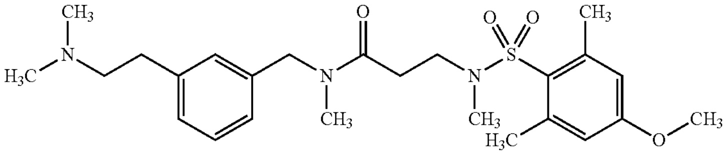 |

-continued
| Example | Structure |
| --- | --- |
| (164) | 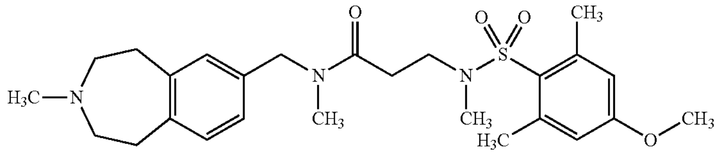 |
| (165) | 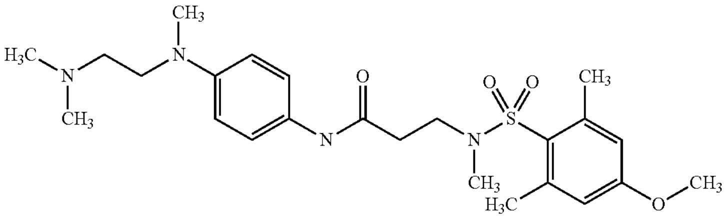 |
| (166) | 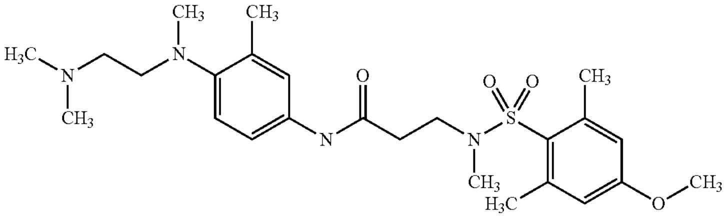 |
| (167) | 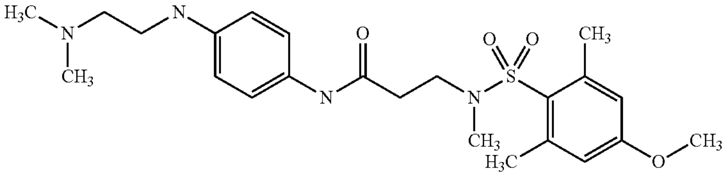 |
| (168) | 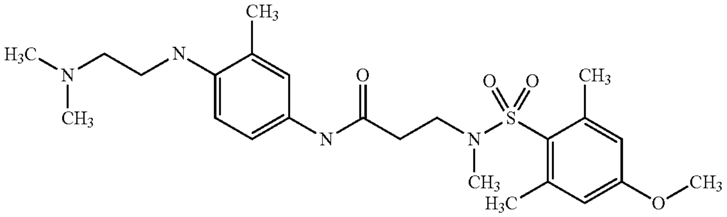 |
| (169) | 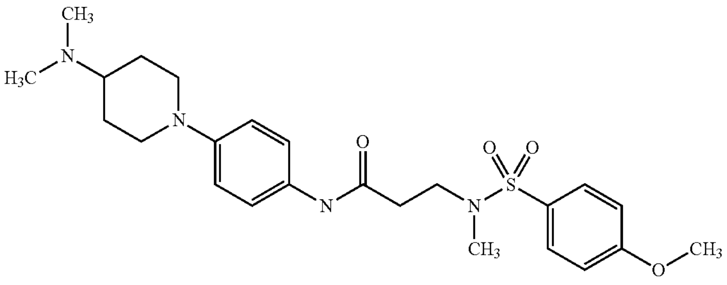 |
| (170) | 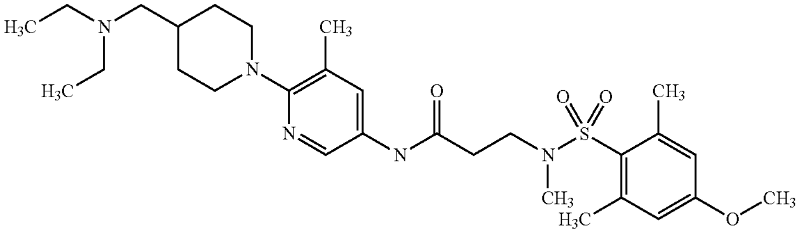 [SMILES: CCN(CC)CC1CCN(c2ncc(NC(=O)CCN(C)S(=O)(=O)c3c(C)cc(OC)cc3C)cc2C)CC1] |

-continued
| Example | Structure |
| --- | --- |
| (171) | 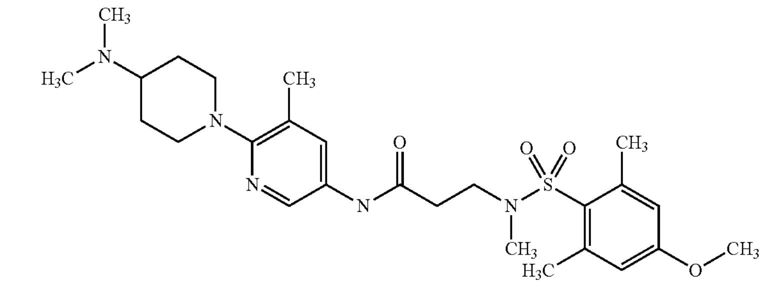 |
| (172) | 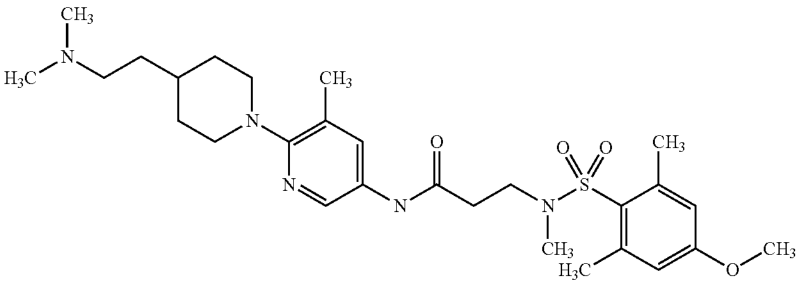 |
| (173) | 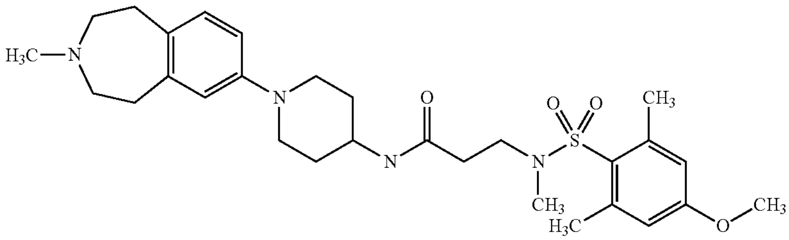 |
| (174) | 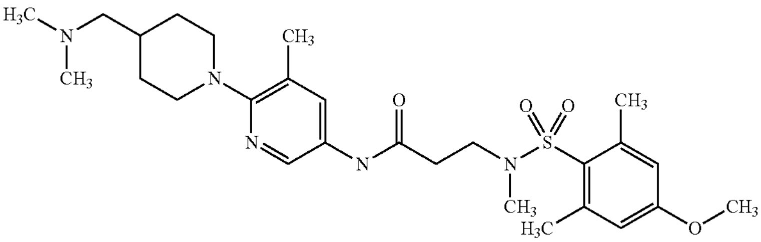 |
| (175) | 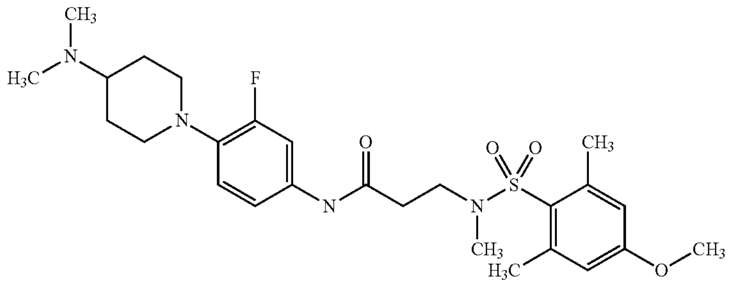 |
| (176) | 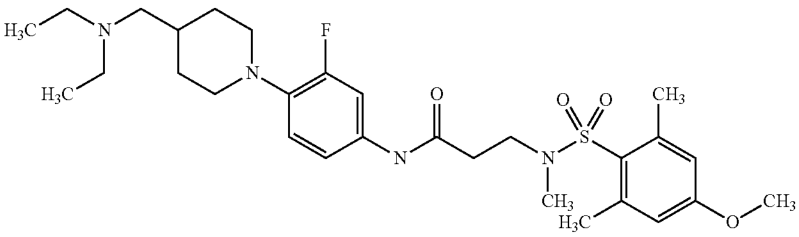 [SMILES: CCN(CC)CC1CCN(c2ccc(NC(=O)CCN(C)S(=O)(=O)c3c(C)cc(OC)cc3C)cc2F)CC1] |

-continued
| Example | Structure |
| --- | --- |
| (177) | 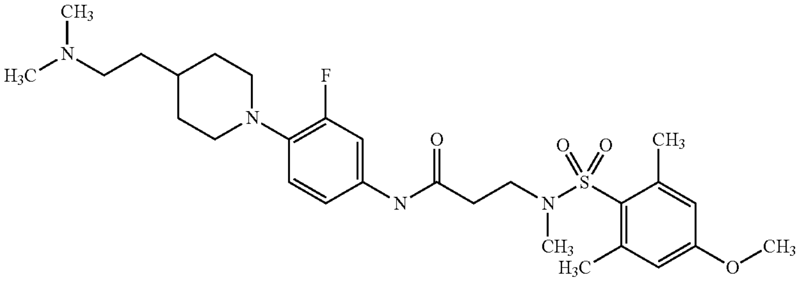 |
| (178) | 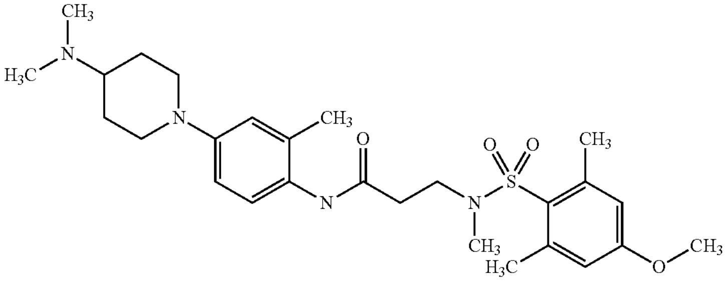 |
| (179) | 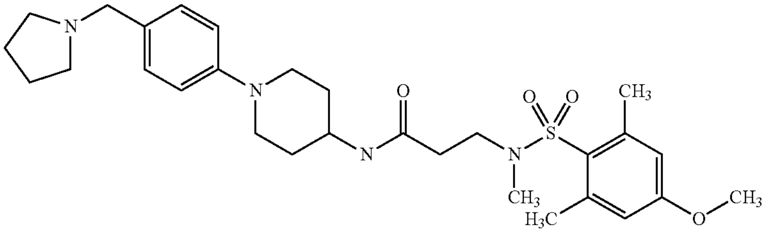 |
| (180) | 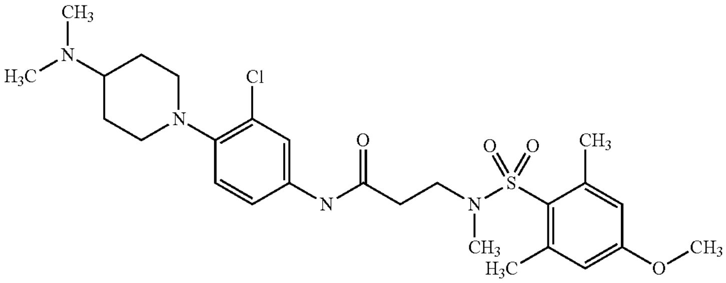 |
| (181) | 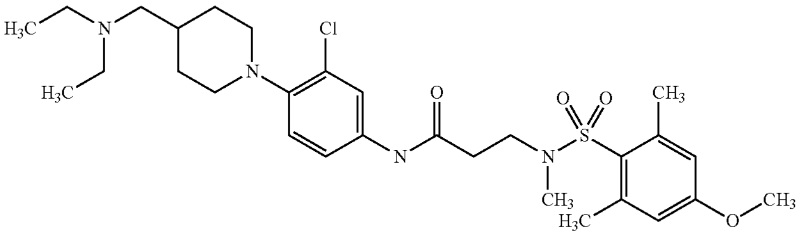 |

-continued
| Example | Structure |
| --- | --- |
| (182) | 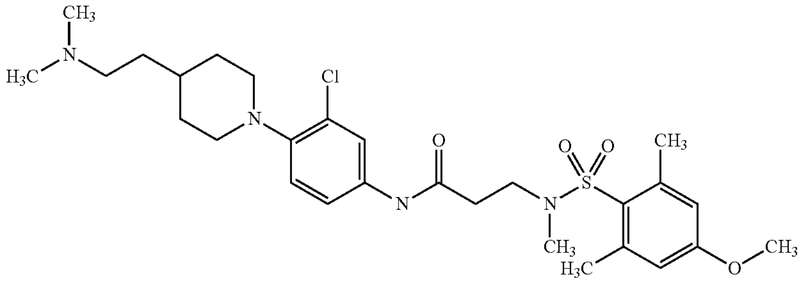 |
| (183) | 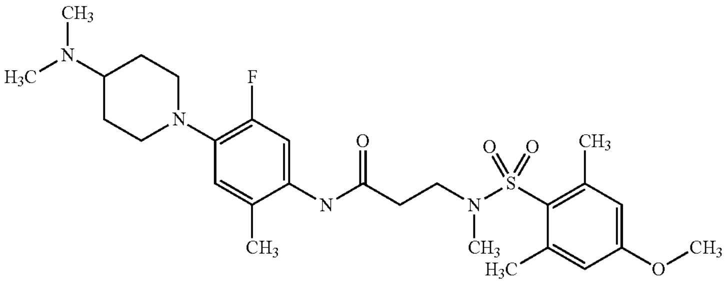 |
| (184) | 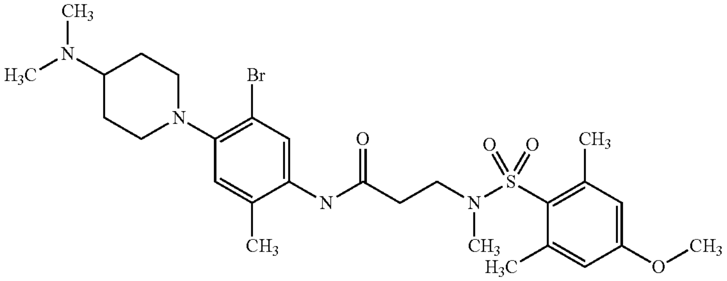 |
| (185) | 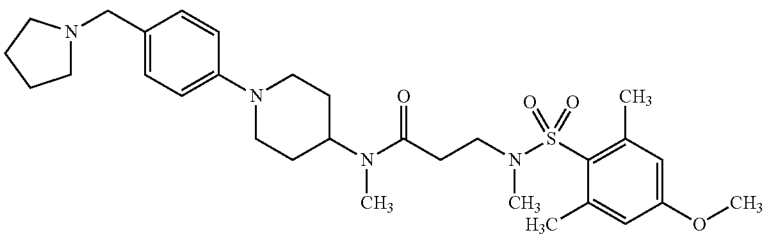 [SMILES: COc1cc(C)c(S(=O)(=O)N(C)CCC(=O)N(C)C2CCN(c3ccc(CN4CCCC4)cc3)CC2)c(C)c1] |
| (186) | 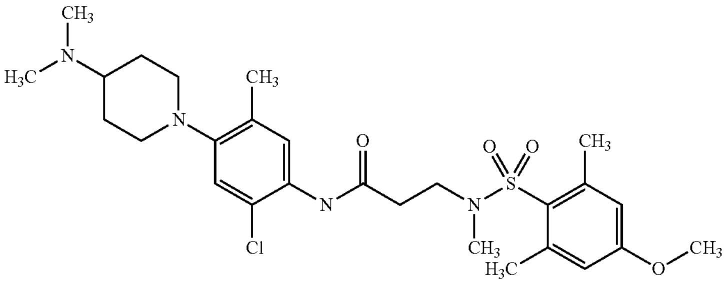 |

-continued
| Example | Structure |
|---|---|
| (187) | 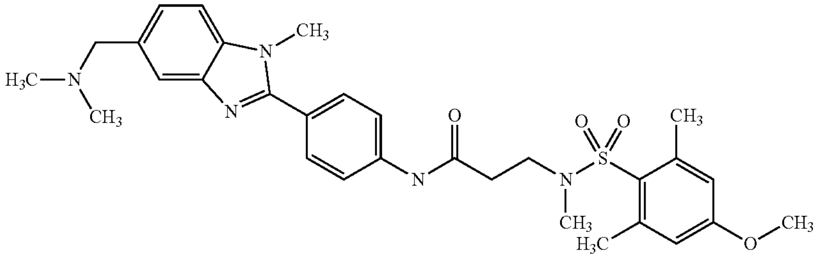 |
| (188) | 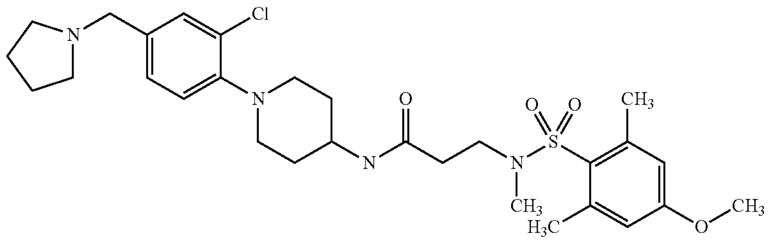 [SMILES: COc1cc(C)c(S(=O)(=O)N(C)CCC(=O)NC2CCN(c3ccc(CN4CCCC4)cc3Cl)CC2)c(C)c1] |
| (189) | 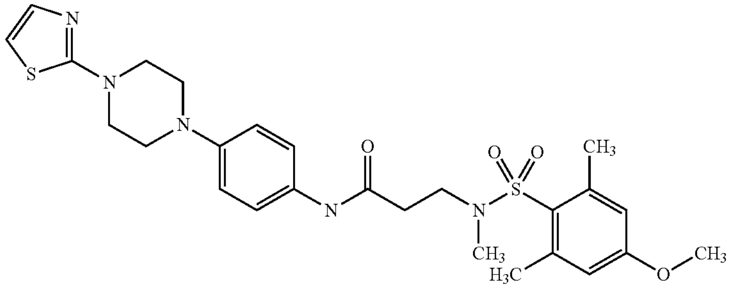 [SMILES: COc1cc(C)c(S(=O)(=O)N(C)CCC(=O)Nc2ccc(N3CCN(c4nccs4)CC3)cc2)c(C)c1] |
| (190) | 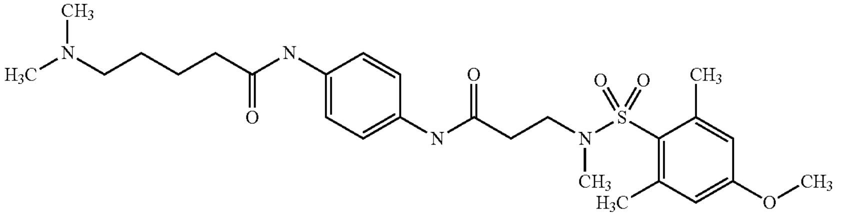 |
| (191) | 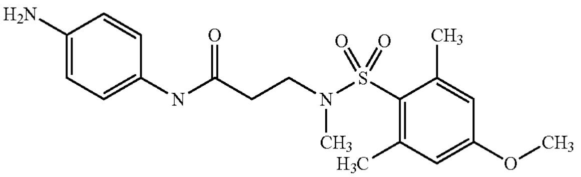 [SMILES: COc1cc(C)c(S(=O)(=O)N(C)CCC(=O)Nc2ccc(N)cc2)c(C)c1] |
| (192) | 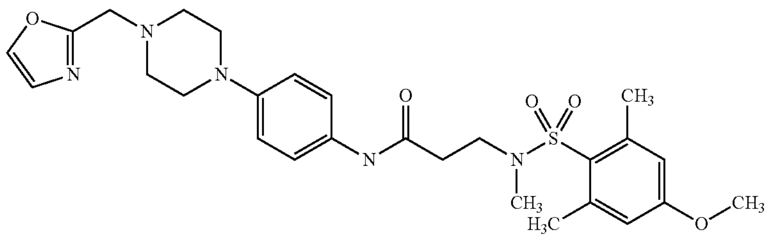 [SMILES: COc1cc(C)c(S(=O)(=O)N(C)CCC(=O)Nc2ccc(N3CCN(Cc4ncco4)CC3)cc2)c(C)c1] |

-continued
| Example | Structure |
| --- | --- |
| (193) | 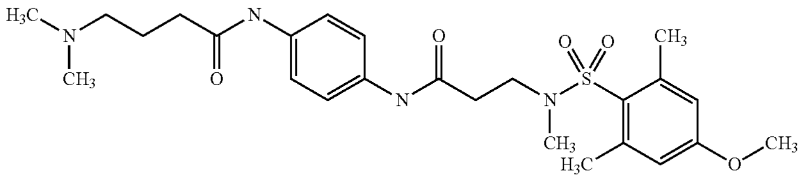 |
| (194) | 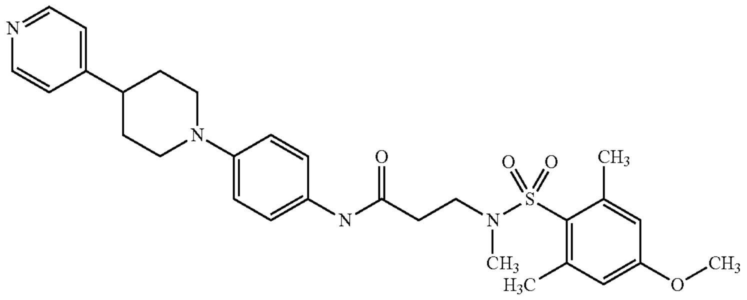 [SMILES: COc1cc(C)c(S(=O)(=O)N(C)CCC(=O)Nc2ccc(N3CCC(c4ccncc4)CC3)cc2)c(C)c1] |
| (195) | 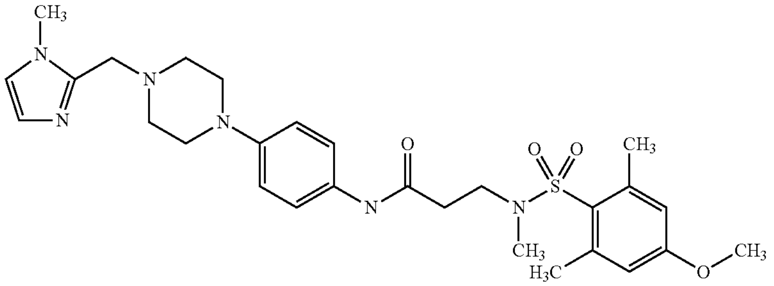 [SMILES: COc1cc(C)c(S(=O)(=O)N(C)CCC(=O)Nc2ccc(N3CCN(Cc4nccn4C)CC3)cc2)c(C)c1] |
| (196) | 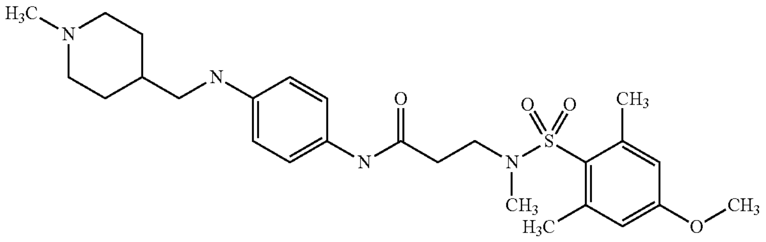 |
| (197) | 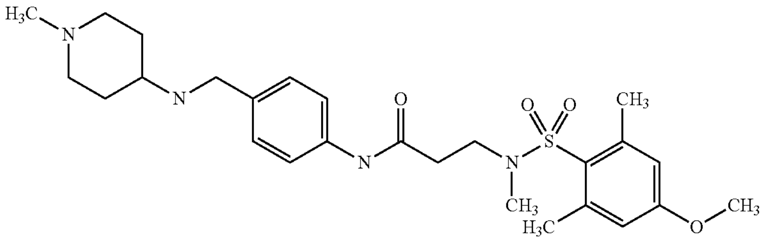 |
| (198) | 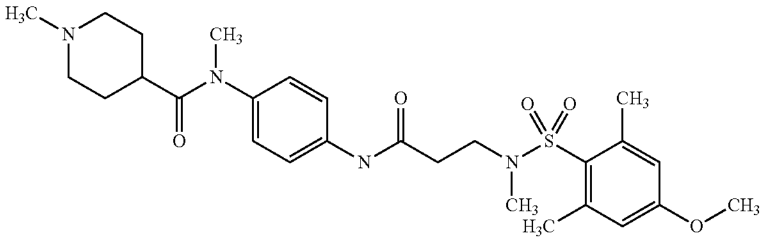 |

-continued
| Example | Structure |
|---|---|
| (199) | 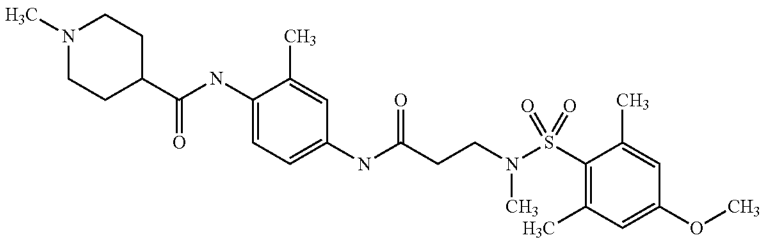 |
| (200) | 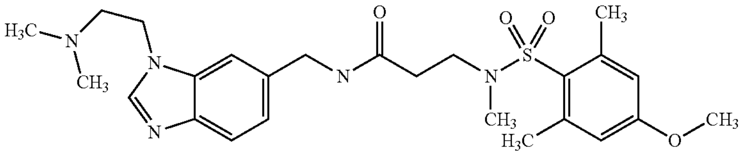 |
| (201) | 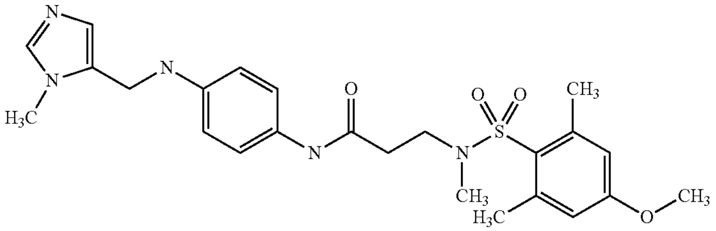 [SMILES: COc1cc(C)c(S(=O)(=O)N(C)CCC(=O)Nc2ccc(NCc3cncn3C)cc2)c(C)c1] |
| (202) | 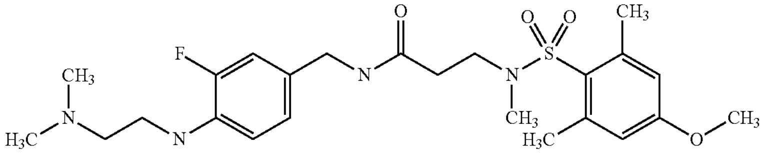 |
| (203) | 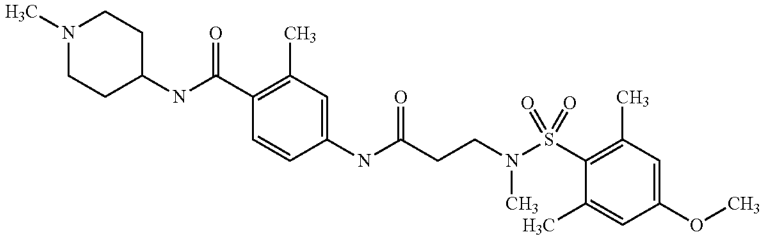 |
| (204) | 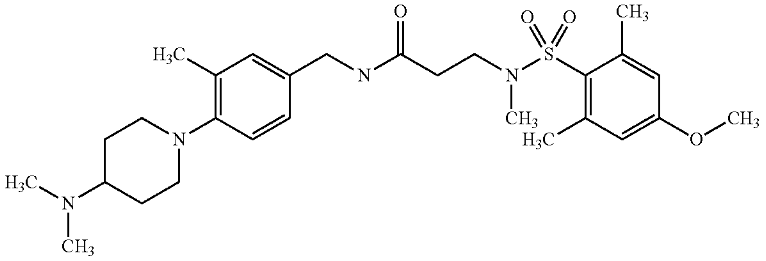 |
| (205) | 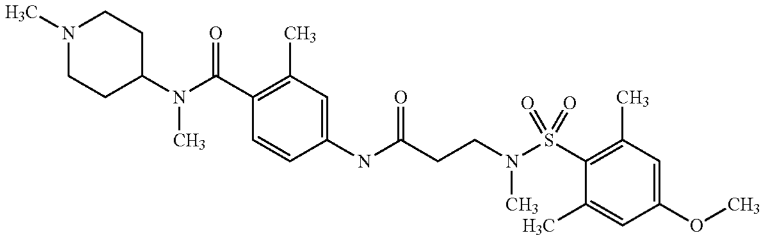 |

-continued
| Example | Structure |
|---|---|
| (206) | 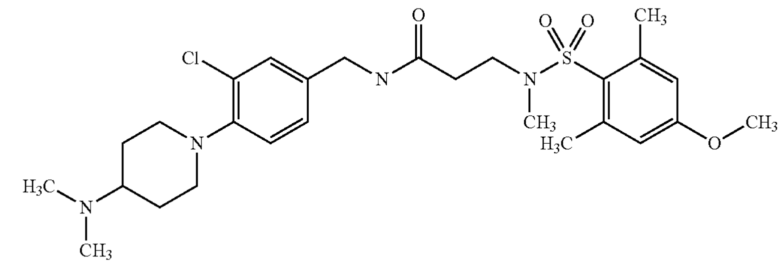 |
| (207) | 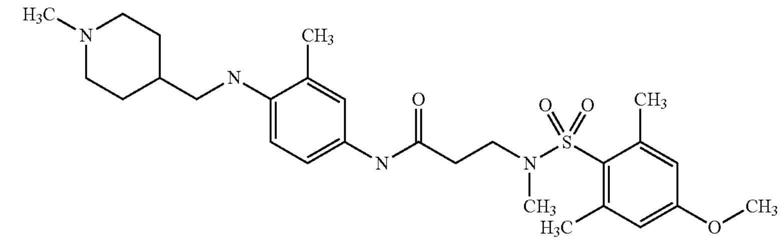 |
| (208) | 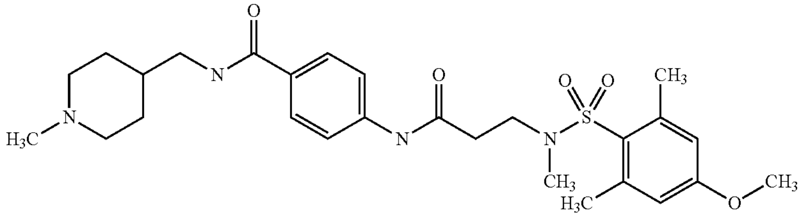 |
| (209) | 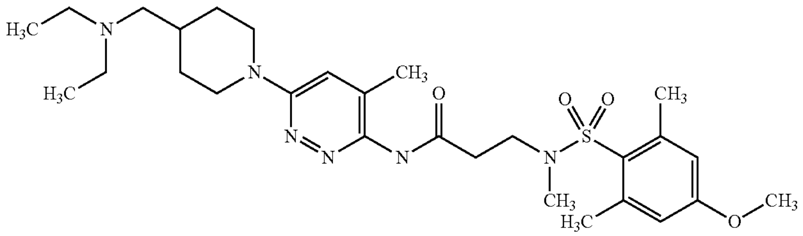 [SMILES: CCN(CC)CC1CCN(c2cc(C)c(NC(=O)CCN(C)S(=O)(=O)c3c(C)cc(OC)cc3C)nn2)CC1] |
| (210) | 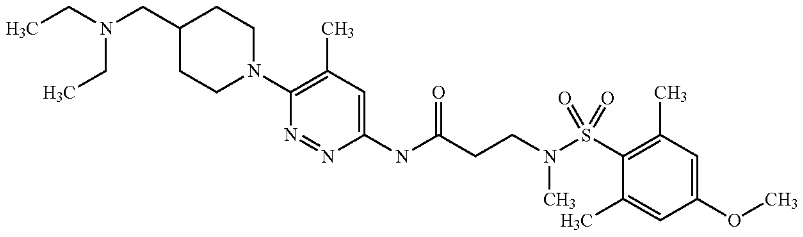 [SMILES: CCN(CC)CC1CCN(c2nnc(NC(=O)CCN(C)S(=O)(=O)c3c(C)cc(OC)cc3C)cc2C)CC1] |
| (211) | 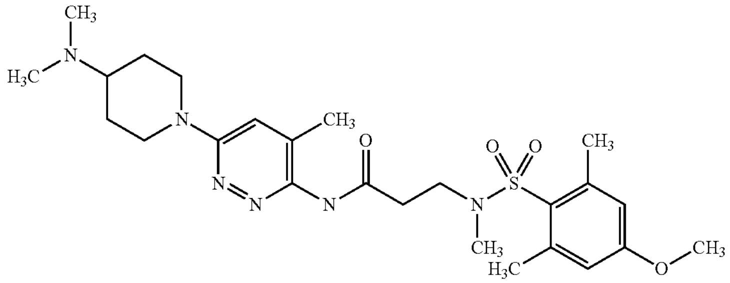 |

-continued
| Example | Structure |
| --- | --- |
| (212) | 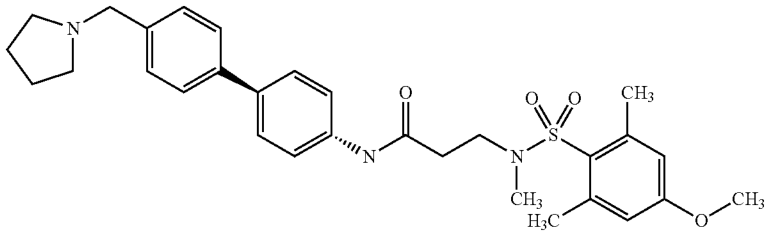 |
| (213) | 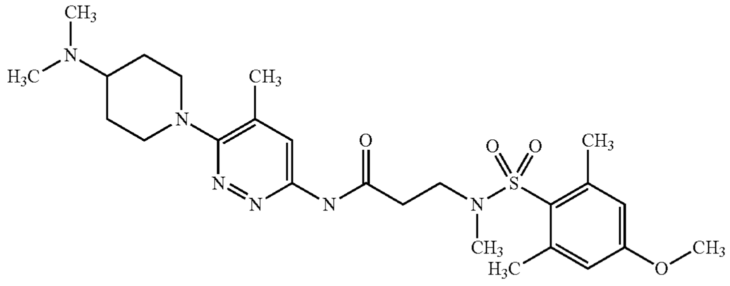 |
| (214) | 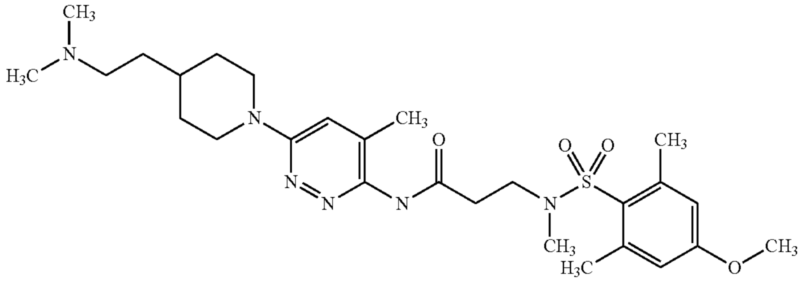 |
| (215) | 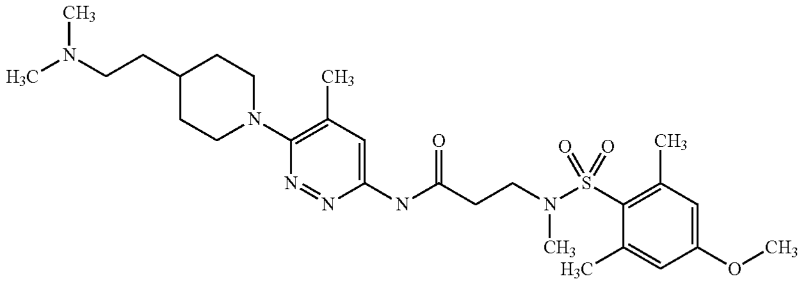 |
| (216) | 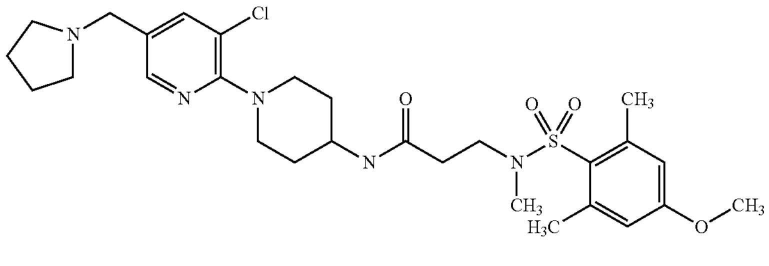 [SMILES: COc1cc(C)c(S(=O)(=O)N(C)CCC(=O)NC2CCN(c3ncc(CN4CCCC4)cc3Cl)CC2)c(C)c1] |
| (217) | 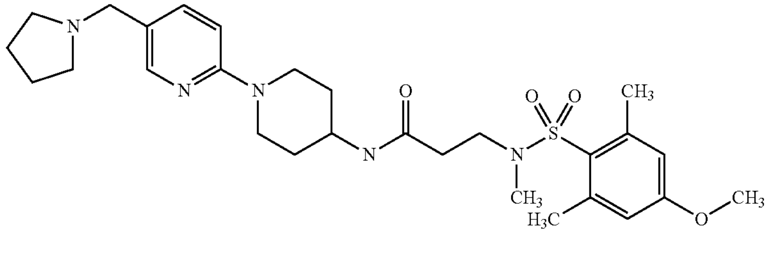 [SMILES: COc1cc(C)c(S(=O)(=O)N(C)CCC(=O)NC2CCN(c3ccc(CN4CCCC4)cn3)CC2)c(C)c1] |

-continued
| Example | Structure |
| --- | --- |
| (218) | 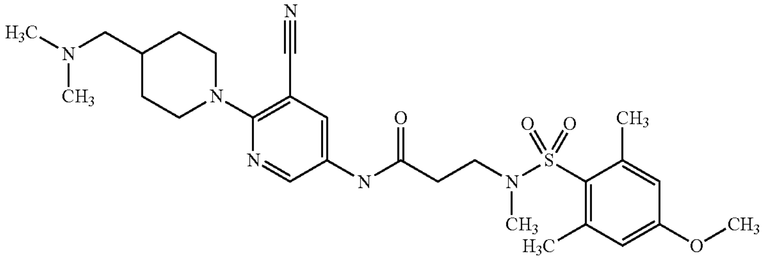 |
| (219) | 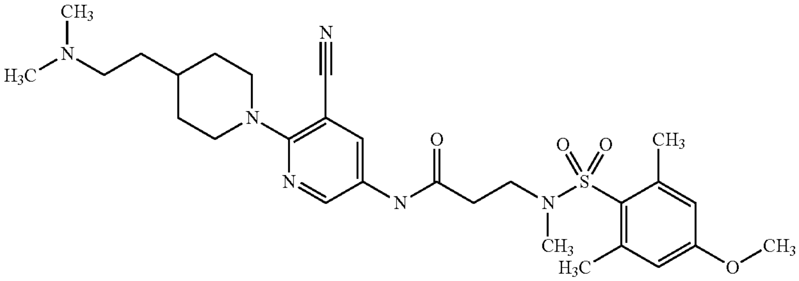 |
| (220) | 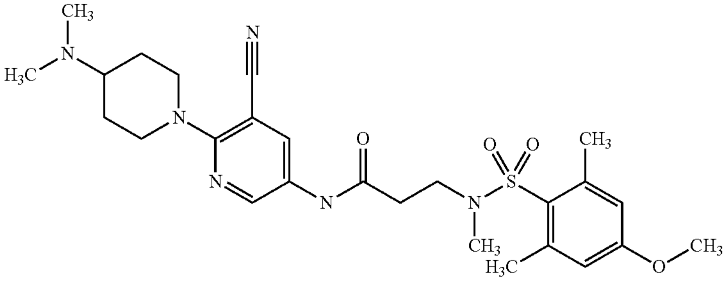 |
| (221) | 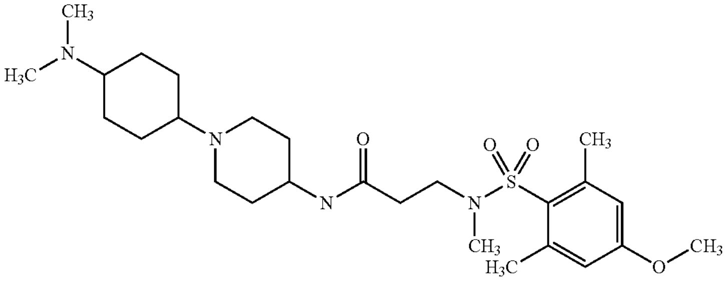 |
| (222) | 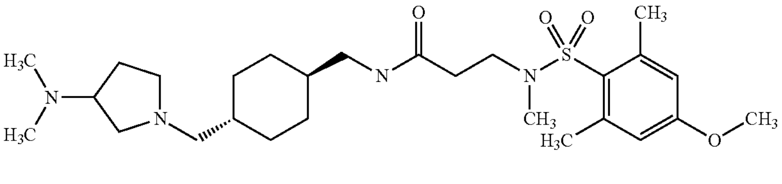 |
| (223) | 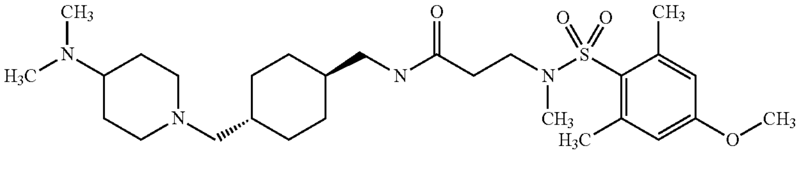 |

-continued
| Example | Structure |
|---|---|
| (224) | 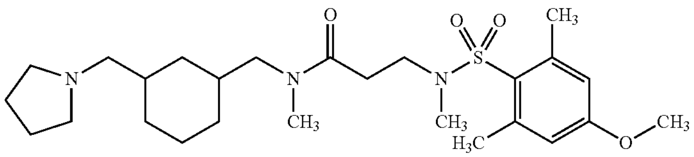 [SMILES: COc1cc(C)c(S(=O)(=O)N(C)CCC(=O)N(C)CC2CCCC(CN3CCCC3)C2)c(C)c1] |
| (225) | 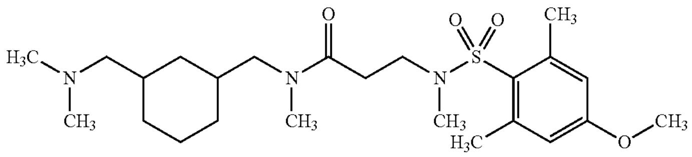 |
| (226) | 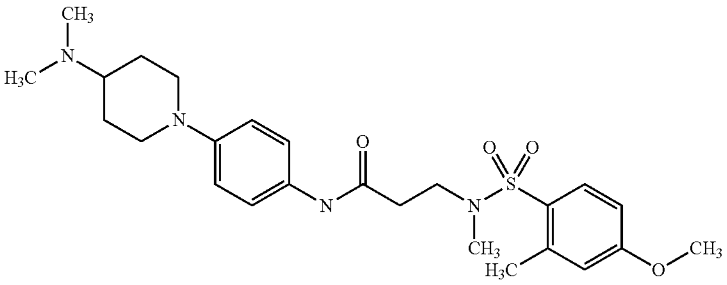 |
| (227) | 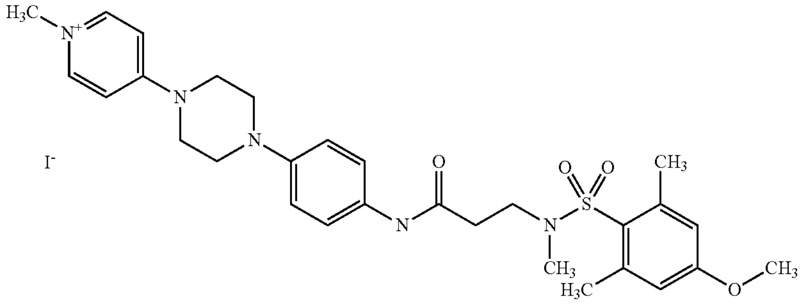 |
| (228) | 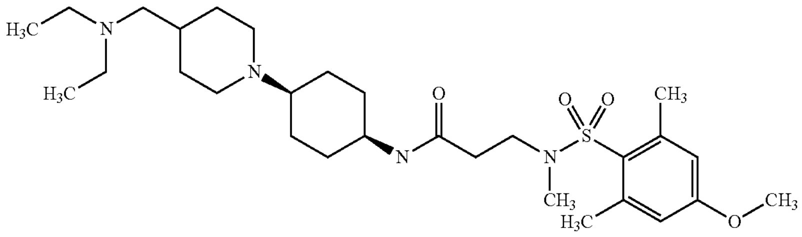 [SMILES: CCN(CC)CC1CCN([C@H]2CC[C@@H](NC(=O)CCN(C)S(=O)(=O)c3c(C)cc(OC)cc3C)CC2)CC1] |
| (229) | 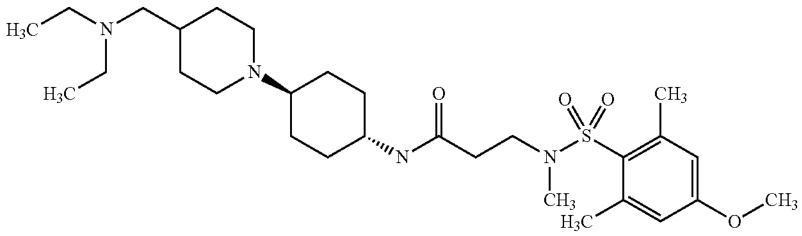 [SMILES: CCN(CC)CC1CCN([C@H]2CC[C@H](NC(=O)CCN(C)S(=O)(=O)c3c(C)cc(OC)cc3C)CC2)CC1] |

-continued
| Example | Structure |
|---|---|
| (230) | 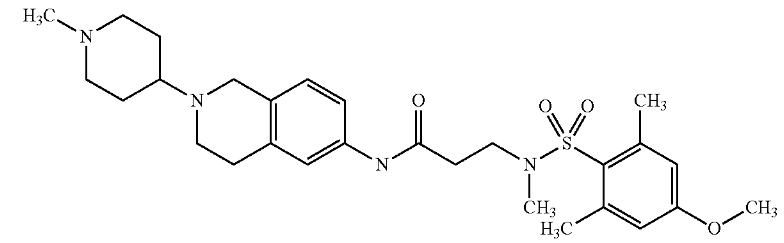 |
| (231) | 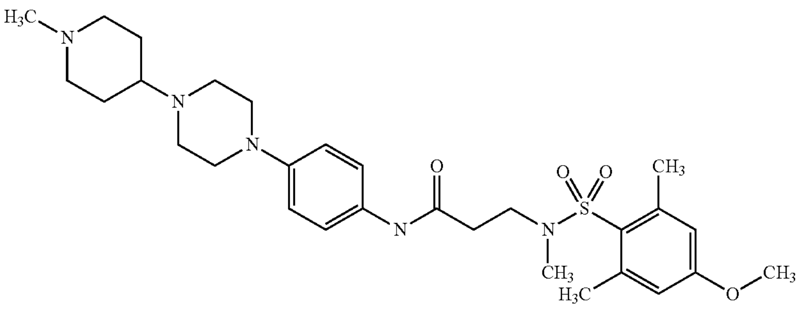 |
| (232) | 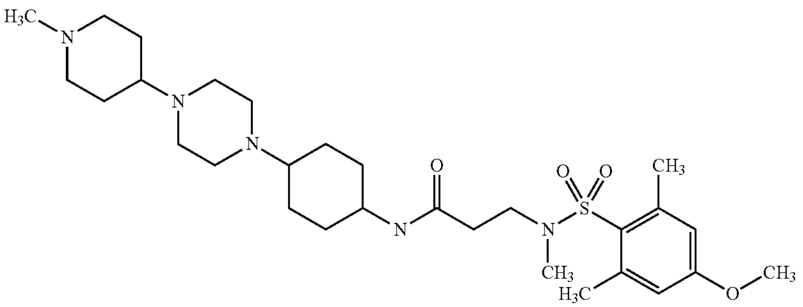 |
| (233) | 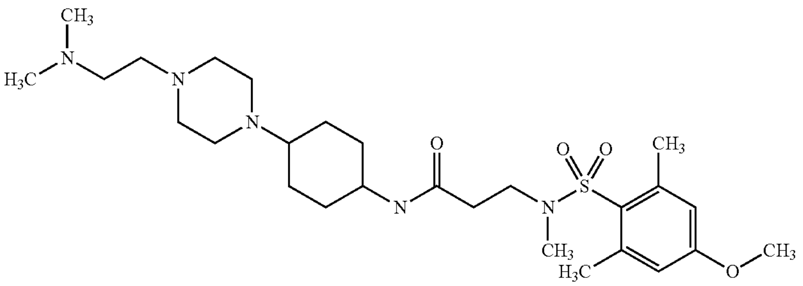 |
| (234) | 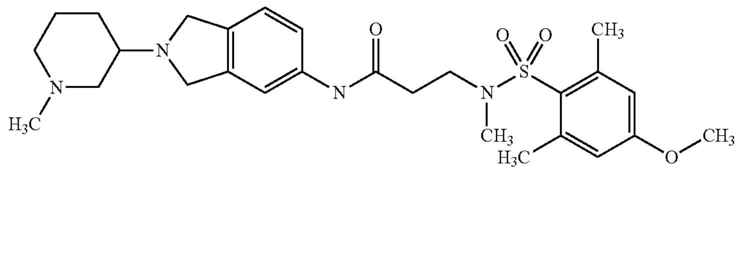 [SMILES: COc1cc(C)c(S(=O)(=O)N(C)CCC(=O)Nc2ccc3c(c2)CN(C2CCCN(C)C2)C3)c(C)c1] |

-continued
| Example | Structure |
| --- | --- |
| (235) | 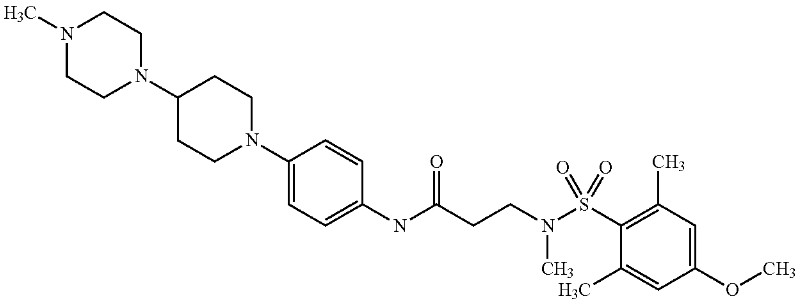 |
| (236) | 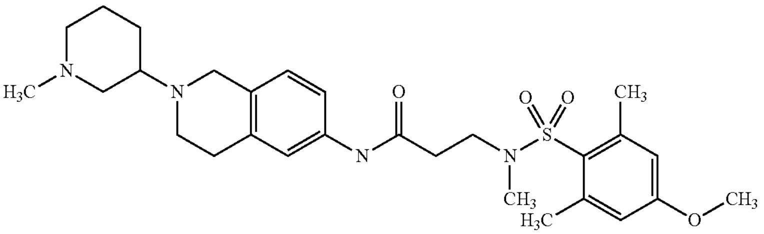 |
| (237) | 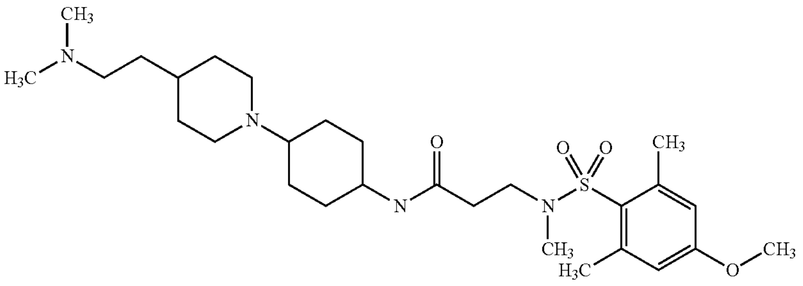 |
| (238) | 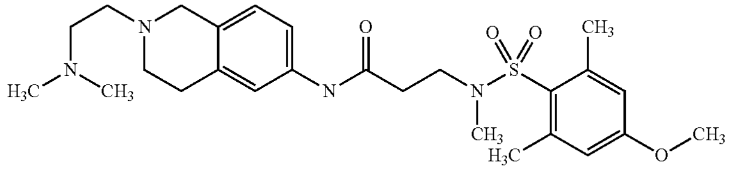 |
| (239) | 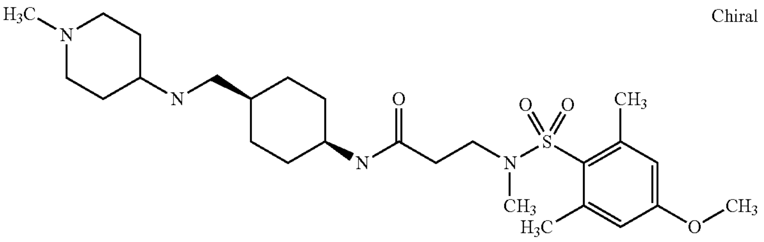 Chiral |
| (240) | 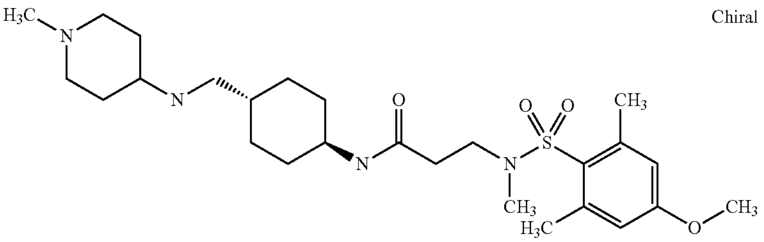 Chiral |

-continued
| Example | Structure |
| --- | --- |
| (241) | Chiral 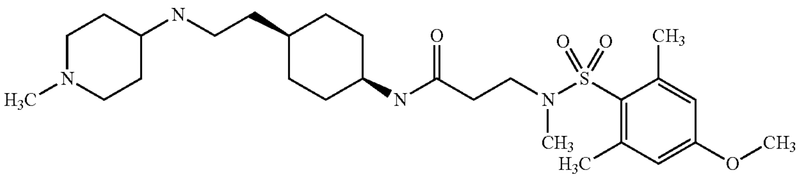 |
| (242) | Chiral 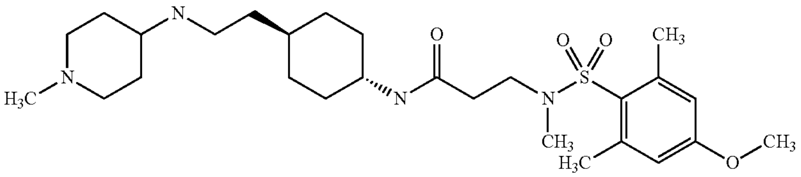 |
| (243) | 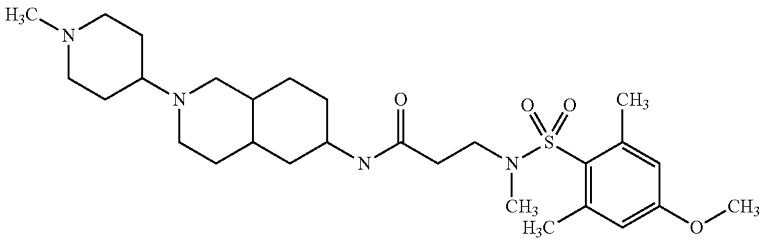 |
| (244) | Chiral 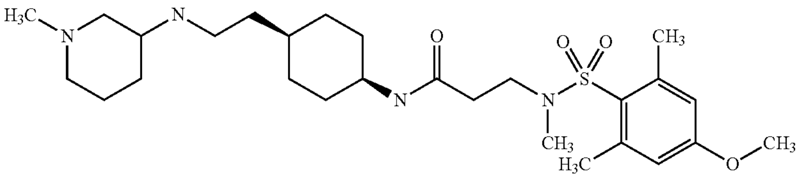 |
| (245) | Chiral 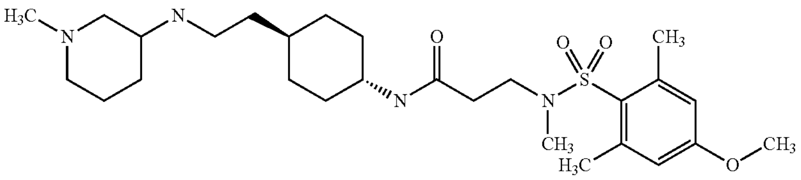 |
| (246) | 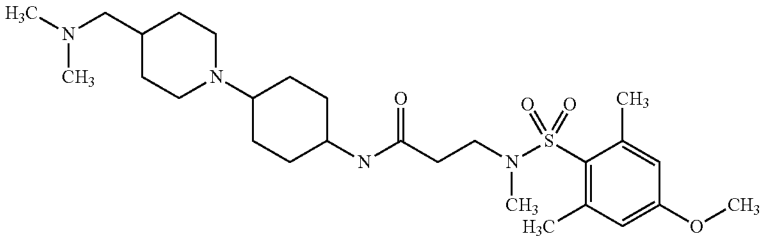 |

-continued
| Example | Structure |
|---|---|
| (247) | 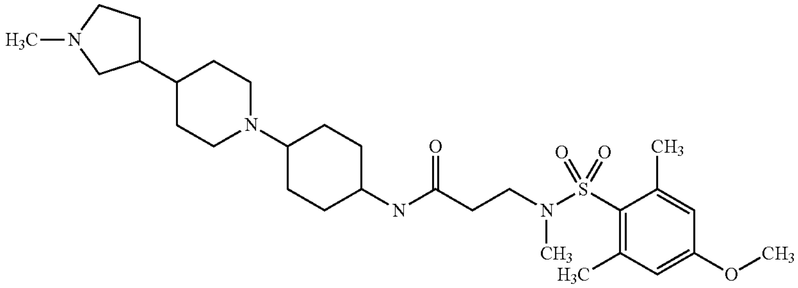 |
| (248) | 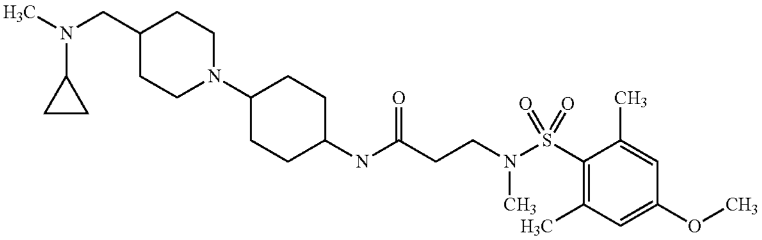 |
| (249) | 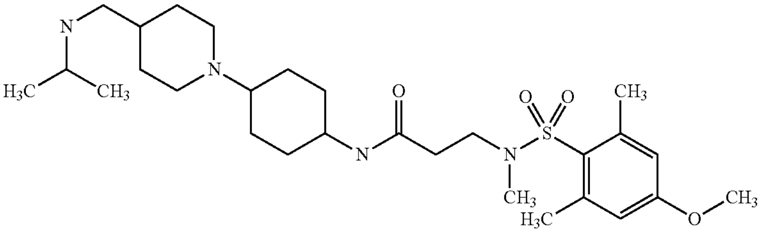 [SMILES: COc1cc(C)c(S(=O)(=O)N(C)CCC(=O)NC2CCC(N3CCC(CNC(C)C)CC3)CC2)c(C)c1] |
| (250) | 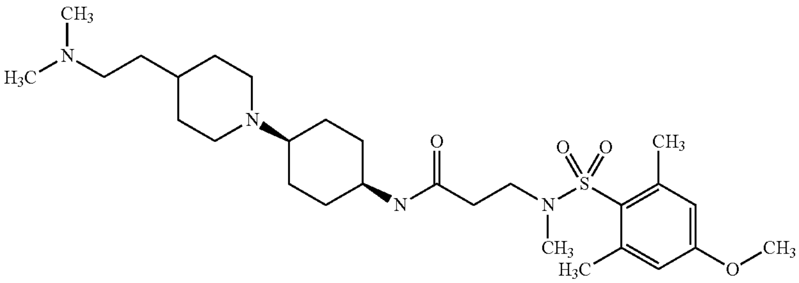 |
| (251) | 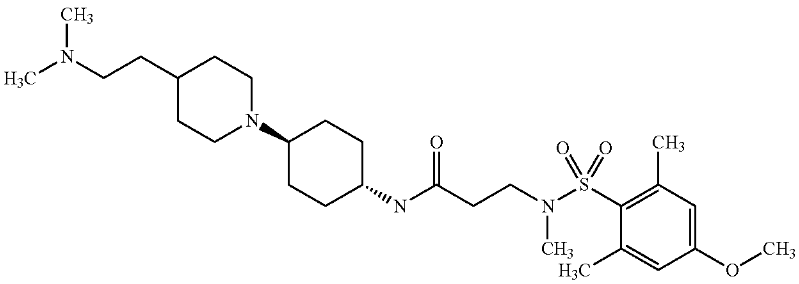 |

-continued
| Example | Structure |
| --- | --- |
| (252) | 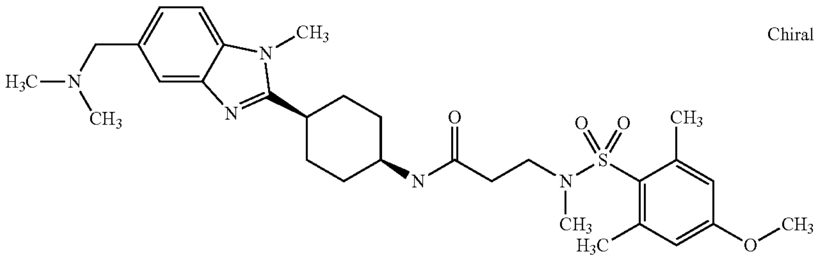 Chiral |
| (253) | 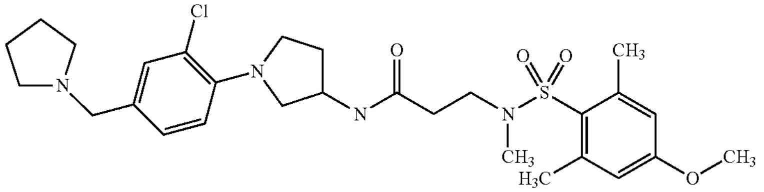 [SMILES: COc1cc(C)c(S(=O)(=O)N(C)CCC(=O)NC2CCN(c3ccc(CN4CCCC4)cc3Cl)C2)c(C)c1] |
| (254) | 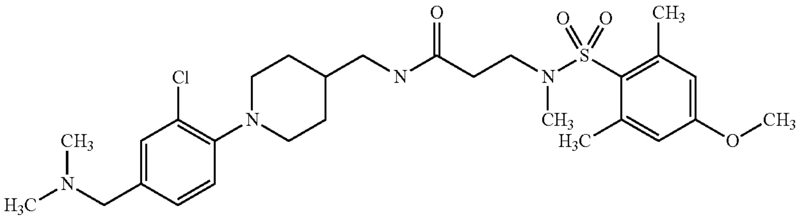 |
| (255) | 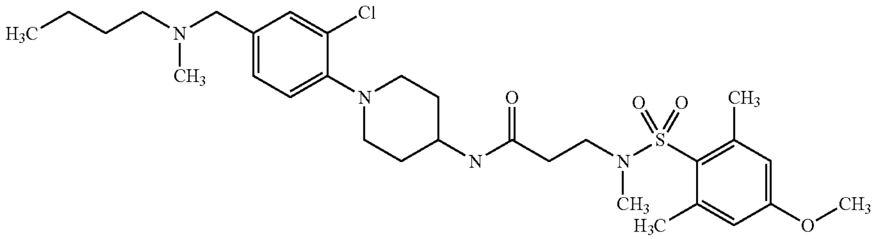 [SMILES: CCCCN(C)Cc1ccc(N2CCC(NC(=O)CCN(C)S(=O)(=O)c3c(C)cc(OC)cc3C)CC2)c(Cl)c1] |
| (256) | 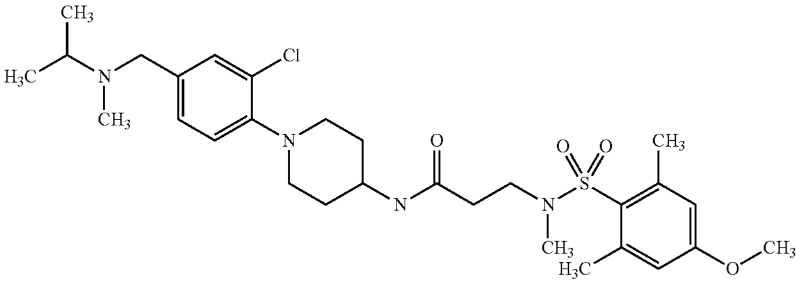 [SMILES: COc1cc(C)c(S(=O)(=O)N(C)CCC(=O)NC2CCN(c3ccc(CN(C)C(C)C)cc3Cl)CC2)c(C)c1] |
| (257) | 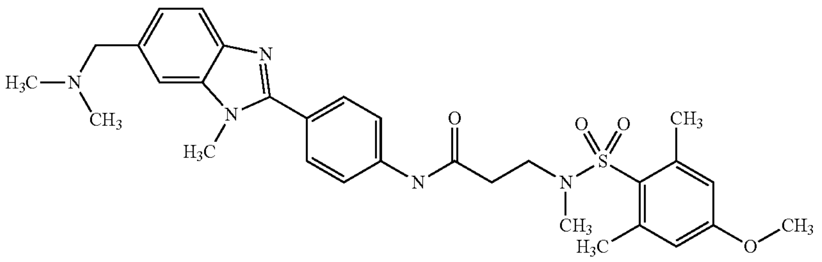 |

-continued
| Example | Structure | |
|---|---|---|
| (258) | 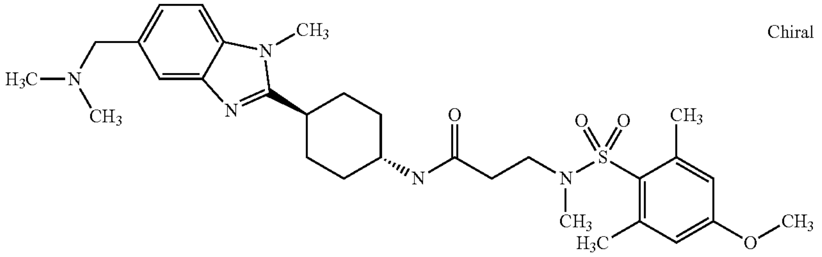 | Chiral |
| (259) | 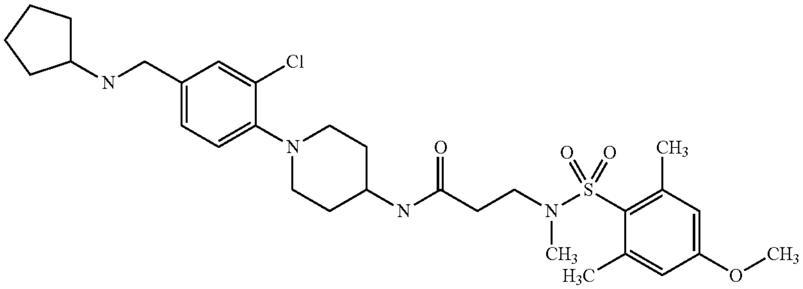 [SMILES: COc1cc(C)c(S(=O)(=O)N(C)CCC(=O)NC2CCN(c3ccc(CNC4CCCC4)cc3Cl)CC2)c(C)c1] | |
| (260) | 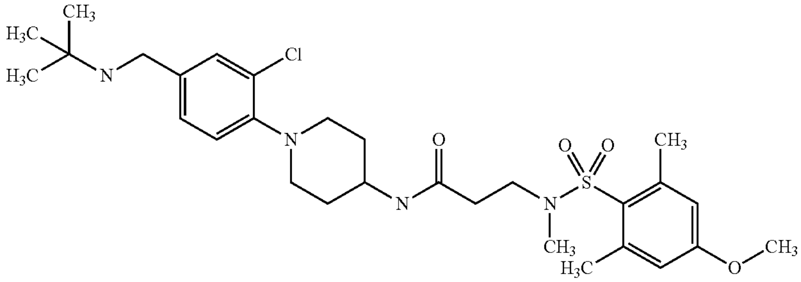 [SMILES: COc1cc(C)c(S(=O)(=O)N(C)CCC(=O)NC2CCN(c3ccc(CNC(C)(C)C)cc3Cl)CC2)c(C)c1] | |
| (261) | 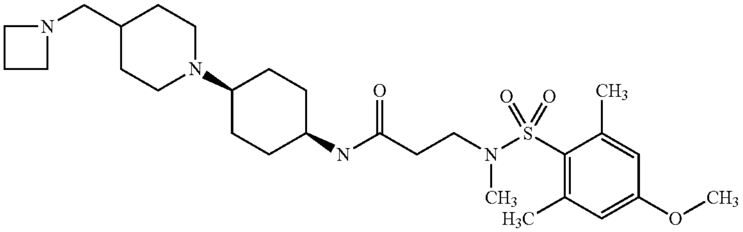 [SMILES: COc1cc(C)c(S(=O)(=O)N(C)CCC(=O)N[C@H]2CC[C@@H](N3CCC(CN4CCC4)CC3)CC2)c(C)c1] | |
| (262) | 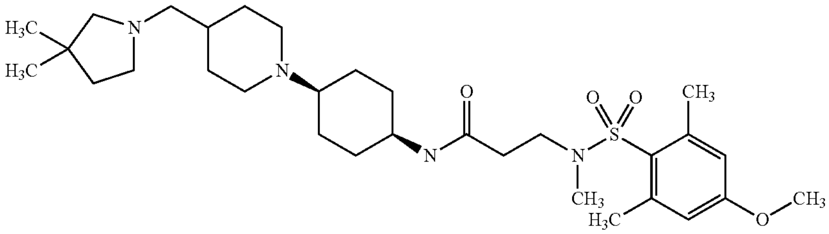 | |
| (263) | 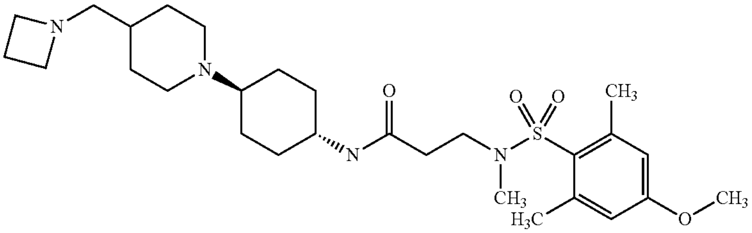 [SMILES: COc1cc(C)c(S(=O)(=O)N(C)CCC(=O)N[C@H]2CC[C@H](N3CCC(CN4CCC4)CC3)CC2)c(C)c1] | |

-continued
| Example | Structure |
|---|---|
| (264) | 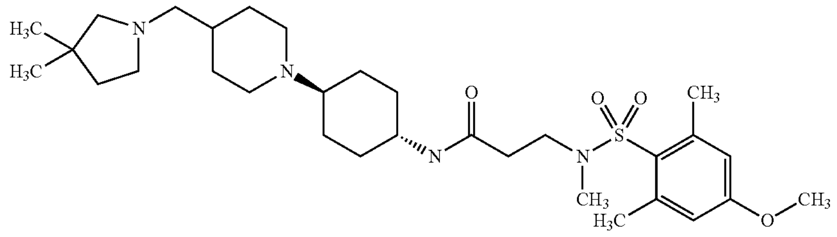 |
| (265) | 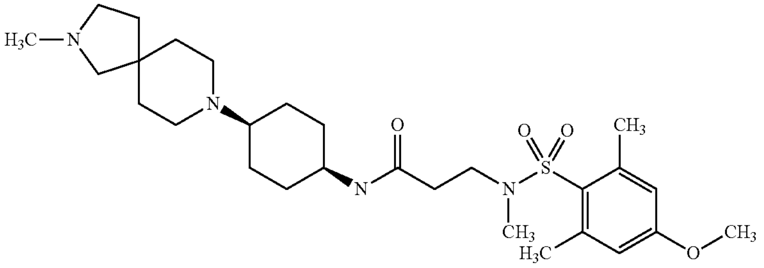 |
| (266) | 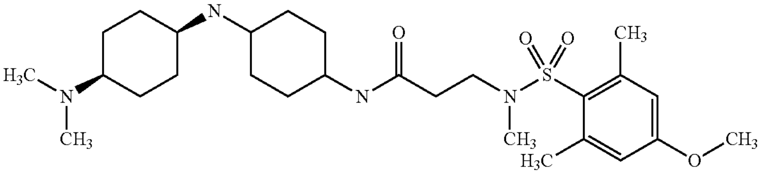 |
| (267) | 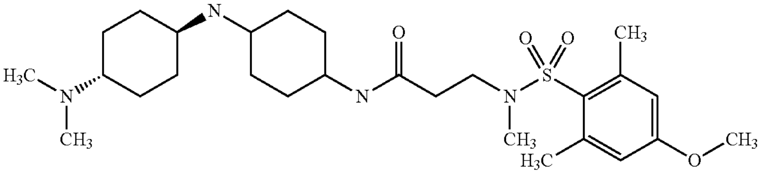 |
| (268) | 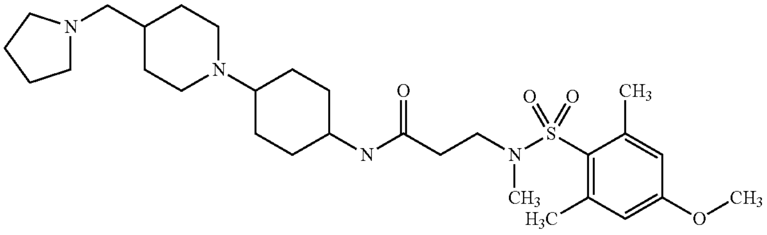 [SMILES: COc1cc(C)c(S(=O)(=O)N(C)CCC(=O)NC2CCC(N3CCC(CN4CCCC4)CC3)CC2)c(C)c1] |
| (269) | 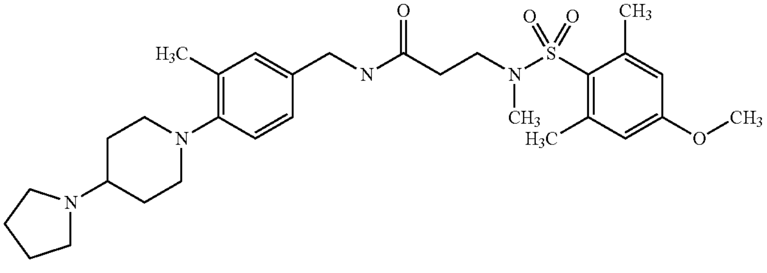 [SMILES: COc1cc(C)c(S(=O)(=O)N(C)CCC(=O)NCc2ccc(N3CCC(N4CCCC4)CC3)c(C)c2)c(C)c1] |

-continued
| Example | Structure |
|---|---|
| (270) | 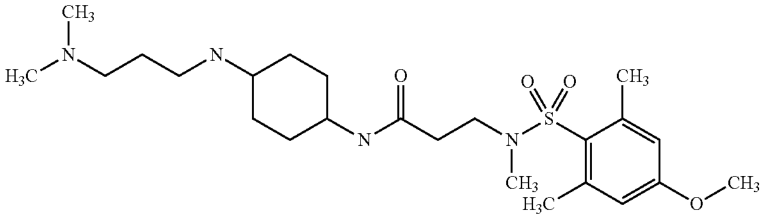 |
| (271) | 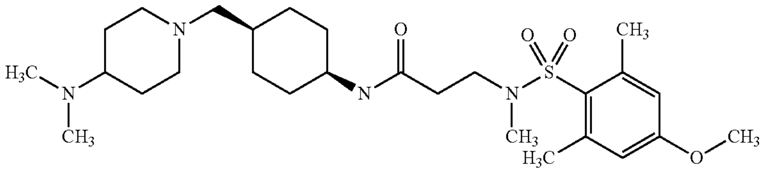 |
| (272) | 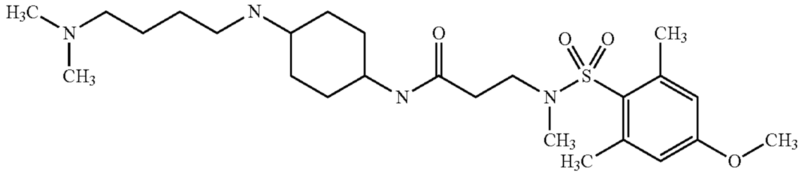 |
| (273) | Chiral 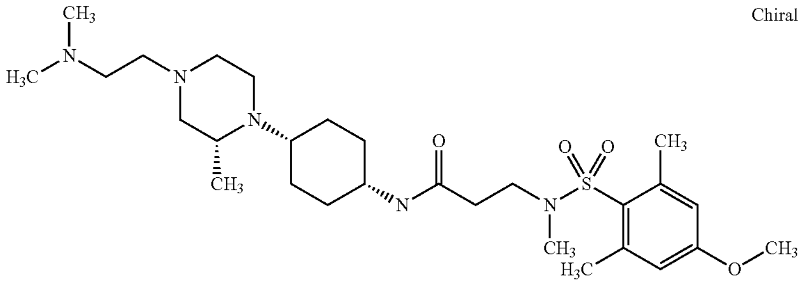 |
| (274) | 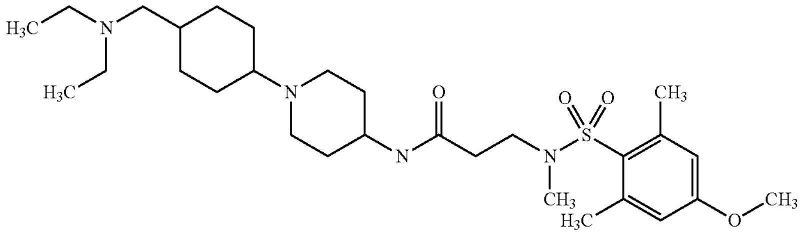 |
| (275) | 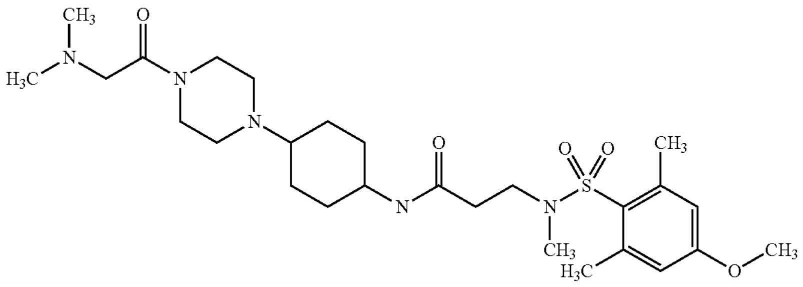 |
| (276) | 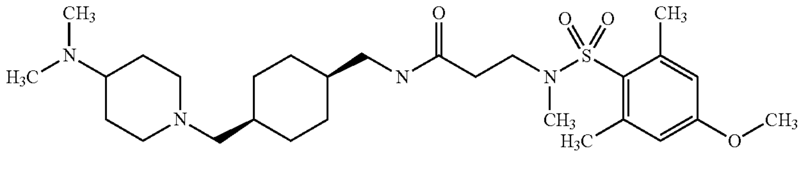 |

-continued
| Example | Structure |
| --- | --- |
| (277) | 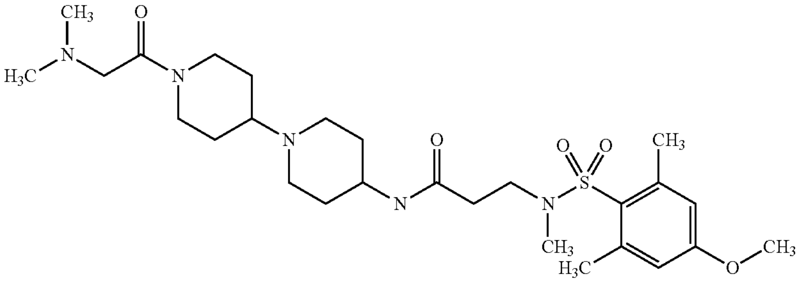 |
| (278) | 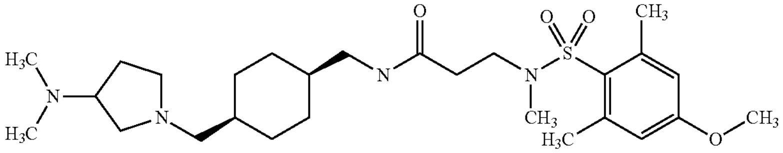 |
| (279) | 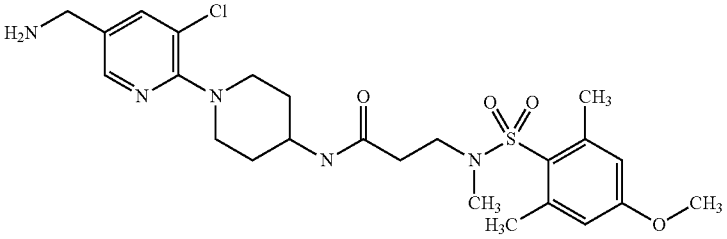 [SMILES: COc1cc(C)c(S(=O)(=O)N(C)CCC(=O)NC2CCN(c3ncc(CN)cc3Cl)CC2)c(C)c1] |
| (280) | 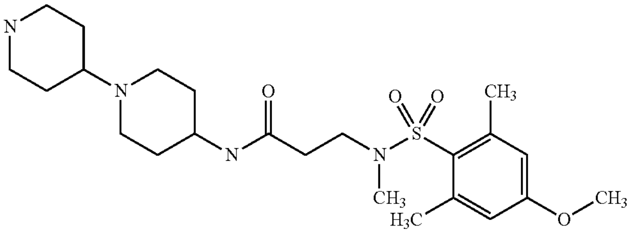 [SMILES: COc1cc(C)c(S(=O)(=O)N(C)CCC(=O)NC2CCN(C3CCNCC3)CC2)c(C)c1] |
| (281) | 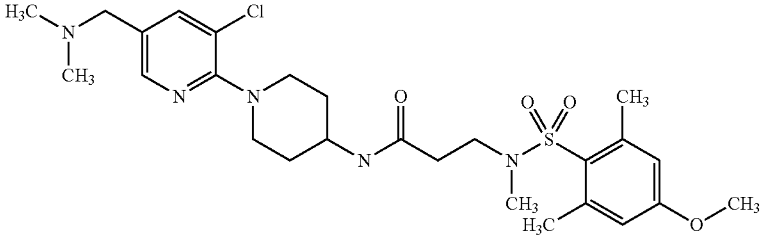 |
| (282) | 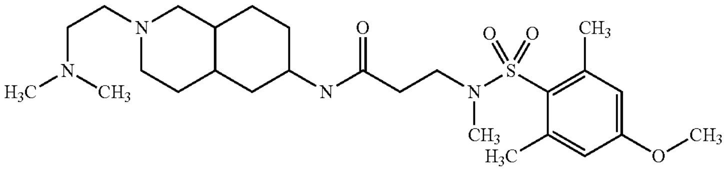 |
| (283) | 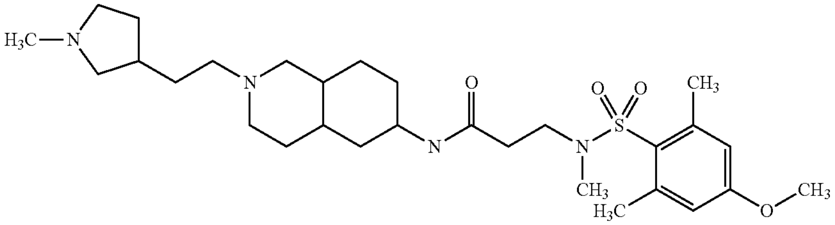 |

-continued
| Example | Structure |
|---|---|
| (284) | 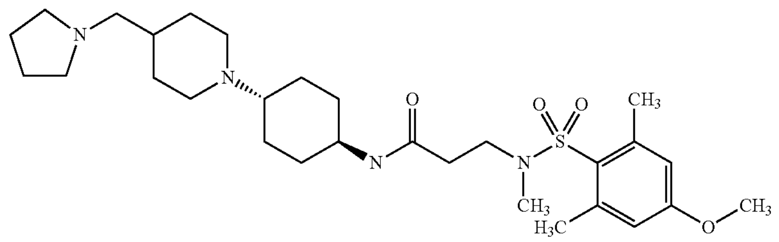 [SMILES: COc1cc(C)c(S(=O)(=O)N(C)CCC(=O)N[C@H]2CC[C@H](N3CCC(CN4CCCC4)CC3)CC2)c(C)c1] |
| (285) | 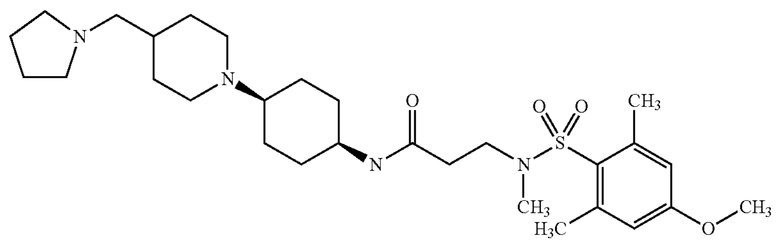 [SMILES: COc1cc(C)c(S(=O)(=O)N(C)CCC(=O)N[C@H]2CC[C@@H](N3CCC(CN4CCCC4)CC3)CC2)c(C)c1] |
| (286) | 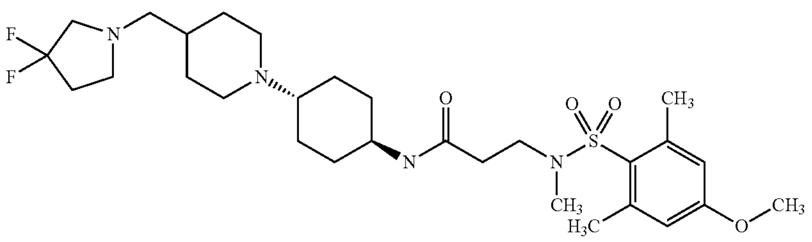 [SMILES: COc1cc(C)c(S(=O)(=O)N(C)CCC(=O)N[C@H]2CC[C@H](N3CCC(CN4CCC(F)(F)C4)CC3)CC2)c(C)c1] |
| (287) | Chiral 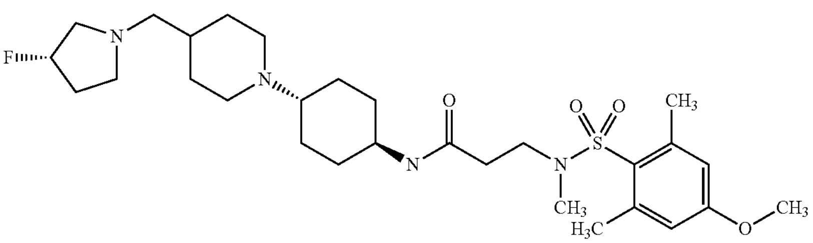 |
| (288) | Chiral 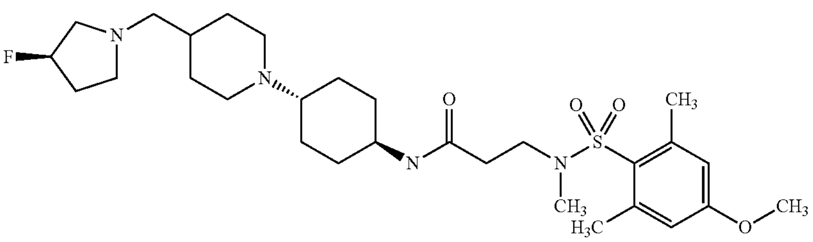 |
| (289) | 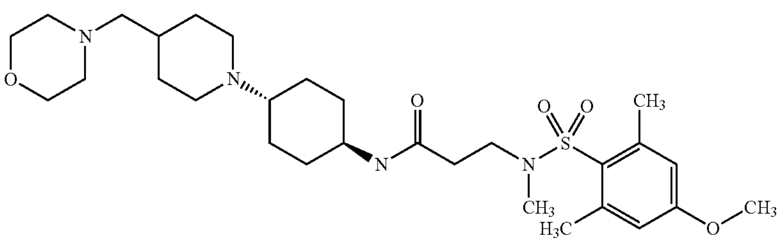 [SMILES: COc1cc(C)c(S(=O)(=O)N(C)CCC(=O)N[C@H]2CC[C@H](N3CCC(CN4CCOCC4)CC3)CC2)c(C)c1] |

-continued
| Example | Structure |
|---|---|
| (290) | 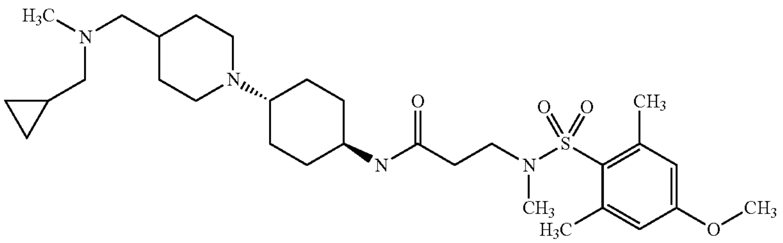 [SMILES: COc1cc(C)c(S(=O)(=O)N(C)CCC(=O)N[C@H]2CC[C@H](N3CCC(CN(C)CC4CC4)CC3)CC2)c(C)c1] |
| (291) | 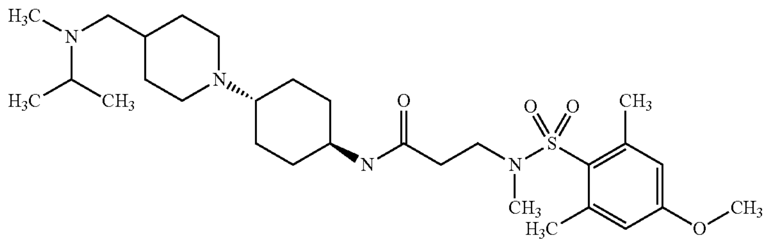 |
| (292) | 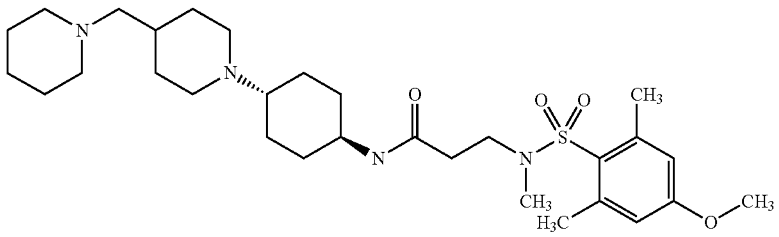 [SMILES: COc1cc(C)c(S(=O)(=O)N(C)CCC(=O)N[C@H]2CC[C@H](N3CCC(CN4CCCCC4)CC3)CC2)c(C)c1] |
| (293) | 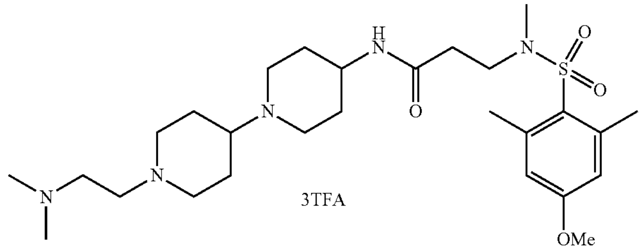 |
| (294) | 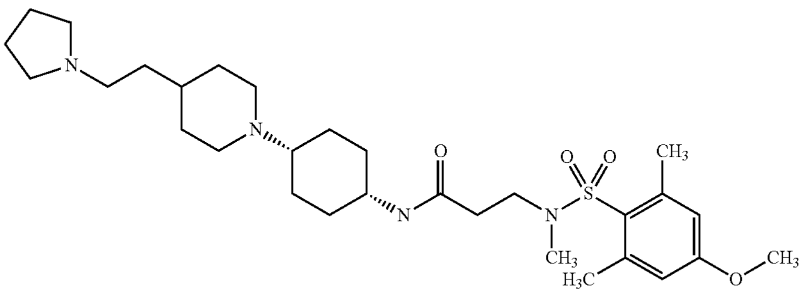 [SMILES: COc1cc(C)c(S(=O)(=O)N(C)CCC(=O)N[C@H]2CC[C@@H](N3CCC(CCN4CCCC4)CC3)CC2)c(C)c1] |
| (295) | 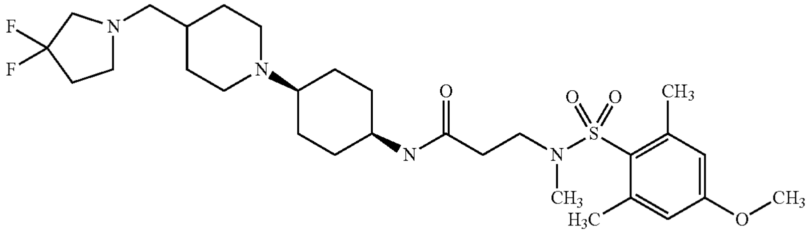 [SMILES: COc1cc(C)c(S(=O)(=O)N(C)CCC(=O)N[C@H]2CC[C@@H](N3CCC(CN4CCC(F)(F)C4)CC3)CC2)c(C)c1] |

-continued
| Example | Structure |
| --- | --- |
| (296) | Chiral 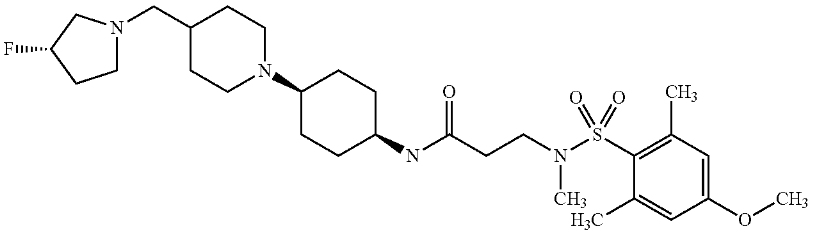 |
| (297) | Chiral 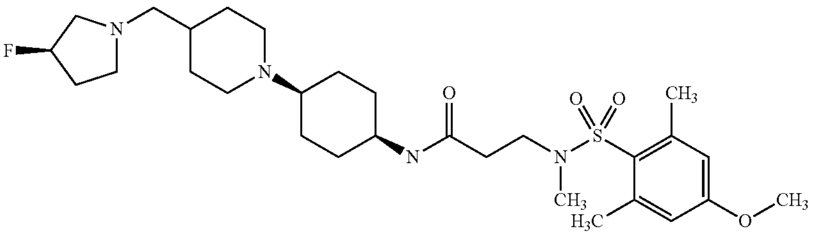 |
| (298) | 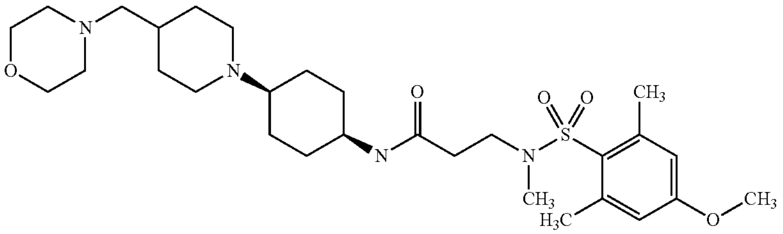 [SMILES: COc1cc(C)c(S(=O)(=O)N(C)CCC(=O)N[C@H]2CC[C@@H](N3CCC(CN4CCOCC4)CC3)CC2)c(C)c1] |
| (299) | 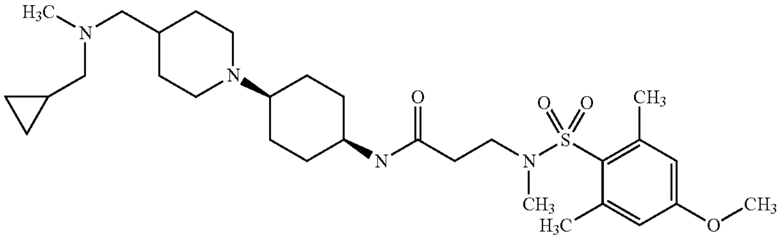 [SMILES: COc1cc(C)c(S(=O)(=O)N(C)CCC(=O)N[C@H]2CC[C@@H](N3CCC(CN(C)CC4CC4)CC3)CC2)c(C)c1] |
| (300) | 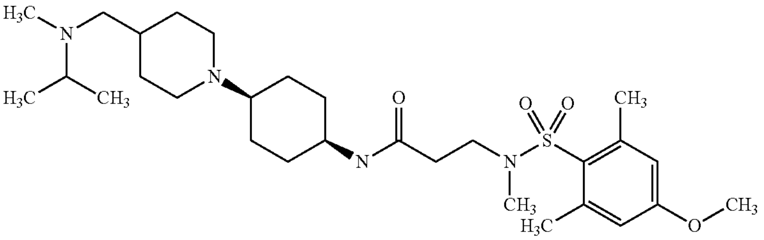 |
| (301) | 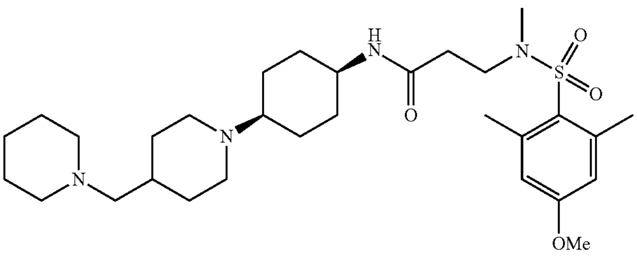 [SMILES: COc1cc(C)c(S(=O)(=O)N(C)CCC(=O)N[C@H]2CC[C@@H](N3CCC(CN4CCCCC4)CC3)CC2)c(C)c1] |

-continued
| Example | Structure |
| --- | --- |
| (302) | 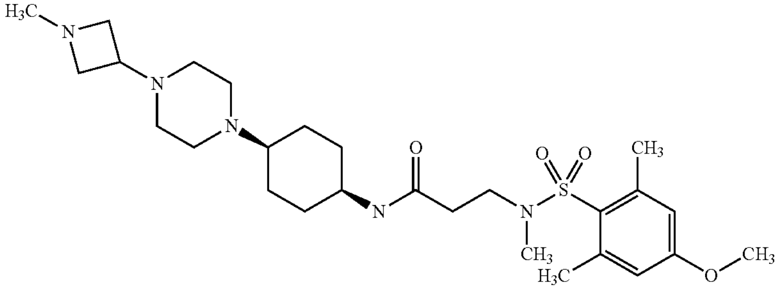 |
| (303) | 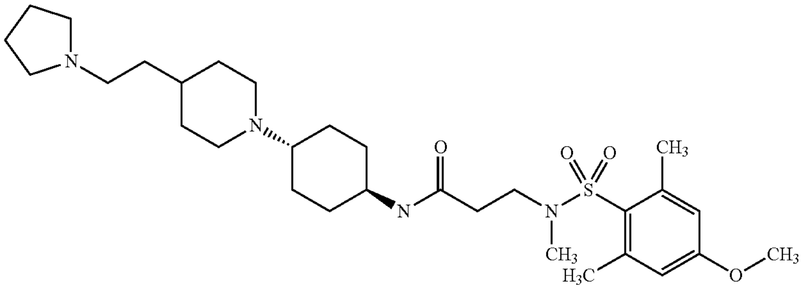 [SMILES: COc1cc(C)c(S(=O)(=O)N(C)CCC(=O)N[C@H]2CC[C@H](N3CCC(CCN4CCCC4)CC3)CC2)c(C)c1] |
| (304) | 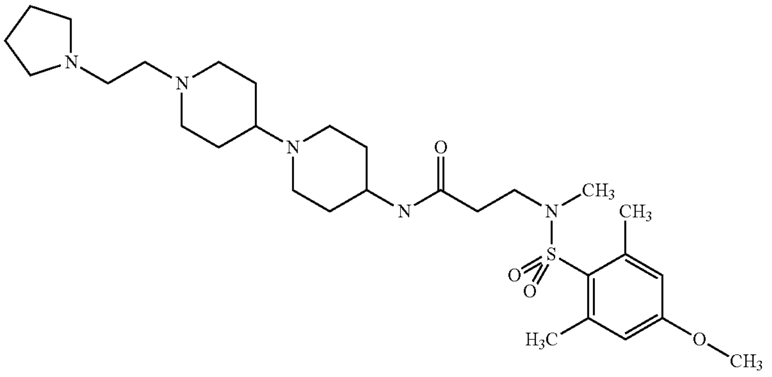 [SMILES: COc1cc(C)c(S(=O)(=O)N(C)CCC(=O)NC2CCN(C3CCN(CCN4CCCC4)CC3)CC2)c(C)c1] |
| (305) | 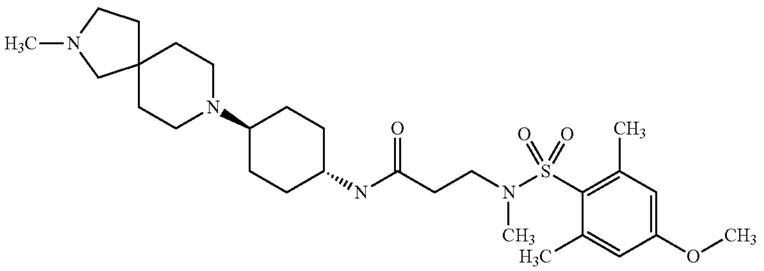 |
| (306) | 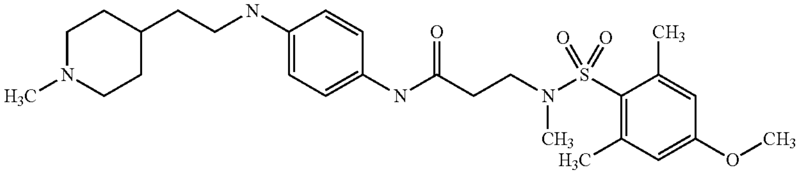 |

-continued
| Example | Structure |
| --- | --- |
| (307) | 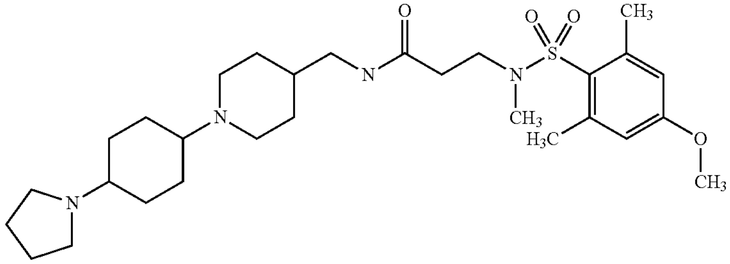 [SMILES: COc1cc(C)c(S(=O)(=O)N(C)CCC(=O)NCC2CCN(C3CCC(N4CCCC4)CC3)CC2)c(C)c1] |
| (308) | 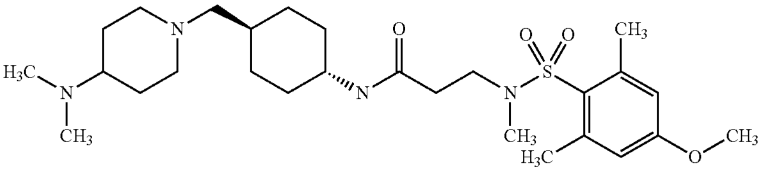 |
| (309) | 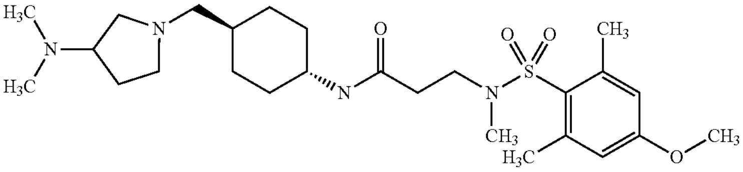 |
| (310) | 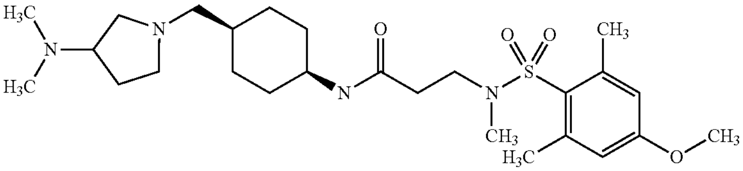 |
| (311) | 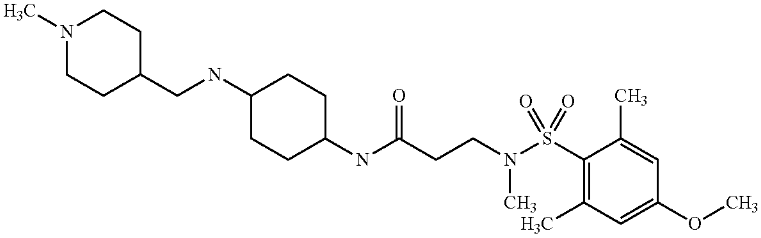 |
| (312) | 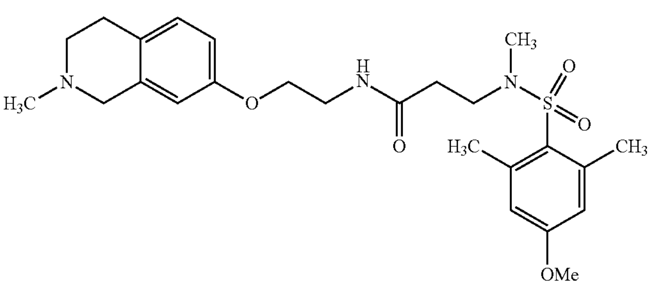 |

-continued
| Example | Structure |
| --- | --- |
| (313) | 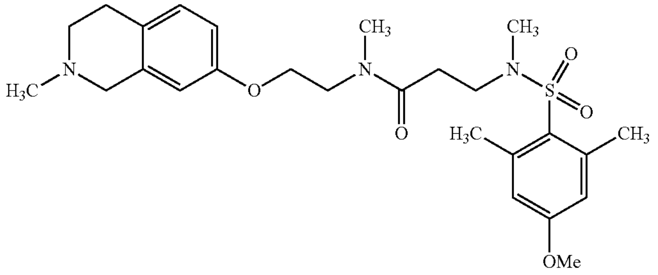 |
| (314) | 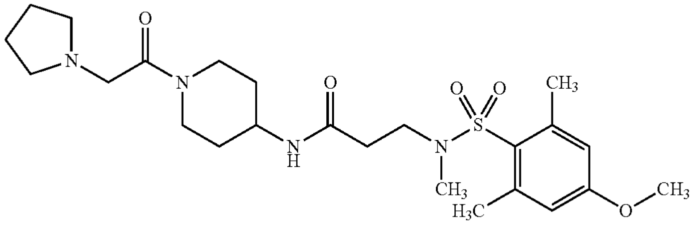 [SMILES: COc1cc(C)c(S(=O)(=O)N(C)CCC(=O)NC2CCN(C(=O)CN3CCCC3)CC2)c(C)c1] |
| (315) | 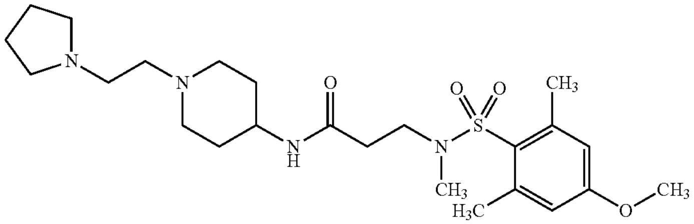 [SMILES: COc1cc(C)c(S(=O)(=O)N(C)CCC(=O)NC2CCN(CCN3CCCC3)CC2)c(C)c1] |
| (316) | 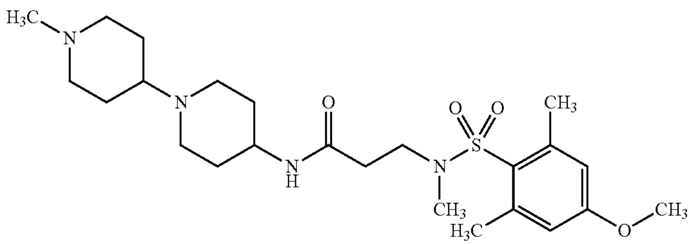 |
| (317) | 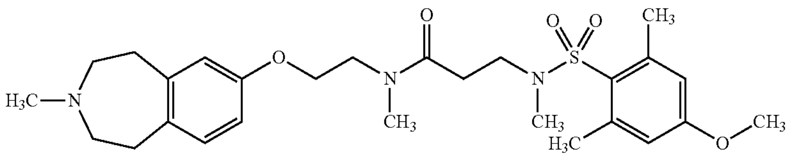 |
| (318) | 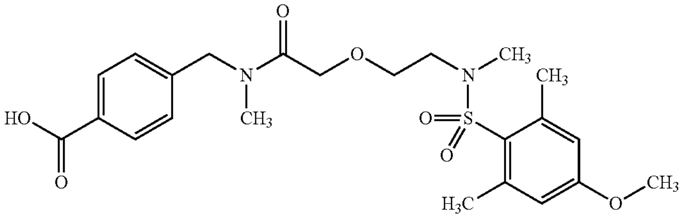 [SMILES: COc1cc(C)c(S(=O)(=O)N(C)CCOCC(=O)N(C)Cc2ccc(C(=O)O)cc2)c(C)c1] |

-continued
| Example | Structure |
|---|---|
| (319) | 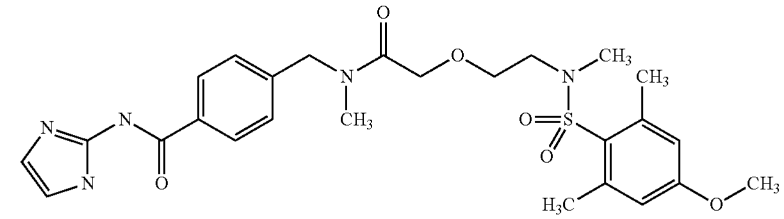 [SMILES: COc1cc(C)c(S(=O)(=O)N(C)CCOCC(=O)N(C)Cc2ccc(C(=O)Nc3ncc[nH]3)cc2)c(C)c1] |
| (320) | 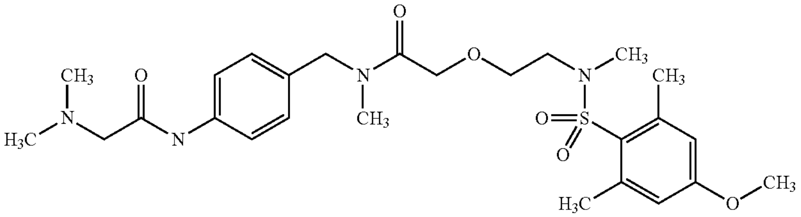 |
| (321) | 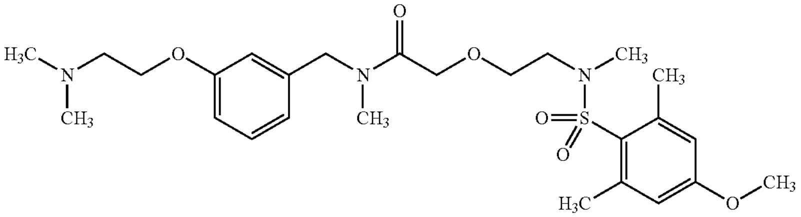 |
| (322) | 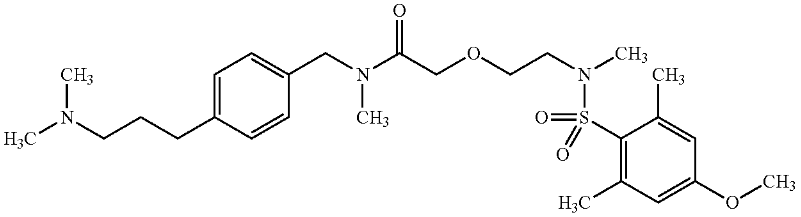 |
| (323) | 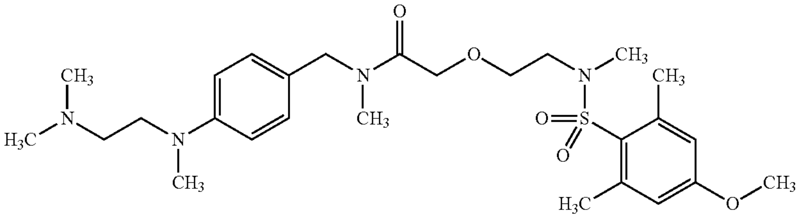 |
| (324) | 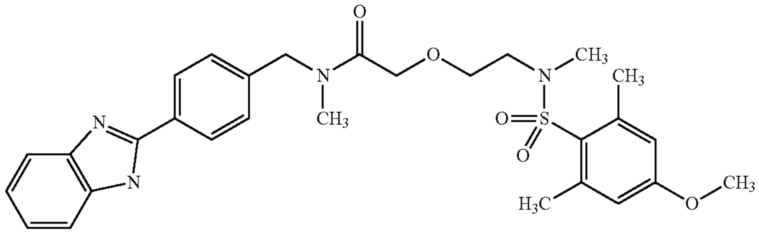 [SMILES: COc1cc(C)c(S(=O)(=O)N(C)CCOCC(=O)N(C)Cc2ccc(-c3nc4ccccc4[nH]3)cc2)c(C)c1] |
| (325) | 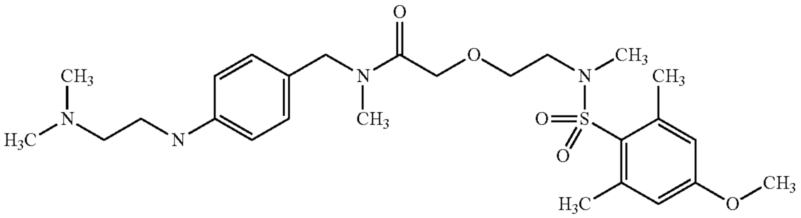 |

-continued
| Example | Structure |
| --- | --- |
| (326) | 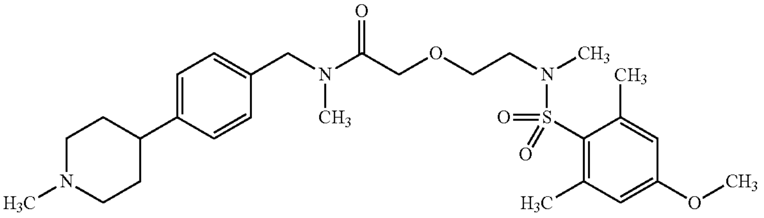 |
| (327) | 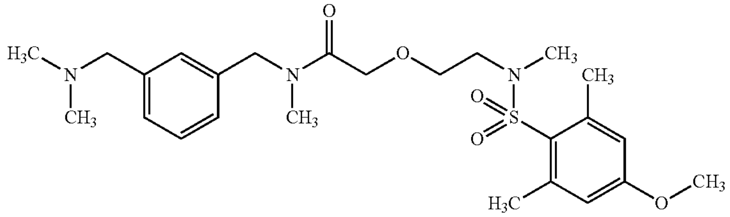 |
| (328) | 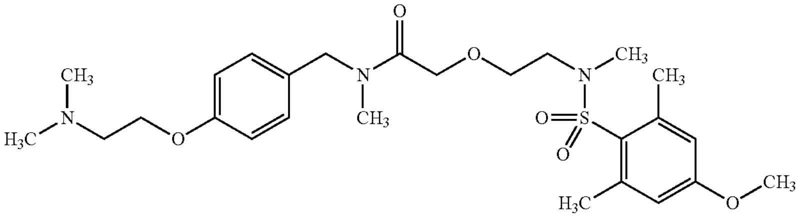 |
| (329) | 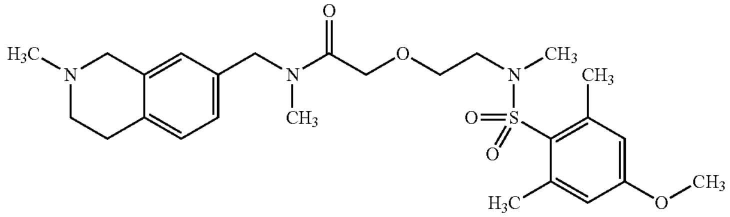 |
| (330) | 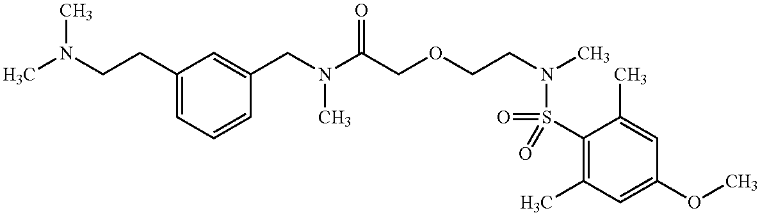 |
| (331) | 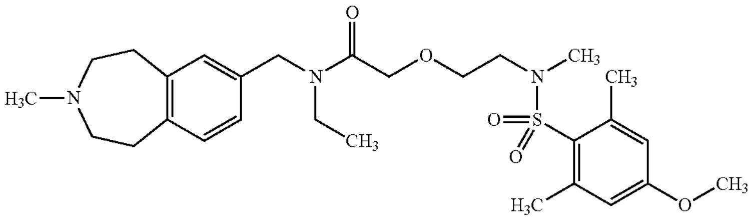 |
| (332) | 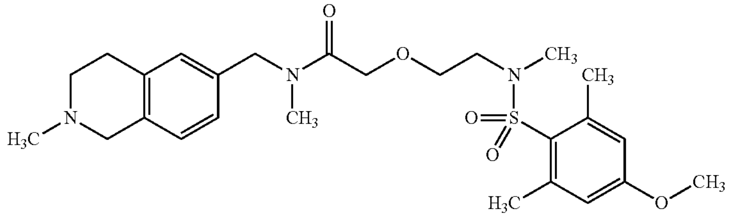 |

-continued
| Example | Structure |
|---|---|
| (333) | 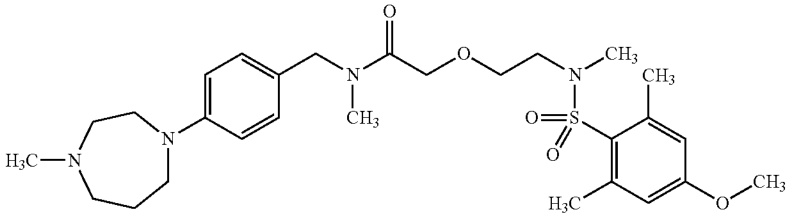 |
| (334) | 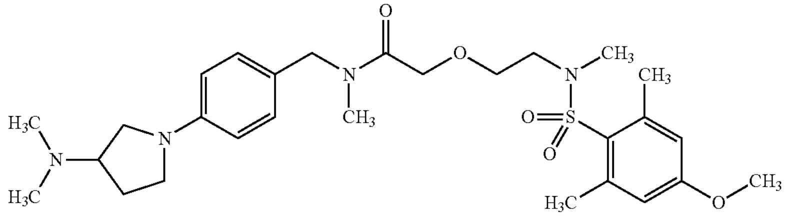 |
| (335) | 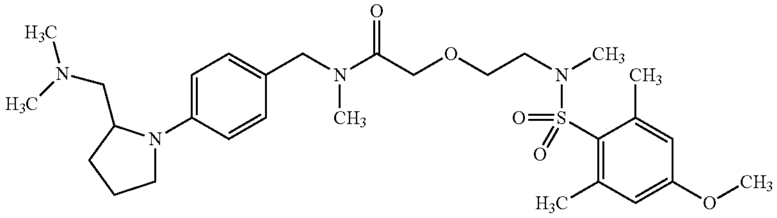 |
| (336) | Chiral 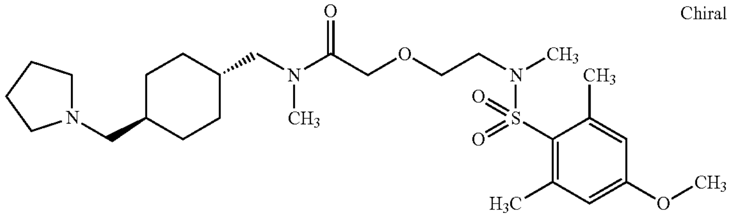 [SMILES: COc1cc(C)c(S(=O)(=O)N(C)CCOCC(=O)N(C)C[C@H]2CC[C@H](CN3CCCC3)CC2)c(C)c1] |
| (337) | 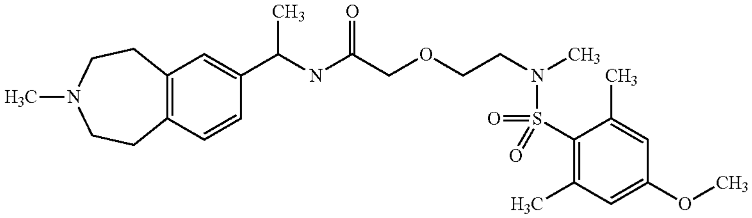 |
| (338) | 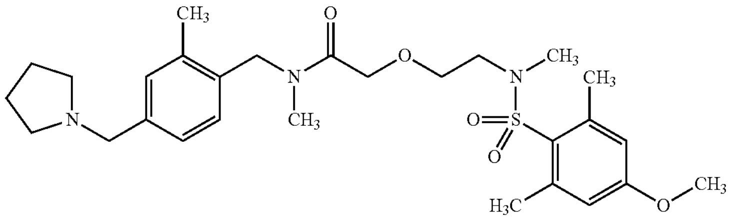 [SMILES: COc1cc(C)c(S(=O)(=O)N(C)CCOCC(=O)N(C)Cc2ccc(CN3CCCC3)cc2C)c(C)c1] |

-continued
| Example | Structure |
|---|---|
| (339) | 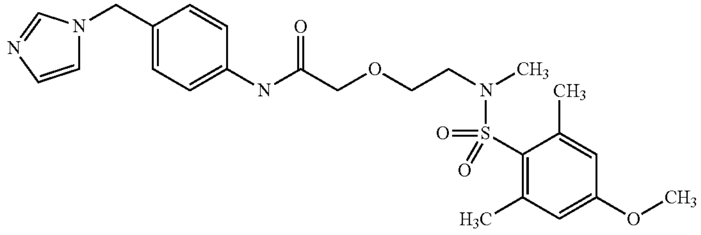 [SMILES: COc1cc(C)c(S(=O)(=O)N(C)CCOCC(=O)Nc2ccc(Cn3ccnc3)cc2)c(C)c1] |
| (340) | 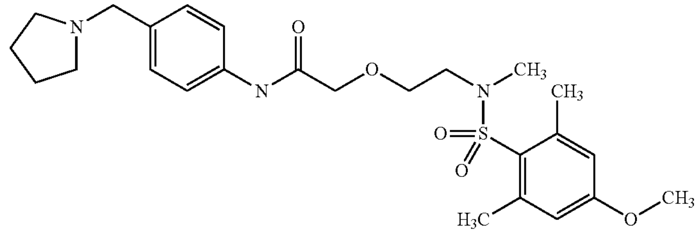 [SMILES: COc1cc(C)c(S(=O)(=O)N(C)CCOCC(=O)Nc2ccc(CN3CCCC3)cc2)c(C)c1] |
| (341) | 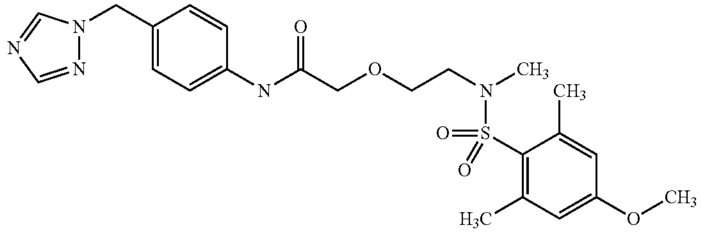 [SMILES: COc1cc(C)c(S(=O)(=O)N(C)CCOCC(=O)Nc2ccc(Cn3cncn3)cc2)c(C)c1] |
| (342) | 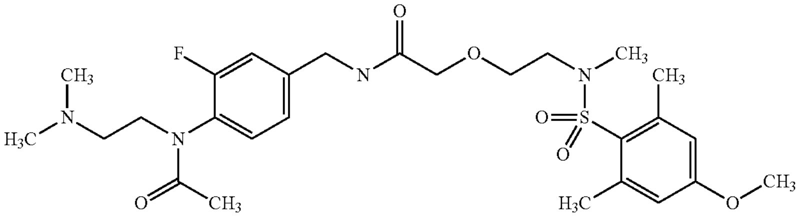 |
| (343) | 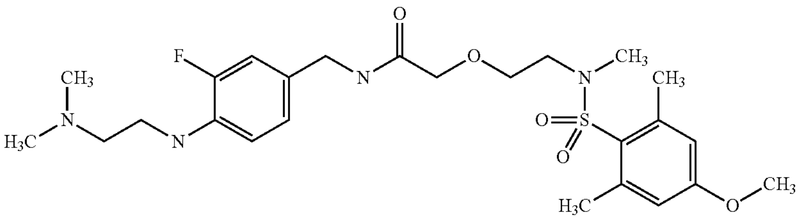 |
| (344) | 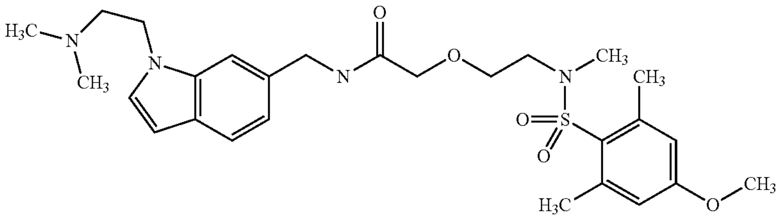 |

-continued
| Example | Structure |
|---|---|
| (345) | 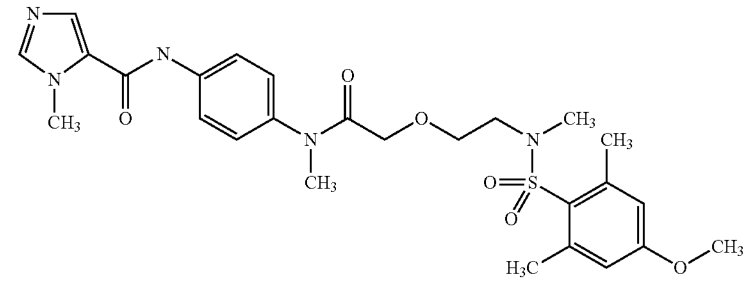 [SMILES: COc1cc(C)c(S(=O)(=O)N(C)CCOCC(=O)N(C)c2ccc(NC(=O)c3cncn3C)cc2)c(C)c1] |
| (346) | 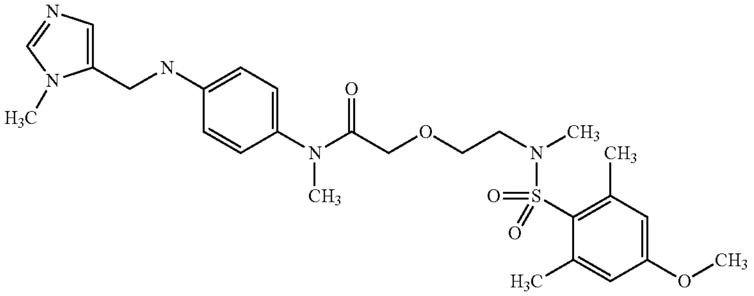 [SMILES: COc1cc(C)c(S(=O)(=O)N(C)CCOCC(=O)N(C)c2ccc(NCc3cncn3C)cc2)c(C)c1] |
| (347) | 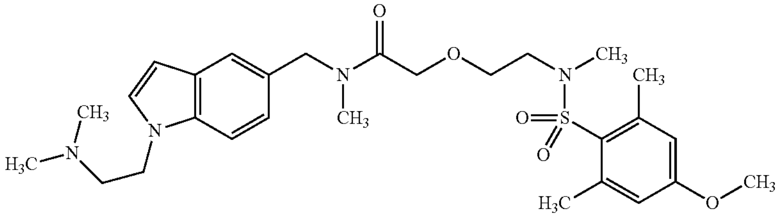 |
| (348) | 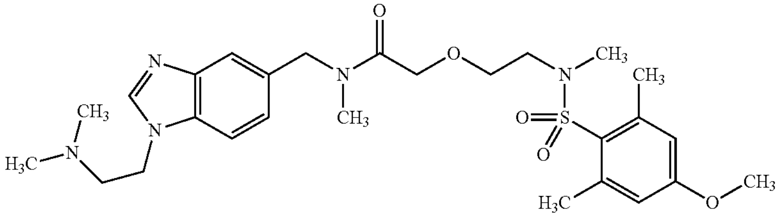 |
| (349) | 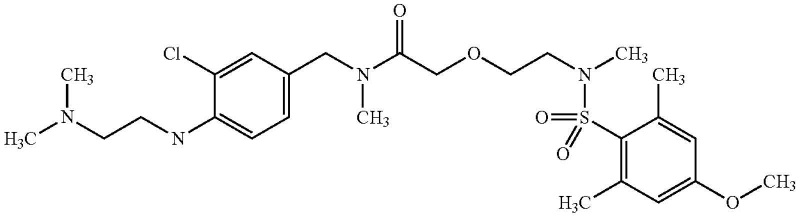 |
| (350) | 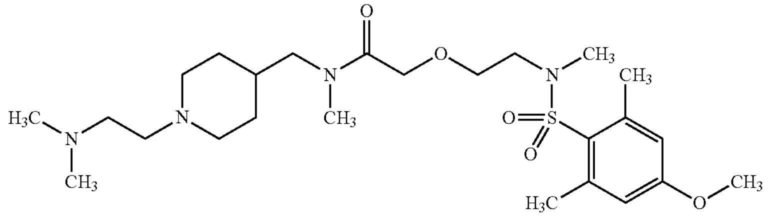 |

-continued
| Example | Structure |
|---|---|
| (351) | 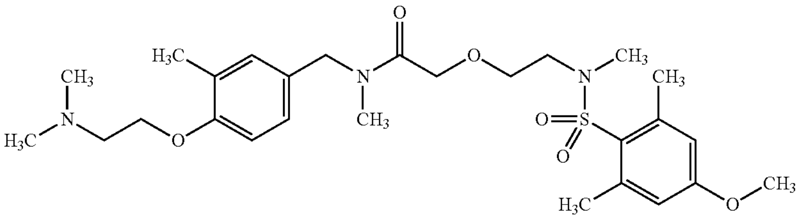 |
| (352) | 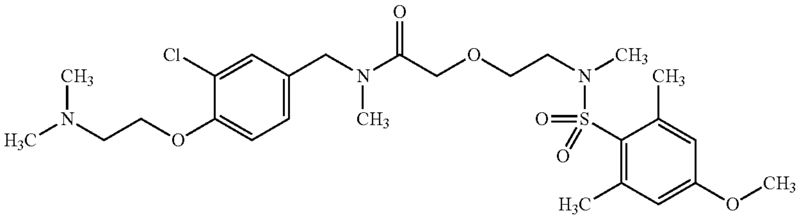 |
| (353) | 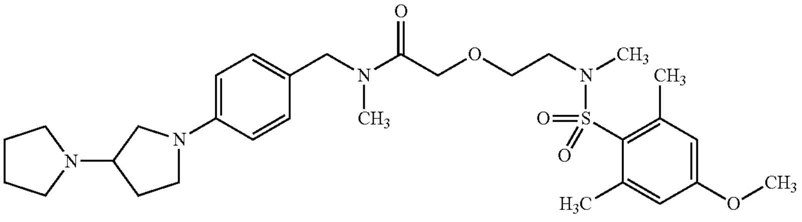 [SMILES: COc1cc(C)c(S(=O)(=O)N(C)CCOCC(=O)N(C)Cc2ccc(N3CCC(N4CCCC4)C3)cc2)c(C)c1] |
| (354) | 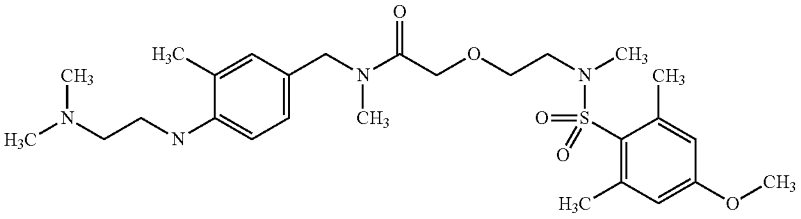 |
| (355) | 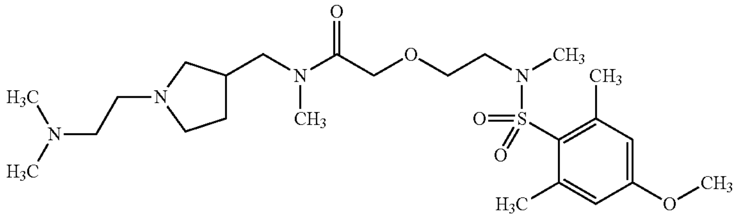 |
| (356) | 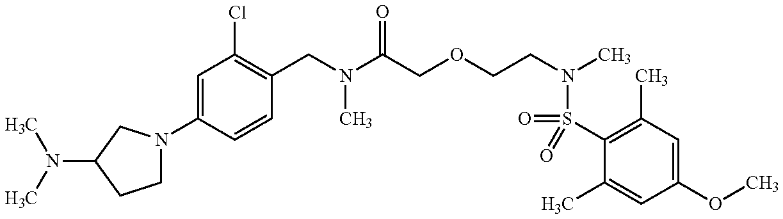 |
| (357) | 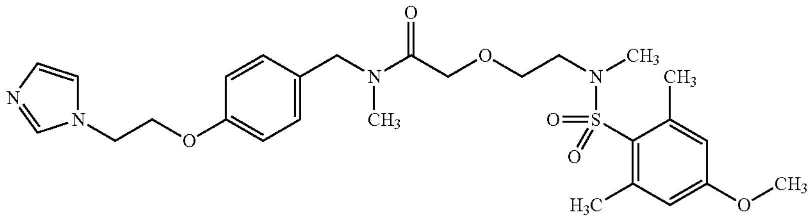 [SMILES: COc1cc(C)c(S(=O)(=O)N(C)CCOCC(=O)N(C)Cc2ccc(OCCn3ccnc3)cc2)c(C)c1] |

-continued
| Example | Structure |
| --- | --- |
| (358) | 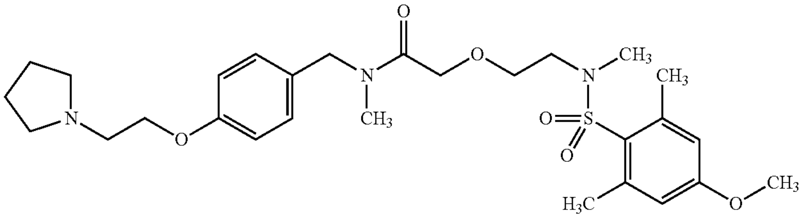 [SMILES: COc1cc(C)c(S(=O)(=O)N(C)CCOCC(=O)N(C)Cc2ccc(OCCN3CCCC3)cc2)c(C)c1] |
| (359) | 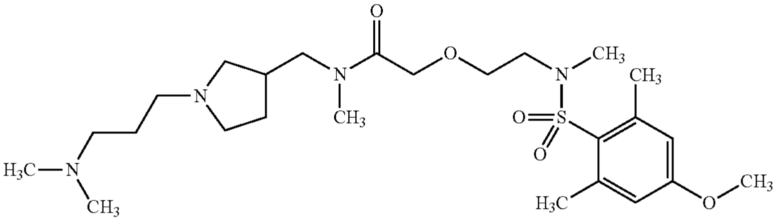 |
| (360) | 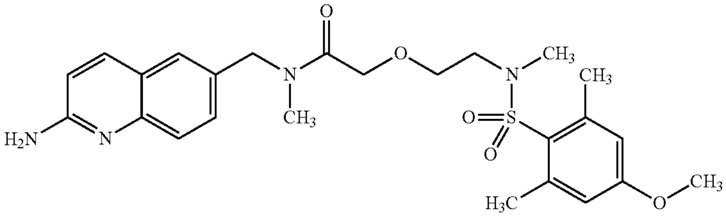 [SMILES: COc1cc(C)c(S(=O)(=O)N(C)CCOCC(=O)N(C)Cc2ccc3nc(N)ccc3c2)c(C)c1] |
| (361) | 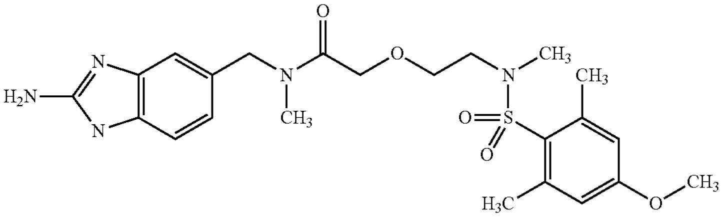 [SMILES: COc1cc(C)c(S(=O)(=O)N(C)CCOCC(=O)N(C)Cc2ccc3[nH]c(N)nc3c2)c(C)c1] |
| (362) | 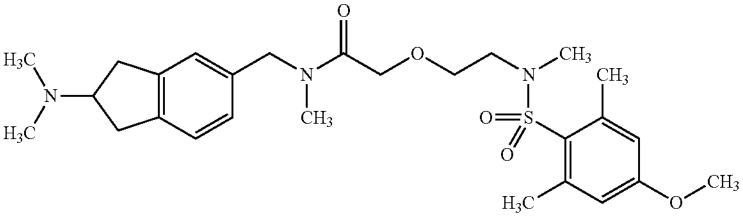 |
| (363) | 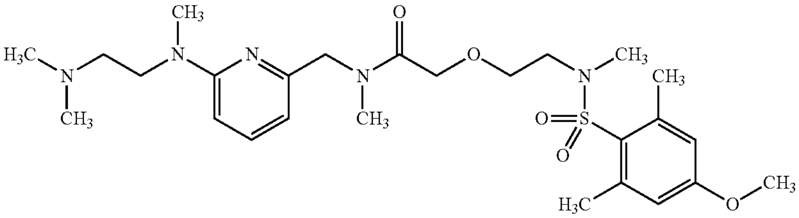 |

-continued
| Example | Structure |
| --- | --- |
| (364) | 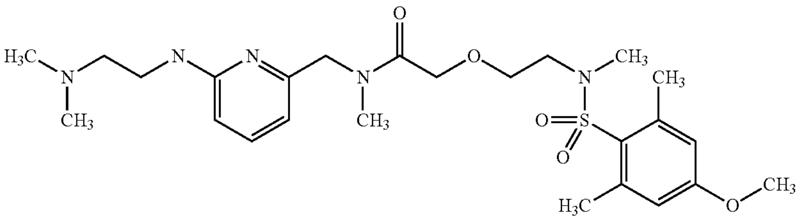 |
| (365) | 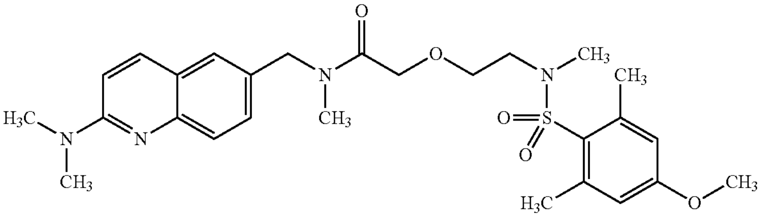 |
| (366) | 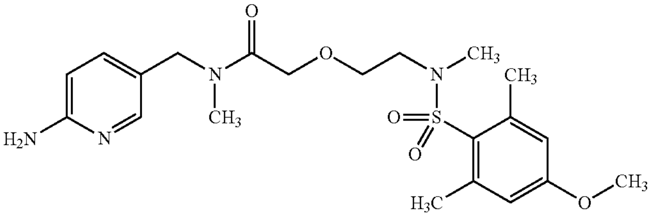 [SMILES: COc1cc(C)c(S(=O)(=O)N(C)CCOCC(=O)N(C)Cc2ccc(N)nc2)c(C)c1] |
| (367) | 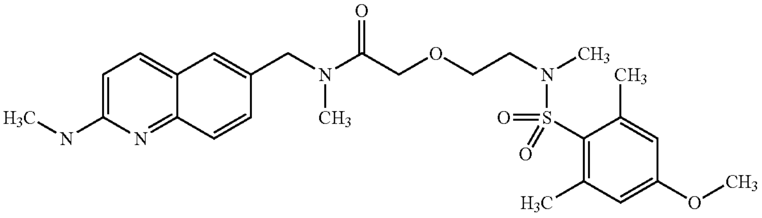 |
| (368) | 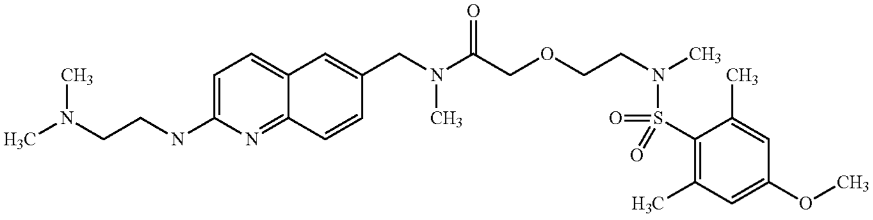 |
| (369) | 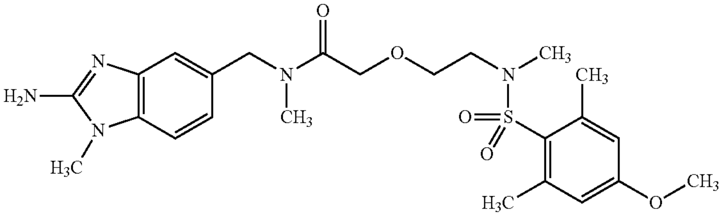 [SMILES: COc1cc(C)c(S(=O)(=O)N(C)CCOCC(=O)N(C)Cc2ccc3c(c2)nc(N)n3C)c(C)c1] |
| (370) | 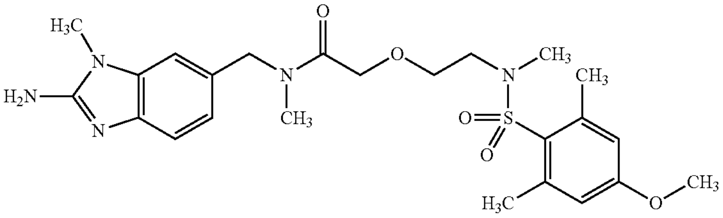 [SMILES: COc1cc(C)c(S(=O)(=O)N(C)CCOCC(=O)N(C)Cc2ccc3nc(N)n(C)c3c2)c(C)c1] |

-continued
| Example | Structure |
| --- | --- |
| (371) | 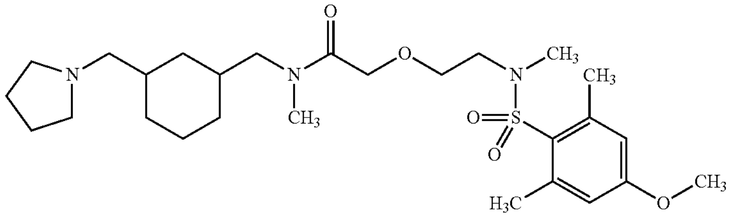 [SMILES: COc1cc(C)c(S(=O)(=O)N(C)CCOCC(=O)N(C)CC2CCCC(CN3CCCC3)C2)c(C)c1] |
| (372) | 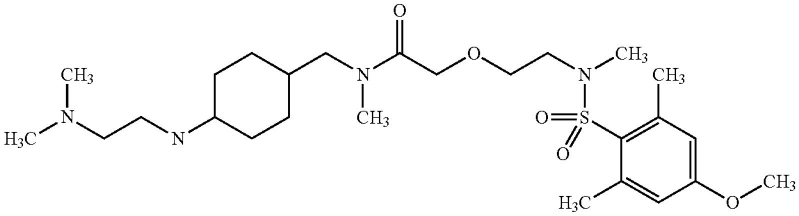 |
| (373) | 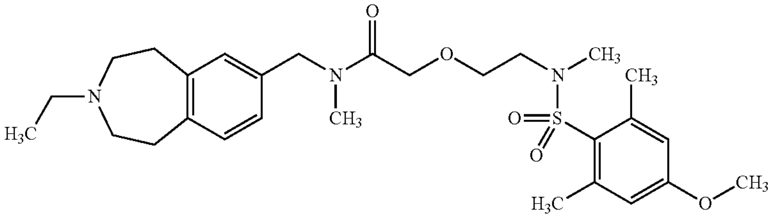 [SMILES: CCN1CCc2ccc(CN(C)C(=O)COCCN(C)S(=O)(=O)c3c(C)cc(OC)cc3C)cc2CC1] |
| (374) | 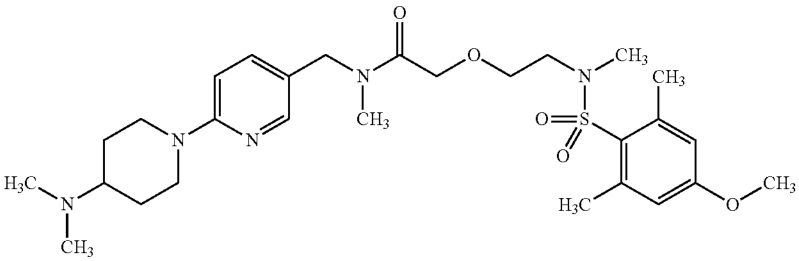 |
| (375) | 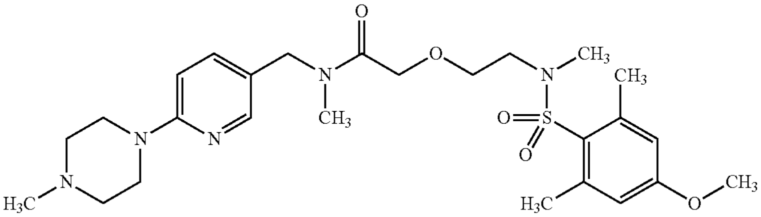 |
| (376) | 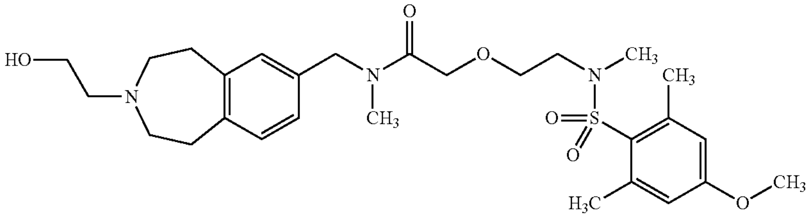 [SMILES: COc1cc(C)c(S(=O)(=O)N(C)CCOCC(=O)N(C)Cc2ccc3c(c2)CCN(CCO)CC3)c(C)c1] |

-continued
| Example | Structure |
|---|---|
| (377) | 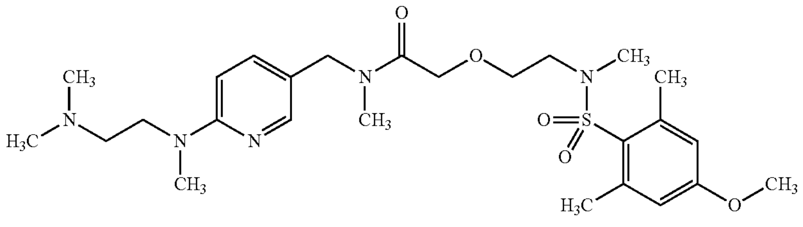 |
| (378) | 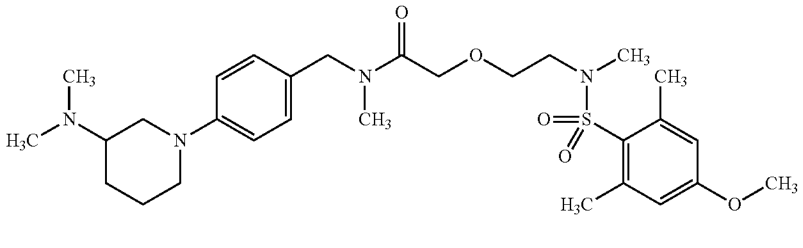 |
| (379) | 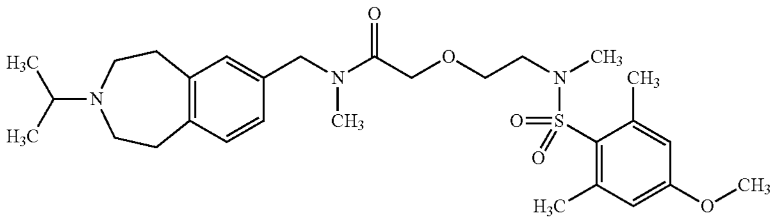 [SMILES: COc1cc(C)c(S(=O)(=O)N(C)CCOCC(=O)N(C)Cc2ccc3c(c2)CCN(C(C)C)CC3)c(C)c1] |
| (380) | 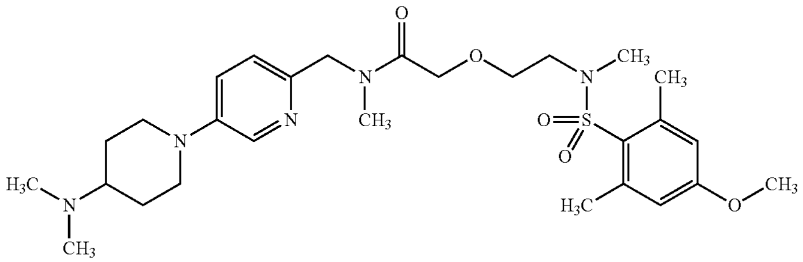 |
| (381) | 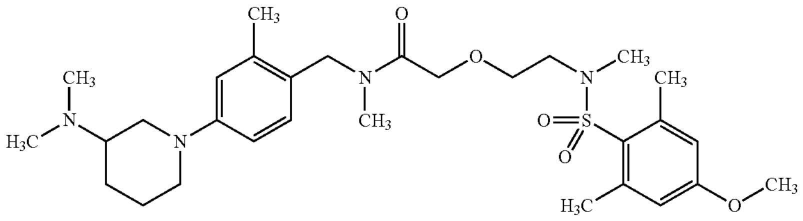 |
| (382) | 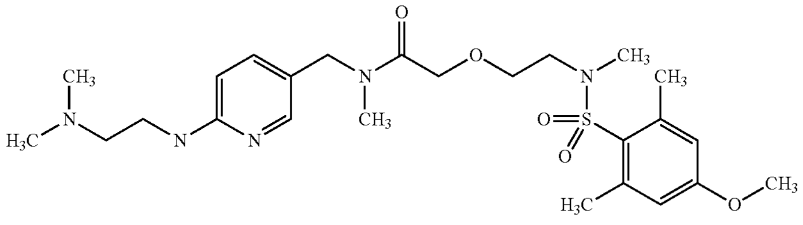 |

-continued
| Example | Structure |
|---|---|
| (383) | 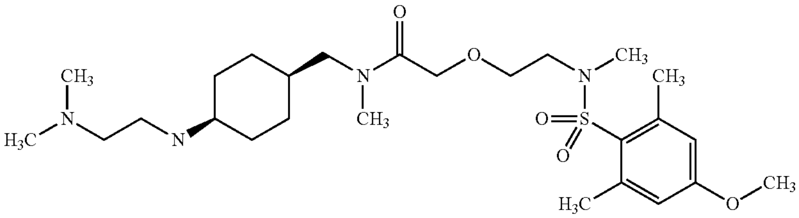 |
| (384) | 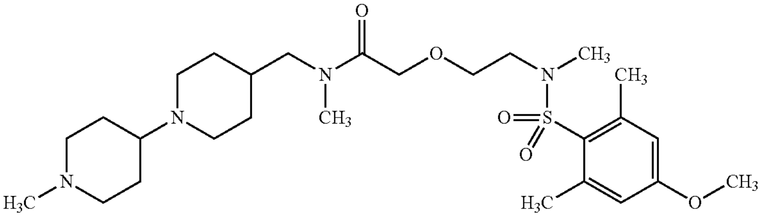 |
| (385) | 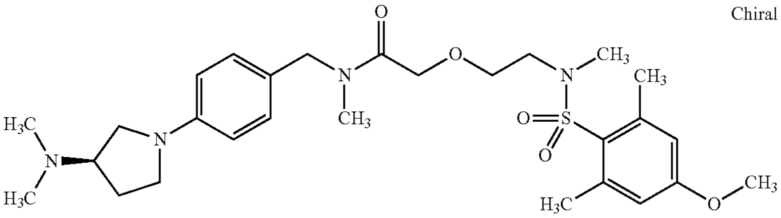 Chiral |
| (386) | 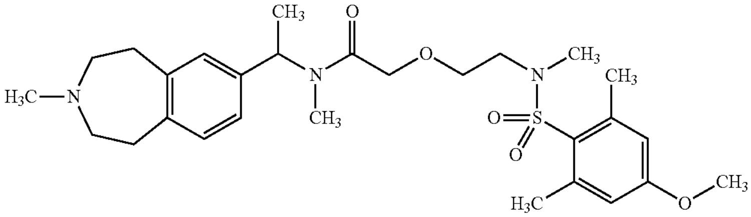 |
| (387) | 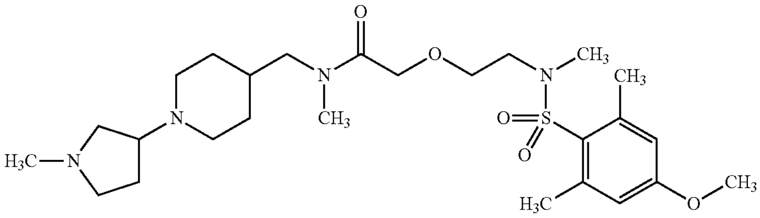 |
| (388) | 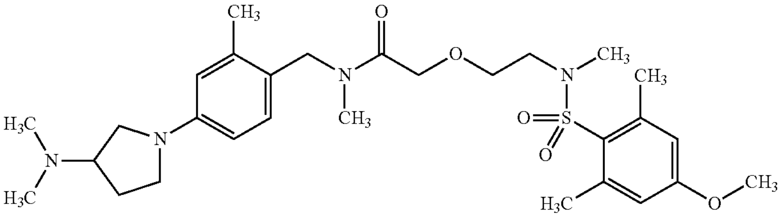 |
| (389) | 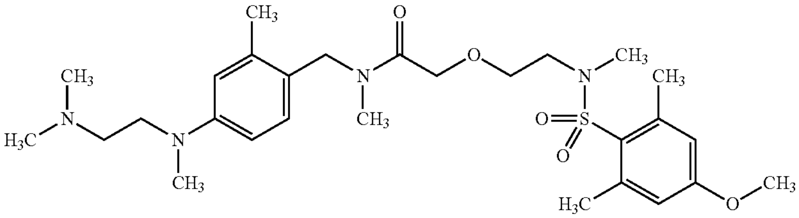 |

-continued
| Example | Structure |
|---|---|
| (390) | 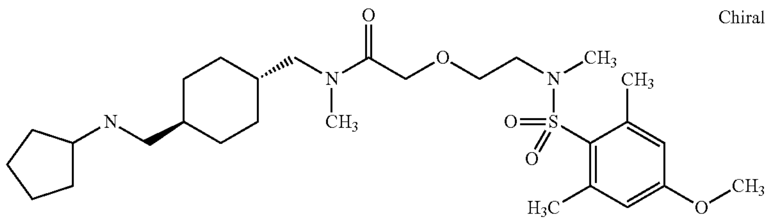 [SMILES: COc1cc(C)c(S(=O)(=O)N(C)CCOCC(=O)N(C)C[C@H]2CC[C@H](CNC3CCCC3)CC2)c(C)c1] Chiral |
| (391) | 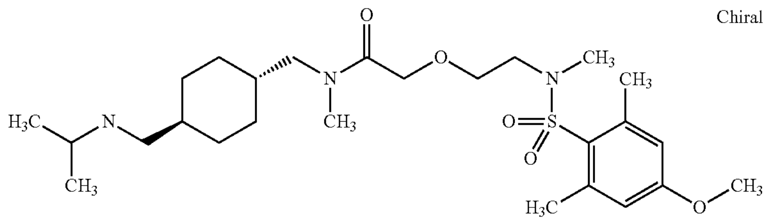 [SMILES: COc1cc(C)c(S(=O)(=O)N(C)CCOCC(=O)N(C)C[C@H]2CC[C@H](CNC(C)C)CC2)c(C)c1] Chiral |
| (392) | 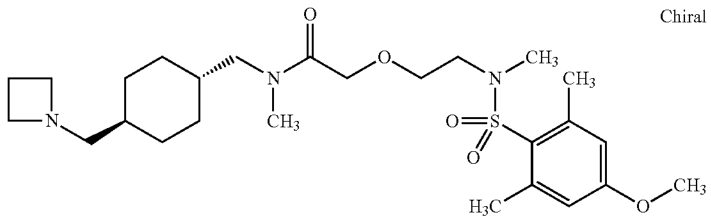 [SMILES: COc1cc(C)c(S(=O)(=O)N(C)CCOCC(=O)N(C)C[C@H]2CC[C@H](CN3CCC3)CC2)c(C)c1] Chiral |
| (393) | 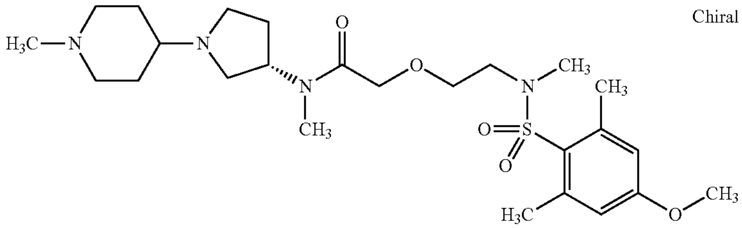 Chiral |
| (394) | 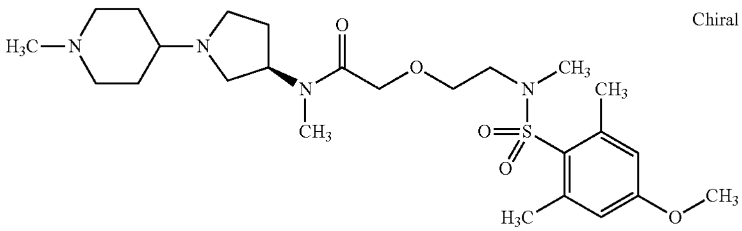 Chiral |
| (395) | 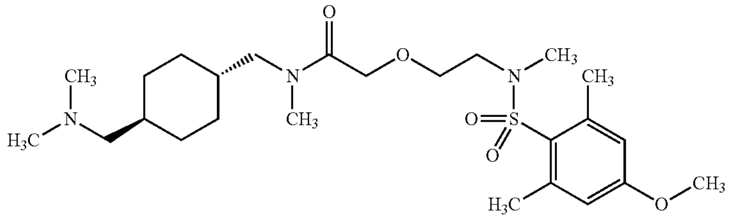 |

-continued
| Example | Structure |
| --- | --- |
| (396) | 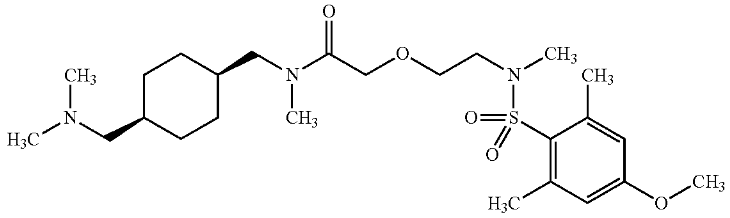 |
| (397) | 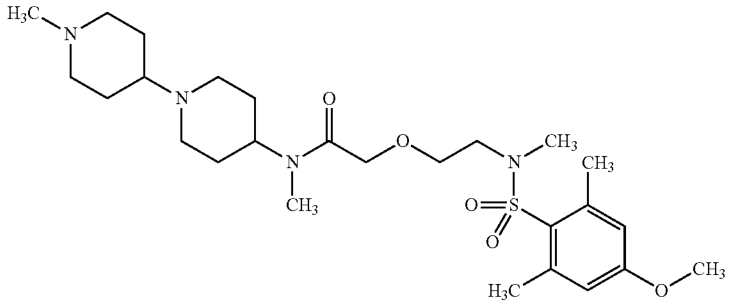 |
| (398) | 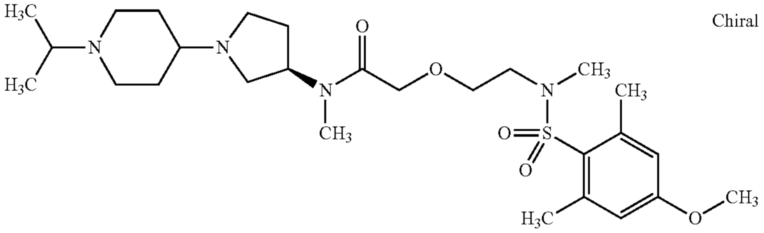 [SMILES: COc1cc(C)c(S(=O)(=O)N(C)CCOCC(=O)N(C)[C@@H]2CCN(C3CCN(C(C)C)CC3)C2)c(C)c1] Chiral |
| (399) | 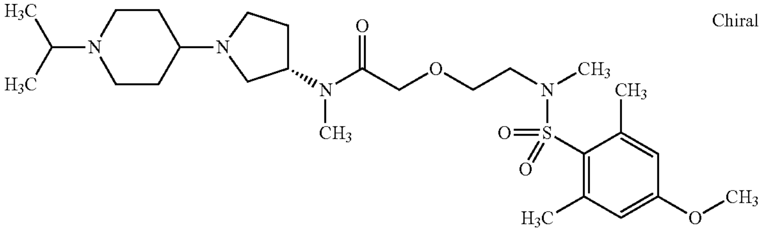 [SMILES: COc1cc(C)c(S(=O)(=O)N(C)CCOCC(=O)N(C)[C@H]2CCN(C3CCN(C(C)C)CC3)C2)c(C)c1] Chiral |
| (400) | 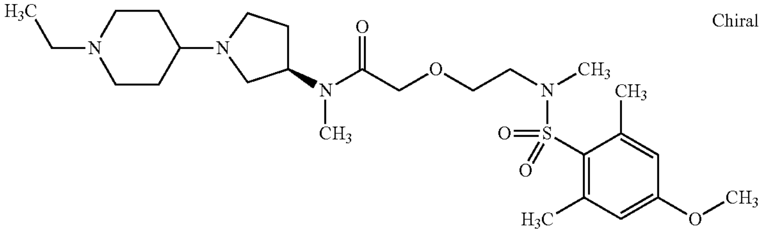 [SMILES: CCN1CCC(N2CC[C@@H](N(C)C(=O)COCCN(C)S(=O)(=O)c3c(C)cc(OC)cc3C)C2)CC1] Chiral |
| (401) | 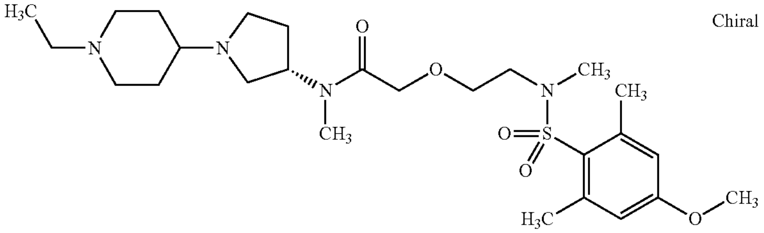 [SMILES: CCN1CCC(N2CC[C@H](N(C)C(=O)COCCN(C)S(=O)(=O)c3c(C)cc(OC)cc3C)C2)CC1] Chiral |

-continued
| Example | Structure |
|---|---|
| (402) | 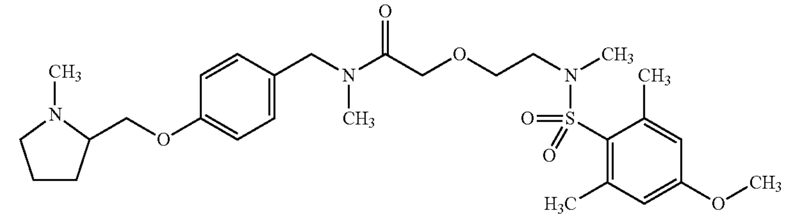 [SMILES: COc1cc(C)c(S(=O)(=O)N(C)CCOCC(=O)N(C)Cc2ccc(OCC3CCCN3C)cc2)c(C)c1] |
| (403) | 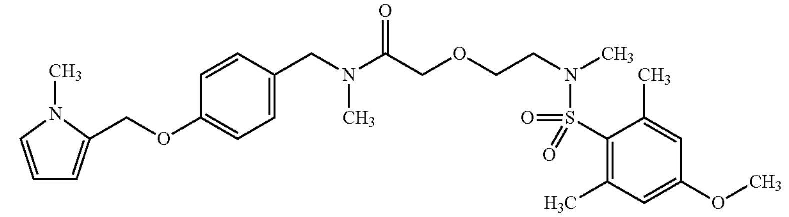 [SMILES: COc1cc(C)c(S(=O)(=O)N(C)CCOCC(=O)N(C)Cc2ccc(OCc3cccn3C)cc2)c(C)c1] |
| (404) | 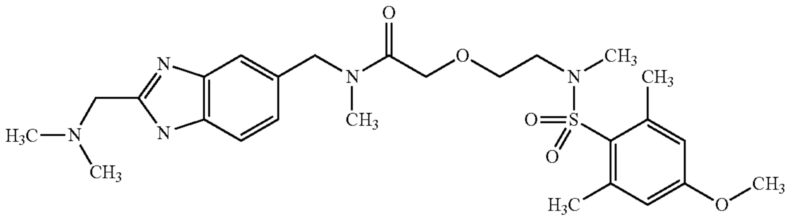 |
| (405) | 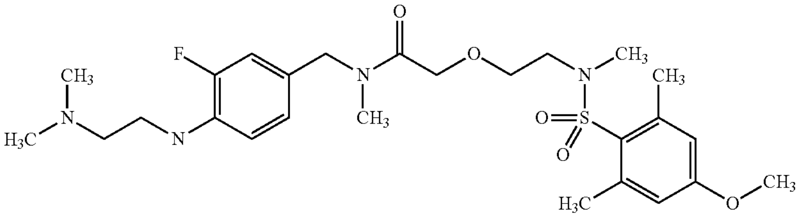 |
| (406) | Chiral 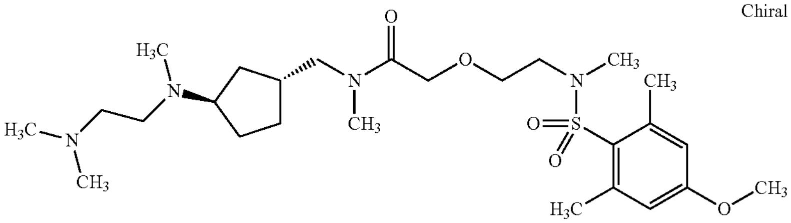 |
| (407) | Chiral 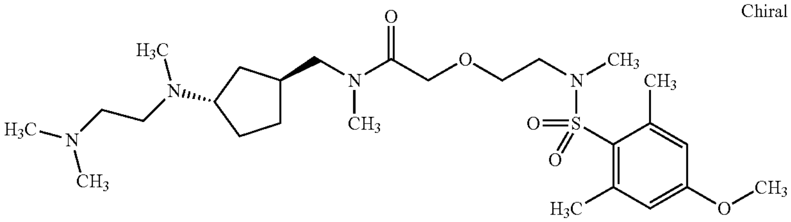 |
| (408) | 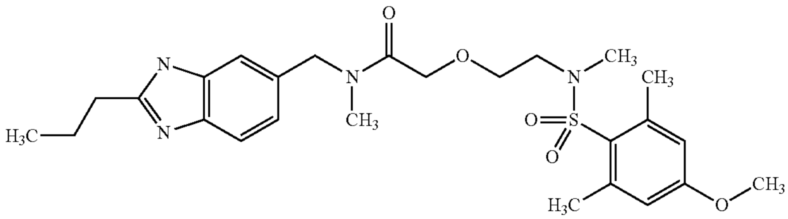 [SMILES: CCCc1nc2ccc(CN(C)C(=O)COCCN(C)S(=O)(=O)c3c(C)cc(OC)cc3C)cc2[nH]1] |

-continued
| Example | Structure |
| --- | --- |
| (409) | 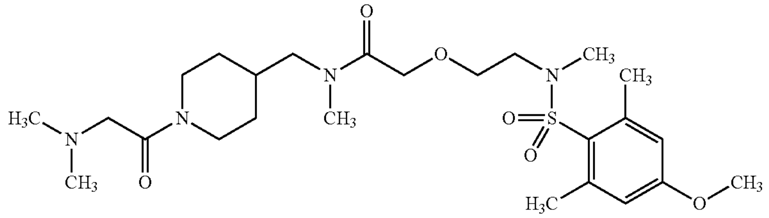 |
| (410) | 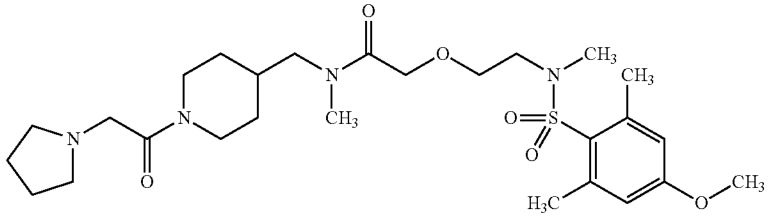 [SMILES: COc1cc(C)c(S(=O)(=O)N(C)CCOCC(=O)N(C)CC2CCN(C(=O)CN3CCCC3)CC2)c(C)c1] |
| (411) | 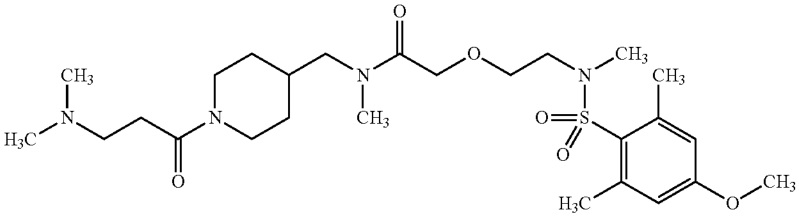 |
| (412) | 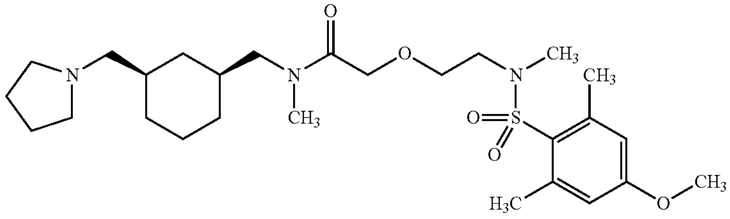 [SMILES: COc1cc(C)c(S(=O)(=O)N(C)CCOCC(=O)N(C)C[C@H]2CCC[C@@H](CN3CCCC3)C2)c(C)c1] |
| (413) | 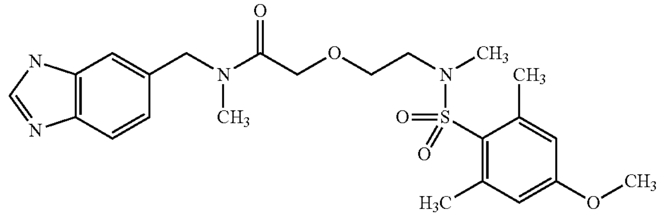 [SMILES: COc1cc(C)c(S(=O)(=O)N(C)CCOCC(=O)N(C)Cc2ccc3nc[nH]c3c2)c(C)c1] |
| (414) | 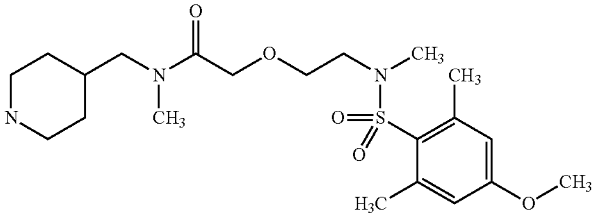 [SMILES: COc1cc(C)c(S(=O)(=O)N(C)CCOCC(=O)N(C)CC2CCNCC2)c(C)c1] |
| (415) | 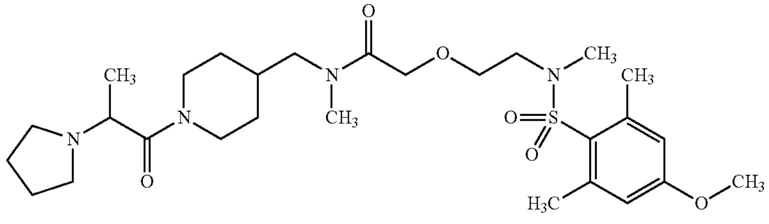 [SMILES: COc1cc(C)c(S(=O)(=O)N(C)CCOCC(=O)N(C)CC2CCN(C(=O)C(C)N3CCCC3)CC2)c(C)c1] |

-continued
| Example | Structure |
| --- | --- |
| (416) | 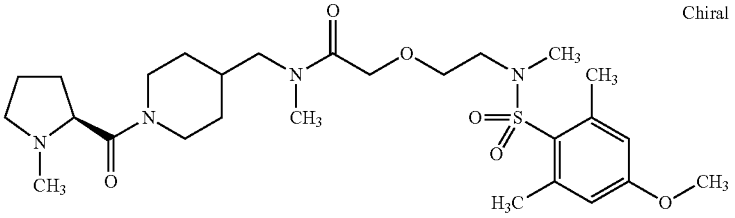 [SMILES: COc1cc(C)c(S(=O)(=O)N(C)CCOCC(=O)N(C)CC2CCN(C(=O)[C@@H]3CCCN3C)CC2)c(C)c1] Chiral |
| (417) | 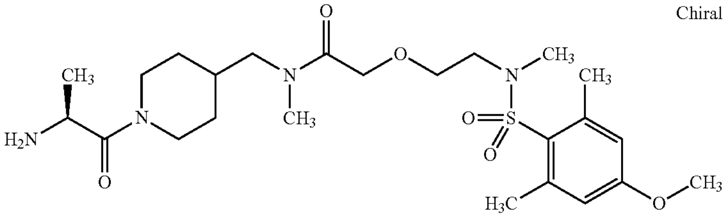 [SMILES: COc1cc(C)c(S(=O)(=O)N(C)CCOCC(=O)N(C)CC2CCN(C(=O)[C@H](C)N)CC2)c(C)c1] Chiral |
| (418) | 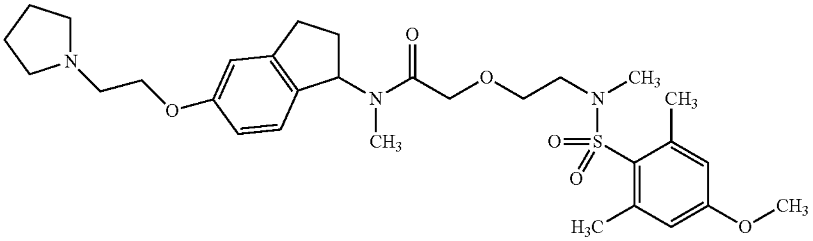 [SMILES: COc1cc(C)c(S(=O)(=O)N(C)CCOCC(=O)N(C)C2CCc3cc(OCCN4CCCC4)ccc32)c(C)c1] |
| (419) | 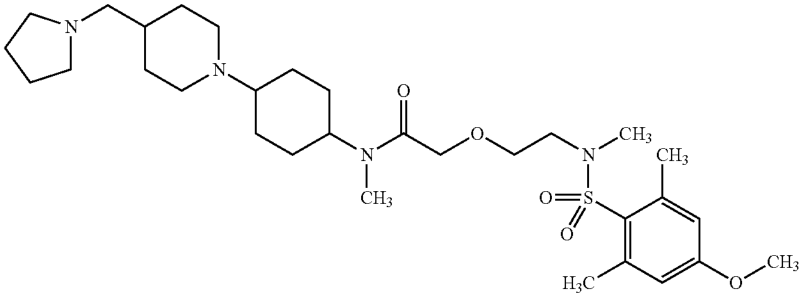 [SMILES: COc1cc(C)c(S(=O)(=O)N(C)CCOCC(=O)N(C)C2CCC(N3CCC(CN4CCCC4)CC3)CC2)c(C)c1] |
| (420) | 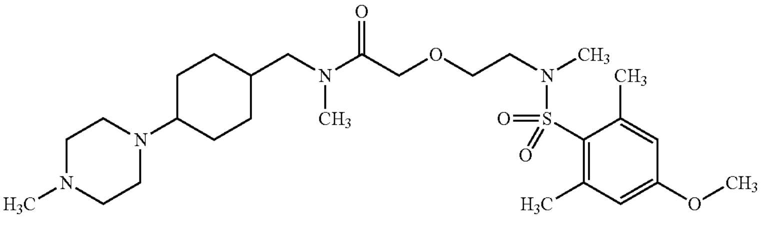 |
| (421) | 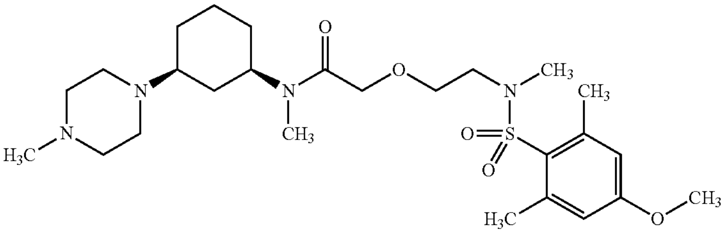 |

-continued
| Example | Structure |
|---|---|
| (422) | 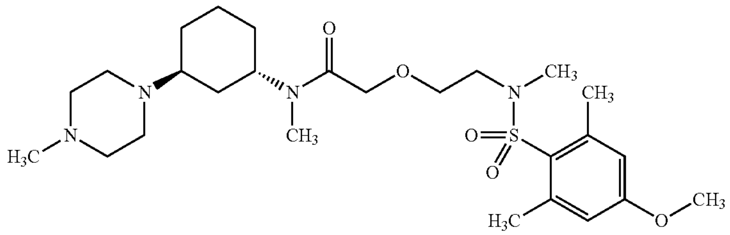 |
| (423) | Chiral 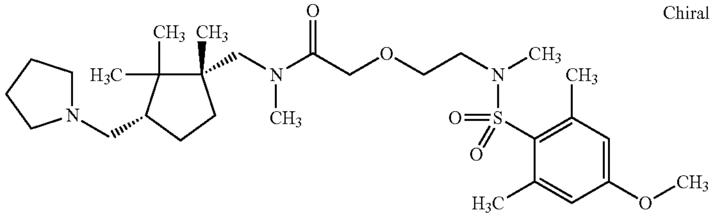 [SMILES: COc1cc(C)c(S(=O)(=O)N(C)CCOCC(=O)N(C)C[C@]2(C)CC[C@H](CN3CCCC3)C2(C)C)c(C)c1] |
| (424) | 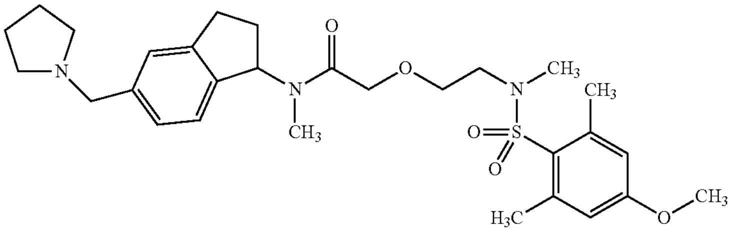 [SMILES: COc1cc(C)c(S(=O)(=O)N(C)CCOCC(=O)N(C)C2CCc3cc(CN4CCCC4)ccc32)c(C)c1] |
| (425) | Chiral 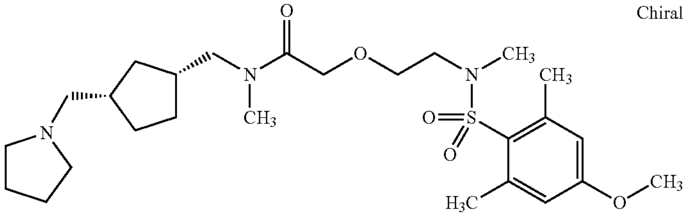 [SMILES: COc1cc(C)c(S(=O)(=O)N(C)CCOCC(=O)N(C)C[C@@H]2CC[C@H](CN3CCCC3)C2)c(C)c1] |
| (426) | 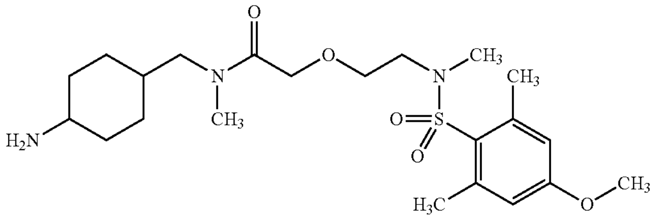 [SMILES: COc1cc(C)c(S(=O)(=O)N(C)CCOCC(=O)N(C)CC2CCC(N)CC2)c(C)c1] |
| (427) | 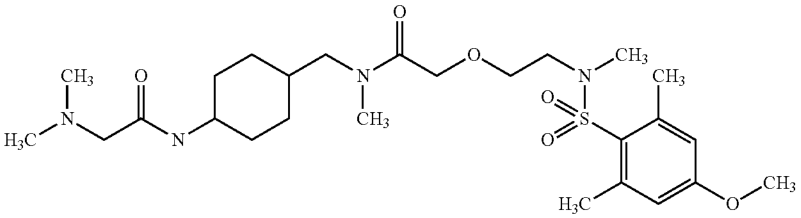 |

-continued
| Example | Structure |
| --- | --- |
| (428) | 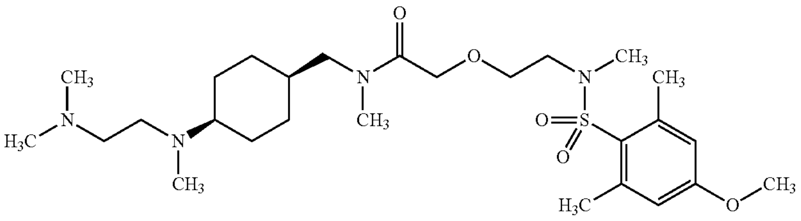 |
| (429) | 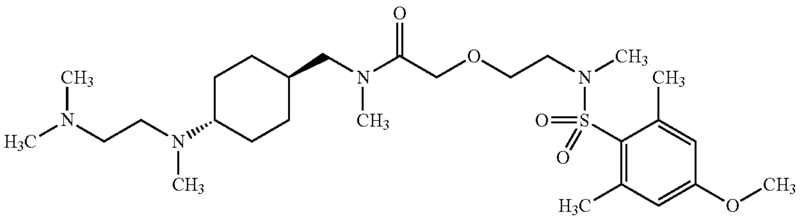 |
| (430) | 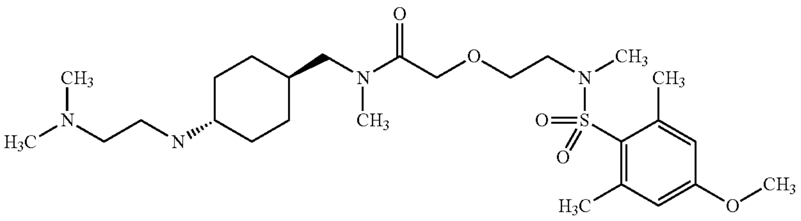 |
| (431) | 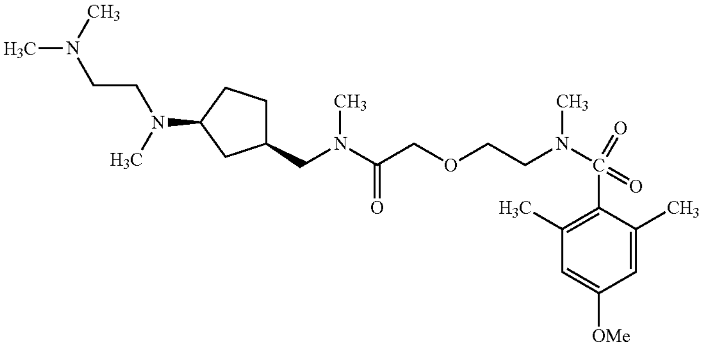 |
| (432) | 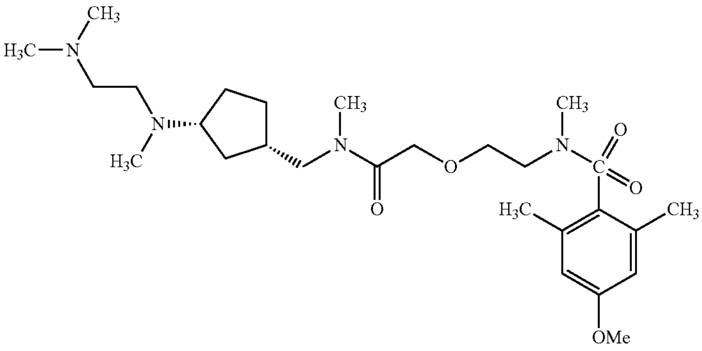 |

-continued
| Example | Structure |
|---|---|
| (433) | 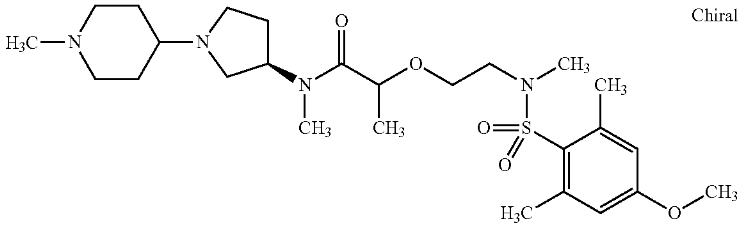 Chiral |
| (434) | 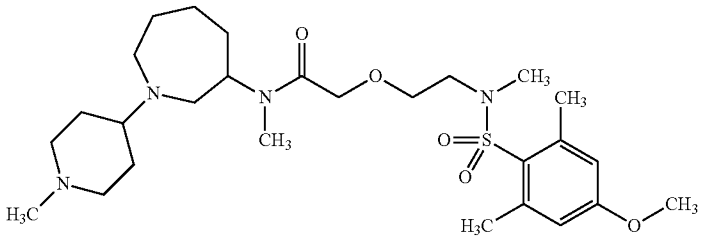 |
| (435) | 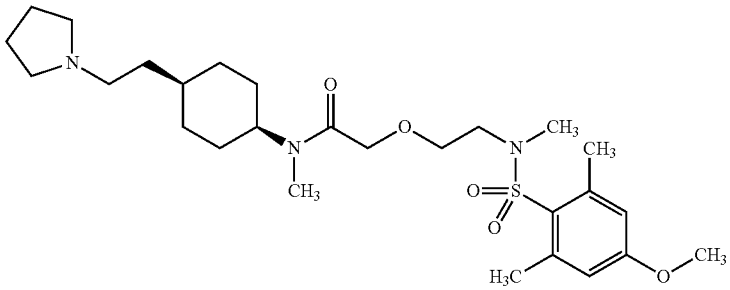 [SMILES: COc1cc(C)c(S(=O)(=O)N(C)CCOCC(=O)N(C)[C@H]2CC[C@@H](CCN3CCCC3)CC2)c(C)c1] |
| (436) | 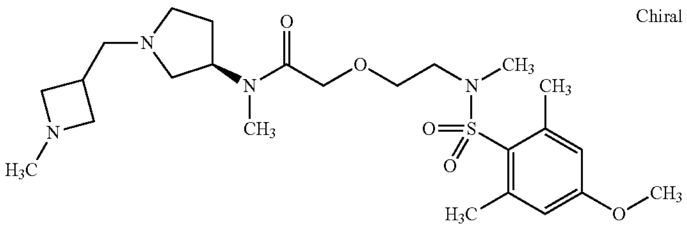 Chiral |
| (437) | 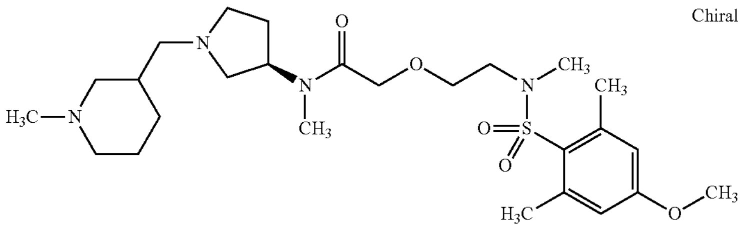 Chiral |
| (438) | 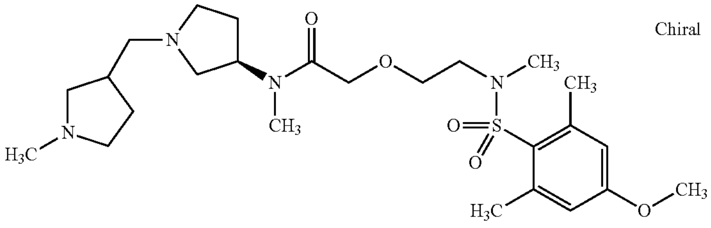 Chiral |

-continued
| Example | Structure |
| --- | --- |
| (439) | 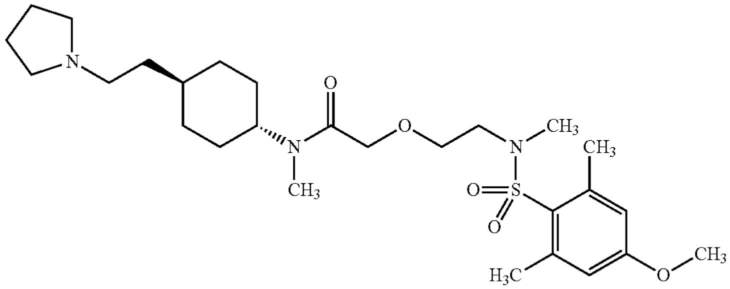 [SMILES: COc1cc(C)c(S(=O)(=O)N(C)CCOCC(=O)N(C)[C@H]2CC[C@H](CCN3CCCC3)CC2)c(C)c1] |
| (440) | 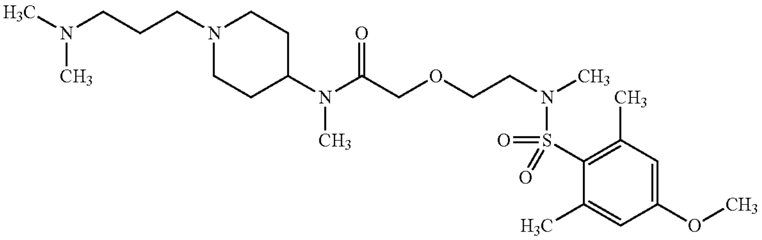 |
| (441) | 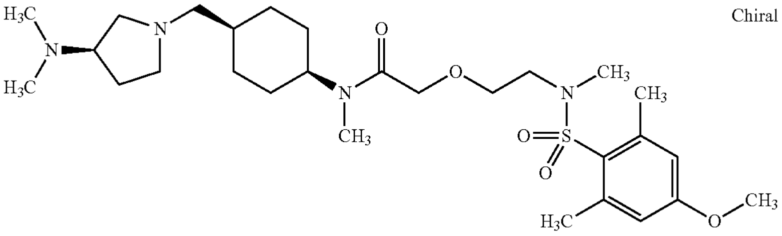 Chiral |
| (442) | 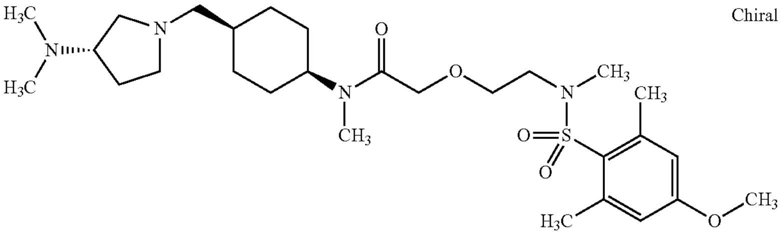 Chiral |
| (443) | 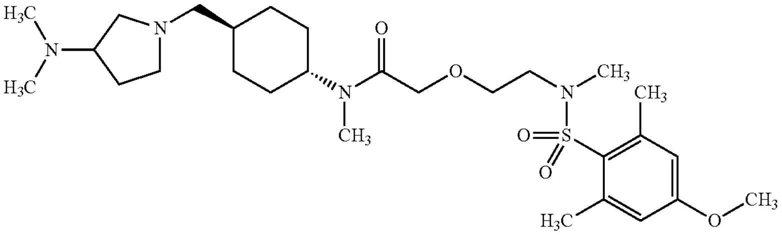 |
| (444) | 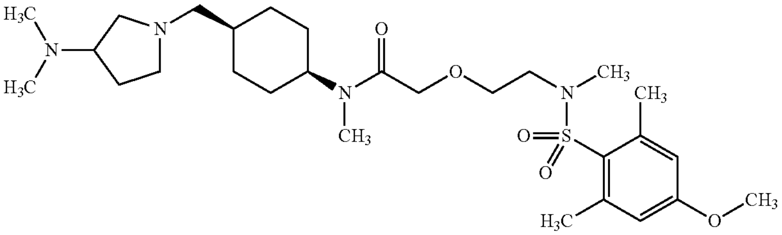 |

-continued
| Example | Structure |
|---|---|
| (445) | 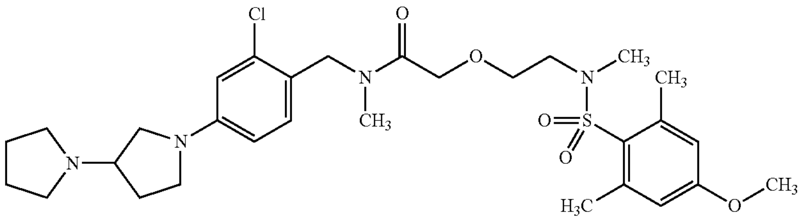 [SMILES: COc1cc(C)c(S(=O)(=O)N(C)CCOCC(=O)N(C)Cc2ccc(N3CCC(N4CCCC4)C3)cc2Cl)c(C)c1] |
| (446) | Chiral 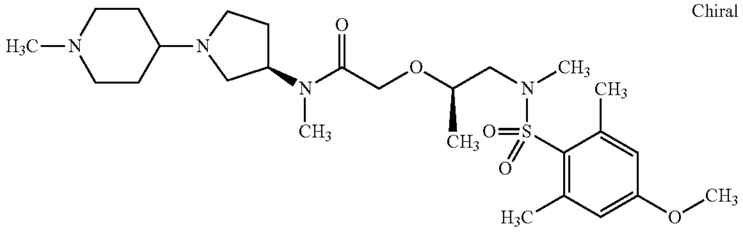 |
| (447) | Chiral 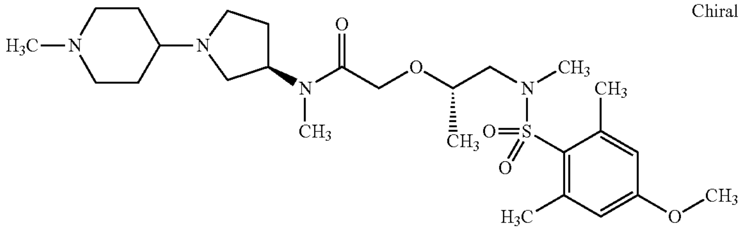 |
| (448) | Chiral 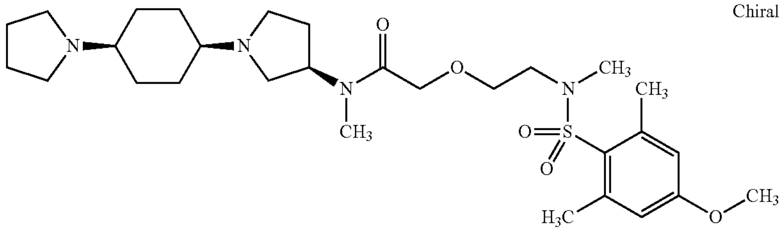 [SMILES: COc1cc(C)c(S(=O)(=O)N(C)CCOCC(=O)N(C)[C@@H]2CCN([C@H]3CC[C@@H](N4CCCC4)CC3)C2)c(C)c1] |
| (449) | Chiral 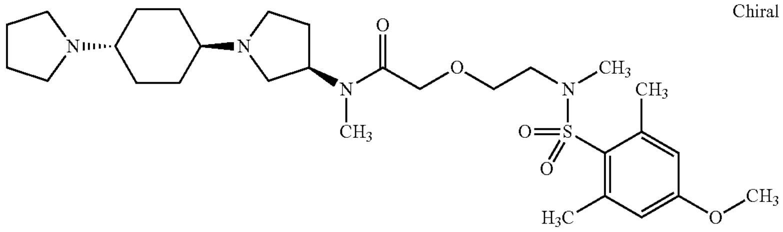 [SMILES: COc1cc(C)c(S(=O)(=O)N(C)CCOCC(=O)N(C)[C@@H]2CCN([C@H]3CC[C@H](N4CCCC4)CC3)C2)c(C)c1] |
| (450) | 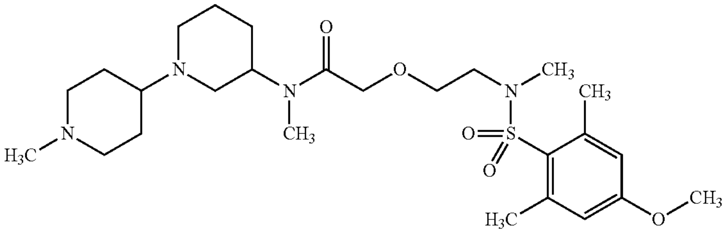 |

-continued
| Example | Structure |
|---|---|
| (451) | 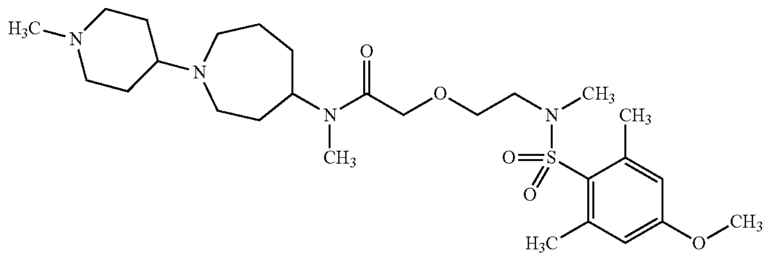 |
| (452) | 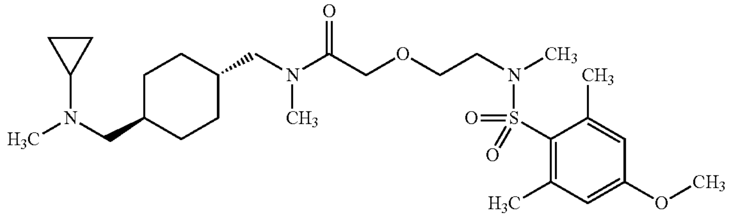 |
| (453) | 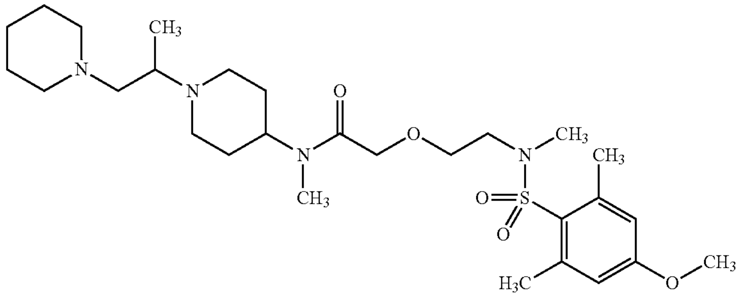 [SMILES: COc1cc(C)c(S(=O)(=O)N(C)CCOCC(=O)N(C)C2CCN(C(C)CN3CCCCC3)CC2)c(C)c1] |
| (454) | 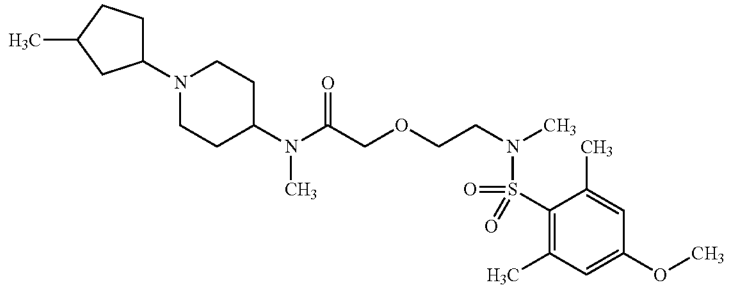 |
| (455) | 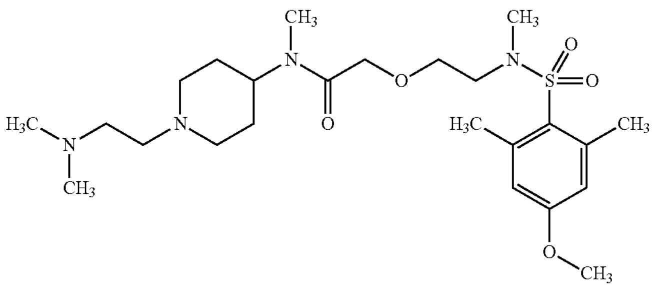 |

-continued
| Example | Structure |
| --- | --- |
| (456) | 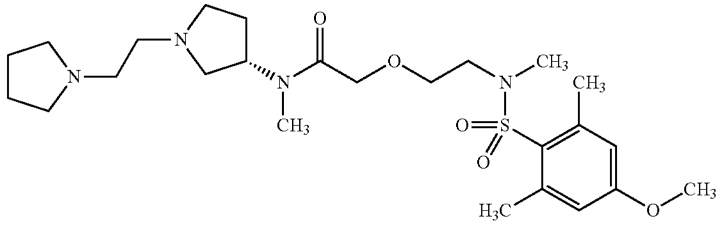 [SMILES: COc1cc(C)c(S(=O)(=O)N(C)CCOCC(=O)N(C)[C@H]2CCN(CCN3CCCC3)C2)c(C)c1] |
| (457) | 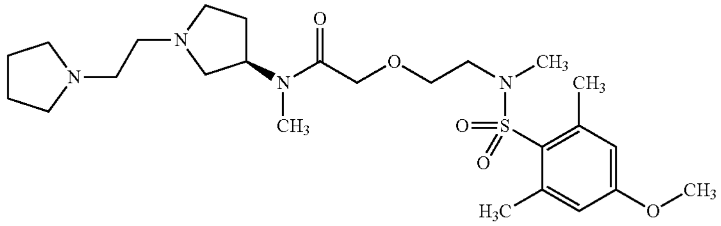 [SMILES: COc1cc(C)c(S(=O)(=O)N(C)CCOCC(=O)N(C)[C@@H]2CCN(CCN3CCCC3)C2)c(C)c1] |
| (458) | 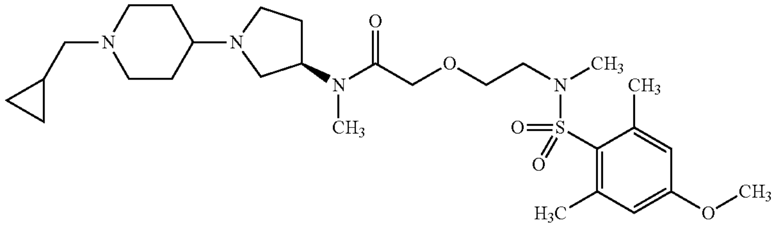 [SMILES: COc1cc(C)c(S(=O)(=O)N(C)CCOCC(=O)N(C)[C@@H]2CCN(C3CCN(CC4CC4)CC3)C2)c(C)c1] |
| (459) | 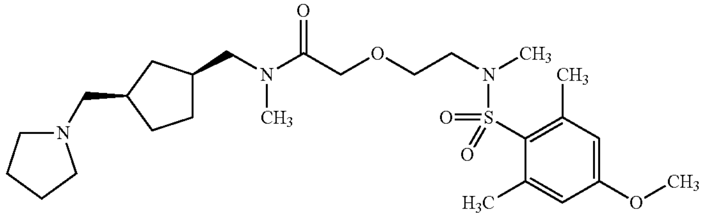 [SMILES: COc1cc(C)c(S(=O)(=O)N(C)CCOCC(=O)N(C)C[C@H]2CC[C@@H](CN3CCCC3)C2)c(C)c1] |
| (460) | 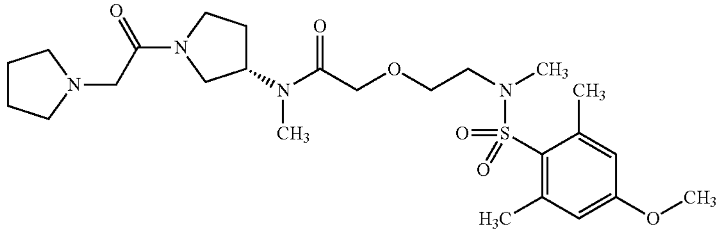 [SMILES: COc1cc(C)c(S(=O)(=O)N(C)CCOCC(=O)N(C)[C@H]2CCN(C(=O)CN3CCCC3)C2)c(C)c1] |
| (461) | 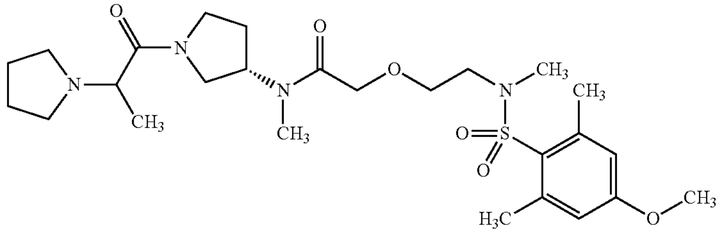 [SMILES: COc1cc(C)c(S(=O)(=O)N(C)CCOCC(=O)N(C)[C@H]2CCN(C(=O)C(C)N3CCCC3)C2)c(C)c1] |

-continued
| Example | Structure |
| --- | --- |
| (462) | 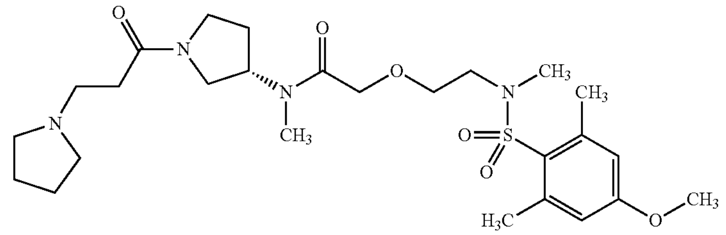 [SMILES: COc1cc(C)c(S(=O)(=O)N(C)CCOCC(=O)N(C)[C@H]2CCN(C(=O)CCN3CCCC3)C2)c(C)c1] |
| (463) | 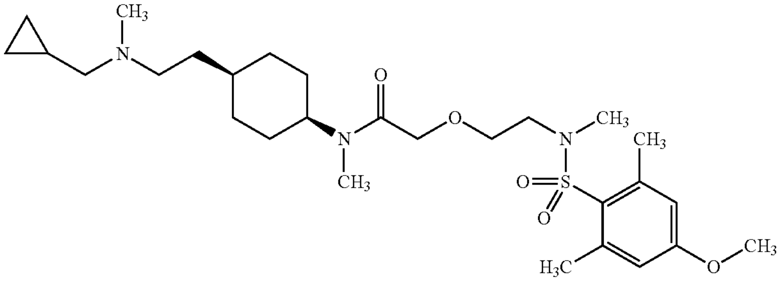 [SMILES: COc1cc(C)c(S(=O)(=O)N(C)CCOCC(=O)N(C)[C@H]2CC[C@@H](CCN(C)CC3CC3)CC2)c(C)c1] |
| (464) | 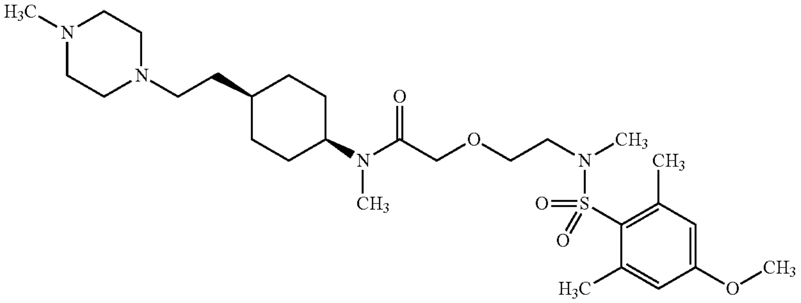 |
| (465) | 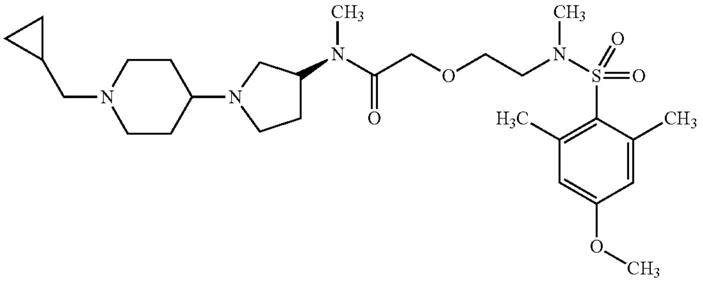 |
| (466) | 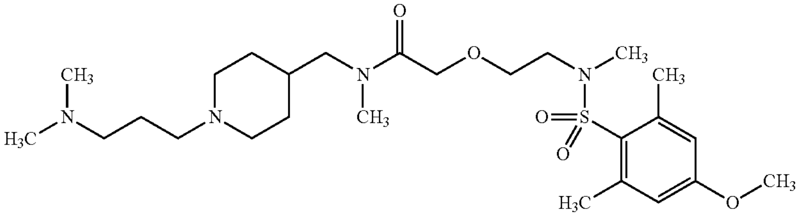 |
| (467) | 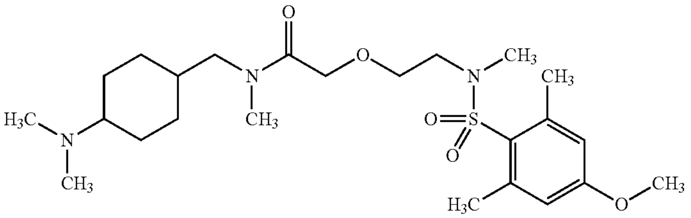 |

-continued
| Example | Structure |
|---|---|
| (468) | 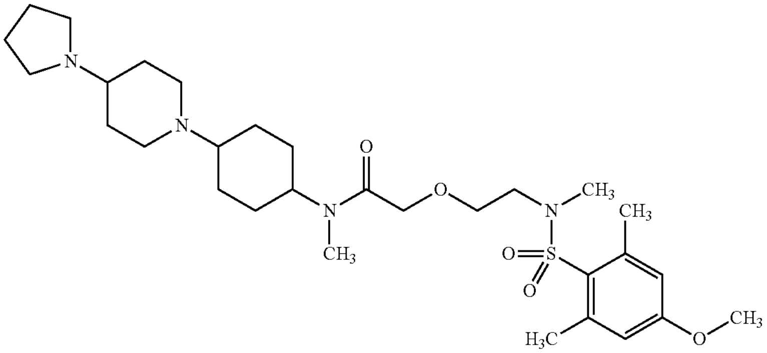 [SMILES: COc1cc(C)c(S(=O)(=O)N(C)CCOCC(=O)N(C)C2CCC(N3CCC(N4CCCC4)CC3)CC2)c(C)c1] |
| (469) | 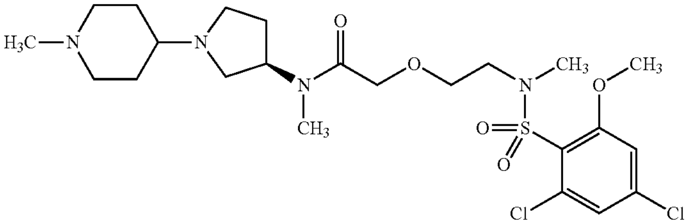 [SMILES: COc1cc(Cl)cc(Cl)c1S(=O)(=O)N(C)CCOCC(=O)N(C)[C@@H]1CCN(C2CCN(C)CC2)C1] |
| (470) | 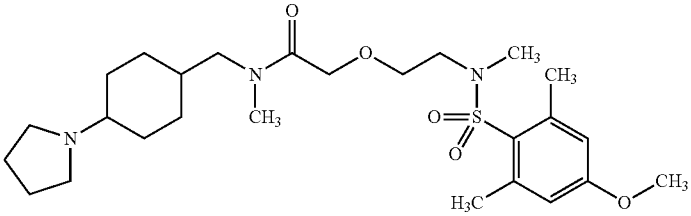 [SMILES: COc1cc(C)c(S(=O)(=O)N(C)CCOCC(=O)N(C)CC2CCC(N3CCCC3)CC2)c(C)c1] |
| (471) | 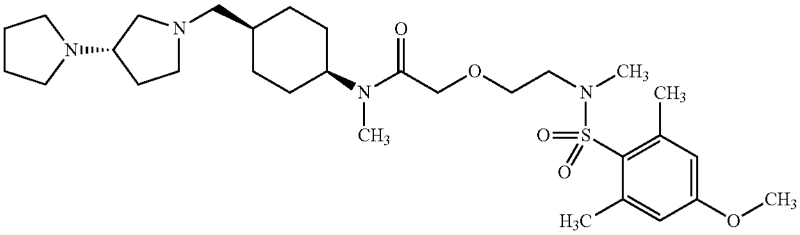 [SMILES: COc1cc(C)c(S(=O)(=O)N(C)CCOCC(=O)N(C)[C@H]2CC[C@@H](CN3CC[C@H](N4CCCC4)C3)CC2)c(C)c1] |
| (472) | 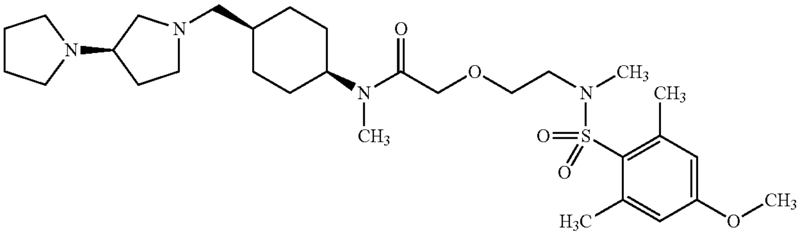 [SMILES: COc1cc(C)c(S(=O)(=O)N(C)CCOCC(=O)N(C)[C@H]2CC[C@@H](CN3CC[C@@H](N4CCCC4)C3)CC2)c(C)c1] |
| (473) | 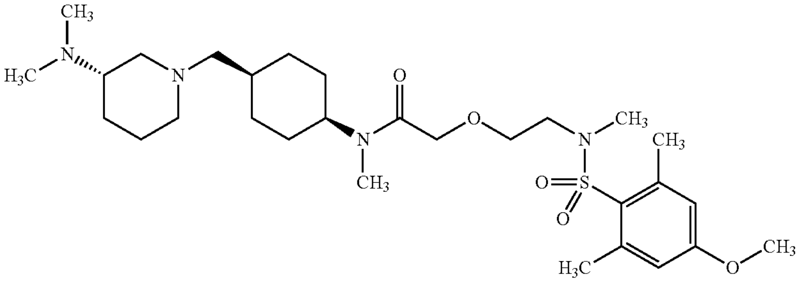 |

-continued
| Example | Structure |
|---|---|
| (474) | 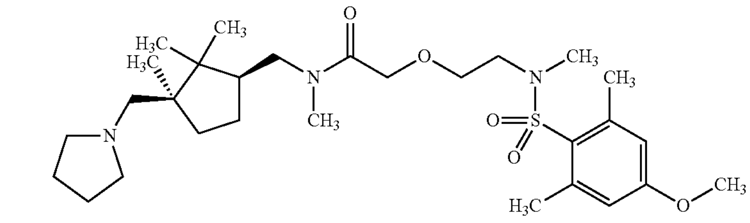 [SMILES: COc1cc(C)c(S(=O)(=O)N(C)CCOCC(=O)N(C)C[C@H]2CC[C@@](C)(CN3CCCC3)C2(C)C)c(C)c1] |
| (475) | 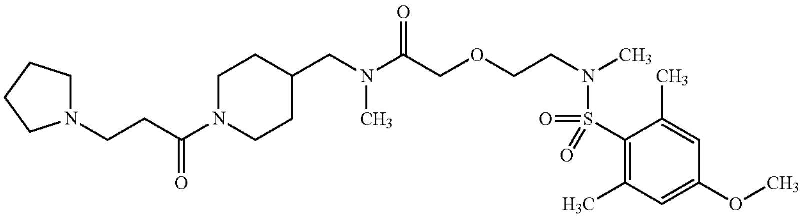 [SMILES: COc1cc(C)c(S(=O)(=O)N(C)CCOCC(=O)N(C)CC2CCN(C(=O)CCN3CCCC3)CC2)c(C)c1] |
| (476) | 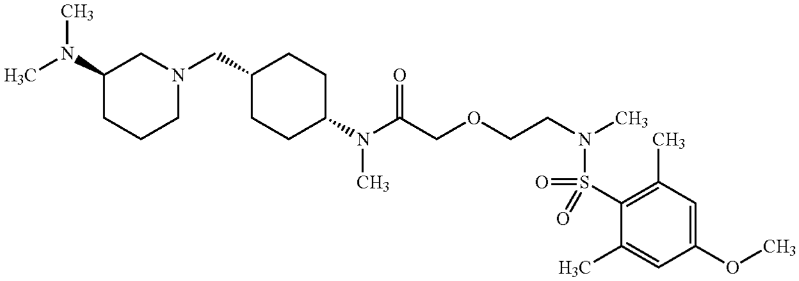 |
| (477) | 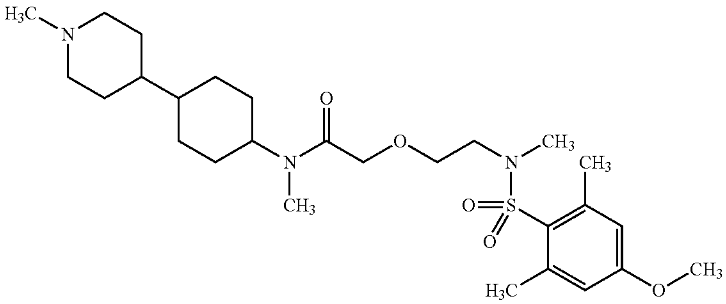 |
| (478) | 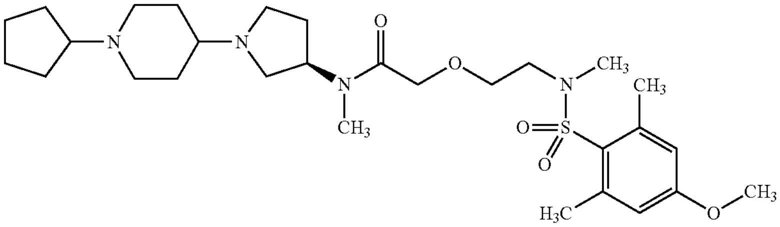 [SMILES: COc1cc(C)c(S(=O)(=O)N(C)CCOCC(=O)N(C)[C@@H]2CCN(C3CCN(C4CCCC4)CC3)C2)c(C)c1] |
| (479) | 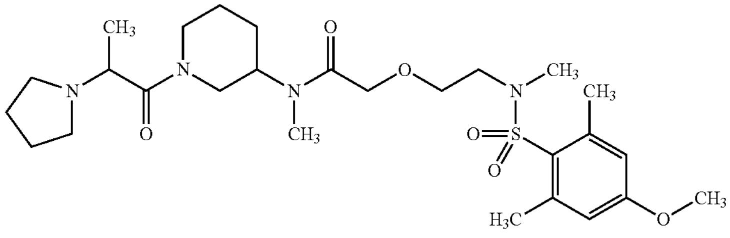 [SMILES: COc1cc(C)c(S(=O)(=O)N(C)CCOCC(=O)N(C)C2CCCN(C(=O)C(C)N3CCCC3)C2)c(C)c1] |

-continued
| Example | Structure |
| --- | --- |
| (480) | 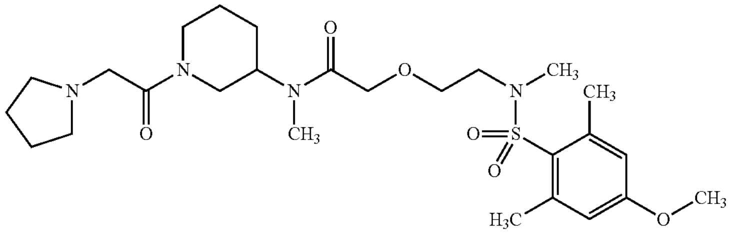 [SMILES: COc1cc(C)c(S(=O)(=O)N(C)CCOCC(=O)N(C)C2CCCN(C(=O)CN3CCCC3)C2)c(C)c1] |
| (481) | 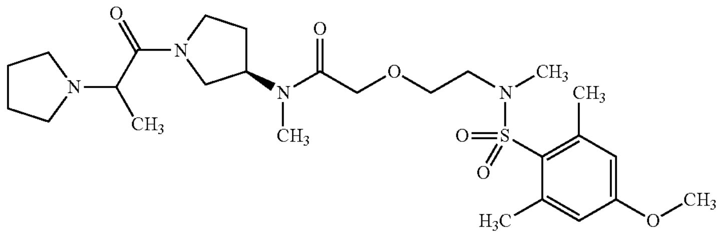 [SMILES: COc1cc(C)c(S(=O)(=O)N(C)CCOCC(=O)N(C)[C@@H]2CCN(C(=O)C(C)N3CCCC3)C2)c(C)c1] |
| (482) | 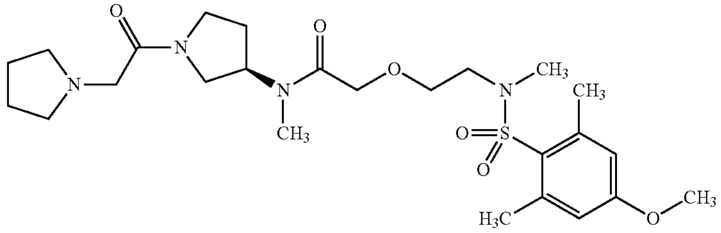 [SMILES: COc1cc(C)c(S(=O)(=O)N(C)CCOCC(=O)N(C)[C@@H]2CCN(C(=O)CN3CCCC3)C2)c(C)c1] |
| (483) | 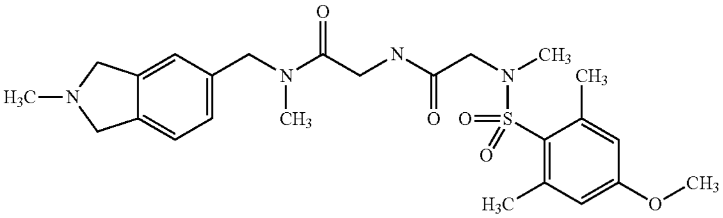 |
| (484) | 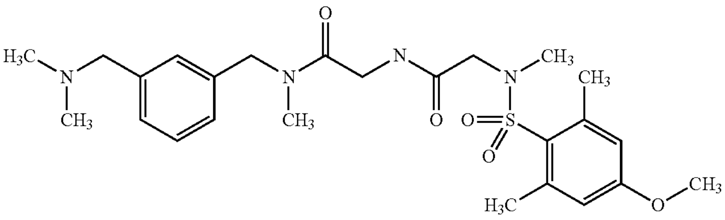 |
| (485) | 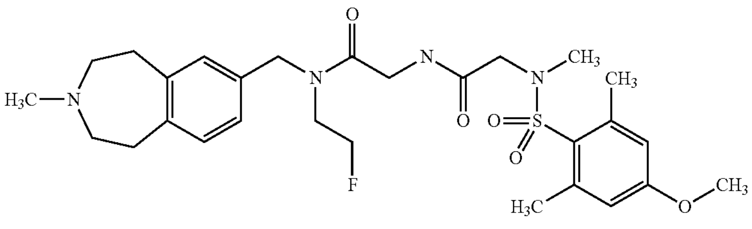 |

-continued
| Example | Structure |
| --- | --- |
| (486) | 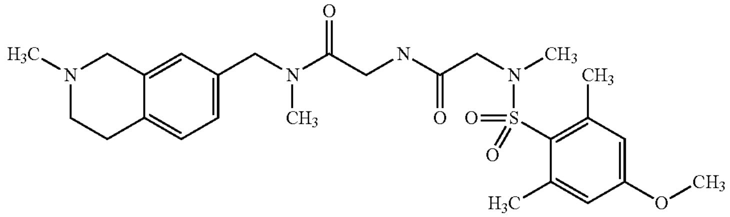 |
| (487) | 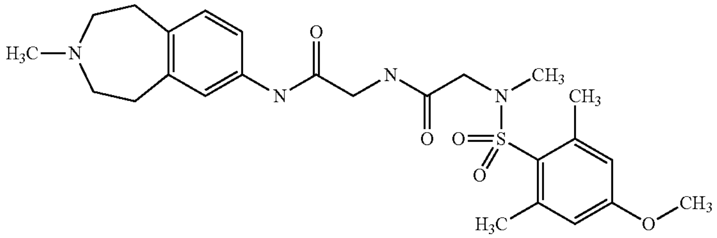 |
| (488) | 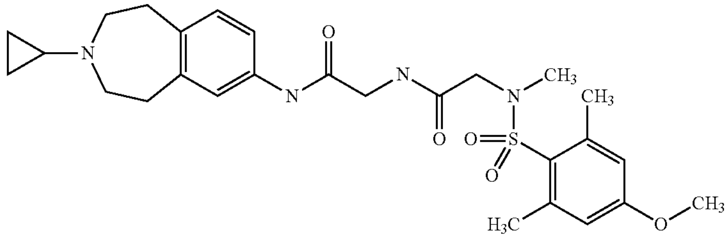 [SMILES: COc1cc(C)c(S(=O)(=O)N(C)CC(=O)NCC(=O)Nc2ccc3c(c2)CCN(C2CC2)CC3)c(C)c1] |
| (489) | 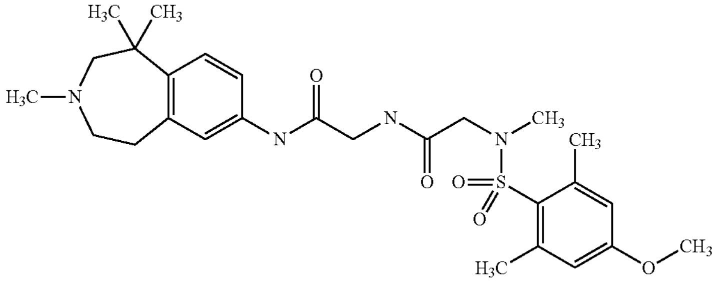 |
| (490) | 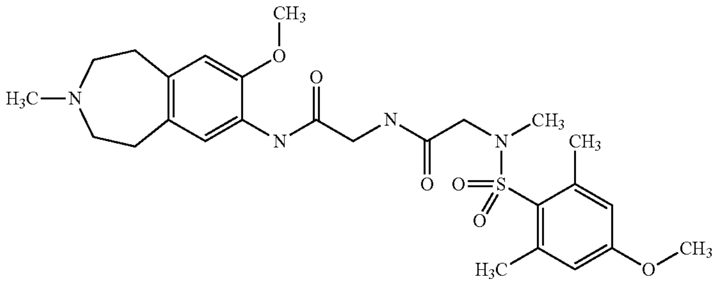 |
| (491) | 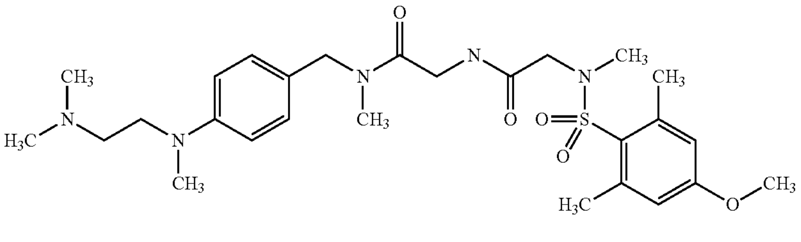 |

-continued
| Example | Structure |
| --- | --- |
| (492) | 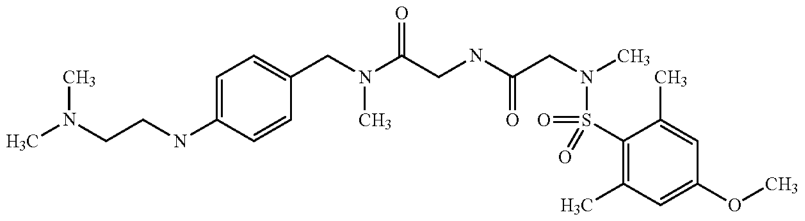 |
| (493) | 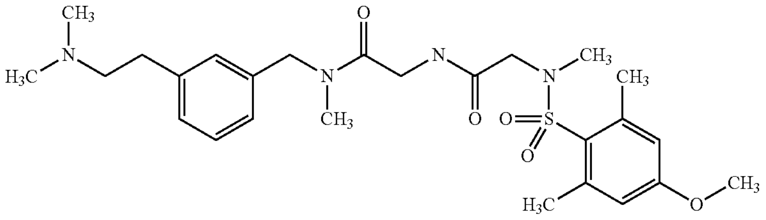 |
| (494) | 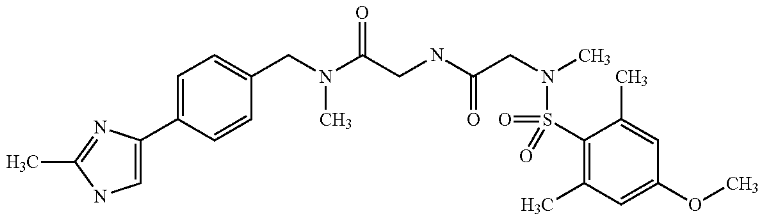 |
| (495) | 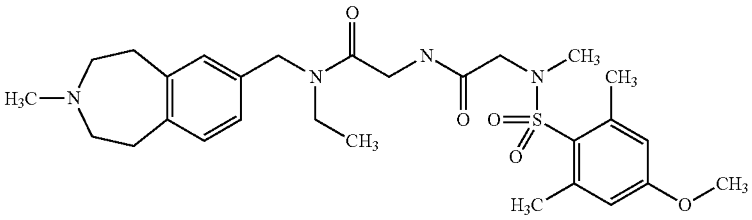 |
| (496) | 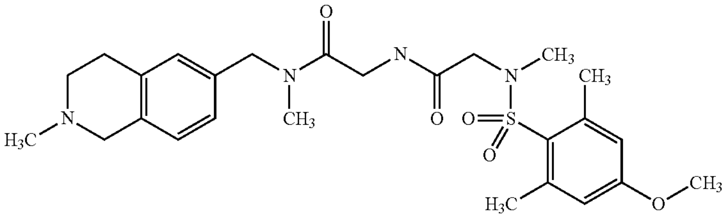 |
| (497) | 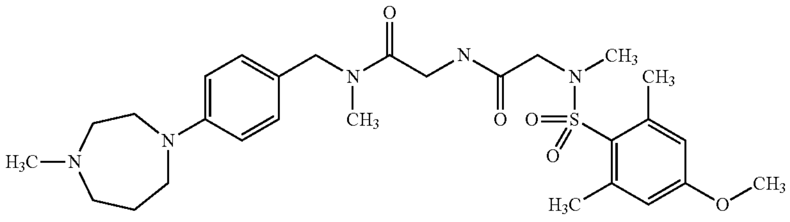 |
| (498) | 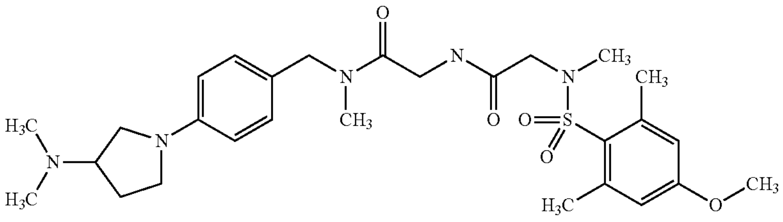 |

-continued
| Example | Structure |
|---|---|
| (499) | 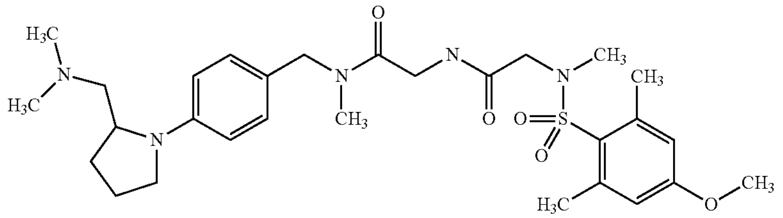 |
| (500) | 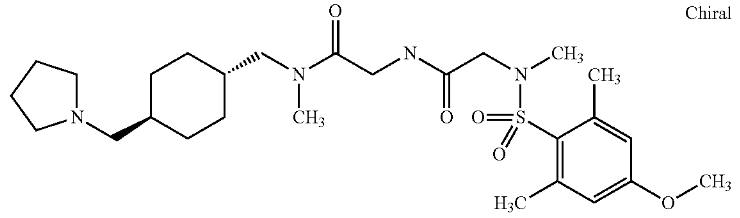 [SMILES: COc1cc(C)c(S(=O)(=O)N(C)CC(=O)NCC(=O)N(C)C[C@H]2CC[C@H](CN3CCCC3)CC2)c(C)c1] Chiral |
| (501) | 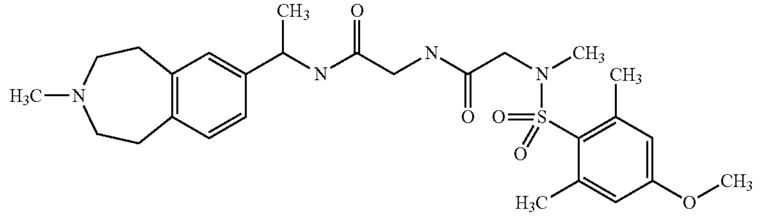 |
| (502) | 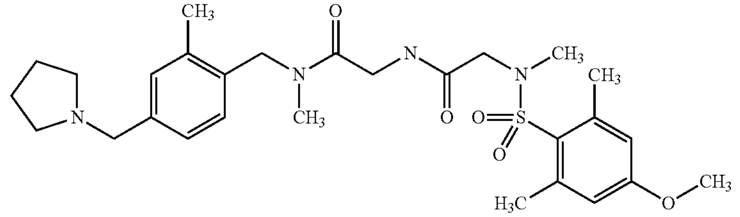 [SMILES: COc1cc(C)c(S(=O)(=O)N(C)CC(=O)NCC(=O)N(C)Cc2ccc(CN3CCCC3)cc2C)c(C)c1] |
| (503) | 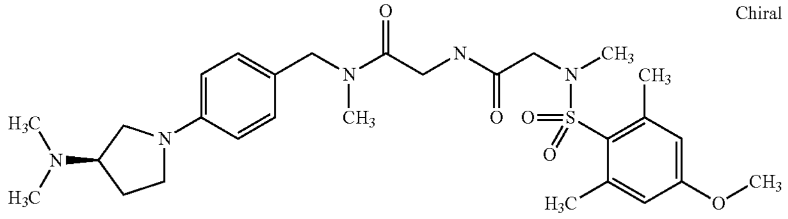 Chiral |
| (504) | 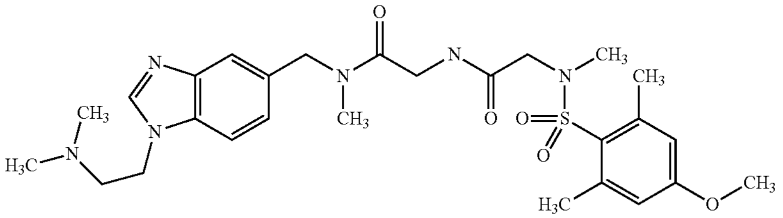 |

-continued
| Example | Structure |
|---|---|
| (505) | 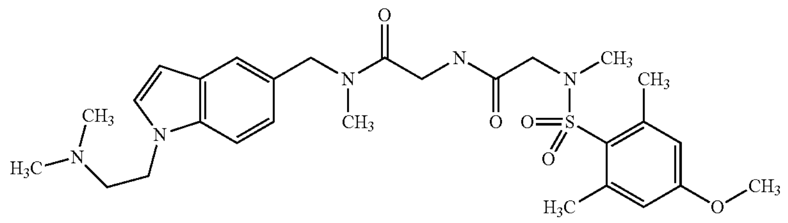 |
| (506) | 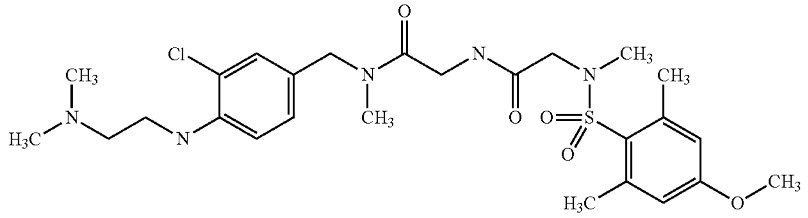 |
| (507) | 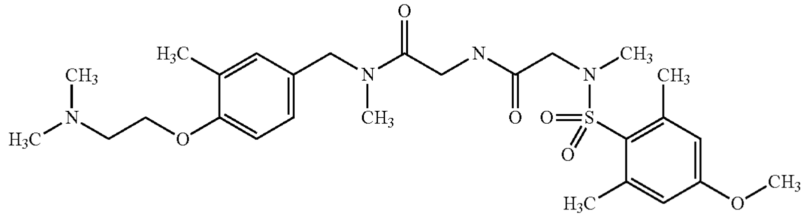 |
| (508) | 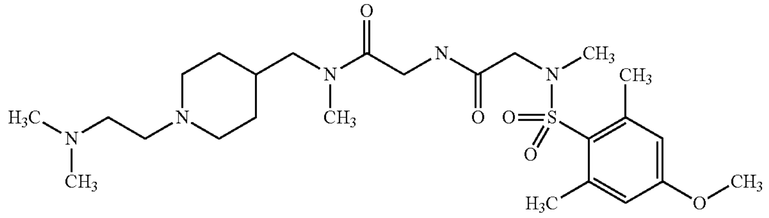 |
| (509) | 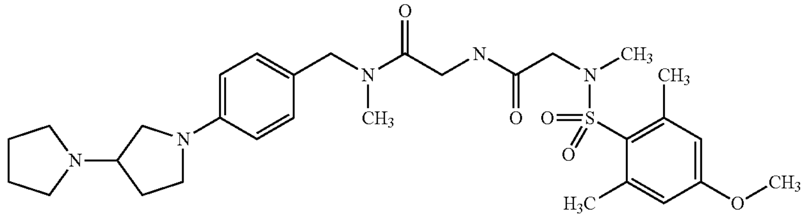 [SMILES: COc1cc(C)c(S(=O)(=O)N(C)CC(=O)NCC(=O)N(C)Cc2ccc(N3CCC(N4CCCC4)C3)cc2)c(C)c1] |
| (510) | 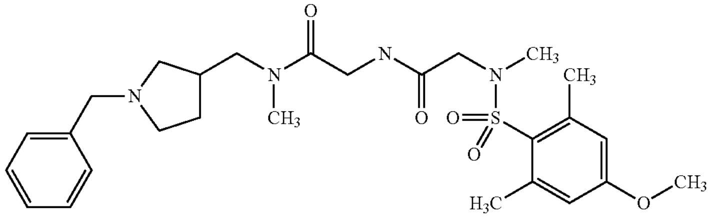 [SMILES: COc1cc(C)c(S(=O)(=O)N(C)CC(=O)NCC(=O)N(C)CC2CCN(Cc3ccccc3)C2)c(C)c1] |
| (511) | 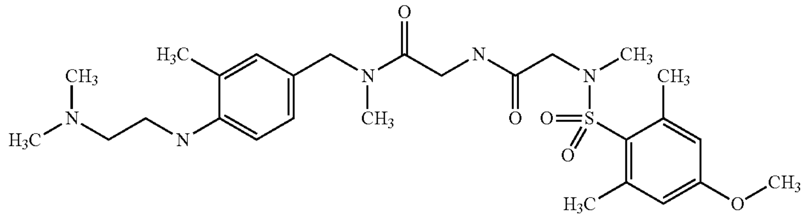 |

-continued
| Example | Structure |
| --- | --- |
| (512) | 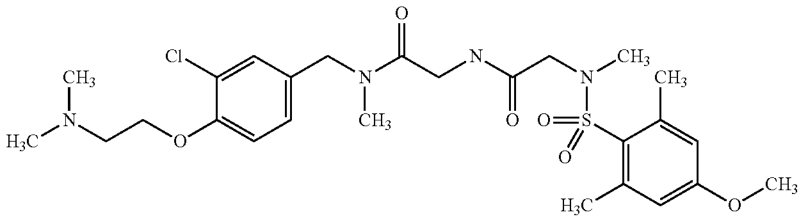 |
| (513) | 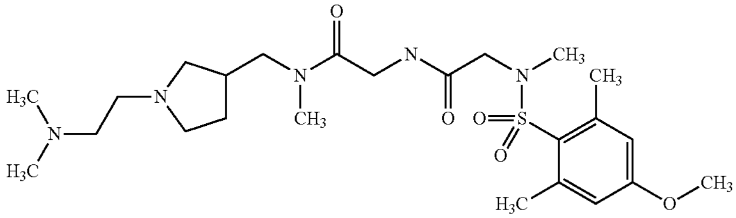 |
| (514) | 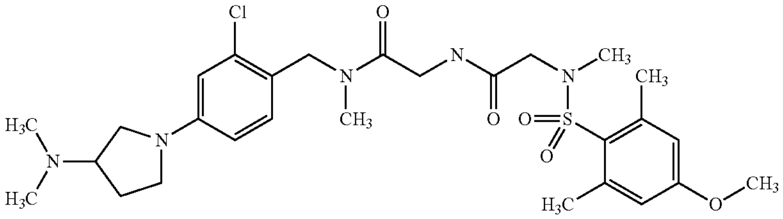 |
| (515) | 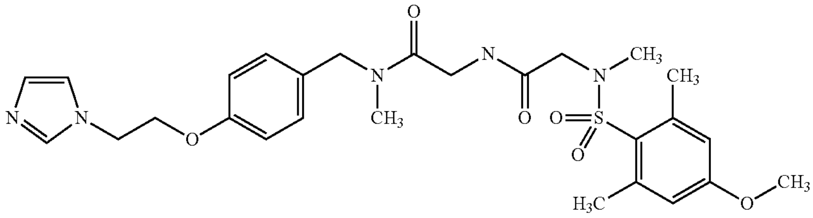 [SMILES: COc1cc(C)c(S(=O)(=O)N(C)CC(=O)NCC(=O)N(C)Cc2ccc(OCCn3ccnc3)cc2)c(C)c1] |
| (516) | 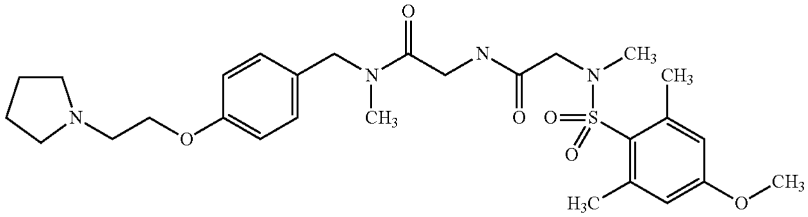 [SMILES: COc1cc(C)c(S(=O)(=O)N(C)CC(=O)NCC(=O)N(C)Cc2ccc(OCCN3CCCC3)cc2)c(C)c1] |
| (517) | 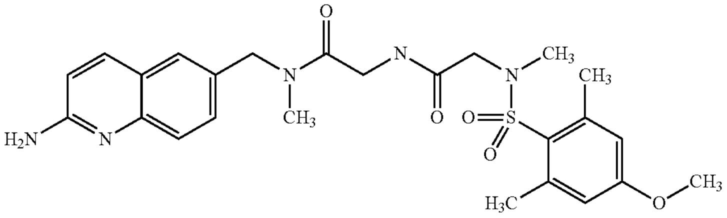 [SMILES: COc1cc(C)c(S(=O)(=O)N(C)CC(=O)NCC(=O)N(C)Cc2ccc3nc(N)ccc3c2)c(C)c1] |
| (518) | 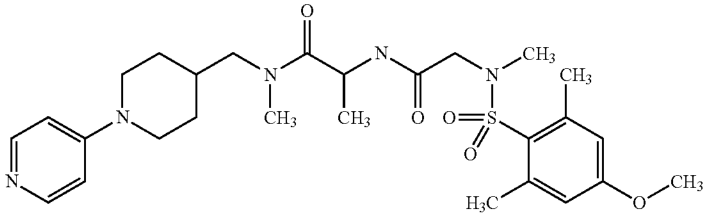 [SMILES: COc1cc(C)c(S(=O)(=O)N(C)CC(=O)NC(C)C(=O)N(C)CC2CCN(c3ccncc3)CC2)c(C)c1] |

-continued
| Example | Structure |
| --- | --- |
| (519) | 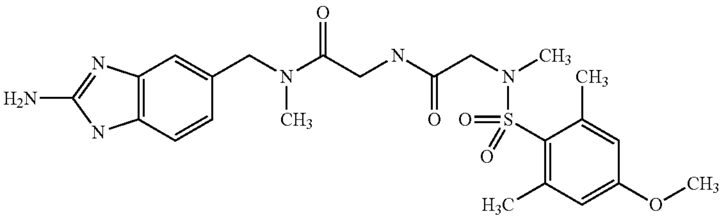 [SMILES: COc1cc(C)c(S(=O)(=O)N(C)CC(=O)NCC(=O)N(C)Cc2ccc3[nH]c(N)nc3c2)c(C)c1] |
| (520) | 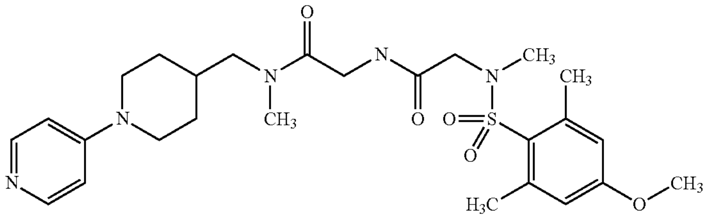 [SMILES: COc1cc(C)c(S(=O)(=O)N(C)CC(=O)NCC(=O)N(C)CC2CCN(c3ccncc3)CC2)c(C)c1] |
| (521) | 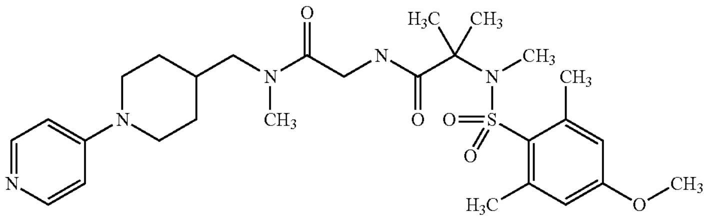 [SMILES: COc1cc(C)c(S(=O)(=O)N(C)C(C)(C)C(=O)NCC(=O)N(C)CC2CCN(c3ccncc3)CC2)c(C)c1] |
| (522) | 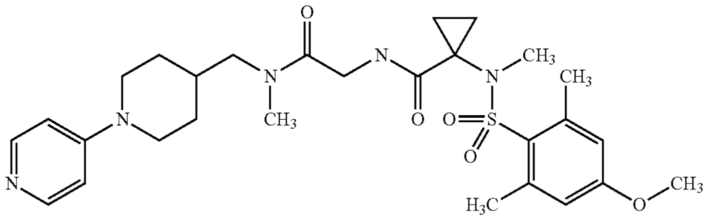 [SMILES: COc1cc(C)c(S(=O)(=O)N(C)C2(C(=O)NCC(=O)N(C)CC3CCN(c4ccncc4)CC3)CC2)c(C)c1] |
| (523) | 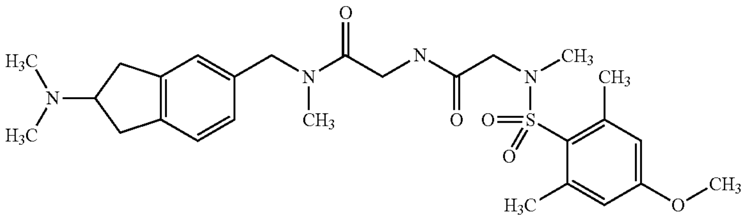 |
| (524) | 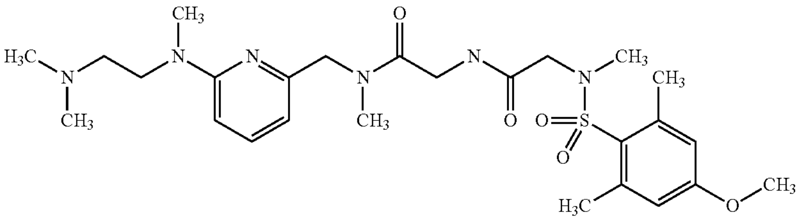 |
| (525) | 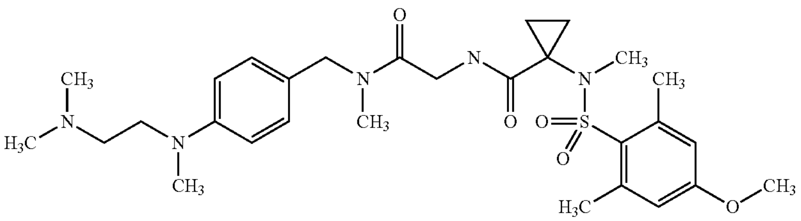 |

-continued
| Example | Structure |
|---|---|
| (526) | 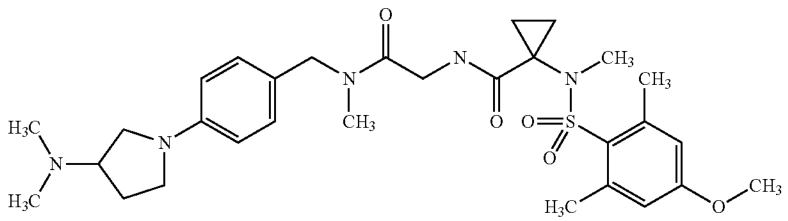 |
| (527) | 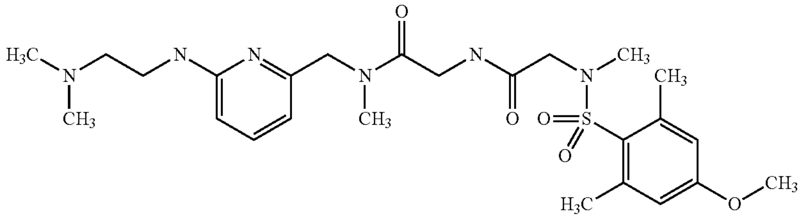 |
| (528) | 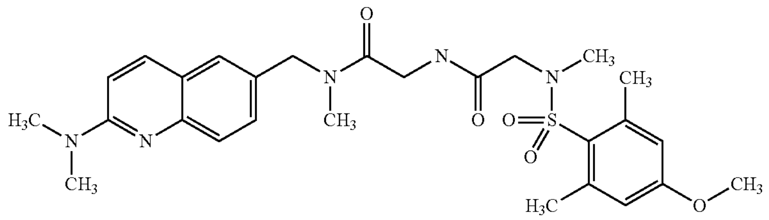 |
| (529) | 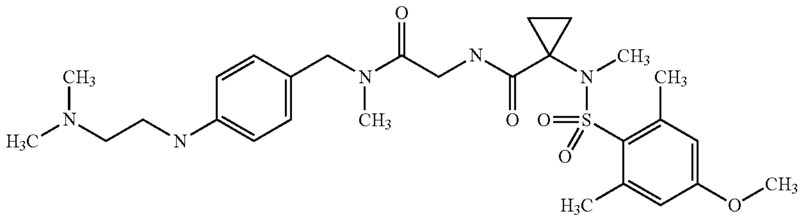 |
| (530) | 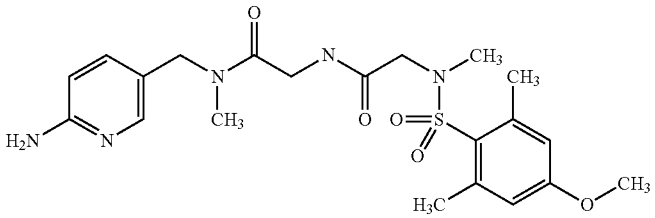 [SMILES: COc1cc(C)c(S(=O)(=O)N(C)CC(=O)NCC(=O)N(C)Cc2ccc(N)nc2)c(C)c1] |
| (531) | 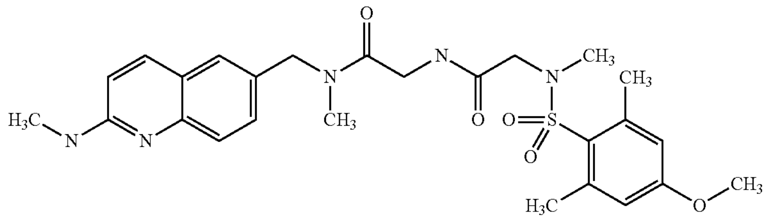 |
| (532) | 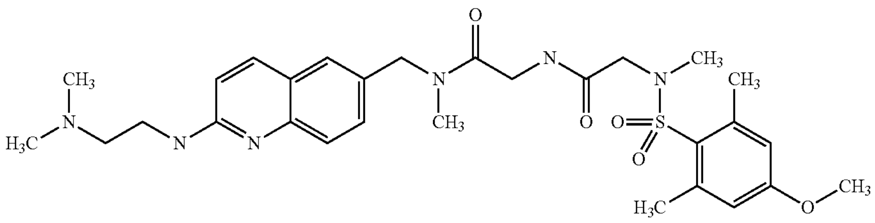 |

-continued
| Example | Structure |
|---|---|
| (533) | 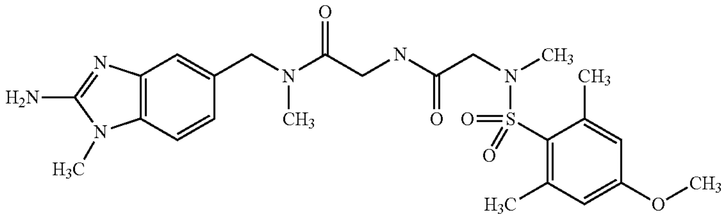 [SMILES: COc1cc(C)c(S(=O)(=O)N(C)CC(=O)NCC(=O)N(C)Cc2ccc3c(c2)nc(N)n3C)c(C)c1] |
| (534) | 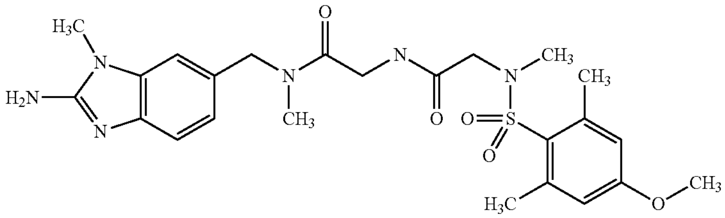 [SMILES: COc1cc(C)c(S(=O)(=O)N(C)CC(=O)NCC(=O)N(C)Cc2ccc3nc(N)n(C)c3c2)c(C)c1] |
| (535) | 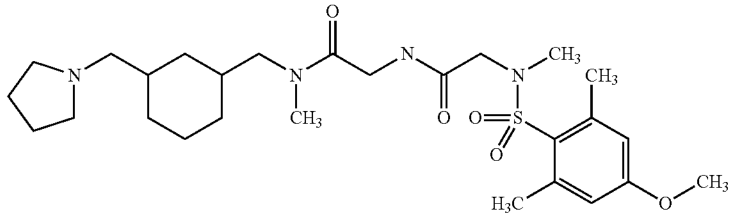 [SMILES: COc1cc(C)c(S(=O)(=O)N(C)CC(=O)NCC(=O)N(C)CC2CCCC(CN3CCCC3)C2)c(C)c1] |
| (536) | 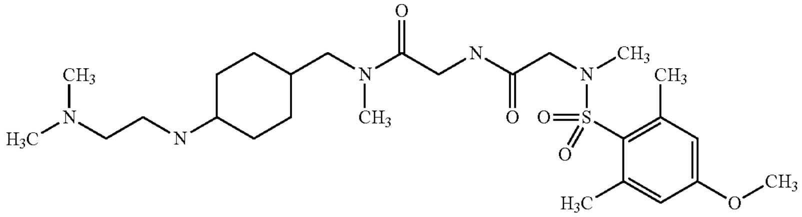 |
| (537) | 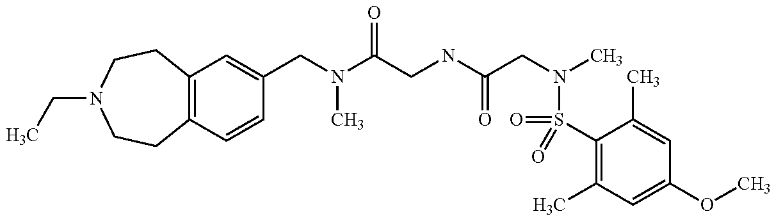 [SMILES: CCN1CCc2ccc(CN(C)C(=O)CNC(=O)CN(C)S(=O)(=O)c3c(C)cc(OC)cc3C)cc2CC1] |
| (538) | 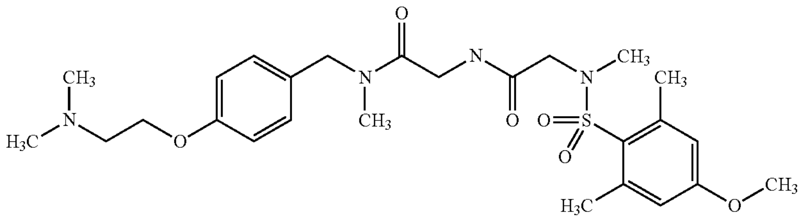 |

-continued
| Example | Structure |
| --- | --- |
| (539) | 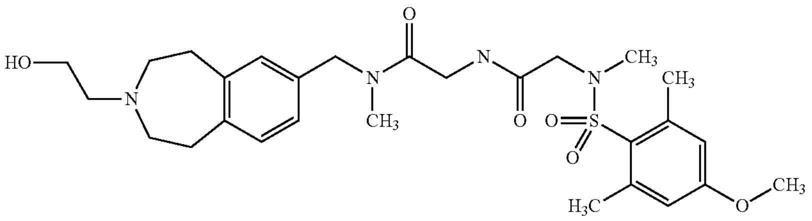 [SMILES: COc1cc(C)c(S(=O)(=O)N(C)CC(=O)NCC(=O)N(C)Cc2ccc3c(c2)CCN(CCO)CC3)c(C)c1] |
| (540) | 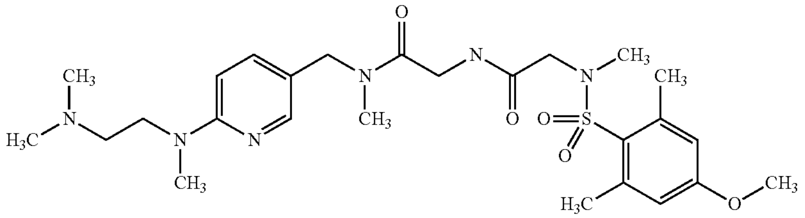 |
| (541) | 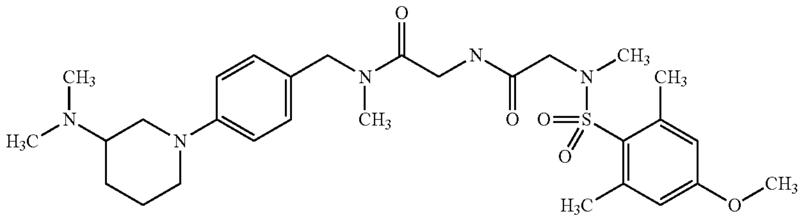 |
| (542) | 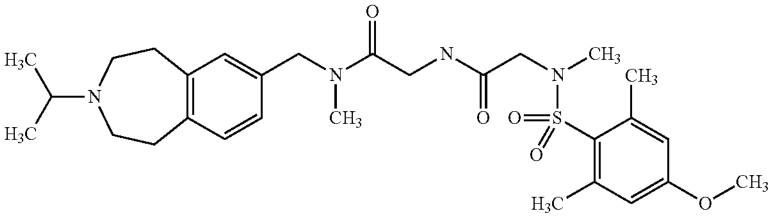 [SMILES: COc1cc(C)c(S(=O)(=O)N(C)CC(=O)NCC(=O)N(C)Cc2ccc3c(c2)CCN(C(C)C)CC3)c(C)c1] |
| (543) | 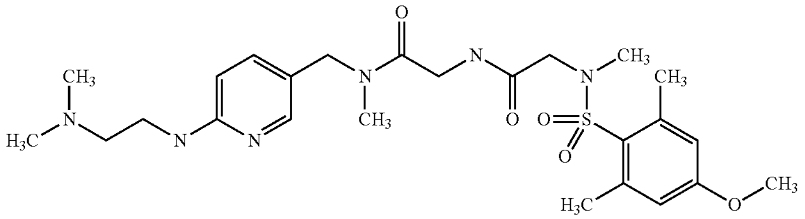 |
| (544) | 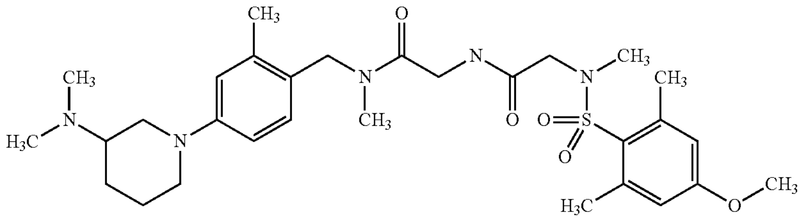 |
| (545) | 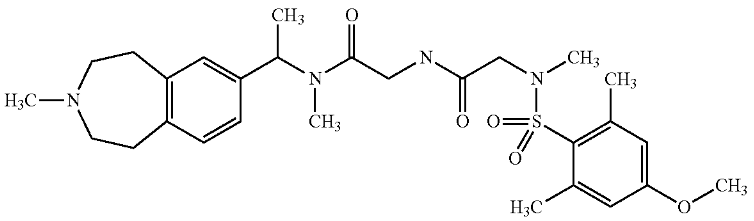 |

-continued
| Example | Structure |
| --- | --- |
| (546) | 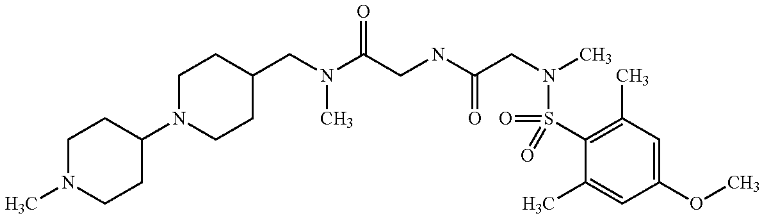 |
| (547) | 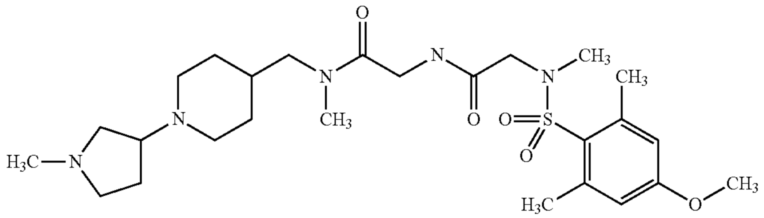 |
| (548) | 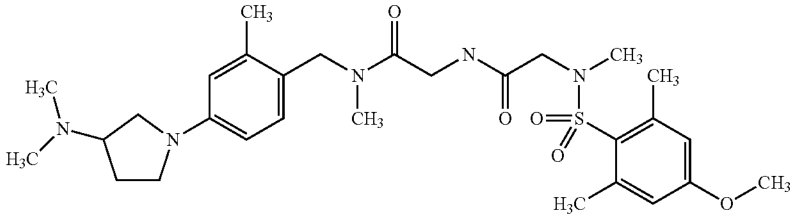 |
| (549) | 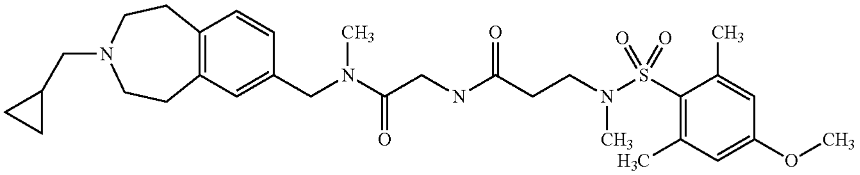 [SMILES: COc1cc(C)c(S(=O)(=O)N(C)CCC(=O)NCC(=O)N(C)Cc2ccc3c(c2)CCN(CC2CC2)CC3)c(C)c1] |
| (550) | 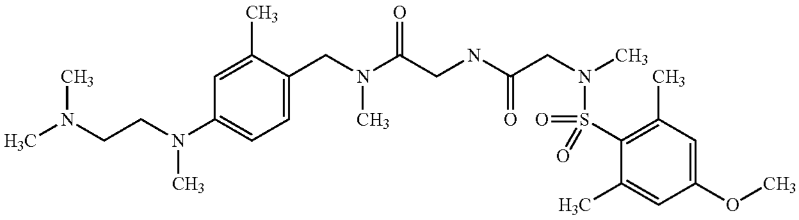 |
| (551) | 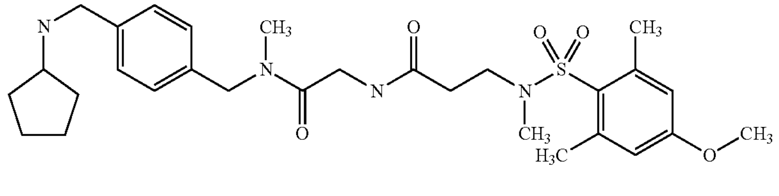 [SMILES: COc1cc(C)c(S(=O)(=O)N(C)CCC(=O)NCC(=O)N(C)Cc2ccc(CNC3CCCC3)cc2)c(C)c1] |
| (552) | 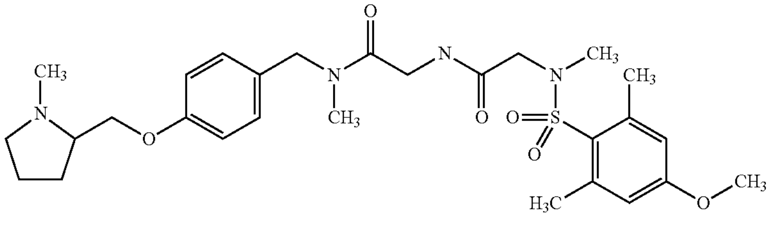 [SMILES: COc1cc(C)c(S(=O)(=O)N(C)CC(=O)NCC(=O)N(C)Cc2ccc(OCC3CCCN3C)cc2)c(C)c1] |

-continued
| Example | Structure |
| --- | --- |
| (553) | 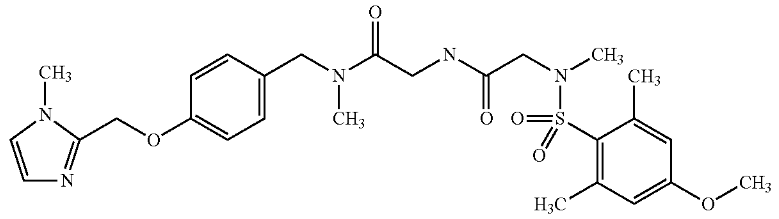 [SMILES: COc1cc(C)c(S(=O)(=O)N(C)CC(=O)NCC(=O)N(C)Cc2ccc(OCc3nccn3C)cc2)c(C)c1] |
| (554) | 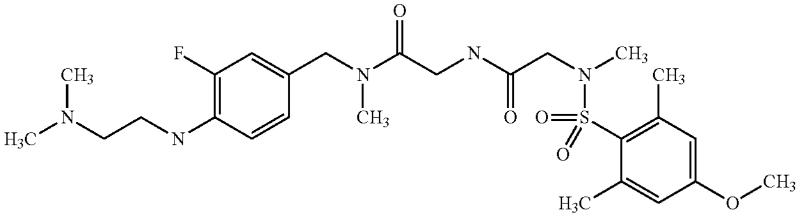 |
| (555) | 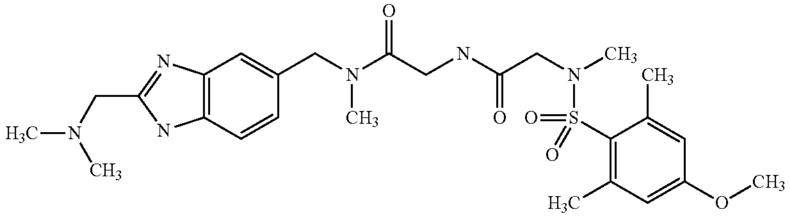 |
| (556) | 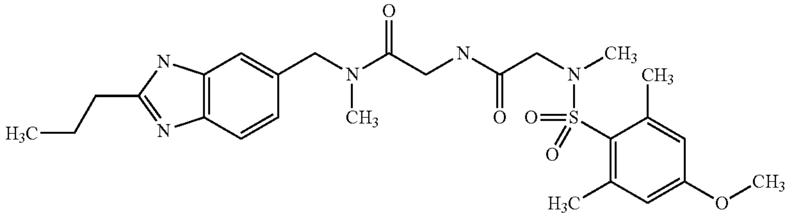 [SMILES: CCCc1nc2ccc(CN(C)C(=O)CNC(=O)CN(C)S(=O)(=O)c3c(C)cc(OC)cc3C)cc2[nH]1] |
| (557) | 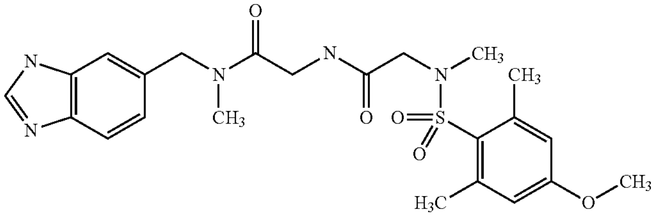 [SMILES: COc1cc(C)c(S(=O)(=O)N(C)CC(=O)NCC(=O)N(C)Cc2ccc3nc[nH]c3c2)c(C)c1] |
| (558) | 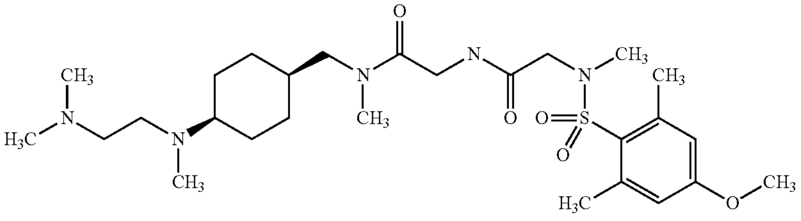 |
| (559) | 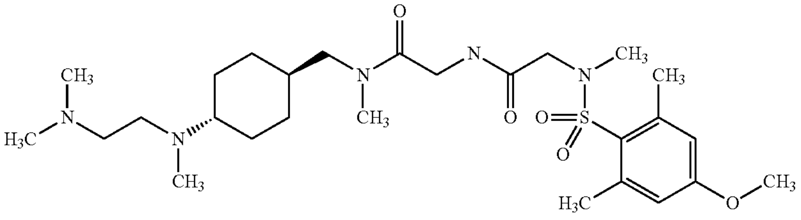 |

-continued
| Example | Structure |
|---|---|
| (560) | 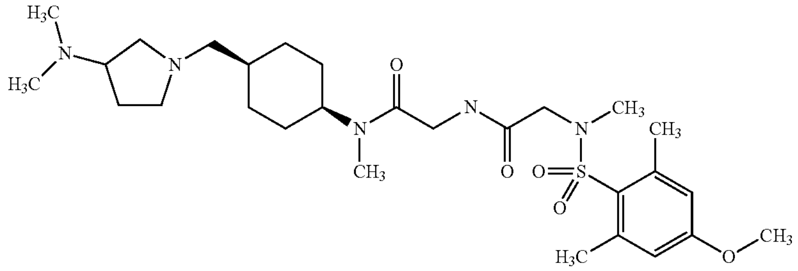 |
| (561) | 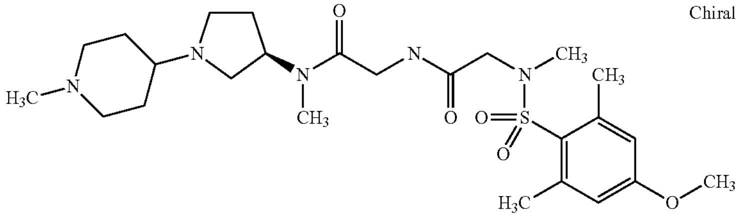 Chiral |
| (562) | 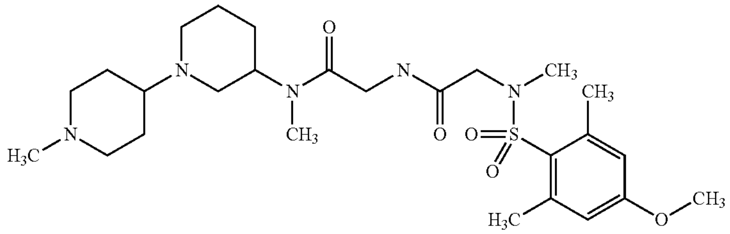 |
| (563) | 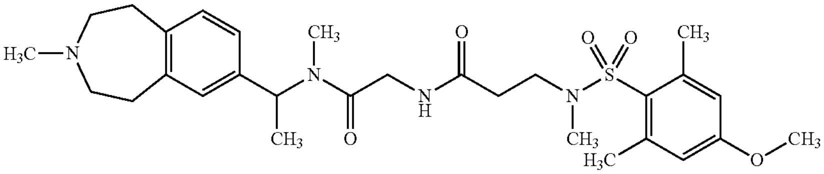 |
| (564) | 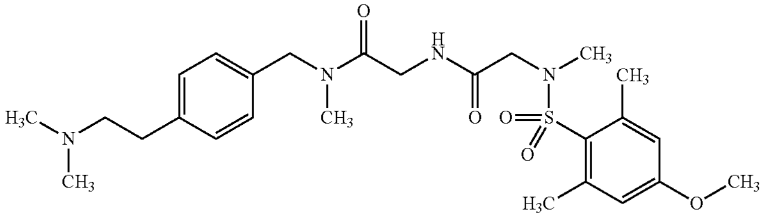 |
| (565) | 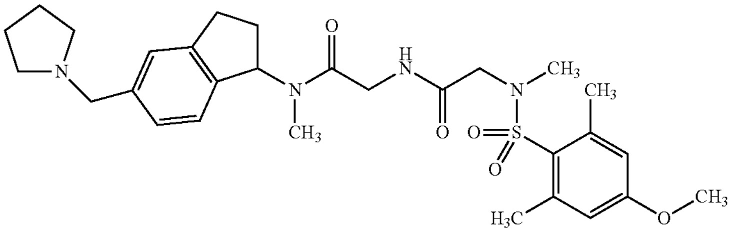 [SMILES: COc1cc(C)c(S(=O)(=O)N(C)CC(=O)NCC(=O)N(C)C2CCc3cc(CN4CCCC4)ccc32)c(C)c1] |

-continued
| Example | Structure |
|---|---|
| (566) | 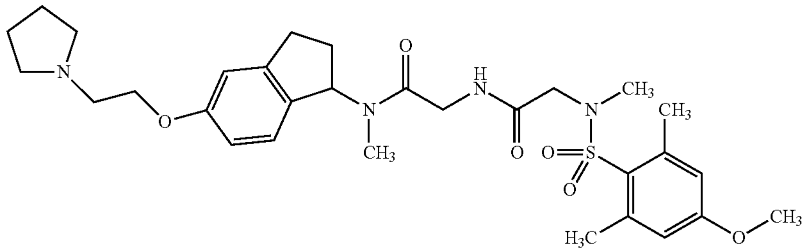 [SMILES: COc1cc(C)c(S(=O)(=O)N(C)CC(=O)NCC(=O)N(C)C2CCc3cc(OCCN4CCCC4)ccc32)c(C)c1] |
| (567) | 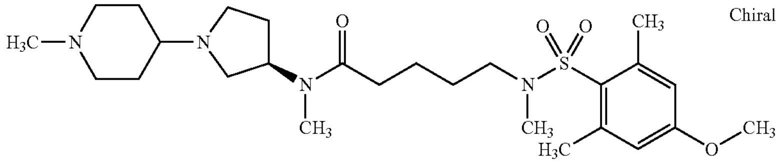 Chiral |
| (568) | 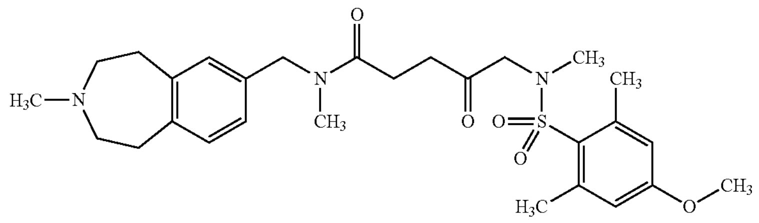 |
| (569) | 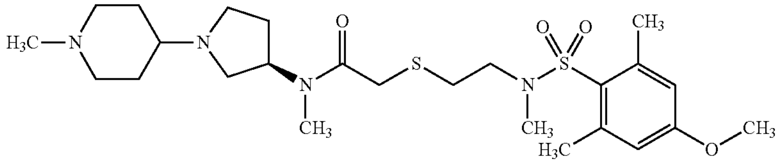 |
| (570) | 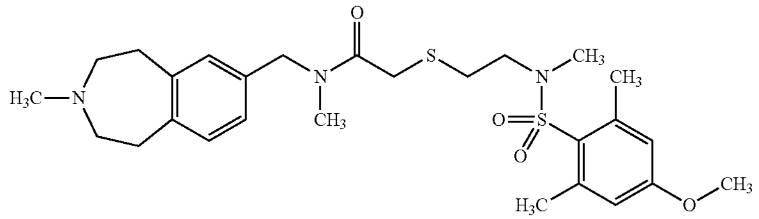 |
| (571) | 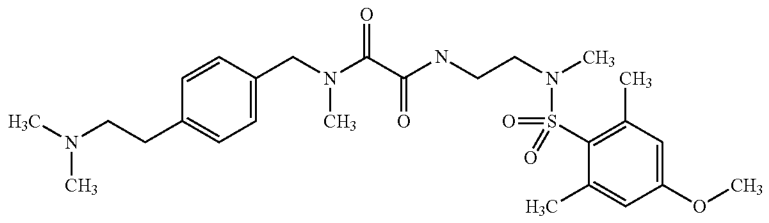 |
| (572) | 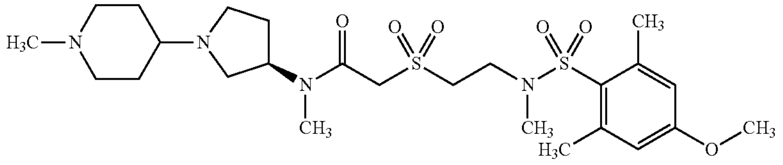 |

-continued
| Example | Structure |
| --- | --- |
| (573) | 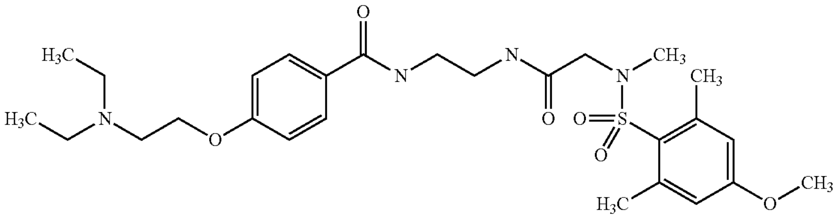 [SMILES: CCN(CC)CCOc1ccc(C(=O)NCCNC(=O)CN(C)S(=O)(=O)c2c(C)cc(OC)cc2C)cc1] |
| (574) | 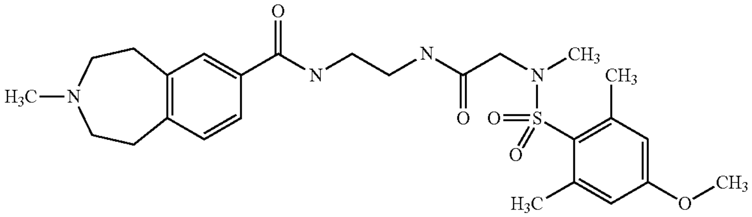 |
| (575) | 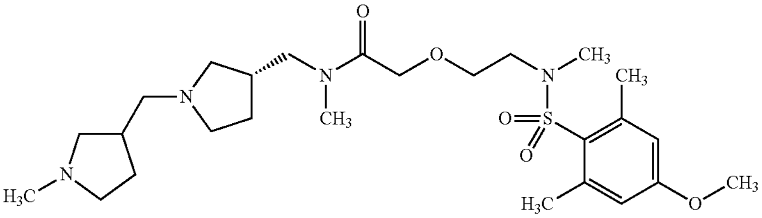 |
| (576) | 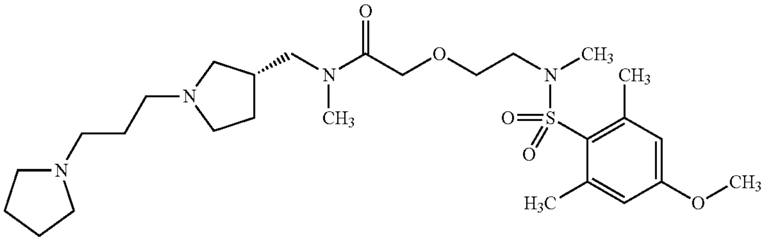 [SMILES: COc1cc(C)c(S(=O)(=O)N(C)CCOCC(=O)N(C)C[C@@H]2CCN(CCCN3CCCC3)C2)c(C)c1] |
| (577) | 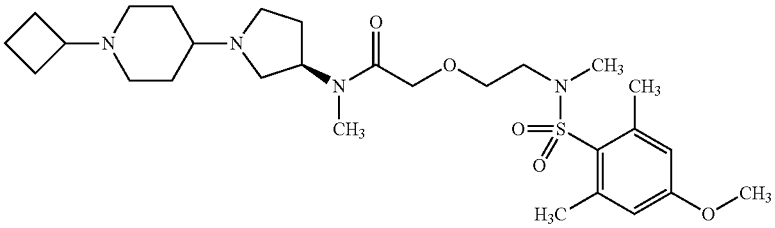 [SMILES: COc1cc(C)c(S(=O)(=O)N(C)CCOCC(=O)N(C)[C@@H]2CCN(C3CCN(C4CCC4)CC3)C2)c(C)c1] |
| (578) | 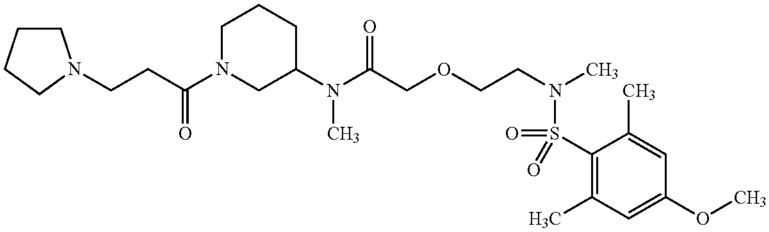 [SMILES: COc1cc(C)c(S(=O)(=O)N(C)CCOCC(=O)N(C)C2CCCN(C(=O)CCN3CCCC3)C2)c(C)c1] |

-continued
| Example | Structure |
| --- | --- |
| (579) | 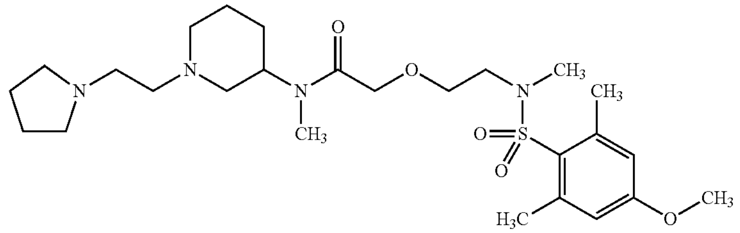 [SMILES: COc1cc(C)c(S(=O)(=O)N(C)CCOCC(=O)N(C)C2CCCN(CCN3CCCC3)C2)c(C)c1] |
| (580) | 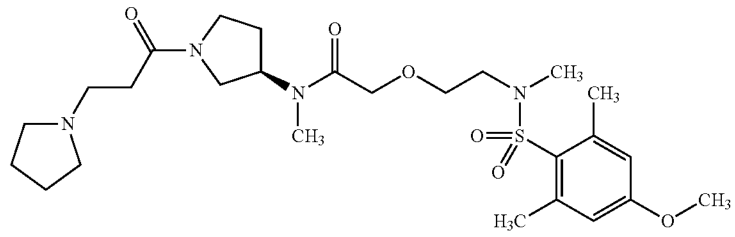 [SMILES: COc1cc(C)c(S(=O)(=O)N(C)CCOCC(=O)N(C)[C@@H]2CCN(C(=O)CCN3CCCC3)C2)c(C)c1] |
| (581) | 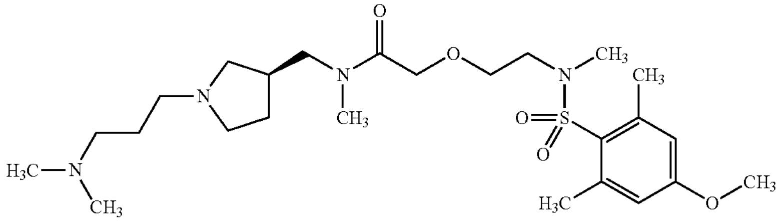 |
| (582) | 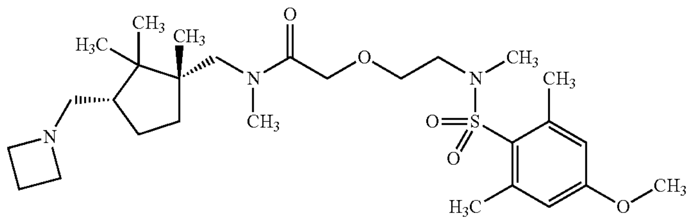 [SMILES: COc1cc(C)c(S(=O)(=O)N(C)CCOCC(=O)N(C)C[C@]2(C)CC[C@H](CN3CCC3)C2(C)C)c(C)c1] |
| (583) | 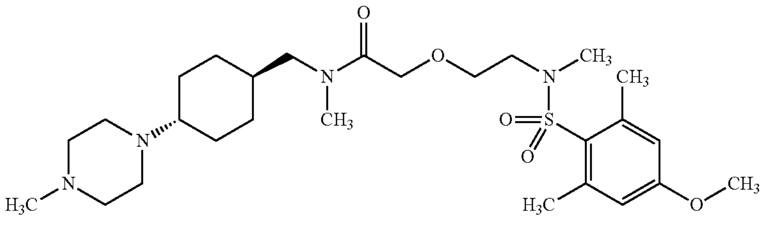 |
| (584) | 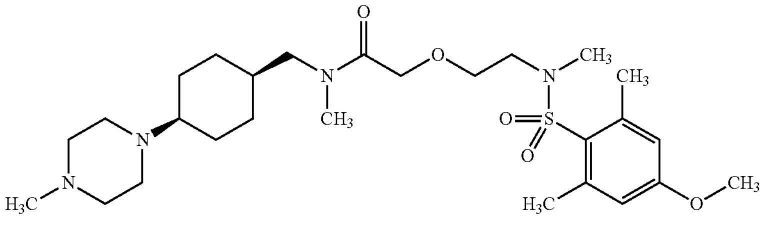 |

-continued
| Example | Structure |
| --- | --- |
| (585) | 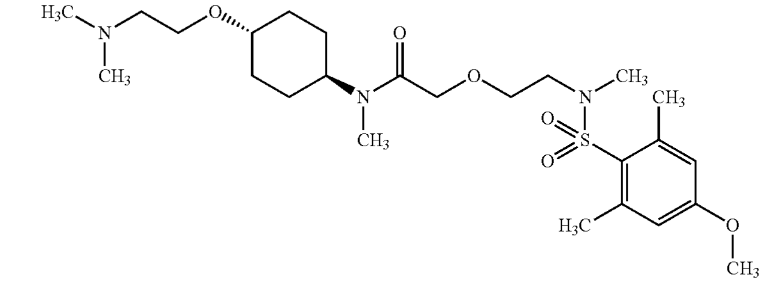 |
| (586) | 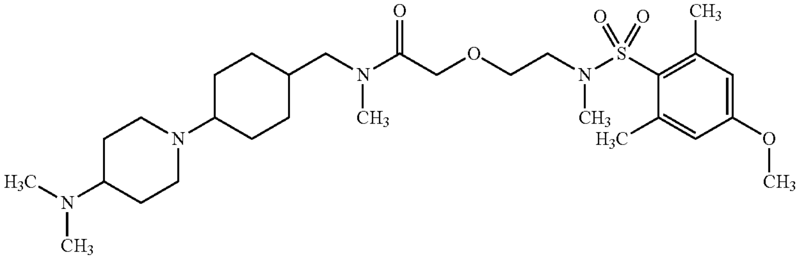 |
| (587) | 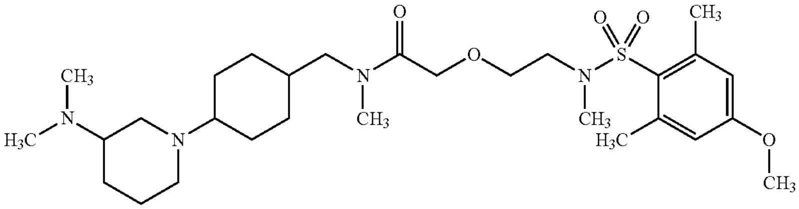 |
| (588) | 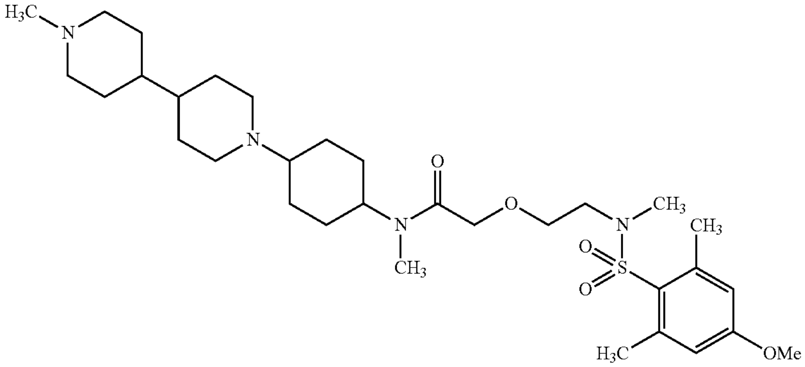 [SMILES: COc1cc(C)c(S(=O)(=O)N(C)CCOCC(=O)N(C)C2CCC(N3CCC(C4CCN(C)CC4)CC3)CC2)c(C)c1] |
| (589) | 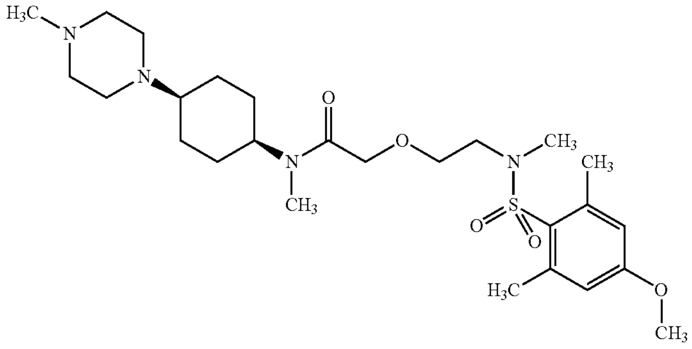 |

-continued
| Example | Structure |
|---|---|
| (590) | 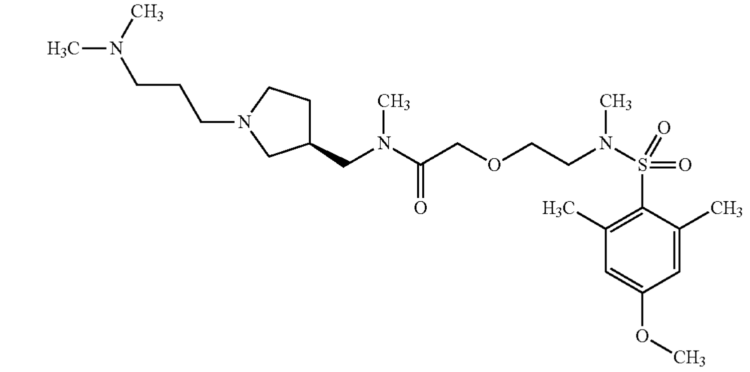 |
| (591) | 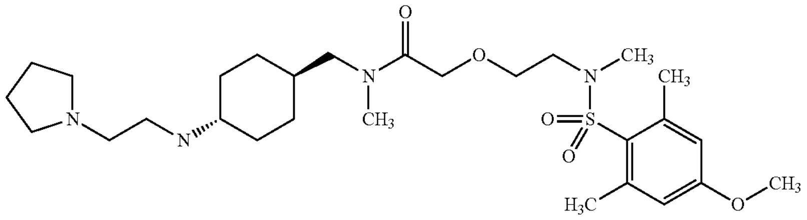 [SMILES: COc1cc(C)c(S(=O)(=O)N(C)CCOCC(=O)N(C)C[C@H]2CC[C@H](NCCN3CCCC3)CC2)c(C)c1] |
| (592) | 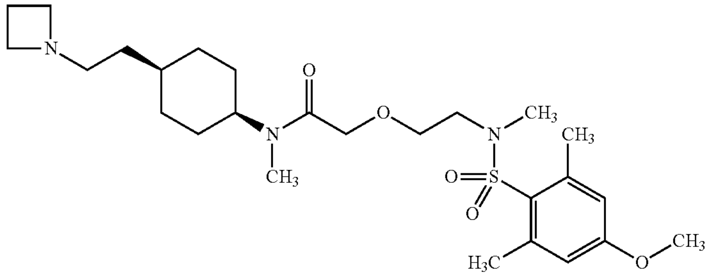 [SMILES: COc1cc(C)c(S(=O)(=O)N(C)CCOCC(=O)N(C)[C@H]2CC[C@@H](CCN3CCC3)CC2)c(C)c1] |
| (593) | 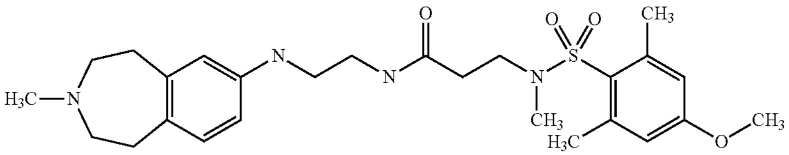 |
| (594) | 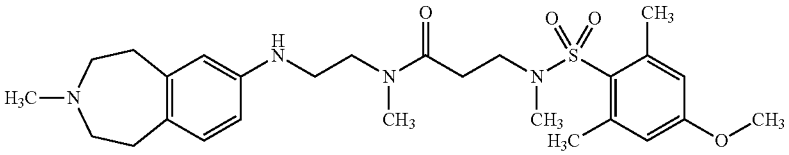 |
| (595) | 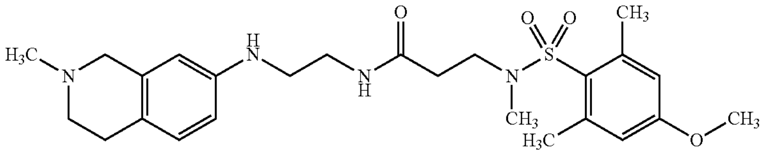 |
| (596) | 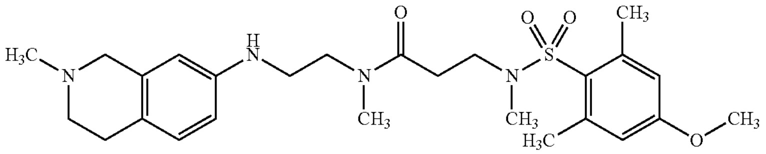 |

-continued
| Example | Structure |
| --- | --- |
| (597) | 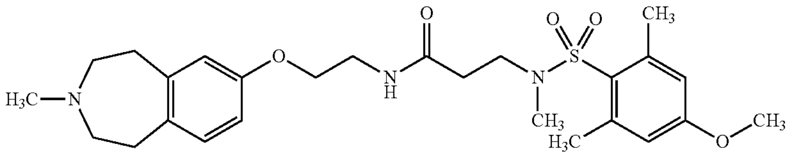 |
| (598) | 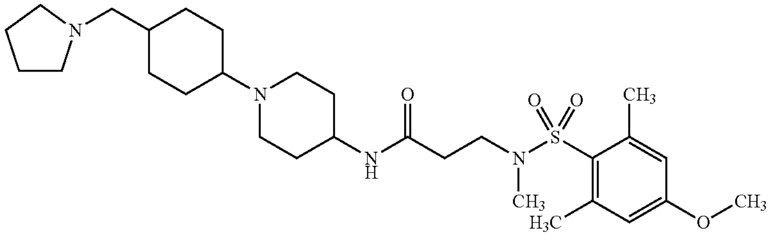 [SMILES: COc1cc(C)c(S(=O)(=O)N(C)CCC(=O)NC2CCN(C3CCC(CN4CCCC4)CC3)CC2)c(C)c1] |
| (599) | 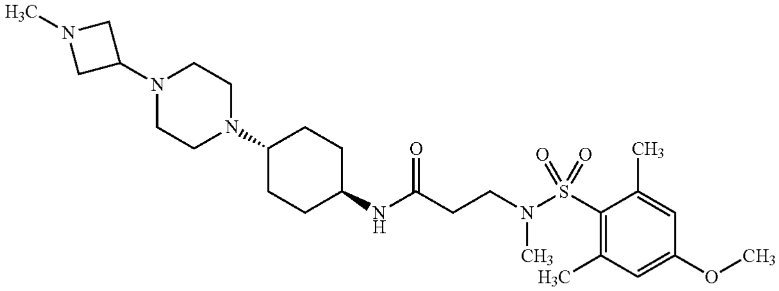 |
| (600) | 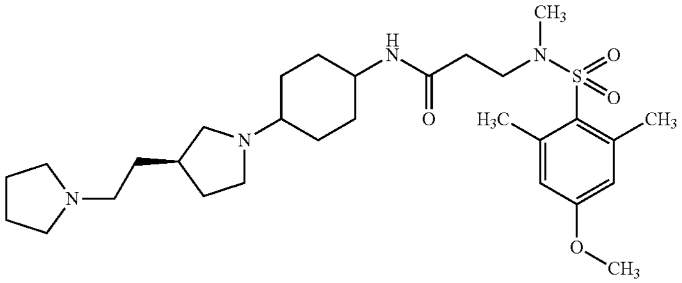 [SMILES: COc1cc(C)c(S(=O)(=O)N(C)CCC(=O)NC2CCC(N3CC[C@@H](CCN4CCCC4)C3)CC2)c(C)c1] |
| (601) | 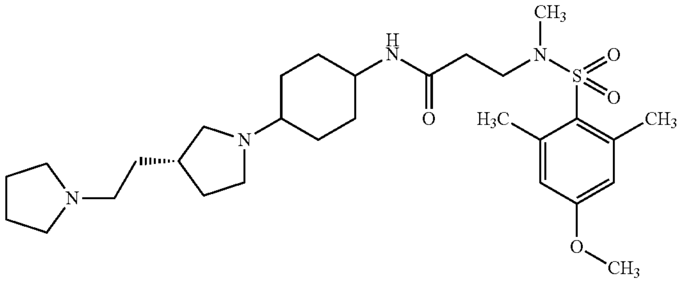 [SMILES: COc1cc(C)c(S(=O)(=O)N(C)CCC(=O)NC2CCC(N3CC[C@H](CCN4CCCC4)C3)CC2)c(C)c1] |
| (602) | 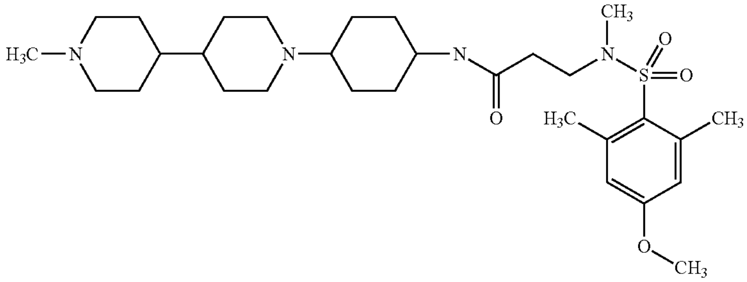 |

-continued
| Example | Structure |
|---|---|
| (603) | 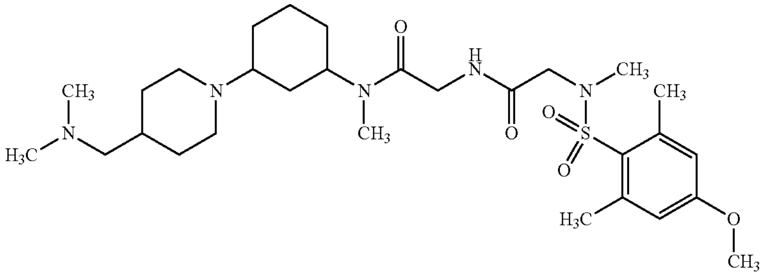 |
| (604) | 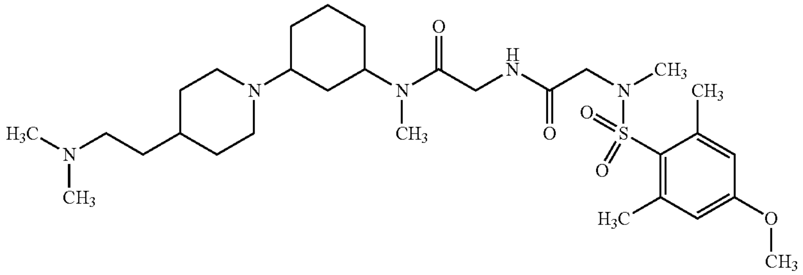 |
| (605) | 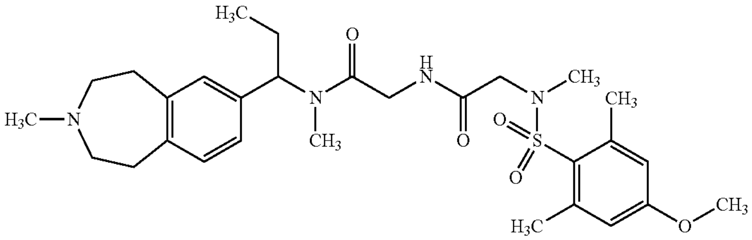 |
| (606) | 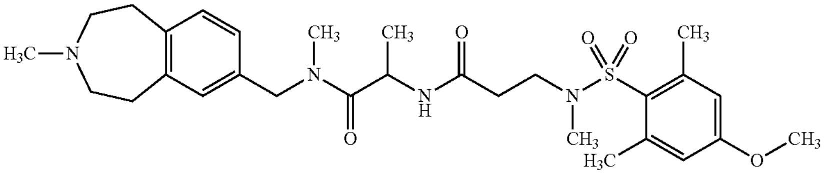 |
| (607) | 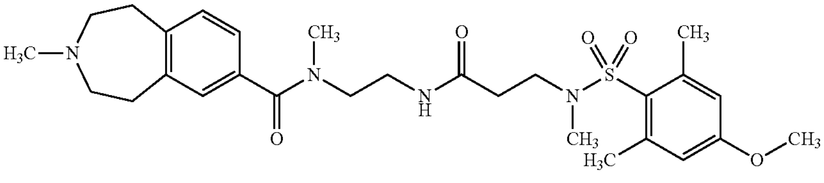 |
| (608) | 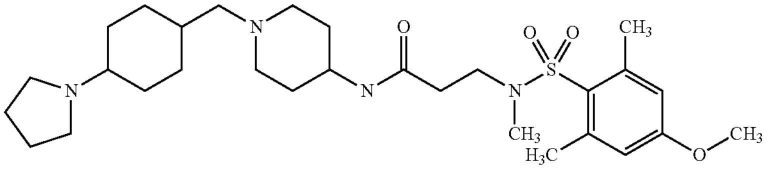 [SMILES: COc1cc(C)c(S(=O)(=O)N(C)CCC(=O)NC2CCN(CC3CCC(N4CCCC4)CC3)CC2)c(C)c1] |

-continued
| Example | Structure |
|---|---|
| (609) | 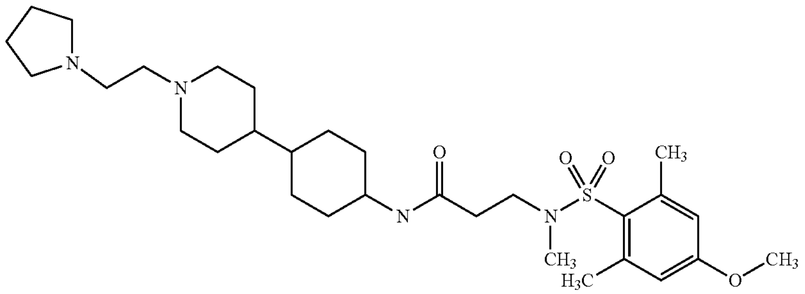 [SMILES: COc1cc(C)c(S(=O)(=O)N(C)CCC(=O)NC2CCC(C3CCN(CCN4CCCC4)CC3)CC2)c(C)c1] |
| (610) | 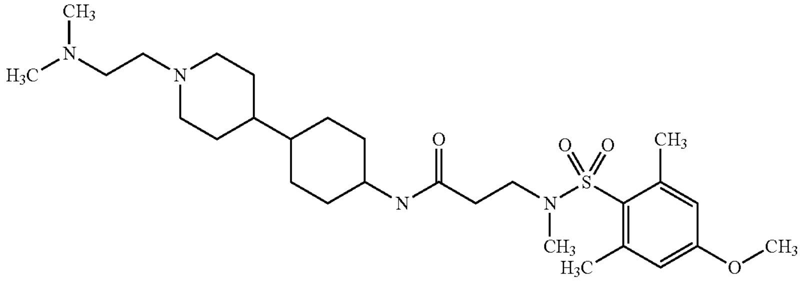 |
| (611) | 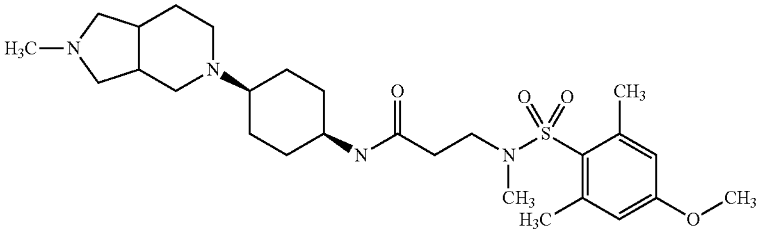 |
| (612) | 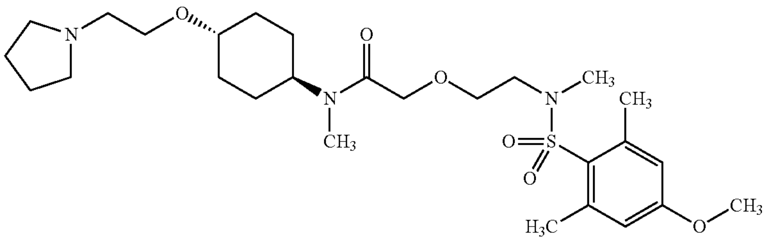 [SMILES: COc1cc(C)c(S(=O)(=O)N(C)CCOCC(=O)N(C)[C@H]2CC[C@H](OCCN3CCCC3)CC2)c(C)c1] |
| (613) | 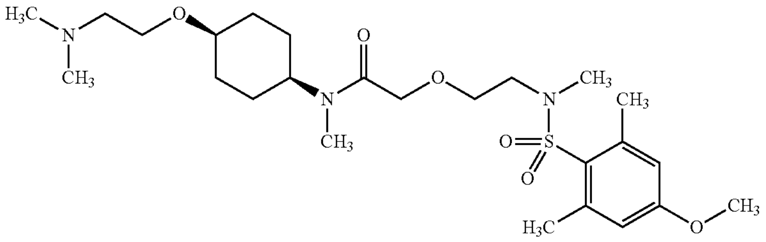 |
| (614) | 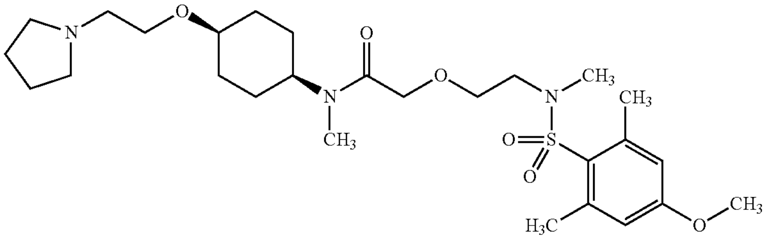 [SMILES: COc1cc(C)c(S(=O)(=O)N(C)CCOCC(=O)N(C)[C@H]2CC[C@@H](OCCN3CCCC3)CC2)c(C)c1] |

-continued
| Example | Structure |
| --- | --- |
| (615) | 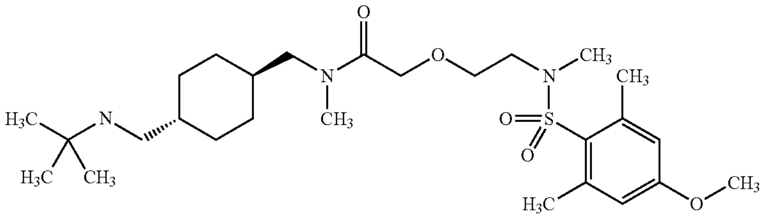 [SMILES: COc1cc(C)c(S(=O)(=O)N(C)CCOCC(=O)N(C)C[C@H]2CC[C@H](CNC(C)(C)C)CC2)c(C)c1] |
| (616) | 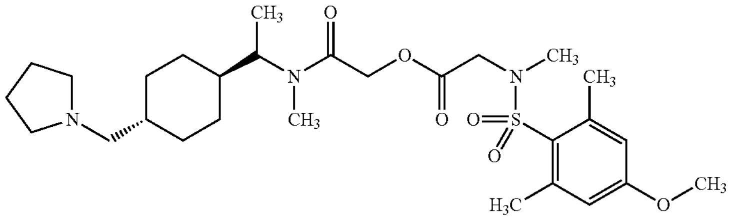 [SMILES: COc1cc(C)c(S(=O)(=O)N(C)CC(=O)OCC(=O)N(C)C(C)[C@H]2CC[C@H](CN3CCCC3)CC2)c(C)c1] |
| (617) | 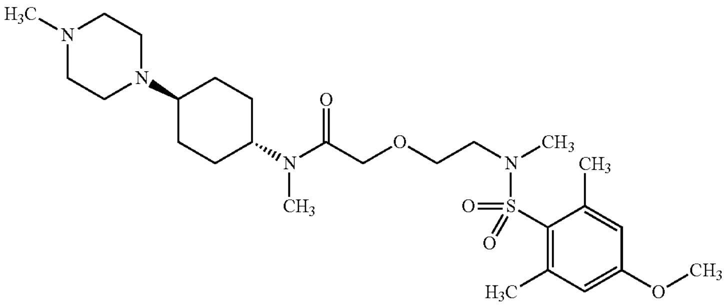 |
| (618) | 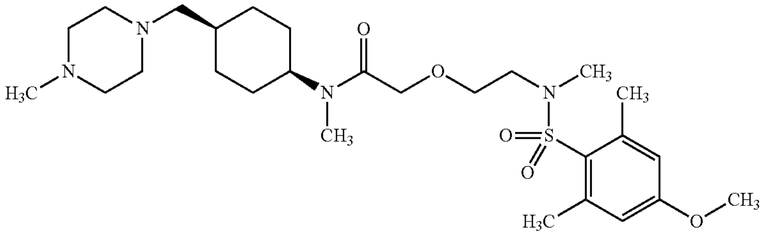 |
| (619) | 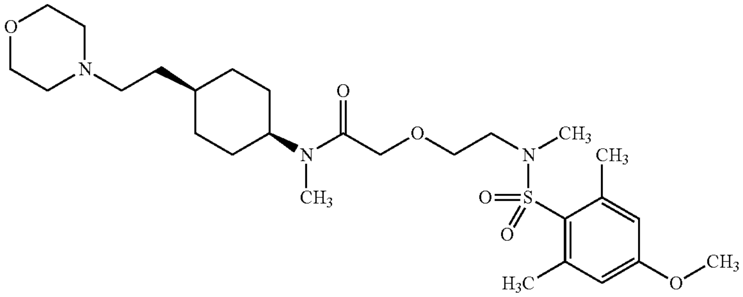 [SMILES: COc1cc(C)c(S(=O)(=O)N(C)CCOCC(=O)N(C)[C@H]2CC[C@@H](CCN3CCOCC3)CC2)c(C)c1] |
| (620) | 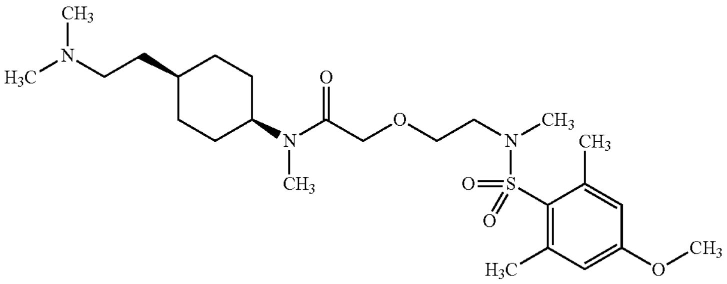 |

-continued
| Example | Structure |
| --- | --- |
| (621) | 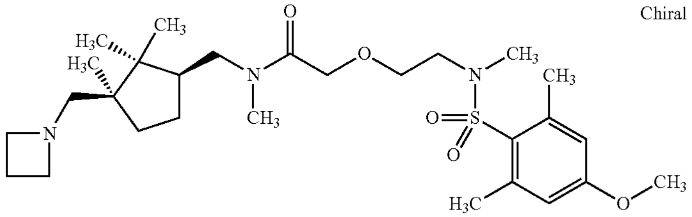 Chiral |
| (622) | 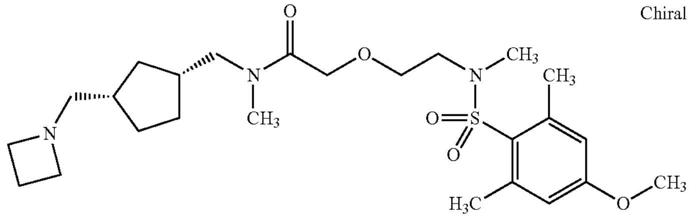 [SMILES: COc1cc(C)c(S(=O)(=O)N(C)CCOCC(=O)N(C)C[C@@H]2CC[C@H](CN3CCC3)C2)c(C)c1] Chiral |
| (623) | 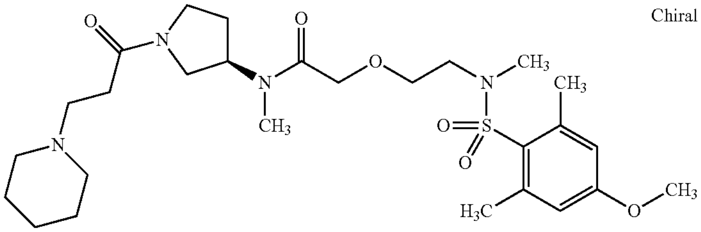 [SMILES: COc1cc(C)c(S(=O)(=O)N(C)CCOCC(=O)N(C)[C@@H]2CCN(C(=O)CCN3CCCCC3)C2)c(C)c1] Chiral |
| (624) | 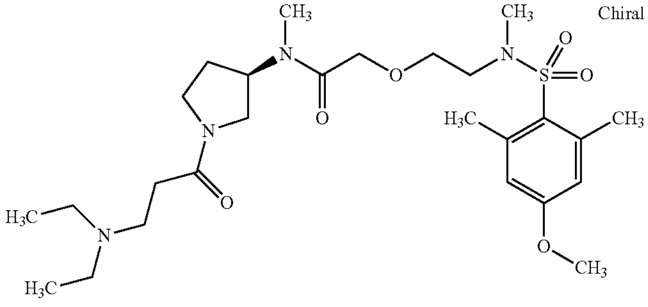 [SMILES: CCN(CC)CCC(=O)N1CC[C@@H](N(C)C(=O)COCCN(C)S(=O)(=O)c2c(C)cc(OC)cc2C)C1] Chiral |
| (625) | 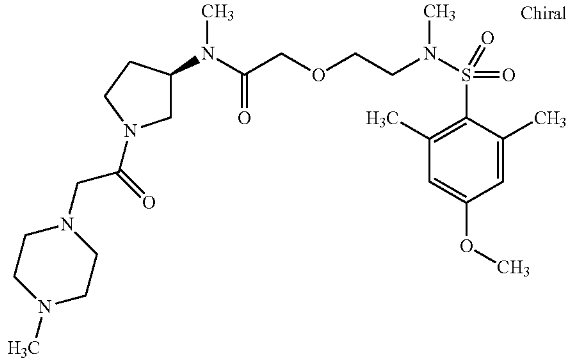 [SMILES: COc1cc(C)c(S(=O)(=O)N(C)CCOCC(=O)N(C)[C@@H]2CCN(C(=O)CN3CCN(C)CC3)C2)c(C)c1] Chiral |

-continued
| Example | Structure |
| --- | --- |
| (626) | 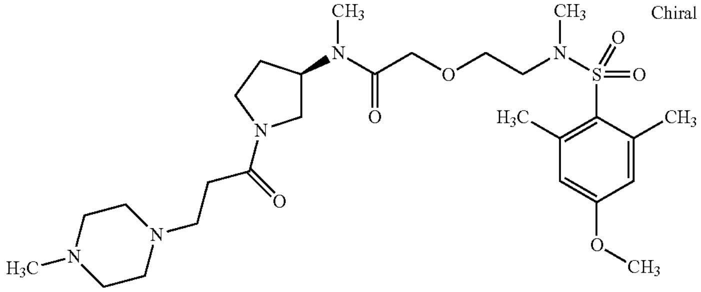 |
| (627) | 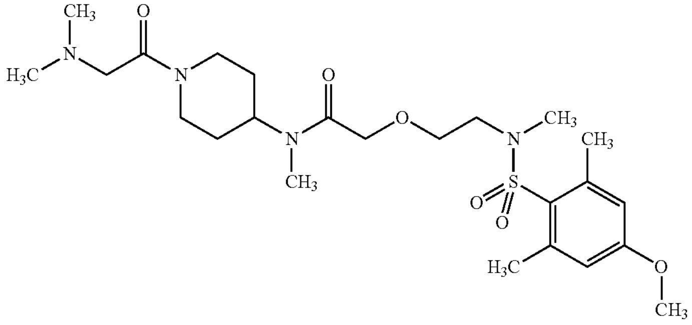 |
| (628) | 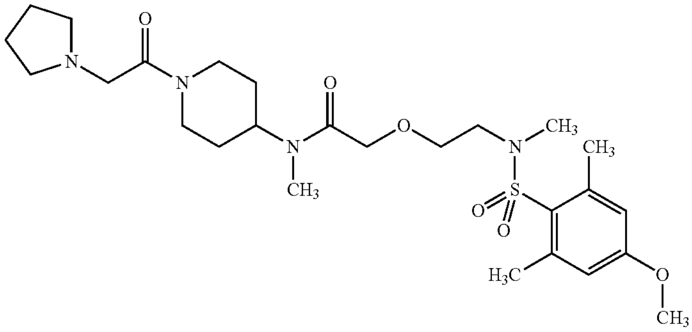 [SMILES: COc1cc(C)c(S(=O)(=O)N(C)CCOCC(=O)N(C)C2CCN(C(=O)CN3CCCC3)CC2)c(C)c1] |
| (629) | 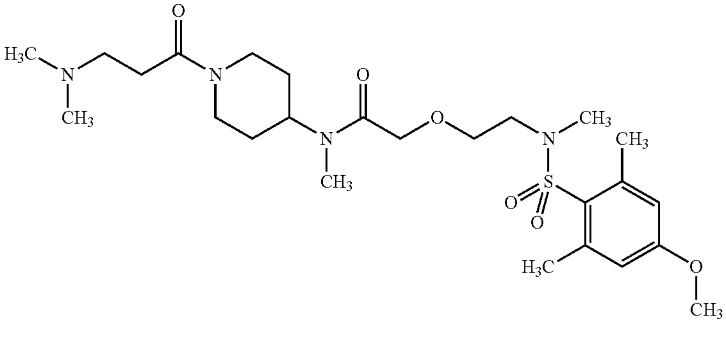 |
| (630) | 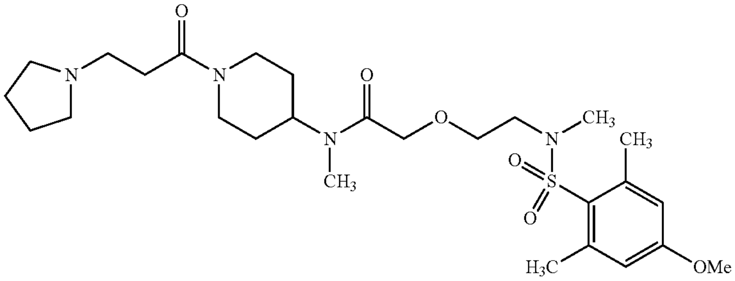 [SMILES: COc1cc(C)c(S(=O)(=O)N(C)CCOCC(=O)N(C)C2CCN(C(=O)CCN3CCCC3)CC2)c(C)c1] |

-continued
| Example | Structure |
| --- | --- |
| (631) | 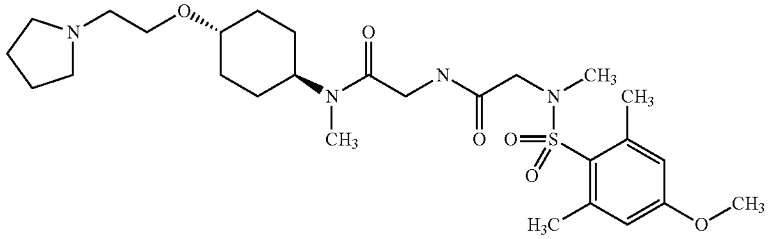 [SMILES: COc1cc(C)c(S(=O)(=O)N(C)CC(=O)NCC(=O)N(C)[C@H]2CC[C@H](OCCN3CCCC3)CC2)c(C)c1] |
| (632) | 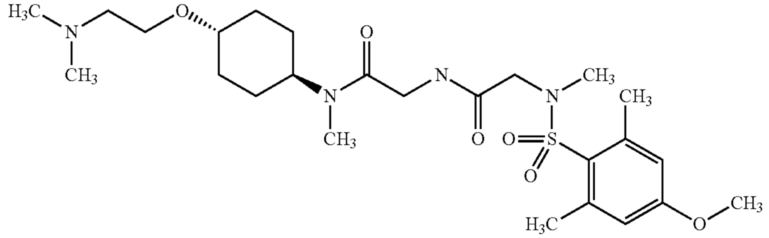 |
| (633) | 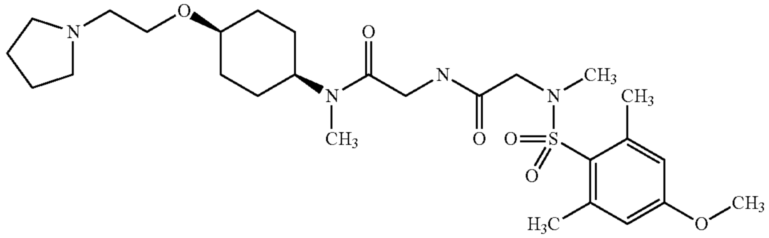 [SMILES: COc1cc(C)c(S(=O)(=O)N(C)CC(=O)NCC(=O)N(C)[C@H]2CC[C@@H](OCCN3CCCC3)CC2)c(C)c1] |
| (634) | 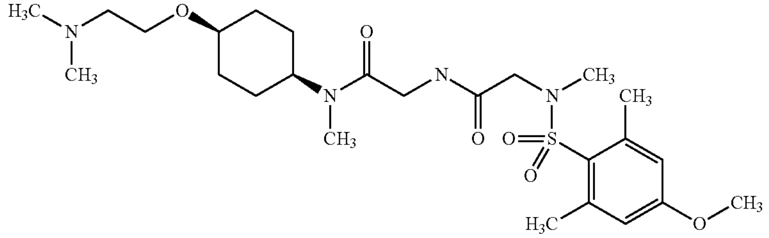 |
| (635) | 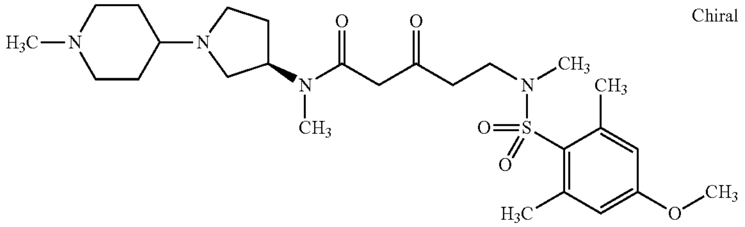 Chiral |
| (636) | 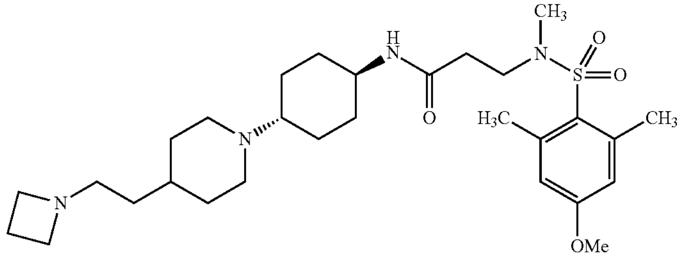 [SMILES: COc1cc(C)c(S(=O)(=O)N(C)CCC(=O)N[C@H]2CC[C@H](N3CCC(CCN4CCC4)CC3)CC2)c(C)c1] |

-continued
| Example | Structure |
|---|---|
| (637) | 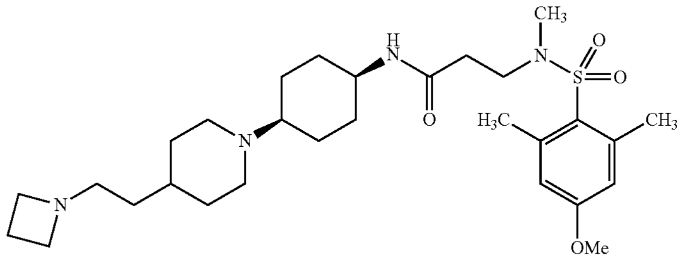 [SMILES: COc1cc(C)c(S(=O)(=O)N(C)CCC(=O)N[C@H]2CC[C@@H](N3CCC(CCN4CCC4)CC3)CC2)c(C)c1] |
| (638) | 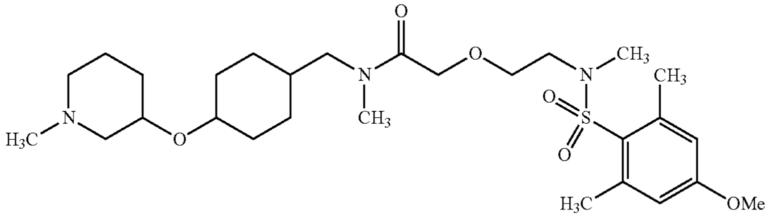 [SMILES: COc1cc(C)c(S(=O)(=O)N(C)CCOCC(=O)N(C)CC2CCC(OC3CCCN(C)C3)CC2)c(C)c1] |
| (639) | 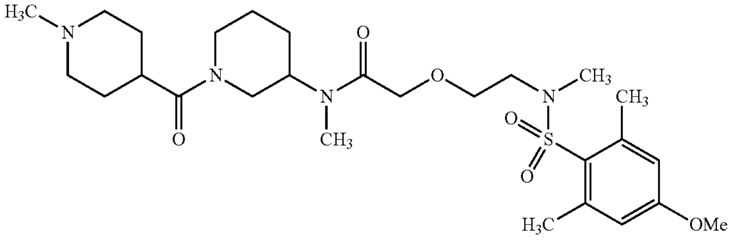 [SMILES: COc1cc(C)c(S(=O)(=O)N(C)CCOCC(=O)N(C)C2CCCN(C(=O)C3CCN(C)CC3)C2)c(C)c1] |
| (640) | 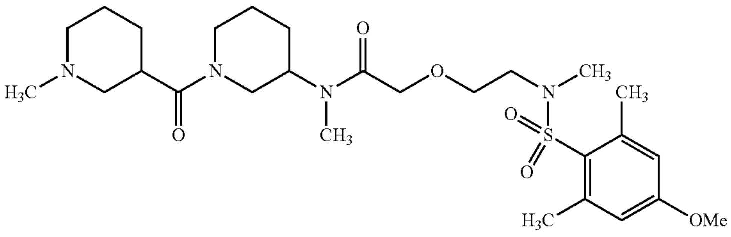 [SMILES: COc1cc(C)c(S(=O)(=O)N(C)CCOCC(=O)N(C)C2CCCN(C(=O)C3CCCN(C)C3)C2)c(C)c1] |
| (641) | 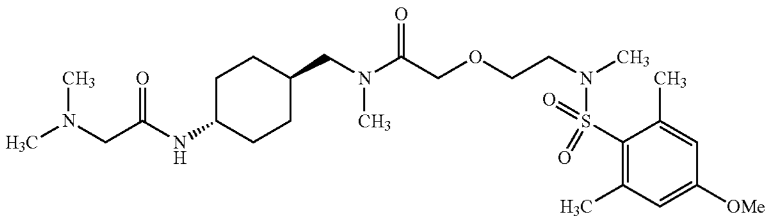 [SMILES: COc1cc(C)c(S(=O)(=O)N(C)CCOCC(=O)N(C)C[C@H]2CC[C@H](NC(=O)CN(C)C)CC2)c(C)c1] |
| (642) | 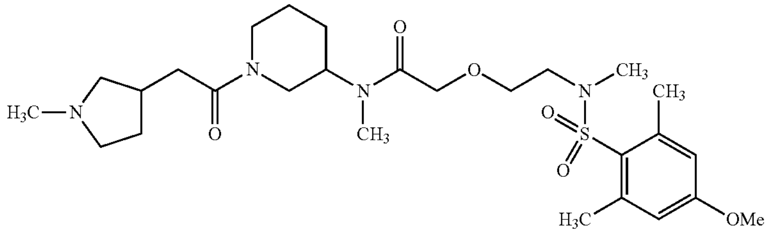 [SMILES: COc1cc(C)c(S(=O)(=O)N(C)CCOCC(=O)N(C)C2CCCN(C(=O)CC3CCN(C)C3)C2)c(C)c1] |

-continued
| Example | Structure |
|---|---|
| (643) | 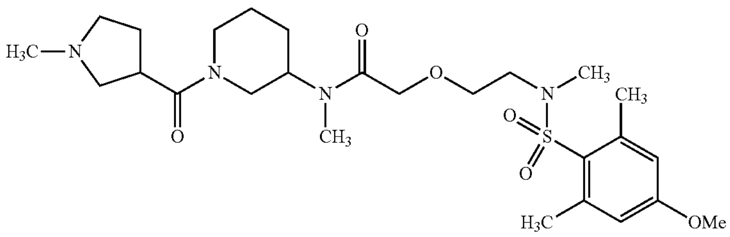 [SMILES: COc1cc(C)c(S(=O)(=O)N(C)CCOCC(=O)N(C)C2CCCN(C(=O)C3CCN(C)C3)C2)c(C)c1] |
| (644) | 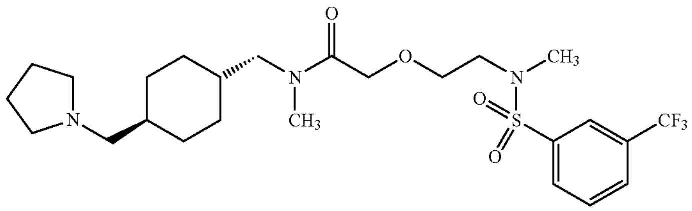 |
| (645) | 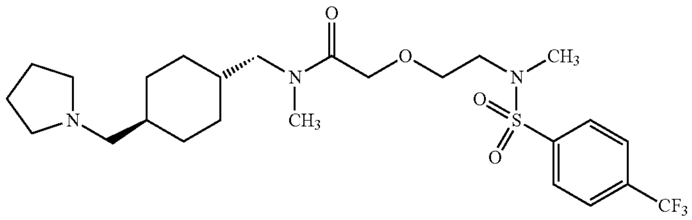 |
| (646) | 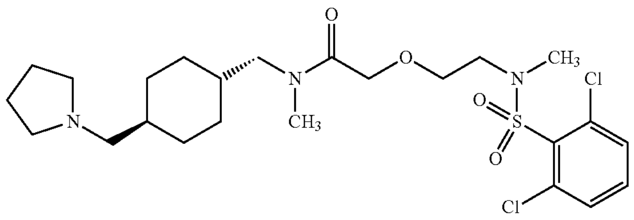 |
| (647) | 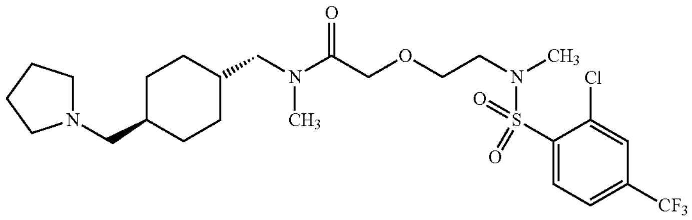 |
| (648) | 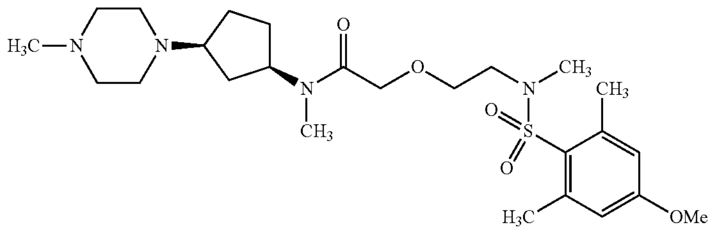 [SMILES: COc1cc(C)c(S(=O)(=O)N(C)CCOCC(=O)N(C)[C@@H]2CC[C@H](N3CCN(C)CC3)C2)c(C)c1] |

-continued
| Example | Structure |
| --- | --- |
| (649) | 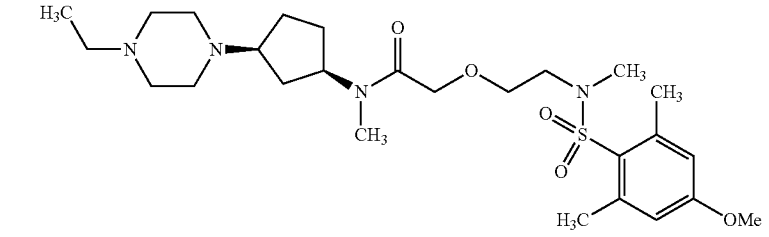 [SMILES: CCN1CCN([C@H]2CC[C@@H](N(C)C(=O)COCCN(C)S(=O)(=O)c3c(C)cc(OC)cc3C)C2)CC1] |
| (650) | 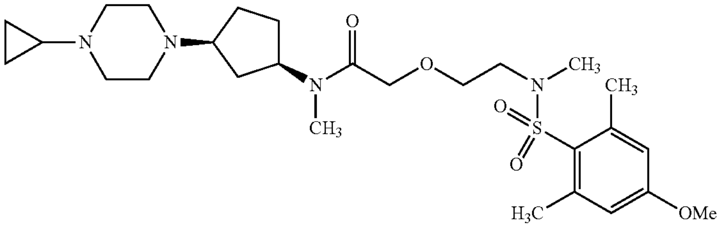 [SMILES: COc1cc(C)c(S(=O)(=O)N(C)CCOCC(=O)N(C)[C@@H]2CC[C@H](N3CCN(C4CC4)CC3)C2)c(C)c1] |
| (651) | 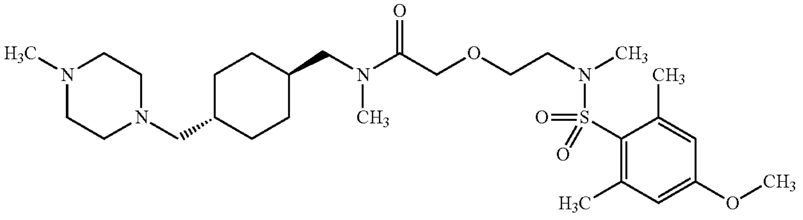 |
| (652) | 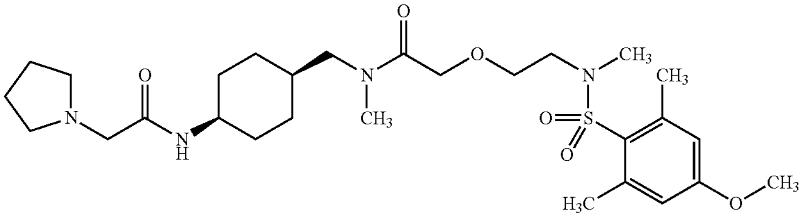 [SMILES: COc1cc(C)c(S(=O)(=O)N(C)CCOCC(=O)N(C)C[C@H]2CC[C@@H](NC(=O)CN3CCCC3)CC2)c(C)c1] |
| (653) | 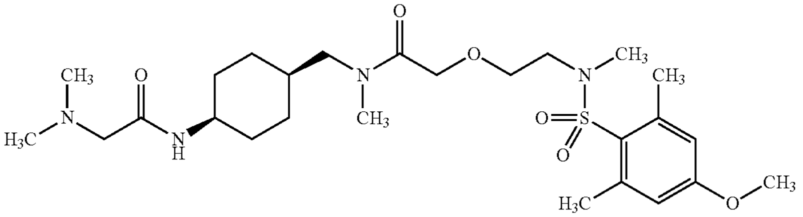 |
| (654) | 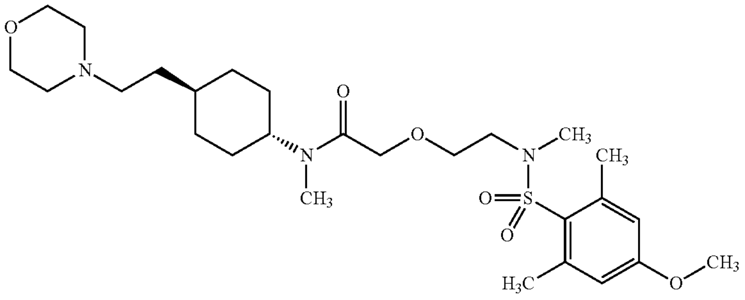 [SMILES: COc1cc(C)c(S(=O)(=O)N(C)CCOCC(=O)N(C)[C@H]2CC[C@H](CCN3CCOCC3)CC2)c(C)c1] |

-continued
| Example | Structure |
| --- | --- |
| (655) | 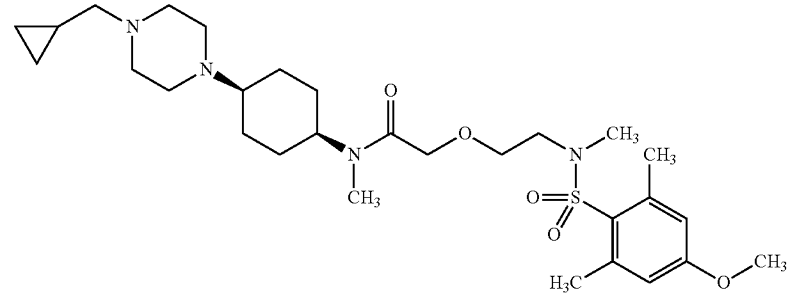 [SMILES: COc1cc(C)c(S(=O)(=O)N(C)CCOCC(=O)N(C)[C@H]2CC[C@@H](N3CCN(CC4CC4)CC3)CC2)c(C)c1] |
| (656) | 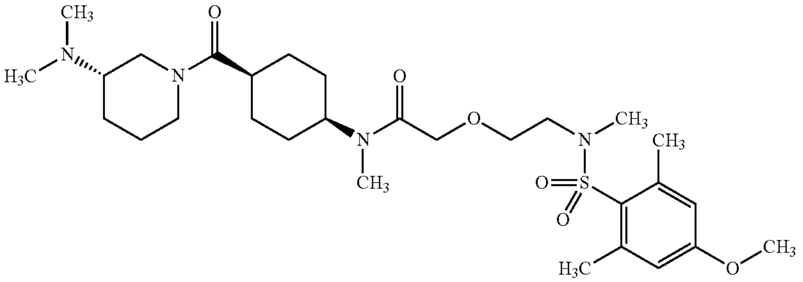 |
| (657) | 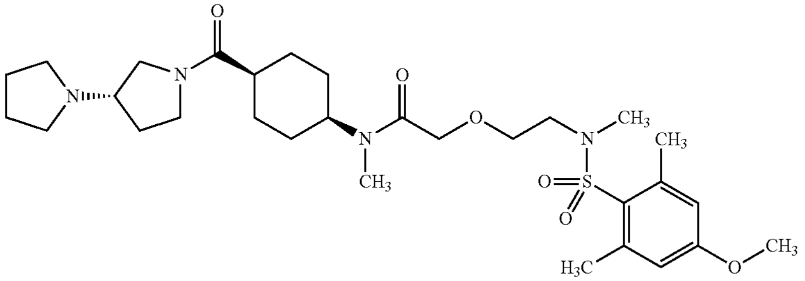 [SMILES: COc1cc(C)c(S(=O)(=O)N(C)CCOCC(=O)N(C)[C@H]2CC[C@@H](C(=O)N3CC[C@H](N4CCCC4)C3)CC2)c(C)c1] |
| (658) | 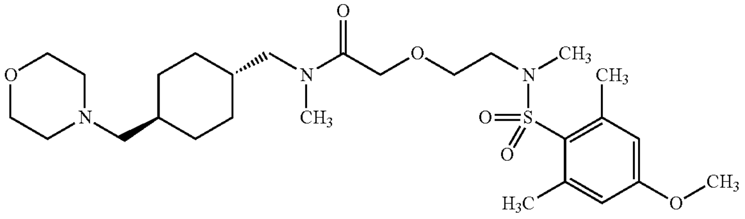 [SMILES: COc1cc(C)c(S(=O)(=O)N(C)CCOCC(=O)N(C)C[C@H]2CC[C@H](CN3CCOCC3)CC2)c(C)c1] |
| (659) | 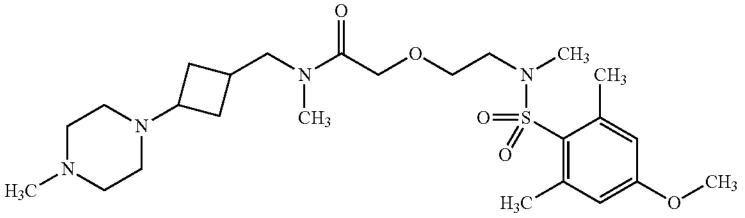 |
| (660) | 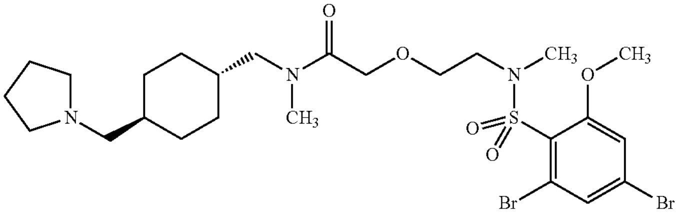 [SMILES: COc1cc(Br)cc(Br)c1S(=O)(=O)N(C)CCOCC(=O)N(C)C[C@H]1CC[C@H](CN2CCCC2)CC1] |

-continued
| Example | Structure |
| --- | --- |
| (661) | 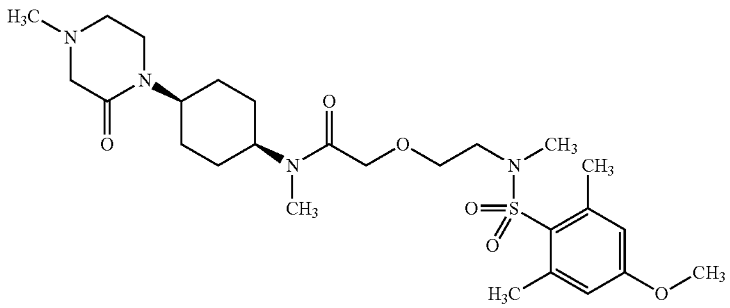 |
| (662) | 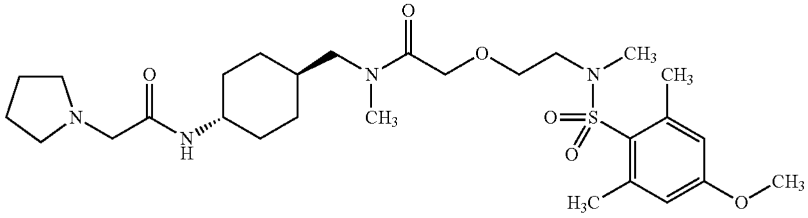 [SMILES: COc1cc(C)c(S(=O)(=O)N(C)CCOCC(=O)N(C)C[C@H]2CC[C@H](NC(=O)CN3CCCC3)CC2)c(C)c1] |
| (663) | 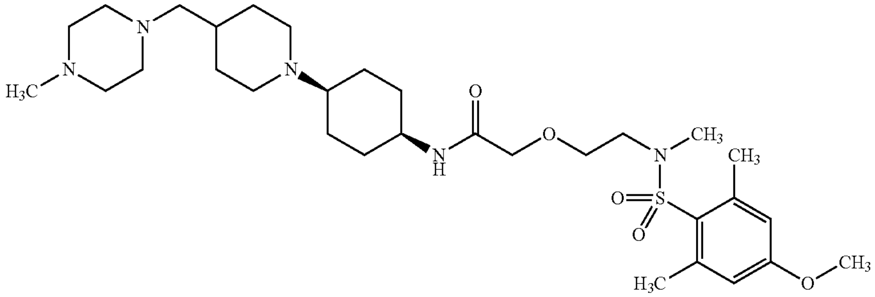 |
| (664) | 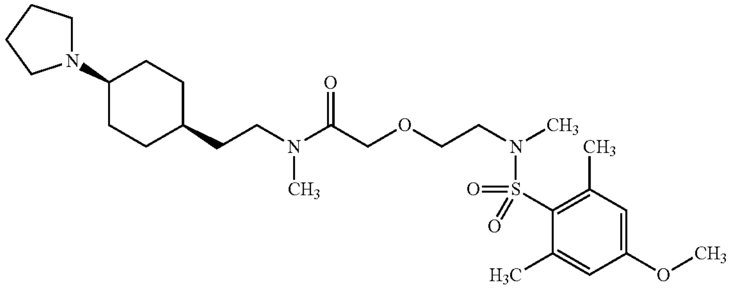 [SMILES: COc1cc(C)c(S(=O)(=O)N(C)CCOCC(=O)N(C)CC[C@H]2CC[C@@H](N3CCCC3)CC2)c(C)c1] |
| (665) | 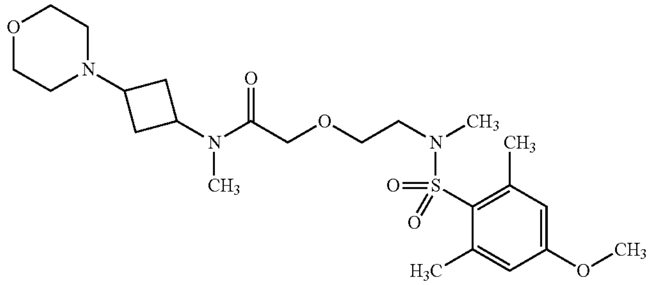 [SMILES: COc1cc(C)c(S(=O)(=O)N(C)CCOCC(=O)N(C)C2CC(N3CCOCC3)C2)c(C)c1] |

-continued
| Example | Structure |
|---|---|
| (666) | 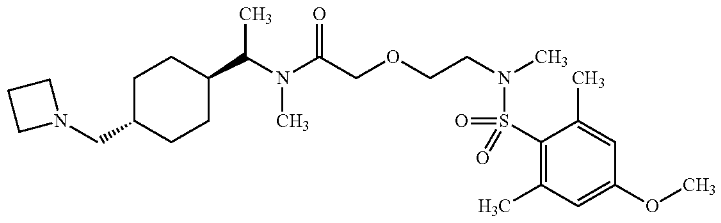 [SMILES: COc1cc(C)c(S(=O)(=O)N(C)CCOCC(=O)N(C)C(C)[C@H]2CC[C@H](CN3CCC3)CC2)c(C)c1] |
| (667) | 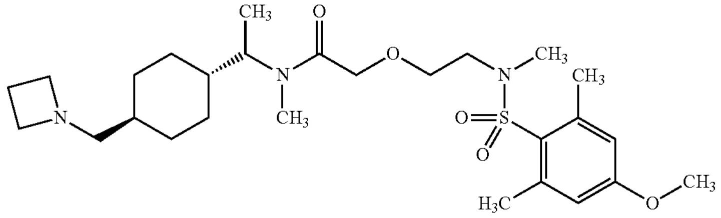 [SMILES: COc1cc(C)c(S(=O)(=O)N(C)CCOCC(=O)N(C)C(C)[C@H]2CC[C@H](CN3CCC3)CC2)c(C)c1] |
| (668) | 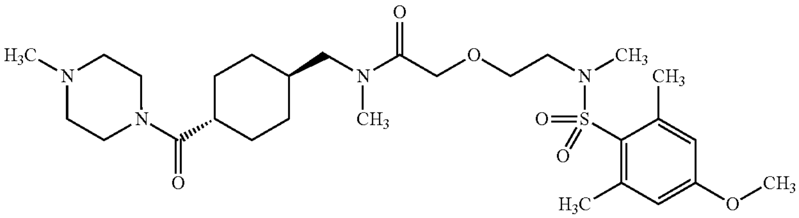 |
| (669) | 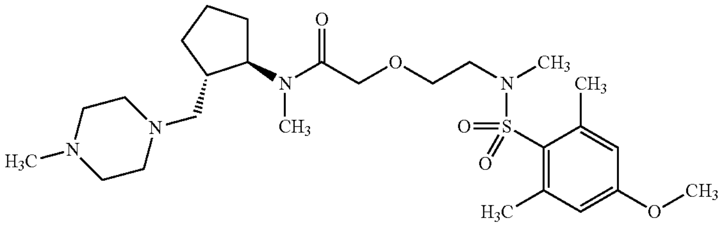 |
| (670) | 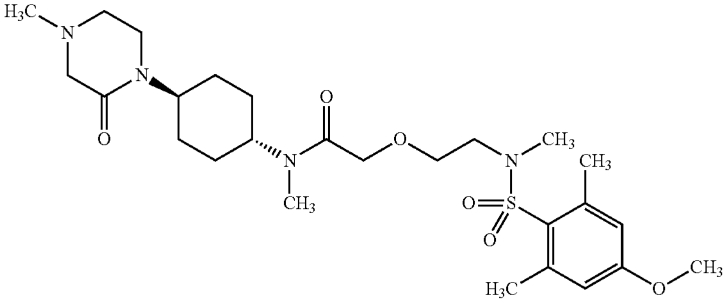 |
| (671) | 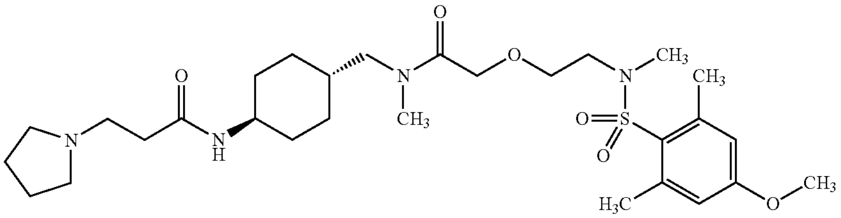 [SMILES: COc1cc(C)c(S(=O)(=O)N(C)CCOCC(=O)N(C)C[C@H]2CC[C@H](NC(=O)CCN3CCCC3)CC2)c(C)c1] |

-continued
| Example | Structure |
|---|---|
| (672) | 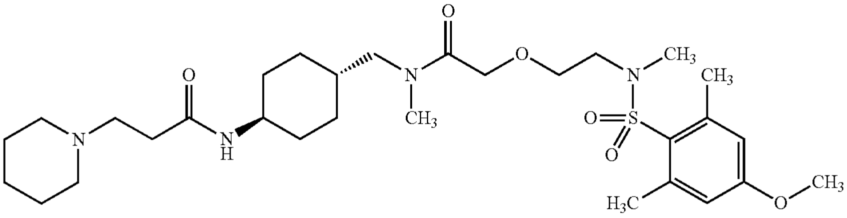 [SMILES: COc1cc(C)c(S(=O)(=O)N(C)CCOCC(=O)N(C)C[C@H]2CC[C@H](NC(=O)CCN3CCCCC3)CC2)c(C)c1] |
| (673) | 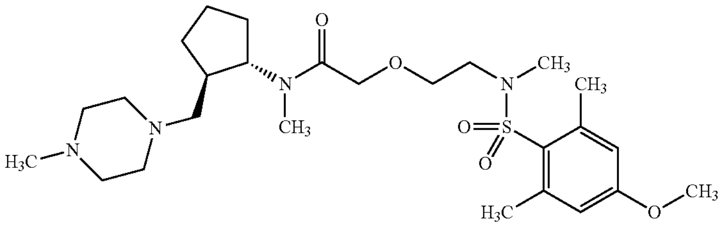 |
| (674) | 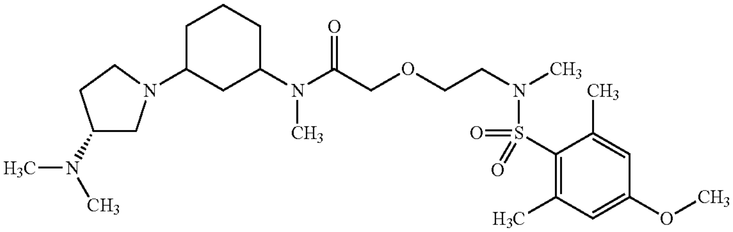 |
| (675) | 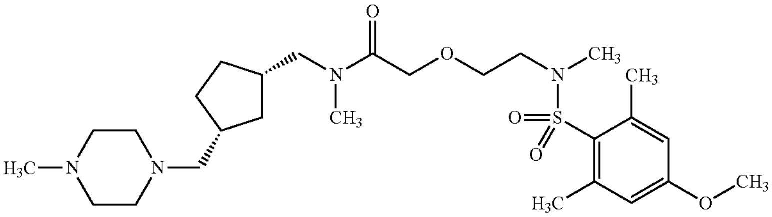 |
| (676) | 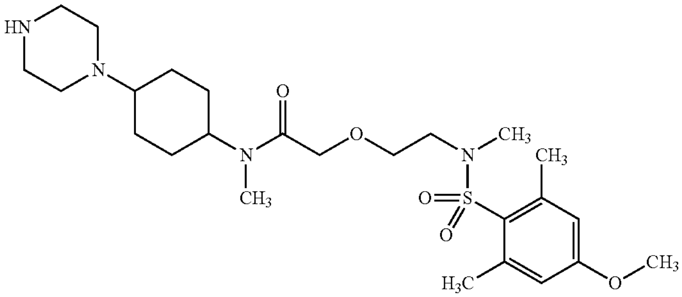 [SMILES: COc1cc(C)c(S(=O)(=O)N(C)CCOCC(=O)N(C)C2CCC(N3CCNCC3)CC2)c(C)c1] |
| (677) | 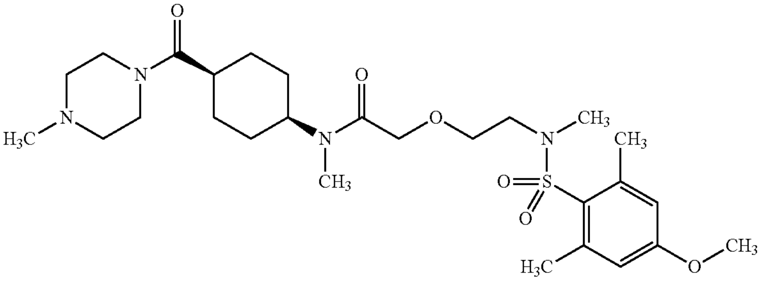 |

-continued
| Example | Structure |
| --- | --- |
| (678) | 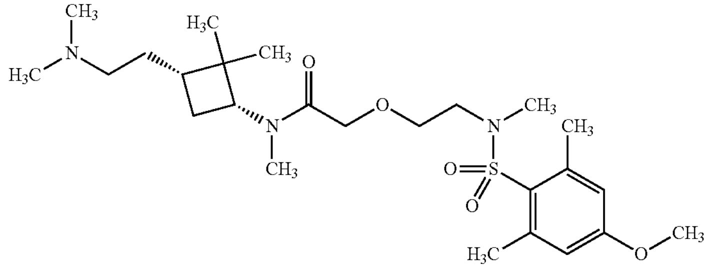 |
| (679) | 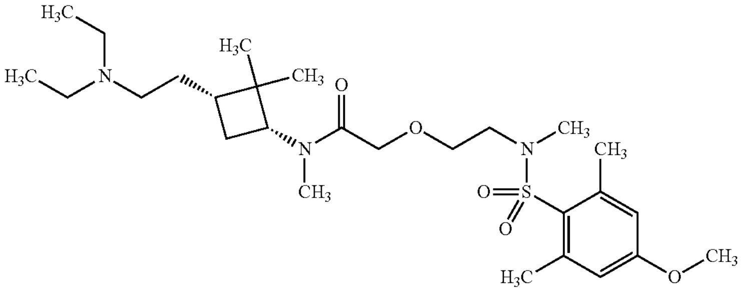 [SMILES: CCN(CC)CC[C@H]1C[C@@H](N(C)C(=O)COCCN(C)S(=O)(=O)c2c(C)cc(OC)cc2C)C1(C)C] |
| (680) | 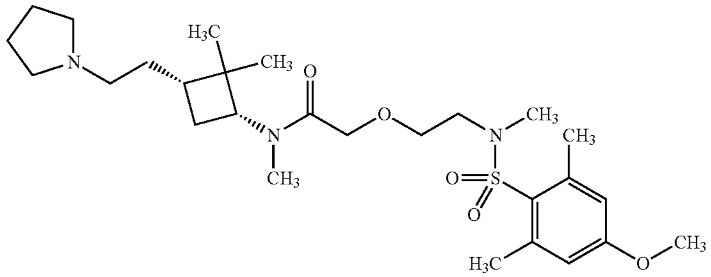 [SMILES: COc1cc(C)c(S(=O)(=O)N(C)CCOCC(=O)N(C)[C@@H]2C[C@H](CCN3CCCC3)C2(C)C)c(C)c1] |
| (681) | 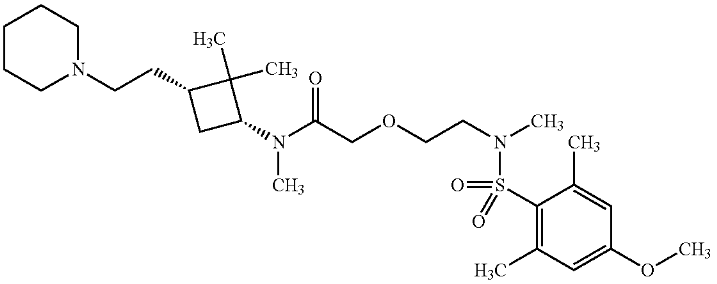 [SMILES: COc1cc(C)c(S(=O)(=O)N(C)CCOCC(=O)N(C)[C@@H]2C[C@H](CCN3CCCCC3)C2(C)C)c(C)c1] |
| (682) | 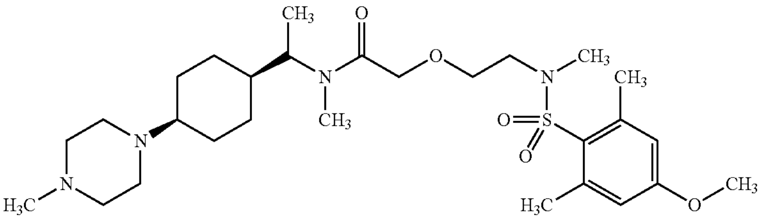 |
| (683) | 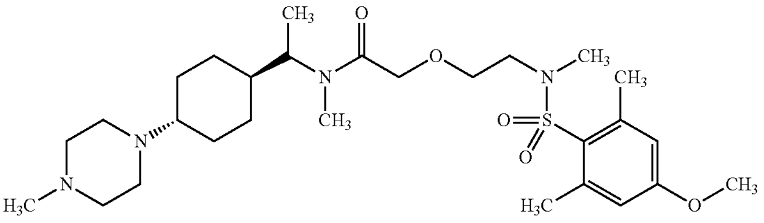 |

-continued
| Example | Structure |
|---|---|
| (684) | 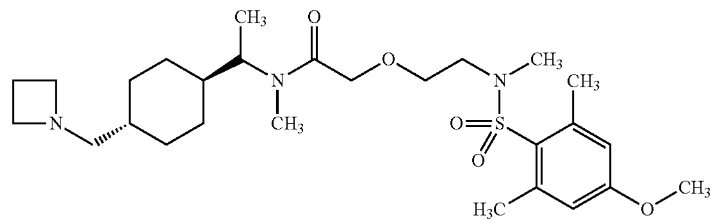 [SMILES: COc1cc(C)c(S(=O)(=O)N(C)CCOCC(=O)N(C)C(C)[C@H]2CC[C@H](CN3CCC3)CC2)c(C)c1] |
| (685) | 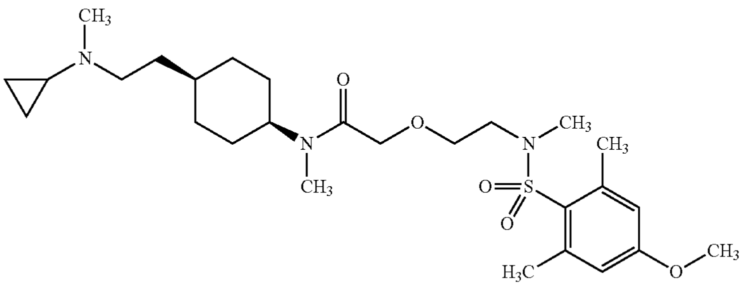 [SMILES: COc1cc(C)c(S(=O)(=O)N(C)CCOCC(=O)N(C)[C@H]2CC[C@@H](CCN(C)C3CC3)CC2)c(C)c1] |
| (686) | 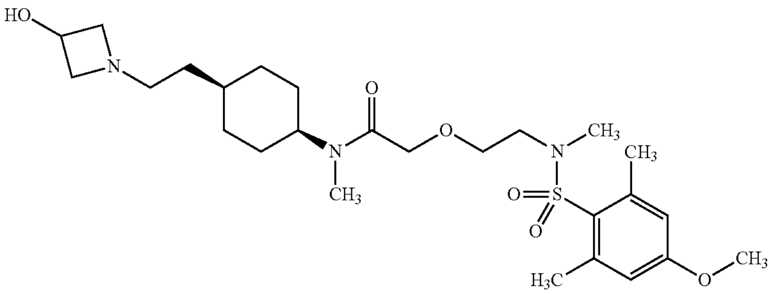 [SMILES: COc1cc(C)c(S(=O)(=O)N(C)CCOCC(=O)N(C)[C@H]2CC[C@@H](CCN3CC(O)C3)CC2)c(C)c1] |
| (687) | 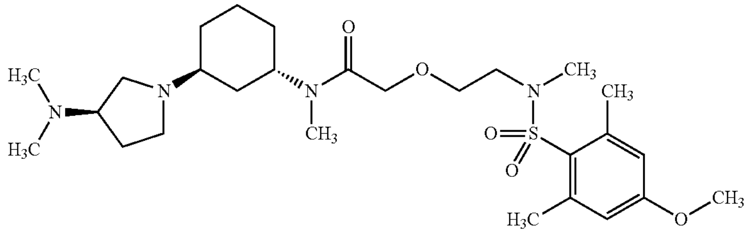 |
| (688) | 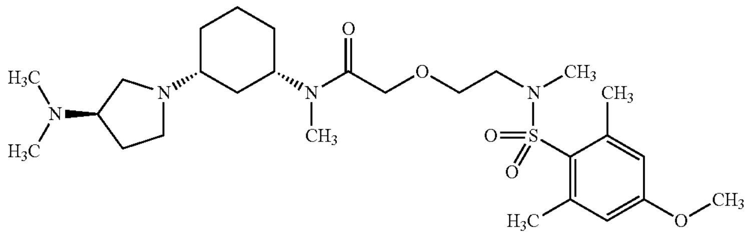 |
| (689) | 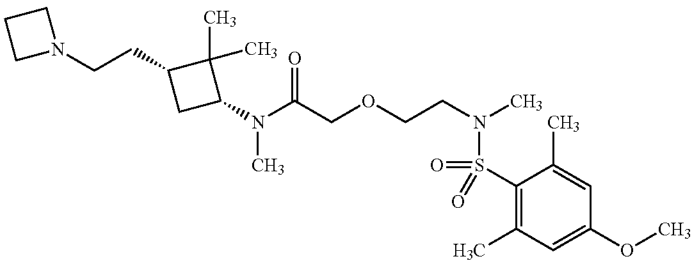 [SMILES: COc1cc(C)c(S(=O)(=O)N(C)CCOCC(=O)N(C)[C@@H]2C[C@H](CCN3CCC3)C2(C)C)c(C)c1] |

-continued
| Example | Structure |
| --- | --- |
| (690) | 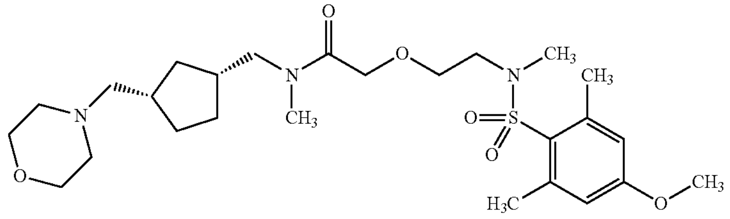 [SMILES: COc1cc(C)c(S(=O)(=O)N(C)CCOCC(=O)N(C)C[C@@H]2CC[C@H](CN3CCOCC3)C2)c(C)c1] |
| (691) | 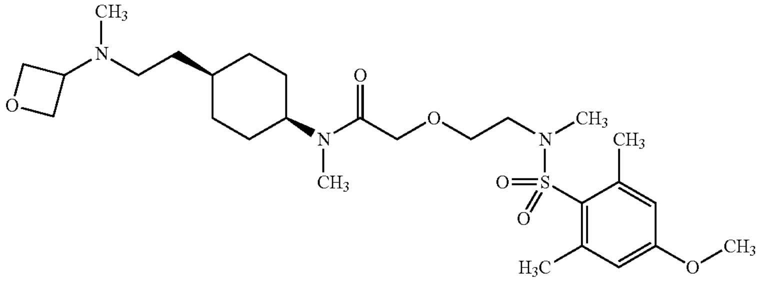 [SMILES: COc1cc(C)c(S(=O)(=O)N(C)CCOCC(=O)N(C)[C@H]2CC[C@@H](CCN(C)C3COC3)CC2)c(C)c1] |
| (692) | 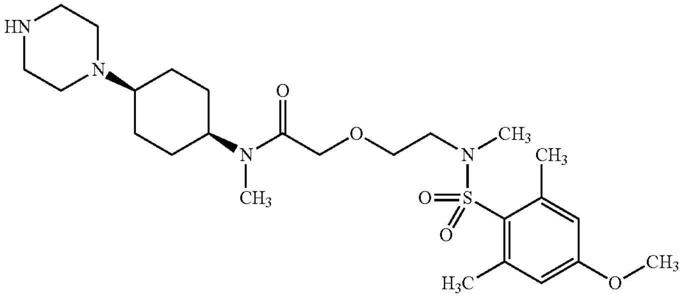 [SMILES: COc1cc(C)c(S(=O)(=O)N(C)CCOCC(=O)N(C)[C@H]2CC[C@@H](N3CCNCC3)CC2)c(C)c1] |
| (693) | 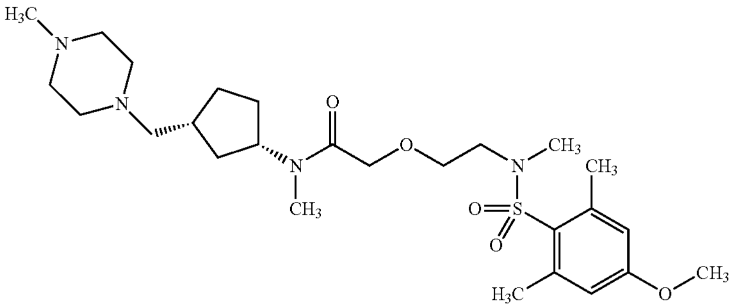 |
| (694) | 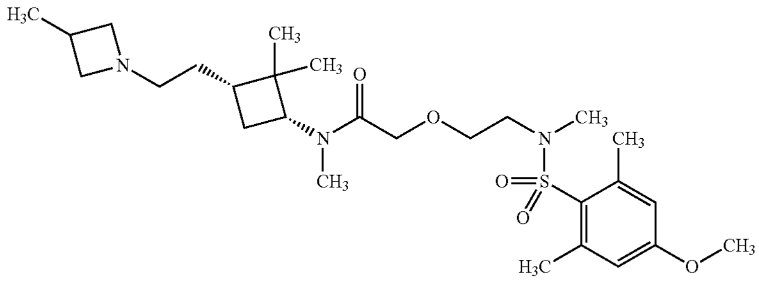 |

-continued
| Example | Structure |
| --- | --- |
| (695) | 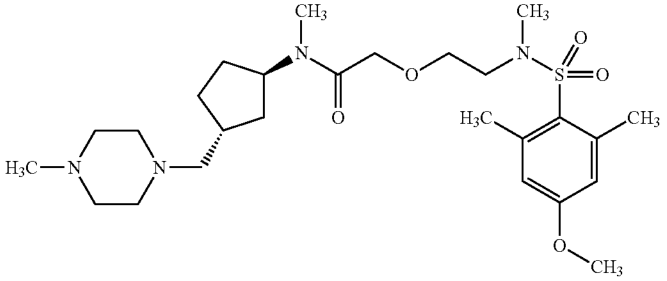 |
| (696) | 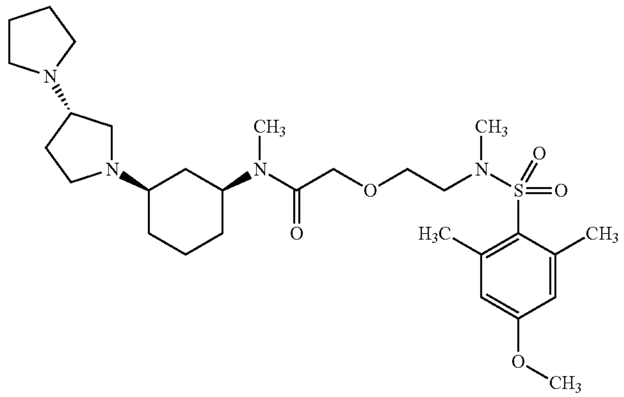 [SMILES: COc1cc(C)c(S(=O)(=O)N(C)CCOCC(=O)N(C)[C@H]2CCC[C@@H](N3CC[C@H](N4CCCC4)C3)C2)c(C)c1] |
| (697) | 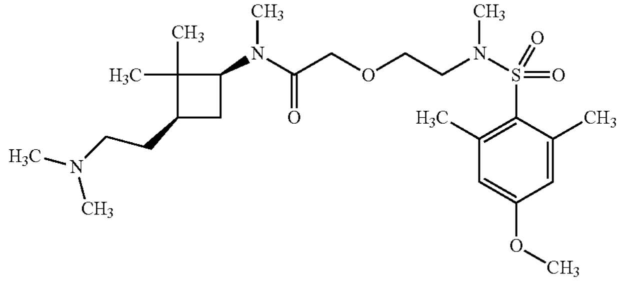 |
| (698) | 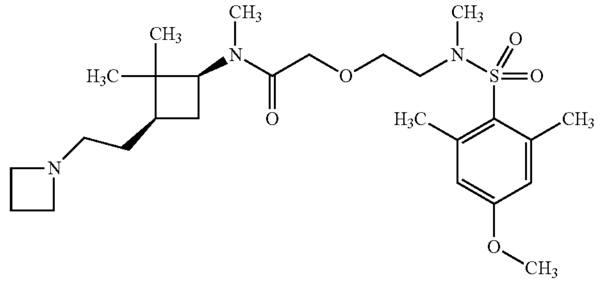 [SMILES: COc1cc(C)c(S(=O)(=O)N(C)CCOCC(=O)N(C)[C@H]2C[C@@H](CCN3CCC3)C2(C)C)c(C)c1] |
| (699) | 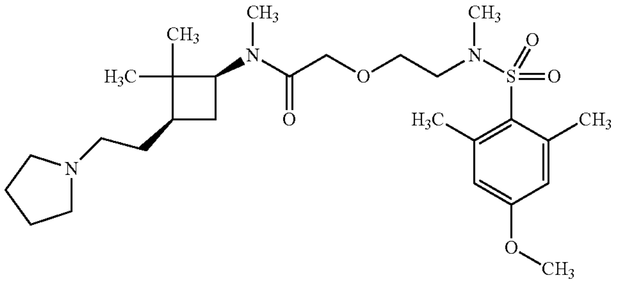 [SMILES: COc1cc(C)c(S(=O)(=O)N(C)CCOCC(=O)N(C)[C@H]2C[C@@H](CCN3CCCC3)C2(C)C)c(C)c1] |

-continued
| Example | Structure |
|---|---|
| (700) | 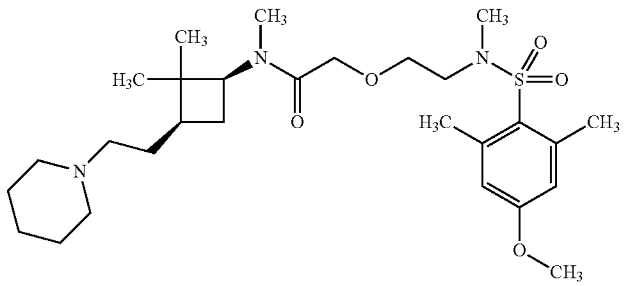 [SMILES: COc1cc(C)c(S(=O)(=O)N(C)CCOCC(=O)N(C)[C@H]2C[C@@H](CCN3CCCCC3)C2(C)C)c(C)c1] |
| (701) | 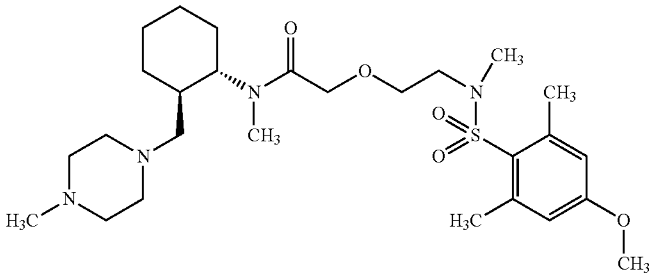 |
| (702) | 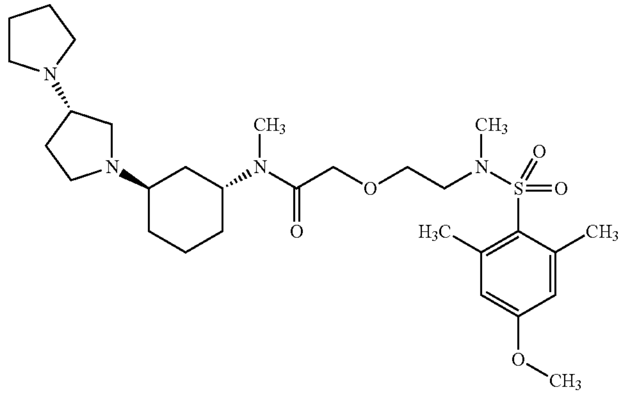 [SMILES: COc1cc(C)c(S(=O)(=O)N(C)CCOCC(=O)N(C)[C@@H]2CCC[C@@H](N3CC[C@H](N4CCCC4)C3)C2)c(C)c1] |
| (703) | 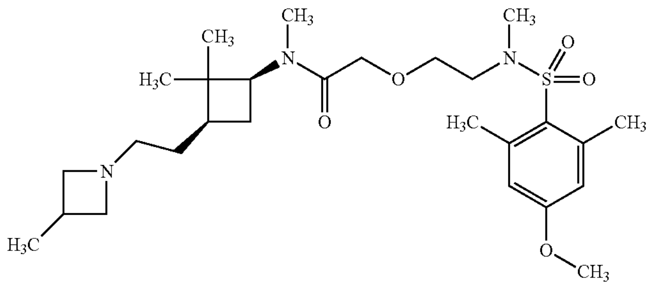 |
| (704) | 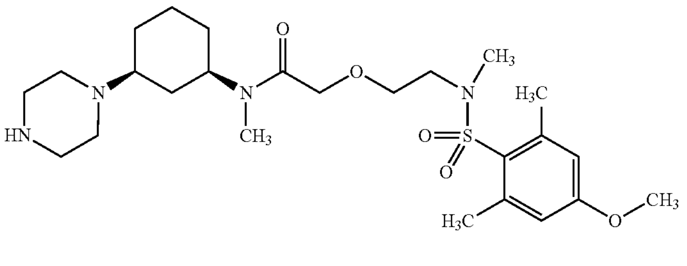 [SMILES: COc1cc(C)c(S(=O)(=O)N(C)CCOCC(=O)N(C)[C@@H]2CCC[C@H](N3CCNCC3)C2)c(C)c1] |

-continued
| Example | Structure |
|---|---|
| (705) | 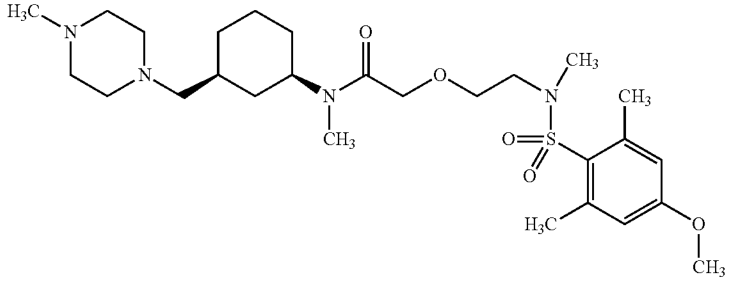 |
| (706) | 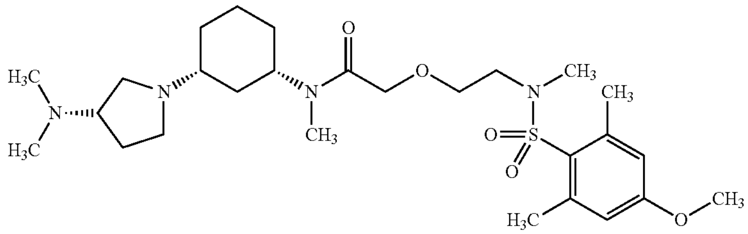 |
| (707a) | 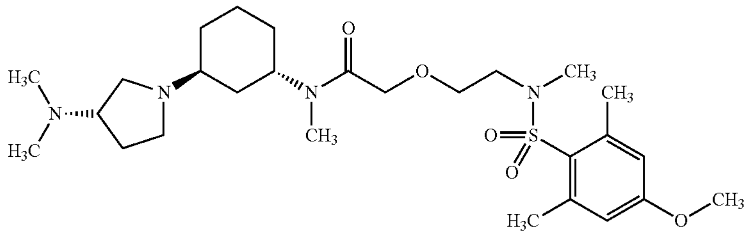 |
| (707b) | 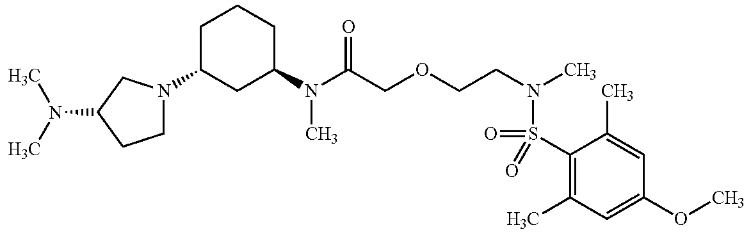 |
| (708) | 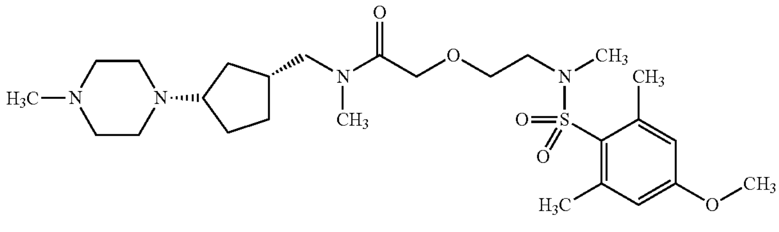 |
| (709) | 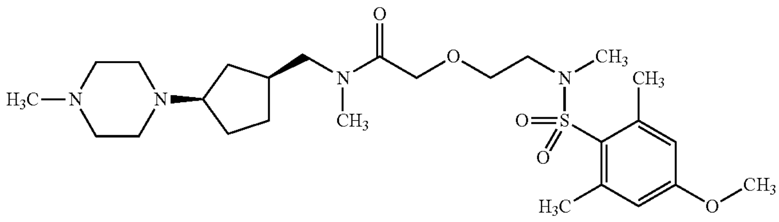 |
the enantiomers, the diastereomers, the mixtures and the salts thereof, particularly the physiologically acceptable salts thereof with organic or inorganic acids or bases.

TERMS AND DEFINITIONS USED

Unless otherwise stated, all the substituents are independent of one another. If for example there are a plurality of $C_{1-6}$-alkyl groups as substituents in one group, in the case of three $C_{1-6}$-alkyl substituents, independently of one another, one may represent methyl, one n-propyl and one tert-butyl.

If in the structural formulae given hereinbefore or hereinafter, in a substituent, there is no evidence of a valency and no other information can be inferred from the name, this valency is occupied by a proton, if this makes sense chemically. This applies particularly to nitrogen substituents.

If in the structural formulae given hereinbefore or hereinafter, in a substituent, there is no evidence of a bond and no other information can be inferred from the name, this bond is occupied by a methyl group, if this makes sense chemically. Examples of this include:

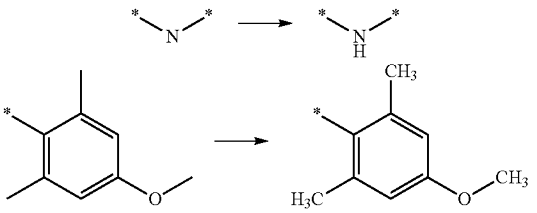

Within the scope of this application, in the definition of possible substituents, these may also be represented in the form of a structural formula. If present, an asterisk (*) in the structural formula of the substituent is to be understood as being the linking point to the rest of the molecule.

The subject-matter of this invention also includes the compounds according to the invention, including the salts thereof, wherein one or more hydrogen atoms, for example one, two, three, four or five hydrogen atoms, are replaced by deuterium.

By the term "$C_{1-2}$-alkyl" (including those which are part of other groups) are meant alkyl groups with 1 to 2 carbon atoms, by the term "$C_{1-3}$-alkyl" are meant branched and unbranched alkyl groups with 1 to 3 carbon atoms, by the term "$C_{1-4}$-alkyl" are meant branched and unbranched alkyl groups with 1 to 4 carbon atoms, by the term "$C_{1-5}$-alkyl" are meant branched and unbranched alkyl groups with 1 to 5 carbon atoms, by the term "$C_{1-6}$-alkyl" are meant branched and unbranched alkyl groups with 1 to 6 carbon atoms and by the term "$C_{1-8}$-alkyl" are meant branched and unbranched alkyl groups with 1 to 8 carbon atoms. Examples include: methyl, ethyl, n-propyl, iso-propyl, n-butyl, iso-butyl, sec-butyl, tert-butyl, n-pentyl, iso-pentyl, neo-pentyl, hexyl, heptyl and octyl. The following abbreviations may optionally also be used for the above-mentioned groups: Me, Et, n-Pr, i-Pr, n-Bu, i-Bu, t-Bu, etc. Unless stated otherwise, the definitions propyl, butyl, pentyl, hexyl, heptyl and octyl include all the possible isomeric forms of the groups in question. Thus, for example, propyl includes n-propyl and iso-propyl, butyl includes iso-butyl, sec-butyl and tert-butyl etc.

Moreover, the terms mentioned above also include those groups wherein each methylene group may be substituted by up to two fluorine atoms and each methyl group may be substituted by up to three fluorine atoms.

By the term "$C_{1-2}$-alkylene" are meant branched and unbranched alkylene groups with 1 or 2 carbon atoms, by the term "$C_{1-3}$-alkylene" (including those which are part of other groups) are meant branched and unbranched alkylene groups with 1 to 3 carbon atoms, by the term "$C_{1-4}$-alkylene" are meant branched and unbranched alkylene groups with 1 to 4 carbon atoms, by the term "$C_{1-6}$-alkylene" are meant branched and unbranched alkylene groups with 1 to 6 carbon atoms and by the term "$C_{2-4}$-alkylene" are meant branched and unbranched alkylene groups with 2 to 4 carbon atoms. Examples include: methylene, ethylene, ethane-1,1-diyl, propylene, propane-2,2-diyl, 1-methylethylene, butylene, 1-methylpropylene, 1,1-dimethylethylene, 1,2-dimethylethylene. Unless stated otherwise, the definitions propylene and butylene include all the possible isomeric forms with the same number of carbons. Thus, for example, propyl also includes 1-methylethylene and butylene includes 1-methylpropylene, 1,1-dimethylethylene, 1,2-dimethylethylene.

In addition, the terms mentioned above also include those groups wherein each methylene group may be substituted by up to two fluorine atoms.

By the term "$C_{3-5}$-cycloalkyl" are meant cyclic alkyl groups with 3 to 5 carbon atoms, by the term "$C_{3-6}$-cycloalkyl" are meant cyclic alkyl groups with 3 to 6 carbon atoms and by the term "$C_{3-7}$-cycloalkyl" (including those which are part of other groups) are meant cyclic alkyl groups with 3 to 7 carbon atoms. Examples include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{3-6}$-cycloalkylene" (including those which are part of other groups) are meant cyclic alkylene groups with 3 to 6 carbon atoms, by the term "$C_{3-7}$-cycloalkylene" are meant cyclic alkylene groups with 3 to 7 carbon atoms and by the term "$C_{4-6}$-cycloalkylene" are meant cyclic alkylene groups with 4 to 6 carbon atoms. Examples include: cyclopropylene, cyclobutylene, cyclopentylene, cyclohexylene or cycloheptylene. Unless otherwise stated, the cyclic alkylene groups may be substituted by one or more groups selected from among methyl, ethyl, iso-propyl, tert-butyl, hydroxy, fluorine, chlorine, bromine and iodine. A $C_4$- or a $C_5$-cycloalkylene group may be linked to the remainder of the molecule in the 1,2 position or in the 1,3 position, preferably in the 1,3 position. A $C_6$- or a $C_7$-cycloalkylene group may be linked to the remainder of the molecule in the 1,2 position, in the 1,3 position or in the 1,4 position, preferably in the 1,3 position.

By the term "$C_{5-7}$-cycloalkenylene" (including those which are part of other groups) are meant cyclic alkenyl groups with 5 to 7 carbon atoms, which contain an unsaturated bond and which are fused to a phenyl ring via this unsaturated bond. Examples include: cyclopentenyl, cyclohexenyl or cycloheptenyl:

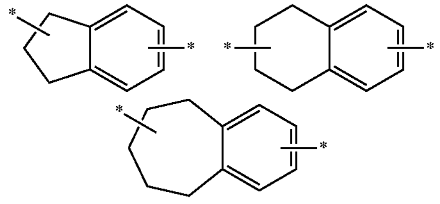

Unless otherwise stated, the cyclic alkenyl groups may be substituted by one or more groups selected from among methyl, ethyl, iso-propyl, tert-butyl, hydroxy, fluorine, chlorine, bromine and iodine.

By the term "saturated heterocyclic rings" are meant four, five, six or seven membered heterocyclic rings which may contain one, two or three heteroatoms selected from among oxygen, sulphur and nitrogen. The ring may be attached to the molecule through a carbon atom and/or—if present—through a nitrogen atom or also through two carbon atoms or through two nitrogen atoms. Although it is encompassed by the term “heterocyclic rings”, the term “heterocyclic non-aromatic rings” denotes five, six or seven membered saturated rings. Examples include:

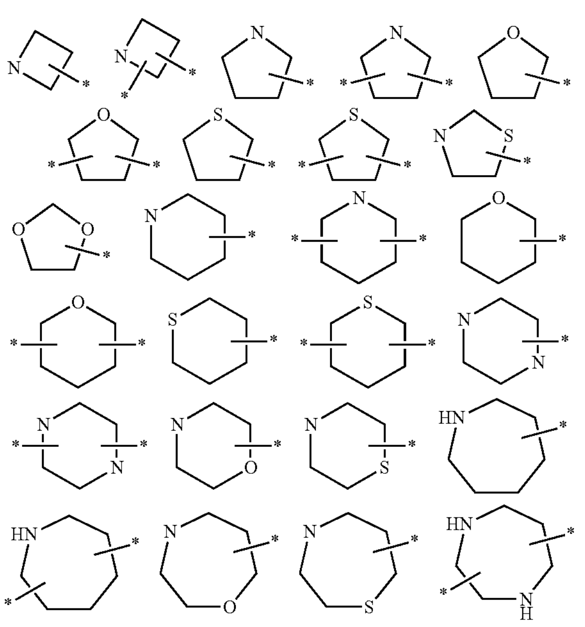

By the term “saturated diaza-heterocycles” are meant six or seven membered heterocyclic rings which contain two nitrogen atoms. The ring is linked to the remainder of the molecule through both nitrogen atoms. Examples include:

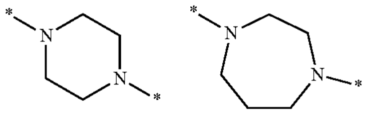 [SMILES: *N1CCN(*)CC1 ; *N1CCCN(*)CC1]

By the term “saturated aza-heterobicycles” are meant eight, nine or ten membered heterobicyclic rings which contain a nitrogen atom. The ring is linked to the remainder of the molecule through a carbon atom and the nitrogen atom. Examples include:

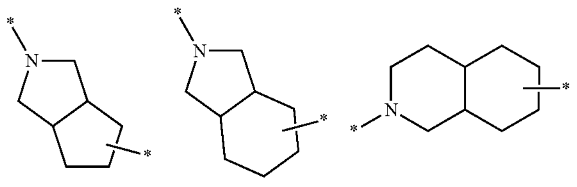

By the term “saturated diaza-heterobicycles” are meant eight, nine or ten membered heterobicyclic rings which contain two nitrogen atoms. The ring is linked to the remainder of the molecule through both nitrogen atoms. Examples include:

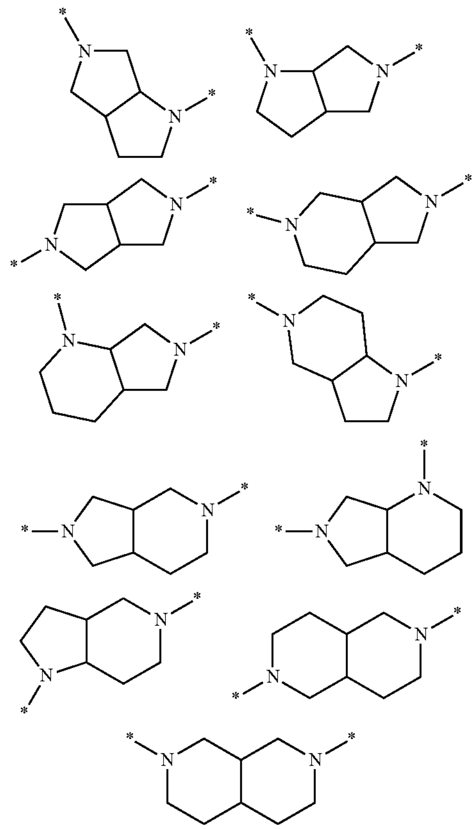

By the term “unsaturated heterocyclic rings” are meant five-, six- or seven-membered, mono- or diunsaturated heterocyclic rings which may contain one, two or three heteroatoms, selected from among oxygen, sulphur and nitrogen and condensed through the unsaturated bonds with one or two phenyl rings. The heterocyclic ring may be linked to the molecule through a carbon atom and/or—if present—through a nitrogen atom or through two carbon atoms or through two nitrogen atoms. Examples include:

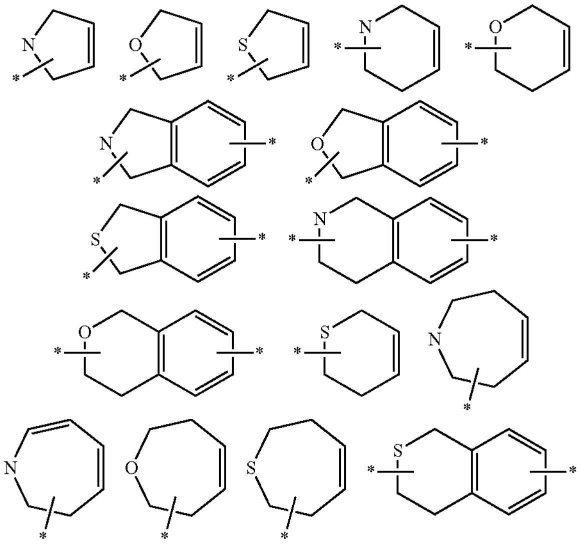

-continued

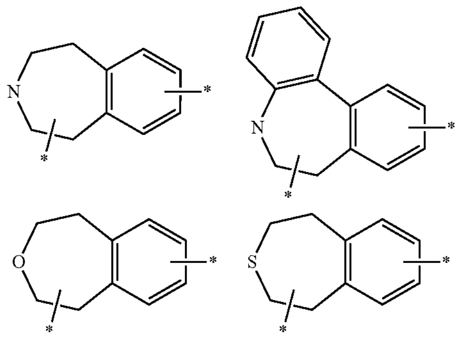

By the term "saturated diaza-spirocycles" are meant nine-, ten- or eleven-membered spirocyclic rings which contain two nitrogen atoms. The spirocyclic group is linked to the remainder of the molecule through the two nitrogen atoms. Examples include:

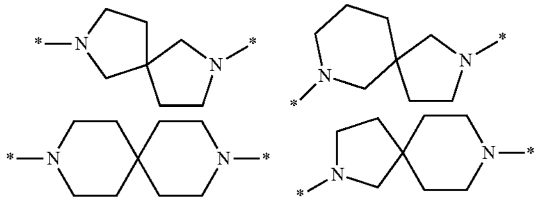

By the term "aryl" (including those which are part of other groups) are meant aromatic ring systems with 6 or 10 carbon atoms. Examples of these are phenyl, 1-naphthyl or 2-naphthyl; preferred aryl groups are phenyl and 1-naphthyl; the particularly preferred aryl group is phenyl. Unless otherwise stated, the aromatic groups may be substituted by one or more groups selected from among methyl, ethyl, n-propyl, iso-propyl, tert-butyl, hydroxy, methoxy, trifluoromethoxy, fluorine, chlorine, bromine and iodine, while the groups may be identical or different.

By the term "heteroaryl" are meant five- or six-membered heterocyclic aromatic groups or 9-11 membered bicyclic heteroaryl rings, which may contain one, two or three heteroatoms, selected from among oxygen, sulphur and nitrogen, and additionally contain sufficient conjugated double bonds to form an aromatic system. Examples of five- or six-membered heterocyclic aromatic groups are as follows:

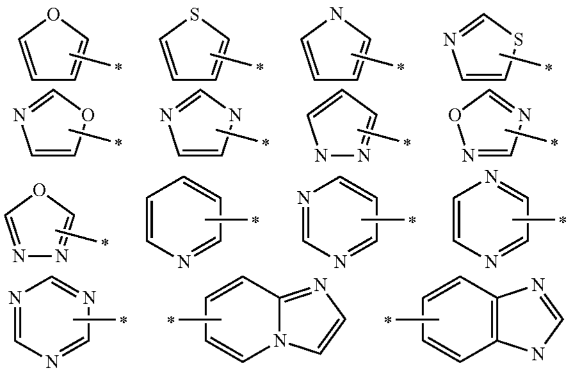

-continued

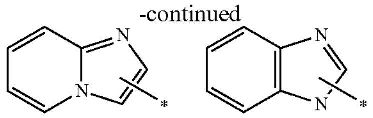

Unless otherwise stated, the heteroaryls mentioned previously may be substituted by one or more groups selected from among methyl, ethyl, n-propyl, iso-propyl, tert-butyl, hydroxy, methoxy, trifluoromethoxy, fluorine, chlorine, bromine and iodine, while the groups may be identical or different.

Bicyclic heteroaryl rings may preferably be substituted in the phenyl group.

By the term "arylene" (including those which are part of other groups) are meant aromatic ring systems with 6 or 10 carbon atoms. Examples include: phenylene, 1-naphthylene or 2-naphthylene, the preferred arylene group being phenylene.

Unless otherwise stated, the aromatic groups may be substituted by one or more groups selected from among methyl, ethyl, n-propyl, iso-propyl, tert-butyl, hydroxy, methoxy, trifluoromethoxy, fluorine, chlorine, bromine and iodine.

These aromatic ring systems are linked to the rest of the molecule at two places independently of one another through a carbon atom in each case.

By the term "heteroarylene" are meant five- or six-membered heterocyclic aromatic groups or 9-11 membered bicyclic heteroaryl rings which may contain one, two or three heteroatoms selected from among oxygen, sulphur and nitrogen, and additionally sufficient conjugated double bonds to form an aromatic system. These heterocyclic aromatic groups are linked at two points independently of one another either through carbon and/or nitrogen.

The following are examples of five- or six-membered heterocyclic aromatic groups:

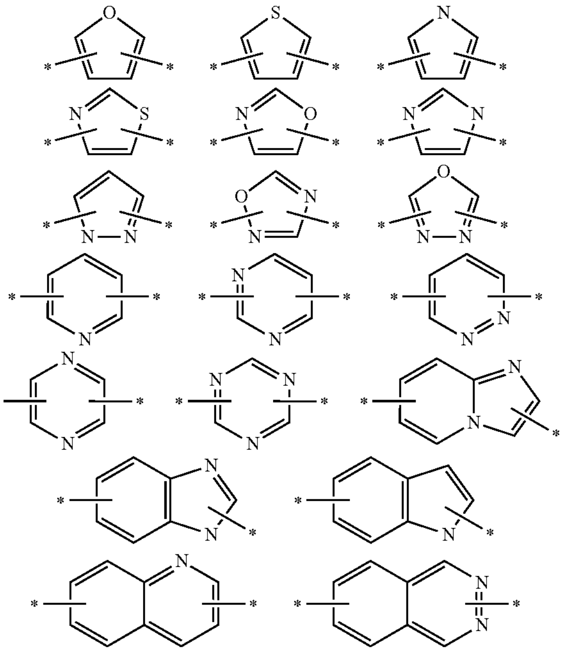

Unless otherwise stated, the heteroaromatic groups may be substituted by one or more groups selected from among methyl, ethyl, n-propyl, iso-propyl, tert-butyl, hydroxy, methoxy, trifluoromethoxy, fluorine, chlorine, bromine and iodine. Preferably, the substituents in the above-mentioned 5-10 membered bicyclic heteroaryl rings are in the phenyl ring.

If they contain suitable basic functions, for example amino groups, compounds of general formula I may be converted, particularly for pharmaceutical use, into the physiologically acceptable salts thereof with inorganic or organic acids. Examples of inorganic acids for this purpose include hydrobromic acid, phosphoric acid, nitric acid, hydrochloric acid, sulphuric acid, methanesulphonic acid, ethanesulphonic acid, benzenesulphonic acid or p-toluenesulphonic acid, while organic acids that may be used include malic acid, succinic acid, acetic acid, fumaric acid, maleic acid, mandelic acid, lactic acid, tartaric acid or citric acid. In addition, any tertiary amino groups present in the molecule may be quaternised. Alkyl halides are used for the reaction. According to the invention methyl iodide is preferably used for the quaternization.

In addition, the compounds of general formula I, if they contain suitable carboxylic acid functions, may if desired be converted into the addition salts thereof with inorganic or organic bases. Examples of inorganic bases include alkali or alkaline earth metal hydroxides, e.g. sodium hydroxide or potassium hydroxide, or carbonates, ammonia, zinc or ammonium hydroxides; examples of organic amines include diethylamine, triethylamine, ethanolamine, diethanolamine, triethanolamine, cyclohexylamine or dicyclohexylamine.

The compounds according to the invention may be present as racemates, provided that they have only one chiral element, but may also be obtained as pure enantiomers, i.e. in the (R) or (S) form.

However, the application also includes the individual diastereomeric pairs of antipodes or mixtures thereof, which are obtained if there is more than one chiral element in the compounds of general formula I, as well as the individual optically active enantiomers of which the above-mentioned racemates are made up. The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

METHODS OF PREPARATION

According to the invention the compounds of general formula I are obtained by methods known per se, for example by the following methods:

Scheme 1

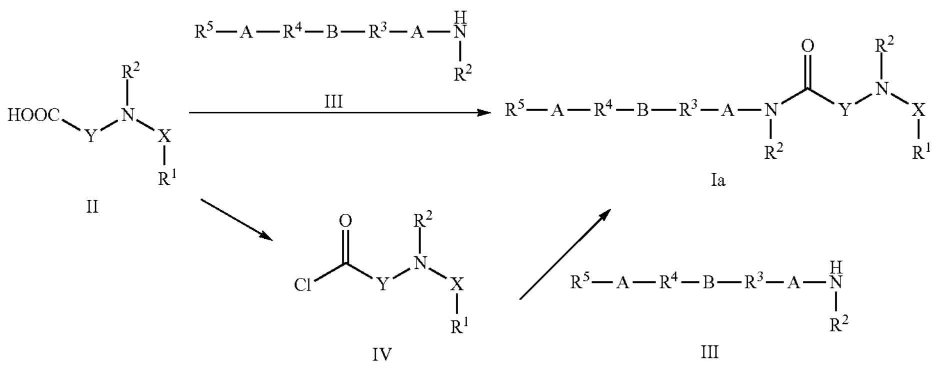

The linking of carboxylic acids of general formula III shown in Scheme 1 wherein all the groups are as hereinbefore defined, with amines of general formula IV, wherein all the groups are as hereinbefore defined, forming carboxylic acid amides of general formula Ia, wherein all the groups are as hereinbefore defined, may be carried out using conventional methods of amide formation.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N',N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30° C. and +30° C., preferably −20° C. and +25° C. If necessary, N-ethyl-diisopropylamine (Hünig base) is preferably used as an additional auxiliary base.

An alternative method of attachment consists in converting a carboxylic acid of general formula III, wherein all the groups are as hereinbefore defined, into a carboxylic acid chloride of general formula V, wherein all the groups are as hereinbefore defined, and subsequent reaction with an amine of general formula IV, wherein all the groups are as hereinbefore defined. The synthesis of a carboxylic acid chloride of general formula V is carried out using methods known from the literature (see e.g. Houben-Weyl, Methoden der Organischen Chemie, vol. E5/1).

The carboxylic acids of general formula III used as starting materials, wherein all the groups are as hereinbefore defined, is obtained using methods known per se from the literature, for example by the methods of synthesis shown in Schemes 2 to 7.

Scheme 2

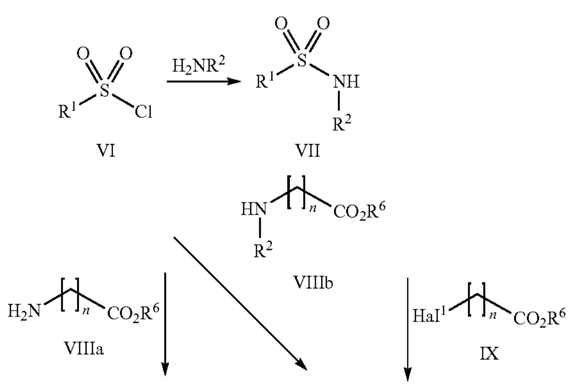

VI, VII, VIIIb, VIIIa, IX

-continued

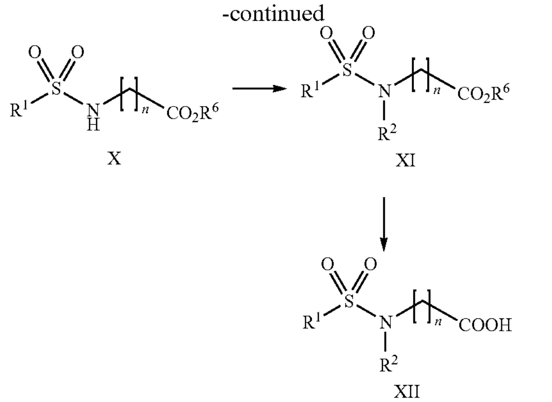

X, XI, XII

The sulphonic acid chlorides of general formula VI, wherein $R^1$ is as hereinbefore defined, are either known from the literature or commercially obtainable. They are reacted under standard reaction conditions with an amine of general formulae $H_2N—R^2$, VIIIa or VIIIb to obtain sulphonic acid amides of general formulae VII, X or XI, wherein $R^1$ and $R^2$ are hereinbefore defined and n denotes a number 1, 2, 3 or 4 and $R^6$ denotes a $C_{1-6}$-alkyl group. The reaction is optionally carried out in the presence of a base such as triethylamine, DIPEA or pyridine and an inert solvent such as dichloromethane or tetrahydrofuran at a temperature of 0° C. to 100° C. with a typical reaction time of one to 24 hours.

The reaction of the sulphonic acid amides of general formula VII with a halide of general formula IX, wherein $Hal^1$ denotes chlorine or bromine, is carried out using methods known from the literature, for example with the aid of a base such as potassium or sodium carbonate in dimethylformamide or tetrahydrofuran at 0° C. to 100° C.

The hydrolysis of the carboxylic acid esters of general formula XI, wherein $R^1$ and $R^2$ are as hereinbefore defined, n denotes a number 1, 2, 3 or 4 and $R^6$ denotes a $C_{1-3}$-alkyl group, to obtain carboxylic acids of general formula XII, wherein $R^1$ and $R^2$ are as hereinbefore defined and n denotes a number 1, 2, 3 or 4 and $R^6$ denotes a $C_{1-3}$-alkyl group, is carried out under known conditions, for example with lithium or sodium carbonate and water in methanol and/or tetrahydrofuran.

Scheme 3

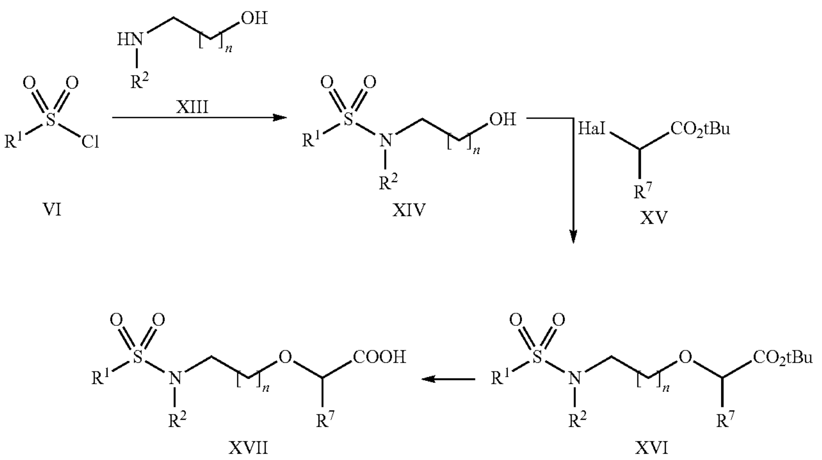

VI, XIII, XIV, XV, XVII, XVI

The preparation of sulphonic acid amides of general formula XIV is carried out as described under Scheme 2.

The alkylation of the hydroxyl function of the sulphonic acid amides of general formula XIV, wherein $R^1$ and $R^2$ are as hereinbefore defined with the proviso that $R^2$ does not denote a hydrogen atom, and n denotes a number 1, 2, 3 or 4 and $R^6$ denotes a $C_{1-3}$-alkyl group, is carried out under reaction conditions known from the literature, for example under 2-phase conditions using a phase transfer catalyst in the presence of a strong inorganic base such as sodium hydroxide solution or potassium hydroxide solution and in an inert solvent such as toluene at 0° C. to 100° C.

The cleaving of the tert-butylester of general formula XVI, wherein $R^1$ and $R^2$ are as hereinbefore defined, n denotes a number 1, 2, 3 or 4 and $R^6$ denotes a $C_{1-3}$-alkyl group and $R^7$ denotes a hydrogen atom or a $C_{1-3}$-alkyl group, is carried out using methods known from the literature (see e.g. Philip J. Kocieński, Protecting Groups, 3rd Edition, 2005, published by Georg Thieme).

Scheme 4

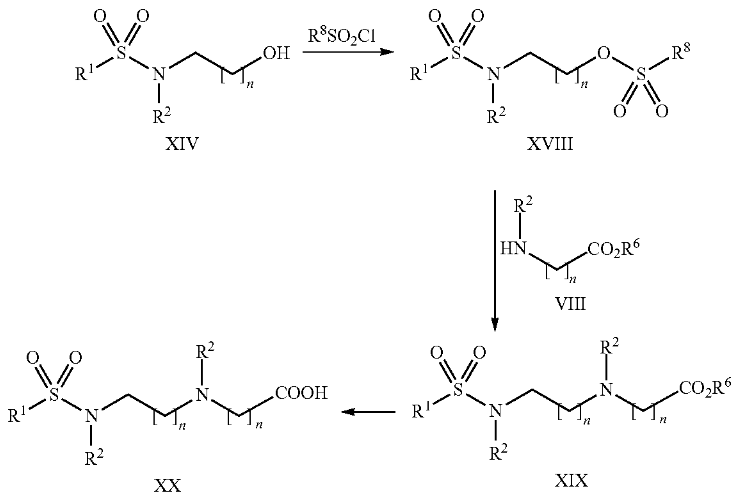

XIV XVIII VIII XIX XX

The sulphonation of the hydroxyl function of a compound of general formula XIV, wherein $R^1$ and $R^2$ are as hereinbefore defined, with the proviso that $R^2$ does not denote a hydrogen atom, and n denotes a number 1, 2, 3 or 4 and $R^6$ denotes a $C_{1-3}$-alkyl group, with a sulphonic acid chloride of general formula $R^8SO_2Cl$, wherein $R^8$ denotes a $C_{1-3}$-alkyl group or a phenyl group optionally substituted by a $C_{1-3}$-alkyl group, to form compounds of general formula XVIII, wherein all the groups are as hereinbefore defined, is carried out under standard reaction conditions, typically in the presence of a base such as DMAP and/or pyridine and an inert solvent such as dichloromethane or THF at −5° C. to 35° C. A liquid base such as pyridine may be used as the base and solvent simultaneously.

The subsequent alkylation of the amines of general formula VII to form compounds of general formula XIX, wherein $R^1$ and $R^2$ are as hereinbefore defined, n denotes a number 1, 2, 3 or 4 and $R^6$ denotes a $C_{1-3}$-alkyl group and $R^6$ denotes a $C_{1-6}$-alkyl group, is conveniently carried out in a solvent such as toluene, chlorobenzene, dimethylformamide, dimethylsulphoxide (DMSO), dichloromethane, acetonitrile or pyridine, for example at temperatures between 0° C. and 150° C. and conveniently in the presence of bases such as pyridine, triethylamine, DIPEA, potassium carbonate, potassium-tert-butoxide or sodium methoxide, the alkylsulphonate serving as the leaving group.

The hydrolysis of the carboxylic acid esters of general formula XIX to form carboxylic acids of general formula XX is carried out as described under Scheme 2.

Scheme 5

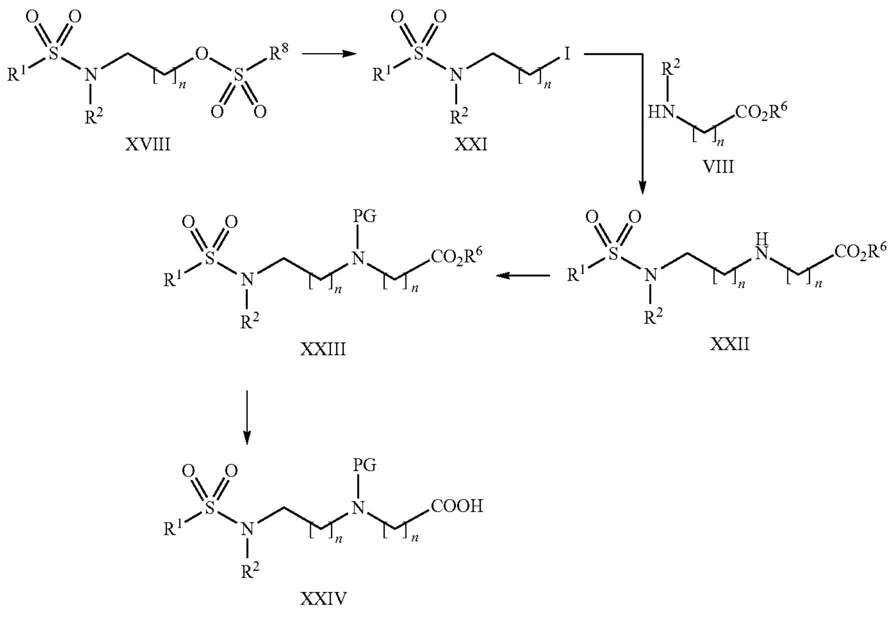

XVIII XXI VIII XXIII XXII XXIV

The Finkelstein reaction of compounds of general formula XVIII, wherein $R^1$ and $R^2$ are as hereinbefore defined, n denotes a number 1, 2, 3 or 4 and $R^6$ denotes a $C_{1-3}$-alkyl group and $R^8$ denotes a $C_{1-3}$-alkyl group or a phenyl group optionally substituted by a $C_{1-3}$-alkyl group, to form halides of general formula XXI, wherein $R^1$ and $R^2$ are as hereinbefore defined and n denotes a number 1, 2, 3 or 4 and $R^6$ denotes a $C_{1-3}$-alkyl group, is carried out under known reaction conditions (see e.g. H. Finkelstein, Berichte der Deutschen Chemischen Gesellschaft 43, 1910, 1528).

The subsequent alkylation of the glycine ester is carried out as described under Scheme 4 ($R^2 \neq H$).

The amino function in the compounds of general formula XXIII is protected by a conventional protective group PG by known methods. The selected protective group is one which can be cleaved under non-hydrogenolytic conditions. A preferred protective group is the Boc group. An overview of the chemistry of protective groups can be found in Theodora W. Greene and Peter G. M. Wuts, Protective Groups in Organic Synthesis, Second Edition, 1991, published by John Wiley and Sons, and in Philip J. Kocieński, Protecting Groups, 3rd Edition, 2005, published by Georg Thieme.

The cleaving of the carboxylic acid esters of general formula XXIII to form carboxylic acids of general formula XXIV is carried out as described under Scheme 2.

Scheme 6

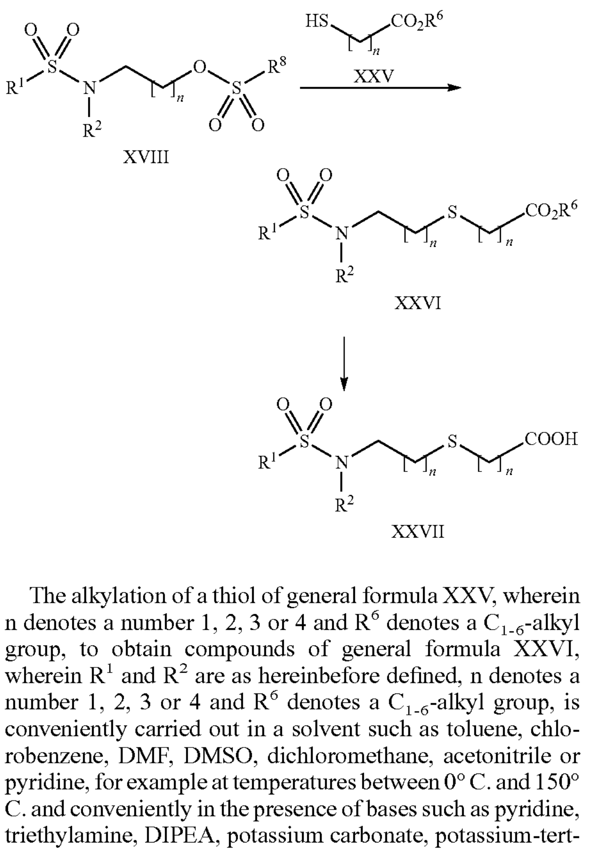

XVIII XXV XXVI XXVII

The alkylation of a thiol of general formula XXV, wherein n denotes a number 1, 2, 3 or 4 and $R^6$ denotes a $C_{1-6}$-alkyl group, to obtain compounds of general formula XXVI, wherein $R^1$ and $R^2$ are as hereinbefore defined, n denotes a number 1, 2, 3 or 4 and $R^6$ denotes a $C_{1-6}$-alkyl group, is conveniently carried out in a solvent such as toluene, chlorobenzene, DMF, DMSO, dichloromethane, acetonitrile or pyridine, for example at temperatures between 0° C. and 150° C. and conveniently in the presence of bases such as pyridine, triethylamine, DIPEA, potassium carbonate, potassium-tert-butoxide or sodium methoxide, while the alkylsulphonate serves as leaving group.

The hydrolysis of the carboxylic acid esters of general formula XXVI to form carboxylic acids of general formula XXVII, wherein all the groups are as hereinbefore defined, is carried out as described under Scheme 2.

Scheme 7

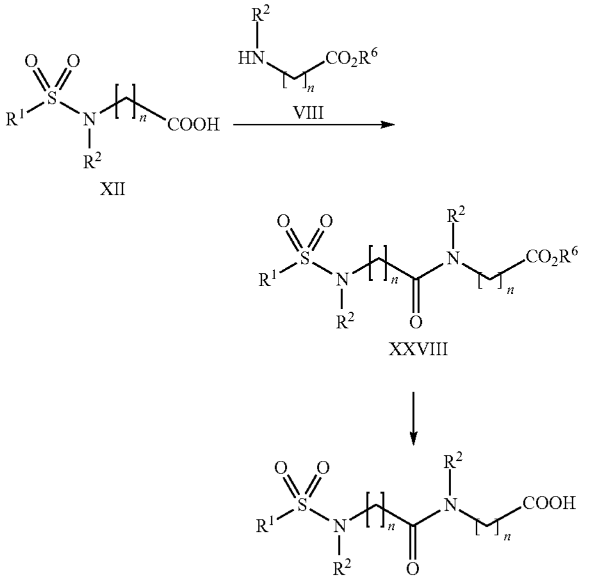

XII VIII XXVIII XXIX

The amide linking of carboxylic acids of general formula XII, wherein $R^1$ and $R^2$ are as hereinbefore defined and n denotes a number 1, 2, 3 or 4, and amino acids of general formula VIII, wherein $R^1$ and $R^2$ are as hereinbefore defined, n denotes a number 1, 2, 3 or 4 and $R^6$ denotes a $C_{1-6}$-alkyl group, to obtain carboxylic acid amides of general formula XXVIII, wherein $R^1$ and $R^2$ are as hereinbefore defined, n denotes a number 1, 2, 3 or 4 and $R^6$ denotes a $C_{1-6}$-alkyl group, is carried out as described under Scheme 1.

As mentioned under Scheme 2, the carboxylic acid ester of general formula XXVIII is cleaved to form carboxylic acid of general formula XXIX, wherein $R^1$ and $R^2$ are as hereinbefore defined and n denotes a number 1, 2, 3 or 4.

The amines of general formula IV used as starting materials are either commercially obtainable, or are obtained using methods known per se from the literature, for example by the methods of synthesis represented in Schemes 8 to 12, wherein $R^{1.1}$ is as hereinbefore defined, $Hal^1$ denotes a chlorine or bromine atom and $Hal^2$ denotes a fluorine, chlorine or bromine atom or a group $R^9$.

Scheme 8

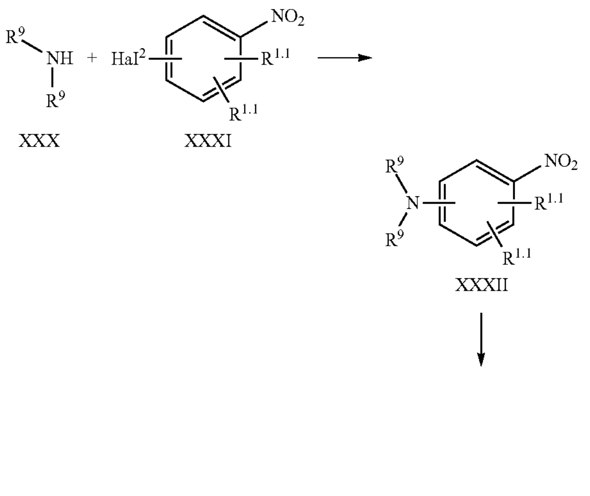

XXX XXXI XXXII

-continued

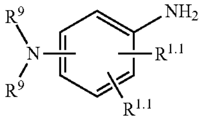

XXXIII

The reaction of an amine of general formula XXX, wherein $R^9$ denotes a $C_{1-3}$-alkyl group, with a halo-nitrobenzene of general formula XXXI, wherein $R^{1.1}$ is as hereinbefore defined and $Hal^2$ denotes a fluorine, chlorine or bromine atom or a group $R^9$, is carried out using known methods, for example in a solvent such as tetrahydrofuran, dimethylformamide or dimethylsulphoxide and conveniently in the presence of a suitable base such as triethylamine or potassium carbonate, at a temperature of 20° C. to 160° C. If the amine of general formula XXX is liquid, the reaction may also be carried out without a solvent and additional base.

The reduction of the nitro group to form anilines of general formula XXXIII, wherein $R^{1.1}$ is as hereinbefore defined and $R^9$ denotes a $C_{1-3}$-alkyl group, is carried out under standard reaction conditions (see e.g. Richard C. Larock, Comprehensive Organic Transformations, 1989, VCH), preferably under standard conditions of catalytic hydrogenolysis with a catalyst such as palladium on charcoal or Raney nickel in a solvent such as methanol or ethanol.

Scheme 9

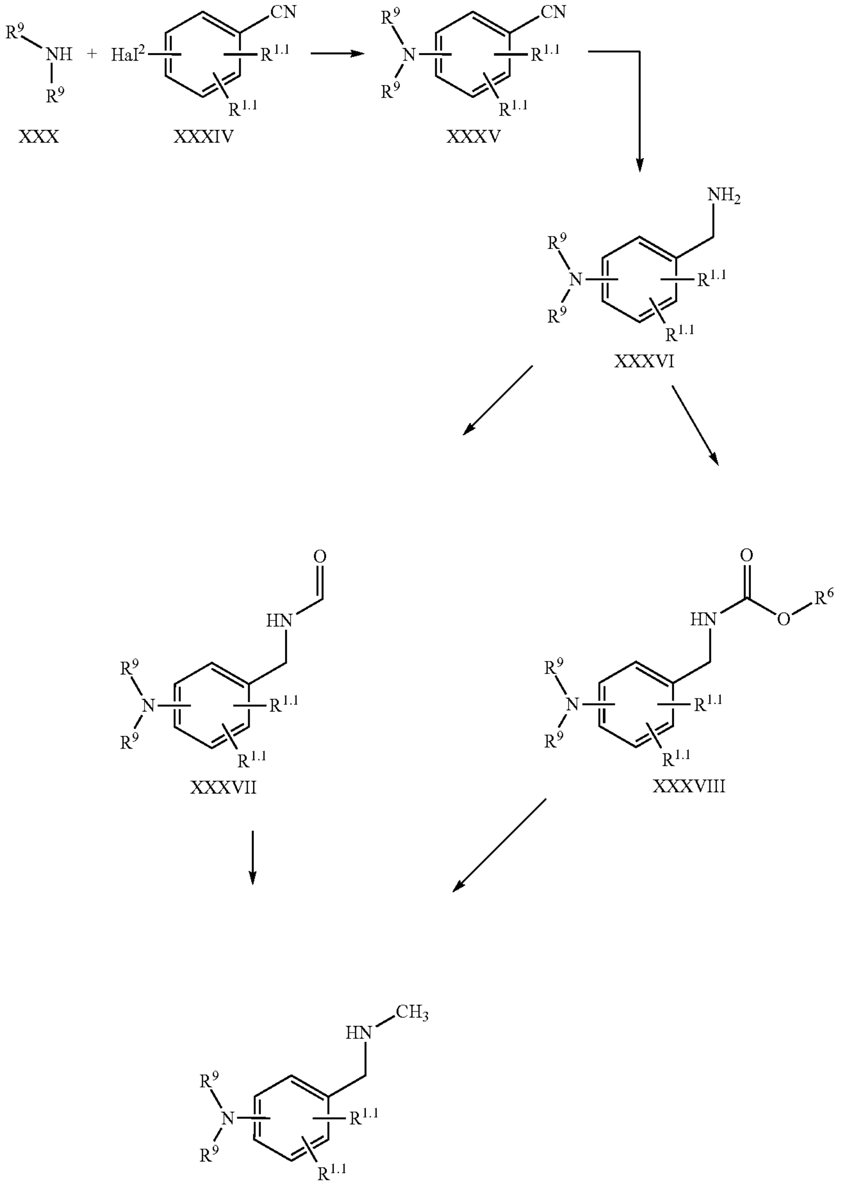

XXX XXXIV XXXV XXXVI XXXVII XXXVIII XXXIX

The reaction of compounds of general formulae XXX, wherein $R^9$ denotes a $C_{1-3}$-alkyl group, with a compound of general formula XXXIV, wherein $R^{1.1}$ is as hereinbefore defined and $Hal^2$ denotes a fluorine, chlorine or bromine atom or a group $R^9$, to obtain compounds of general formula XXXV, wherein $R^{1.1}$ is as hereinbefore defined and $R^9$ denotes a $C_{1-3}$-alkyl group, is carried out as described under Scheme 8.

The reduction of a nitrile of general formula XXXV to form an amine of general formula XXXVI, wherein $R^{1.1}$ is as hereinbefore defined and $R^9$ denotes a $C_{1-3}$-alkyl group, may be carried out under standard conditions of catalytic hydrogenolysis with a catalyst such as for example Raney nickel in a solvent such as ammoniacal methanol or ethanol or with a reducing agent such as lithium aluminium hydride or sodium borohydride in a solvent such as tetrahydrofuran, optionally in the presence of aluminium chloride.

The formylation of an amine of general formula XXXVI to obtain a compound of general formula XXXVII, wherein $R^{1.1}$ is as hereinbefore defined and $R^9$ denotes a $C_{1-3}$-alkyl group, is conveniently carried out in a solvent such as dichloromethane, for example at temperatures from 40° C. to 70° C. and in the presence of acetic anhydride and formic acid.

The carbamate formation to obtain compounds of general formula XXXVIII, wherein $R^{1.1}$ is as hereinbefore defined, $R^6$ denotes a $C_{1-6}$-alkyl and $R^9$ denotes a $C_{1-3}$-alkyl group is carried out by known methods, for example with a chloroformic acid ester or Boc-anhydride in the presence of a base such as triethylamine or sodium hydroxide solution and a solvent such as THF or dioxane.

The reduction of the formyl or of the carbamate to obtain compounds of general formula XXXIX, wherein $R^{11}$ is as hereinbefore defined and $R^9$ denotes a $C_{1-3}$-alkyl group, is carried out under standard reaction conditions, preferably with a reducing agent such as lithium aluminium hydride and in a solvent such as tetrahydrofuran at a temperature of 50° C. to 100° C.

Scheme 10

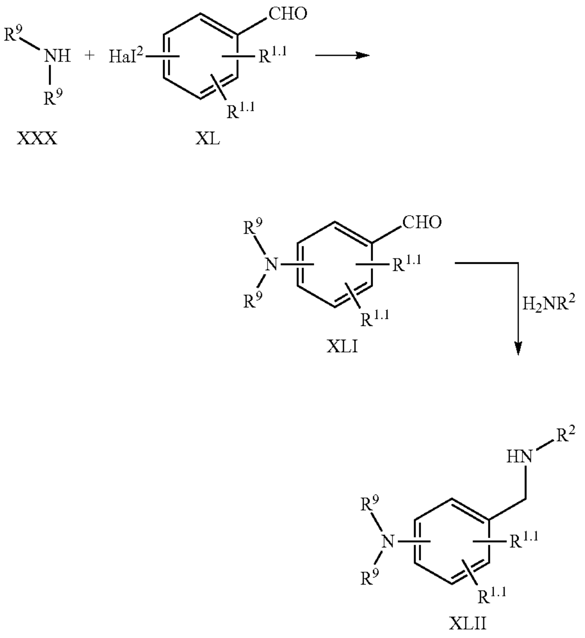

XXX XL XLI XLII

The halogen-nitrogen exchange in compounds of general formulae XXX, wherein $R^9$ denotes a $C_{1-3}$-alkyl group, and XL, wherein $R^{1.1}$ is as hereinbefore defined and $Hal^2$ denotes a fluorine, chlorine or bromine atom or a group $R^9$, for preparing compounds of general formula XLI, wherein $R^{1.1}$ is as hereinbefore defined and $R^9$ denotes a $C_{1-3}$-alkyl group, is carried out as described under Scheme 8.

The reaction of benzaldehydes of general formula XLI, wherein $R^{1.1}$ is as hereinbefore defined and $R^9$ denotes a $C_{1-3}$-alkyl group, with an amine of general formula $H_2NR^2$, wherein $R^2$ is as hereinbefore defined, to obtain a compound of general formula XLII, wherein $R^{1.1}$ and $R^2$ are as hereinbefore defined and $R^9$ denotes a $C_{1-3}$-alkyl group, is a reductive amination. It is carried out by known methods, for example with a reducing agent such as sodium triacetoxyborohydride, sodium borohydride or sodium cyanoborohydride, conveniently in a solvent such as tetrahydrofuran or dichloromethane, optionally with the addition of acetic acid.

Scheme 11

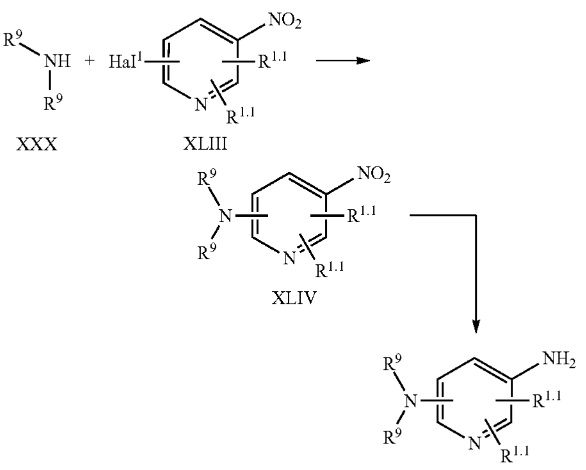

XXX XLIII XLIV XLV

The reaction of an amine of general formula XXX, wherein $R^9$ denotes a $C_{1-3}$-alkyl group, with a halogen-nitropyridine of general formula XLIII, wherein $R^{1.1}$ is as hereinbefore defined and $Hal^1$ denotes a chlorine or bromine atom, is carried out by known methods, for example in a solvent such as tetrahydrofuran, dichloromethane, methanol or DMSO and conveniently in the presence of a suitable base such as triethylamine, sodium hydroxide solution or potassium carbonate and at a temperature of 20° C. to 100° C.

The subsequent reduction of the nitro group of a compound of general formula XLIV, wherein $R^{1.1}$ is as hereinbefore defined and $R^9$ denotes a $C_{1-3}$-alkyl group, to obtain compounds of general formula XLV, wherein $R^{1.1}$ is as hereinbefore defined and $R^9$ denotes a $C_{1-3}$-alkyl group, is carried out as described under Scheme 8.

Scheme 12

$$R^5—A—R^4—B—R^3—COOH \xrightarrow{H_2NR^2}$$

XLVI

-continued

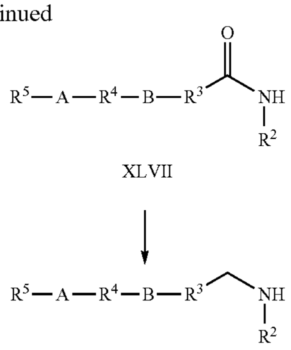

XLVII

XLVIII

The amide linking of carboxylic acids of general formula XLVI, wherein all the groups are as hereinbefore defined, and amines of general formula $H_2NR^2$, wherein $R^2$ is as hereinbefore defined, to form carboxylic acid amides of general formula XLVII, wherein all the groups are as hereinbefore defined, is carried out as described under Scheme 1.

The reduction of carboxylic acid amides of general formula XLVII to obtain amines of general formula XLVIII, wherein all the groups are as hereinbefore defined, is carried out under standard reaction conditions, preferably in the presence of a reducing agent such as lithium aluminium hydride and a solvent such as tetrahydrofuran at 40° C. to 100° C.

Description of the Method of hBK1 Receptor Binding

CHO cells expressing the hBK1 receptor are cultivated in Dulbecco's modified medium. The medium from confluent cultures is removed and the cells are washed with PBS buffer, scraped off and isolated by centrifugation. The cells are then homogenized in suspension and the homogenate is centrifuged and resuspended. The protein content is determined and the membrane preparation obtained in this manner is then frozen at −80° C.

After thawing, 200 μl of the homogenate (50 to 100 μg of proteins/assay) are incubated at room temperature with 0.5 to 1.0 nM of kallidin (DesArg10, Leu9), [3,4-prolyl-3,43H(N)] and increasing concentrations of the test substance in a total volume of 250 μl for 60 minutes. The incubation is terminated by rapid filtration through GF/B glass fibre filters which had been pretreated with polyethyleneimine (0.3%). The protein-bound radioactivity is measured in a TopCount NXT. Non-specific binding is defined as radioactivity bound in the presence of 1.0 μM of kallidin (DesArg10, Leu9), [3,4-prolyl-3,43H(N)]. The concentration/binding curve is analysed using a computer-assisted nonlinear curve fitting. The K which corresponds to the test substance is determined using the data obtained in this manner.

To demonstrate that the compounds of general formula I with different structural elements show good to very good bradykinin-B1-receptor antagonistic effects, the following Table gives the $K_i$ values obtained according to the test method described above. It is pointed out that the compounds were selected for their different structural elements and not in order to emphasise specific compounds:

| Example | $K_i$ [nM] |
|---|---|
| (1) | 6.2 |
| (13) | 2.1 |
| (22) | 7 |
| (53) | 2.4 |
| (55) | 0.7 |
| (59) | 6.3 |
| (61) | 3.3 |
| (66) | 4.6 |
| (67) | 0.4 |
| (72) | 2.8 |
| (73) | 6.8 |
| (77) | 8.7 |
| (78) | 5.8 |
| (97) | 6.7 |
| (102) | 5.0 |
| (109) | 6.0 |
| (114) | 4.4 |
| (117) | 0.99 |
| (130) | 5.7 |
| (180) | 5.2 |
| (181) | 7.1 |
| (182) | 4.8 |
| (183) | 6.6 |
| (184) | 1.3 |
| (186) | 3.4 |
| (188) | 9.4 |
| (216) | 4.9 |
| (227) | 4.8 |
| (269) | 7.8 |
| (303) | 6.32 |
| (323) | 2.8 |
| (325) | 0.94 |
| (326) | 6.5 |
| (334) | 8.65 |
| (335) | 9.37 |
| (338) | 1.11 |
| (352) | 9.2 |
| (353) | 6.1 |
| (356) | 8.8 |
| (358) | 3.5 |
| (360) | 4.4 |
| (361) | 7.4 |
| (365) | 2.4 |
| (367) | 2.7 |
| (368) | 1.52 |
| (369) | 3.8 |
| (372) | 2.39 |
| (381) | 8.1 |
| (383) | 6.2 |
| (384) | 9.3 |
| (385) | 6.4 |
| (386) | 6.3 |
| (389) | 3.7 |
| (392) | 8.3 |
| (393) | 1.6 |
| (394) | 1.04 |
| (397) | 7.5 |
| (398) | 0.74 |
| (399) | 3 |
| (400) | 0.79 |
| (401) | 2.7 |
| (402) | 9.3 |
| (404) | 2.8 |
| (418) | 1.2 |
| (419) | 0.65 |
| (420) | 9.1 |
| (421) | 8.7 |
| (423) | 3.4 |
| (424) | 1.4 |
| (425) | 8.3 |
| (428) | 6.3 |
| (435) | 1.5 |
| (439) | 7.5 |
| (441) | 4.6 |
| (444) | 6.9 |
| (445) | 5.6 |
| (448) | 0.82 |
| (451) | 9 |
| (458) | 4.3 |
| (463) | 2 |
| (464) | 1.5 |
| (465) | 3.8 |

-continued

| Example | $K_i$ [nM] |
|---|---|
| (468) | 1 |
| (469) | 8 |
| (471) | 4.1 |
| (472) | 0.68 |
| (473) | 1.8 |
| (474) | 1.4 |
| (475) | 2.4 |
| (476) | 2.35 |
| (477) | 5.8 |
| (478) | 1 |
| (492) | 3.2 |
| (576) | 0.85 |
| (577) | 0.34 |
| (580) | 6.2 |
| (582) | 9.3 |
| (584) | 9.0 |
| (586) | 5.1 |
| (587) | 9.5 |
| (588) | 1.5 |
| (589) | 5.1 |
| (591) | 1.9 |
| (592) | 2.8 |
| (613) | 9.7 |
| (614) | 2 |
| (616) | 3.7 |
| (619) | 1.2 |
| (620) | 5.9 |
| (621) | 5.8 |
| (623) | 3.4 |
| (624) | 8 |
| (630) | 5.5 |

INDICATIONS

By virtue of their pharmacological properties, the novel compounds and their physiologically acceptable salts are suitable for treating diseases and symptoms of diseases caused at least to some extent by stimulation of bradykinin-B1 receptors.

In view of their pharmacological effect the substances are suitable for the treatment of (a) acute pain such as e.g. toothache, peri- and postoperative pain, traumatic pain, muscle pain, the pain caused by burns, sunburn, trigeminal neuralgia, pain caused by colic, as well as spasms of the gastro-intestinal tract or uterus;

(b) visceral pain such as e.g. chronic pelvic pain, gynecological pain, pain before and during menstruation, pain caused by pancreatitis, peptic ulcers, interstitial cystitis, renal colic, angina pectoris, pain caused by irritable bowel, non-ulcerative dyspepsia and gastritis, non-cardiac thoracic pain and pain caused by myocardial ischaemia and cardiac infarct;

(c) neuropathic pain such as e.g. painful neuropathies, pain of diabetic neuropathy, AIDS-associated neuropathic pain, pain of lumbago, non-herpes-associated neuralgia, post-zoster neuralgia, nerve damage, cerebro-cranial trauma, pain of nerve damage caused by toxins or chemotherapy, phantom pain, pain of multiple sclerosis, nerve root tears and painful traumatically-caused damage to individual nerves;

(d) inflammatory/pain receptor-mediated pain in connection with diseases such as osteoarthritis, rheumatoid arthritis, rheumatic fever, tendo-synovitis, tendonitis, gout, vulvodynia, damage to and diseases of the muscles and fascia (muscle injury, fibromyalgia), osteoarthritis, juvenile arthritis, spondylitis, gout-arthritis, psoriasis-arthritis, fibromyalgia, myositis, migraine, dental disease, influenza and other virus infections such as colds, systemic lupus erythematodes, (e) tumour pain associated with cancers such as lymphatid or myeloid leukaemia, Hodgkin's disease, non-Hodgkin's lymphomas, lymphogranulomatosis, lymphosarcomas, solid malignant tumours and extensive metastases;

(f) headache diseases such as e.g. headache of various origins, cluster headaches, migraine (with or without aura) and tension headaches.

The compounds are also suitable for treating (g) inflammatory changes connected with diseases of the airways such as bronchial asthma, including allergic asthma (atopic and non-atopic) as well as bronchospasm on exertion, occupationally induced asthma, viral or bacterial exacerbation of an existing asthma and other non-allergically induced asthmatic diseases;

chronic obstructive pulmonary disease (COPD) including pulmonary emphysema, acute adult respiratory distress syndrome (ARDS), bronchitis, lung inflammation, allergic rhinitis (seasonal and all year round), vasomotor rhinitis and diseases caused by dust in the lungs such as aluminosis, anthracosis, asbestosis, chalicosis, siderosis, silicosis, tabacosis and byssinosis;

(h) inflammatory phenomena caused by sunburn and burns, oedema after burns trauma, cerebral oedema and angiooedema, intestinal complaints including Crohn's diseases and ulcerative colitis, irritable bowel syndrome, pancreatitis, nephritis, cystitis (interstitial cystitis), uveitis; inflammatory skin diseases (such as e.g. psoriasis and eczema), vascular diseases of the connective tissue, lupus, sprains and fractures;

(i) diabetes mellitus and its effects (such as e.g. diabetic vasculopathy, diabetic neuropathy, diabetic retinopathy) and diabetic symptoms in insulitis (e.g. hyperglycaemia, diuresis, proteinuria and increased renal excretion of nitrite and kallikrein);

(j) neurodegenerative diseases such as Parkinson's disease and Alzheimer's disease;

(k) sepsis and septic shock after bacterial infections or after trauma;

(l) syndromes that cause itching and allergic skin reactions;

(m) osteoporosis;

(n) epilepsy;

(o) damage to the central nervous system;

(p) wounds and tissue damage;

(q) inflammation of the gums;

(r) benign prostatic hyperplasia and hyperactive bladder;

(s) pruritus;

(t) vitiligo;

(u) disorders of the motility of respiratory, genito-urinary, gastro-intestinal or vascular regions and (v) post-operative fever.

In addition to being suitable as human therapeutic agents, these substances are also useful in the veterinary treatment of domestic animals, exotic animals and farm animals.

For treating pain, it may be advantageous to combine the compounds according to the invention with stimulating substances such as caffeine or other pain-alleviating active compounds. If active compounds suitable for treating the cause of the pain are available, these can be combined with the compounds according to the invention. If, independently of the pain treatment, other medical treatments are also indicated, for example for high blood pressure or diabetes, the active compounds required can be combined with the compounds according to the invention.

The following compounds may be used for combination therapy, for example:

Non-steroidal antirheumatics (NSAR): COX-2 inhibitors such as propionic acid derivatives (alminoprofen, benoxaprofen, bucloxic acid, carprofen, fenhufen, fenoprofen, fiuprofen, fiulbiprofen, ibuprofen, indoprofen, ketoprofen, miroprofen, naproxen, oxaprozin, pirprofen, pranoprofen, suprofen, tiaprofenic acid, tioxaprofen), acetic acid derivatives (indomethacin, acemetacin, alcofenac, isoxepac, oxpinax, sulindac, tiopinac, tolmetin, zidometacin, zomepirac) fenamic derivatives (meclofenamic acid, mefenamic acid, tolfenamic acid), biphenyl-carboxylic acid derivatives, oxicams (isoxicam, meloxicam, piroxicam, sudoxicam and tenoxicam), salicylic acid derivatives (acetylsalicylic acid, sulphasalazin, why not also mesalazin, olsalazin, and pyrazolone (apazone, bezpiperylone, feprazone, mofebutazone, oxyphenbutazone, phenylbutazone, why not also propyphenazone and metamizol, and coxibs (celecoxib, valecoxib, rofecoxib, etoricoxib).

Opiate receptor agonists such as e.g. morphine, propoxyphen (Darvon), tramadol, buprenorphine.

Cannabinoid agonists such as e.g. GW-1000, KDS-2000, SAB-378, SP-104, NVP001-GW-843166, GW-842166X, PRS-211375.

Sodium channel blockers such as e.g. carbamazepine, mexiletin, lamotrigin, pregabalin, tectin, NW-1029, CGX-1002.

N-type calcium channel blockers such as e.g. ziconitide, NMED-160, SP1-860.

Serotonergic and noradrenergic modulators such as e.g. SR-57746, paroxetine, duloxetine, clonidine, amitriptyline, citalopram.

Corticosteroids such as e.g. betamethasone, budesonide, cortisone, dexamethasone, hydrocortisone, methylprednisolone, prednisolone, prednisone and triamcinolone.

Histamine H1-receptor antagonists such as e.g. bromopheniramine, chloropheniramine, dexchlorpheniramine, triprolidine, clemastine, diphenhydramine, diphenylpyraline, tripelennamine, hydroxyzine, methdilazine, promethazine, trimeprazine azatadine, cyproheptadine, antazoline, pheniramine, pyrilamine, astemizole, terfenadine, loratadine, cetirizine, desloratadine, fexofenadine, levocetirizine.

Histamine H2-receptor antagonists such as e.g. cimetidine, famotidine, and ranitidine.

Proton pump inhibitors such as e.g. omeprazole, pantoprazole, esomeprazole. Leukotriene antagonists and 5-lipoxygenasehemmer such as e.g. zafirlukast, montelukast, pranlukast and zileuton.

Local anaesthetics such as e.g. ambroxol, lidocaine.

VR1 agonists and antagonists such as e.g. NGX-4010, WL-1002, ALGRX-4975, WL-10001, AMG-517.

Nicotine receptor agonists such as e.g. ABT-202, A-366833, ABT-594, BTG-102, A-85380, CGX1204.

P2X3-receptor antagonists such as e.g. A-317491, ISIS-13920, AZD-9056.

NGF agonists and antagonists such as e.g. RI-724, RI-1024, AMG-819, AMG-403, PPH 207.

NK1 and NK2 antagonists such as e.g. DA-5018, R-116301, CP-728663, ZD-2249.

NMDA antagonists such as e.g. NER-MD-11, CNS-5161, EAA-090, AZ-756, CNP-3381.

potassium channel modulators such as e.g. CL-888, ICA-69673, retigabin.

GABA modulators such as e.g. lacosamide.

Serotonergic and noradrenergic modulators such as e.g. SR-57746, paroxetine, duloxetine, clonidine, amitriptyline, citalopram, flibanserine.

Anti-migraine drugs such as e.g. sumatriptan, zolmitriptan, naratriptan, eletriptan.

The dosage necessary for obtaining a pain-alleviating effect is, in the case of intravenous administration, expediently from 0.01 to 3 mg/kg of body weight, preferably from 0.1 to 1 mg/kg, and, in the case of oral administration, from 0.1 to 8 mg/kg of body weight, preferably from 0.5 to 3 mg/kg, in each case 1 to 3 times per day. The compounds prepared according to the invention can be administered intravenously, subcutaneously, intramuscularly, intrarectally, intranasally, by inhalation, transdermally or orally, aerosol formulations being particularly suitable for inhalation. They can be incorporated into customary pharmaceutical preparations, such as tablets, coated tablets, capsules, powders, suspensions, solutions, metered-dose aerosols or suppositories, if appropriate together with one or more customary inert carriers and/or diluents, for example with maize starch, lactose, cane sugar, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances, such as hardened fat, or suitable mixtures thereof.

EXPERIMENTAL SECTION

Generally, there are IR, $^1$H NMR and/or mass spectra for the compounds that were prepared. The ratios given for the eluants are in volume units of the solvents in question. For ammonia, the given volume units are based on a concentrated solution of ammonia in water.

Unless indicated otherwise, the acid, base and salt solutions used for working up the reaction solutions are aqueous systems having the stated concentrations. For chromatographic purification, silica gel from Millipore (MATREX™, 35-70 μm) or Alox (E. Merck, Darmstadt, Alumina 90 standardized, 63-200 μm, article No. 1.01097.9050) are used.

In the descriptions of the experiments, the following abbreviations are used:

| | |
|---|---|
| CDI | 1,1'-carbonyldiimidazole |
| TLC | thin layer chromatogram |
| DIPEA | diisopropylethylamine |
| DMAP | 4-dimethylaminopyridine |
| DMF | dimethylformamide |
| DMSO | dimethylsulphoxide |
| HATU | O-(7-azabenzotriazol-1-yl)-N,N,N',N'-tetramethyluronium hexafluorophosphate |
| tert | tertiary |
| TBTU | 2-(1H-benzotriazol-1-yl)-1,1,3,3-tetramethyluronium-tetrafluoroborate |
| THF | tetrahydrofuran |

The following analytical HPLC methods were used:

Method 1:

| | | | | |
|---|---|---|---|---|
| column: | XTerra ™ MS C18, 2.5 μM, 4.6 × 30 mm | | | |
| detection: | 210-420 nm | | | |
| eluant A: | water/0.1% formic acid | | | |
| eluant B: | acetonitrile/0.1% formic acid | | | |
| gradient: | time in min | % A | % B | flow rate in mL/min |
| | 0.0 | 95.0 | 5.0 | 1.0 |
| | 0.1 | 95.0 | 5.0 | 1.0 |
| | 3.1 | 2.0 | 98.0 | 1.0 |
| | 4.5 | 2.0 | 98.0 | 1.0 |
| | 5.0 | 95.0 | 5.0 | 1.0 |

Method 2:

| | |
|---|---|
| column: | Microsorb C18, 3 μM, 4.6 × 50 mm |
| detection: | 220-320 nm |
| eluant A: | water/0.1% TFA |
| eluant B: | acetonitrile/0.1% TFA |

-continued

| gradient: | time in min | % A | % B | flow rate in mL/min |
|---|---|---|---|---|
| | 0.0 | 95.0 | 5.0 | 1.5 |
| | 0.5 | 95.0 | 5.0 | 1.5 |
| | 3.8 | 2.0 | 98.0 | 1.5 |
| | 4.3 | 2.0 | 98.0 | 1.5 |
| | 4.35 | 95.0 | 5.0 | 1.5 |
| | 4.6 | 95.0 | 5.0 | 1.5 |

Method 3:

column: XTerra ™ MS C18, 3.5 μM, 4.6 × 50 mm
detection: 210-420 nm
eluant A: water/0.1% formic acid
eluant B: acetonitrile/0.1% formic acid

| gradient: | time in min | % A | % B | flow rate in mL/min |
|---|---|---|---|---|
| | 0.0 | 95.0 | 5.0 | 1.0 |
| | 0.1 | 95.0 | 5.0 | 1.0 |
| | 7.1 | 2.0 | 98.0 | 1.0 |
| | 7.9 | 2.0 | 98.0 | 1.0 |
| | 8.0 | 95.0 | 5.0 | 1.0 |

Method 4:

column: Zorbax Stable Bond C18, 3.5 μM, 4.6 × 75 mm
detection: 230-360 nm
eluant A: water/0.1% formic acid
eluant B: acetonitrile/0.1% formic acid

| gradient: | time in min | % A | % B | flow rate in mL/min |
|---|---|---|---|---|
| | 0.0 | 95.0 | 5.0 | 1.6 |
| | 0.1 | 95.0 | 5.0 | 1.6 |
| | 4.5 | 10.0 | 90.0 | 1.6 |
| | 5.09 | 10.0 | 90.0 | 1.6 |
| | 5.5 | 90.0 | 10.0 | 1.6 |

Method 5:

column: Interchim Strategy C18, 5 μM, 4.6 × 50 mm
detection: 220-320 nm
eluant A: water/0.1% TFA
eluant B: acetonitrile

| gradient: | time in min | % A | % B | flow rate in mL/min |
|---|---|---|---|---|
| | 0.0 | 95.0 | 5.0 | 3.0 |
| | 0.3 | 95.0 | 5.0 | 3.0 |
| | 2.0 | 2.0 | 98.0 | 3.0 |
| | 2.4 | 2.0 | 98.0 | 3.0 |
| | 2.45 | 95.0 | 5.0 | 3.0 |
| | 2.8 | 95.0 | 5.0 | 3.0 |

Method 6:

column: Merck Cromolith Speed ROD RP18e, 4.6 × 50 mm
detection: 190-400 nm
eluant A: water/0.1% formic acid
eluant B: acetonitrile/0.1% formic acid

| gradient: | time in min | % A | % B | flow rate in mL/min |
|---|---|---|---|---|
| | 0.0 | 90.0 | 10.0 | 1.5 |
| | 4.5 | 10.0 | 90.0 | 1.5 |
| | 5.0 | 10.0 | 90.0 | 1.5 |
| | 5.5 | 90.0 | 10.0 | 1.5 |

Method 7:

column: Waters SunFire C18, 3.5 μM, 4.6 × 50 mm
detection: 210-500 nm
eluant A: water/0.1% TFA
eluant B: acetonitrile/0.1% TFA

| gradient: | time in min | % A | % B | flow rate in mL/min |
|---|---|---|---|---|
| | 0.0 | 95.0 | 5.0 | 1.5 |
| | 2.0 | 2.0 | 98.0 | 1.5 |
| | 3.0 | 2.0 | 98.0 | 1.5 |
| | 3.4 | 95.0 | 5.0 | 1.5 |

Method 8:

column: Waters XBridge C18, 3.5 μM, 4.6 × 50 mm
detection: 210-500 nm
eluant A: water/0.1% TFA
eluant B: acetonitrile/0.1% TFA -continued

| gradient: | time in min | % A | % B | flow rate in mL/min |
|---|---|---|---|---|
| | 0.0 | 95.0 | 5.0 | 1.0 |
| | 0.1 | 95.0 | 5.0 | 1.0 |
| | 5.1 | 2.0 | 98.0 | 1.0 |
| | 6.5 | 2.0 | 98.0 | 1.0 |
| | 7.0 | 95.0 | 5.0 | 1.0 |

Method 9:

column: Merck Chromolith ™ Flash RP18e, 4.6 × 25 mm
detection: 190-400 nm
eluant A: water/0.1% formic acid
eluant B: acetonitrile/0.1% formic acid

| gradient: | time in min | % A | % B | flow rate in mL/min |
|---|---|---|---|---|
| | 0.0 | 90.0 | 10.0 | 1.6 |
| | 2.7 | 10.0 | 90.0 | 1.6 |
| | 3.0 | 10.0 | 90.0 | 1.6 |
| | 3.3 | 90.0 | 10.0 | 1.6 |

Method 10:

column: Merck Chromolith ™ Flash RP18e, 4.6 × 25 mm
detection: 210-400 nm
eluant A: water/0.1% TFA
eluant B: acetonitrile/0.1% TFA

| gradient: | time in min | % A | % B | flow rate in mL/min |
|---|---|---|---|---|
| | 0.0 | 95.0 | 5.0 | 2.5 |
| | 0.2 | 95.0 | 5.0 | 2.5 |
| | 1.5 | 2.0 | 98.0 | 2.5 |
| | 1.7 | 2.0 | 98.0 | 2.5 |
| | 1.9 | 95.0 | 5.0 | 2.5 |
| | 2.2 | 95.0 | 5.0 | 2.5 |

Method 11:

column: Waters XBridge C18, 3.5 μM, 4.6 × 50 mm
detection: 210-500 nm
eluant A: water/0.1% TFA
eluant B: acetonitrile/0.1% TFA

| gradient: | time in min | % A | % B | flow rate in mL/min |
|---|---|---|---|---|
| | 0.0 | 95.0 | 5.0 | 1.5 |
| | 2.0 | 0.0 | 100.0 | 1.5 |
| | 3.0 | 0.0 | 100.0 | 1.5 |
| | 3.4 | 95.0 | 5.0 | 1.5 |

Method 12:

column: YMC-Pack ODS-AQ, 3.0 μM, 4.6 × 75 mm
detection: 230-360 nm
eluant A: water/0.1% formic acid
eluant B: acetonitrile/0.1% formic acid

| gradient: | time in min | % A | % B | flow rate in mL/min |
|---|---|---|---|---|
| | 0.0 | 95.0 | 5.0 | 1.6 |
| | 4.5 | 10.0 | 90.0 | 1.6 |
| | 5.0 | 10.0 | 90.0 | 1.6 |
| | 5.5 | 90.0 | 10.0 | 1.6 |

Methode 13:

column: Varian C18 Pursuit XRs, 10 μM, 50 × 250 mm
detection: UV controlled
eluant A: water/0.2% ammonia
eluant B: acetonitrile

| gradient: | time in min | % A | % B | flow rate in mL/min |
|---|---|---|---|---|
| | 0.0 | 90.0 | 10.0 | 100.00 |
| | 1.0 | 90.0 | 10.0 | 100.00 |
| | 1.5 | 90.0 | 10.0 | 180.00 |
| | 13.0 | 0 | 100.0 | 180.00 |
| | 15.5 | 0 | 100.0 | 180.00 |
| | 15.75 | 90.0 | 10.0 | 180.00 |
| | 19.0 | 90.0 | 10.0 | 180.00 |

Methode 14:

column: Waters Xbridge C18, 2.5 μM, 3.0 × 30 mm
detection: 230-360 nm
eluant A: water/0.1% ammonia
eluant B: acetonitrile/0.1% ammonia -continued

| gradient: | time in min | % A | % B | flow rate in mL/min |
|---|---|---|---|---|
| | 0.0 | 95.0 | 5.0 | 1.4 |
| | 1.6 | 50.0 | 5.0 | 1.4 |
| | 1.8 | 10.0 | 90.0 | 1.4 |
| | 2.0 | 10.0 | 90.0 | 1.4 |
| | 2.2 | 95 | 10 | 1.4 |

The following microwave apparatus was used: Biotage EmrysOptimizer™

Preparation of the End Compounds

Example 1

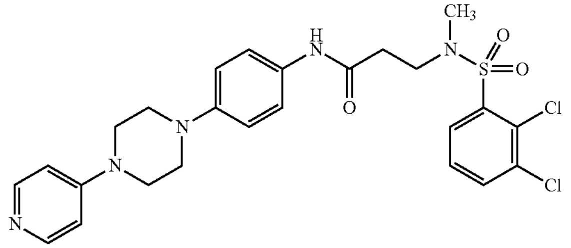

1a)

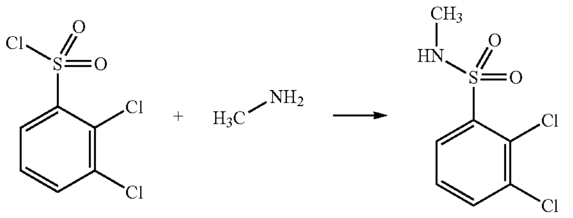

A mixture of 1.0 g (4.07 mmol) of 2,3-dichlorobenzene-sulphonic acid chloride, 0.33 g (4.89 mmol) of methylamine hydrochloride, 2.73 ml (19.55 mmol) of triethylamine and 20 ml dichloromethane is stirred overnight at ambient temperature. The reaction mixture is then washed once with 1N HCl, saturated sodium hydrogen carbonate solution, water and saturated sodium chloride solution, dried on sodium sulphate and then evaporated to dryness.

$C_7H_7Cl_2NO_2S$ (240.11)

[M+H]+=240/242/244

TLC: silica gel, petroleum ether/ethyl acetate 2:1, Rf value=0.50

1b)

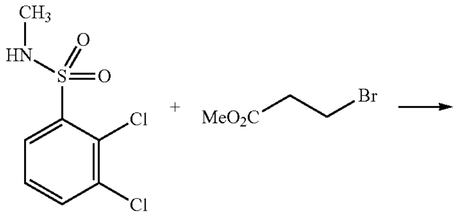

-continued

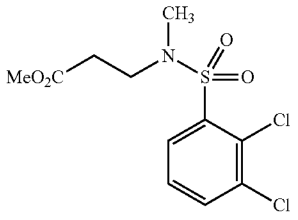

A mixture of 0.9 g (3.75 mmol) of product from 1a and 20 ml DMF is taken and combined with 1.55 g (11.24 mmol) of potassium carbonate and 0.49 ml (4.50 mmol) of ethyl 3-bromopropionate. The reaction mixture is stirred overnight at ambient temperature and then mixed with water. It is extracted twice with ethyl acetate. The organic extracts are washed three times with water and once with saturated sodium chloride solution, dried on sodium sulphate and evaporated to dryness.

$C_{11}H_{13}Cl_2NO_4S$ (326.20)

[M+H]+=326/328/330

TLC: silica gel, petroleum ether/ethyl acetate 2:1, Rf value=0.45

1c)

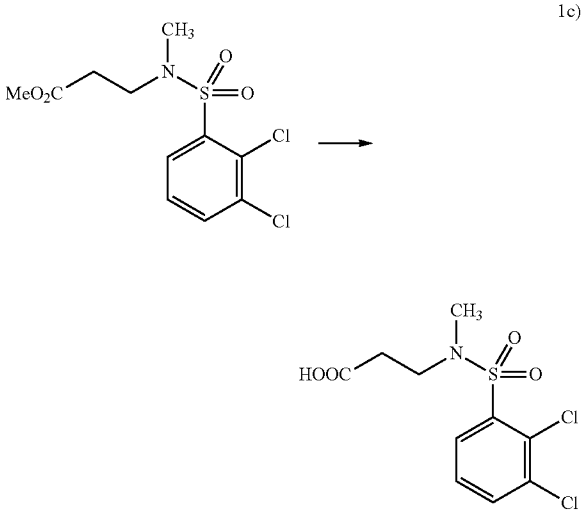

A mixture of 1.15 g (3.53 mmol) of product from 1b, 0.74 g (17.63 mmol) of lithium hydroxide monohydrate, 15 ml THF and 15 ml of water is stirred for one hour at ambient temperature. Then the THF is eliminated in vacuo and the residue is acidified with concentrated HCl. The reaction mixture is then extracted three times with ethyl acetate. The organic extracts are washed with saturated sodium chloride solution, dried on sodium sulphate and evaporated to dryness. The crude product is triturated with diethyl ether and suction filtered.

$C_{10}H_{11}Cl_2NO_4S$ (312.17)

[M+H]+=310/312/314

TLC: silica gel, petroleum ether/ethyl acetate 2:1, Rf value=0.03

1d)

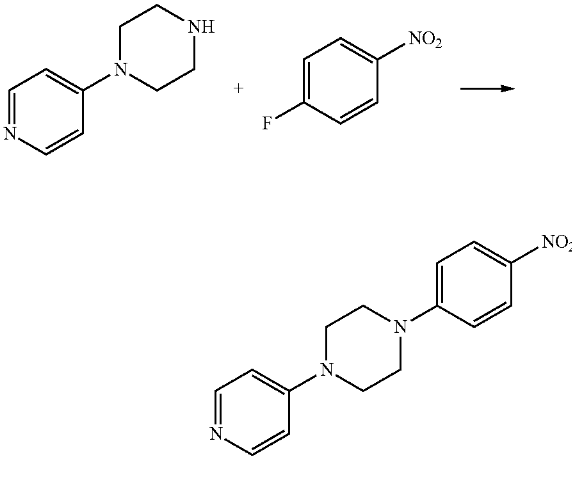

A mixture of 5.0 g (30.63 mmol) of 1-pyridin-4-yl-piperazine, 4.32 g (30.63 mmol) of 1-fluoro-4-nitrobenzene (Aldrich), 10.62 ml (76.59 mmol) of triethylamine and 100 ml DMF is heated for 50 min at reflux temperature and then evaporated to dryness. The crude product thus obtained is purified by column chromatography through silica gel (eluant: dichloromethane/ethanol/ammonia 12:1:0.1 to 10:1:0.1).

$C_{15}H_{16}N_4O_2$ (284.31)

[M+H]+=285

TLC: silica gel, dichloromethane/methanol/ammonia 9:1:0.1, Rf value=0.52

1e)

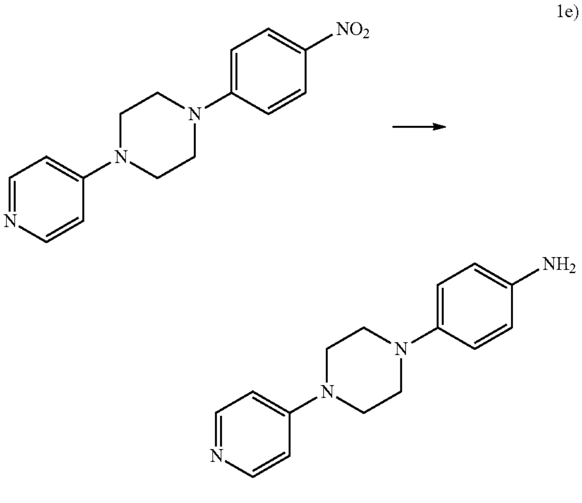

A mixture of 4.95 g (17.41 mmol) of product from 1d, 0.6 g palladium on charcoal (10%), 120 ml dichloromethane and 20 ml of methanol is hydrogenated for five hours in the autoclave at ambient temperature. Then the mixture is suction filtered and the filter cake is decocted another six times with dichloromethane/methanol 1:1 and suction filtered again. The combined filtrates are evaporated to dryness in vacuo.

$C_{15}H_{18}N_4$ (254.33)

[M+H]+=255

1f)

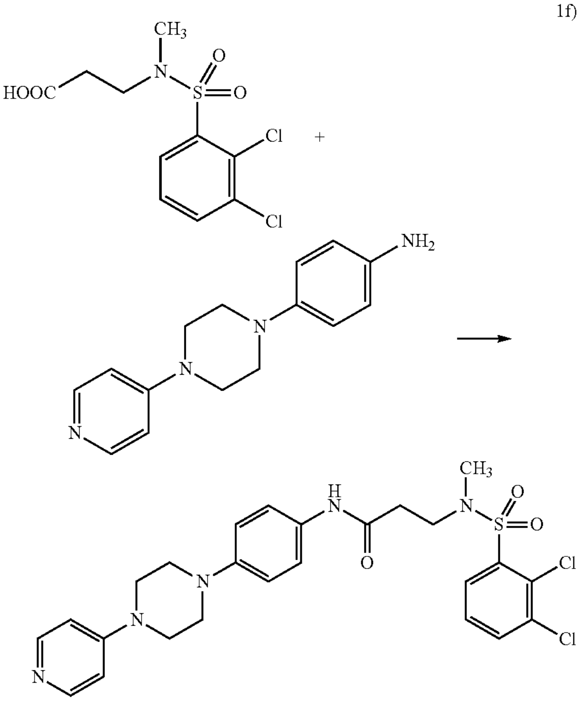

A mixture of 1.25 g (4.00 mmol) of product from 1c, 2.0 ml (14.34 mmol) of triethylamine, 1.28 g (4.00 mmol) of TBTU and 7 ml DMF is stirred for 45 min at ambient temperature. Then 1.0 g (3.93 mmol) of product from 1e is added and the mixture is stirred overnight at ambient temperature. Then the reaction mixture is poured into water and extracted with dichloromethane. The organic extracts are washed with water, dried on $Na_2SO_4$ and evaporated to dryness. The crude product thus obtained was purified by column chromatography through silica gel (eluant: dichloromethane with 5-20% methanol).

$C_{25}H_{27}Cl_2N_5O_3S$ (548.49)

[M+H]+=548/550/552

TLC: silica gel, dichloromethane/methanol 4:1, Rf value=0.65

Example 2

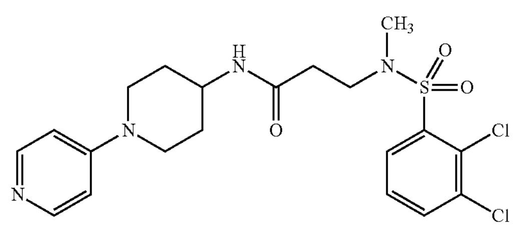

2a)

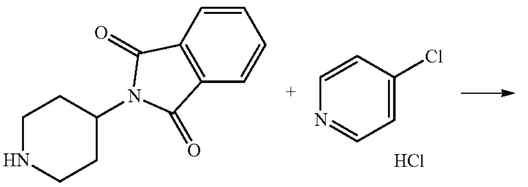

-continued

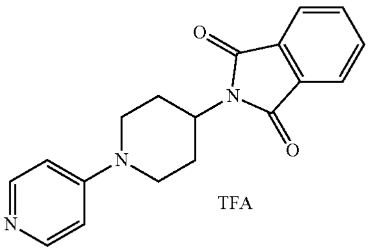

A mixture of 0.5 g (2.17 mmol) of N-(1-benzylpiperidin-4-yl)-phthalimide (Bioorg. Med. Chem. Lett. 11, 2001, 2325-2330), 0.33 g (2.17 mmol) of 4-chloropyridine hydrochloride, 1.2 ml (8.69 mmol) of triethylamine and 2.4 ml of absolute ethanol is heated in the microwave to 150° C. for one hour. The reaction mixture is then diluted with ethanol, the precipitate formed is filtered off. The filtrates are evaporated to dryness and the crude product is purified by preparative HPLC.

$C_{18}H_{17}N_3O_2 \times C_2HF_3O_2$ (421.37)

[M+H]+=308

HPLC (Method 1): retention time=2.07 min

2b)

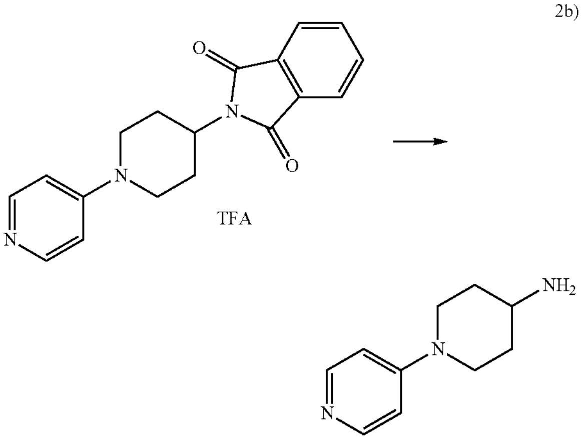

A mixture of 0.3 g (0.71 mmol) of product from 2a, 0.09 g (1.42 mmol) of hydrazine hydrate 80% and 6 ml of absolute ethanol is refluxed for four hours. The reaction mixture is then cooled to 0° C., the precipitate formed is filtered off. The filtrates are evaporated to dryness.

$C_{10}H_{15}N_3$ (177.25)

[M+H]+=178

2c)

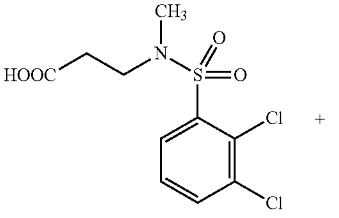

-continued

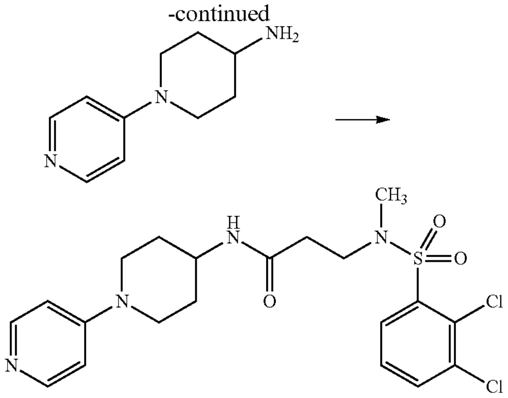

Example 2 is prepared analogously to 1f from 0.22 g (0.71 mmol) of product from 1c, 0.24 g (1.35 mmol) of product from 2b, 0.3 ml (2.13 mmol) of triethylamine and 0.23 g (0.71 mmol) of TBTU in 5.5 ml DMF.

$C_{20}H_{24}Cl_2N_4O_3S$ (471.40)

[M+H]+=471/473/475

TLC: silica gel, dichloromethane/methanol 9:1, Rf value=0.2

Example 3

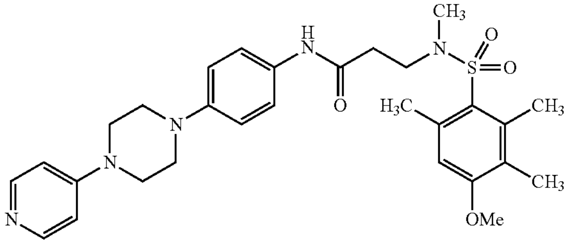

3a)

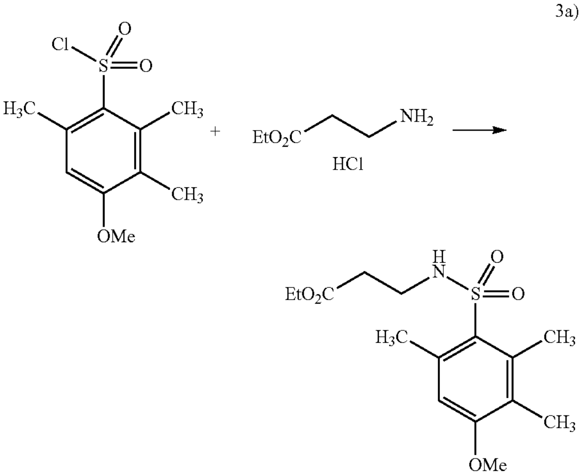

A mixture of 0.99 g (4.00 mmol) of 4-methoxy-2,3,6-trimethyl-benzenesulphonyl chloride, 0.69 g (4.51 mmol) of β-alanine ethylester hydrochloride, 2.23 ml (15.98 mmol) of triethylamine and 20 ml dichloromethane is stirred overnight at ambient temperature. The reaction mixture is then washed with 0.5 M HCl, saturated sodium hydrogen carbonate solution, water and saturated sodium chloride solution, dried on sodium sulphate and evaporated to dryness in vacuo.

$C_{15}H_{23}NO_5S$ (329.41)

[M+H]+=330

TLC: silica gel, petroleum ether/ethyl acetate 2:1, Rf value=0.43

3b)

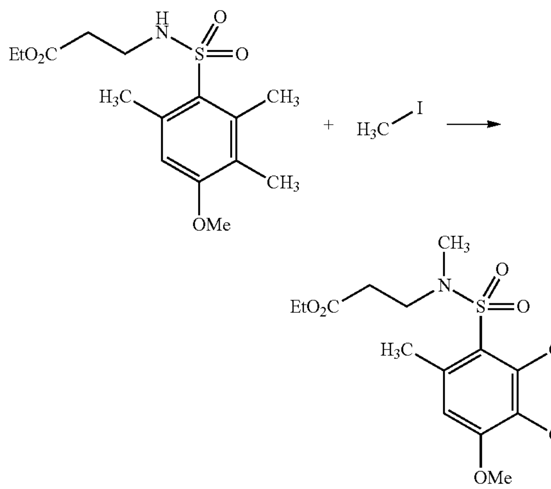

A mixture of 1.24 g (3.76 mmol) of product from 3a, 0.84 ml (13.55 mmol) of methyl iodide, 1.04 g (7.53 mmol) of anhydrous potassium carbonate and 10 ml DMF is stirred for five hours at ambient temperature. The reaction mixture is then evaporated to dryness in vacuo, the residue is taken up in ethyl acetate. It is washed with water, saturated sodium hydrogen carbonate solution and saturated sodium chloride solution, dried on sodium sulphate and evaporated to dryness in vacuo.

$C_{16}H_{25}NO_5S$ (343.44)

[M+H]+=344

TLC: silica gel, petroleum ether/ethyl acetate 2:1, Rf value=0.52

3c)

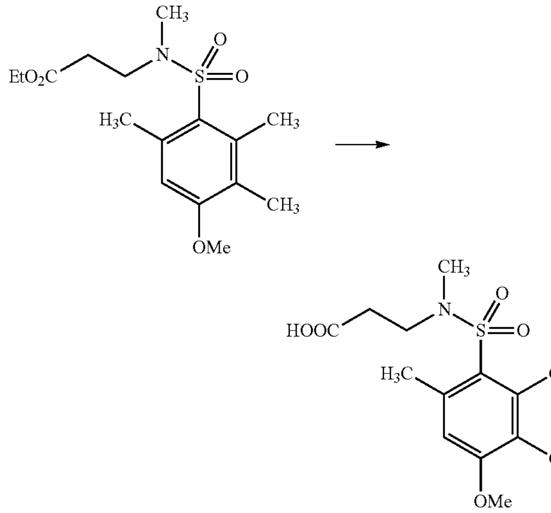

The acid is prepared analogously to 1c from 1.29 g (3.76 mmol) of product from 3b, 0.79 g (18.80 mmol) of lithium hydroxide monohydrate, 15 ml THF and 15 ml of water.

$C_{14}H_{21}NO_5S$ (315.39)

[M+H]+=316

TLC: silica gel, petroleum ether/ethyl acetate 2:1, Rf value=0.07

3d)

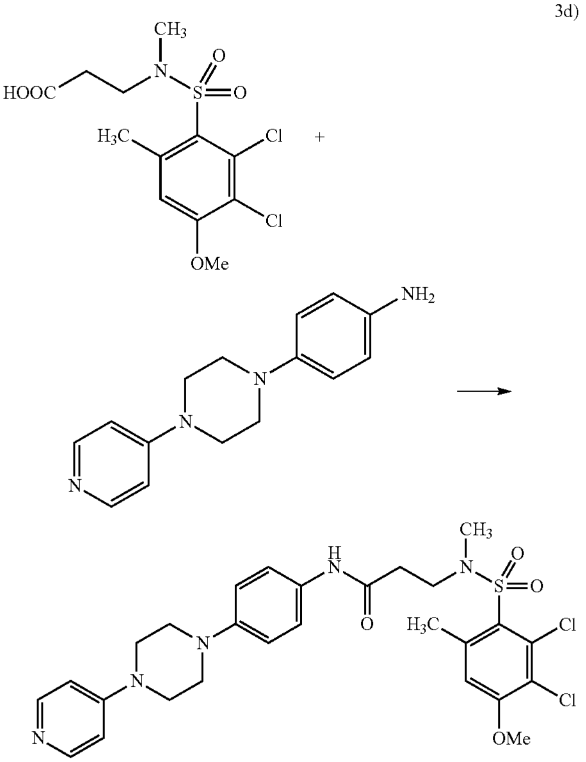

Example 3 is prepared analogously to 1f from 0.15 g (0.47 mmol) of product from 3c, 0.12 g (0.47 mmol) of product from 1e, 0.2 ml (1.43 mmol) of triethylamine and 0.15 g (0.48 mmol) of TBTU in 8 ml DMF.

$C_{29}H_{37}N_{15}O_4S$ (551.70)

[M+H]+=552

TLC: silica gel, dichloromethane/methanol 9:1, Rf value=0.38

Example 4

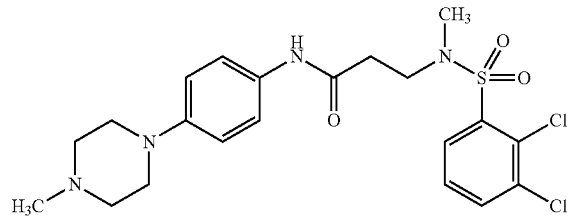

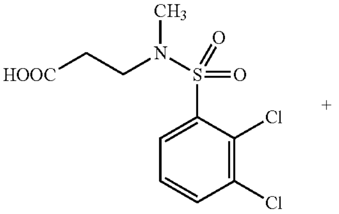

-continued

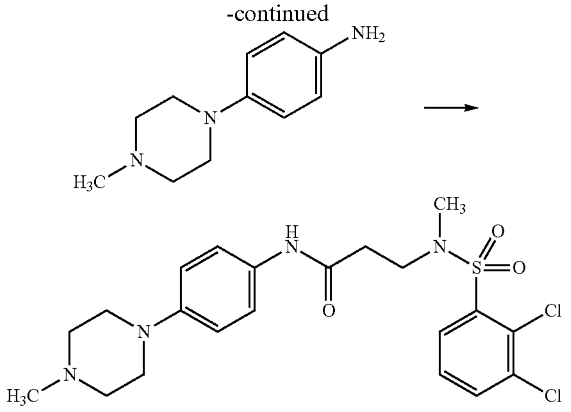

Example 4 is prepared analogously to 1f from 0.39 g (1.26 mmol) of product from 1c, 0.24 g (1.26 mmol) of 4-(4-methylpiperazin-1-yl)aniline (J. Med. Chem. SIR 48, 7, 2005, 2371-2387), 0.35 ml (2.51 mmol) of triethylamine and 0.50 g (1.32 mmol) of HATU in 5 ml DMF.

$C_{21}H_{26}CL_2N_4O_3S$ (485.43)

[M+H]+=485/487/489

HPLC (Method 2): retention time=2.64 min

Example 5

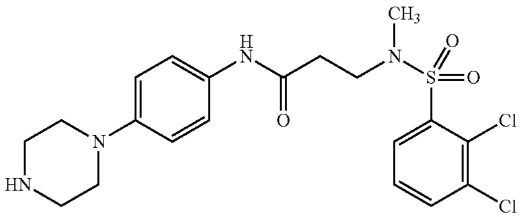

5a)

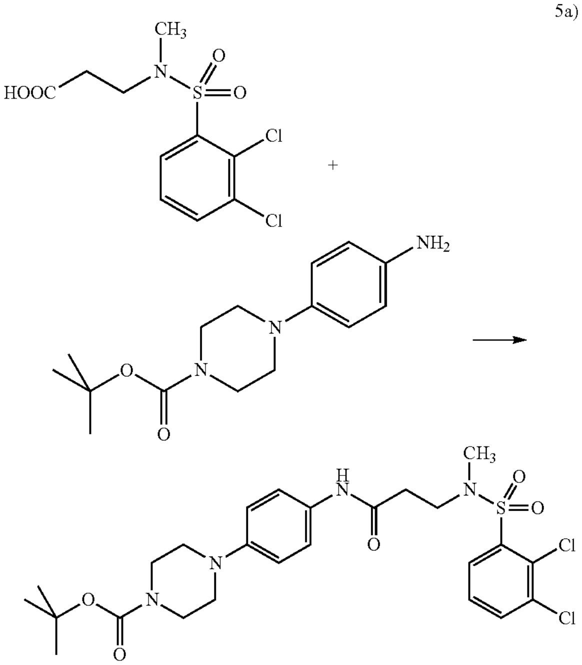

5a is prepared analogously to 1f from 0.39 g (1.26 mmol) of product from 1c, 0.24 g (1.26 mmol) of 4-(4-methylpiperazin-1-yl)aniline (J. Med. Chem. SIR 48, 7, 2005, 2371-2387), 0.35 ml (2.51 mmol) of triethylamine and 0.50 g (1.32 mmol) of HATU in 5 ml DMF.

$C_{25}H_{32}CL_2N_4O_5S$ (571.52)

5b)

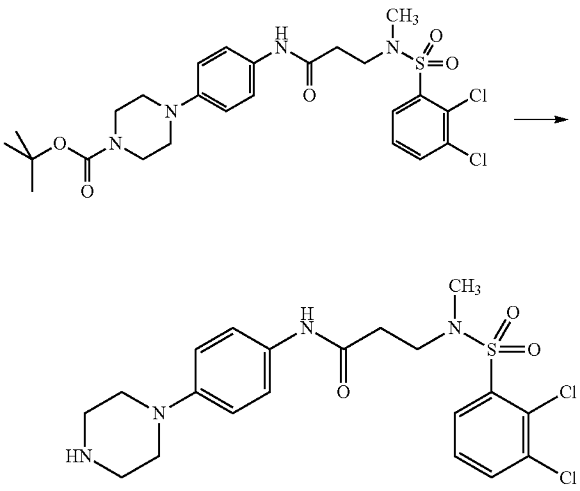

A mixture of 0.60 g (1.05 mmol) of product from 5a, 3 ml TFA and 3 ml dichloromethane is stirred for two hours at ambient temperature. The reaction mixture is evaporated to dryness and the crude product is purified by preparative HPLC.

$C_{20}H_{24}Cl_2N_4O_3S$ (471.40)

[M+H]+=471/473/475

HPLC (Method 2): retention time=2.58 min

Example 6

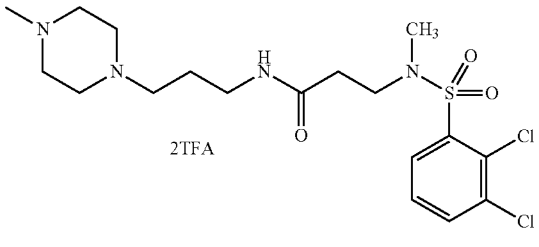

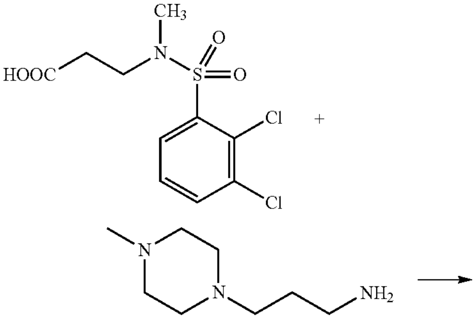

-continued

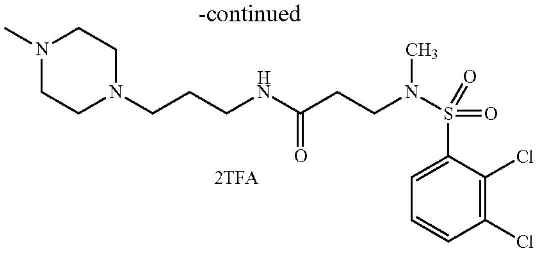

2TFA

Example 6 is prepared analogously to 1f from 0.22 g (0.71 mmol) of product from 1c, 0.12 g (0.78 mmol) of 3-(4-methylpiperazin-1-yl)-propylamine (Bioorg. Med. Chem. Lett. 13, 2003, 2131-2136), 0.30 ml (2.13 mmol) of triethylamine and 0.23 g (0.71 mmol) of TBTU in 5.5 ml THF.

$C_{18}H_{28}Cl_2N_4O_3S \times 2C_2HF_3O_2$ (679.46)

[M+H]+=451/453/455

HPLC (Method 5): retention time=1.37 min

Example 7

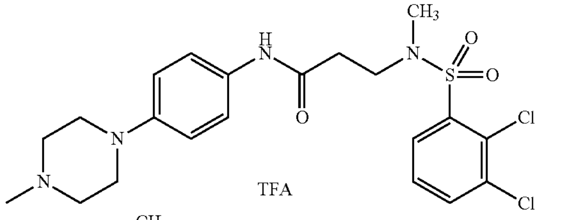

TFA

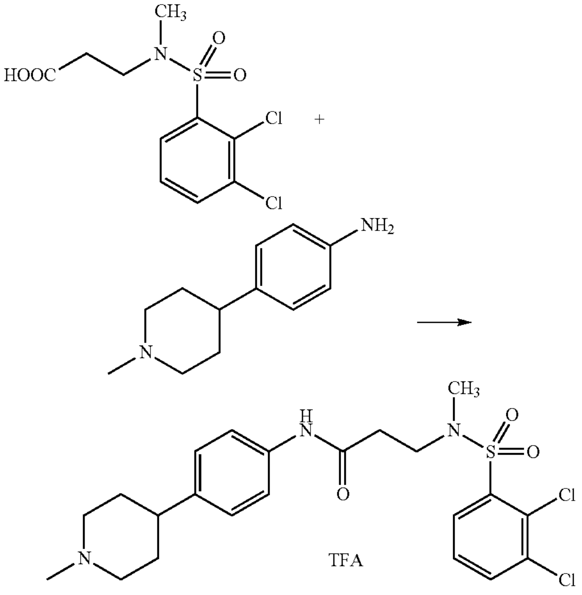

TFA

Example 7 is prepared analogously to 1f from 0.22 g (0.71 mmol) of product from 1c, 0.14 g (0.71 mmol) of 4-(1-methylpiperidin-4-yl)-aniline (JW Pharmlab), 0.30 ml (2.13 mmol) of triethylamine and 0.23 g (0.71 mmol) of TBTU in 5.5 ml THF.

$C_{22}H_{27}Cl_2N_3O_3S \times C_2HF_3O_2$ (598.46)

[M+H]+=484/486/488

HPLC (Method 5): retention time=1.57 min

Example 8

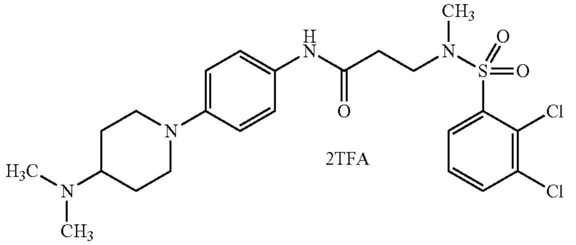

2TFA

8a)

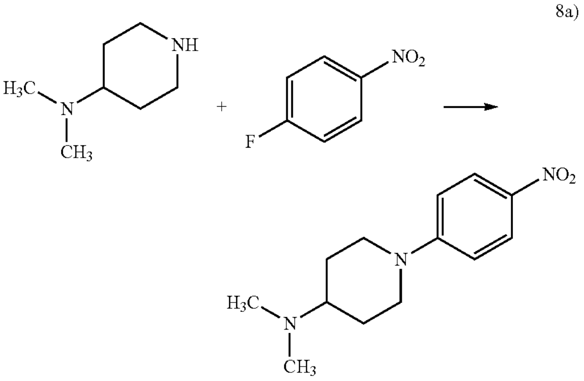

8a is prepared analogously to 1d from 0.5 g (3.90 mmol) of 4-dimethylamino-piperidine (Alfa Aesar), 0.44 g (4.18 mmol) of 1-fluoro-4-nitrobenzene (Aldrich) and 1.33 ml (76.59 mmol) of triethylamine in 12 ml DMF.

$C_{13}H_{19}N_3O_2$ (249.31)

[M+H]+=250

8b)

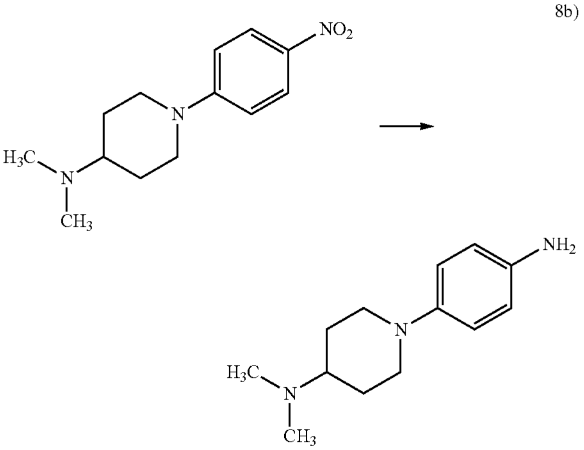

A mixture of 1.66 g (6.67 mmol) of product from 8a, 0.17 g palladium on charcoal (5%) and 132 ml of ethanol is hydrogenated in the autoclave at ambient temperature. Then the catalyst is removed by suction filtering and the filtrate is evaporated to dryness in vacuo.

$C_{13}H_{21}N_3$ (219.33)

[M+H]+=220

TLC: silica gel, dichloromethane/methanol 9:1, Rf value=0.1

8c)

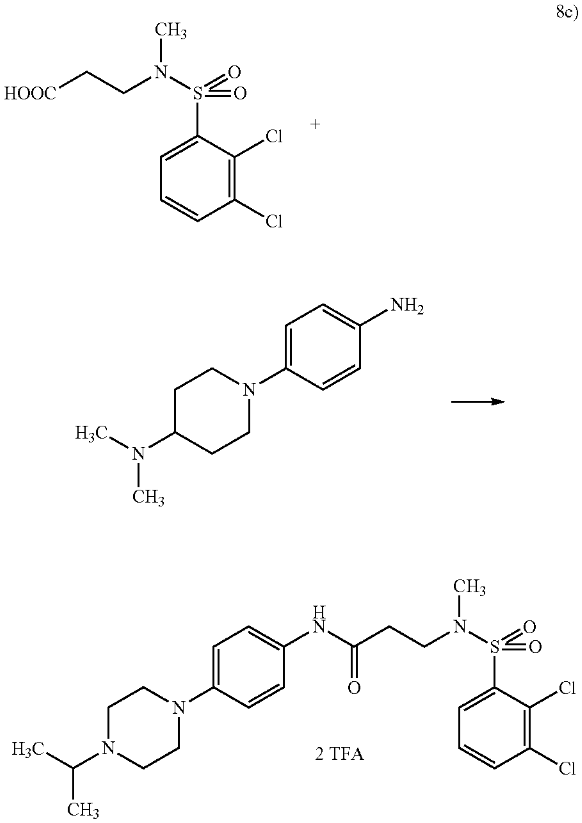

Example 8 is prepared analogously to 1f from 0.22 g (0.71 mmol) of product from 1c, 0.16 g (0.71 mmol) of product from 8b, 0.30 ml (2.13 mmol) of triethylamine and 0.23 g (0.71 mmol) of TBTU in 5.5 ml THF.

$C_{23}H_{30}Cl_2N_4O_3S\times2C_2HF_3O_2$ (741.53)

[M+H]+=513/515/517

HPLC (Method 5): retention time=1.46 min

Example 9

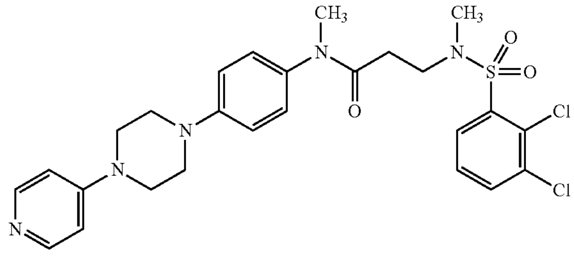

9a)

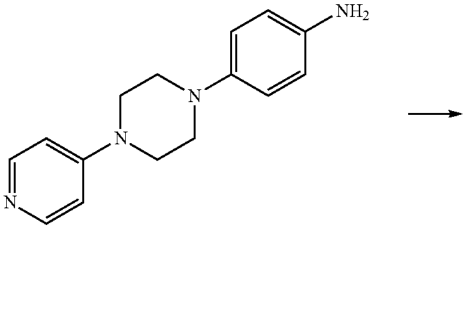

-continued

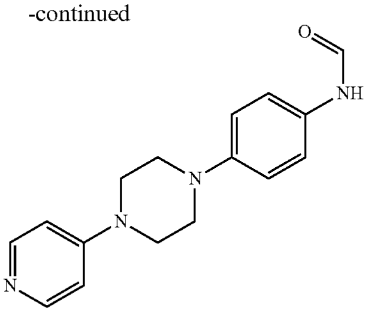

13 ml acetic anhydride are taken and 8 ml formic acid are slowly added thereto. The reaction mixture is heated for 1.5 hours to 50° C. and then combined with 80 ml dichloromethane. While cooling with the ice bath 5.0 g (19.66 mmol) are then added. The mixture is stirred for one hour at ambient temperature and then evaporated to dryness. The residue is combined with semisaturated sodium hydrogen carbonate solution and extracted twice with dichloromethane. The organic extracts are washed with saturated sodium chloride solution, dried on sodium sulphate and evaporated to dryness. The crude product thus obtained is purified by column chromatography through silica gel (eluant: dichloromethane/methanol/ammonia 9:1:0.1).

$C_{16}H_{18}N_4O$ (282.34)

[M+H]+=283

9b)

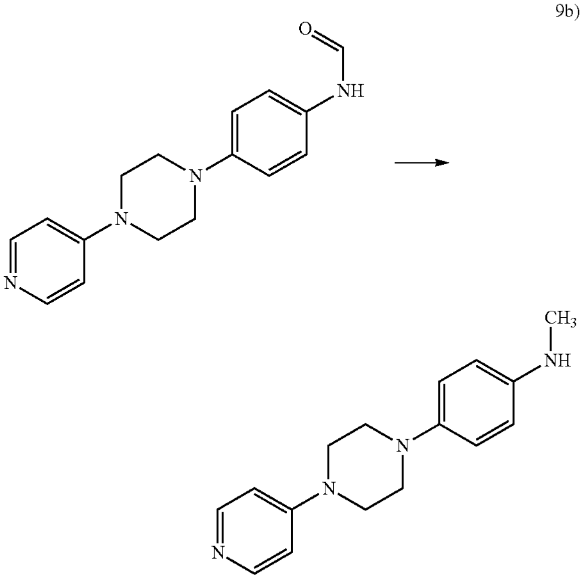

At 60° C. a mixture of 10.63 ml lithium aluminium hydride 2 M in THF (21.25 mmol) and 50 ml THF is slowly combined with 3.0 g (10.63 mmol) of product from 9a. The reaction mixture is stirred for eight hours at 60° C. and four hours at ambient temperature. While cooling with the ice bath 20 ml of water are then added. The mixture is filtered through Celite and washed with THF and dichloromethane. The filtrate is evaporated to dryness. The residue is combined with dichloromethane, washed with water and 1 M sodium hydroxide solution, dried on sodium sulphate solution and evaporated to dryness. The crude product thus obtained is purified by column chromatography through silica gel (eluant: dichloromethane/methanol/ammonia 9:1:0.1)

$C_{16}H_{20}N_4$ (268.36).

9c)

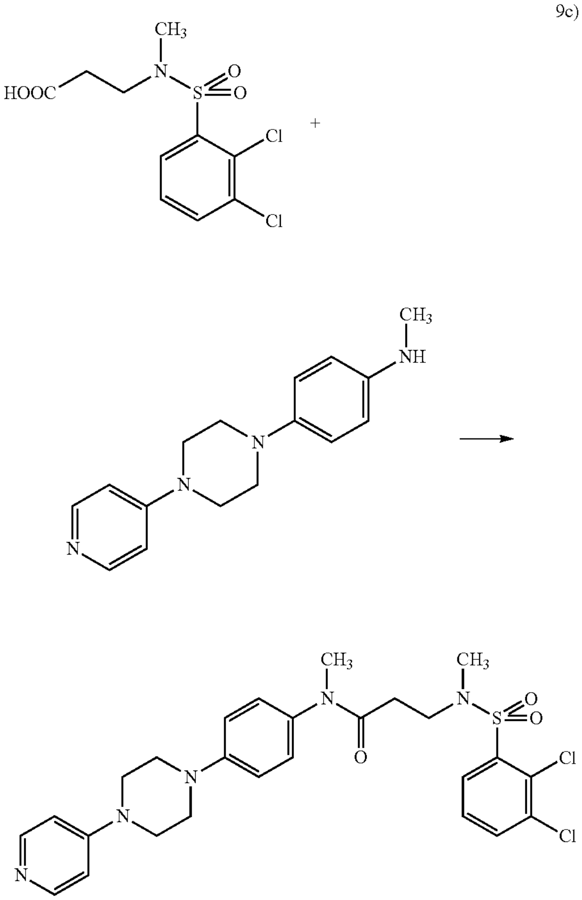

Example 9 is prepared analogously to 1f from 0.15 g (0.48 mmol) of product from 1c, 0.14 g (0.51 mmol) of product from 9b, 0.13 ml (0.96 mmol) of triethylamine and 0.19 g (0.51 mmol) of HATU in 5 ml DMF.

$C_{26}H_{29}Cl_2N_5O_3S$ (562.51)

[M+H]+=562/564/566

HPLC (Method 2): retention time=2.86 min

Example 10

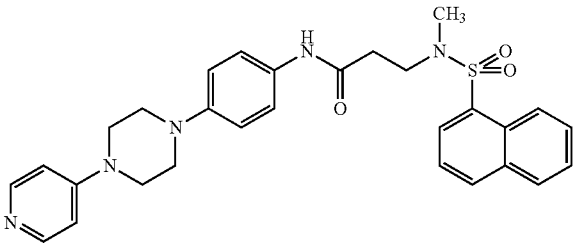

10a)

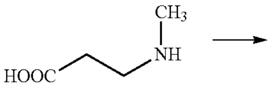

-continued

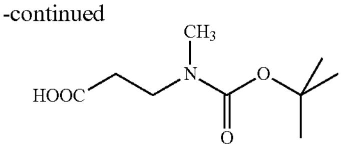

A mixture of 1.0 g (9.70 mmol) of N-methyl-β-alanine (Convertex), 24 ml dioxane, 12 ml of water and 2.68 g (19.38 mmol) of anhydrous potassium carbonate is combined with 2.33 g (10.66 mmol) of Boc-anhydride while cooling with an ice bath. The reaction mixture is stirred for three days at ambient temperature. Then the dioxane is eliminated in vacuo. The aqueous residue is extracted with ethyl acetate (ethyl acetate phases are discarded), then acidified slightly with 1 M hydrochloric acid and then extracted with dichloromethane. The organic dichloromethane extracts are washed with saturated sodium chloride solution, dried on sodium sulphate and evaporated to dryness.

$C_9H_{17}NO_4$ (203.24)

[M+H]+=204

10b)

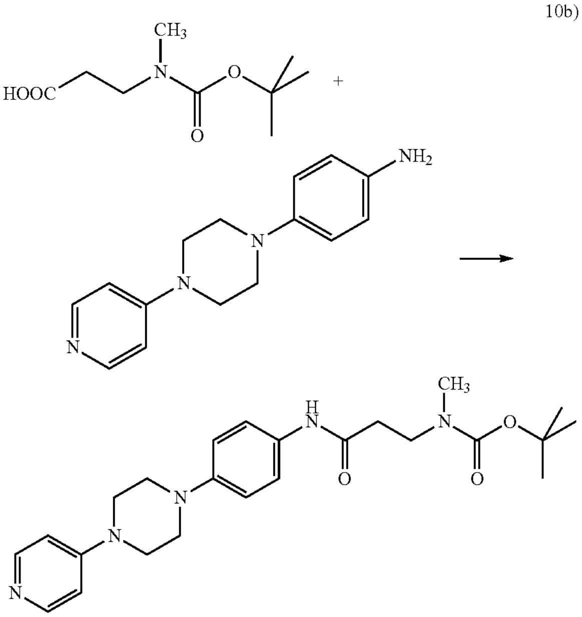

10b is prepared analogously to 1f from 1.85 g (9.10 mmol) of product from 10a, 2.32 g (9.10 mmol) of product from 1e, 3.81 ml (27.31 mmol) of triethylamine and 2.92 g (9.10 mmol) of TBTU in 80 ml DMF.

$C_{24}H_{33}N_5O_3$ (439.55)

[M+H]+=440

TLC: silica gel, dichloromethane/methanol 9:1, Rf value=0.49

10c)

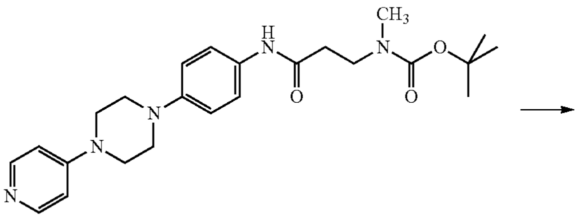

-continued

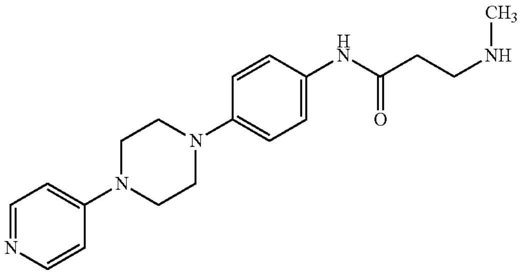

A mixture of 3.20 g (7.28 mmol) of product from 10b, 20 ml TFA and 60 ml dichloromethane is stirred for 30 min at ambient temperature. Then the reaction mixture is evaporated to dryness in vacuo. The crude product thus obtained is purified by column chromatography through silica gel (eluant: dichloromethane/ethanol/ammonia 9:1:0.1 to 4:1:0.1).

$C_{19}H_{25}N_5O$ (339.43)

[M+H]+=340

TLC: silica gel, dichloromethane/methanol/ammonia 9:1:0.1, Rf value=0.25

10d)

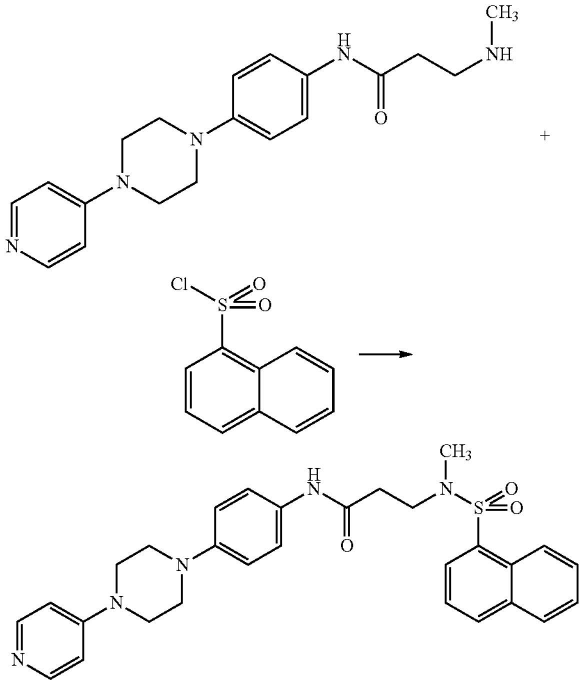

A mixture of 0.1 g (0.30 mmol) of product from 10c, 0.056 g (0.25 mmol) of 1-naphthylsulphonic acid chloride, 0.137 ml (0.98 mmol) of triethylamine and 5 ml dichloromethane is stirred overnight at ambient temperature. Then the reaction mixture is evaporated to dryness in vacuo. The crude product thus obtained is purified by column chromatography through silica gel (eluant: dichloromethane/ethanol/ammonia 12:1:0.1).

$C_{29}H_{31}N_5O_3S$ (529.65)

[M+H]+=530

TLC: silica gel, dichloromethane/methanol/ammonia 9:1:0.1, Rf value=0.44

Example 11

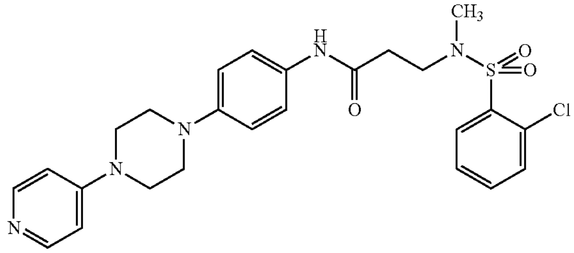

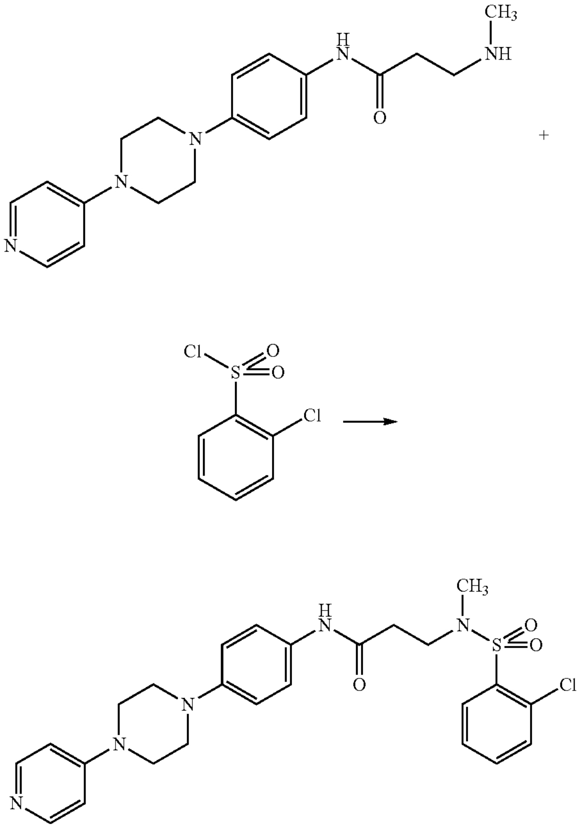

Example 11 is prepared analogously to 10d from 0.10 g (0.30 mmol) of product from 10c, 0.052 g (0.25 mmol) of 2-chlorobenzenesulphonic acid chloride, 0.14 ml (98 mmol) of triethylamine in 5 ml dichloromethane.

$C_{25}H_{28}ClN_5O_3S$ (514.04)

[M+H]+=514/516

TLC: silica gel, dichloromethane/methanol/ammonia 9:1:0.1, Rf value=0.47

Example 12

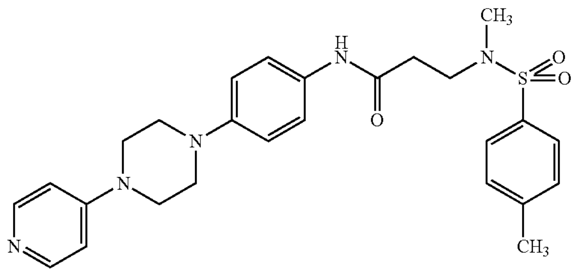

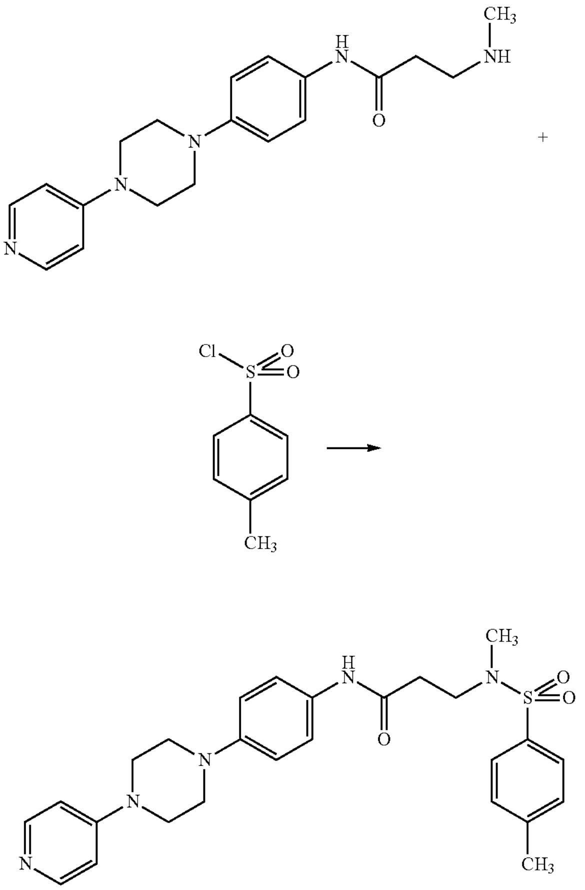

Example 12 is prepared analogously to 10d from 0.10 g (0.30 mmol) of product from 10c, 0.047 g (0.25 mmol) of p-toluenesulphonic acid chloride, 0.14 ml (98 mmol) of triethylamine in 5 ml dichloromethane.

$C_{26}H_{31}N_5O_3S$ (493.62)

[M+H]+=494

TLC: silica gel, dichloromethane/methanol/ammonia 9:1:0.1, Rf value=0.43

Example 13

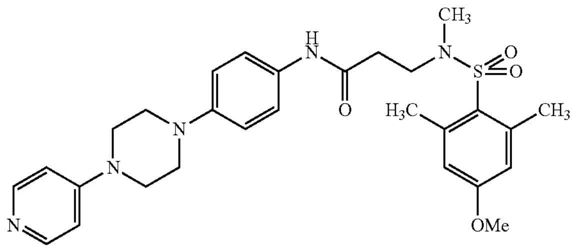

13a)

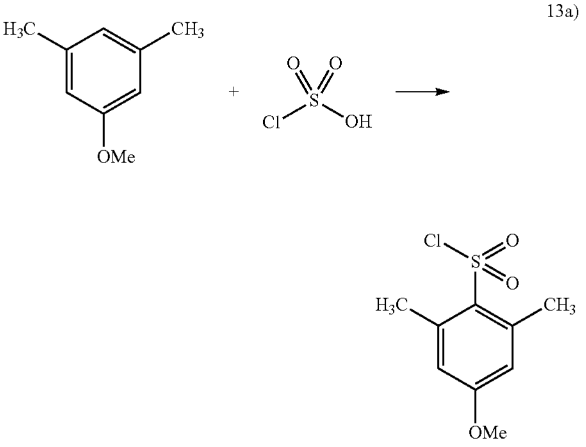

A mixture of 2.0 g (14.69 mmol) of 3,5-dimethylanisol and 20 ml dichloromethane is combined with 5.85 ml (88.0 mmol) of chlorosulphonic acid while cooling with an ice bath. The reaction mixture is then stirred for 20 min at ambient temperature and then poured onto 50 ml ice water. The mixture is extracted with 100 ml dichloromethane. The organic extracts are washed with 5% sodium hydrogen carbonate solution, dried on sodium sulphate and evaporated to dryness.

$C_9H_{11}ClO_3S$ (234.70)

[M+H]+=234/236

TLC: silica gel, petroleum ether/ethyl acetate 9:1, Rf value=0.46

13b)

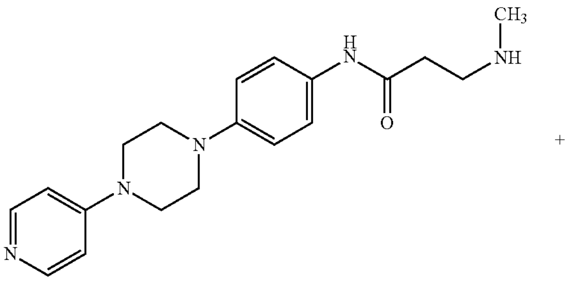

-continued

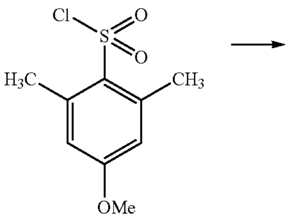

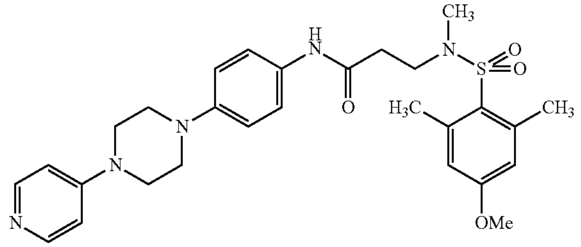

Example 13 is prepared analogously to 10d from 0.10 g (0.30 mmol) of product from 10c, 0.058 g (0.25 mmol) of product from 13a, 0.14 ml (98 mmol) of triethylamine in 5 ml dichloromethane.

$C_{28}H_{35}N_5O_4S$ (537.67)

[M+H]+=538

TLC: silica gel, dichloromethane/methanol/ammonia 9:1: 0.1, Rf value=0.62

Example 14

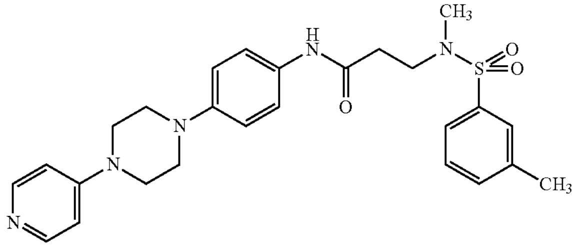

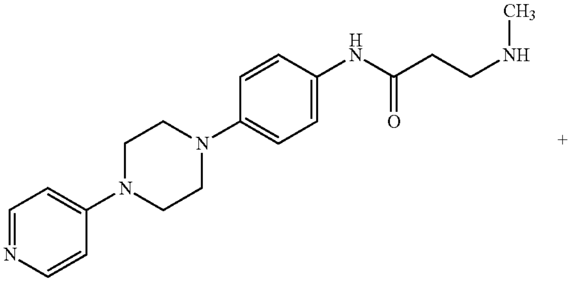

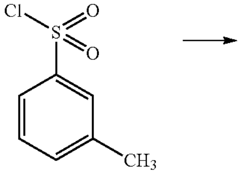

-continued

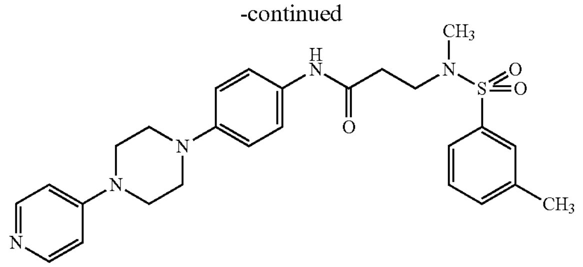

Example 14 is prepared analogously to 10d from 0.10 g (0.30 mmol) of product from 10c, 0.047 g (0.25 mmol) of m-toluenesulphonic acid chloride, 0.14 ml (98 mmol) of triethylamine in 5 ml dichloromethane.

$C_{26}H_{31}N_5O_3S$ (493.62)

[M+H]+=494

TLC: silica gel, dichloromethane/methanol/ammonia 9:1: 0.1, Rf value=0.47

Example 15

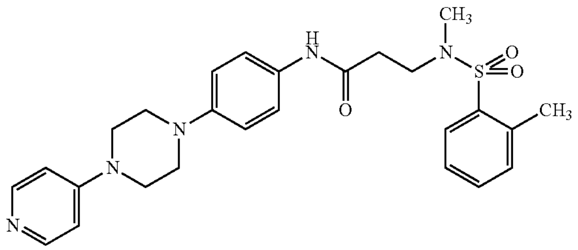

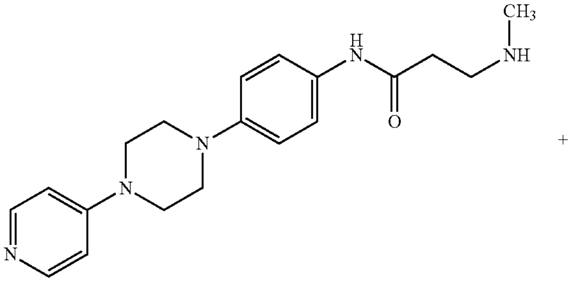

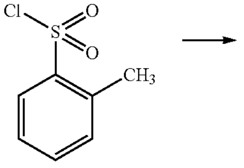

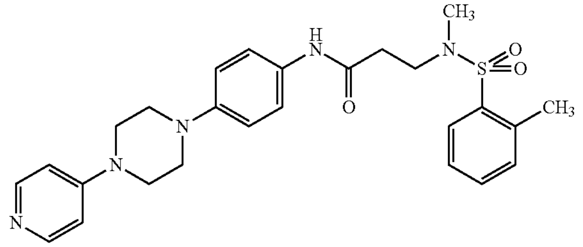

Example 15 is prepared analogously to 10d from 0.10 g (0.30 mmol) of product from 10c, 0.047 g (0.25 mmol) of o-toluenesulphonic acid chloride, 0.14 ml (98 mmol) of triethylamine in 5 ml dichloromethane.

$C_{26}H_{31}N_5O_3S$ (493.62)

[M+H]+=494

HPLC (Method 1): retention time=2.37 min

Example 16

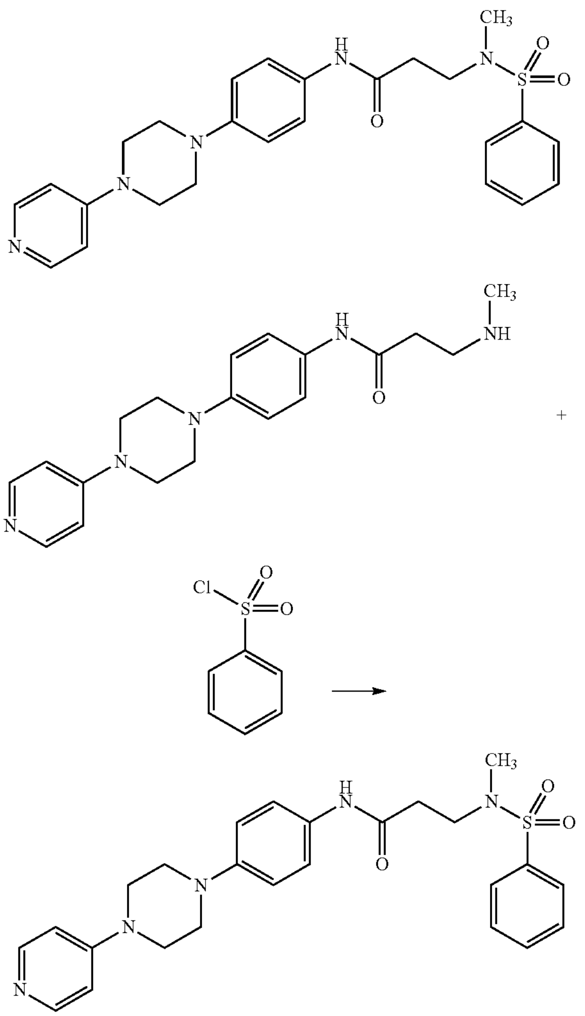

Example 16 is prepared analogously to 10d from 0.10 g (0.30 mmol) of product from 10c, 0.043 g (0.25 mmol) of benzenesulphonic acid chloride, 0.14 ml (98 mmol) of triethylamine in 5 ml dichloromethane.

$C_{25}H_{29}N_5O_3S$ (479.60)

[M+H]+=480

HPLC (Method 1): retention time=2.40 min

Example 17

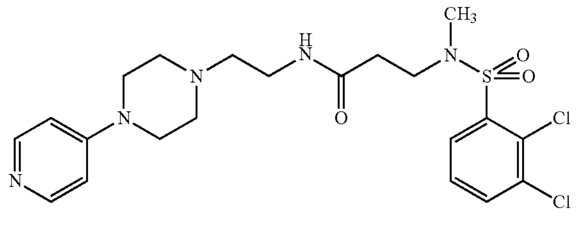

-continued

17a)

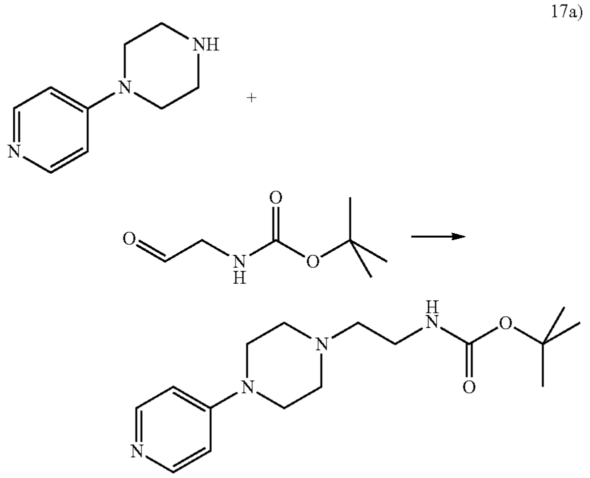

A mixture of 1.03 g (6.28 mmol) of 1-(4-pyridyl)-piperazine (Girindus) and 50 ml dichloromethane is combined with 1.0 g (6.28 mmol) of tert-butyl-N-(2-oxoethyl)-carbamate (Aldrich). The reaction mixture is then stirred for 30 min at ambient temperature, then combined with 2.66 g (12.56 mmol) of sodium-triacetoxyborohydride while cooling with an ice bath and then stirred overnight at ambient temperature. Another 60 ml dichloromethane are added and the reaction mixture is washed with saturated sodium hydrogen carbonate solution and saturated sodium chloride solution. The organic phase is dried on sodium sulphate and evaporated to dryness. The crude product thus obtained is purified by column chromatography through silica gel (eluant: dichloromethane/ethanol/ammonia 14:1:0.1 to 10:1:0.1).

$C_{16}H_{26}N_4O_2$ (306.40)

[M+H]+=307

17b)

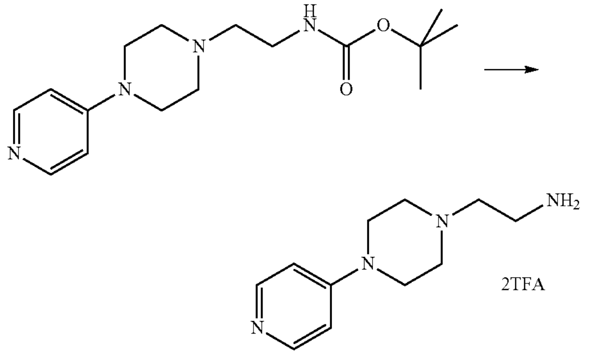

A mixture of 0.36 g (1.19 mmol) of product from 17a, 1.19 ml (15.50 mmol) of TFA and 2 ml dichloromethane is stirred for two hours at ambient temperature. Then the reaction mixture is evaporated to dryness in vacuo.

$C_{11}H_{18}N_4 \times 2C_2HF_3O_2$ (434.33)

[M+H]+=207

HPLC (Method 2): retention time=0.98 min

17c)

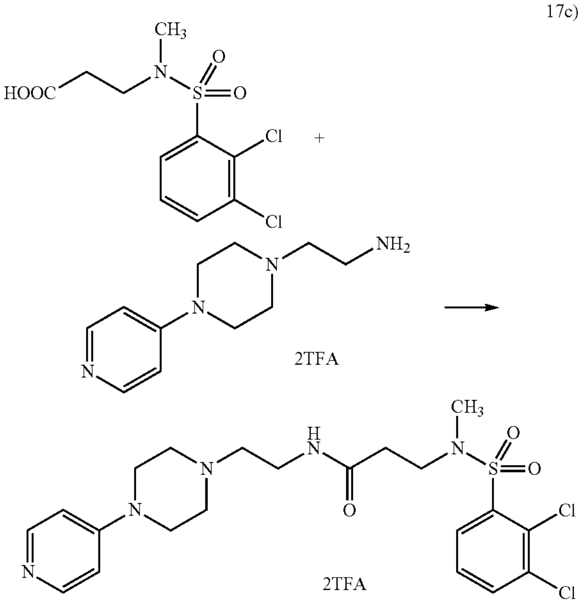

Example 17 is prepared analogously to 1f from 0.22 g (0.71 mmol) of product from 1c, 0.34 g (0.78 mmol) of product from 17b, 0.50 ml (3.56 mmol) of triethylamine and 0.23 g (0.71 mmol) of TBTU in 5.5 ml THF.

$C_{21}H_{27}Cl_2N_5O_3S{\times}2C_2HF_3O_2$ (728.49)

[M+H]+=500/502/504

HPLC (Method 2): retention time=3.14 min

Example 18

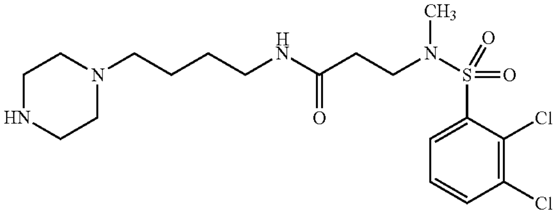

-continued

18a)

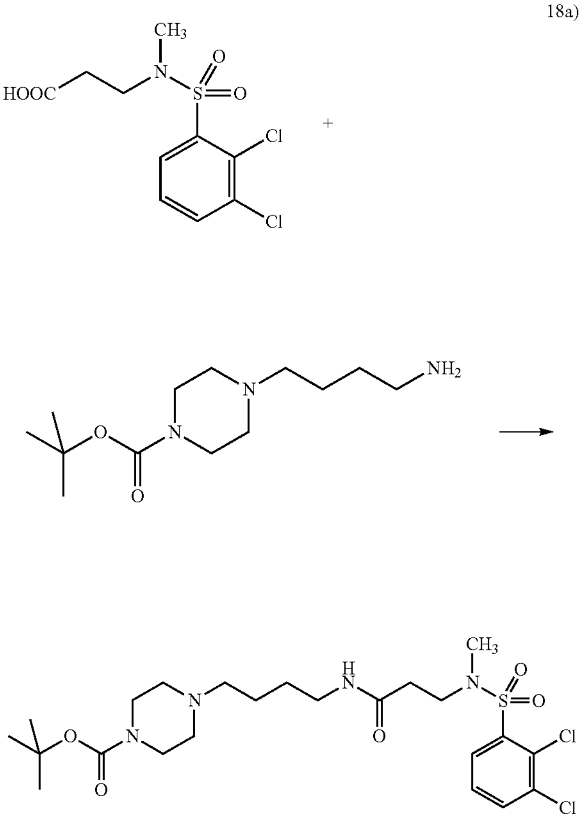

18a is prepared analogously to 1f from 0.20 g (0.64 mmol) of product from 1c, 0.17 g (0.64 mmol) of tert-butyl 4-(4-aminobutyl)-piperazine-1-carboxylate (J. Med. Chem. 47, 2004, 4300-4315), 0.27 ml (1.92 mmol) of triethylamine and 0.21 g (0.64 mmol) of TBTU in 5 ml THF.

$C_{23}H_{36}CL_2N_4O_5S$ (551.53)

M+H]+=551/553/555

TLC: silica gel, dichloromethane/methanol 30:1, Rf value=0.1

18b)

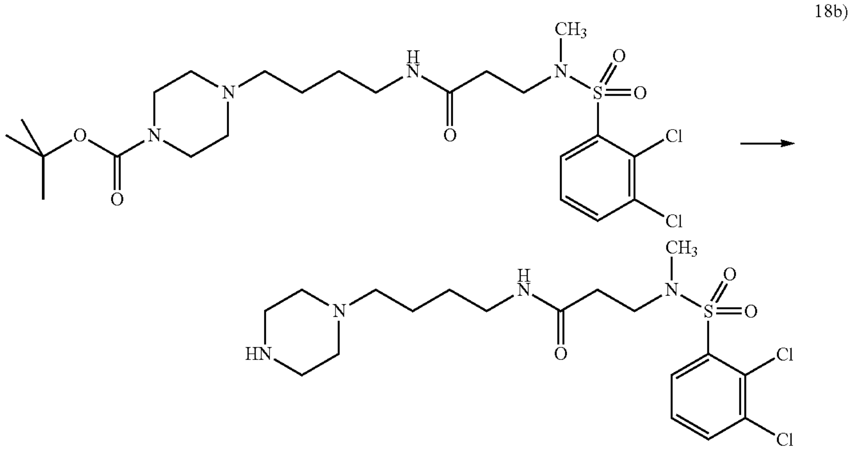

A mixture of 0.29 g (0.53 mmol) of product from 18a, 0.53 ml TFA and 1 ml dichloromethane is stirred for two hours at ambient temperature. The reaction mixture is washed with saturated sodium hydrogen carbonate solution. After the phase separation the aqueous phase is extracted three times more with dichloromethane. The organic extracts are dried on sodium sulphate and evaporated to dryness in vacuo.

$C_{18}H_{28}Cl_2N_4O_3S$ (451.41)

[M+H]+=451/453/455

HPLC (Method 2): retention time=2.22 min

Example 19

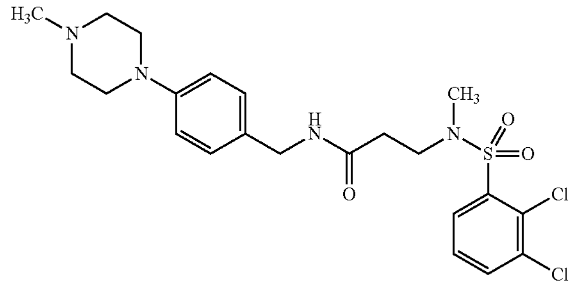

19a)

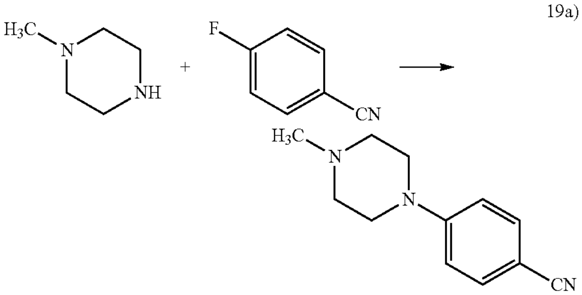

A mixture of 5.0 ml (45.13 mmol) of N-methylpiperazine and 0.73 g (6.00 mmol) of 4-fluorobenzonitrile (Aldrich) is heated for 12 hours to 80° C. Then it is evaporated to dryness and the residue is mixed with water. It is extracted three times with ethyl acetate. The organic extracts are dried on sodium sulphate and evaporated to dryness in vacuo.

$C_{12}H_{15}N_3$ (201.27)

M+H]+=202

TLC: silica gel, dichloromethane/ethanol 95:5, Rf value=0.31

19b)

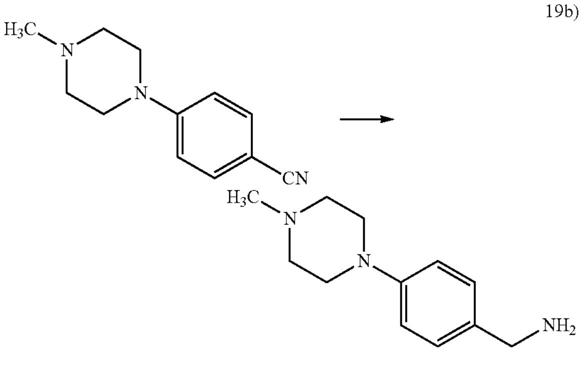

A mixture of 1.17 g (5.81 mmol) of product from 19a, 0.3 g Raney nickel and 50 ml of methanolic ammonia solution is hydrogenated at 50° C. in the autoclave. Then the catalyst is filtered off and the filtrate is evaporated to dryness in vacuo.

$C_{12}H_{19}N_3$ (205.30)

M+H]+=206

19c)

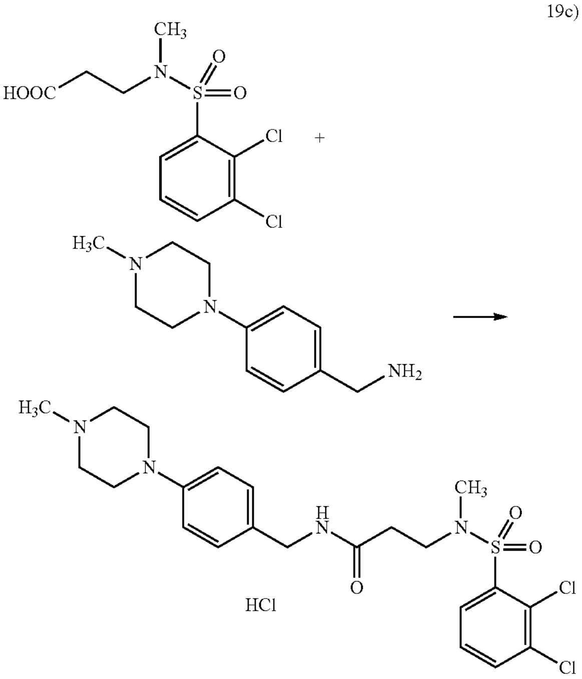

Example 19 is prepared analogously to 1f from 0.16 g (0.50 mmol) of product from 1c, 0.10 g (0.50 mmol) of product from 19b, 0.14 ml (1.00 mmol) of triethylamine and 0.16 g (0.50 mmol) of TBTU in 3 ml DMF.

$C_{22}H_{28}Cl_2N_4O_3S \times HCl$ (535.91)

[M+H]+=499/501/503

HPLC (Method 3): retention time=3.49 min

Example 20

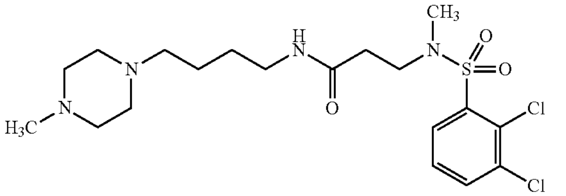

20a)

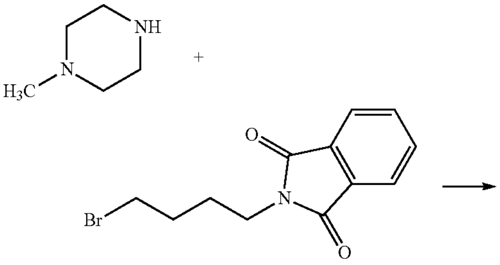

-continued

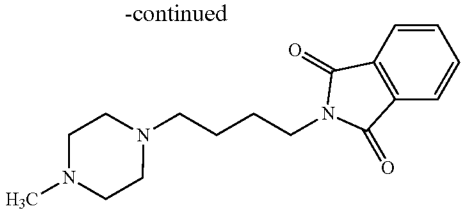

A mixture of 0.5 g (4.99 mmol) of N-methylpiperazine (Aldrich), 1.41 g (4.99 mmol) of N-(4-bromobutyl)-phthalimide (Fluka), 0.86 ml (4.99 mmol) of DIPEA and 9.3 ml acetonitrile is heated for 45 min in the microwave to 120° C. Then it is evaporated to dryness. The crude product thus obtained is purified by column chromatography through silica gel (eluant: dichloromethane/methanol 98:2).

$C_{17}H_{23}N_3O_2$ (301.38)

M+H]+=302

20b)

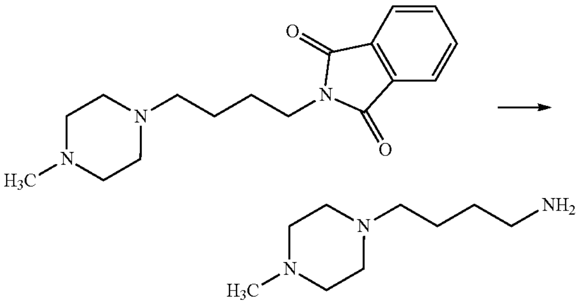

A mixture of 1.94 g (6.44 mmol) of product from 20a, 1.61 g (25.75 mmol) of hydrazine hydrate hydrate and 15 ml of absolute ethanol is heated for 5.5 hours in the autoclave to 120° C. The precipitate formed is filtered off. Then the filtrate is evaporated to dryness.

$C_9H_{21}N_3$ (171.28)

20c)

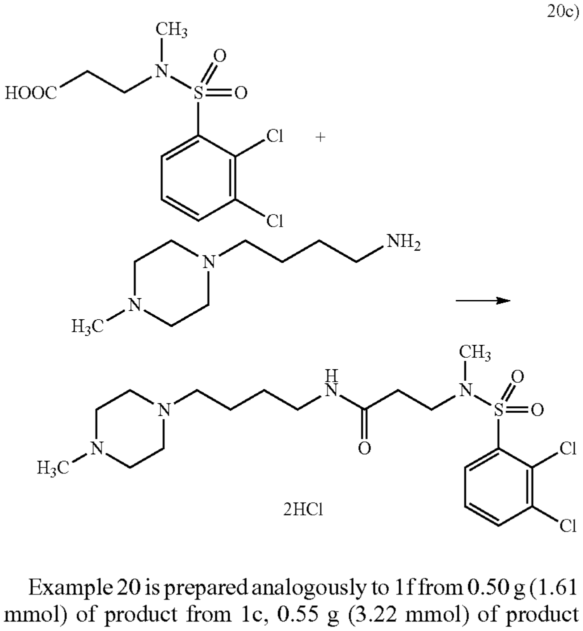

Example 20 is prepared analogously to 1f from 0.50 g (1.61 mmol) of product from 1c, 0.55 g (3.22 mmol) of product from 20b, 0.67 ml (4.83 mmol) of triethylamine and 0.52 g (1.61 mmol) of TBTU in 30 ml DMF.

$C_{19}H_{30}Cl_2N_4O_3S$x2HCl (538.36)

[M+H]+=465/467/469

HPLC (Method 1): retention time=2.15 min

Example 21

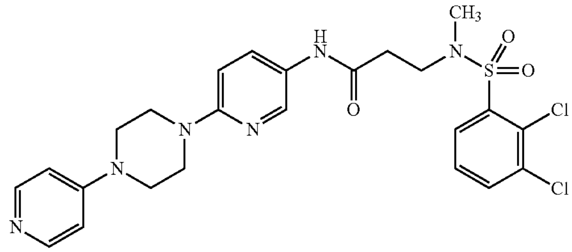

21a)

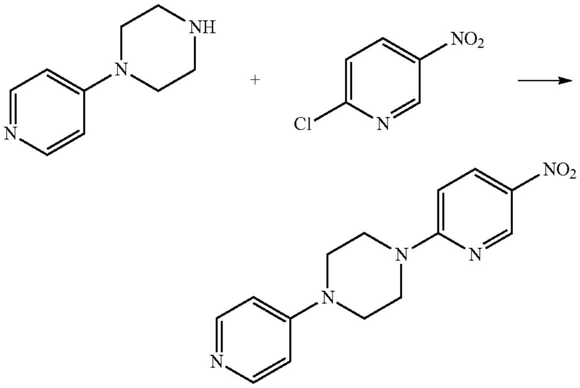

A mixture of 2.06 g (12.62 mmol) of 1-pyridin-4-yl-piperazine (Girindus), 2.00 g (12.62 mmol) of 2-chloro-5-nitropyridine (Fluka) and 50 ml dichloromethane is stirred for 15 min at ambient temperature and then combined with 6.31 ml (12.62 mmol) of 2 M sodium hydroxide solution. The reaction mixture is stirred for 20 hours at ambient temperature and then combined with 300 ml dichloromethane and 100 ml 5% sodium hydrogen carbonate solution. After the phase separation the organic phase is dried on sodium sulphate and evaporated to dryness in vacuo. The crude product is stirred with 100 ml diethyl ether/ethanol 2:1, filtered off and dried.

$C_{14}H_{15}N_5O_2$ (285.30)

[M+H]+=286

TLC: silica gel, dichloromethane/ethanol 9:1, Rf value=0.10

21b)

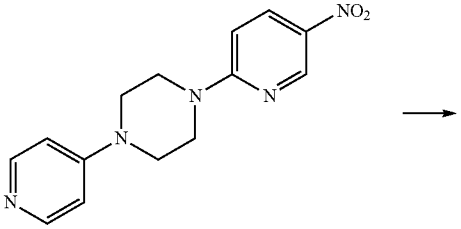

-continued

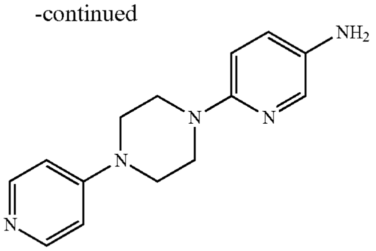

A mixture of 1.75 g (6.13 mmol) of product from 21a, 0.4 g palladium on charcoal (10%), 100 ml dichloromethane and 50 ml of methanol is hydrogenated for five hours in the autoclave at ambient temperature. Then the catalyst is removed by suction filtering and the filtrate is evaporated to dryness in vacuo. The residue is stirred with 100 ml diethyl ether/ethanol 2:1 and suction filtered. The crude product thus obtained is purified by column chromatography through silica gel (eluant: dichloromethane/methanol/ammonia 95:5: 0.5).

$C_{14}H_{17}N_5$ (255.32)

[M+H]+=256

TLC: silica gel, dichloromethane/methanol/ammonia 9:1: 0.1, Rf value=0.37

21c)

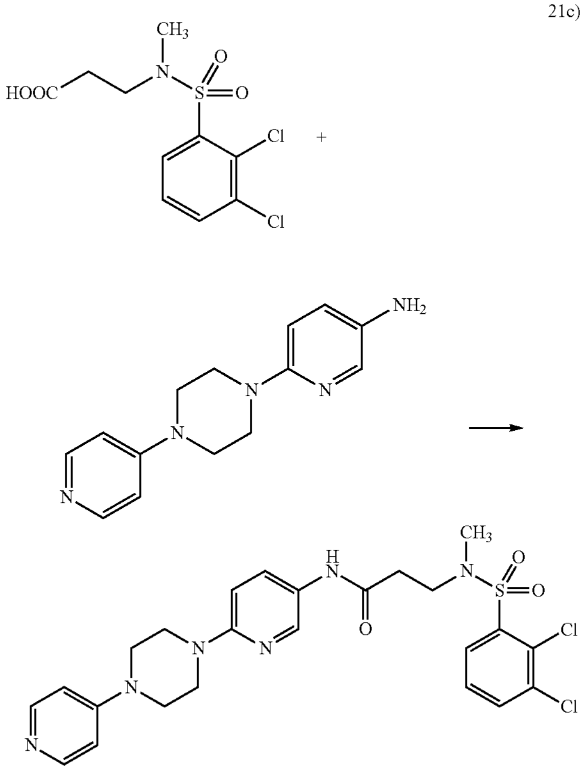

Example 21 is prepared analogously to 1f from 0.11 g (0.35 mmol) of product from 1c, 0.089 g (0.35 mmol) of product from 21b, 0.098 ml (0.70 mmol) of triethylamine and 0.13 g (0.42 mmol) of TBTU in 15 ml THF.

$C_{24}H_{26}Cl_2N_6O_3S$ (549.47)

[M+H]+=549/551/553

HPLC (Method 4): retention time=2.7 min

Example 22

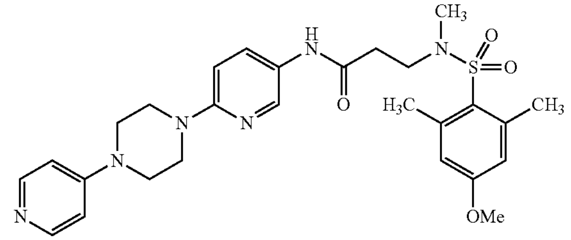

22a)

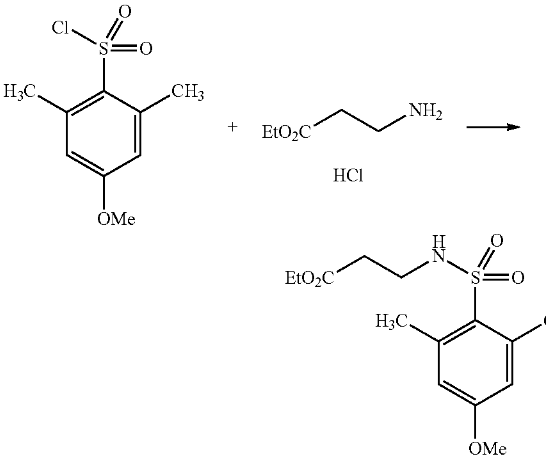

22a is prepared analogously to 3a from 3.00 g (12.78 mmol) of product from 13a, 2.16 g (14.06 mmol) of β-alanine ethylester hydrochloride, 7.13 ml (51.13 mmol) of triethylamine in 70 ml dichloromethane.

$C_{14}H_{21}NO_5S$ (315.39)

[M+H]+=316

TLC: silica gel, petroleum ether/ethyl acetate 2:1, Rf value=0.23

22b)

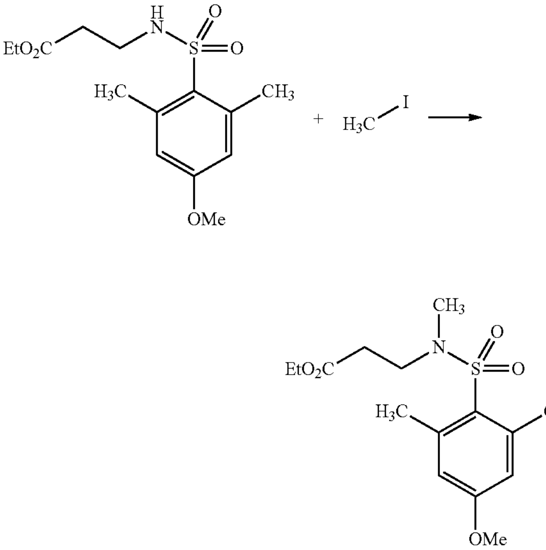

22b is prepared analogously to 3b from 4.06 g (12.87 mmol) of product from 22a, 2.40 ml (38.62 mmol) of methyl iodide, 3.56 g (25.75 mmol) of potassium carbonate anhydrous in 40 ml DMF.

$C_{15}H_{23}NO_5S$ (329.41)

[M+H]+=330

TLC: silica gel, petroleum ether/ethyl acetate 2:1, Rf value=0.36

22c)

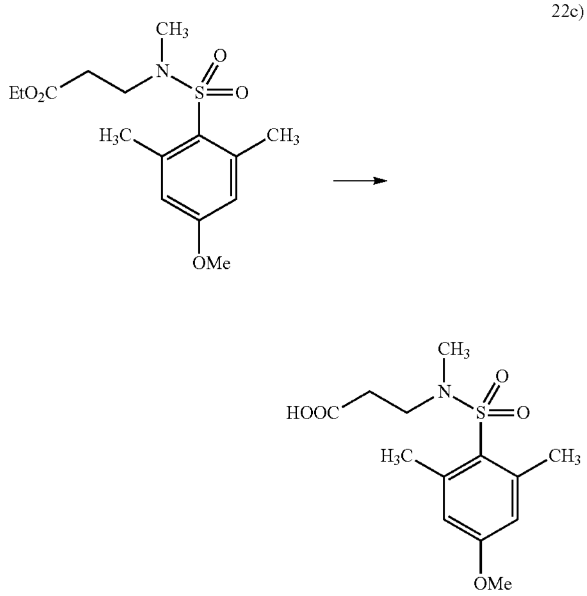

The acid is prepared analogously to 1c from 3.83 g (11.63 mmol) of product from 22b, 2.44 g (58.13 mmol) of lithium hydroxide monohydrate in 30 ml THF and 30 ml of water.

$C_{13}H_{19}NO_5S$ (301.36)

[M+H]+=302

TLC: silica gel, petroleum ether/ethyl acetate 1:1, Rf value=0.12

22d)

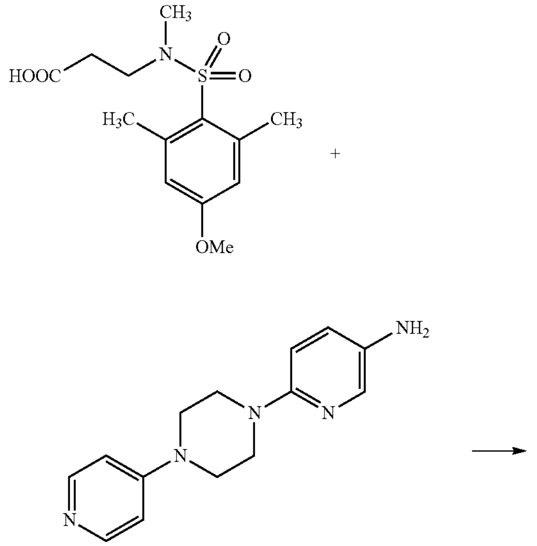

-continued

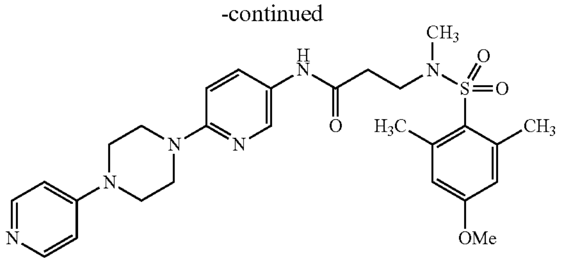

Example 22 is prepared analogously to 1f from 0.13 g (0.42 mmol) of product from 22c, 0.089 g (0.35 mmol) of product from 21b, 0.098 ml (0.70 mmol) of triethylamine and 0.13 g (0.42 mmol) of TBTU in 15 ml THF.

$C_{27}H_{34}N_6O_4S$ (538.66)

[M+H]+=539

HPLC (Method 4): retention time=2.6 min

Example 23

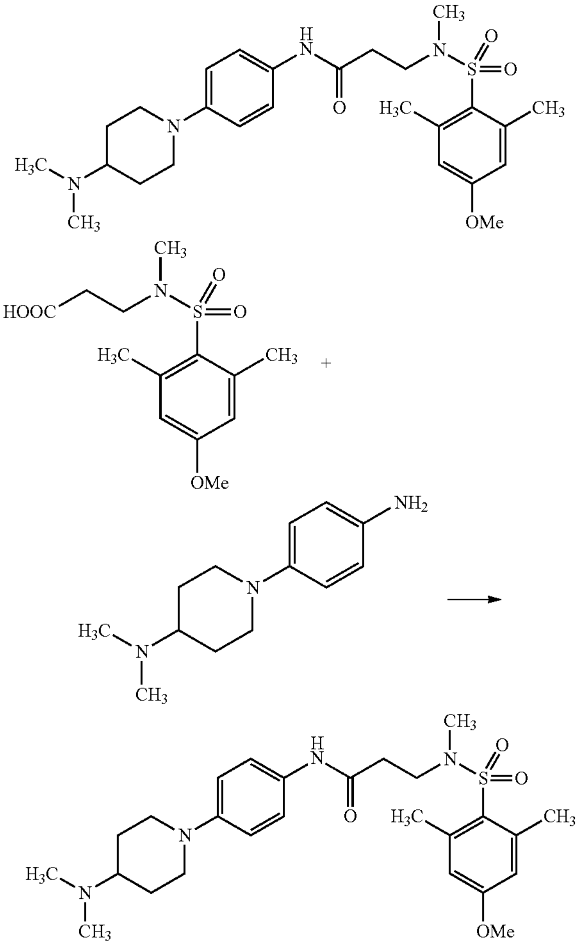

Example 23 is prepared analogously to 1f from 0.30 g (1.00 mmol) of product from 22c, 0.22 g (1.00 mmol) of product from 8b, 0.42 ml (2.99 mmol) of triethylamine and 0.32 g (1.00 mmol) of TBTU in 15 ml DMF.

$C_{26}H_{38}N_4O_4S$ (502.67)

[M+H]+=503

HPLC (Method 1): retention time=2.47 min

Example 24

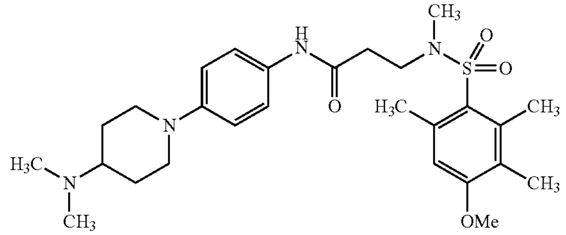

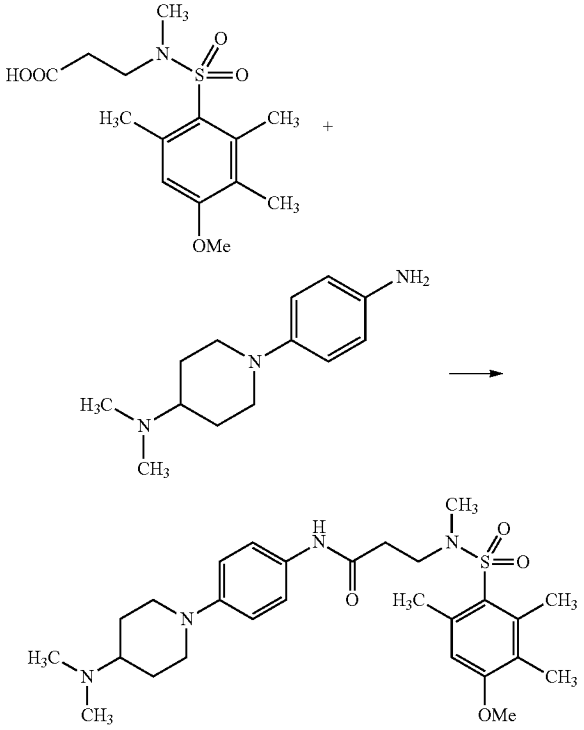

Example 24 is prepared analogously to 1f from 0.25 g (0.80 mmol) of product from 3c, 0.18 g (0.80 mmol) of product from 8b, 0.33 ml (2.39 mmol) of triethylamine and 0.26 g (0.80 mmol) of TBTU in 10 ml DMF.

$C_{27}H_{40}N_4O_4S$ (516.70)

[M+H]+=517

HPLC (Method 1): retention time=2.50 min

Example 25

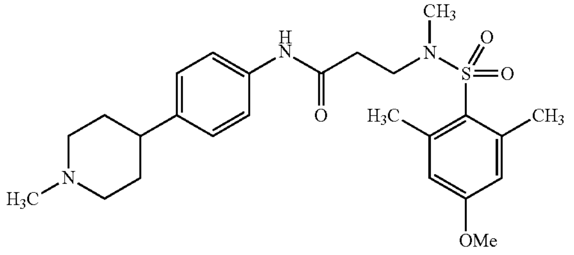

-continued

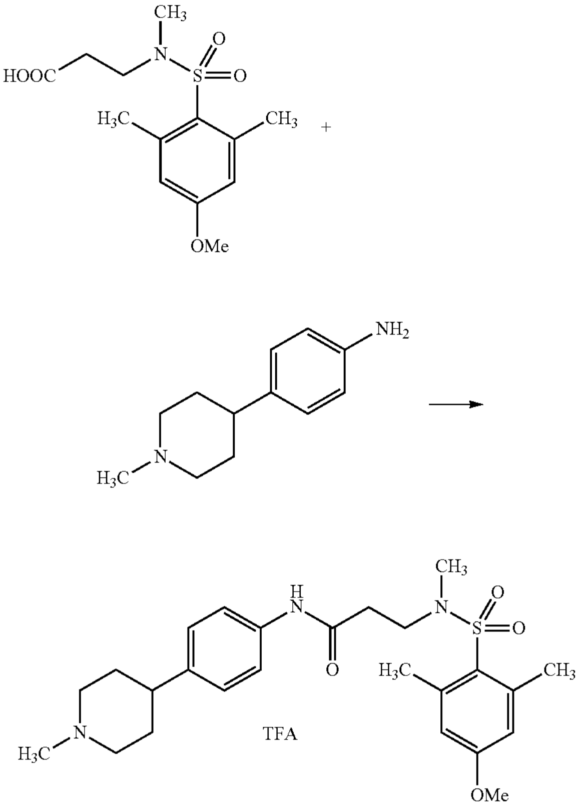

Example 25 is prepared analogously to 1f from 0.20 g (0.66 mmol) of product from 22c, 0.14 g (0.73 mmol) of 4-(1-methylpiperidin-4-yl)-aniline (JW Pharmlab), 0.28 ml (1.99 mmol) of triethylamine and 0.21 g (0.66 mmol) of TBTU in 50 ml THF.

$C_{27}H_{40}N_4O_4S \times C_2HF_3O_2$ (587.65)

[M+H]+=474

HPLC (Method 2): retention time=3.03 min

Example 26

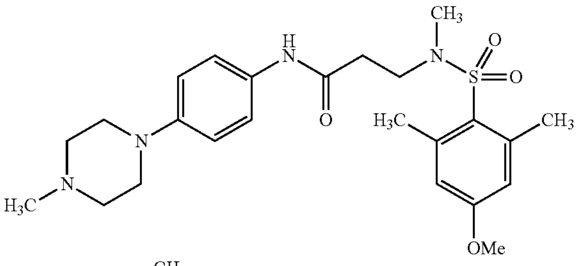

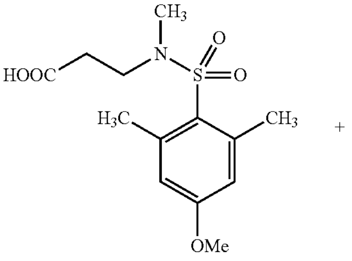

-continued

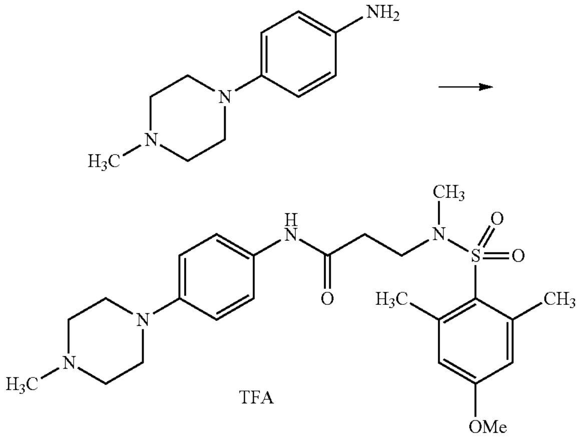

Example 26 is prepared analogously to 1f from 0.20 g (0.66 mmol) of product from 22c, 0.14 g (0.73 mmol) of 4-(4-methylpiperazin-1-yl)aniline (J. Med. Chem. SIR 48, 7, 2005, 2371-2387), 0.28 ml (1.99 mmol) of triethylamine and 0.21 g (0.66 mmol) of TBTU in 5 ml THF.

$C_{24}H_{34}N_4O_4S \times C_2HF_3O_2$ (588.65)

[M+H]+=475

HPLC (Method 5): retention time=1.50 min

Example 27

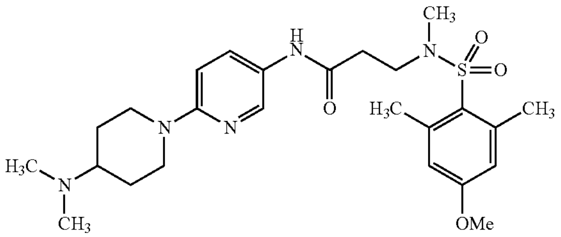

27a)

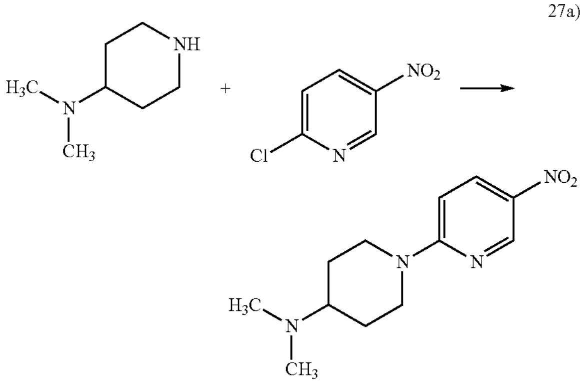

A mixture of 1.00 g (6.31 mmol) of 2-chloro-5-nitropyridine (Fluka), 1.32 ml (9.46 mmol) of triethylamine and 2 ml of methanol is taken and slowly combined with 1.13 g (8.83 mmol) of 4-dimethylamino-piperidine (Alfa Aesar). The reaction solution is then quenched with semisaturated sodium chloride, the precipitate formed is suction filtered and dried.

$C_{12}H_{18}N_4O_2$ (250.30)

27b)

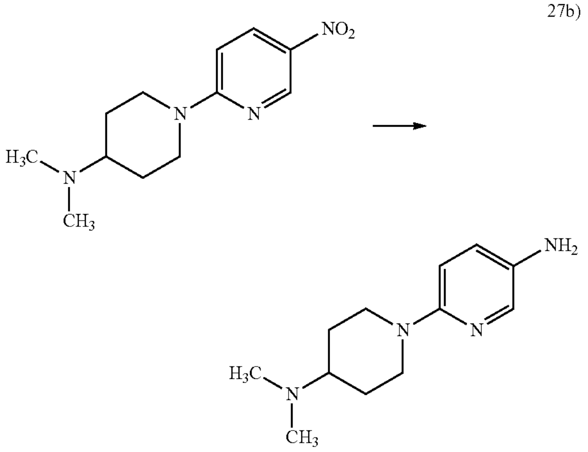

27b is prepared analogously to 8b from 1.50 g (5.99 mmol) of product from 27a, 0.20 g palladium on charcoal (10%) and 15 ml of methanol.

$C_{12}H_{20}N_4$ (220.31)

27c)

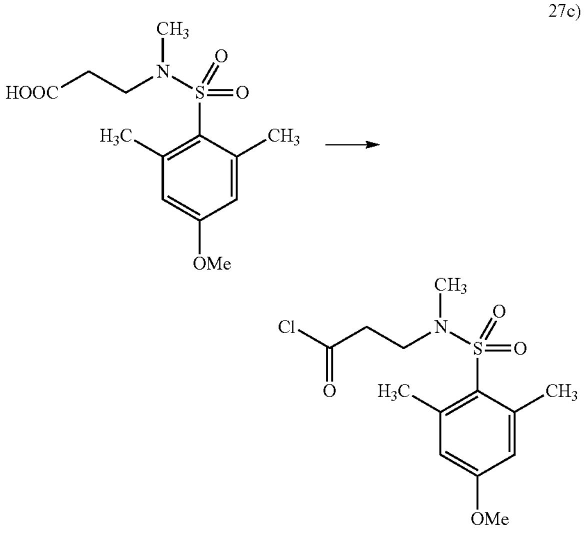

A mixture of 0.11 g (0.35 mmol) of product from 22c and 2.0 ml of thionyl chloride is stirred for two hours at ambient temperature. The reaction mixture is then evaporated to dryness in vacuo.

$C_{13}H_{18}ClNO_4S$ (319.81)

27d)

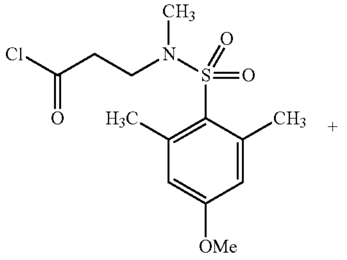

-continued

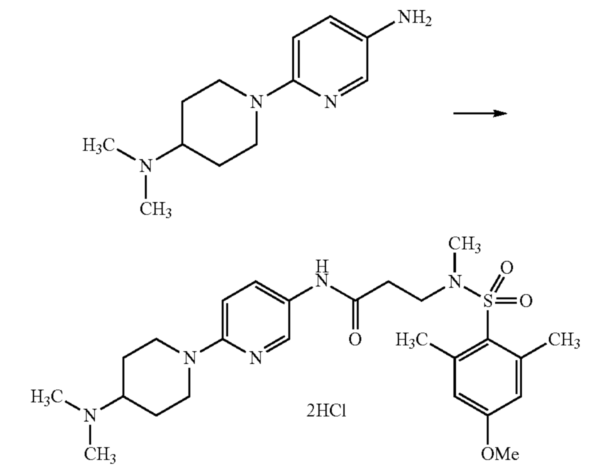

A mixture of 0.11 g (0.34 mmol) of product from 27c, 0.091 g (0.41 mmol) of product from 27b, 0.18 ml (1.03 mmol) of DIPEA and 45 ml THF is stirred for two hours at ambient temperature. The reaction mixture is then evaporated to dryness in vacuo. The crude product is purified by preparative HPLC. Then the hydrochloride is prepared using 4 M HCl in dioxane.

$C_{25}H_{37}N_5O_4S$x2HCl (576.58)

[M+H]+=504

HPLC (Method 2): retention time=2.73 min

Example 28

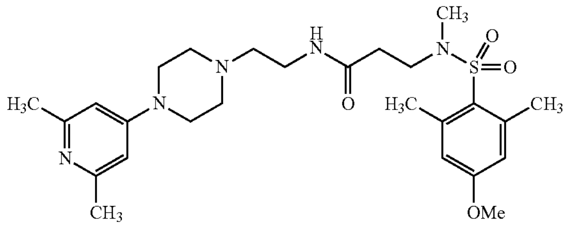

28a)

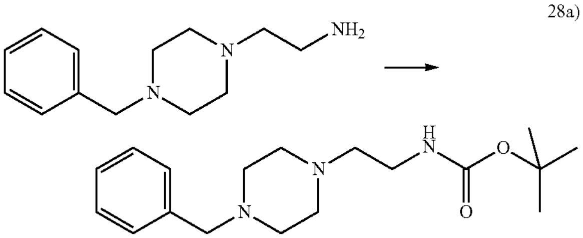

A mixture of 1.50 g (6.84 mmol) of 1-(2-aminoethyl)-4-benzylpiperazine (Maybridge), 1.64 g (7.52 mmol) of Boc-anhydride and 30 ml dichloromethane is stirred for one hour at ambient temperature. Then the reaction solution is diluted with 100 ml dichloromethane and washed with 1 M sodium hydroxide solution and water. The organic phase is dried on sodium sulphate and evaporated to dryness in vacuo.

$C_{18}H_{29}N_3O_2$ (319.44)

HPLC (Method 4): retention time=2.6 min

28b)

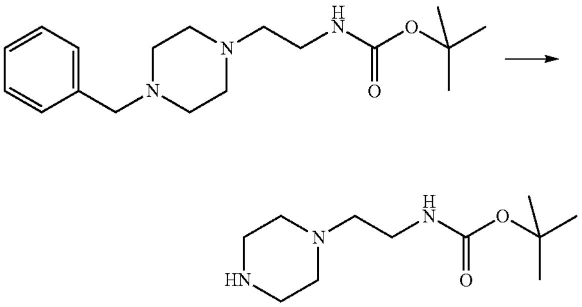

A mixture of 2.10 g (6.57 mmol) of product from 28a, 0.25 g palladium on charcoal (10%) and 30 ml of methanol is hydrogenated for 15 hours at ambient temperature in the autoclave. Then the catalyst is removed by suction filtering and the filtrate is evaporated to dryness in vacuo.

$C_{11}H_{23}N_3O_4$ (229.32)

[M+H]+=230

TLC: silica gel, dichloromethane/ethanol 9:1, Rf value=0.08

28c)

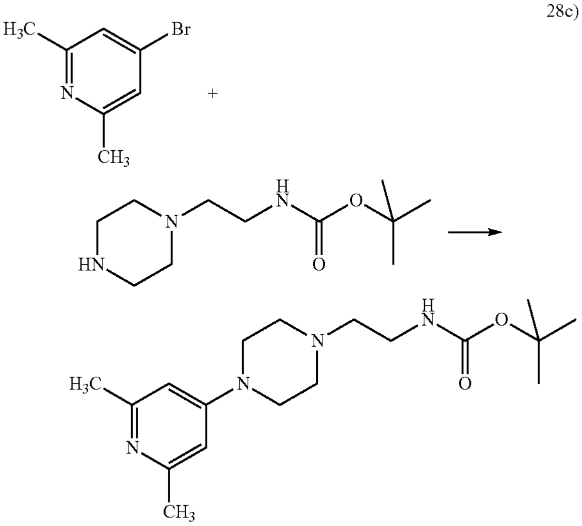

A mixture of 1.18 g (6.32 mmol) of 4-bromo-2,6-dimethylpyridine (Acta Chem. Scand. Ser. B 42, 1988, 373-377), 1.45 g (6.32 mmol) of product from 28b and 2.2 ml DIPEA is heated for 50 min to 130° C. in the microwave. The reaction mixture is combined with ethyl acetate and semisaturated potassium carbonate solution and then the phases are separated. The organic phase is dried on sodium sulphate and evaporated to dryness in vacuo. The crude product thus obtained is purified by column chromatography through silica gel (eluant: dichloromethane/methanol/ammonia 95:5:0.5).

$C_{18}H_{30}N_4O_2S$ (334.46)

[M+H]+=335

TLC: silica gel, dichloromethane/methanol/ammonia 9:1:0.1, Rf value=0.37

28d)

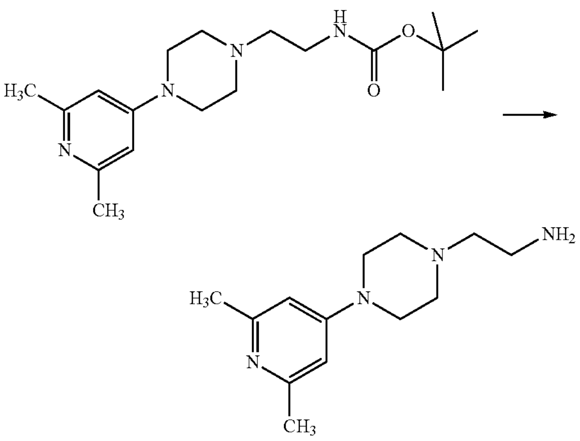

A mixture of 1.61 g (4.81 mmol) of product from 28c, 3.70 ml TFA and 30 ml dichloromethane is stirred for six hours at ambient temperature. The reaction mixture is then diluted with dichloromethane and washed with 5% sodium hydrogen carbonate solution. The aqueous phase is extracted twice more with ethyl acetate. The combined organic phases are dried on sodium sulphate and evaporated to dryness in vacuo. The crude product thus obtained is purified by column chromatography through silica gel (eluant: dichloromethane/methanol/ammonia 90:10:1).

$C_{13}H_{22}N_4$ (234.34)

[M+H]+=235

TLC: silica gel, dichloromethane/methanol/ammonia 9:1:0.1, Rf value=0.10

28e)

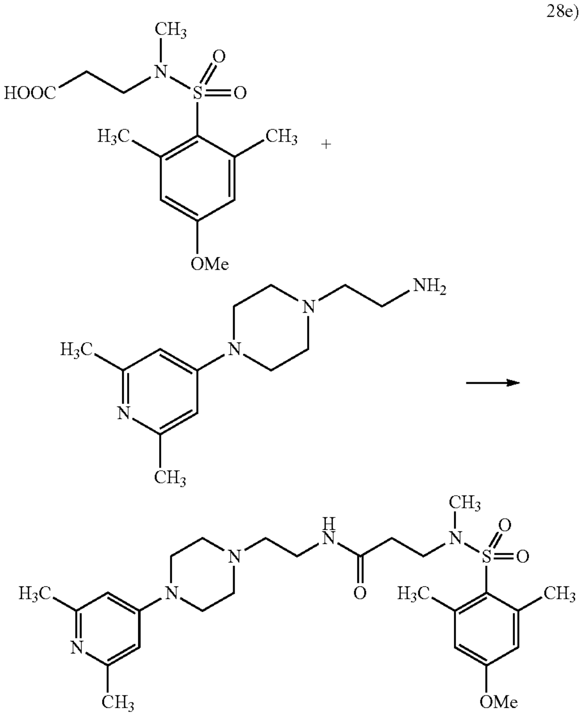

Example 28 is prepared analogously to 1f from 0.11 g (0.35 mmol) of product from 22c, 0.082 g (0.35 mmol) of product from 28d, 0.098 ml (0.70 mmol) of triethylamine and 0.13 g (0.42 mmol) of TBTU in 7 ml THF and 1 ml DMF.

$C_{26}H_{39}N_5O_4S$ (517.69)

[M+H]+=518

HPLC (Method 4): retention time=2.4 min

Example 29

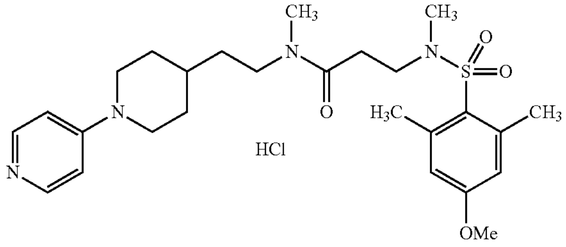

29a)

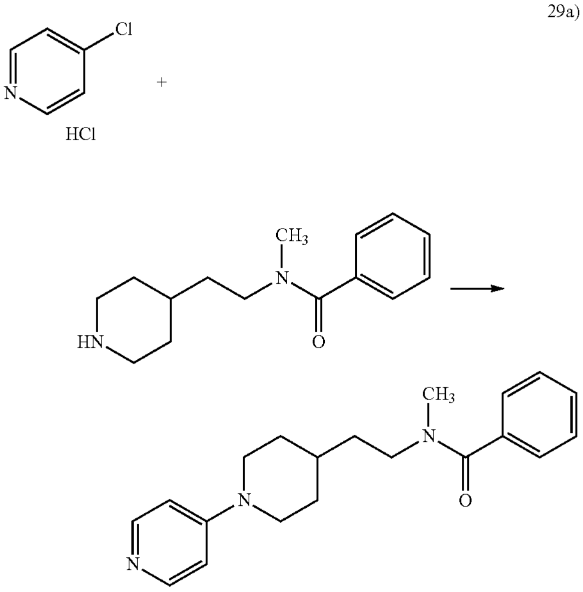

29a is prepared analogously to 28c from 0.12 g (0.80 mmol) of 4-chloropyridine hydrochloride (Aldrich), 0.20 g (0.80 mmol) of N-methyl-N-(2-piperidin-4-yl-ethyl)-benzamide (J. Med. Chem. 33, 1990, 1880-1887), 0.23 ml (1.68 mmol) of triethylamine in 5 ml of ethanol.

$C_{20}H_{25}N_3O$ (323.43)

[M+H]+=324

29b)

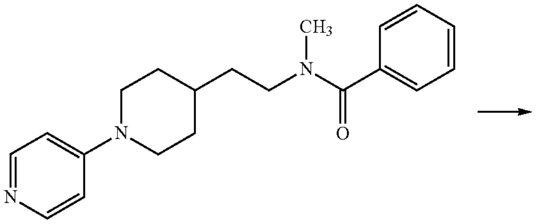

-continued

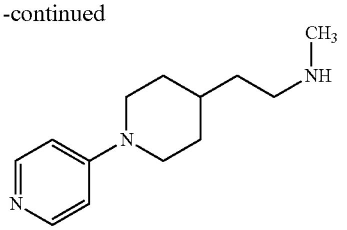

A mixture of 0.52 g (1.61 mmol) of product from 29a, 10 ml of 2 M potassium hydroxide solution and 10 ml of ethanol is refluxed for 30 hours. The reaction mixture is evaporated down by half in vacuo and then extracted with dichloromethane. The organic extracts are dried on sodium sulphate and evaporated to dryness in vacuo.

$C_{13}H_{21}N_3$ (219.33)

[M+H]+=220

TLC: silica gel, dichloromethane/methanol/ammonia 8:2:0.01, Rf value=0.46

29c)

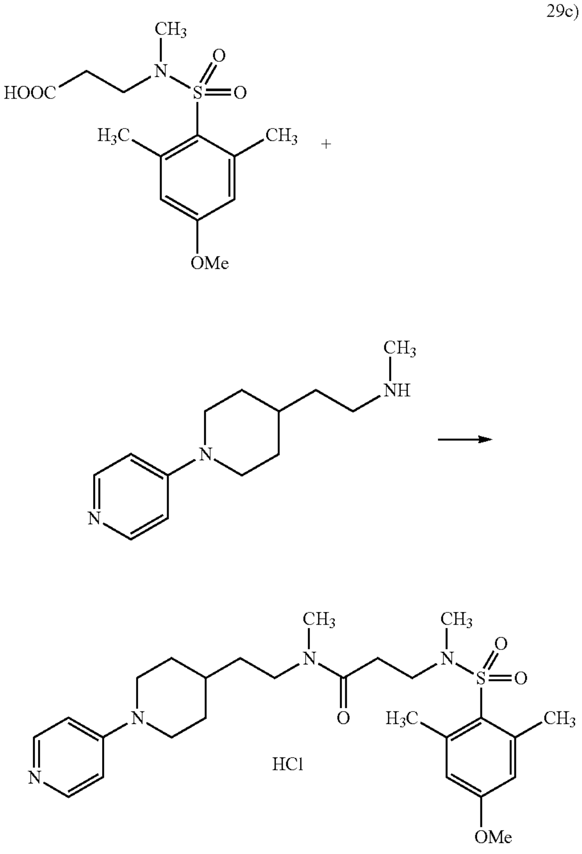

Example 29 is prepared analogously to 1f from 0.14 g (0.46 mmol) of product from 22c, 0.10 g (0.46 mmol) of product from 29b, 0.15 ml (1.09 mmol) of triethylamine and 0.16 g (0.50 mmol) of TBTU in 30 ml THF and 5 ml DMF.

$C_{26}H_{38}N_4O_4S \times HCl$ (539.13)

[M+H]+=503

TLC: silica gel, dichloromethane/methanol/ammonia 8:2:0.01, Rf value=0.41

Example 30

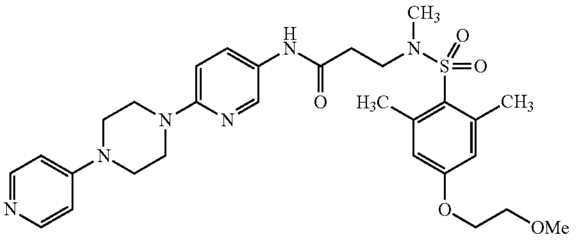

30a)

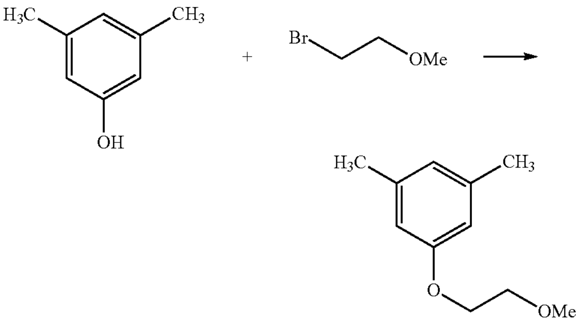

A mixture of 3.25 g (26.60 mmol) of 3,5-dimethylphenol (Aldrich), 3.20 g (28.52 mmol) of potassium-tert-butoxide and 40 ml DMSO is stirred for one hour at ambient temperature. Then 3.80 g (27.34 mmol) of bromoethylmethylether (Aldrich) is added dropwise thereto and the mixture is stirred for another two hours at ambient temperature. The reaction mixture is poured onto water and extracted with diethyl ether. The organic extracts are washed with water and saturated sodium chloride solution, dried on sodium sulphate and evaporated to dryness in vacuo.

$C_{11}H_{16}O_2$ (180.24)

[M+H]+=181

TLC: silica gel, petroleum ether/ethyl acetate 9:1, Rf value=0.31

30b)

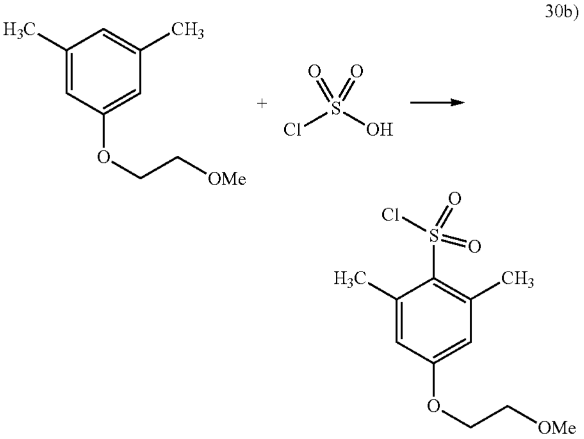

30b is prepared analogously to 13a from 4.30 g (23.86 mmol) of product from 30a and 5.60 g (48.06 mmol) of chlorosulphonic acid in 100 ml dichloromethane.

$C_{11}H_{15}ClO_4S$ (278.75)

TLC: silica gel, petroleum ether/ethyl acetate 9:1, Rf value=0.06

30c)

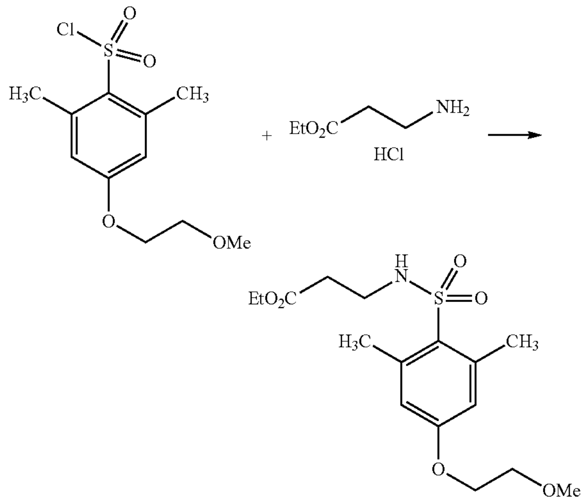

30a is prepared analogously to 3a from 1.70 g (6.10 mmol) of product from 30b, 1.20 g (7.81 mmol) of R-alanine ethylester hydrochloride, 2.60 ml (18.65 mmol) of triethylamine in 30 ml dichloromethane.

$C_{16}H_{25}NO_6S$ (359.44)

[M+H]+=360

TLC: silica gel, dichloromethane/methanol 19:1, Rf value=0.51

30d)

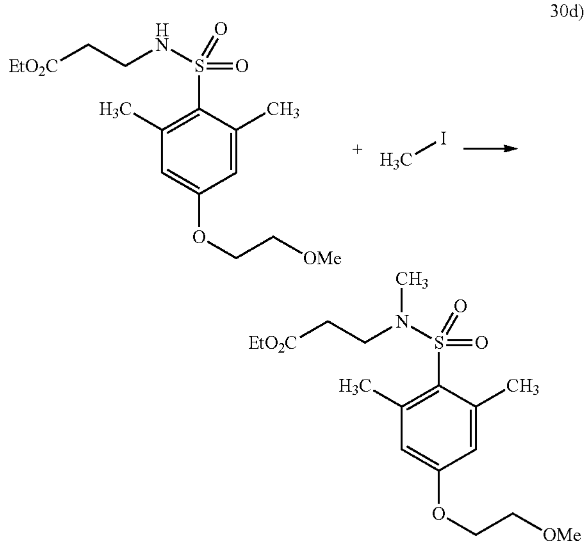

30d is prepared analogously to 3b from 1.90 g (5.29 mmol) of product from 30c, 1.10 g (7.75 mmol) of methyl iodide, 1.50 g (10.85 mmol) of anhydrous potassium carbonate in 30 ml DMF.

$C_{17}H_{27}NO_6S$ (373.47)

[M+H]+=374

30e)

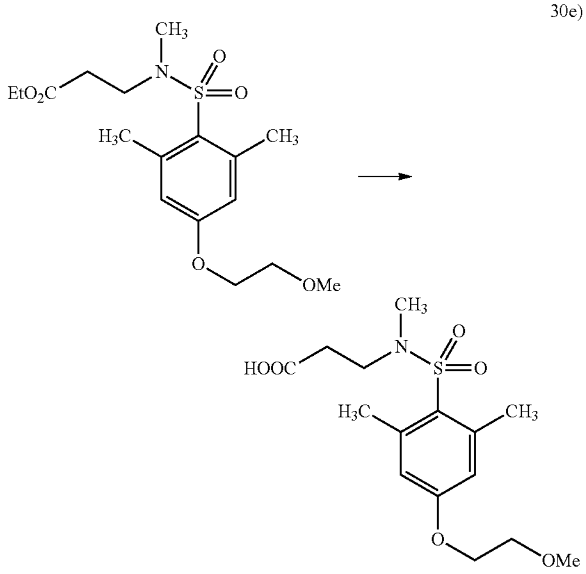

The acid is prepared analogously to 1c from 1.70 g (4.55 mmol) of product from 30d, 0.80 g (20.00 mmol) of sodium hydroxide in 30 ml of ethanol and 10 ml of water.

$C_{15}H_{23}NO_6S$ (345.41)

[M+H]+=346

30f)

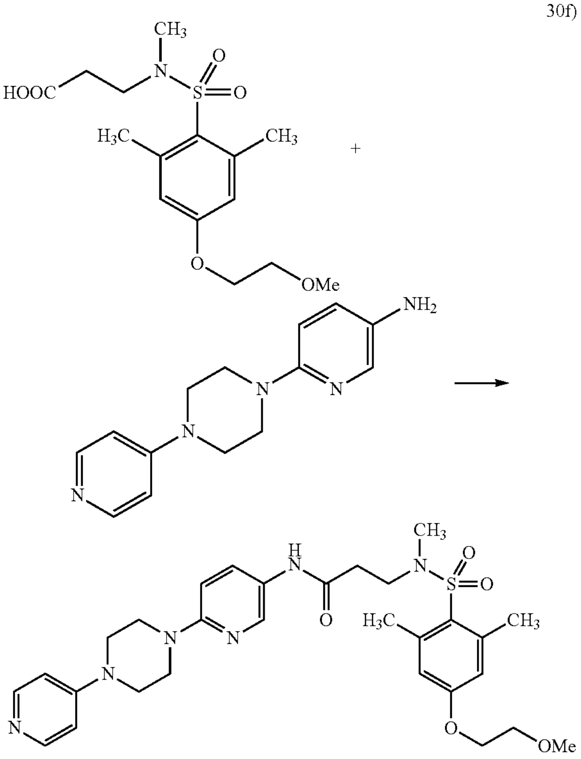

Example 30 is prepared analogously to 1f from 0.14 g (0.39 mmol) of product from 30e, 0.10 g (0.39 mmol) of product from 21b, 0.10 ml (0.99 mmol) of triethylamine and 0.14 g (0.44 mmol) of TBTU in 30 ml THF and 5 ml DMF.

$C_{29}H_{38}N_6O_5S$ (582.72)

[M+H]+=583

TLC: silica gel, dichloromethane/methanol/ammonia 8:2: 0.01, Rf value=0.44

Example 31

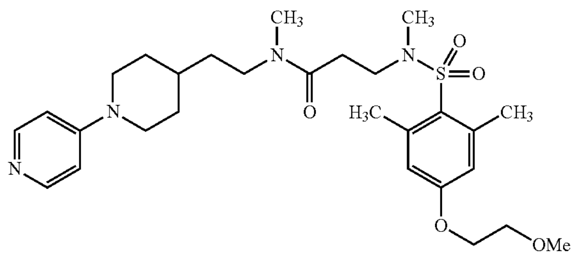

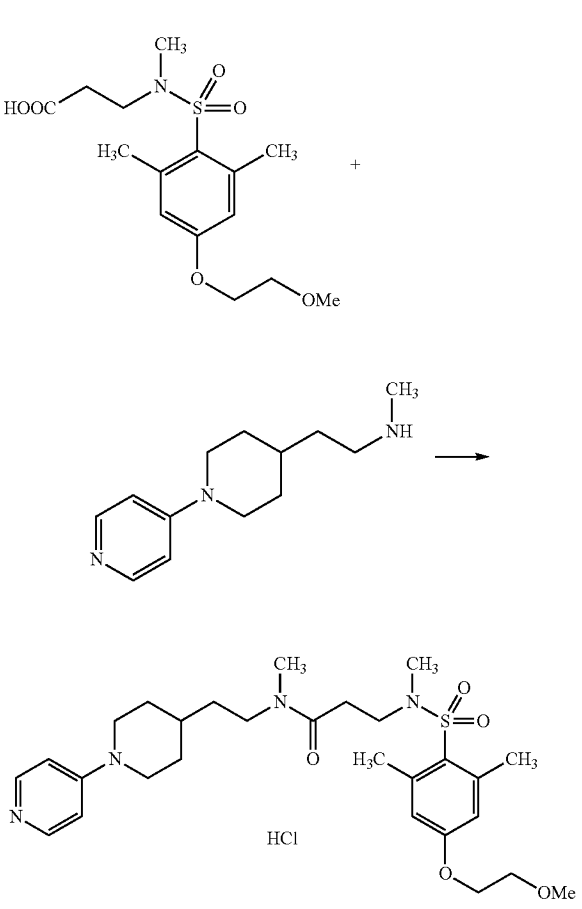

Example 31 is prepared analogously to 1f from 0.16 g (0.46 mmol) of product from 30e, 0.10 g (0.46 mmol) of product from 29b, 0.11 ml (1.09 mmol) of triethylamine and 0.16 g (0.50 mmol) of TBTU in 30 ml THF and 5 ml DMF.

$C_{28}H_{42}N_4O_5S \times HCl$ (583.18)

[M+H]+=547

TLC: silica gel, dichloromethane/methanol/ammonia 8:2: 0.01, Rf value=0.52

Example 32

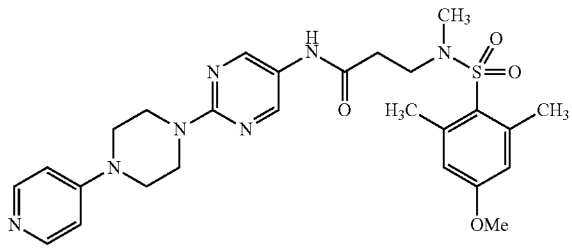

32a)

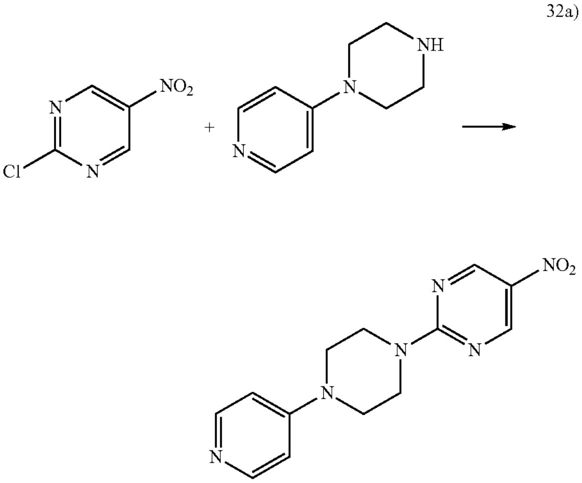

A mixture of 3.00 g (18.81 mmol) of 2-chloro-5-nitropyrimidine (Apin), 3.07 g (18.81 mmol) of 1-(4-pyridyl)-piperazine (Girindus), 9.40 ml (18.81 mmol) of 2 M sodium hydroxide solution in 80 ml dichloromethane is stirred for 2.5 hours at ambient temperature. Then the reaction mixture is diluted with 100 ml dichloromethane and washed with 5% sodium hydrogen carbonate solution. The organic phase is dried on sodium sulphate and evaporated to dryness in vacuo. The crude product is triturated with a mixture of 50 ml of water and 30 ml ethyl acetate, filtered off and dried.

$C_{13}H_{14}N_6O_2$ (286.29)

[M+H]+=287

HPLC (Method 4): retention time=2.6 min

32b)

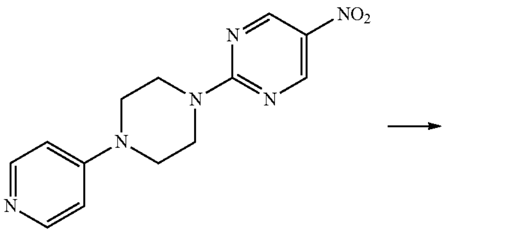

-continued

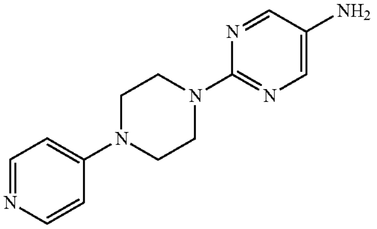

32b is prepared analogously to 21b from 1.93 g (6.74 mmol) of product from 32a and 0.3 g palladium on charcoal (10%) in 60 ml dichloromethane and 30 ml of methanol.

$C_{13}H_{16}N_6$ (256.31)

[M+H]+=257

TLC: silica gel, dichloromethane/methanol 8:2, Rf value=0.11

32c)

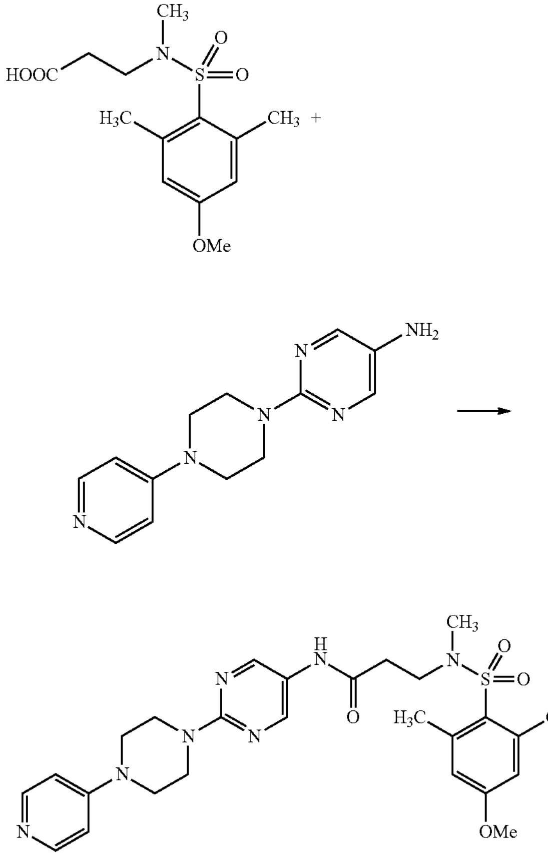

Example 32 is prepared analogously to 1f from 0.11 g (0.35 mmol) of product from 22c, 0.090 g (0.35 mmol) of product from 32b, 0.098 ml (0.70 mmol) of triethylamine and 0.13 g (0.42 mmol) of TBTU in 7 ml THF and 1 ml DMF.

$C_{26}H_{33}N_7O_4S$ (539.65)

[M+H]+=540

HPLC (Method 4): retention time=2.9 min

Example 33

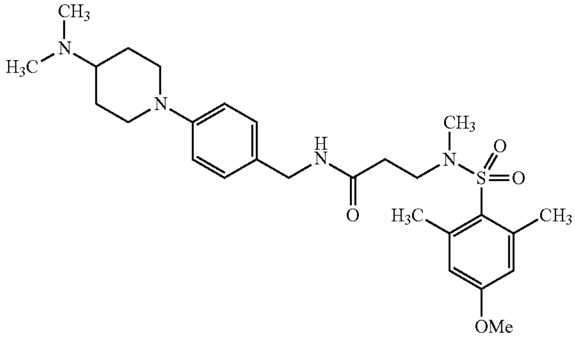

33a)

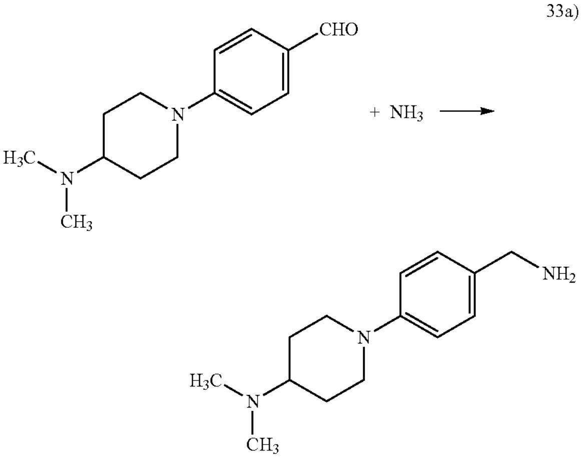

A mixture of 0.68 g (2.91 mmol) of 4-(4-dimethylamino-piperidin-1-yl)-benzaldehyde (Tetrahedron 57, 2001, 4781-4785), 15 ml of 2 M ammonia in ethanol and 0.10 g Raney nickel is hydrogenated at ambient temperature in the autoclave. Then the catalyst is filtered off and the filtrate is evaporated to dryness in vacuo.

$C_{14}H_{23}N_3$ (233.35)

33b)

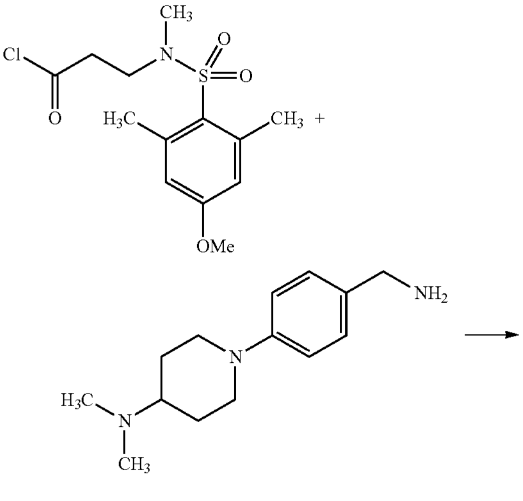

-continued

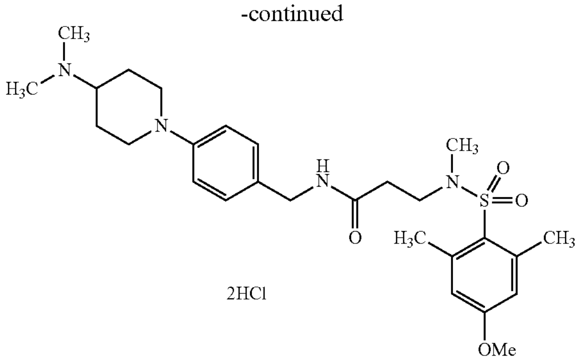

2HCl

Example 33 is prepared analogously to 27d from 0.27 g (0.84 mmol) of product from 27c, 0.63 g (2.68 mmol) of product from 33a, 0.22 ml (1.26 mmol) of DIPEA in 3 ml dichloromethane.

$C_{27}H_{40}N_4O_4S \times 2HCl$ (589.62)

[M+H]+=517

HPLC (Method 5): retention time=1.46 min

Example 34

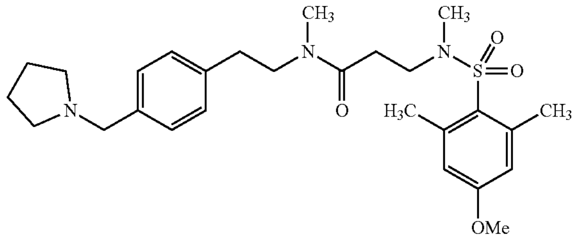

34a)

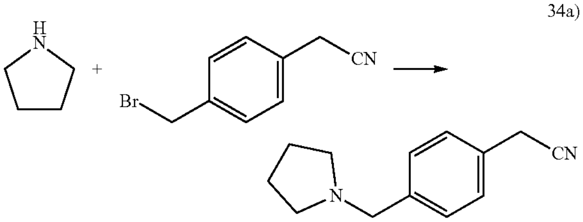

A mixture of 4.97 ml (59.50 mmol) of pyrrolidine and 100 ml dichloromethane is slowly combined with 5.00 g (23.80 mmol) of (4-bromomethyl-phenyl)-acetonitrile (Tetrahedron 47, 1991, 3969-3980) while cooling with an ice bath. Then the reaction mixture is heated to ambient temperature, washed with water, dried on magnesium sulphate and evaporated to dryness in vacuo.

$C_{13}H_{16}N_2$ (200.28)

[M+H]+=201

TLC: silica gel, dichloromethane/methanol/ammonia 9:1:0.1, Rf value=0.58

34b)

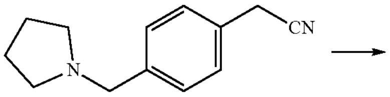

-continued

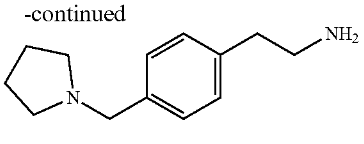

A mixture of 4.70 g (23.47 mmol) of product from 34a, 0.5 g Raney nickel and 50 ml of methanolic ammonia solution is hydrogenated in the autoclave at 50° C. Then the catalyst is filtered off and the filtrate is evaporated to dryness in vacuo.

$C_{13}H_{20}N_2$ (204.31)

[M+H]+=205

34c)

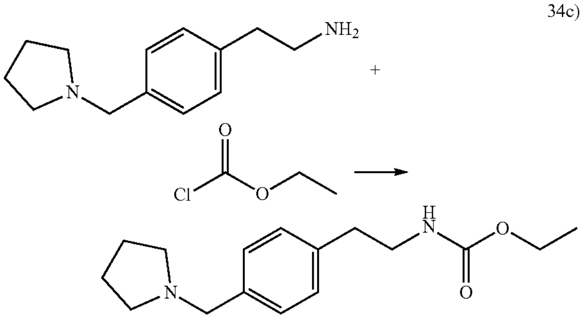

A mixture of 4.09 g (20.00 mmol) of product from 34b, 5.62 ml (40.00 mmol) of triethylamine and 100 ml dichloromethane is slowly combined with 2.17 ml (22.00 mmol) of ethyl chloroformate (Aldrich) while cooling with an ice bath. Then the mixture is stirred for five hours at ambient temperature. The reaction mixture is then quenched with water and extracted with MTB-ether. The organic extracts are washed twice with water, dried on magnesium sulphate and evaporated to dryness in vacuo. The crude product thus obtained is purified by column chromatography through silica gel (eluant: dichloromethane/methanol/ammonia 9:1:0.1).

$C_{16}H_{24}N_2O_2$ (276.37)

[M+H]α=277

34d)

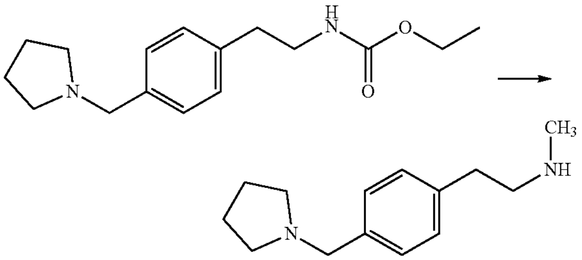

A mixture of 3.60 g (13.03 mmol) of product from 34c and 25 ml THF is slowly combined with 51.05 ml (51.05 mmol) of 1 M lithium aluminium hydride in THF (Aldrich). Then the mixture is stirred for two hours at ambient temperature and two hours at 70° C. The reaction mixture is then quenched with water and 15% sodium hydroxide solution and stirred for another hour at ambient temperature. The precipitate formed is filtered off and the filtrate is evaporated to dryness in vacuo. The crude product thus obtained is purified by column chromatography through silica gel (eluant: dichloromethane/methanol/ammonia 9:1:0.1).

$C_{14}H_{22}N_2$ (218.34)

[M+H]+=219

34e)

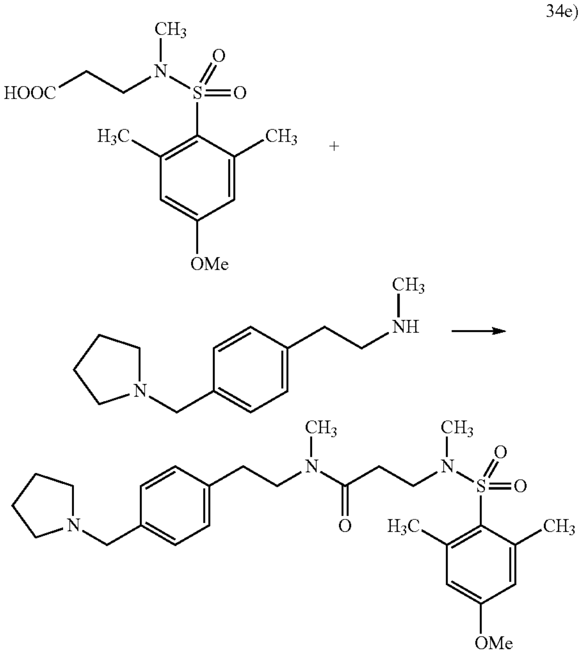

Example 34 is prepared analogously to 1f from 0.11 g (0.35 mmol) of product from 22c, 0.076 g (0.35 mmol) of product from 34d, 0.098 ml (0.70 mmol) of triethylamine and 0.13 g (0.42 mmol) of TBTU in 7 ml THF and 1 ml DMF.

$C_{27}H_{39}N_3O_4S$ (501.68)

[M+H]+=502

HPLC (Method 4): retention time=3.1 min

Example 35

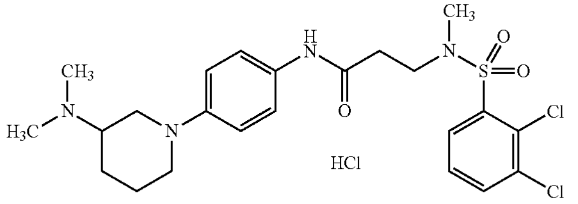

35a)

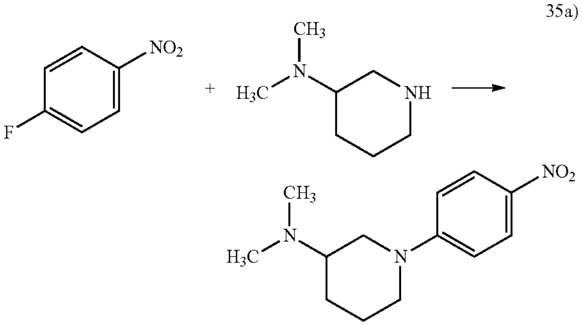

A mixture of 0.33 g (2.34 mmol) of 1-fluoro-4-nitrobenzene (Aldrich), 0.30 g (2.34 mmol) of 3-dimethylamino-piperidine (Chess), 0.46 ml (3.27 mmol) of triethylamine and 4 ml DMF is stirred for six hours at ambient temperature. The reaction mixture is then quenched with water and extracted with dichloromethane. The organic extracts are washed with saturated sodium chloride solution, dried on sodium sulphate and evaporated to dryness in vacuo.

$C_{13}H_{19}N_3O_2$ (249.31)

[M+H]+=250

TLC: silica gel, dichloromethane/methanol/ammonia 9:1:0.1, Rf value=0.56

35b)

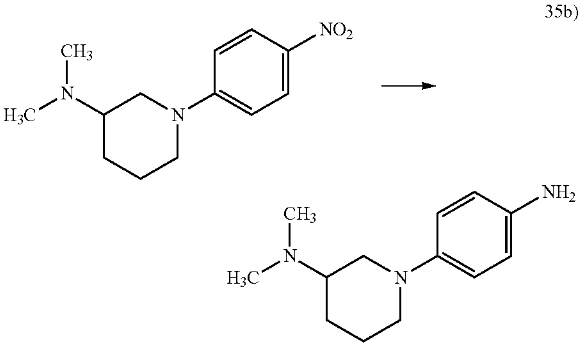

A mixture of 0.25 g (1.00 mmol) of product from 35a, 30 mg Raney nickel and 10 ml ethyl acetate is hydrogenated in the autoclave at ambient temperature. The catalyst is filtered off and the filtrate is evaporated to dryness in vacuo.

$C_{13}H_{21}N_3$ (219.33)

TLC: silica gel, dichloromethane/methanol/ammonia 9:1:0.1, Rf value=0.25

35c)

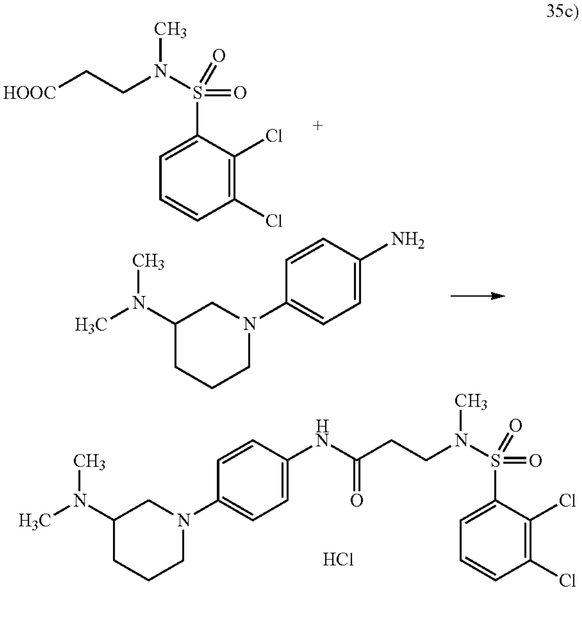

Example 35 is prepared analogously to 1f from 0.16 g (0.50 mmol) of product from 1c, 0.11 g (0.50 mmol) of product from 35b, 0.14 ml (1.00 mmol) of triethylamine and 0.16 g (0.50 mmol) of TBTU in 3 ml DMF.

$C_{23}H_{30}Cl_2N_4O_3S{\times}HCl$ (539.14)

[M+H]+=513/515/517

HPLC (Method 1): retention time=2.43 min

Example 36

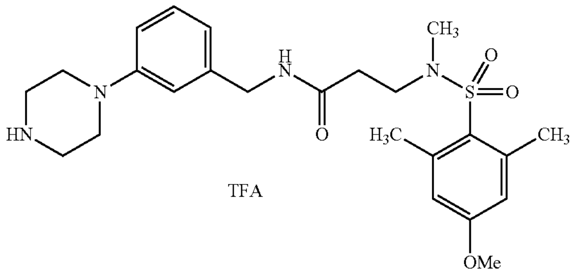

TFA

36a)

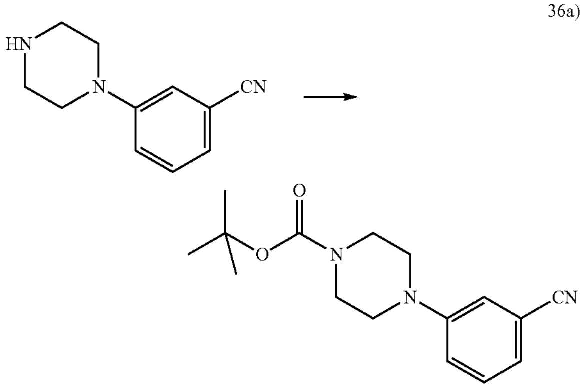

A mixture of 2.50 g (13.35 mmol) of 3-piperazin-1-yl-benzonitrile (Tetrahedron 55, 1999, 13285-13300), 3.00 g (13.75 mmol) of Boc-anhydride, 2.40 ml (13.78 mmol) of DIPEA and 50 ml THF is stirred for four hours at ambient temperature and then evaporated to dryness in vacuo. The residue is taken up in water and extracted with diethyl ether. The organic extracts are dried on sodium sulphate and evaporated to dryness in vacuo.

$C_{16}H_{21}N_3O_2$ (287.36)

[M+Na]+=310

36b)

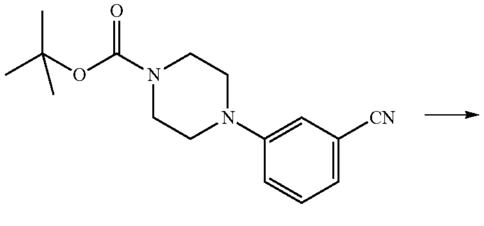

-continued

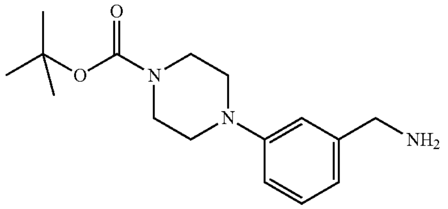

36b is prepared analogously to 34b from 4.40 g (15.31 mmol) of product from 36a, 0.7 g Raney nickel and 45 ml of methanolic ammonia solution.

$C_{16}H_{25}N_3O_2$ (291.39)

[M+H]+=292

36c)

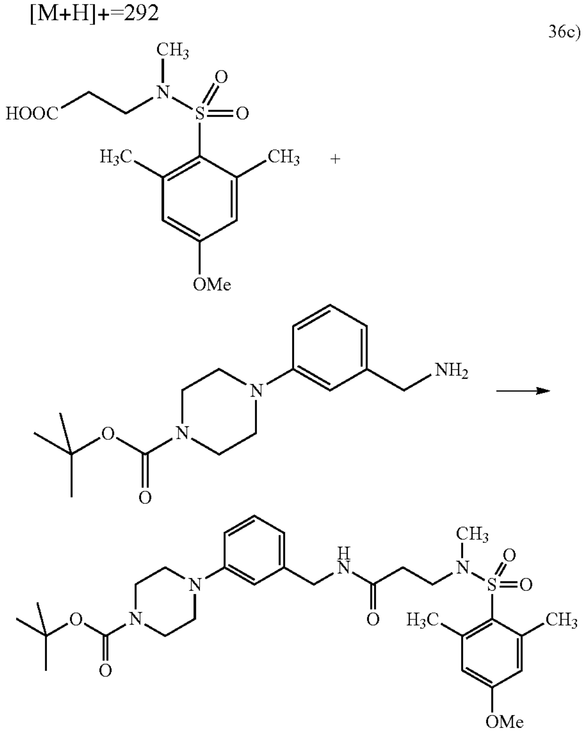

36c is prepared analogously to 1f from 0.40 g (1.33 mmol) of product from 22c, 0.43 g (1.46 mmol) of product from 36b, 0.56 ml (3.98 mmol) of triethylamine and 0.43 g (1.33 mmol) of TBTU in 10 ml THF.

$C_{29}H_{42}N_4O_6S$ (574.73)

M+H]+=575

TLC: silica gel, dichloromethane/methanol 9:1, Rf value=0.53

36d)

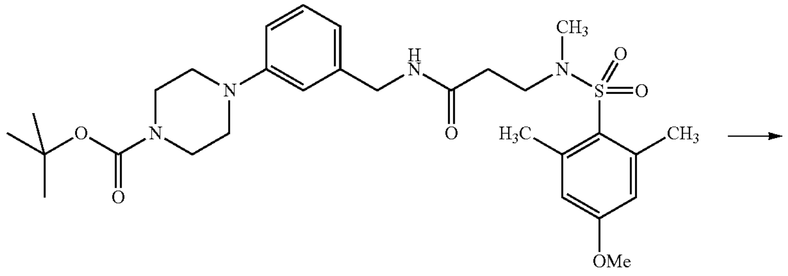

-continued

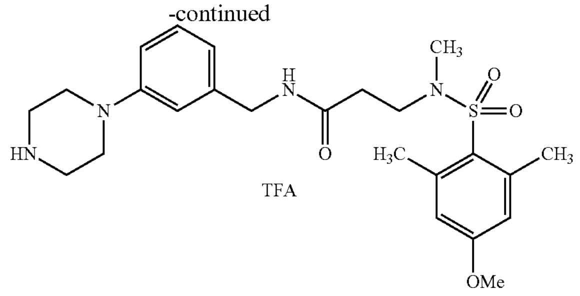

TFA

Example 36 is prepared analogously to 18b from 0.50 g (0.57 mmol) of product from 36c, 0.44 ml TFA in 5 ml dichloromethane.

$C_{18}H_{28}Cl_2N_4O_3S \times C_2HF_3O_2$ (588.64)

[M+H]+=475

HPLC (Method 2): retention time=2.95 min

Example 37

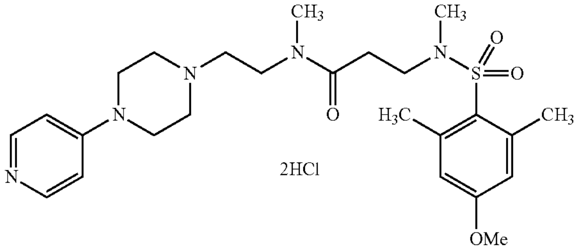

2HCl

37a)

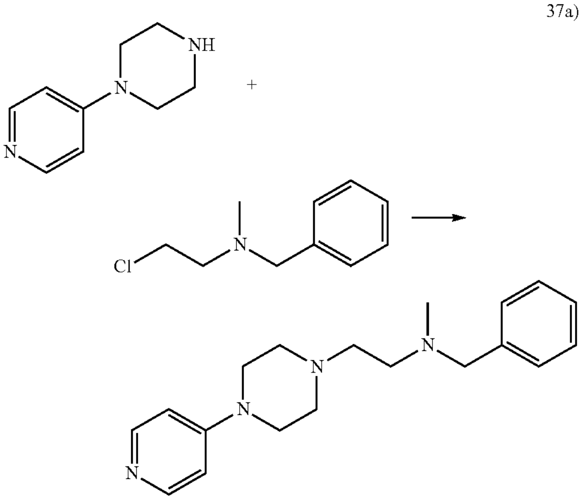

A mixture of 2.00 g (12.25 mmol) of 1-(4-pyridyl)-piperazine (Girindus), 1.65 g (14.70 mmol) of potassium-tert-butoxide and 50 ml DMSO is stirred for 30 min at ambient temperature and then combined with 2.25 g (12.25 mmol) of 1-benzylmethylamino-2-chloroethane (Chem. Pharm. Bull. 45, 1997, 996-1007). The reaction mixture is stirred overnight at ambient temperature and then poured onto ice water. It is extracted four times with dichloromethane. The organic extracts are dried on sodium sulphate and evaporated to dryness in vacuo. The crude product thus obtained is purified by column chromatography through silica gel (eluant: dichloromethane/methanol/ammonia 9:1:0.1).

$C_{19}H_{26}N_4$ (310.44)

[M+H]+=311

TLC: silica gel, dichloromethane/methanol/ammonia 9:1:0.1, Rf value=0.22

37b)

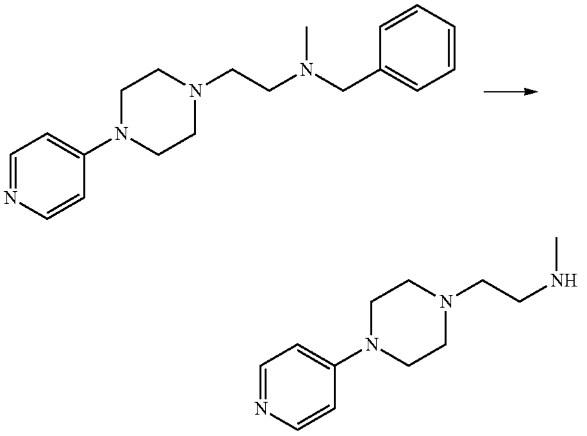

A mixture of 1.78 g (5.73 mmol) of product from 37a, 0.40 g palladium hydroxide and 50 ml of methanol is hydrogenated at 40° C. in the autoclave. The catalyst is filtered off and the filtrate is evaporated to dryness in vacuo. The crude product thus obtained is purified by column chromatography through silica gel (eluant: dichloromethane/methanol/ammonia 9:1:0.1).

$C_{12}H_{20}N_4$ (220.31)

[M+H]+=221

TLC: silica gel, dichloromethane/methanol/ammonia 9:1:0.1, Rf value=0.13

37c)

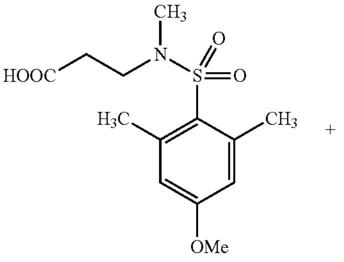

-continued

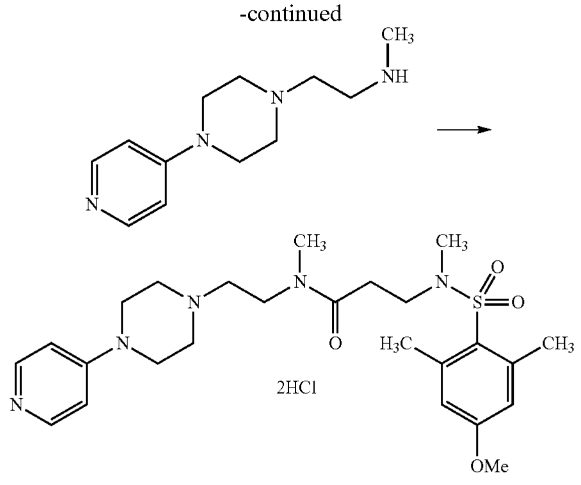

Example 37 is prepared analogously to 1f from 0.11 g (0.35 mmol) of product from 22c, 0.072 g (0.35 mmol) of product from 37b, 0.098 ml (0.70 mmol) of triethylamine and 0.13 g (0.42 mmol) of TBTU in 7 ml THF.

$C_{25}H_{37}N_5O_4S \times 2HCl$ (576.58)

[M+H]+=504

HPLC (Method 4): retention time=2.5 min

Example 38

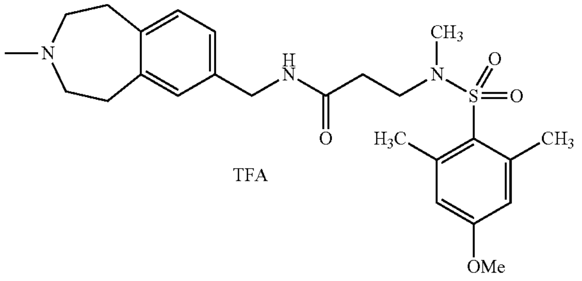

38a)

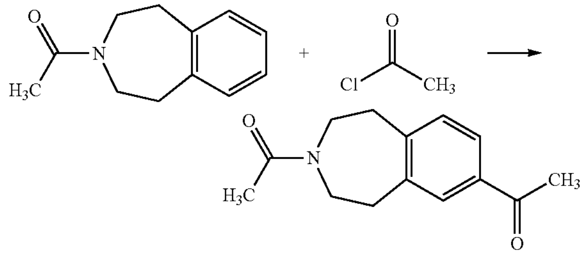

A mixture of 4.44 g (33.29 mmol) of aluminium chloride (Merck) and 16 ml of dichloroethane is taken and 1.24 ml (17.44 mmol) of acetyl chloride (Aldrich) is slowly added while cooling with an ice bath. The mixture is stirred for 30 min at ambient temperature. Then 3.00 g (15.85 mmol) of 1-(1,2,4,5-tetrahydrobenzo[d]azepin-3-yl)-ethanone (J. Med. Chem. 46, 2003, 4952-4964) in 7 ml of dichloroethane slowly added to the reaction mixture. After two hours' stirring at ambient temperature the reaction mixture is poured onto a mixture of 6 M HCl and ice. After the phase separation the aqueous phase is extracted another three times with dichloromethane. The combined organic phases are washed with water, dried on sodium sulphate and evaporated to dryness in vacuo. The crude product thus obtained is triturated with diethyl ether, filtered off and dried.

$C_{14}H_{17}NO_2$ (231.29)

[M+H]+=232

38b)

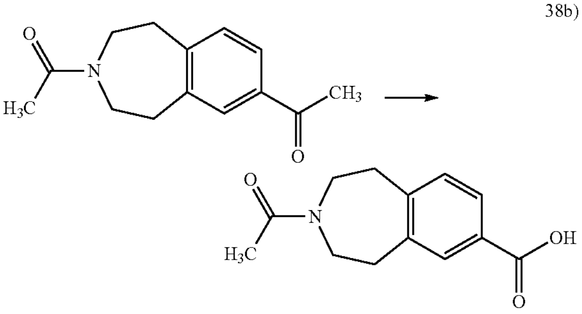

A mixture of 2.86 g (12.37 mmol) of product from 38a and 79 ml 2.5 M sodium hydroxide solution is slowly combined at ambient temperature with 2.48 ml (48.23 mmol) of bromine. The reaction mixture is then stirred for one hour at ambient temperature. The precipitate formed is filtered off and the filtrate is extracted with MTB-ether. The aqueous phase is then mixed with concentrated HCl and a little sodium disulphite solution while cooling with an ice bath. The precipitate formed is filtered off and dried in the circulating air dryer at 30° C.

$C_{13}H_{15}NO_3$ (233.26)

[M+H]+=234

38c)

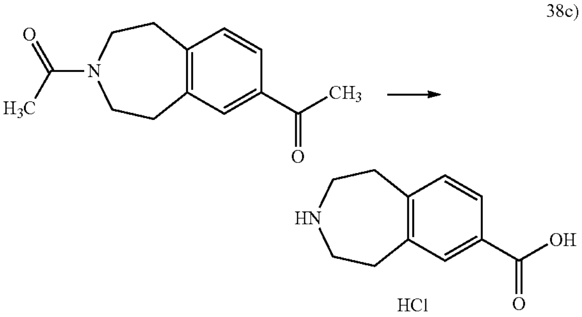

A mixture of 2.12 g (9.09 mmol) of product from 38b and 20 ml 6 M HCl is heated for 3.5 days to 100° C. The reaction mixture is then cooled with a mixture of ice and ethanol. The precipitate formed is filtered off, washed with a little cooled acetone and diethyl ether and dried in the desiccator.

$C_{11}H_{13}NO_2 \times HCl$ (227.69)

[M+H]+=192

38d)

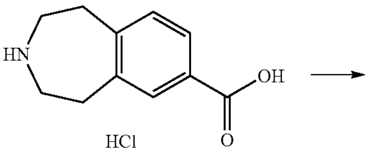

-continued

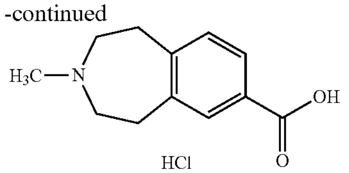

First 0.94 ml (17.83 mmol) of 50% sodium hydroxide solution, then 2.66 ml (35.66 mmol) of 37% formalin solution are slowly added to a mixture of 2.03 g (8.92 mmol) of product from 38c and 3.36 ml (89.16 mmol) of formic acid. The reaction mixture is heated for two hours to 70° C. and then evaporated to dryness in vacuo. The residue is combined with water and concentrated HCl and again evaporated to dryness. The crude product is triturated with a little ice-cold water, filtered off and dried in the circulating air dryer at 60° C.

$C_{12}H_{15}NO_2 \times HCl$ (241.71)

[M+H]+=206

38e)

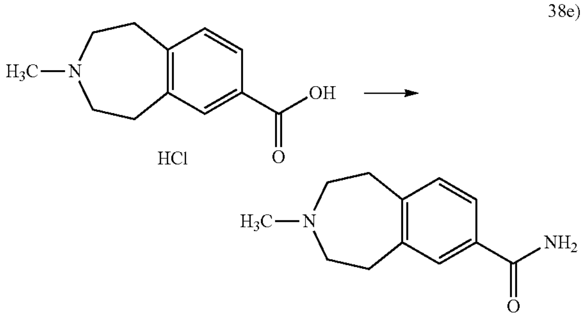

38e is prepared analogously to 1f from 2.00 g (8.27 mmol) of product from 38d, 18.20 ml (9.10 mmol) of ammonia 0.5 M in dioxane (Aldrich), 3.46 ml (24.82 mmol) of triethylamine and 3.19 g (9.93 mmol) of TBTU in 30 ml THF.

$C_{12}H_{16}N_2O$ (204.27)

[M+H]+=205

HPLC (Method 2): retention time=1.54 min

38f)

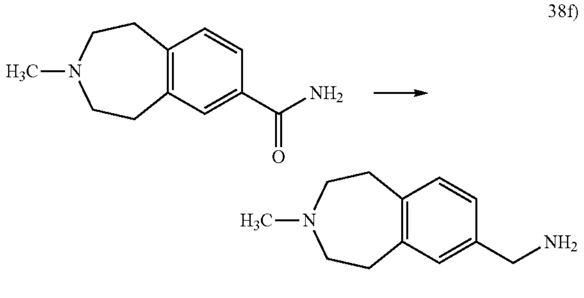

A mixture of 5.20 ml (5.20 mmol) of lithium aluminium hydride 1 M in THF (Aldrich) and 18 ml THF is heated to 50° C. and slowly combined with 0.84 g (2.64 mmol) of product from 38e. The reaction mixture is then stirred for 30 min at 50° C. It is then cooled to −20° C. and the reaction mixture is quenched first with a mixture of water and THF, then with 2 M sodium hydroxide solution. It is stirred for one hour at ambient temperature. The precipitate formed is filtered off, the filtrate is evaporated to dryness in vacuo. The residue is taken up in dichloromethane and washed with saturated sodium hydrogen sulphate solution. The organic phase is dried on sodium sulphate and evaporated to dryness in vacuo.

$C_{12}H_{18}N_2$ (190.28)

[M+H]+=191

HPLC (Method 2): retention time=2.21 min

38g)

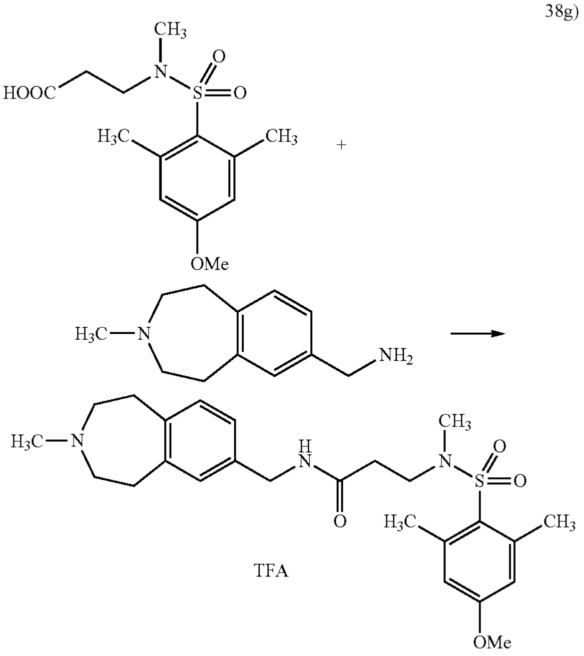

Example 38 is prepared analogously to 1f from 0.19 g (0.63 mmol) of product from 22c, 0.12 g (0.63 mmol) of product from 38f, 0.26 ml (1.89 mmol) of triethylamine and 0.20 g (0.63 mmol) of TBTU in 5 ml THF.

$C_{25}H_{35}N_3O_4S \times C_2HF_3O_2$ (587.65)

[M+H]+=474

HPLC (Method 4): retention time=2.98 min

Example 39

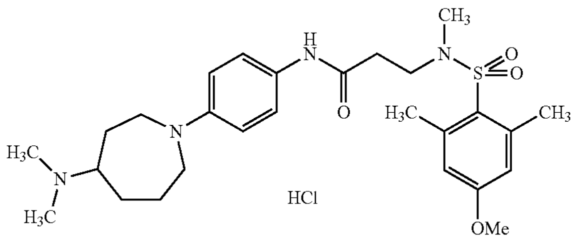

39a)

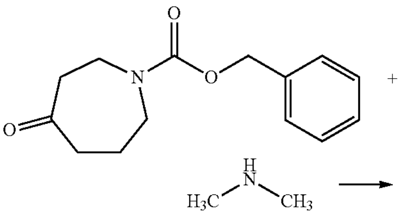

-continued

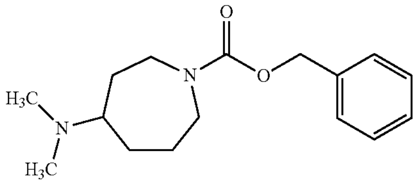

A mixture of 1.50 g (6.07 mmol) of benzyl 4-oxo-azepan-1-carboxylate (Tyger), 20 ml (40.00 mmol) of dimethylamine 2 M in THF (Aldrich) and 0.34 ml (6.07 mmol) of acetic acid is stirred for 20 min at ambient temperature and then combined with 3.82 g (18.00 mmol) of sodium triacetoxyborohydride (Aldrich). The mixture is stirred overnight at ambient temperature. The reaction mixture is then mixed with saturated sodium hydrogen carbonate solution and extracted with ethyl acetate. The organic extracts are washed with saturated sodium chloride solution, dried on sodium sulphate and evaporated to dryness in vacuo. The crude product thus obtained is purified by column chromatography through silica gel (eluant: dichloromethane/4-12% (methanol+10% ammonia)).

$C_{16}H_{24}N_2O_2$ (276.37)

[M+H]+=277

HPLC (Method 1): retention time=2.12 min

39b)

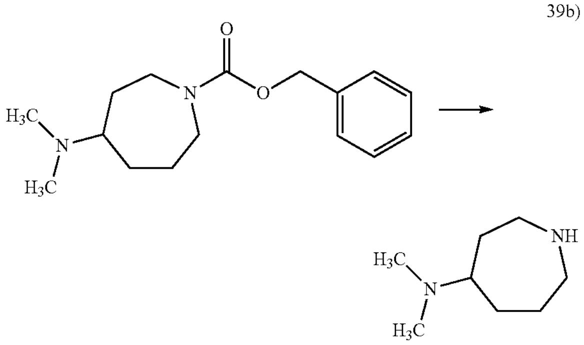

A mixture of 1.00 g (3.62 mmol) of product from 39a, 0.10 g palladium on charcoal (10%) and 30 ml of methanol is hydrogenated at ambient temperature in the autoclave. The catalyst is then filtered off, the filtrate is evaporated to dryness in vacuo.

$C_8H_{18}N_2$ (142.24)

[M+H]+=143

TLC: silica gel, dichloromethane/methanol/ammonia 9:1:0.1, Rf value=0.12

39c)

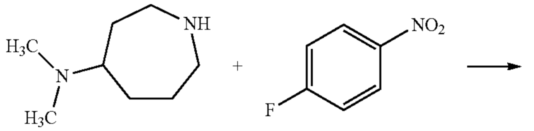

-continued

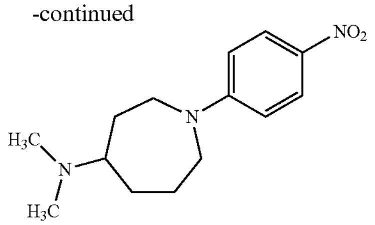

39c is prepared analogously to 1d from 0.56 g (4.37 mmol) of product from 39b, 0.64 g (4.50 mmol) of 4-fluoro-nitrobenzene (Aldrich), 0.65 ml (4.60 mmol) of triethylamine in 5 ml DMF.

$C_{14}H_{21}N_3O_2$ (263.34)

[M+H]+=264

TLC: silica gel, dichloromethane/methanol/ammonia 9:1:0.1, Rf value=0.60

39d)

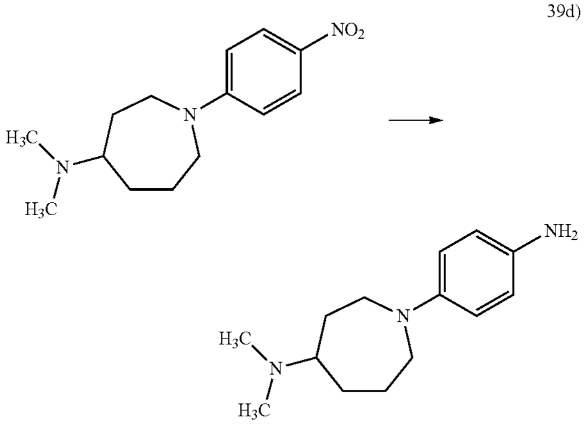

39d is prepared analogously to 8b from 0.94 g (3.55 mmol) of product from 39c and 0.10 g palladium on charcoal (10%) in 30 ml of methanol.

$C_{14}H_{23}N_3O_2$ (233.35)

TLC: silica gel, dichloromethane/methanol/ammonia 9:1:0.1, Rf value=0.15

39e)

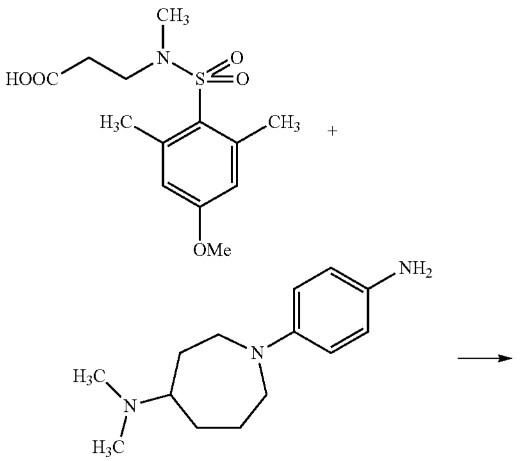

-continued

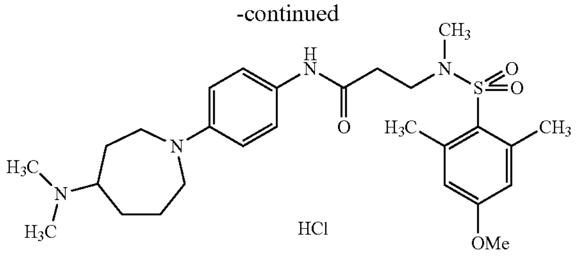

Example 39 is prepared analogously to 1f from 0.30 g (1.00 mmol) of product from 22c, 0.23 g (1.00 mmol) of product from 39d, 0.42 ml (3.00 mmol) of triethylamine and 0.32 g (1.00 mmol) of TBTU in 15 ml DMF.

$C_{27}H_{40}N_4O_4S \times HCl$ (553.16)

[M+H]+=517

TLC: silica gel, dichloromethane/methanol/ammonia 9:1:0.1, Rf value=0.42

HPLC (Method 5): retention time=1.50 min

Example 40

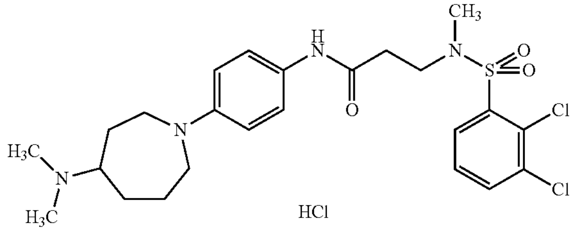

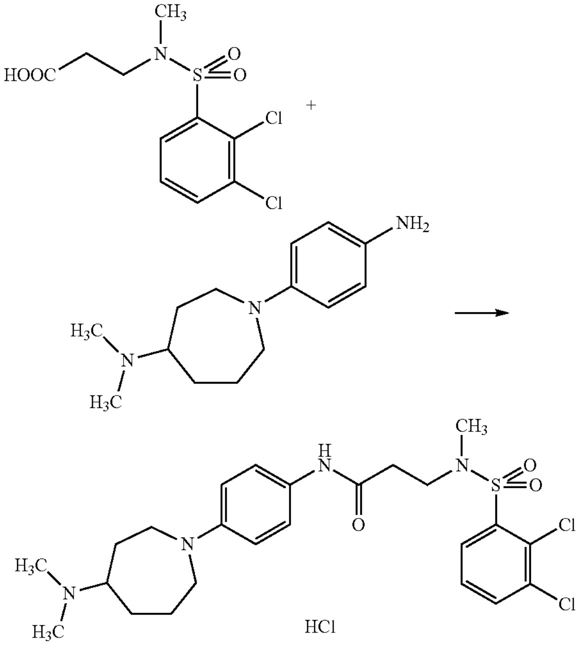

Example 40 is prepared analogously to 1f from 0.16 g (0.50 mmol) of product from 1c, 0.12 g (0.50 mmol) of product from 39d, 0.21 ml (1.50 mmol) of triethylamine and 0.16 g (0.50 mmol) of TBTU in 5 ml DMF.

$C_{24}H_{32}Cl_2N_4O_3S \times HCl$ (563.97)

[M+H]+=527/529/531

TLC: silica gel, dichloromethane/methanol/ammonia 6:1:0.2, Rf value=0.48

HPLC (Method 5): retention time=1.53 min

Example 41

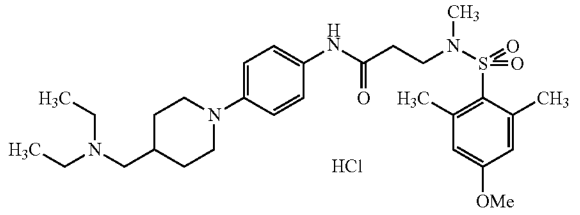

41a)

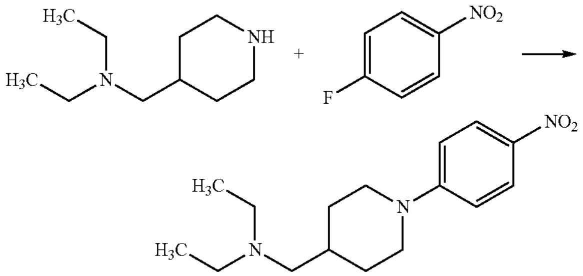

41a is prepared analogously to 1d from 1.00 g (5.87 mmol) of diethyl-piperidin-4-ylmethyl-amine (Chem. Pharm. Bull. 42, 1994, 74-84), 0.83 g (5.87 mmol) of 4-fluoro-nitrobenzene (Aldrich), 1.14 ml (8.20 mmol) of triethylamine in 12 ml DMF.

$C_{16}H_{25}N_3O_2$ (291.39)

[M+H]+=292

TLC: silica gel, dichloromethane/ethanol 9:1, Rf value=0.5

41b)

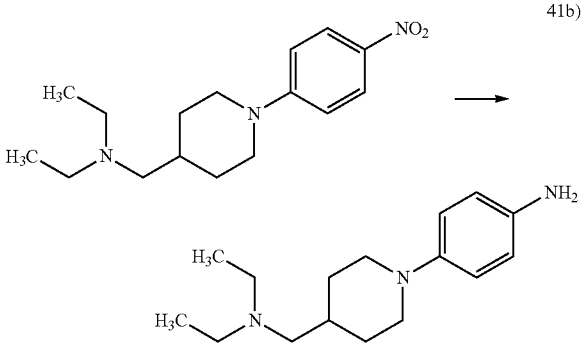

A mixture of 0.40 g (1.37 mmol) of product from 41a, 0.10 g palladium on charcoal (10%) and 30 ml of methanol is hydrogenated at ambient temperature in the autoclave. The catalyst is then filtered off, the filtrate is evaporated to dryness in vacuo.

$C_{16}H_{27}N_3$ (261.41)

TLC: silica gel, dichloromethane/ethanol 9:1, Rf value=0.1

41c)

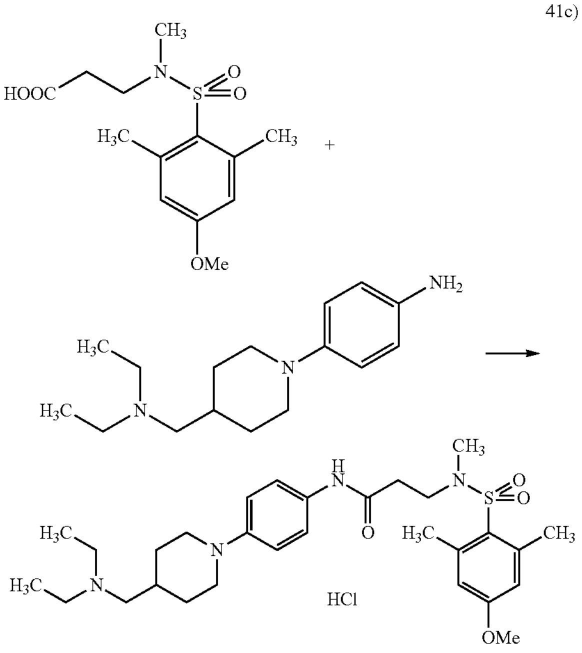

Example 41 is prepared analogously to 1f from 0.40 g (1.34 mmol) of product from 22c, 0.35 g (1.34 mmol) of product from 41b, 0.47 ml (3.35 mmol) of triethylamine and 0.43 g (1.34 mmol) of TBTU in 7 ml THF and 1 ml DMF.

$C_{29}H_{44}N_4O_4S \times HCl$ (581.21)

[M+H]+=545

HPLC (Method 5): retention time=1.42 min

Example 42

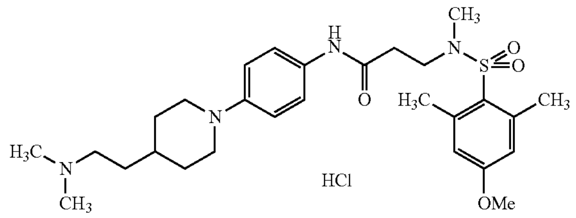

42a)

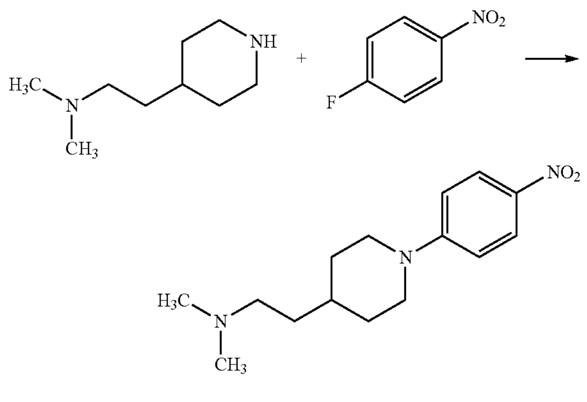

42a is prepared analogously to 1d from 1.88 g (12.00 mmol) of dimethyl-(2-piperidin-4-yl-ethyl)-amine (J. Med. Chem. 36, 1993, 162-165), 1.69 g (12.00 mmol) of 4-fluoronitrobenzene (Aldrich), 2.37 ml (17.00 mmol) of triethylamine in 15 ml DMF.

$C_{15}H_{23}N_3O_2$ (277.36)

[M+H]+=278

TLC: silica gel, dichloromethane/ethanol 9:1, Rf value=0.2

42b)

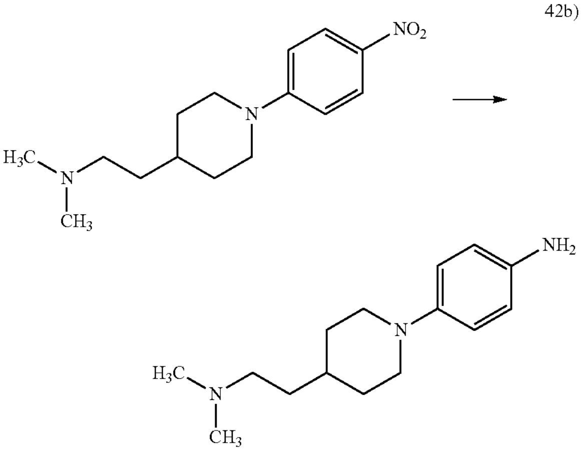

A mixture of 0.30 g (1.08 mmol) of product from 42a, 0.10 g palladium on charcoal (10%) and 30 ml of methanol is hydrogenated at ambient temperature in the autoclave. The catalyst is then filtered off, the filtrate is evaporated to dryness in vacuo.

$C_{15}H_{25}N_3$ (247.38)

42c)

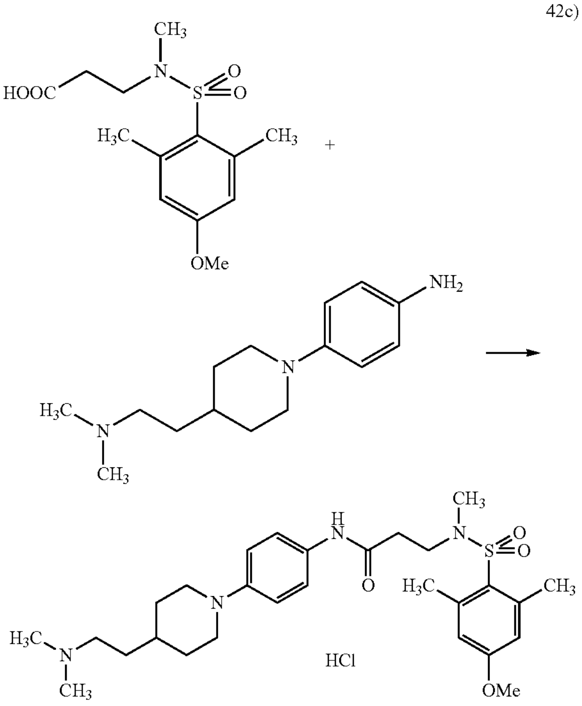

Example 42 is prepared analogously to 1f from 0.33 g (1.08 mmol) of product from 22c, 0.27 g (1.08 mmol) of product from 42b, 0.38 ml (2.70 mmol) of triethylamine and 0.35 g (1.08 mmol) of TBTU in 7 ml THF and 1 ml DMF.

$C_{28}H_{42}N_4O_4S$ (530.72)

[M+H]+=531

HPLC (Method 5): retention time=1.41 min

Example 43

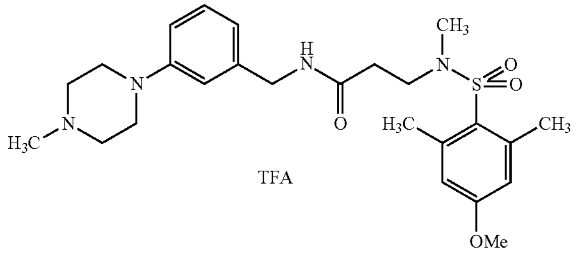

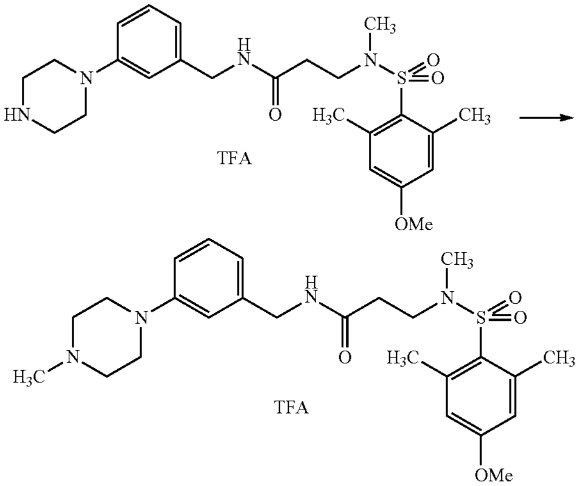

A mixture of 0.15 g (0.25 mmol) of product from 36d, 0.025 ml (0.40 mmol) of methyl iodide (Aldrich), 0.10 ml (0.75 mmol) of potassium carbonate and 5 ml acetonitrile is stirred overnight at ambient temperature. The reaction mixture is then combined with 10% TFA, the product is separated off by preparative HPLC.

$C_{25}H_{36}N_4O_4S \times C_2HF_3O_2$ (602.67)

[M+H]+=489

HPLC (Method 2): retention time=2.99 min

Example 44

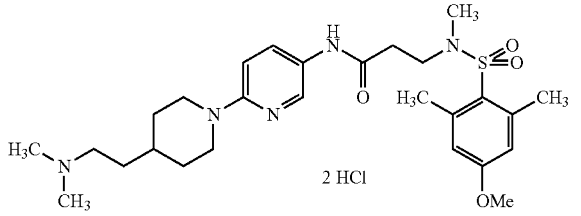

44a)

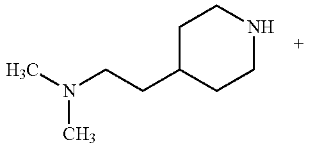

-continued

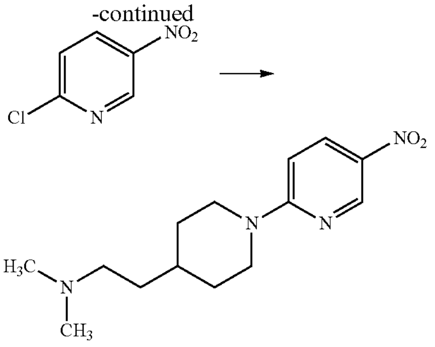

A mixture of 0.72 g (4.61 mmol) of dimethyl-(2-piperidin-4-yl-ethyl)-amine (J. Med. Chem. 36, 1993, 162-165), 0.73 g (4.61 mmol) of 2-chloro-5-nitropyridine (Fluka), 1.30 g (9.41 mmol) of potassium carbonate and 100 ml THF is stirred at ambient temperature over the weekend. The precipitate is filtered off, the filtrate is evaporated to dryness in vacuo. The crude product thus obtained is purified by column chromatography through silica gel (eluant: dichloromethane/methanol 19:1 to 4:1).

$C_{14}H_{22}N_4O_2$ (278.35)

[M+H]+=279

44b)

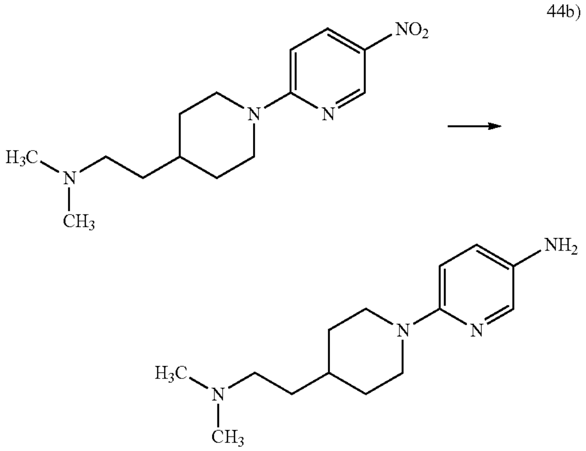

A mixture of 0.26 g (0.93 mmol) of product from 44a, 0.05 g palladium on charcoal (10%) and 30 ml of methanol is hydrogenated at ambient temperature in the autoclave. The catalyst is then filtered off, the filtrate is evaporated to dryness in vacuo.

$C_{14}H_{24}N_4$ (248.37)

[M+H]+=249

44c)

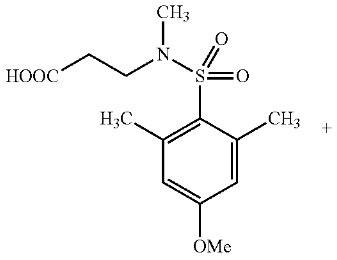

-continued

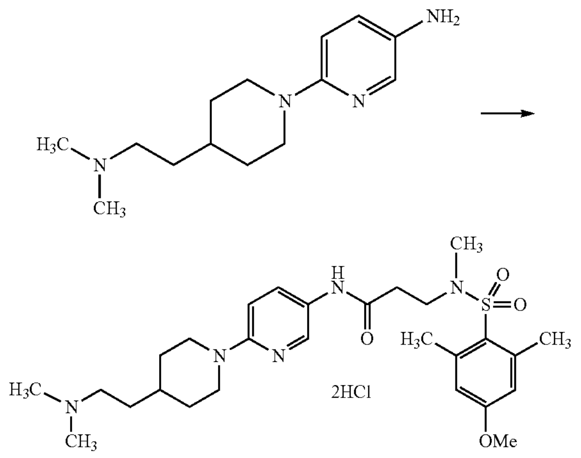

Example 44 is prepared analogously to 1f from 0.12 g (0.40 mmol) of product from 22c, 0.10 g (0.40 mmol) of product from 44b, 0.069 ml (0.50 mmol) of triethylamine and 0.14 g (0.44 mmol) of TBTU in 40 ml THF and 5 ml DMF.

$C_{27}H_{41}N_5O_4S \times 2HCl$ (604.63)

[M+H]+=532

HPLC (Method 5): retention time=1.40 min

Example 45

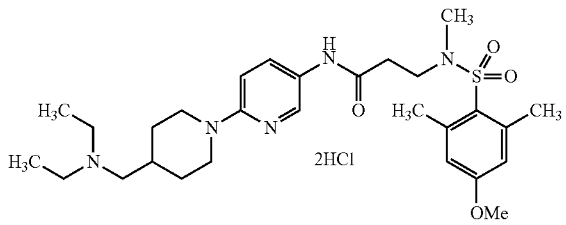

45a)

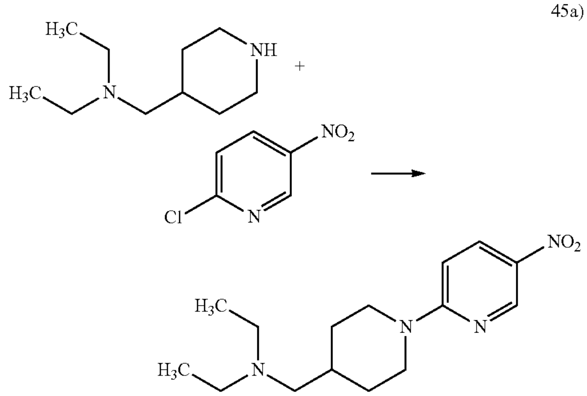

45a is prepared analogously to 44a from 1.00 g (5.87 mmol) of diethyl-piperidin-4-ylmethyl-amine (Chem. Pharm. Bull. 42, 1994, 74-84), 0.93 g (5.87 mmol) of 2-chloro-5-nitropyridine (Fluka) and 1.70 g (12.30 mmol) of potassium carbonate in 100 ml THF.

$C_{15}H_{24}N_4O_2$ (292.38)

[M+H]+=293

45b)

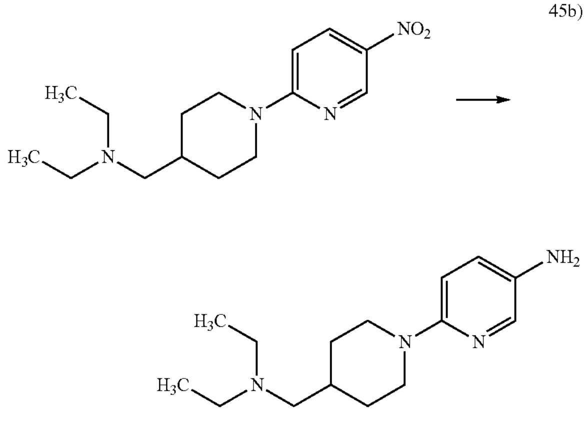

A mixture of 0.20 g (0.68 mmol) of product from 45a, 0.03 g palladium on charcoal (10%) and 30 ml of methanol is hydrogenated at ambient temperature in the autoclave. The catalyst is then filtered off, the filtrate is evaporated to dryness in vacuo.

$C_{15}H_{26}N_4$ (262.39)

[M+H]+=263

45c)

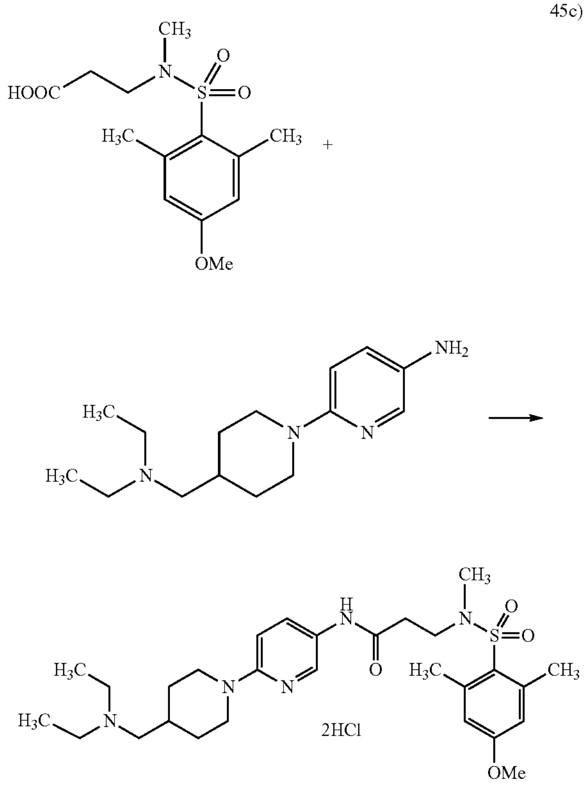

Example 45 is prepared analogously to 1f from 0.16 g (0.53 mmol) of product from 22c, 0.14 g (0.53 mmol) of product from 45b, 0.096 ml (0.69 mmol) of triethylamine and 0.19 g (0.58 mmol) of TBTU in 40 ml THF and 5 ml DMF.

$C_{28}H_{43}N_5O_4S \times 2HCl$ (618.66)

[M+H]+=546

HPLC (Method 5): retention time=1.40 min

Example 46

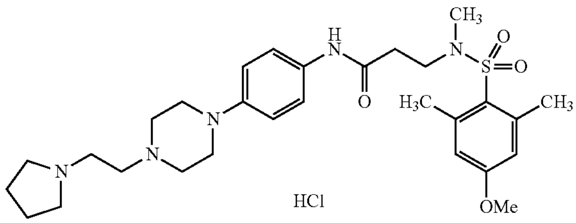

46a)

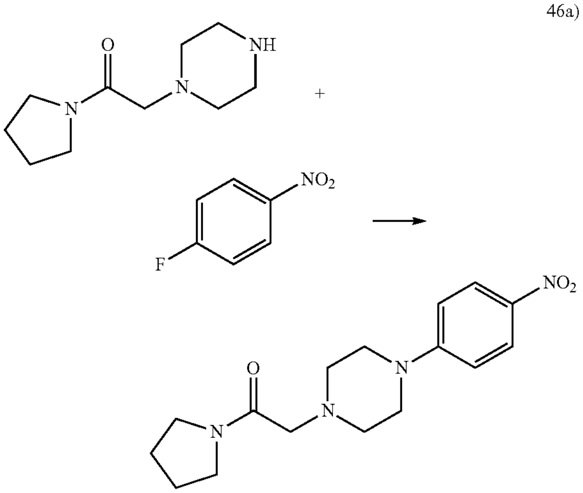

46a is prepared analogously to 1d from 3.00 g (15.21 mmol) of 2-piperazin-1-yl-1-pyrrolidin-1-yl-ethanone (Chess), 2.15 g (15.21 mmol) of 1-fluoro-4-nitrobenzene (Aldrich) and 3.07 ml (22.00 mmol) of triethylamine in 25 ml DMF.

$C_{16}H_{22}N_4O_3$ (318.37)

[M+H]+=319

TLC: silica gel, dichloromethane/ethanol 9:1, Rf value=0.4

46b)

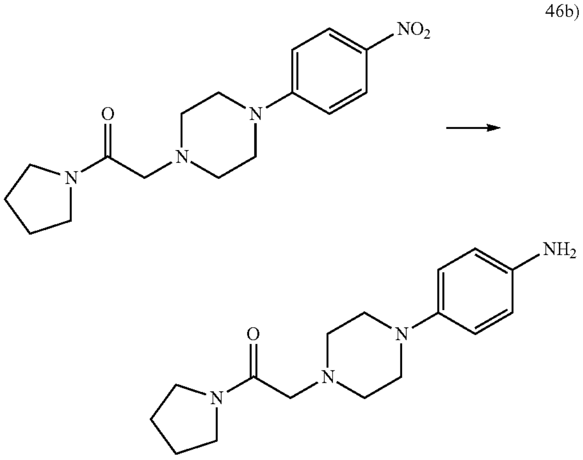

A mixture of 3.00 g (9.42 mmol) of product from 46a, 0.30 g palladium on charcoal (10%) and 200 ml of methanol is hydrogenated at ambient temperature in the autoclave. The catalyst is then filtered off, the filtrate is evaporated to dryness in vacuo.

$C_{16}H_{24}N_4O$ (288.39)

TLC: silica gel, dichloromethane/ethanol 9:1, Rf value=0.42

46c)

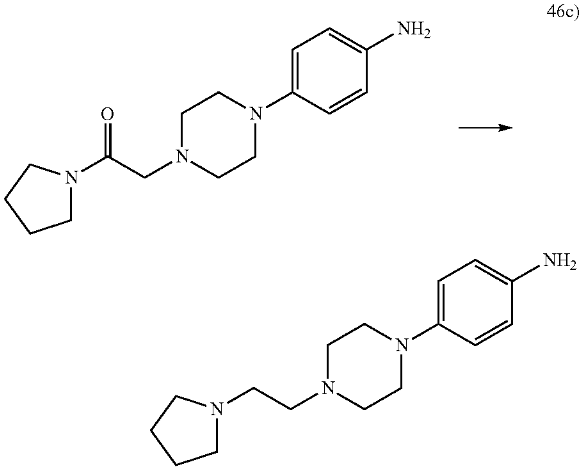 [SMILES: Nc1ccc(N2CCN(CC(=O)N3CCCC3)CC2)cc1 ; Nc1ccc(N2CCN(CCN3CCCC3)CC2)cc1]

30.00 ml (30.00 mmol) of lithium aluminium hydride 1 M in THF (Aldrich) is placed in 50 ml THF and at ambient temperature combined with a mixture of 2.70 g (9.36 mmol) of product from 46b and 20 ml THF. The reaction mixture is then stirred for three hours at ambient temperature and then combined with 20% sodium hydroxide solution while cooling with an ice bath. The precipitate formed is filtered off, the filtrate is evaporated to dryness in vacuo.

$C_{16}H_{26}N_4$ (274.40)

46d)

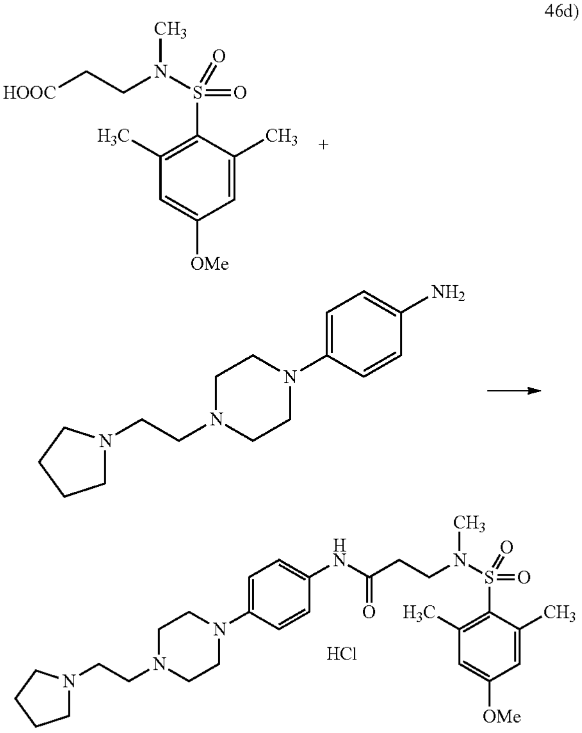 [SMILES: COc1cc(C)c(S(=O)(=O)N(C)CCC(=O)O)c(C)c1 ; Nc1ccc(N2CCN(CCN3CCCC3)CC2)cc1 ; COc1cc(C)c(S(=O)(=O)N(C)CCC(=O)Nc2ccc(N3CCN(CCN4CCCC4)CC3)cc2)c(C)c1 ; Cl]

Example 46 is prepared analogously to 1f from 0.30 g (1.00 mmol) of product from 22c, 0.27 g (1.00 mmol) of product from 46c, 0.35 ml (2.50 mmol) of triethylamine and 0.32 g (1.00 mmol) of TBTU in 7 ml THF and 1 ml DMF.

$C_{29}H_{43}N_5O_4S \times HCl$ (594.21)

[M+H]+=558

HPLC (Method 5): retention time=1.43 min

Example 47

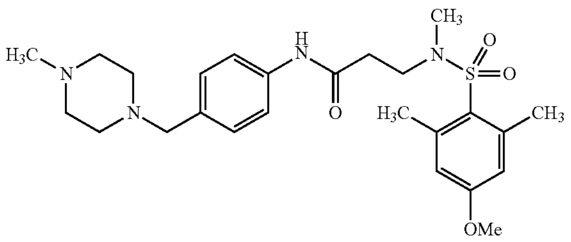

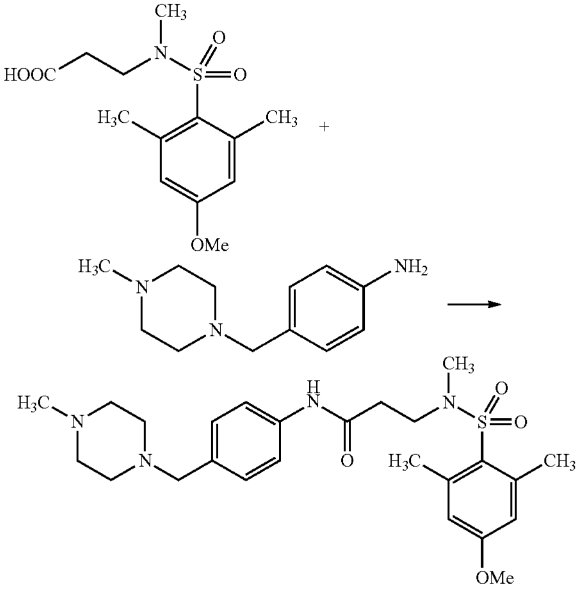

Example 47 is prepared analogously to 1f from 0.20 g (0.66 mmol) of product from 22c, 0.14 g (0.66 mmol) of 4-(4-methyl-piperazin-1-ylmethyl)-phenylamine (Med. Chem. Res. 9, 1999, 149-161), 0.28 ml (1.99 mmol) of triethylamine and 0.21 g (0.66 mmol) of TBTU in 5 ml THF.

$C_{25}H_{36}N_4O_4S$ (488.64)

[M+H]+=489

HPLC (Method 5): retention time=1.42 min

Example 48

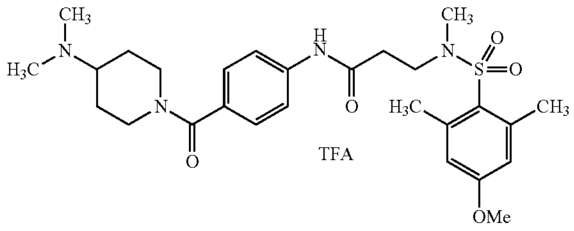

-continued

48a)

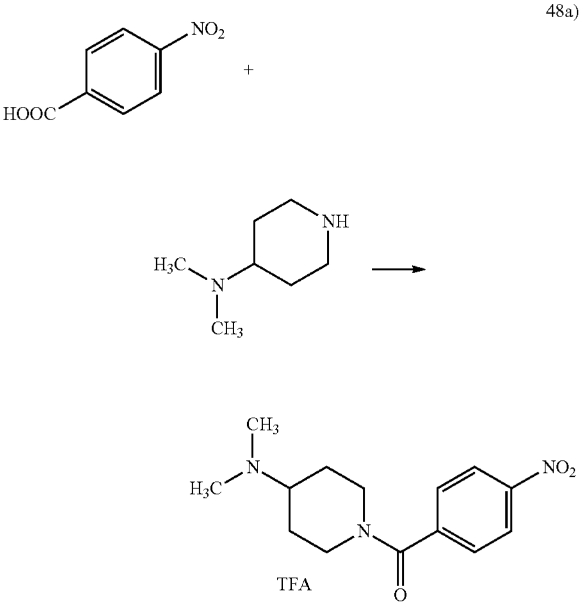

48a is prepared analogously to 1f from 0.24 g (1.45 mmol) of 4-nitrobenzoic acid (Aldrich), 0.19 g (1.45 mmol) of 4-dimethylamino-piperidine (Alfa Aesar), 0.21 ml (1.52 mmol) of triethylamine and 0.49 g (1.52 mmol) of TBTU in 8 ml DMF.

$C_{14}H_{19}N_3O_3 \times C_2HF_3O_2$ (391.34)

[M+H]+=278

HPLC (Method 2): retention time=2.29 min

48b)

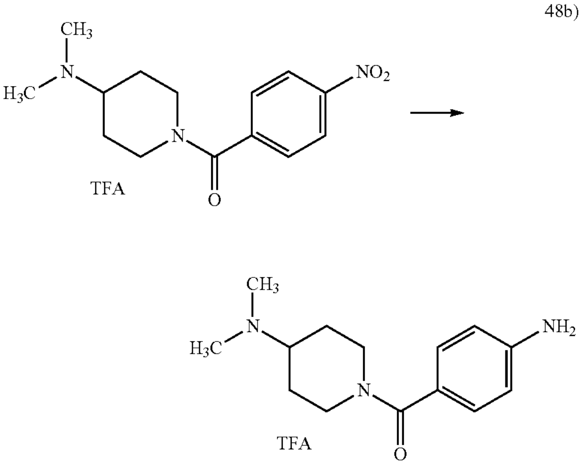

A mixture of 0.36 g (0.92 mmol) of product from 48a, 0.092 g palladium on charcoal (10%) and 5 ml of methanol is hydrogenated at ambient temperature in the autoclave. The catalyst is then filtered off, the filtrate is evaporated to dryness in vacuo.

$C_{14}H_{21}N_3O \times C_2HF_3O_2$ (361.36)

[M+H]+=248

HPLC (Method 2): retention time=0.66 min

48c)

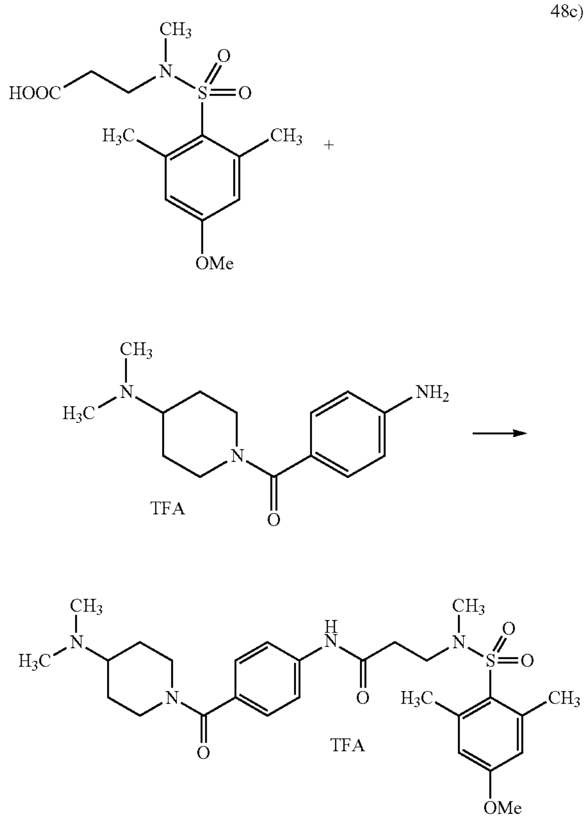

Example 48 is prepared analogously to 1f from 0.15 g (0.50 mmol) of product from 22c, 0.18 g (0.50 mmol) of product from 48b, 0.21 ml (1.49 mmol) of triethylamine and 0.16 g (0.50 mmol) of TBTU in 3 ml THF.

$C_{27}H_{38}N_4O_5S \times C_2HF_3O_2$ (644.70)

[M+H]+=531

HPLC (Method 5): retention time=1.48 min

Example 49

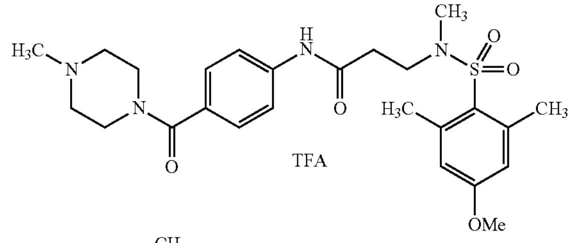

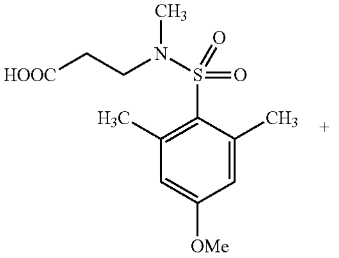

-continued

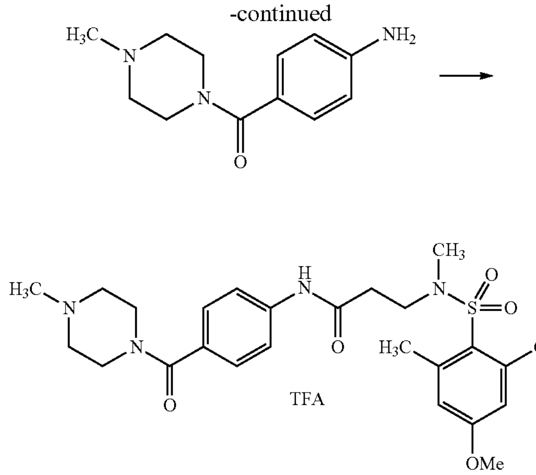

Example 49 is prepared analogously to 1f from 0.15 g (0.50 mmol) of product from 22c, 0.11 g (0.50 mmol) of (4-aminophenyl)-(4-methylpiperazin-1-yl)methanone (J. Org. Chem. 24, 1959, 459-463), 0.21 ml (1.49 mmol) of triethylamine and 0.16 g (0.50 mmol) of TBTU in 3 ml THF.

$C_{25}H_{34}N_4O_5S \times C_2HF_3O_2$ (616.65)

[M+H]+=503

HPLC (Method 5): retention time=1.47 min

Example 50

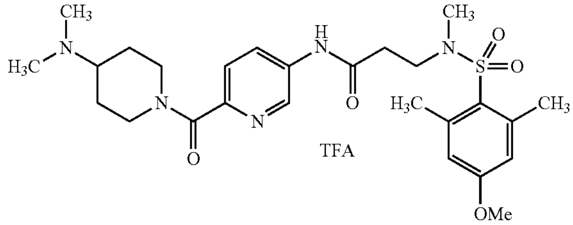

50a)

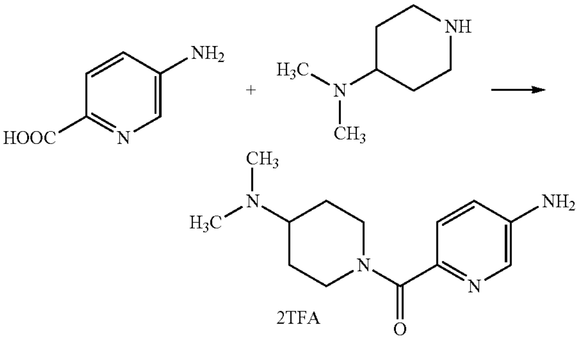

50a is prepared analogously to 1f from 0.60 g (4.34 mmol) of 5-amino-pyridine-2-carboxylic acid (Pharm. Acta Helv. 44, 1969, 637-643), 0.56 g (4.34 mmol) of 4-dimethylamino-piperidine (Alfa Aesar), 0.64 ml (4.56 mmol) of triethylamine and 1.46 g (4.56 mmol) of TBTU in 24 ml DMF.

$C_{13}H_{20}N_4O \times 2C_2HF_3O_2$ (476.37)

HPLC (Method 2): retention time=0.65 min

50b)

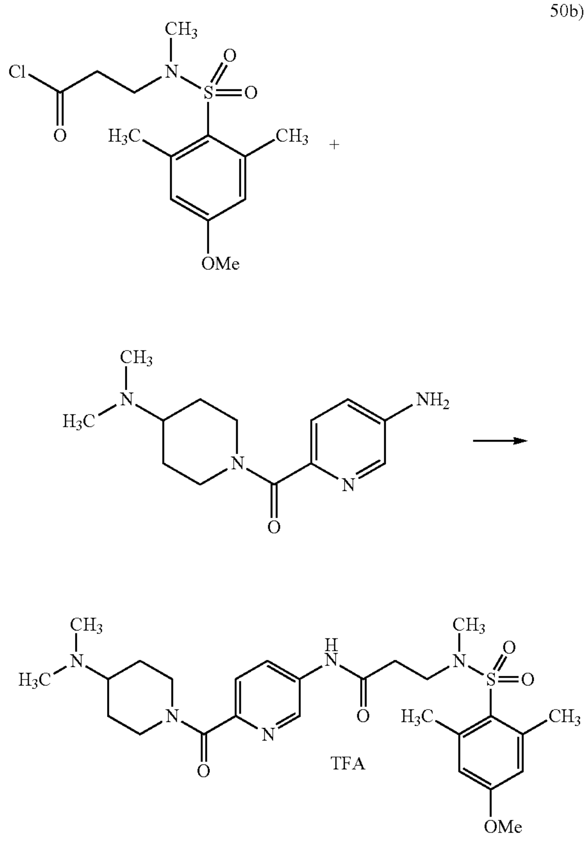

A mixture of 0.64 g (1.99 mmol) of product from 27c, 1.90 g (2.39 mmol) of product from 50a, 0.08 g (0.33 mmol) of DMAP and 16 ml chlorobenzene is heated to 15° C. for 39 hours. The reaction mixture is then evaporated to dryness in vacuo. The product is obtained by preparative HPLC.

$C_{26}H_{37}N_5O_5S \times C_2HF_3O_2$ (645.69)

[M+H]+=532

HPLC (Method 5): retention time=1.44 min

Example 51

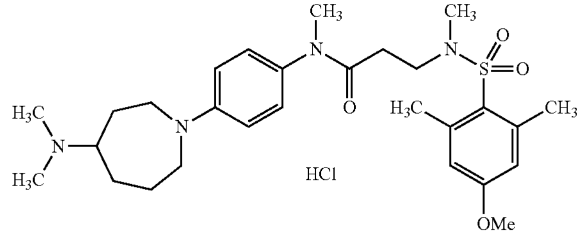

51a)

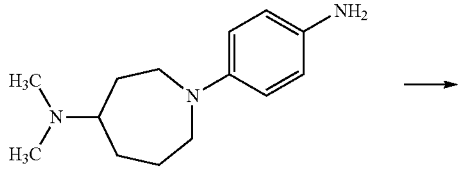

-continued

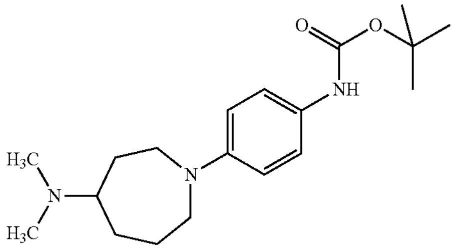

A mixture of 0.26 g (1.11 mmol) of product from 39d, 0.27 g (1.22 mmol) of Boc-anhydride, 0.17 ml (1.22 mmol) of triethylamine and 15 ml dichloromethane is stirred overnight at ambient temperature. Then the reaction mixture is diluted with dichloromethane, washed with saturated sodium hydrogen carbonate solution and saturated sodium chloride solution, dried on sodium sulphate and evaporated to dryness in vacuo.

$C_{19}H_{31}N_3O_2$ (333.47)

[M+H]+=334

HPLC (Method 1): retention time=2.40 min

51b)

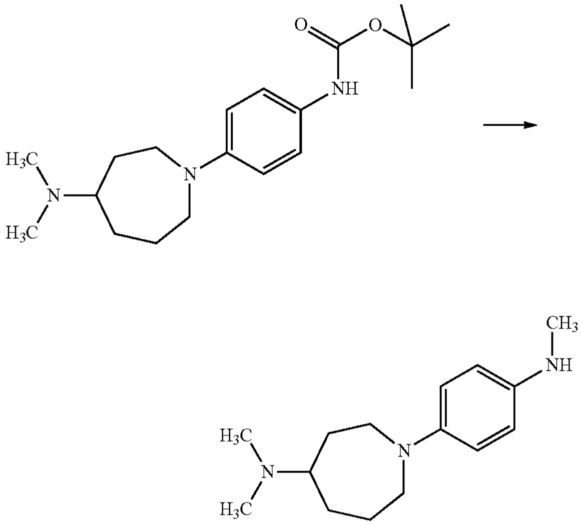

0.13 g (3.40 mmol) of lithium aluminium hydride are placed in 5 ml THF, heated to 60° C. and combined with 0.38 g (1.14 mmol) of product from 51a in 5 ml THF. The reaction mixture is then refluxed for four hours and stirred overnight at ambient temperature. Then the reaction mixture is quenched with water and 1 M sodium hydroxide solution. The precipitate formed is filtered off through Celite, the filtrate is evaporated to dryness in vacuo.

$C_{15}H_{25}N_3$ (247.38)

TLC: silica gel, dichloromethane/methanol/ammonia 4:1:0.2, Rf value=0.68

51c)

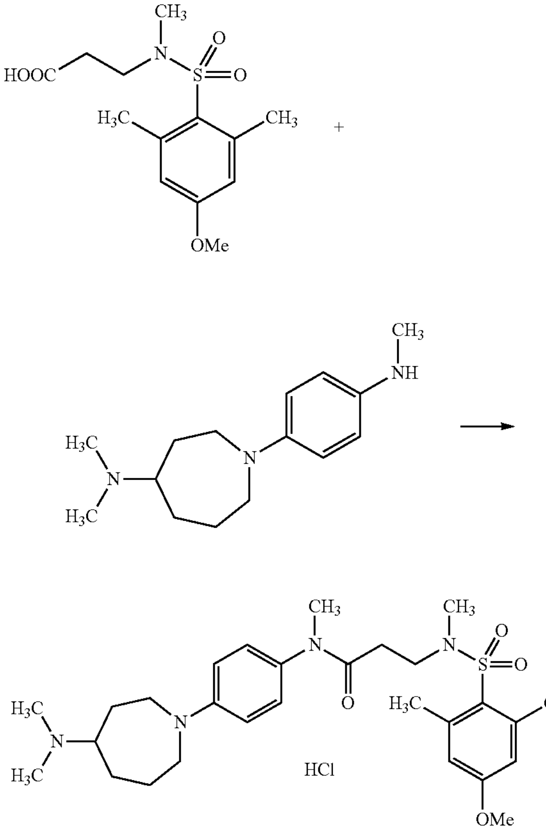

Example 51 is prepared analogously to 1f from 0.15 g (0.50 mmol) of product from 22c, 0.12 g (0.50 mmol) of product from 51b, 0.21 ml (1.50 mmol) of triethylamine and 0.18 g (0.55 mmol) of TBTU in 8 ml DMF.

$C_{28}H_{42}N_4O_4S \times HCl$ (567.18)

[M+H]+=531

HPLC (Method 1): retention time=2.5 min

Example 52

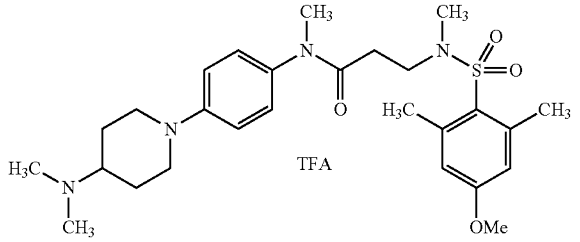

52a)

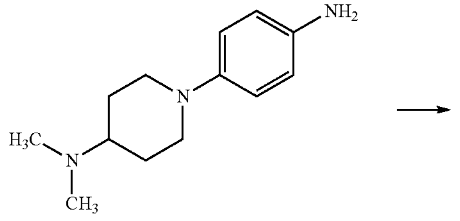

-continued

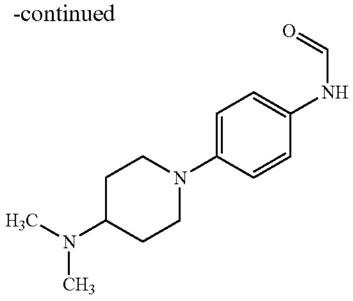

0.70 ml (7.36 mmol) of acetic anhydride are placed under a nitrogen atmosphere and slowly combined with 0.42 ml (9.06 mmol) of formic acid while cooling with an ice bath. The reaction mixture is heated for two hours to 50-60° C. and then combined with 0.50 g (2.28 mmol) of product from 8b in 7 ml dichloromethane while cooling with an ice bath. After 20 minutes' stirring at ambient temperature the reaction mixture is evaporated to dryness in vacuo. The crude product thus obtained is purified by column chromatography through silica gel (eluant: dichloromethane/methanol/ammonia 9:1:0.1).

$C_{14}H_{21}N_3O$ (247.34)

[M+H]+=248

HPLC (Method 5): retention time=0.50 min

52b)

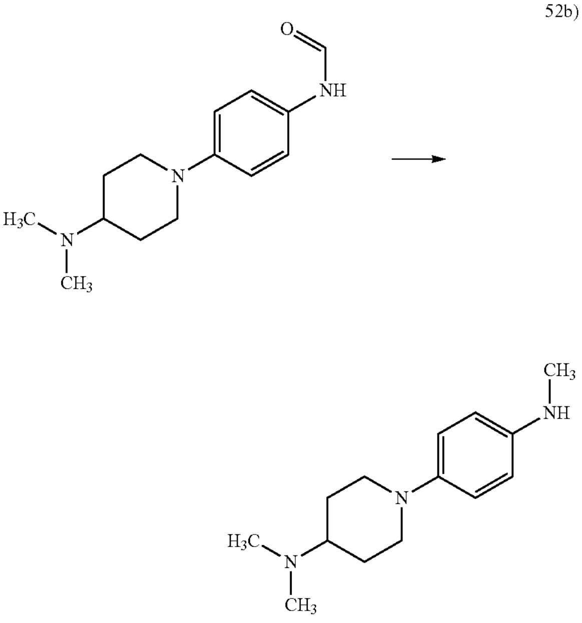 [SMILES: CN(C)C1CCN(c2ccc(NC=O)cc2)CC1 ; CNc1ccc(N2CCC(N(C)C)CC2)cc1]

52b is prepared analogously to 51b from 0.17 g (4.51 mmol) of lithium aluminium hydride and 0.58 g (2.34 mmol) of product from 52a in 10 ml THF.

$C_{14}H_{23}N_3$ (233.35)

TLC: silica gel, dichloromethane/methanol/ammonia 9:1:0.1, Rf value=0.5

52c)

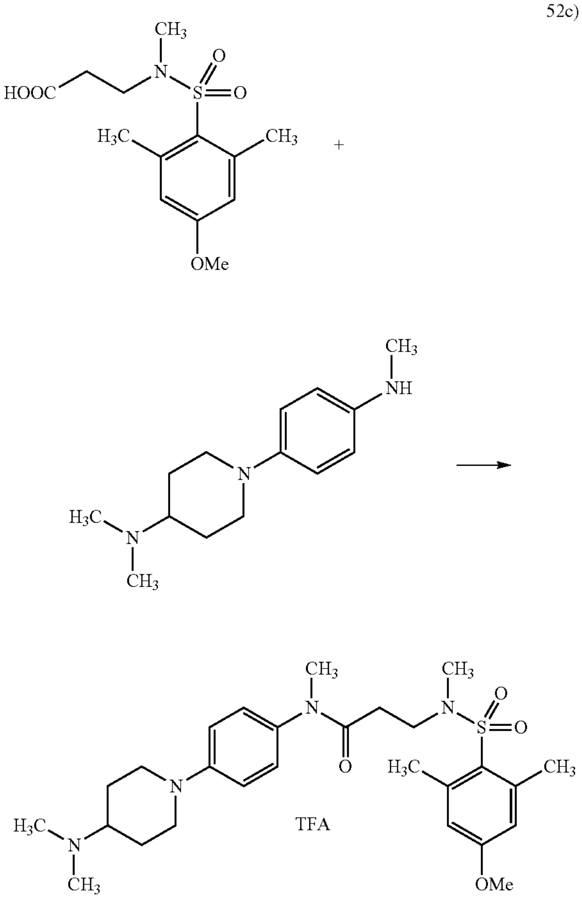

Example 52 is prepared analogously to 1f from 0.21 g (0.68 mmol) of product from 22c, 0.24 g (0.68 mmol) of product from 52b, 0.28 ml (2.04 mmol) of triethylamine and 0.22 g (0.68 mmol) of TBTU in 4 ml THF.

$C_{27}H_{40}N_4O_4S \times C_2HF_3O_2$ (630.72)

[M+H]+=517

HPLC (Method 5): retention time=1.50 min

Example 53

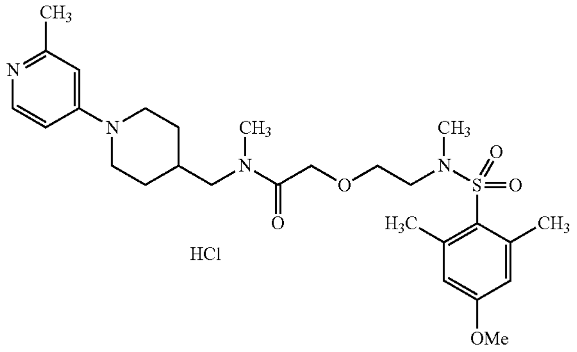

-continued

53a)

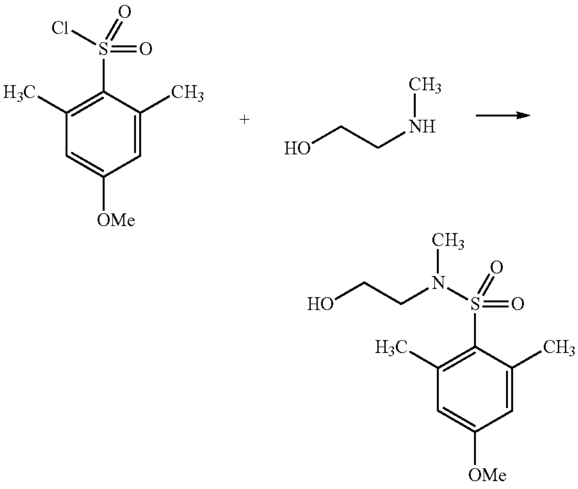

53a is prepared analogously to 3a from 4.50 g (19.17 mmol) of product from 13a, 1.69 g (21.10 mmol) of N-methylaminoethanol (BASF), 6.68 ml (47.90 mmol) of triethylamine in 150 ml dichloromethane.

$C_{12}H_{19}NO_4S$ (273.35)

[M+H]+=274

TLC: silica gel, dichloromethane/ethanol 19:1, Rf value=0.43

53b)

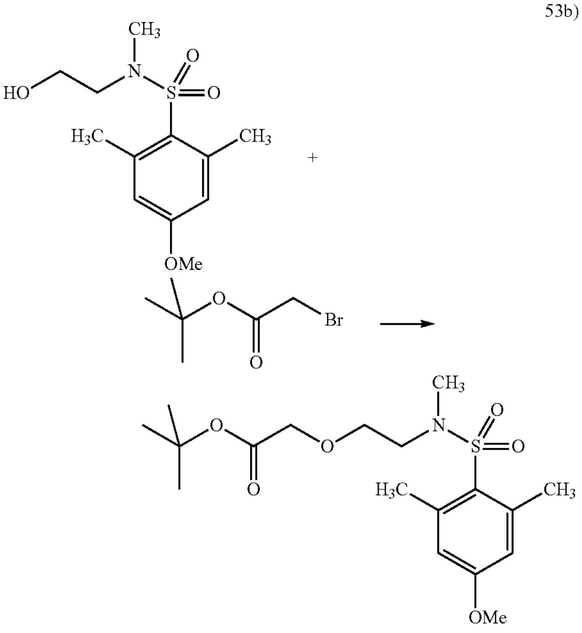

First 100 ml 35% sodium hydroxide solution, then 4.18 ml (28.26 mmol) of tert-butyl bromoacetate in 20 ml of toluene are added to a mixture of 5.15 g (18.84 mmol) of product from 53a, 1.75 g (6.60 mmol) of tetrabutylammonium chloride (Fluka) and 80 ml of toluene at 0° C. The reaction mixture is then stirred for 1.5 hours at ambient temperature, then diluted with diethyl ether. After the phase separation the organic phase is washed four times with water until neutral, dried on sodium sulphate and evaporated to dryness in vacuo. The crude product thus obtained is purified by column chromatography through silica gel (eluant: petroleum ether/ethyl acetate 4:1).

$C_{18}H_{29}NO_6S$ (387.49)

[M+H]+=388

TLC: silica gel, petroleum ether/ethyl acetate 7:3, Rf value=0.59

53c)

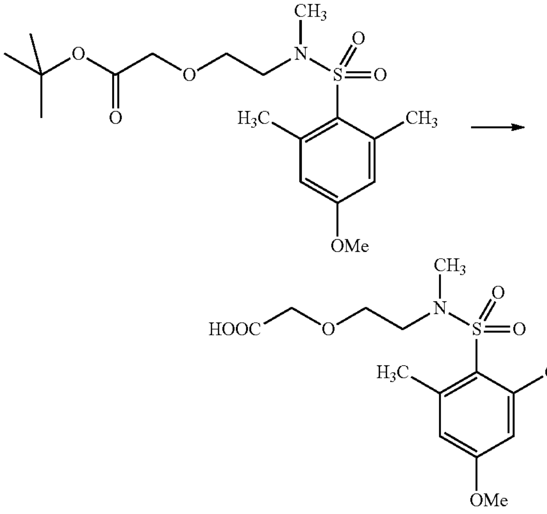

A mixture of 6.80 g (17.55 mmol) of product from 53b, 8 ml TFA and 100 ml dichloromethane is stirred for 2.5 hours at ambient temperature. The reaction mixture is then evaporated to dryness in vacuo. The residue is combined with 1 M sodium hydroxide solution and extracted twice with ethyl acetate (organic extracts are discarded). The aqueous phase is acidified with 2 M HCl, then extracted again with ethyl acetate. The organic extracts are washed with water, dried on sodium sulphate and evaporated to dryness in vacuo.

$C_{14}H_{21}NO_6S$ (331.29)

[M+H]+=332

HPLC (Method 4): retention time=3.4 min

53d)

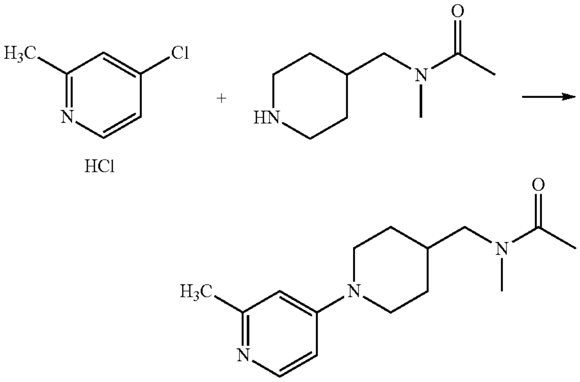

53d is prepared analogously to 28c from 1.00 g (6.10 mmol) of 4-chloro-2-methylpyridine hydrochloride (Alfa Aesar) and 2.08 g (12.20 mmol) of N-methyl-N-piperidin-4-ylmethyl-acetamide (DE 1100635, Rhône-Poulenc, 1961).

$C_{15}H_{23}N_3O$ (261.36)

[M+H]+=262

HPLC (Method 4): retention time=1.9 min

53e)

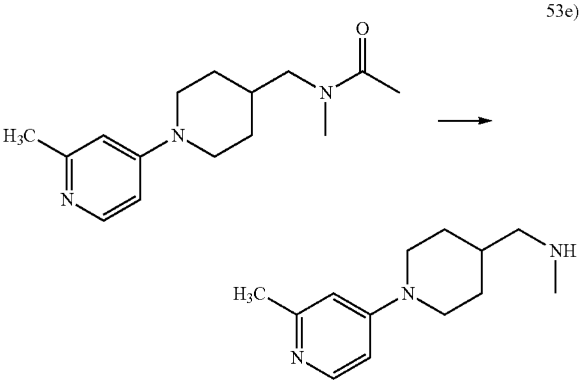

A mixture of 1.37 g (5.24 mmol) of product from 53d and 15 ml semiconcentrated HCl is refluxed for four days. The reaction mixture is made alkaline with 20% sodium hydroxide solution and extracted with dichloromethane. The organic extracts are dried on sodium sulphate and evaporated to dryness in vacuo.

$C_{13}H_{21}N_3$ (219.33)

[M+H]+=220

TLC: silica gel, dichloromethane/methanol/ammonia 8:2:0.2, Rf value=0.48

53f)

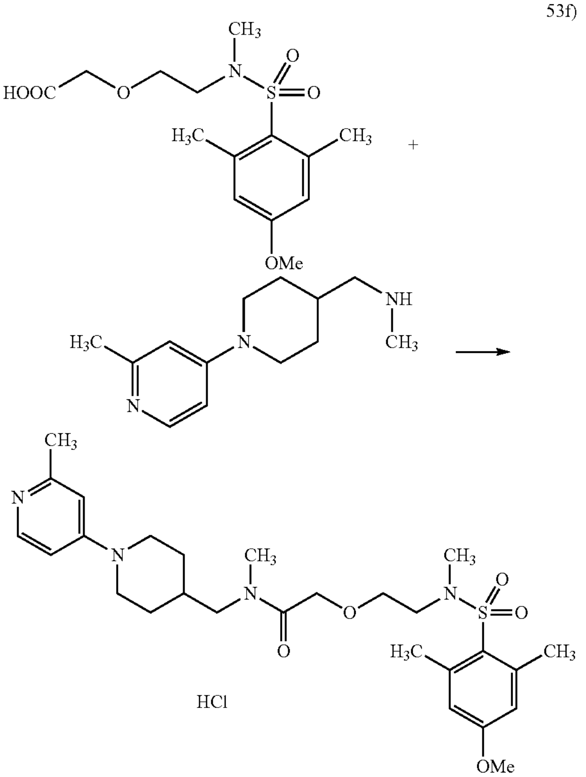

Example 53 is prepared analogously to 1f from 0.099 g (0.30 mmol) of product from 53c, 0.066 g (0.30 mmol) of product from 53e, 0.10 ml (0.75 mmol) of triethylamine and 0.12 g (0.36 mmol) of TBTU in 8 ml THF and 1 ml DMF.

$C_{27}H_{40}N_4O_5S \times HCl$ (569.16)

[M+H]+=533

HPLC (Method 4): retention time=3.1 min

Example 54

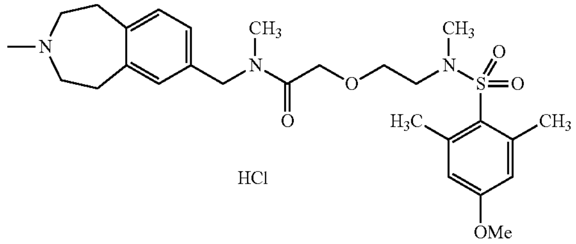

54a)

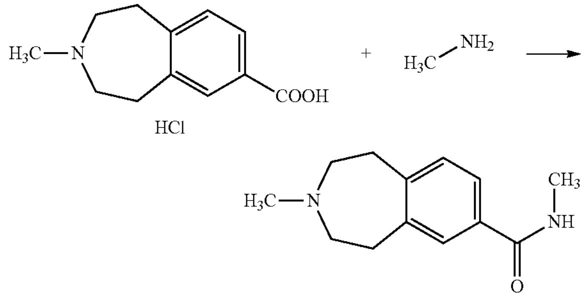

54a is prepared analogously to 1f from 2.00 g (8.27 mmol) of product from 38d, 8.28 ml (16.55 mmol) of methylamine 2 M in THF (Aldrich), 3.46 ml (24.82 mmol) of triethylamine and 3.19 g (9.93 mmol) of TBTU in 30 ml THF.

$C_{13}H_{18}N_2O$ (218.29)

[M+H]+=219

TLC: silica gel, dichloromethane/methanol 8:2, Rf value=0.14

54b)

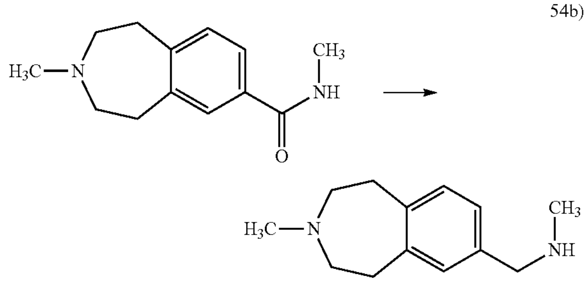

54b is prepared analogously to 38f from 1.00 g (4.58 mmol) of product from 54a and 9.00 ml (9.00 mmol) of lithium aluminium hydride 1 M in THF (Aldrich) in 30 ml THF.

$C_{13}H_{20}N_2$ (204.31)

[M+H]+=205

TLC: silica gel, dichloromethane/methanol 8:2, Rf value=0.07

54c)

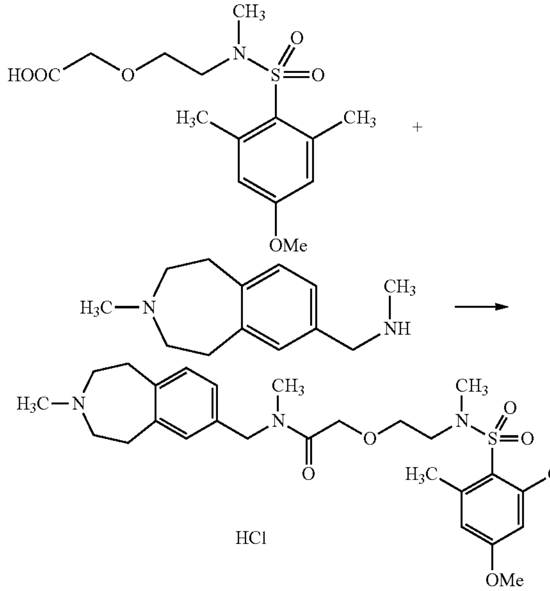

Example 54 is prepared analogously to 1f from 0.099 g (0.30 mmol) of product from 53c, 0.088 g (0.30 mmol) of product from 54b, 0.10 ml (0.75 mmol) of triethylamine and 0.12 g (0.36 mmol) of TBTU in 7 ml THF and 1 ml DMF.

$C_{27}H_{39}N_3O_5S \times HCl$ (554.14)

[M+H]+=518

HPLC (Method 4): retention time=3.1 min

Example 55

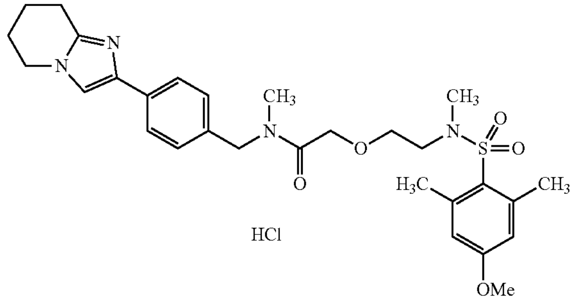

55a)

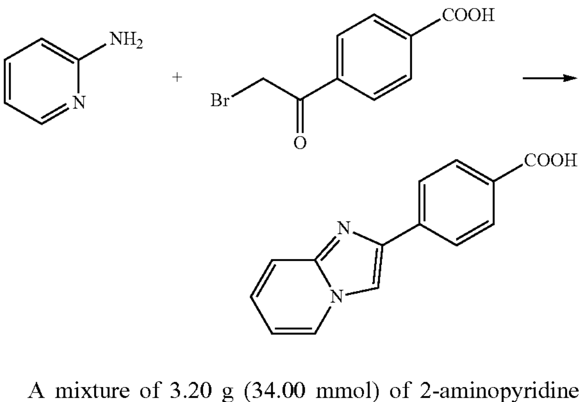

A mixture of 3.20 g (34.00 mmol) of 2-aminopyridine (Aldrich), 2.75 g (11.31 mmol) of 4-bromoacetylbenzoic acid (Fluorochem) and 100 ml of ethanol is refluxed for six hours at reflux temperature and stirred overnight at ambient temperature. The precipitate formed is filtered off and dried.

$C_{14}H_{10}N_2O_2$ (238.24)

[M+H]+=239

55b)

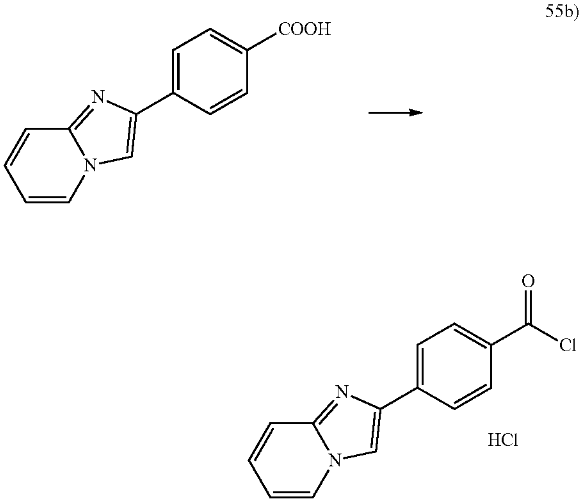 [SMILES: O=C(O)c1ccc(-c2cn3ccccc3n2)cc1 ; O=C(Cl)c1ccc(-c2cn3ccccc3n2)cc1 ; Cl]

55b is prepared analogously to 27c from 1.7 g (7.14 mmol) of product from 55a and 30 ml of thionyl chloride.

$C_{14}H_9ClN_2O \times HCl$ (293.15)

55c)

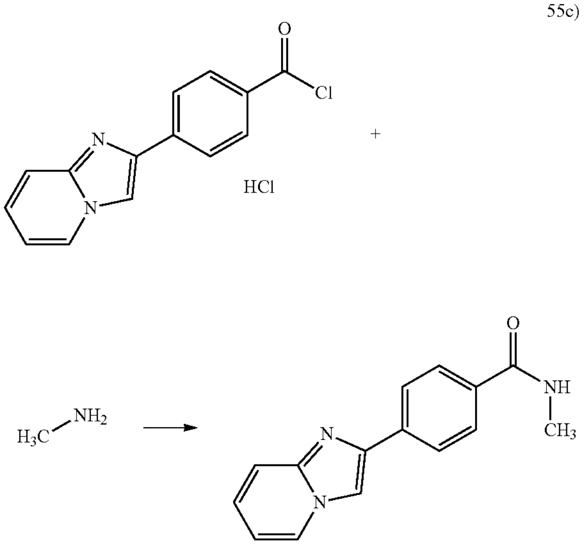

2.10 g (7.14 mmol) of product from 55b in 100 ml dichloromethane are combined with 25 ml (50.00 mmol) of methylamine 2 M in THF (Aldrich) while cooling with an ice bath. The reaction mixture is then stirred for two hours at ambient temperature and then evaporated to dryness in vacuo. The residue is triturated with water, filtered off and dried. The crude product thus obtained is purified by column chromatography through silica gel (eluant: dichloromethane/methanol 97:3).

$C_{15}H_{13}N_3O$ (251.28)

[M+H]+=252

55d)

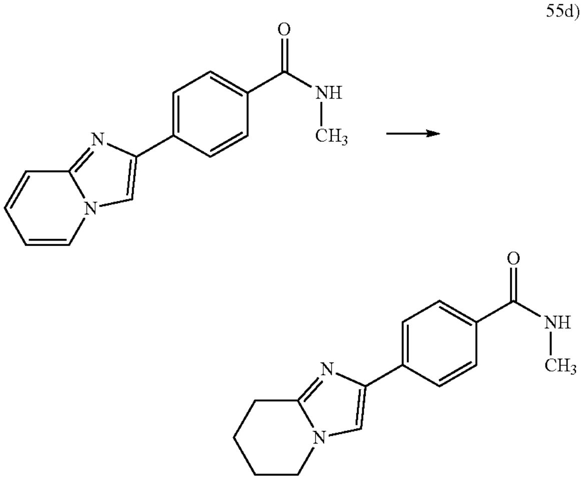

A mixture of 0.70 g (2.79 mmol) of product from 55c, 0.15 g palladium on charcoal (20%), 100 ml of methanol and 30 ml dichloromethane is hydrogenated at ambient temperature in the autoclave. The catalyst is filtered off, the filtrate is evaporated to dryness in vacuo.

$C_{15}H_{17}N_3O$ (255.32)

[M+H]+=256

55e)

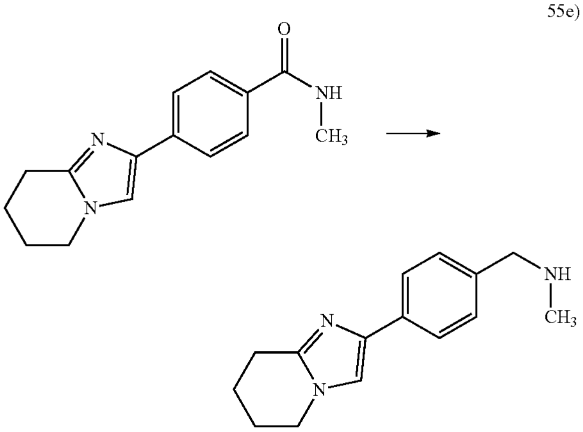

55e is prepared analogously to 38f from 0.80 g (3.13 mmol) of product from 55d and 20.00 ml (20.00 mmol) of lithium aluminium hydride 1 M in THF (Aldrich) in 50 ml of pyridine.

$C_{15}H_{19}N_3$ (241.33)

[M+H]+=242

55f)

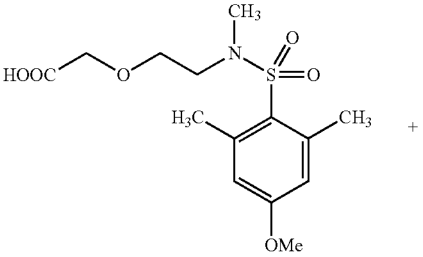

-continued

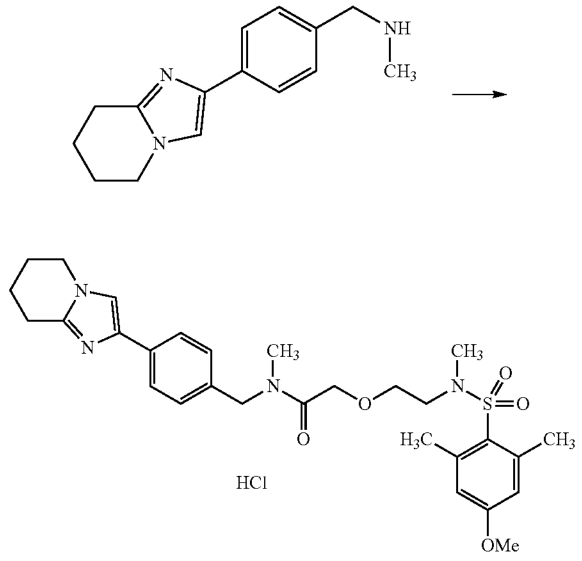

Example 55 is prepared analogously to 1f from 0.14 g (0.42 mmol) of product from 53c, 0.10 g (0.41 mmol) of product from 55e, 0.14 ml (0.99 mmol) of triethylamine and 0.15 g (0.46 mmol) of TBTU in 30 ml THF and 5 ml DMF.

$C_{29}H_{38}N_4O_5S \times HCl$ (591.16)

[M+H]+=555

TLC: silica gel, dichloromethane/methanol 9:1, Rf value=0.26

Example 56

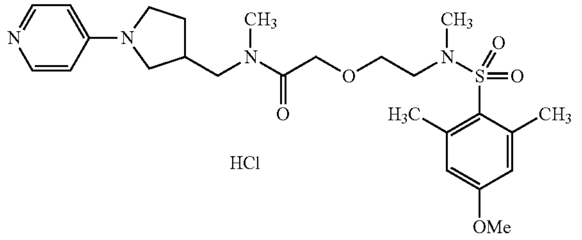

56a)

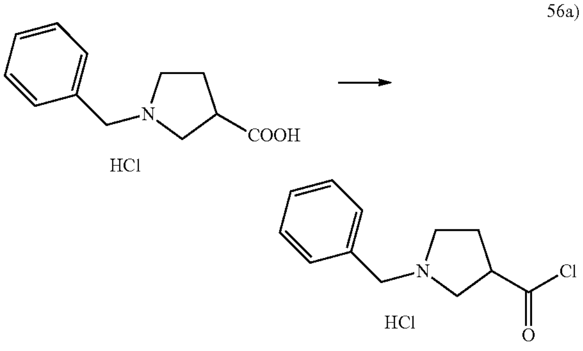

56a is prepared analogously to 27c from 1.35 g (5.59 mmol) of 1-benzyl-pyrrolidine-3-carboxylic acid (J. Org. Chem. 33, 1968, 3637-3639) and 10 ml of thionyl chloride.

$C_{12}H_{14}ClNO \times HCl$ (260.16)

56b)

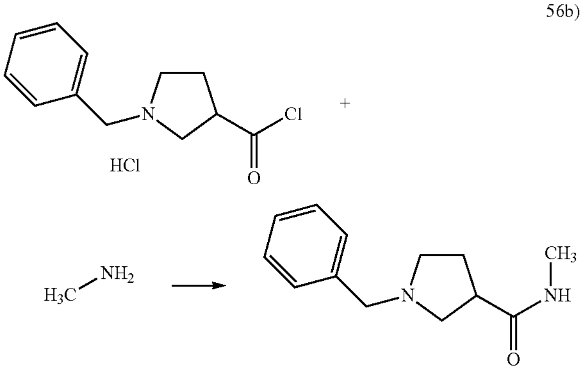

56b is prepared analogously to 55c from 1.45 g (5.57 mmol) of product from 56a, 10 ml (50.00 mmol) of methylamine 2 M in THF (Aldrich) in 50 ml THF.

$C_{13}H_{18}N_2O$ (218.29)

[M+H]+=219

56c)

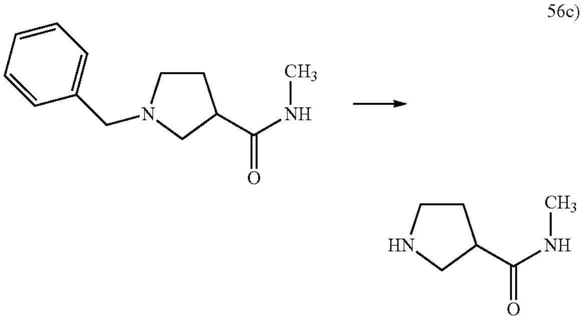

A mixture of 1.10 g (5.04 mmol) of product from 56b, 0.20 g palladium hydroxide and 40 ml of methanol is hydrogenated at 50° C. in the autoclave. The catalyst is filtered off, the filtrate is evaporated to dryness in vacuo.

$C_6H_{12}N_2O$ (128.17)

[M+H]+=129

56d)

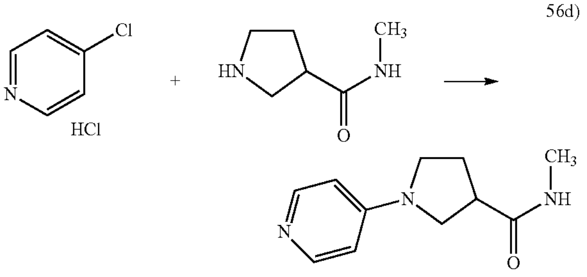

56d is prepared analogously to 28c from 0.76 g (5.08 mmol) of 4-chloropyridine hydrochloride (Aldrich), 0.65 g (5.07 mmol) of product from 56c and 1.52 ml (10.88 mmol) of triethylamine in 10 ml of ethanol.

$C_{11}H_{15}N_3O$ (205.26)

[M+H]+=206

56e)

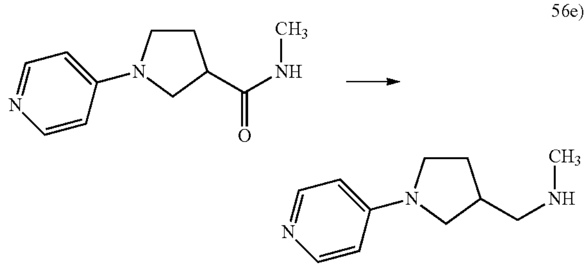

56e is prepared analogously to 38f from 0.45 g (2.19 mmol) of product from 56d and 7.00 ml (7.00 mmol) of lithium aluminium hydride 1 M in THF (Aldrich) in 30 ml THF.

$C_{11}H_{17}N_3$ (191.27)

[M+H]+=192

56f)

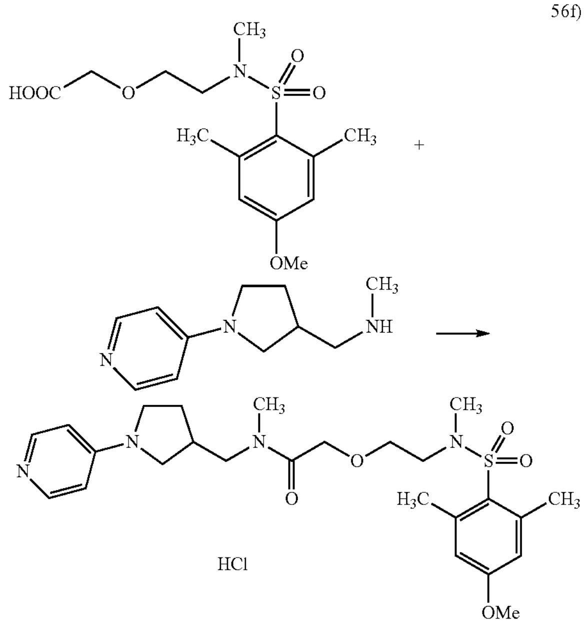

Example 56 is prepared analogously to 1f from 0.14 g (0.42 mmol) of product from 53c, 0.10 g (0.42 mmol) of product from 56e, 0.18 ml (1.29 mmol) of triethylamine and 0.18 g (0.56 mmol) of TBTU in 30 ml THF and 5 ml DMF.

$C_{25}H_{36}N_4O_5S{\times}HCl$ (541.10)

[M+H]+=505

HPLC (Method 5): retention time=1.51 min

Example 57

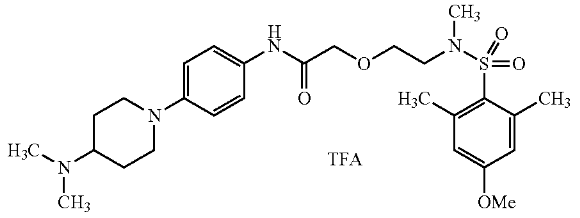

-continued

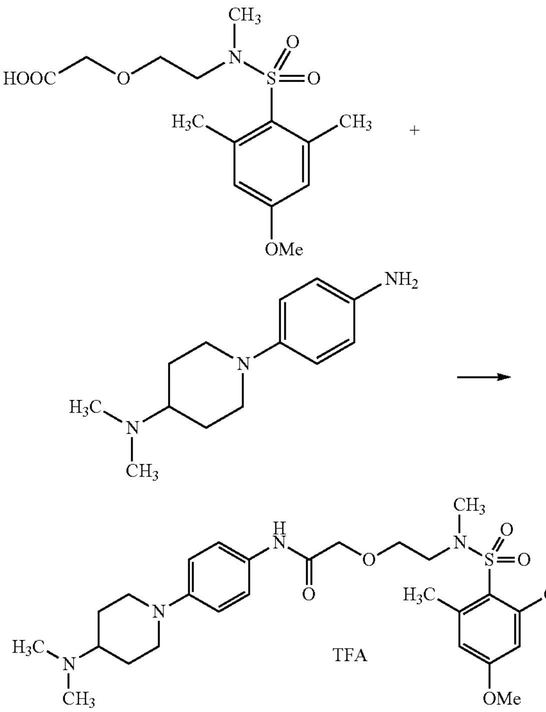

Example 57 is prepared analogously to 1f from 0.10 g (0.30 mmol) of product from 53c, 0.066 g (0.30 mmol) of product from 8b, 0.13 ml (0.91 mmol) of triethylamine and 0.097 g (0.30 mmol) of TBTU in 5 ml DMF.

$C_{27}H_{40}N_4O_5S{\times}C_2HF_3O_2$ (646.72)

[M+H]+=533

HPLC (Method 5): retention time=1.51 min

Example 58

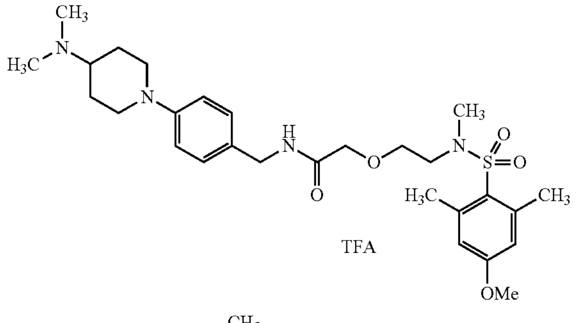

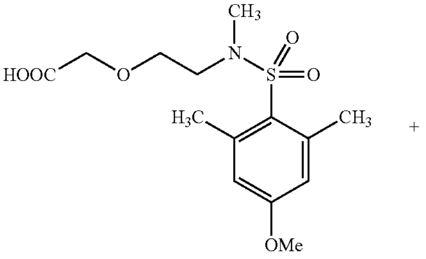

-continued

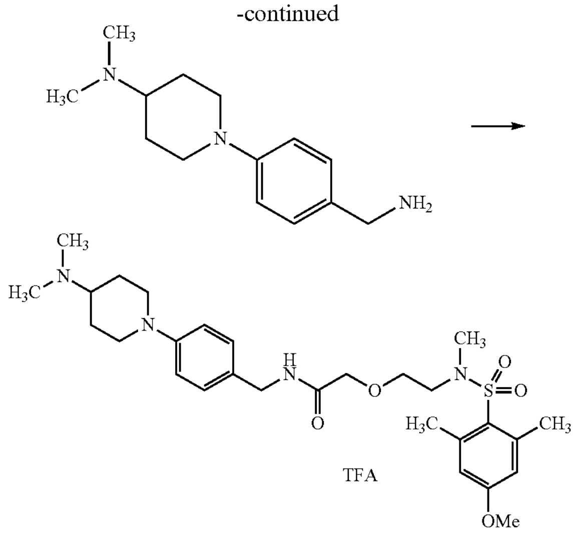

Example 58 is prepared analogously to 1f from 0.10 g (0.30 mmol) of product from 53c, 0.07 g (0.30 mmol) of product from 33a, 0.13 ml (0.91 mmol) of triethylamine and 0.097 g (0.30 mmol) of TBTU in 5 ml DMF.

$C_{28}H_{42}N_4O_5S \times C_2HF_3O_2$ (660.75)

[M+H]+=547

HPLC (Method 5): retention time=1.48 min

Example 59

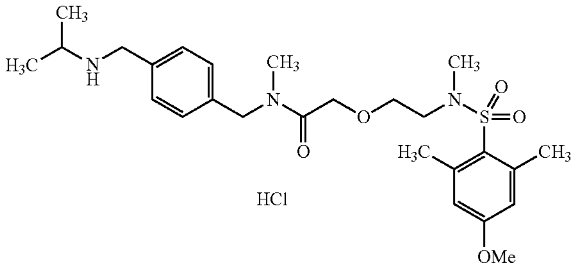

59a)

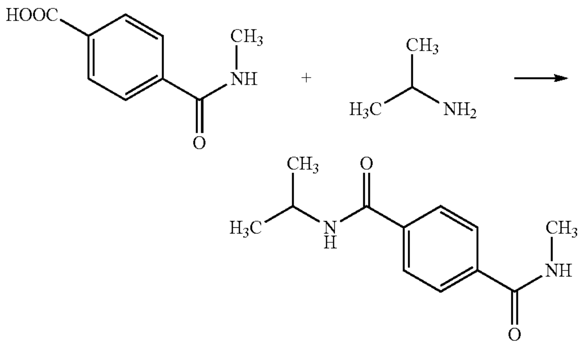

59a is prepared analogously to 1f from 2.00 g (11.16 mmol) of terephthalic acid monomethylamide (EMKA), 1.90 ml (22.32 mmol) of isopropylamine (Aldrich), 3.11 ml (22.32 mmol) of triethylamine and 4.30 g (13.40 mmol) of TBTU in 60 ml THF.

$C_{12}H_{16}N_2O_2$ (220.27)

[M+H]+=221

HPLC (Method 4): retention time=2.3 min

59b)

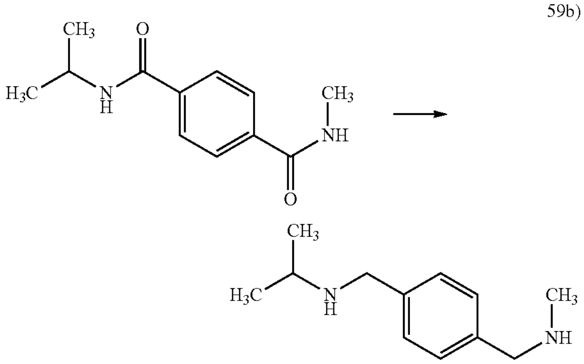

59b is prepared analogously to 38f from 1.34 g (6.08 mmol) of product from 59a and 25.00 ml (25.00 mmol) of lithium aluminium hydride 1 M in THF (Aldrich) in 150 ml THF.

$C_{12}H_{20}N_2$ (192.30)

[M+H]+=193

TLC: silica gel, dichloromethane/methanol/ammonia 9:1:0.1, Rf value=0.17

59c)

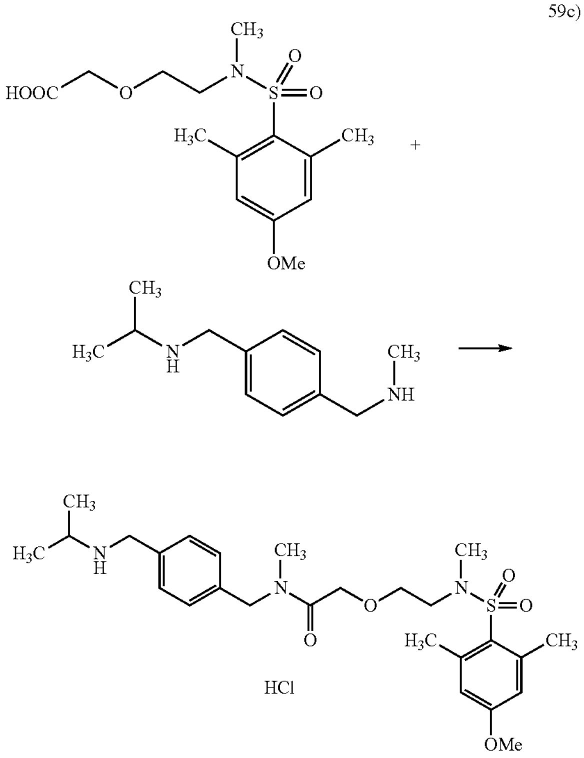

Example 59 is prepared analogously to 1f from 0.099 g (0.30 mmol) of product from 53c, 0.058 g (0.30 mmol) of product from 59b, 0.10 ml (0.75 mmol) of triethylamine and 0.12 g (0.36 mmol) of TBTU in 8 ml THF.

$C_{26}H_{39}N_3O_5S \times HCl$ (542.13)

[M+H]+=506

HPLC (Method 4): retention time=3.1 min

Example 60

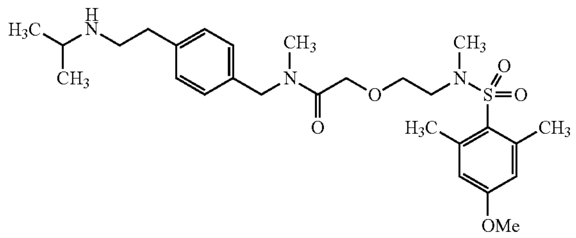

60a)

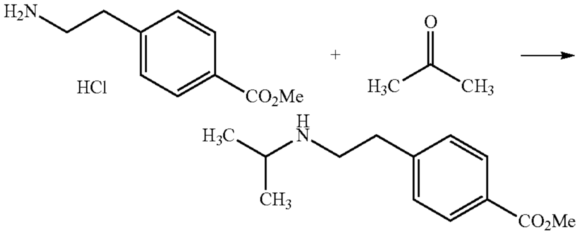

A mixture of 3.00 g (13.91 mmol) of methyl 4-aminoethylbenzoate (EMKA), 1.94 ml (13.91 mmol) of triethylamine and 50 ml THF is stirred for 10 min at ambient temperature and then combined with 1.13 ml (15.30 mmol) of acetone. The reaction mixture is stirred for another 30 min at ambient temperature, then 3.24 g (15.30 mmol) of sodium triacetoxyborohydride and 1.19 ml (20.86 mmol) of acetic acid are added. The mixture is stirred for 16 hours at ambient temperature. The reaction mixture is evaporated to dryness in vacuo, the residue is taken up in 1 M HCl and extracted with ethyl acetate (organic phase is discarded). The aqueous phase is made alkaline with saturated potassium carbonate solution and extracted with ethyl acetate. The organic extracts are dried on sodium sulphate and evaporated to dryness in vacuo.

$C_{13}H_{19}NO_2$ (221.30)

[M+H]+=222

HPLC (Method 4): retention time=2.2 min

60b)

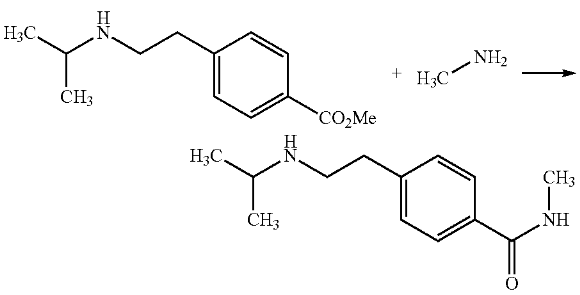

A mixture of 2.52 g (11.39 mmol) of product from 60a, 11.40 ml (22.80 mmol) of methylamine 2 M in THF (Aldrich), 0.54 g (5.70 mmol) of magnesium chloride (Aldrich) and 100 ml THF is stirred for 17 hours at 120° C. in the autoclave. The reaction mixture is filtered, the filtrate is evaporated to dryness in vacuo. The crude product thus obtained is purified by column chromatography through silica gel (eluant: dichloromethane/methanol/ammonia 9:1:0.1).

$C_{13}H_{20}N_2O$ (220.31)

[M+H]+=221

TLC: silica gel, dichloromethane/methanol/ammonia 9:1:0.1, Rf value=0.21

60c)

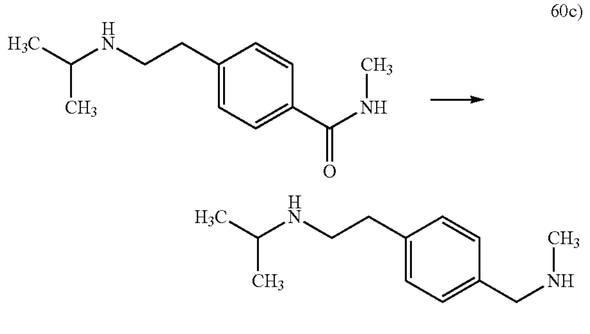

60c is prepared analogously to 38f from 1.49 g (6.76 mmol) of product from 60b and 10.00 ml (10.00 mmol) of lithium aluminium hydride 1 M in THF (Aldrich) in 60 ml THF.

$C_{13}H_{22}N_2$ (206.33)

[M+H]+=207

TLC: silica gel, dichloromethane/methanol/ammonia 9:1:0.1, Rf value=0.10

60d)

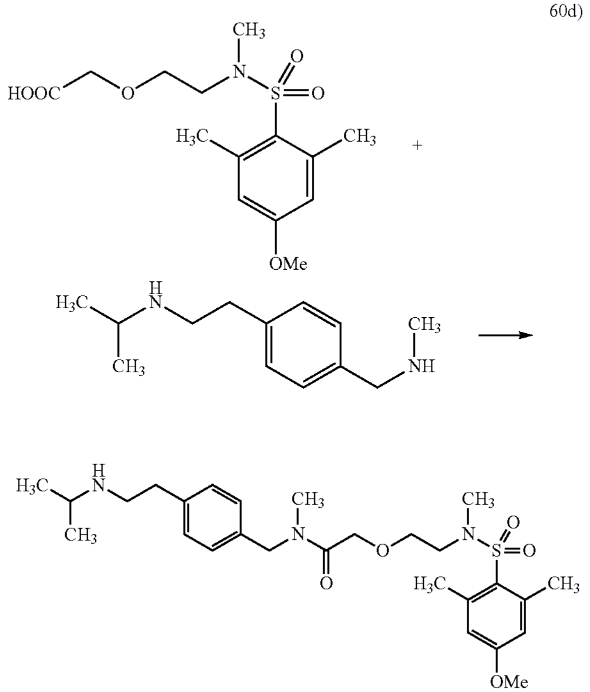

Example 60 is prepared analogously to 1f from 0.099 g (0.30 mmol) of product from 53c, 0.062 g (0.30 mmol) of product from 60c, 0.083 ml (0.60 mmol) of triethylamine and 0.12 g (0.36 mmol) of TBTU in 8 ml THF.

$C_{27}H_{41}N_3O_5S$ (519.70)

[M+H]+=520

HPLC (Method 4): retention time=3.2 min

Example 61

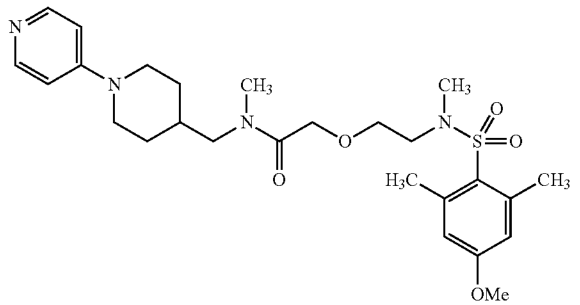

61a)

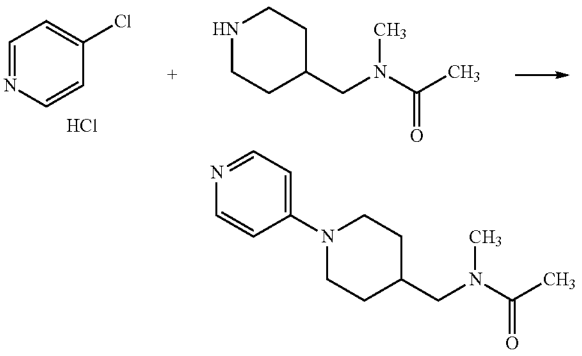

61a is prepared analogously to 28c from 1.00 g (6.67 mmol) of 4-chloropyridine hydrochloride (Aldrich) and 2.55 g (15.00 mmol) of N-methyl-N-piperidin-4-ylmethyl-acetamide (DE 110635, Rhône-Poulenc, 1961) in 1 ml of water.

$C_{14}H_{21}N_3O$ (247.34)

[M+H]+=248

61b)

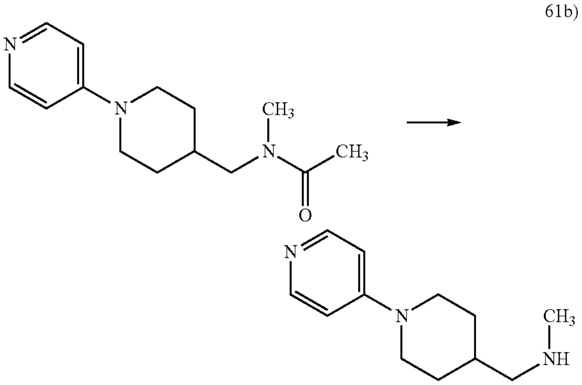

A mixture of 1.00 g (4.04 mmol) of product from 61a and 10 ml semiconcentrated HCl is refluxed for three days. The reaction mixture is then diluted with water, made alkaline with 20% sodium hydroxide solution and extracted with ethyl acetate. The organic extracts are dried on sodium sulphate and evaporated to dryness in vacuo.

$C_{12}H_{19}N_3$ (205.30)

TLC: silica gel, dichloromethane/ethanol 9:1, Rf value=0.2

61c)

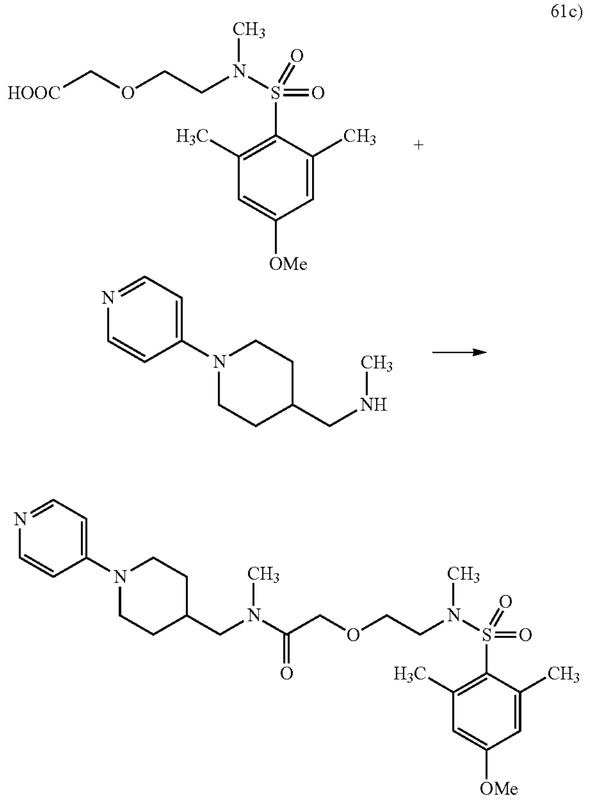

Example 61 is prepared analogously to 1f from 0.099 g (0.30 mmol) of product from 53c, 0.062 g (0.30 mmol) of product from 61b, 0.083 ml (0.60 mmol) of triethylamine and 0.12 g (0.36 mmol) of TBTU in 8 ml THF and 1 ml DMF.

$C_{26}H_{38}N_4O_5S$ (518.67)

[M+H]+=519

HPLC (Method 4): retention time=3.2 min

Example 62

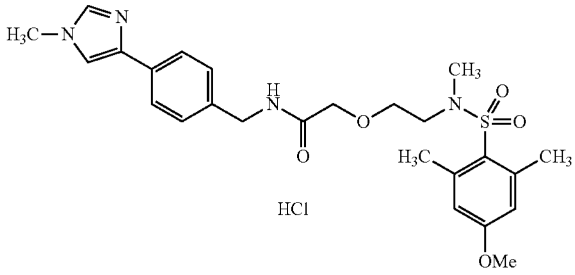

62a)

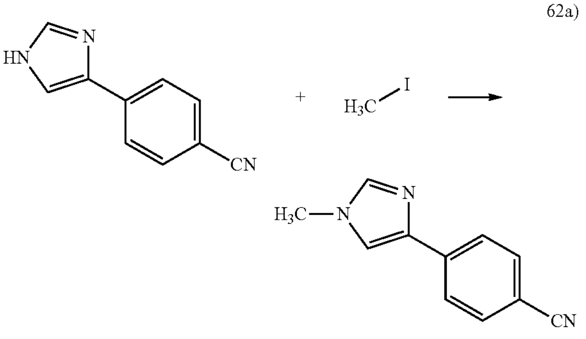

A mixture of 1.69 g (10.00 mmol) of 4-(1H-imidazol-4-yl)-benzonitrile (J. Am. Chem. Soc. 93, 1971, 4256-4263), 1.12 g (10.00 mmol) of potassium-tert-butoxide and 25 ml DMSO is first stirred for 30 min at ambient temperature, then slowly combined with 0.62 ml (10.00 mmol) of methyl iodide and stirred for another 2.5 hours at ambient temperature. The reaction mixture is then added to water, the precipitate formed is filtered off and dried in vacuo. The crude product thus obtained is purified by column chromatography through silica gel (eluant: dichloromethane/ethanol 19:1).

$C_{11}H_9N_3$ (183.21)

[M+H]+=184

HPLC (Method 4): retention time=1.9 min

62b)

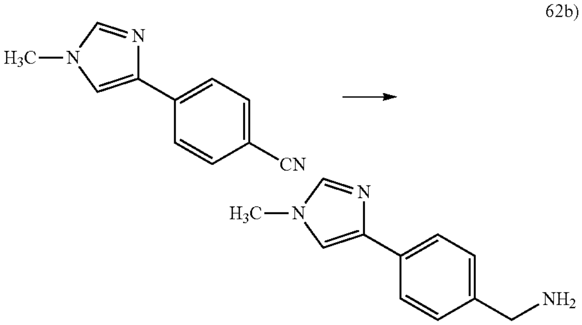

62b is prepared analogously to 34b from 1.02 g (5.57 mmol) of product from 62a, 0.20 g Raney nickel and 30 ml of methanolic ammonia solution.

$C_{11}H_{13}N_3$ (187.24)

TLC: silica gel, dichloromethane/methanol/ammonia 9:1:0.1, Rf value=0.27

62c)

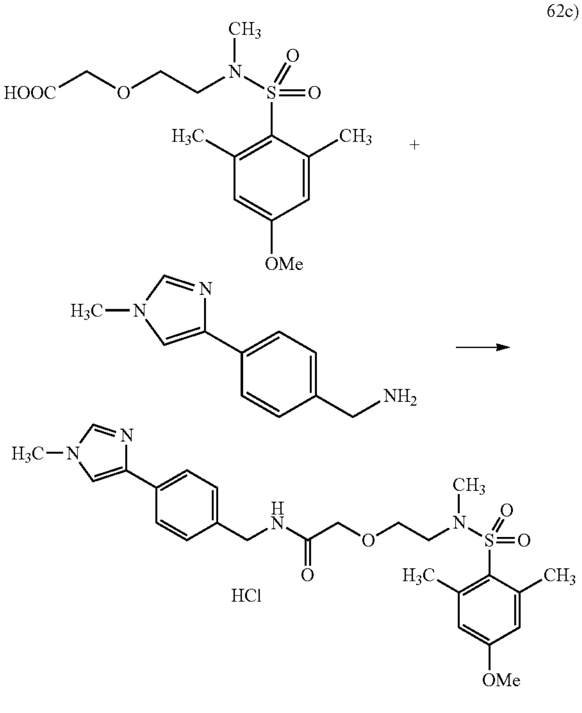

Example 62 is prepared analogously to 1f from 0.099 g (0.30 mmol) of product from 53c, 0.056 g (0.30 mmol) of product from 62b, 0.083 ml (0.60 mmol) of triethylamine and 0.12 g (0.36 mmol) of TBTU in 7 ml THF and 1 ml DMF.

$C_{25}H_{32}N_4O_5S{\times}HCl$ (537.07)

[M+H]+=501

HPLC (Method 4): retention time=3.2 min

Example 63

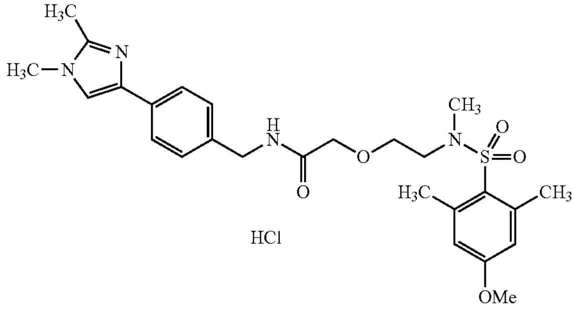

63a)

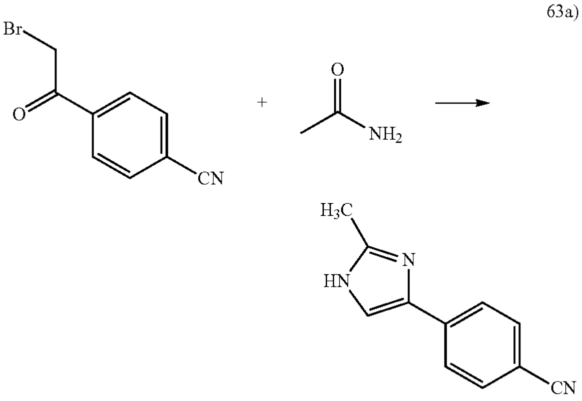

5.00 g (22.32 mmol) of 2-bromo-4'-cyano-acetophenone (Aldrich) and 10.00 g (169.29 mmol) of acetamide (Merck) are heated together with stirring for two hours to 210° C. After cooling, the reaction mixture is stirred into water and acidified with 2 M HCl. The precipitate is filtered off and discarded. The filtrate is made alkaline with concentrated ammonia solution, the precipitate is filtered off and dried in vacuo. The crude product thus obtained is purified by column chromatography through silica gel (eluant: dichloromethane/ethanol 9:1).

$C_{11}H_9N_3$ (183.21)

[M-H]-=182

HPLC (Method 4): retention time=1.9 min

63b)

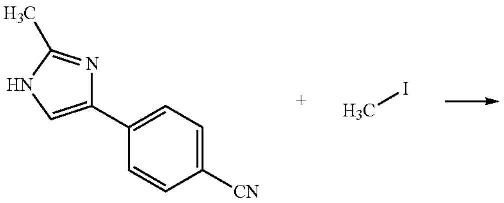

-continued

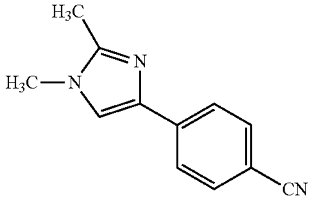

63b is prepared analogously to 62a from 2.39 g (13.05 mmol) of product from 63a, 1.46 g (13.05 mmol) of potassium-tert-butoxide and 0.81 ml (13.05 mmol) of methyl iodide in 50 ml DMSO.

$C_{12}H_{11}N_3$ (197.24)

[M+H]+=198

HPLC (Method 4): retention time=1.9 min

63c)

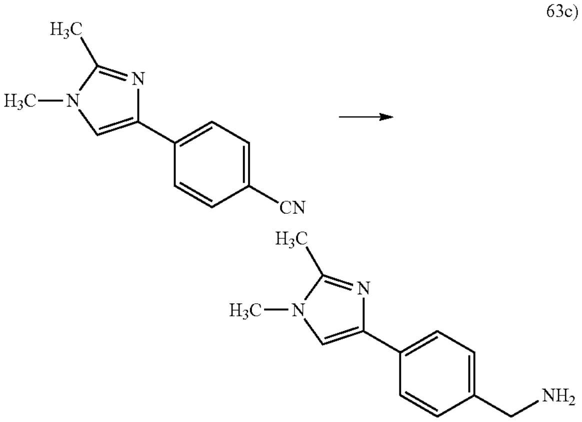

63c is prepared analogously to 34b from 2.04 g (10.34 mmol) of product from 63b, 0.40 g Raney nickel and 50 ml of methanolic ammonia solution.

$C_{12}H_{15}N_3$ (201.27)

TLC: silica gel, dichloromethane/methanol/ammonia 9:1:0.1, Rf value=0.19

63d)

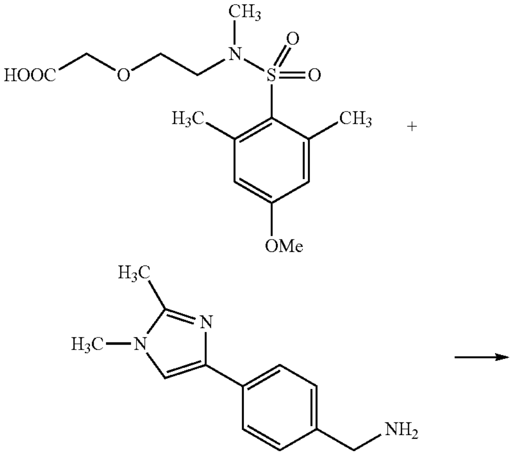

-continued

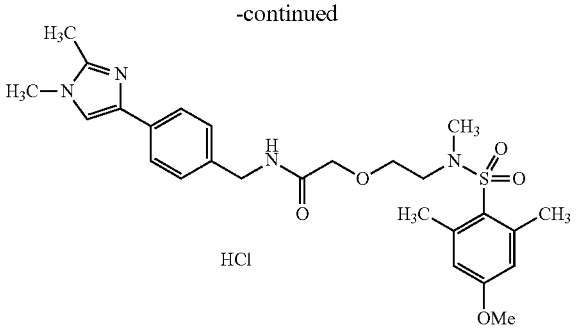

HCl

Example 63 is prepared analogously to 1f from 0.099 g (0.30 mmol) of product from 53c, 0.060 g (0.30 mmol) of product from 63c, 0.083 ml (0.60 mmol) of triethylamine and 0.12 g (0.36 mmol) of TBTU in 7 ml THF and 1 ml DMF.

$C_{26}H_{34}N_4O_5S \times HCl$ (551.10)

[M+H]+=515

HPLC (Method 4): retention time=3.2 min

Example 64

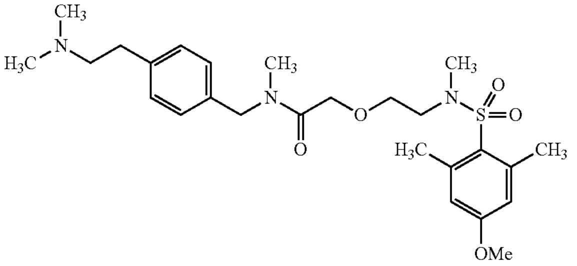

64a)

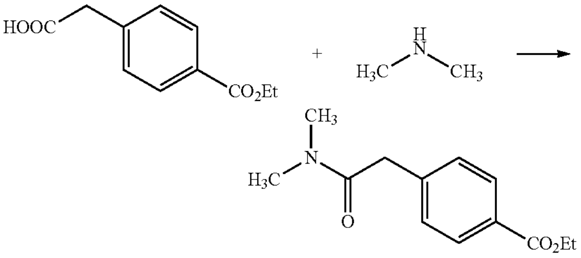

64a is prepared analogously to 1f from 4.00 g (19.21 mmol) of ethyl 4-carboxymethyl-benzoate (J. Med. Chem. 41, 1998, 5219-5246), 19.21 ml (38.42 mmol) of dimethylamine 2 M in THF (Aldrich), 5.36 ml (38.42 mmol) of triethylamine and 7.39 g (23.00 mmol) of TBTU in 100 ml THF.

$C_{13}H_{17}NO_3$ (235.28)

[M+H]+=236

HPLC (Method 4): retention time=3.3 min

64b)

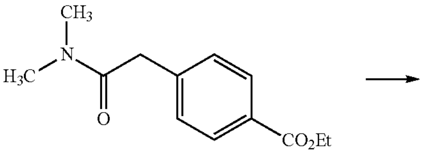

-continued

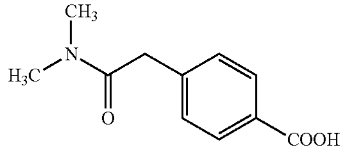

A mixture of 3.07 g (13.05 mmol) of product from 64a, 9.75 ml (39.00 mmol) of 4 M sodium hydroxide solution, 9.75 ml of water and 50 ml of ethanol is stirred overnight at ambient temperature. Then the ethanol is eliminated in vacuo. The aqueous residue is acidified with 4 M HCl and extracted with ethyl acetate. The organic extracts are dried on sodium sulphate and evaporated to dryness in vacuo. The product thus obtained is triturated with diethyl ether and dried.

$C_{11}H_{13}NO_3$ (207.23)

[M+H]+=208

HPLC (Method 4): retention time=2.3 min

64c)

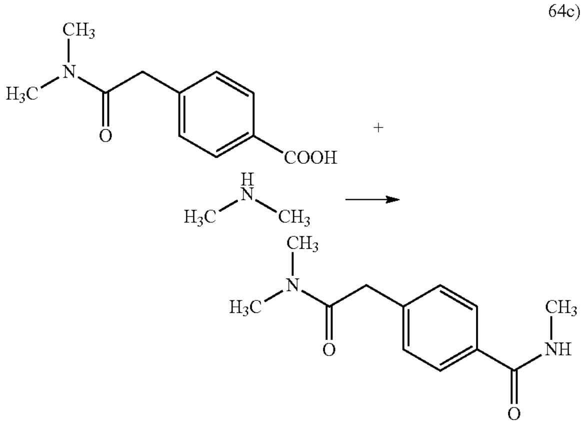

64c is prepared analogously to 1f from 2.30 g (11.10 mmol) of product from 64b, 11.10 ml (22.20 mmol) of dimethylamine 2 M in THF (Aldrich), 3.09 ml (22.20 mmol) of triethylamine and 4.28 g (13.32 mmol) of TBTU in 70 ml THF.

$C_{12}H_{16}N_2O_2$ (220.27)

[M+H]+=221

TLC: silica gel, dichloromethane/methanol/ammonia 9:1:0.1, Rf value=0.44

64d)

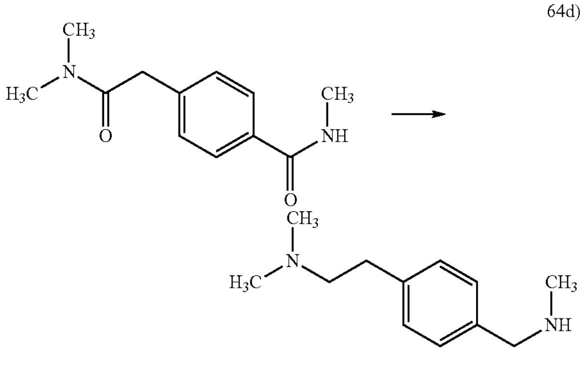

64d is prepared analogously to 38f from 1.92 g (8.72 mmol) of product from 64c and 40.00 ml (40.00 mmol) of lithium aluminium hydride 1 M in THF (Aldrich) in 150 ml THF.

$C_{12}H_{20}N_2$ (192.30)

[M+H]+=193

TLC: silica gel, dichloromethane/methanol/ammonia 9:1:0.1, Rf value=0.10

64e)

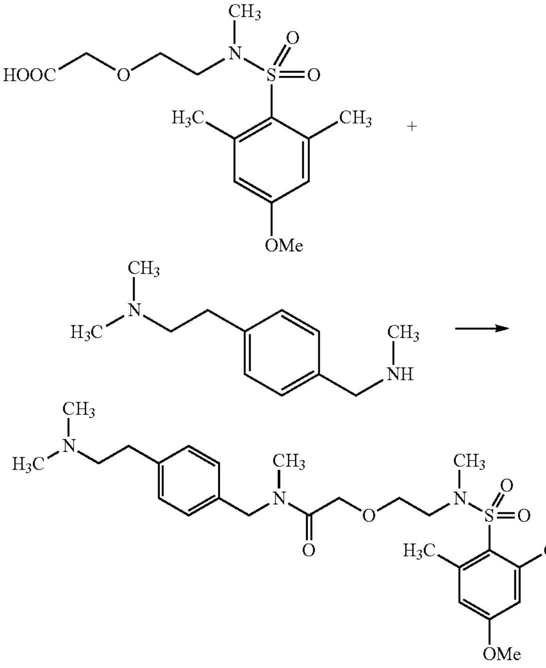

Example 64 is prepared analogously to 1f from 0.099 g (0.30 mmol) of product from 53c, 0.058 g (0.30 mmol) of product from 64d, 0.083 ml (0.60 mmol) of triethylamine and 0.12 g (0.36 mmol) of TBTU in 7 ml THF and 1 ml DMF.

$C_{26}H_{39}N_3O_5S$ (505.67)

[M+H]+=508

HPLC (Method 4): retention time=3.0 min

Example 65

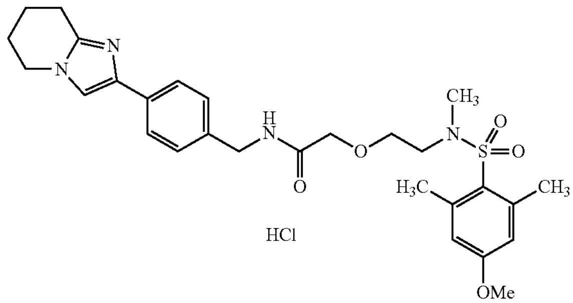

65a)

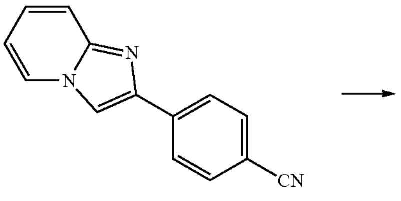

-continued

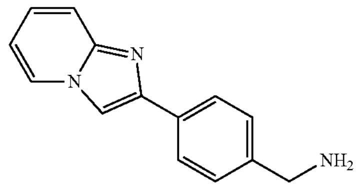

65a is prepared analogously to 34b from 0.40 g (1.82 mmol) of 4-imidazo[1,2-a]pyridin-2-yl-benzonitrile (J. Med. Chem. 41, 1998, 4317-4328), 0.10 g Raney nickel and 40 ml of methanolic ammonia solution.

$C_{14}H_{13}N_3$ (223.27)

[M+H]+=224

TLC: silica gel, dichloromethane/methanol 9:1, Rf value=0.06

65b)

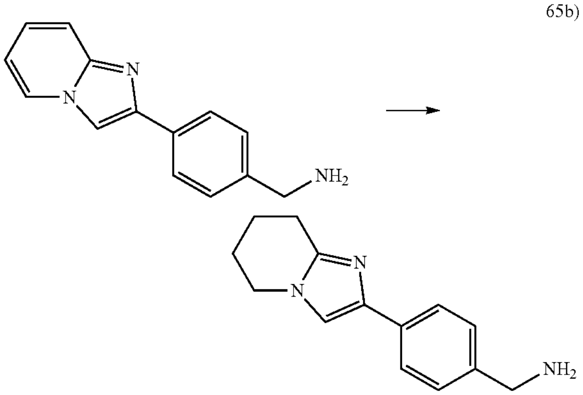

A mixture of 0.40 g (1.79 mmol) of product from 65a, 0.05 g platinum oxide and 40 ml of methanol is hydrogenated at 50° C. in the autoclave. The catalyst is filtered off, the filtrate is evaporated to dryness in vacuo.

$C_{14}H_{17}N_3$ (227.30)

[M+H]+=228

65c)

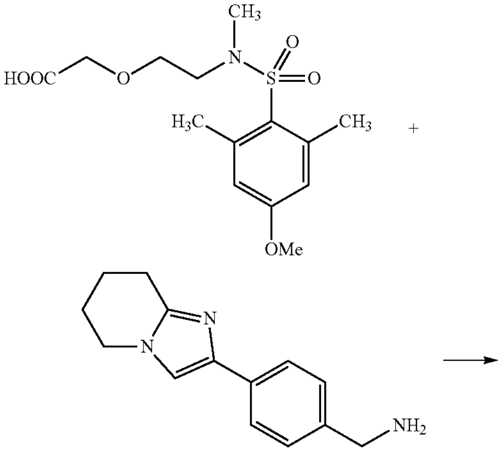

-continued

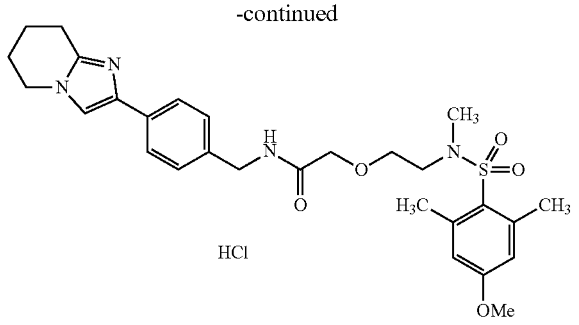

Example 65 is prepared analogously to 1f from 0.15 g (0.44 mmol) of product from 53c, 0.10 g (0.44 mmol) of product from 65b, 0.15 ml (1.09 mmol) of triethylamine and 0.16 g (0.48 mmol) of TBTU in 30 ml THF and 10 ml DMF.

$C_{28}H_{36}N_4O_5S \times HCl$ (577.14)

[M+H]+=541

HPLC (Method 5): retention time=1.57 min

Example 66

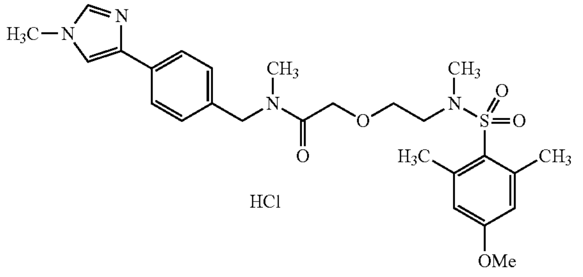

66a)

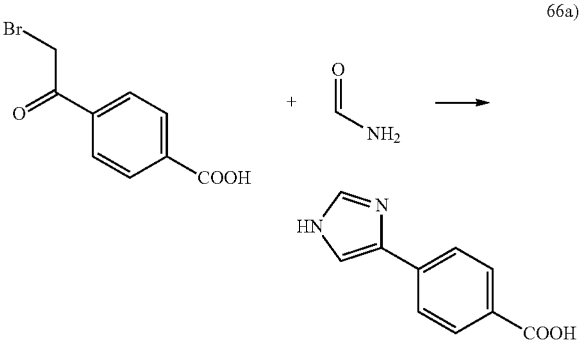

A mixture of 0.50 g (2.06 mmol) of 4-bromoacetylbenzoic acid (Fluorochem) and 5 ml formamide is stirred for one hour at 150° C. in the microwave. After cooling the precipitated product is filtered off, washed with diethyl ether and dried.

$C_{10}H_8N_2O_2$ (188.18)

[M+H]+=189

66b)

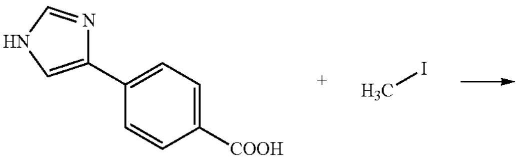

-continued

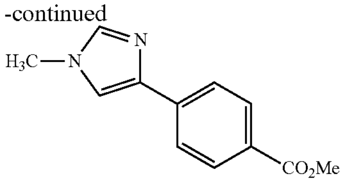

A mixture of 1.60 g (8.50 mmol) of product from 66a, 5.40 g (38.04 mmol) of methyl iodide, 7.00 g (25.33 mmol) of potassium carbonate and 30 ml DMF is stirred overnight at ambient temperature. The reaction mixture is filtered, the filtrate is evaporated to dryness in vacuo. The crude product thus obtained is purified by column chromatography through silica gel (eluant: dichloromethane/methanol 100:1 to 75:1).

$C_{12}H_{12}N_2O_2$ (216.24)

[M+H]+=217

66c)

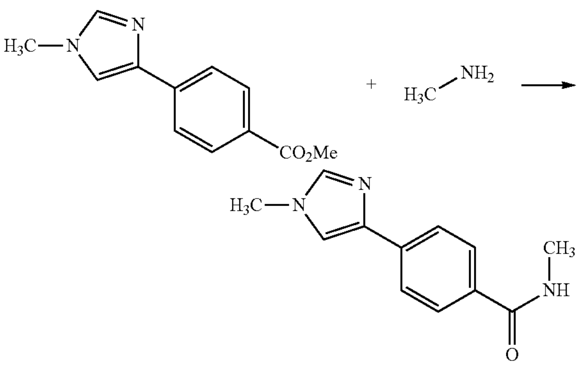

A mixture of 0.75 g (3.47 mmol) of product from 66b and 20 ml methylamine 33% in ethanol (Fluka) is heated to 160° C. overnight in the autoclave. The reaction mixture is evaporated to dryness in vacuo. The crude product thus obtained is purified by column chromatography through silica gel (eluant: dichloromethane/methanol 50:1 to 25:1).

$C_{12}H_{13}N_3O$ (215.25)

[M+H]+=216

66d)

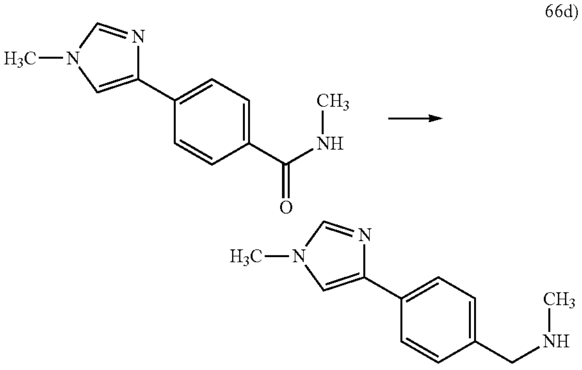

66d is prepared analogously to 38f from 0.41 g (1.91 mmol) of product from 66c and 3.00 ml (3.00 mmol) of lithium aluminium hydride 1 M in THF (Aldrich) in 70 ml THF.

$C_{12}H_{15}N_3$ (201.27)

[M+H]+=202

TLC: silica gel, dichloromethane/methanol/ammonia 8:2:0.01, Rf value=0.16

66e)

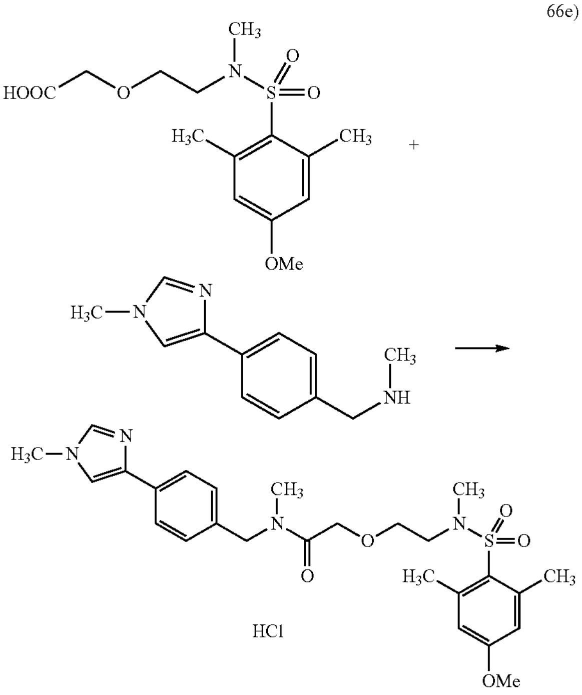

Example 66 is prepared analogously to 1f from 0.15 g (0.45 mmol) of product from 53c, 0.09 g (0.45 mmol) of product from 66d, 0.11 ml (1.09 mmol) of triethylamine and 0.16 g (0.50 mmol) of TBTU in 30 ml THF and 5 ml DMF.

$C_{26}H_{34}N_4O_5S \times HCl$ (551.10)

[M+H]+=515

TLC: silica gel, dichloromethane/methanol 9:1, Rf value=0.52

Example 67

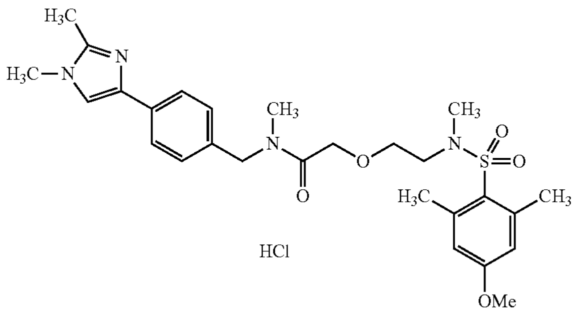

67a)

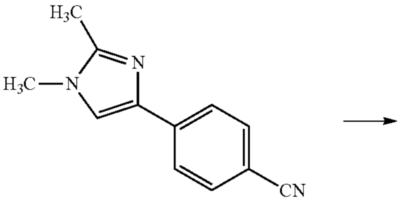

-continued

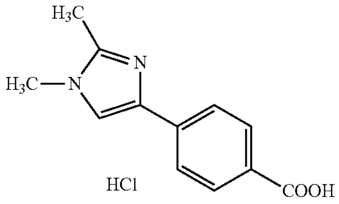

A mixture of 1.21 g (6.14 mmol) of product from 63b, 20 ml 20% sodium hydroxide solution and 40 ml of ethanol is refluxed overnight with stirring. The ethanol is eliminated in vacuo. The residue is diluted with water and acidified with 4 M HCl. The precipitated product is filtered off and dried at 50° C. in the circulating air dryer.

$C_{12}H_{12}N_2O_2$ (252.70)

[M+H]+=217

HPLC (Method 4): retention time=1.7 min

67b)

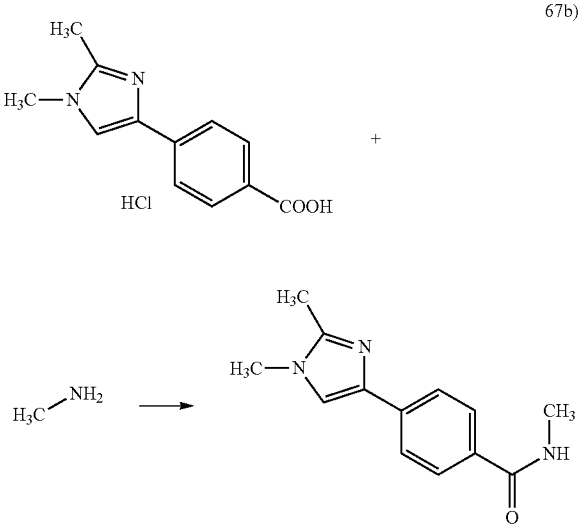

67b is prepared analogously to 1f from 1.55 g (6.13 mmol) of product from 67a, 4.60 ml (9.20 mmol) of methylamine 2 M in THF (Aldrich), 1.71 ml (12.30 mmol) of triethylamine and 2.38 g (7.40 mmol) of TBTU in 50 ml THF.

$C_{13}H_{15}N_3O$ (229.28)

[M+H]+=230

TLC: silica gel, dichloromethane/methanol 9:1, Rf value=0.47

67c)

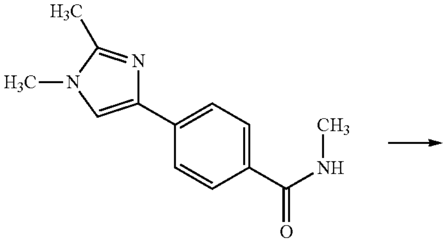

-continued

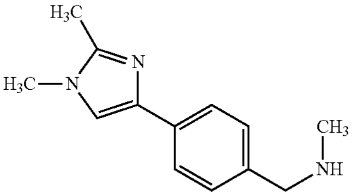

67c is prepared analogously to 38f from 1.33 g (5.80 mmol) of product from 67b and 15.00 ml (15.00 mmol) of lithium aluminium hydride 1 M in THF (Aldrich) in 80 ml THF.

$C_{13}H_{17}N_3$ (215.29)

[M+H]+=216

TLC: silica gel, dichloromethane/methanol/ammonia 9:1:0.1, Rf value=0.29

67d)

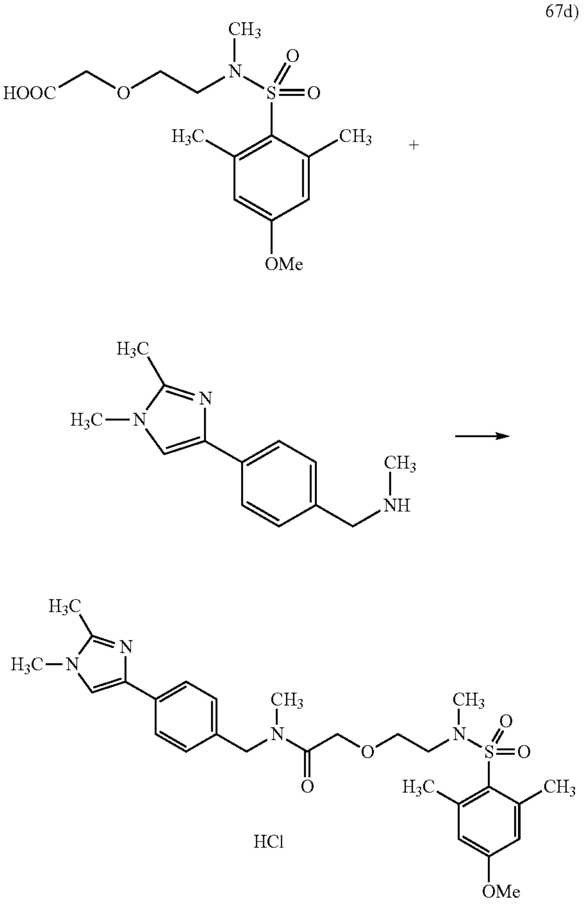

Example 67 is prepared analogously to 1f from 0.099 g (0.30 mmol) of product from 53c, 0.065 g (0.30 mmol) of product from 67c, 0.083 ml (0.60 mmol) of triethylamine and 0.12 g (0.36 mmol) of TBTU in 7 ml THF and 1 ml DMF.

$C_{27}H_{36}N_4O_5S \times HCl$ (565.13)

[M+H]+=529

HPLC (Method 4): retention time=3.1 min

Example 68

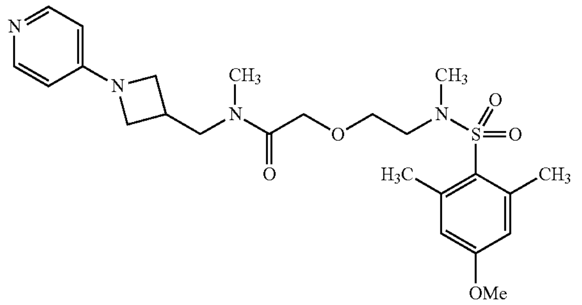

68a)

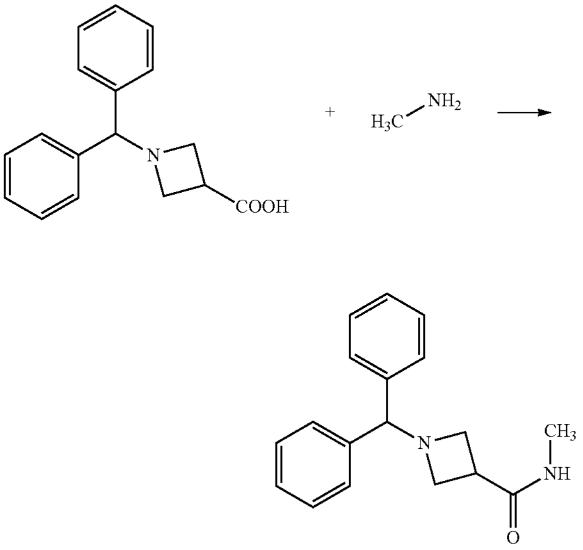

68a is prepared analogously to 1f from 5.39 g (20.16 mmol) of 1-benzhydryl-azetidine-3-carboxylic acid (Acros), 15 ml (30.00 mmol) of methylamine 2 M in THF (Aldrich), 5.58 ml (40.00 mmol) of triethylamine and 7.71 g (24.00 mmol) of TBTU in 150 ml THF.

$C_{18}H_{20}N_2O$ (280.36)

HPLC (Method 4): retention time=2.5 min

68b)

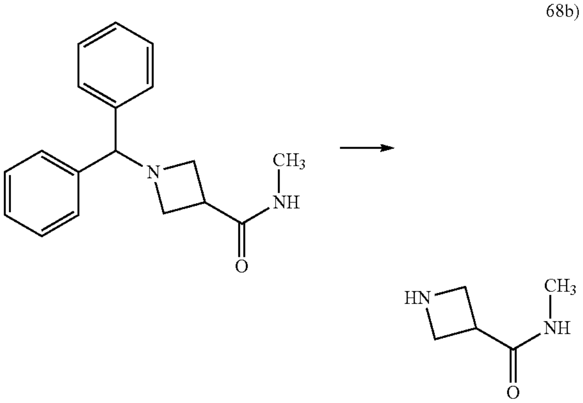

A mixture of 5.32 g (18.98 mmol) of product from 68a, 0.50 g palladium on charcoal (10%) and 100 ml of methanol is hydrogenated for 24 hours at ambient temperature in the autoclave. The catalyst is filtered off, the filtrate is evaporated to dryness in vacuo. The crude product thus obtained is purified by column chromatography through silica gel (eluant: dichloromethane/methanol/ammonia 70:30:3).

$C_5H_{10}N_2O$ (114.15)

TLC: silica gel, dichloromethane/methanol/ammonia 7:3: 0.3, Rf value=0.17

68c)

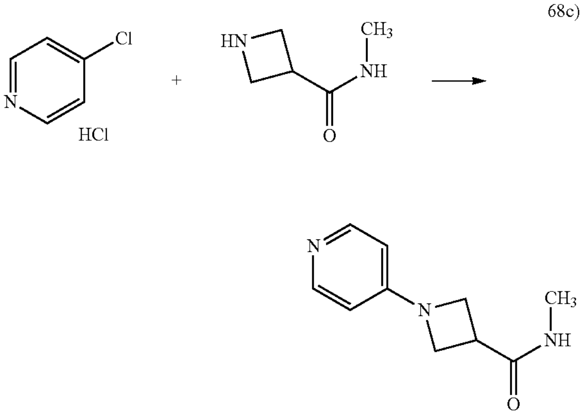

68c is prepared analogously to 28c from 1.31 g (8.76 mmol) of 4-chloropyridine hydrochloride (Aldrich), 1.00 g (8.76 mmol) of product from 68b and 2.40 ml (17.22 mmol) of triethylamine in 5 ml of ethanol.

$C_{10}H_{13}N_3O$ (191.23)

[M+H]+=192

TLC: silica gel, dichloromethane/methanol/ammonia 9:1: 0.1, Rf value=0.25

68d)

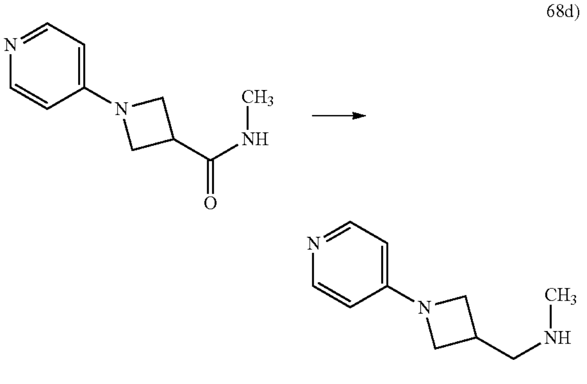

68d is prepared analogously to 38f from 0.46 g (2.41 mmol) of product from 68c and 5.00 ml (5.00 mmol) of lithium aluminium hydride 1 M in THF (Aldrich) in 20 ml THF.

$C_{10}H_{15}N_3$ (177.25)

[M+H]+=178

TLC: silica gel, dichloromethane/methanol/ammonia 8:2: 0.2, Rf value=0.40

68e)

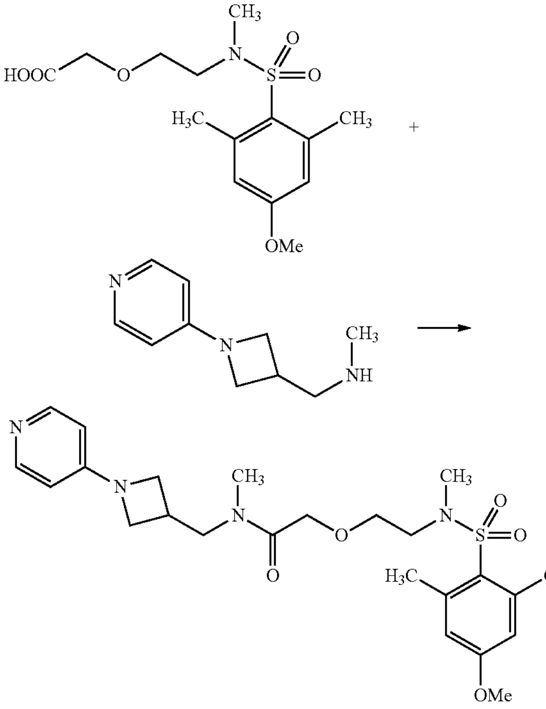

Example 68 is prepared analogously to 1f from 0.083 g (0.25 mmol) of product from 53c, 0.044 g (0.25 mmol) of product from 68d, 0.070 ml (0.50 mmol) of triethylamine and 0.096 g (0.30 mmol) of TBTU in 7 ml THF and 1 ml DMF.

$C_{24}H_{34}N_4O_5S$ (490.62)

[M+H]+=491

HPLC (Method 4): retention time=2.9 min

Example 69

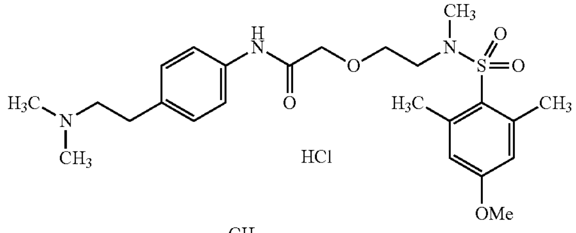

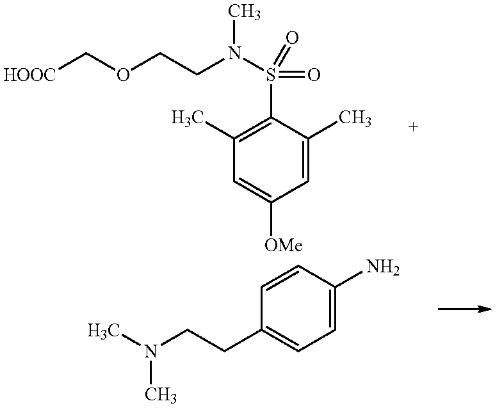

-continued

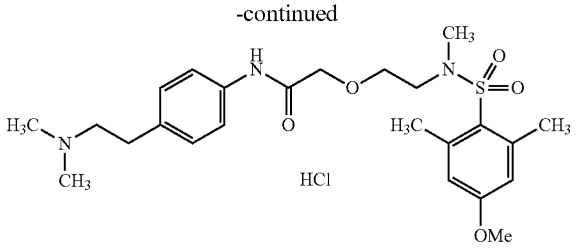

Example 69 is prepared analogously to 1f from 0.083 g (0.25 mmol) of product from 53c, 0.041 g (0.25 mmol) of 4-(2-dimethylamino-ethyl)-phenylamine (JW Pharmlab), 0.070 ml (0.50 mmol) of triethylamine and 0.096 g (0.30 mmol) of TBTU in 7 ml THF and 1 ml DMF.

$C_{24}H_{35}N_3O_5S \times HCl$ (514.08)

[M+H]+=478

HPLC (Method 4): retention time=3.1 min

Example 70

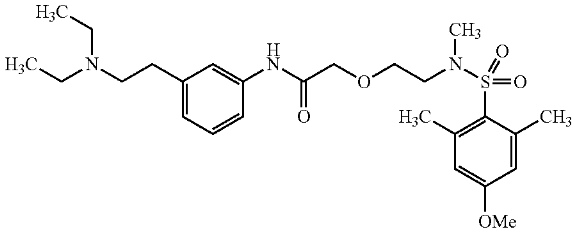

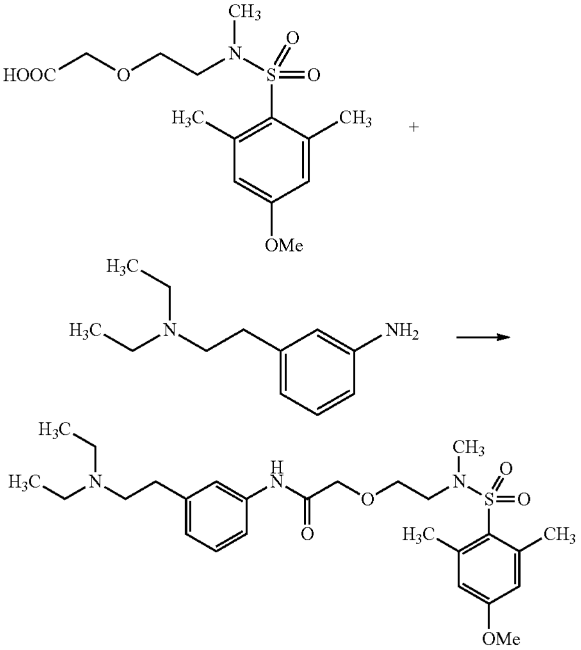

Example 70 is prepared analogously to 1f from 0.083 g (0.25 mmol) of product from 53c, 0.048 g (0.25 mmol) of 3-(2-diethylamino-ethyl)-phenylamine (analogously to J. Med. Chem. 28, 1985, 1533-1536), 0.070 ml (0.50 mmol) of triethylamine and 0.096 g (0.30 mmol) of TBTU in 7 ml THF and 1 ml DMF.

$C_{26}H_{39}N_3O_5S$ (505.67)

[M+H]+=506

HPLC (Method 4): retention time=3.4 min

Example 71

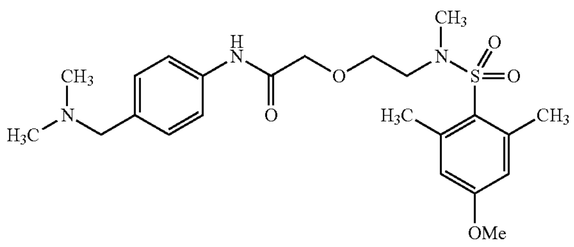

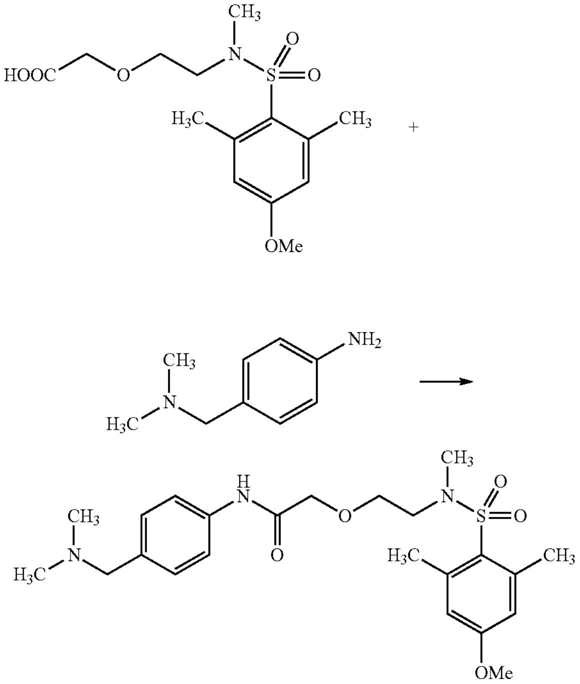

Example 71 is prepared analogously to 1f from 0.083 g (0.25 mmol) of product from 53c, 0.038 g (0.25 mmol) of 4-dimethylaminomethyl-phenylamine (J. Chem. Soc. 1935, 871), 0.070 ml (0.50 mmol) of triethylamine and 0.096 g (0.30 mmol) of TBTU in 7 ml THF and 1 ml DMF.

$C_{23}H_{33}N_3O_5S$ (463.59)

[M+H]+=464

HPLC (Method 4): retention time=3.1 min

Example 72

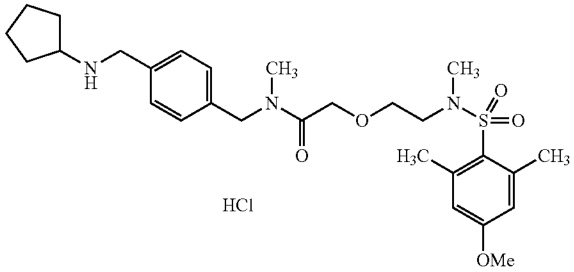

HCl

-continued

72a)

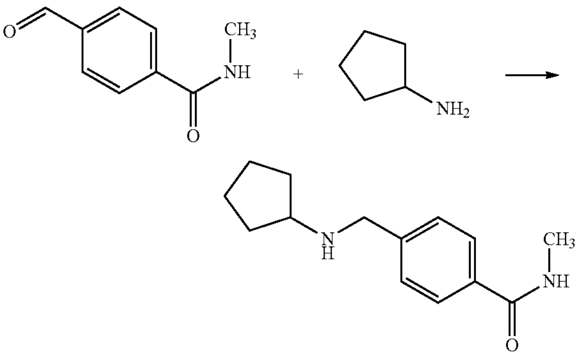

72a is prepared analogously to 60a from 0.82 g (5.00 mmol) of 4-formyl-benzoic acid methylamide (EMKA), 0.50 ml (5.00 mmol) of cyclopentylamine (Aldrich), 0.37 ml (6.50 mmol) of acetic acid and 1.59 g (7.50 mmol) of sodium triacetoxyborohydride in 30 ml THF.

$C_{14}H_{20}N_2O$ (232.32)

TLC: silica gel, dichloromethane/ethanol 9:1, Rf value=0.15

72b)

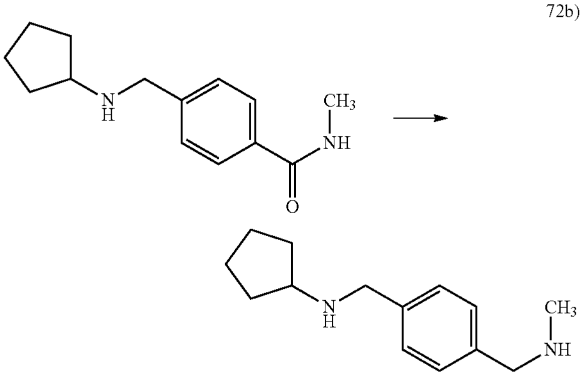

72b is prepared analogously to 38f from 1.00 g (4.30 mmol) of product from 72a and 9.00 ml (9.00 mmol) of lithium aluminium hydride 1 M in THF (Aldrich) in 40 ml THF.

$C_{14}H_{22}N_2$ (218.34) [M+H]+=219

TLC: silica gel, dichloromethane/ethanol 9:1, Rf value=0.2

72c)

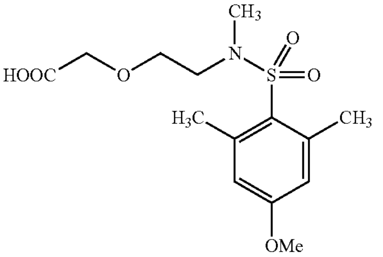

+

-continued

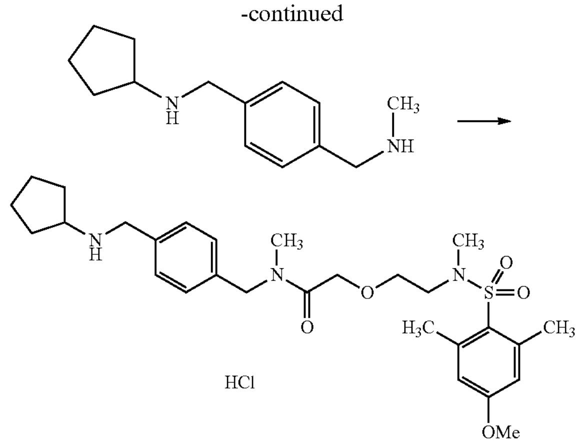

Example 72 is prepared analogously to 1f from 0.20 g (0.60 mmol) of product from 53c, 0.13 g (0.60 mmol) of product from 72b, 0.21 ml (1.50 mmol) of triethylamine and 0.23 g (0.72 mmol) of TBTU in 10 ml THF.

$C_{28}H_{41}N_3O_5S \times HCl$ (568.17)

[M+H]+=532

HPLC (Method 5): retention time=1.60 min

Example 73

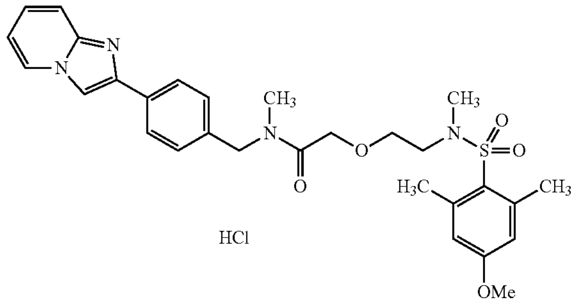

73a)

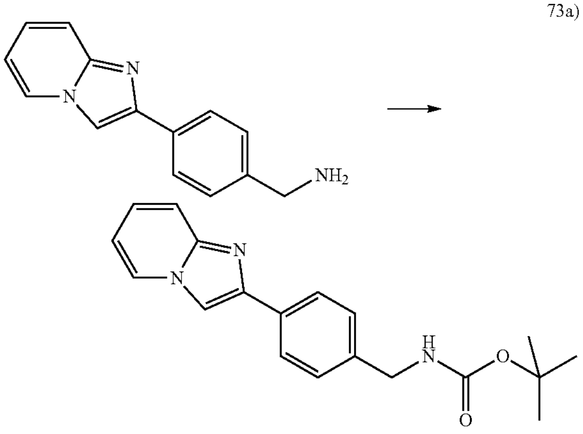

A mixture of 2.60 g (11.65 mmol) of product from 65a, 2.55 g (11.68 mmol) of Boc-anhydride and 100 ml DMF is stirred for two hours at ambient temperature. Then 100 ml of water are slowly added thereto. The precipitated product is filtered off, washed with water and petroleum ether and dried.

$C_{19}H_{21}N_3O_2$ (323.39)

[M+H]+=324

TLC: silica gel, dichloromethane/methanol 9:1, Rf value=0.78

73b)

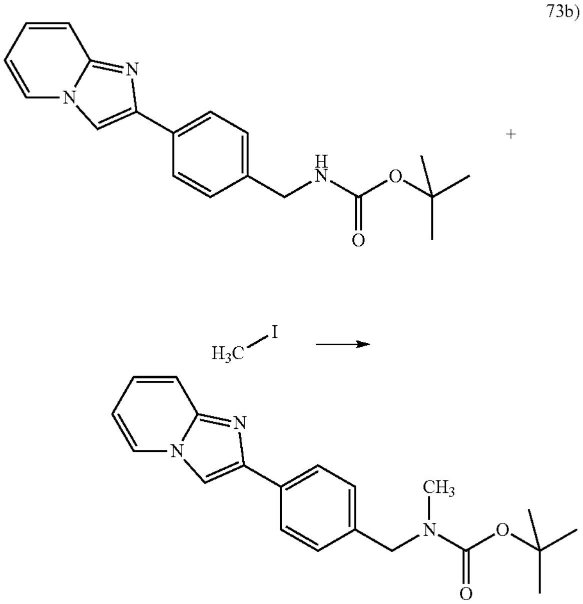

73b is prepared analogously to 62a from 1.00 g (3.09 mmol) of product from 73a, 0.70 g (6.24 mmol) of potassium-tert-butoxide and 0.98 ml (6.90 mmol) of methyl iodide in 30 ml DMSO.

$C_{17}H_{17}N_3O_2$ (295.34)

[M+H]+=296

73c)

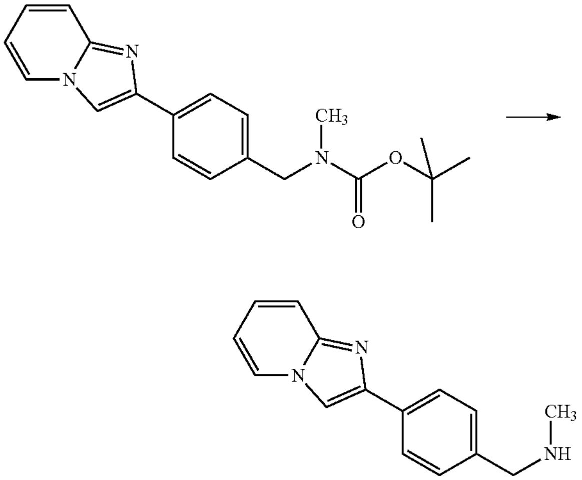

A mixture of 0.59 g (1.75 mmol) of product from 73b, 2 ml TFA and 30 ml dichloromethane is stirred for three hours at ambient temperature. The reaction mixture is then washed with water, dried on sodium sulphate and evaporated to dryness in vacuo.

$C_{15}H_{15}N_3$ (237.30)

[M+H]+=238

73d)

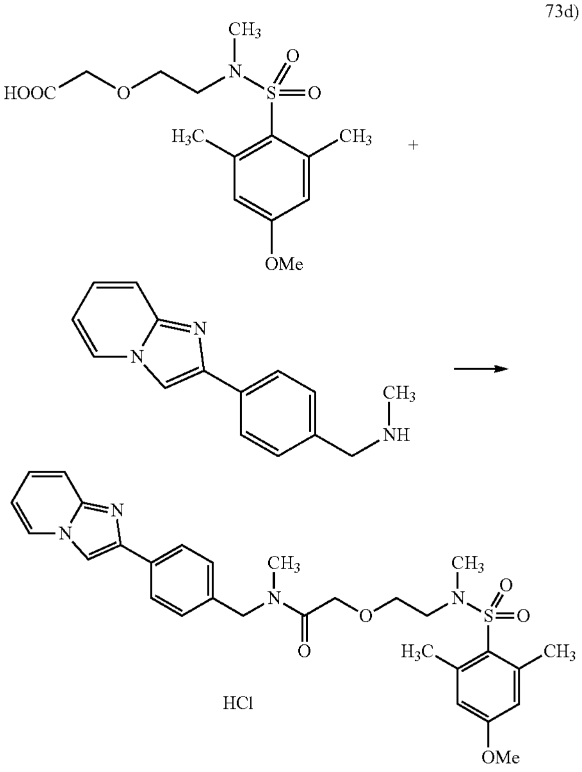

Example 73 is prepared analogously to 1f from 0.14 g (0.42 mmol) of product from 53c, 0.10 g (0.42 mmol) of product from 73c, 0.10 ml (0.99 mmol) of triethylamine and 0.15 g (0.46 mmol) of TBTU in 30 ml THF and 5 ml DMF.

$C_{29}H_{34}N_4O_5S \times HCl$ (587.13)

[M+H]+=551

HPLC (Method 5): retention time=1.58 min

Example 74

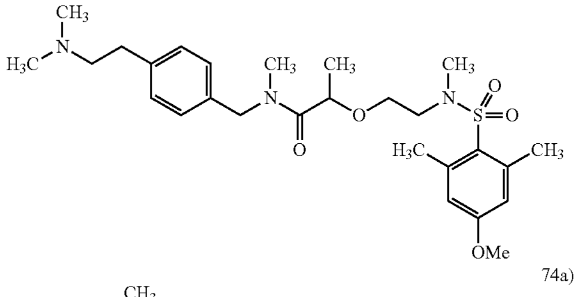

74a)

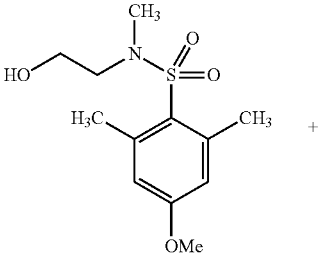

-continued

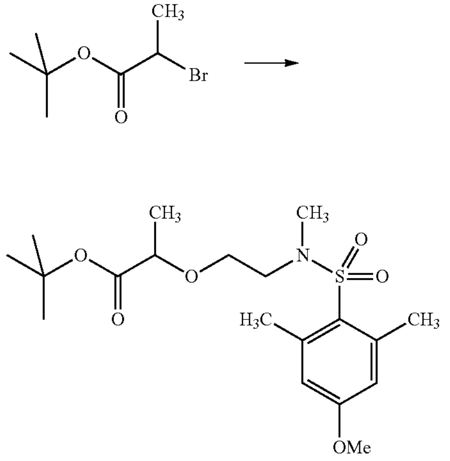

74a is prepared analogously to 53b from 4.08 g (14.93 mmol) of product from 53a, 4.68 g (22.39 mmol) of tert-butyl 2-bromopropionate (TCI), 1.38 g (4.98 mmol) of tetrabutylammonium chloride (Fluka) and 70 ml of 35% sodium hydroxide solution in 70 ml of toluene.

$C_{19}H_{31}NO_6S$ (401.52)

[M+H]+=402

TLC: silica gel, petroleum ether/ethyl acetate 7:3, Rf value=0.69

74b)

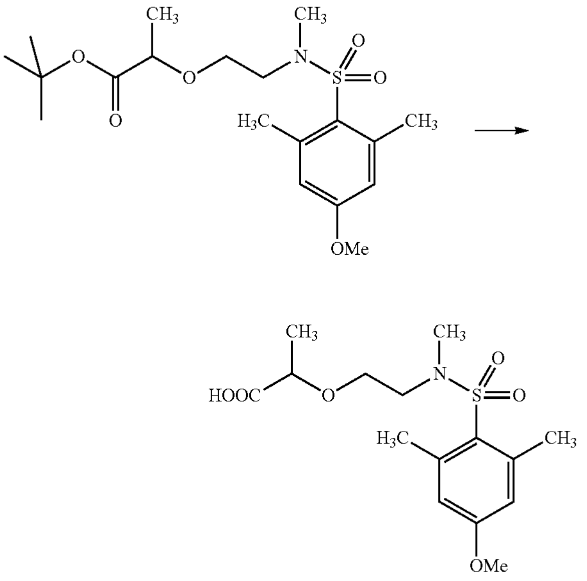

74b is prepared analogously to 53c from 5.12 g (12.75 mmol) of product from 74a and 5.89 ml TFA in 80 ml dichloromethane.

$C_{15}H_{23}NO_6S$ (345.41)

[M+H]+=346

TLC: silica gel, dichloromethane/ethanol 19:1, Rf value=0.25

74c)

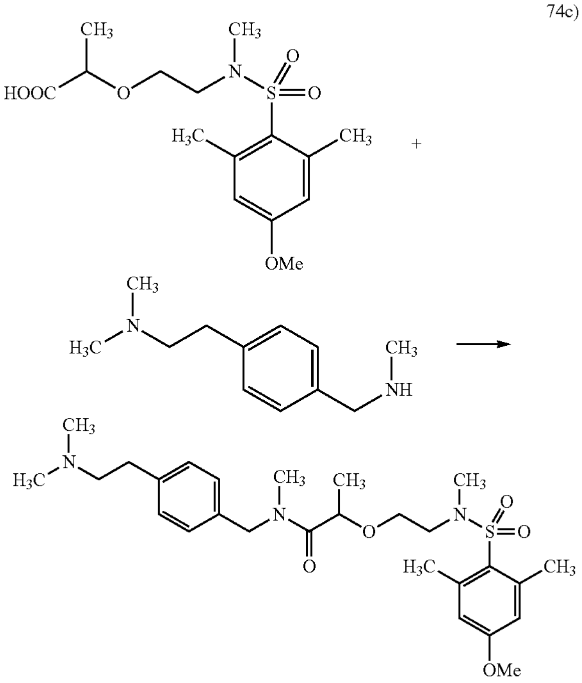

Example 74 is prepared analogously to 1f from 0.10 g (0.30 mmol) of product from 74b, 0.058 g (0.30 mmol) of product from 64d, 0.084 ml (0.60 mmol) of triethylamine and 0.12 g (0.36 mmol) of TBTU in 7 ml THF and 1 ml DMF.

$C_{27}H_{41}N_3O_5S$ (519.70)

[M+H]+=520

HPLC (Method 4): retention time=3.1 min

Example 75

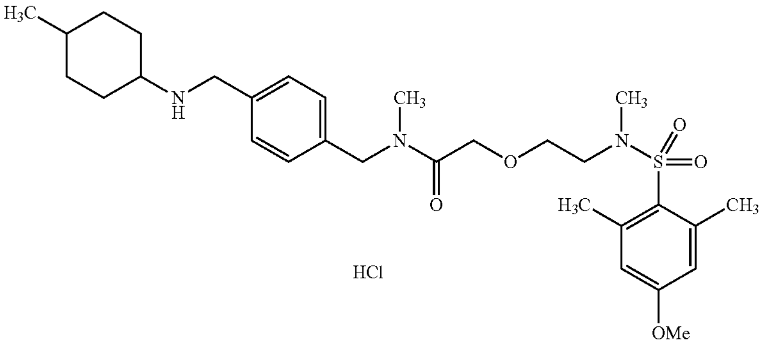

75a)

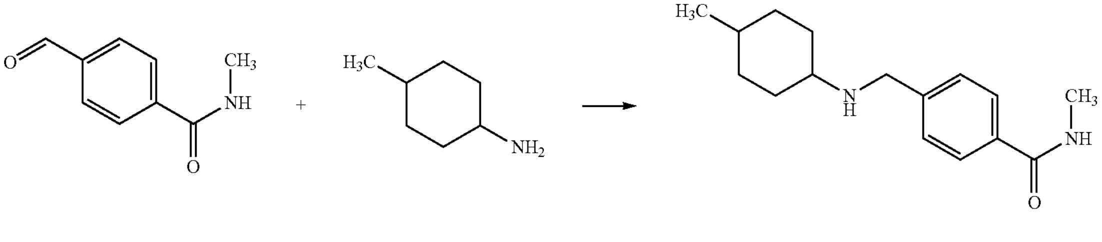

75a is prepared analogously to 60a from 0.82 g (5.00 mmol) of 4-formyl-benzoic acid methylamide (EMKA), 0.67 ml (5.00 mmol) of 4-methylcyclohexylamine cis/trans mixture (Acros), 0.37 ml (6.50 mmol) of acetic acid and 1.59 g (7.50 mmol) of sodium triacetoxyborohydride in 30 ml THF.

$C_{16}H_{24}N_2O$ (260.37)

TLC: silica gel, dichloromethane/ethanol 9:1, Rf value=0.25

75b)

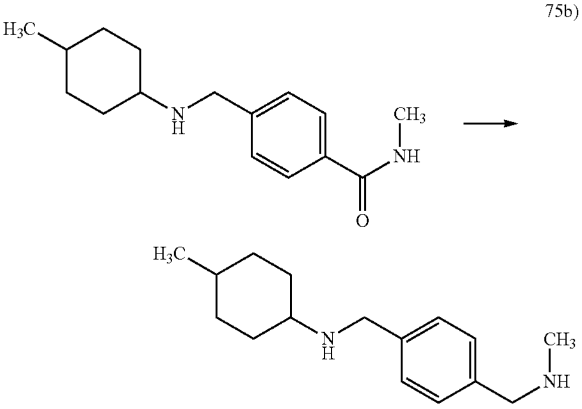

75b is prepared analogously to 38f from 1.30 g (4.99 mmol) of product from 75a and 10.00 ml (10.00 mmol) of lithium aluminium hydride 1 M in THF (Aldrich) in 50 ml THF.

$C_{16}H_{26}N_2$ (246.39)

TLC: silica gel, dichloromethane/ethanol 9:1, Rf value=0.2

75c)

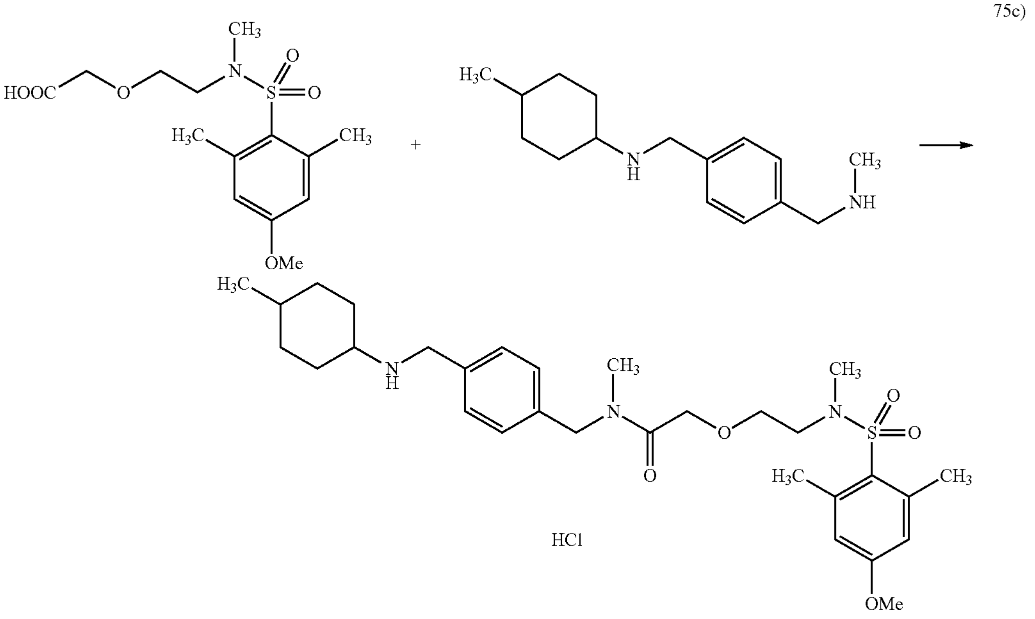

Example 75 is prepared analogously to 1f from 0.20 g (0.60 mmol) of product from 53c, 0.15 g (0.60 mmol) of product from 75b, 0.21 ml (1.50 mmol) of triethylamine and 0.23 g (0.72 mmol) of TBTU in 10 ml THF.

$C_{30}H_{45}N_3O_5S \times HCl$ (596.22)

[M+H]+=560

HPLC (Method 5): retention time=1.65 min

Example 76

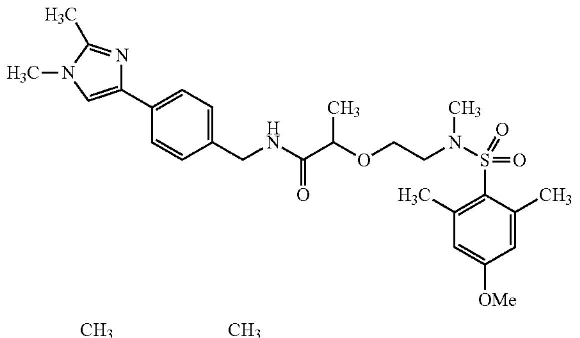

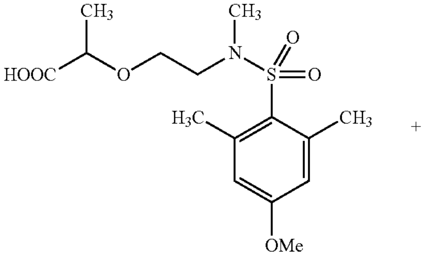

-continued

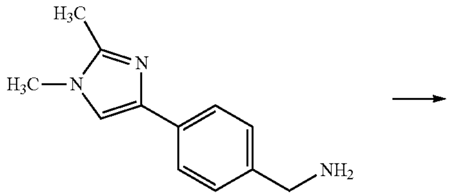

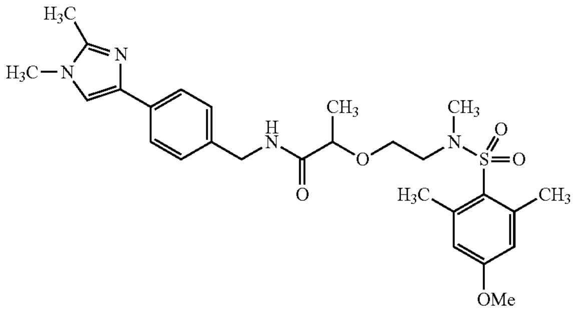

Example 76 is prepared analogously to 1f from 0.10 g (0.30 mmol) of product from 74b, 0.060 g (0.30 mmol) of product from 63c, 0.084 ml (0.60 mmol) of triethylamine and 0.12 g (0.36 mmol) of TBTU in 7 ml THF and 1 ml DMF.

$C_{27}H_{36}N_4O_5S$ (528.66)

[M+H]+=529

HPLC (Method 4): retention time=3.2 min

Example 77

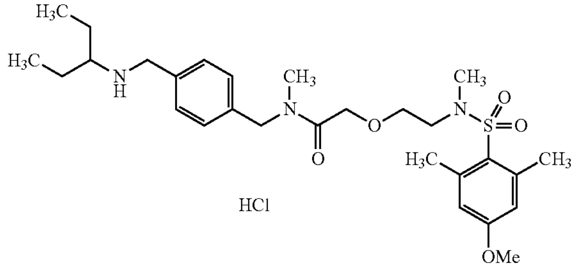

77a)

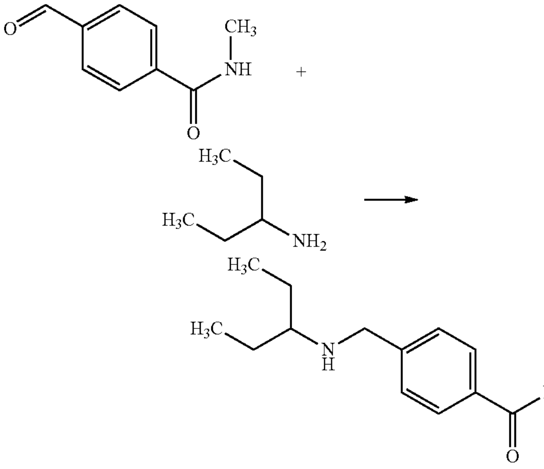

77a is prepared analogously to 60a from 0.82 g (5.00 mmol) of 4-formyl-benzoic acid methylamide (EMKA), 0.58 ml (5.00 mmol) of 3-pentylamine (Aldrich), 0.37 ml (6.50 mmol) of acetic acid and 1.59 g (7.50 mmol) of sodium triacetoxyborohydride in 30 ml THF.

$C_{14}H_{22}N_2O$ (234.34)

[M+H]+=235

TLC: silica gel, dichloromethane/ethanol 9:1, Rf value=0.4

77b)

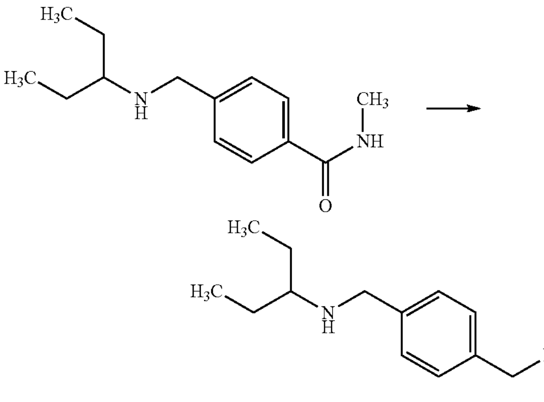

77b is prepared analogously to 38f from 1.10 g (4.69 mmol) of product from 77a and 9.40 ml (9.40 mmol) of lithium aluminium hydride 1 M in THF (Aldrich) in 40 ml THF.

$C_{14}H_{24}N_2$ (220.35)

TLC: silica gel, dichloromethane/ethanol 9:1, Rf value=0.1

77c)

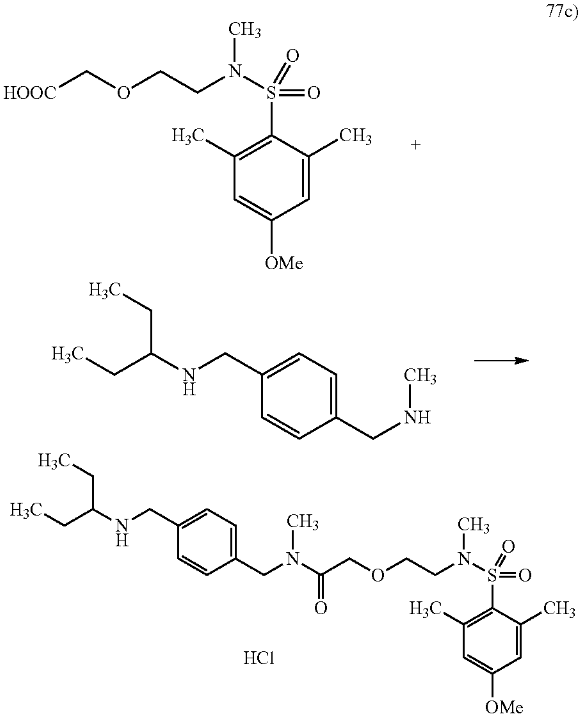

Example 77 is prepared analogously to 1f from 0.20 g (0.60 mmol) of product from 53c, 0.13 g (0.60 mmol) of product from 77b, 0.21 ml (1.50 mmol) of triethylamine and 0.23 g (0.72 mmol) of TBTU in 10 ml THF.

$C_{28}H_{43}N_3O_5S$×HCl (570.18)

[M+H]+=534

TLC: silica gel, dichloromethane/ethanol 9:1, Rf value=0.45

Example 78

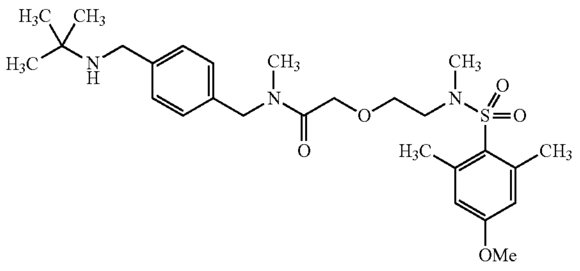

78a)

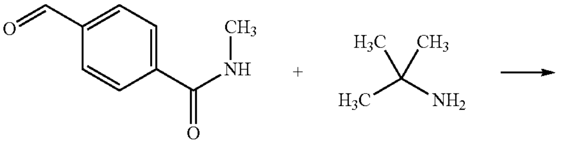

-continued

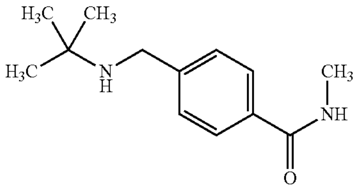

78a is prepared analogously to 60a from 0.82 g (5.00 mmol) of 4-formyl-benzoic acid methylamide (EMKA), 0.53 ml (5.00 mmol) of tert-butylamine (Fluka), 0.37 ml (6.50 mmol) of acetic acid and 1.59 g (7.50 mmol) of sodium triacetoxyborohydride in 30 ml THF.

$C_{13}H_{20}N_2O$ (220.31)

[M+H]+=221

TLC: silica gel, dichloromethane/ethanol 9:1, Rf value=0.15

78b)

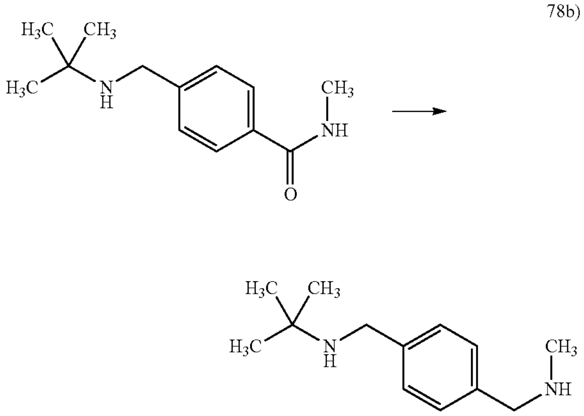

78b is prepared analogously to 38f from 1.00 g (4.54 mmol) of product from 78a and 9.10 ml (9.10 mmol) of lithium aluminium hydride 1 M in THF (Aldrich) in 40 ml THF.

$C_{13}H_{22}N_2$ (206.33)

78c)

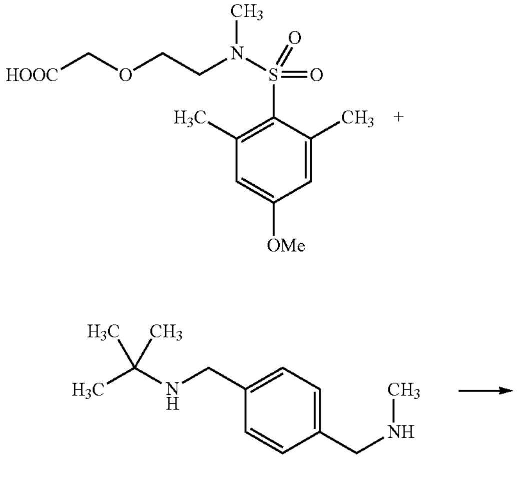

-continued

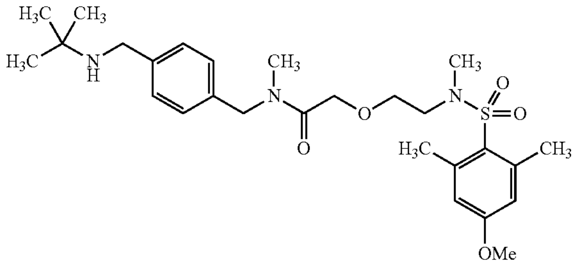

Example 78 is prepared analogously to 1f from 0.20 g (0.60 mmol) of product from 53c, 0.12 g (0.60 mmol) of product from 78b, 0.21 ml (1.50 mmol) of triethylamine and 0.23 g (0.72 mmol) of TBTU in 10 ml THF.

$C_{27}H_{41}N_3O_5S$ (519.70)

[M+H]+=520

HPLC (Method 5): retention time=1.58 min

Example 79

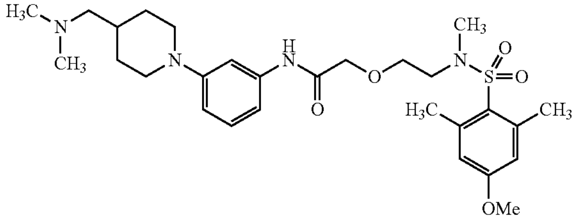

79a)

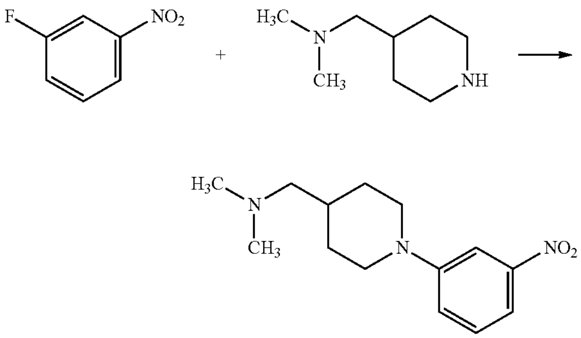

A mixture of 0.50 ml (4.70 mmol) of 1-fluoro-3-nitrobenzene (Fluka), 1.34 g (9.39 mmol) of 4-(N,N-dimethylaminomethyl)-piperidine (Eur. J. Med. Chem. Chim. Ther. 37, 2002, 487-502), 0.65 g (4.70 mmol) of potassium carbonate and 6.6 ml DMSO is stirred for five days at 110° C. The reaction mixture is then poured onto ice, the precipitate formed is filtered off. The product thus obtained is dried overnight in the vacuum desiccator.

$C_{14}H_{21}N_3O_2$ (263.34)

[M+H]+=264

TLC: silica gel, dichloromethane/methanol 9:1, Rf value=0.20

79b)

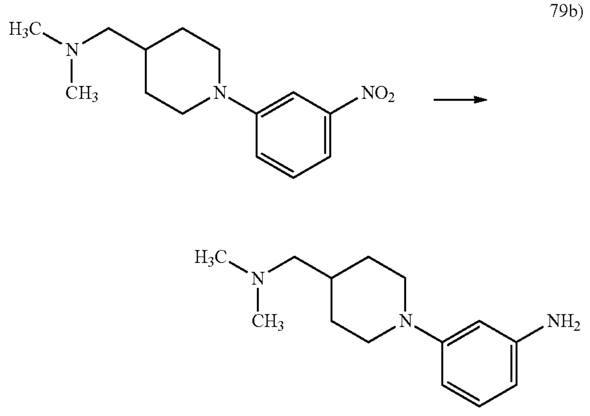

A mixture of 0.95 ml (3.60 mmol) of product from 79a, 0.095 g palladium on charcoal (5%) and 72 ml of ethanol is hydrogenated at ambient temperature in the autoclave. The catalyst is filtered off, the filtrate is evaporated to dryness in vacuo.

$C_{14}H_{23}N_3$ (233.35)

[M+H]+=234

79c)

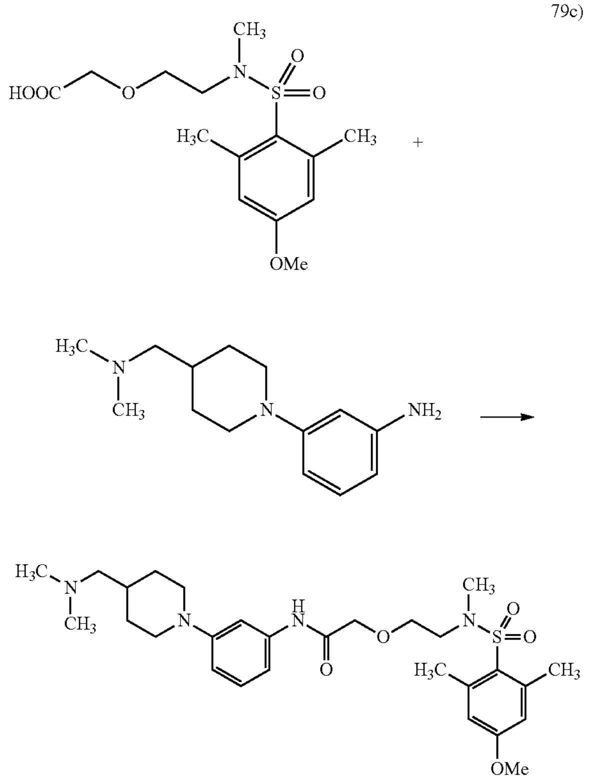

Example 79 is prepared analogously to 1f from 0.15 g (0.46 mmol) of product from 53c, 0.11 g (0.46 mmol) of product from 79b, 0.084 ml (0.60 mmol) of triethylamine and 0.18 g (0.56 mmol) of TBTU in 3 ml DMF.

$C_{28}H_{42}N_4O_5S$ (546.72)

[M+H]+=547

HPLC (Method 5): retention time=1.49 min

Example 80

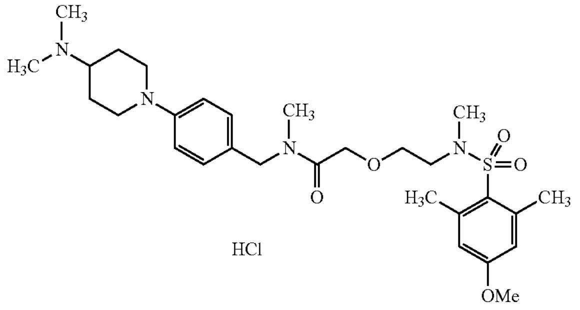

80a)

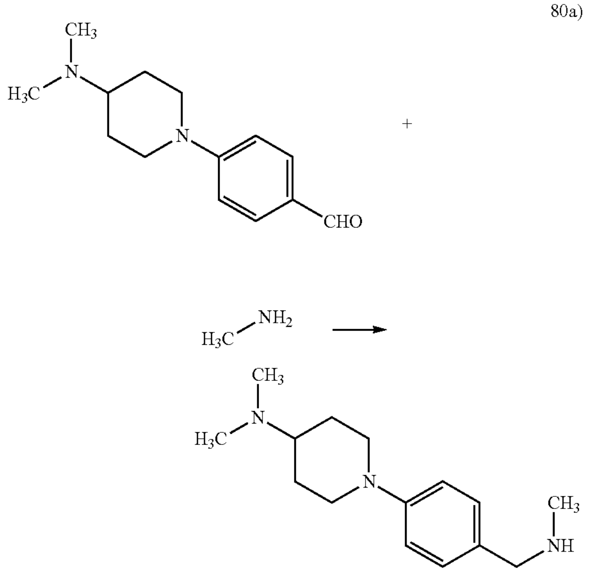

80a is prepared analogously to 33a from 0.70 g (3.01 mmol) of 4-(4-dimethylamino-piperidin-1-yl)-benzaldehyde (Tetrahedron 57, 2001, 4781-4785), 3.00 ml (31.88 mmol) of methylamine 33% in ethanol (Aldrich), 0.20 g Raney nickel in 25 ml of ethanol.

$C_{15}H_{25}N_3$ (247.38)

[M+H]+=248

TLC: silica gel, dichloromethane/methanol/ammonia 9:1:0.1, Rf value=0.16

80b)

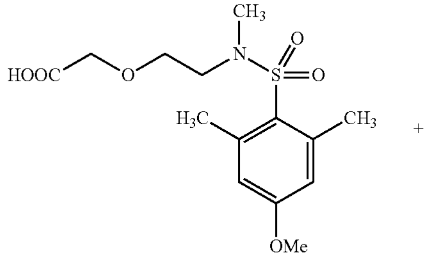

-continued

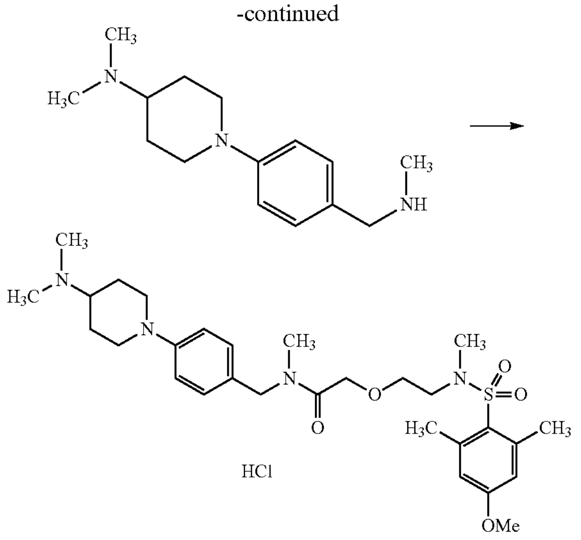

Example 80 is prepared analogously to 1f from 0.15 g (0.45 mmol) of product from 53c, 0.11 g (0.45 mmol) of product from 80a, 0.13 ml (0.90 mmol) of triethylamine and 0.17 g (0.54 mmol) of TBTU in 5 ml DMF.

$C_{29}H_{44}N_4O_5S \times HCl$ (597.21)

[M+H]+=561

HPLC (Method 1): retention time=2.33 min

Example 81

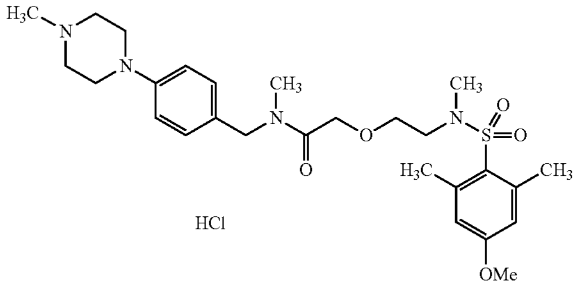

81a)

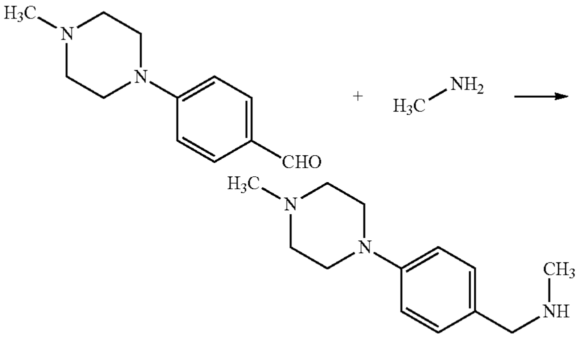

81a is prepared analogously to 33a from 1.00 g (4.90 mmol) of 4-(4-methyl-piperazin-1-yl)-benzaldehyde (Chem. Pharm Bull. 45, 1997, 1458-1469), 4.00 ml (42.50 mmol) of methylamine 33% in ethanol (Aldrich), 0.20 g Raney nickel in 30 ml of ethanol.

$C_{13}H_{21}N_3$ (219.33)

[M+H]+=220

TLC: silica gel, dichloromethane/methanol/ammonia 9:1:0.1, Rf value=0.15

81b)

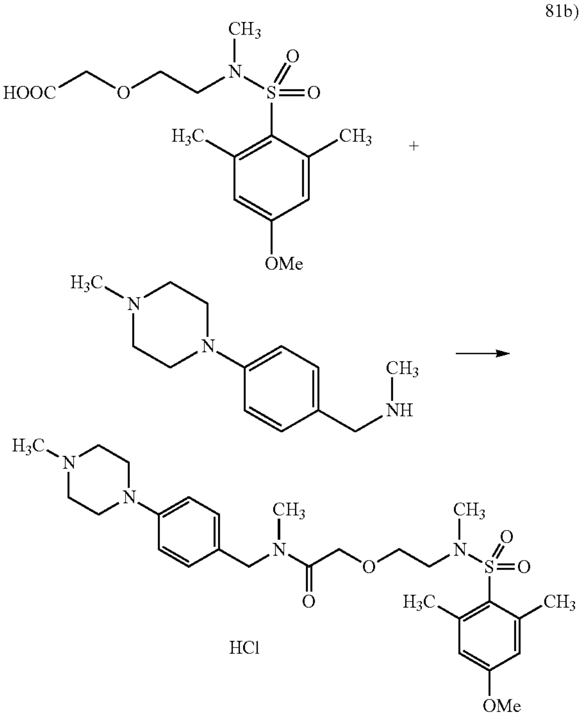

Example 81 is prepared analogously to 1f from 0.15 g (0.45 mmol) of product from 53c, 0.099 g (0.45 mmol) of product from 81a, 0.13 ml (0.90 mmol) of triethylamine and 0.17 g (0.54 mmol) of TBTU in 5 ml DMF.

$C_{27}H_{40}N_4O_5S \times HCl$ (569.16)

[M+H]+=533

HPLC (Method 1): retention time=2.28 min

Example 82

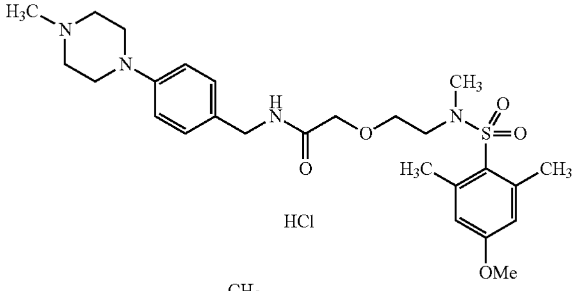

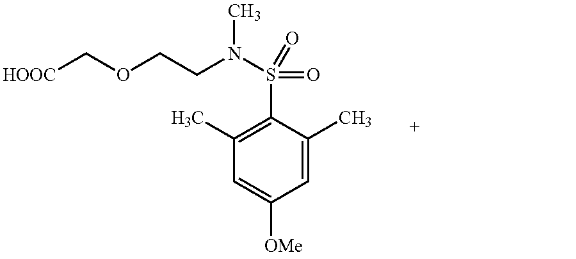

-continued

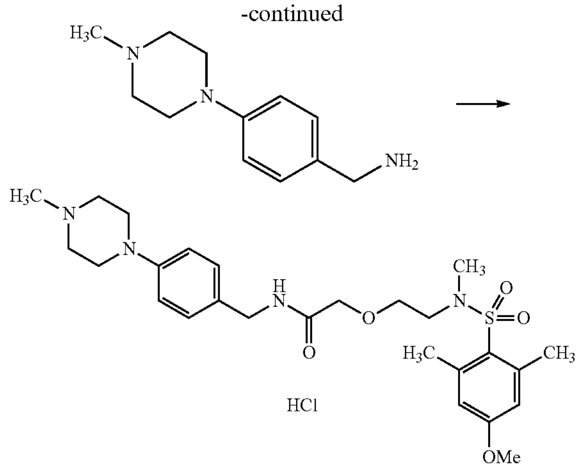

Example 82 is prepared analogously to 1f from 0.15 g (0.45 mmol) of product from 53c, 0.092 g (0.45 mmol) of product from 19b, 0.13 ml (0.90 mmol) of triethylamine and 0.17 g (0.54 mmol) of TBTU in 5 ml DMF.

$C_{26}H_{38}N_4O_5S \times HCl$ (555.13)

[M+H]+=519

HPLC (Method 1): retention time=2.29 min

Example 83

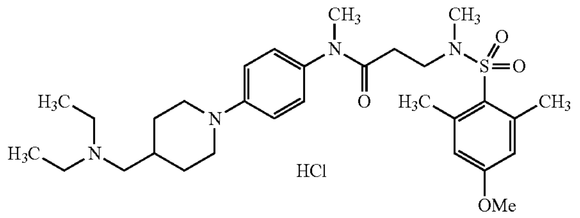

83a)

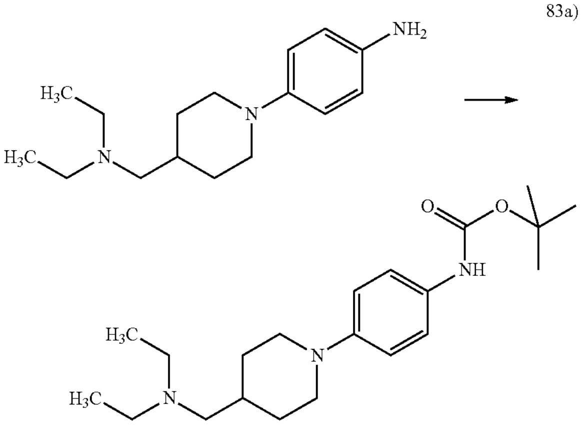

83a is prepared analogously to 51a from 1.35 g (5.16 mmol) of product from 41b, 1.24 g (5.68 mmol) of Boc-anhydride and 0.80 ml (5.68 mmol) of triethylamine in 50 ml dichloromethane.

$C_{21}H_{35}N_3O_2$ (361.52)

[M+H]+=362

TLC: silica gel, dichloromethane/methanol/ammonia 9:1:0.1, Rf value=0.42

83b)

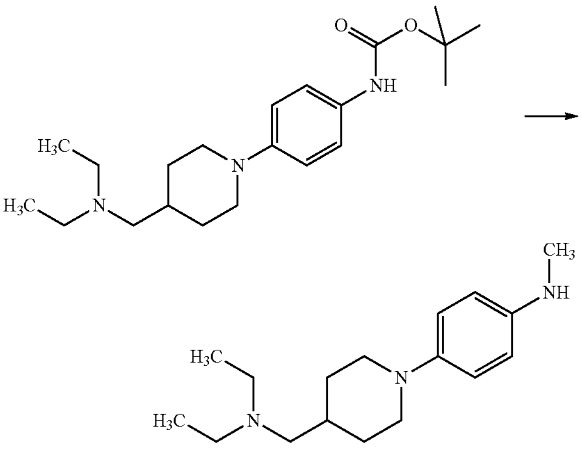

83b is prepared analogously to 51b from 1.80 g (4.98 mmol) of product from 83a and 0.57 g (15.00 mmol) of lithium aluminium hydride (Aldrich) in 25 ml THF.

$C_{17}H_{29}N_3$ (275.43)

[M+H]+=276

HPLC (Method 1): retention time=1.77 min

83c)

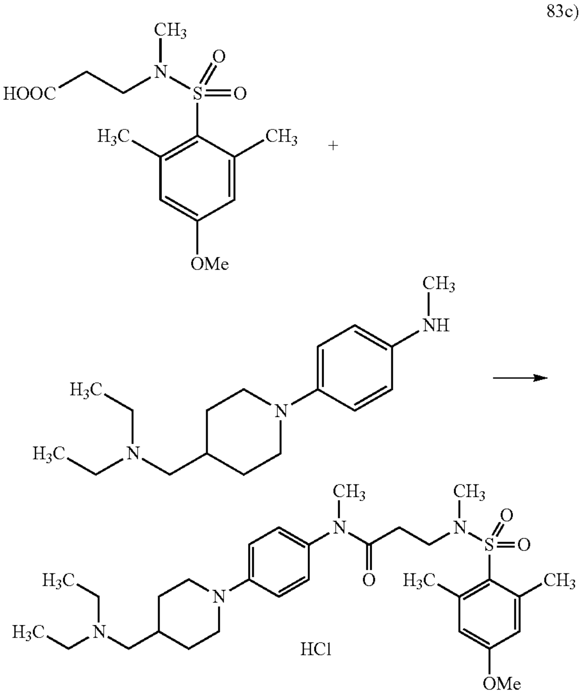

Example 83 is prepared analogously to 1f from 0.14 g (0.50 mmol) of product from 22c, 0.15 g (0.50 mmol) of product from 83b, 0.14 ml (1.00 mmol) of triethylamine and 0.18 g (0.55 mmol) of TBTU in 6 ml DMF.

$C_{30}H_{46}N_4O_4S \times HCl$ (595.24)

[M+H]+=559

HPLC (Method 1): retention time=2.46 min

Example 84

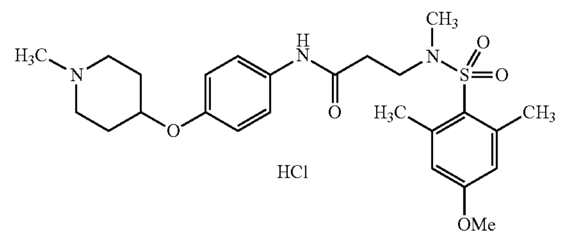

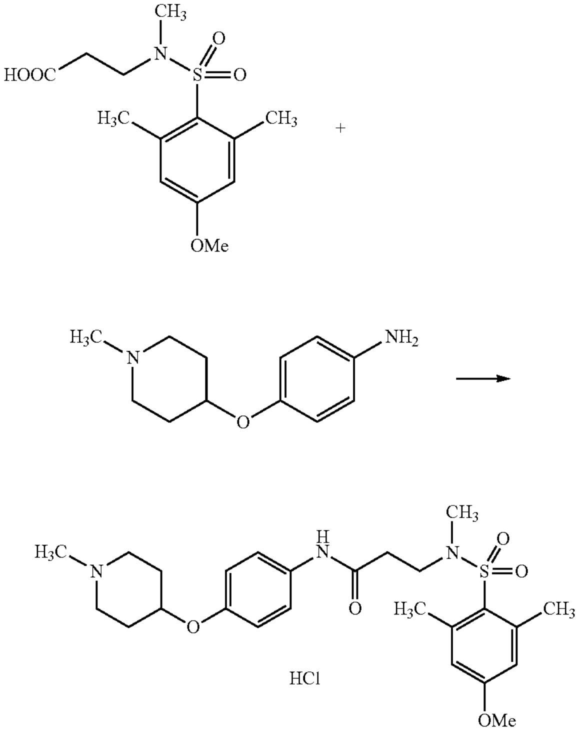

Example 84 is prepared analogously to 1f from 0.15 g (0.50 mmol) of product from 22c, 0.10 g (0.50 mmol) of 4-(1-methylpiperidin-4-yloxy)-phenylamine (ART-CHEM), 0.14 ml (1.00 mmol) of triethylamine and 0.18 g (0.55 mmol) of TBTU in 6 ml DMF.

$C_{25}H_{35}N_3O_5S \times HCl$ (526.09)

[M+H]+=490

HPLC (Method 1): retention time=2.40 min

Example 85

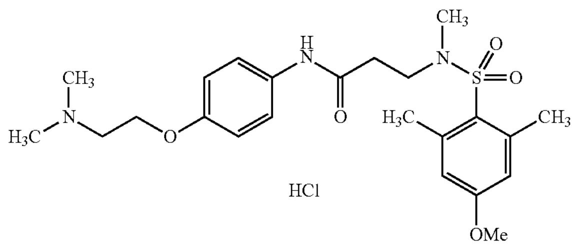

-continued

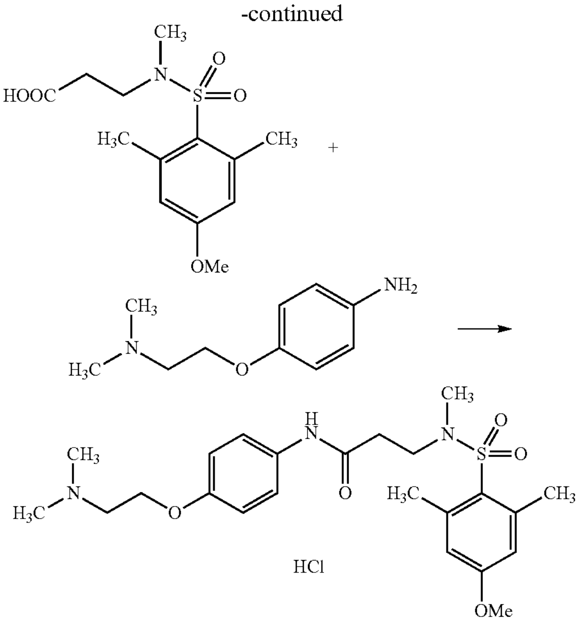

Example 85 is prepared analogously to 1f from 0.15 g (0.50 mmol) of product from 22c, 0.09 g (0.50 mmol) of 4-(2-dimethylamino-ethoxy)-phenylamine (Collect. Czech. Chem. Commun. 55, 1990, 282-295), 0.14 ml (1.00 mmol) of triethylamine and 0.18 g (0.55 mmol) of TBTU in 6 ml DMF.

$C_{23}H_{33}N_3O_5S \times HCl$ (500.05)

[M+H]+=464

HPLC (Method 1): retention time=2.35 min

Example 86

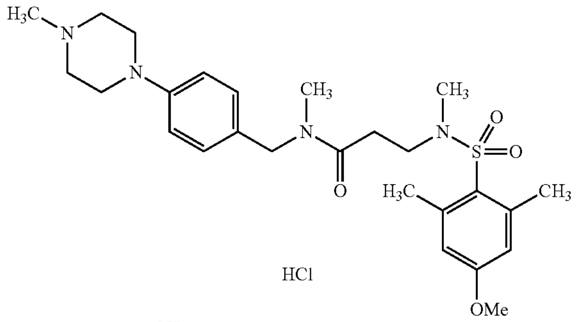

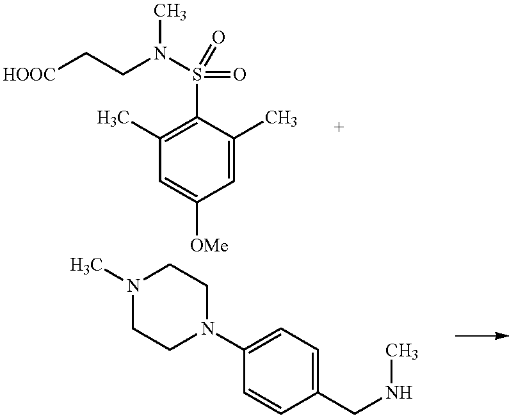

-continued

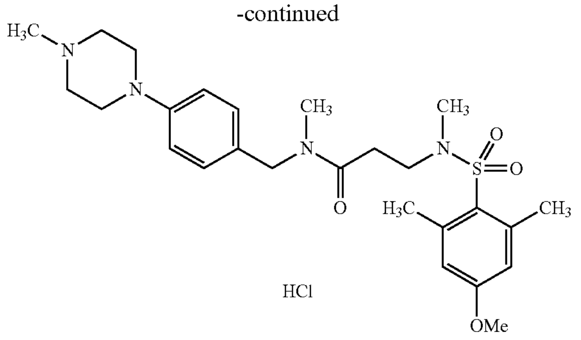

Example 86 is prepared analogously to 1f from 0.14 g (0.45 mmol) of product from 22c, 0.099 g (0.45 mmol) of product from 81a, 0.13 ml (0.90 mmol) of triethylamine and 0.17 g (0.54 mmol) of TBTU in 5 ml DMF.

$C_{26}H_{38}N_4O_5S \times HCl$ (539.13)

[M+H]+=503

HPLC (Method 1): retention time=2.43 min

Example 87

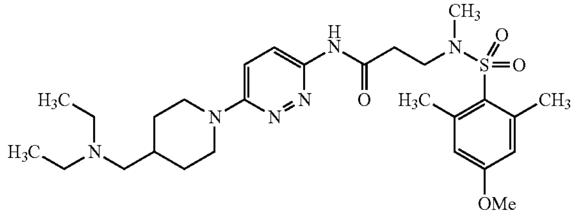

87a)

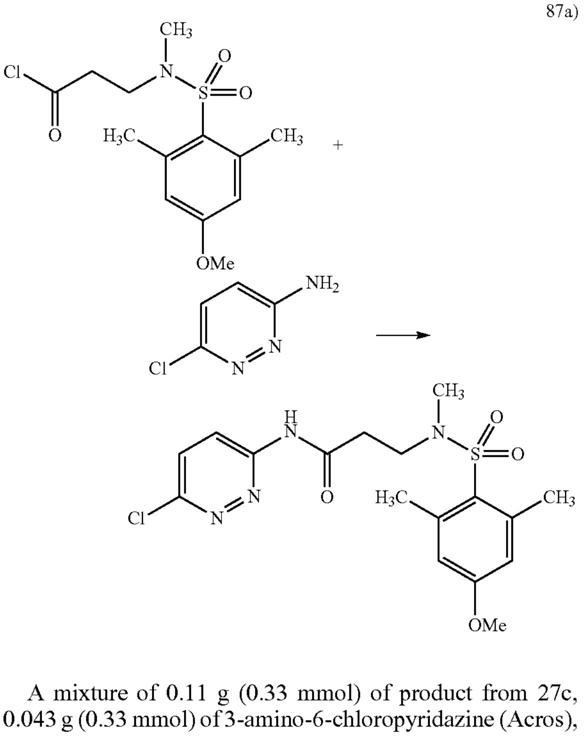

A mixture of 0.11 g (0.33 mmol) of product from 27c, 0.043 g (0.33 mmol) of 3-amino-6-chloropyridazine (Acros), 0.12 ml (0.66 mmol) of DIPEA and 10 ml dichloromethane is refluxed for three days with stirring. The precipitate is then filtered off. The filtrate is evaporated to dryness in vacuo and the crude product is purified by preparative HPLC.

$C_{17}H_{21}ClN_4O_4S$ (412.89)

[M+H]+=413/415

87b)

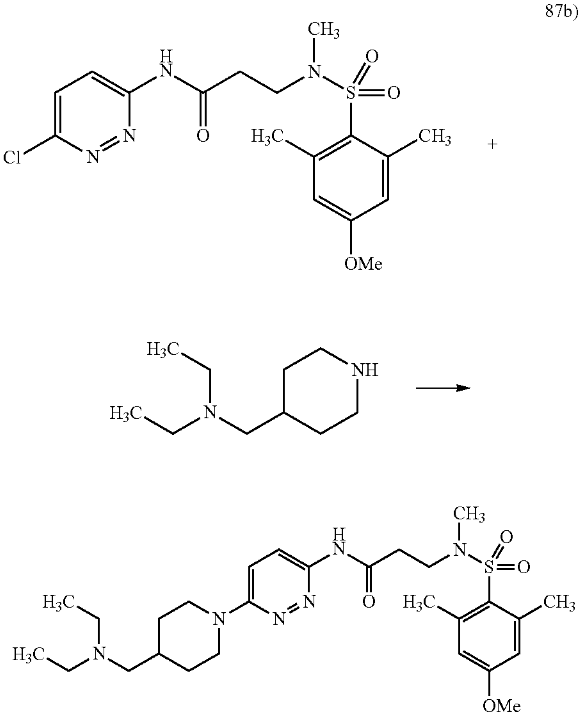

A mixture of 0.03 g (0.073 mmol) of product from 87a and 0.013 g (0.073 mmol) of diethyl-piperidin-4-ylmethyl-amine (Chem. Pharm. Bull. 42, 1994, 74-84) is melted at 173° C. The product is then recovered from the reaction mixture by preparative HPLC.

$C_{27}H_{42}N_6O_4S$ (546.73)

[M+H]+=547

HPLC (Method 6): retention time=2.12 min

Example 88

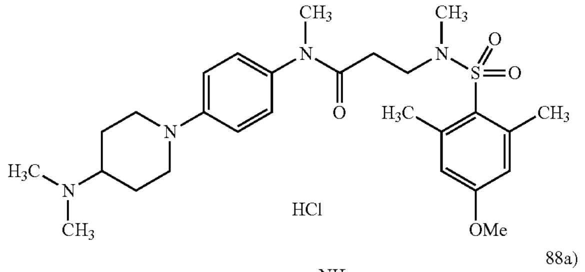

88a)

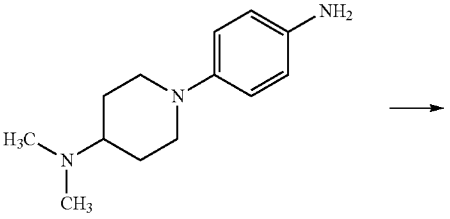

-continued

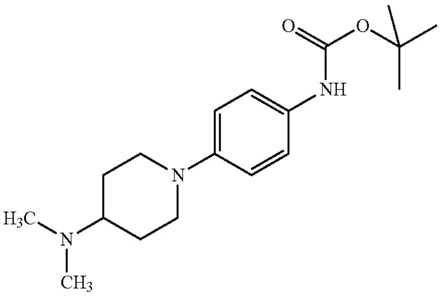

88a is prepared analogously to 51a from 0.70 g (3.18 mmol) of product from 27b, 0.80 g (3.65 mmol) of Boc-anhydride and 5.50 ml (11.00 mmol) of 2 M sodium hydroxide solution in 40 ml dioxane and 20 ml of water.

$C_{17}H_{28}N_4O_2$ (320.43)

[M+H]+=321

TLC: silica gel, dichloromethane/methanol/ammonia 4:1:0.2, Rf value=0.83

88b)

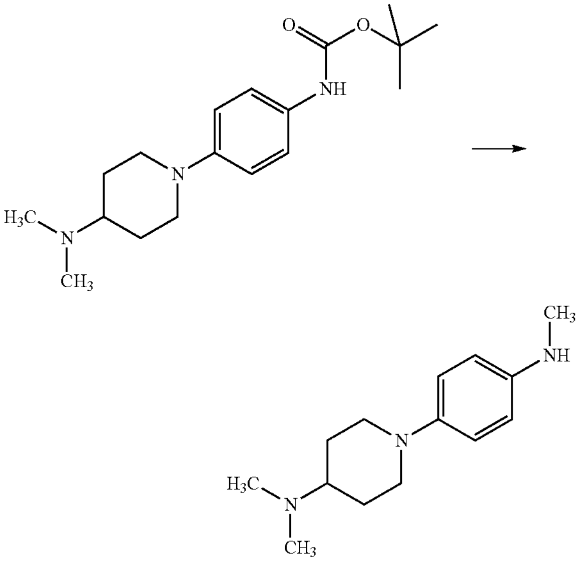

88b is prepared analogously to 51b from 0.60 g (1.87 mmol) of product from 88a and 0.21 g (5.60 mmol) of lithium aluminium hydride (Aldrich) in 20 ml THF.

$C_{13}H_{22}N_4$ (234.34)

[M+H]+=235

TLC: silica gel, dichloromethane/methanol/ammonia 4:1:0.2, Rf value=0.62

88c)

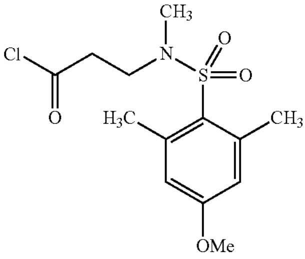

+

-continued

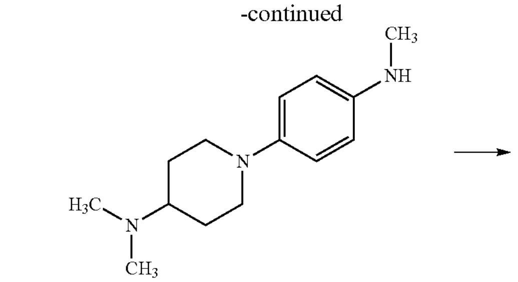

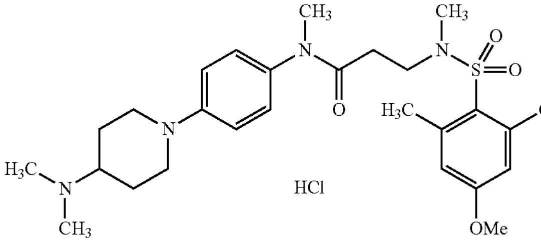

HCl

Example 88 is prepared analogously to 27d from 0.16 g (0.50 mmol) of product from 27c, 0.12 g (0.50 mmol) of product from 88b and 0.17 ml (1.00 mmol) of DIPEA in 5 ml THF.

$C_{26}H_{39}N_5O_4S \times HCl$ (554.15)

[M+H]+=518

TLC: silica gel, dichloromethane/methanol/ammonia 9:1:0.1, Rf value=0.61

Example 89

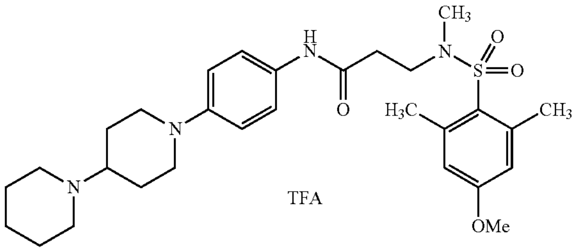

TFA

89a)

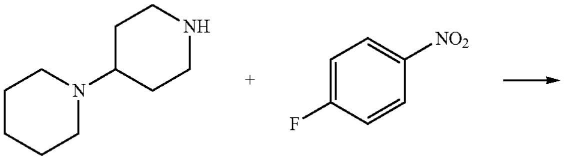

+

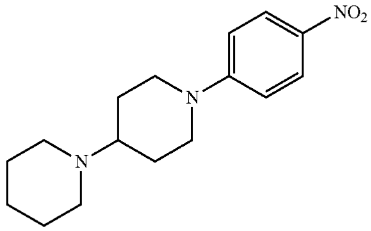

89a is prepared analogously to 8a from 0.70 g (4.18 mmol) of 4-piperidinopiperidine (Aldrich), 0.44 ml (4.18 mmol) of 1-fluoro-4-nitrobenzene (Acros) and 1.33 ml (9.61 mmol) of triethylamine in 12 ml DMF.

$C_{16}H_{23}N_3O_2$ (289.37)

[M+H]+=290

TLC: silica gel, dichloromethane/methanol/ammonia 9:1: 0.1, Rf value=0.3

89b)

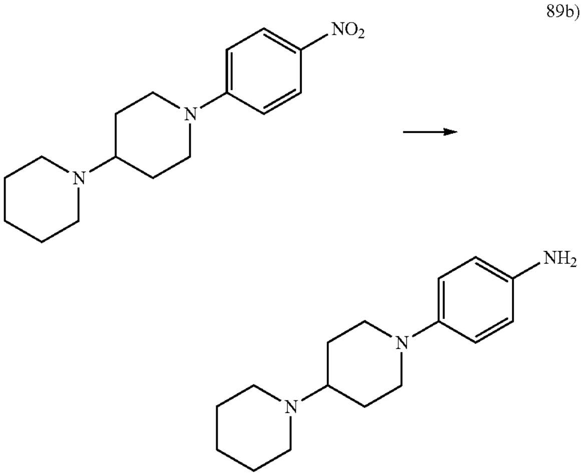

89b is prepared analogously to 8b from 0.96 g (3.32 mmol) of product from 89a and 0.093 g palladium on charcoal (5%) in 45 ml of ethanol.

$C_{16}H_{25}N_3$ (259.39)

[M+H]+=260

TLC: silica gel, dichloromethane/methanol/ammonia 9:1: 0.1, Rf value=0.2

89c)

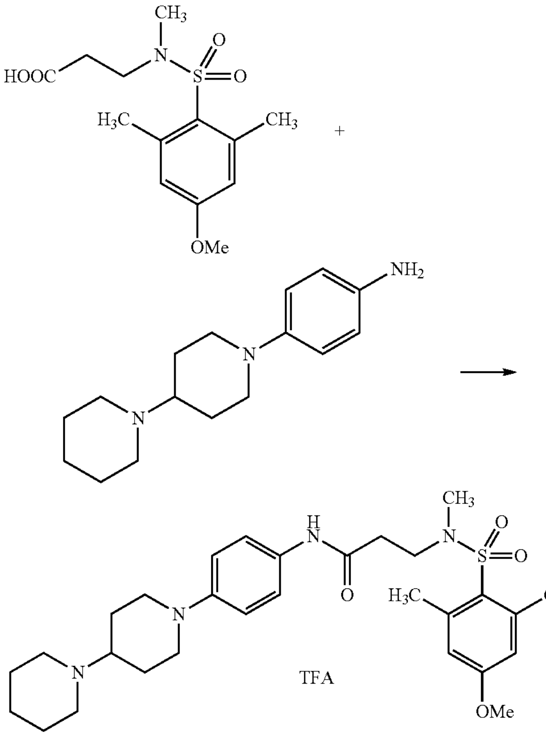

Example 89 is prepared analogously to 1f from 0.10 g (0.33 mmol) of product from 22c, 0.086 g (0.33 mmol) of product from 89b, 0.14 ml (1.00 mmol) of triethylamine and 0.11 g (0.33 mmol) of TBTU in 2 ml THF.

$C_{29}H_{42}N_4O_4S \times C_2HF_3O_2$ (656.76)

[M+H]+=543

HPLC (Method 5): retention time=1.47 min

Example 90

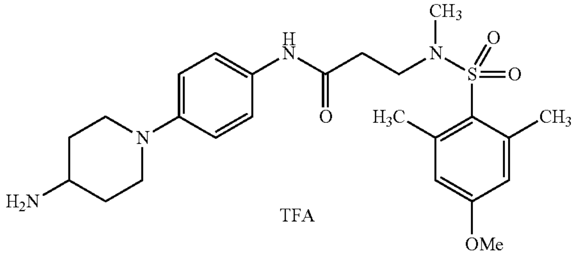

90a)

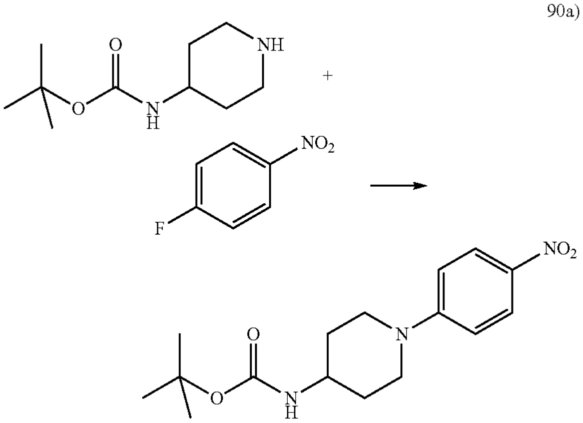

90a is prepared analogously to 8a from 0.84 g (4.18 mmol) of 4-N-Boc-aminopiperidine (Acros), 0.44 ml (4.18 mmol) of 1-fluoro-4-nitrobenzene (Acros) and 1.33 ml (9.61 mmol) of triethylamine in 12 ml DMF.

$C_{16}H_{23}N_3O_4$ (321.37)

[M+H]+=322

90b)

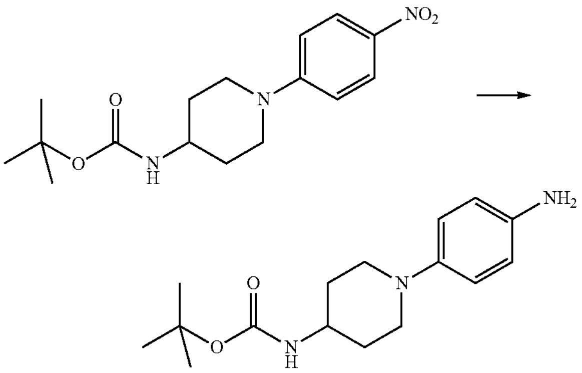

90b is prepared analogously to 8b from 1.01 g (3.43 mmol) of product from 90a and 0.11 g palladium on charcoal (5%) in 45 ml of ethanol.

$C_{16}H_{25}N_3O_2$ (291.39)

[M+H]+=292

90c)
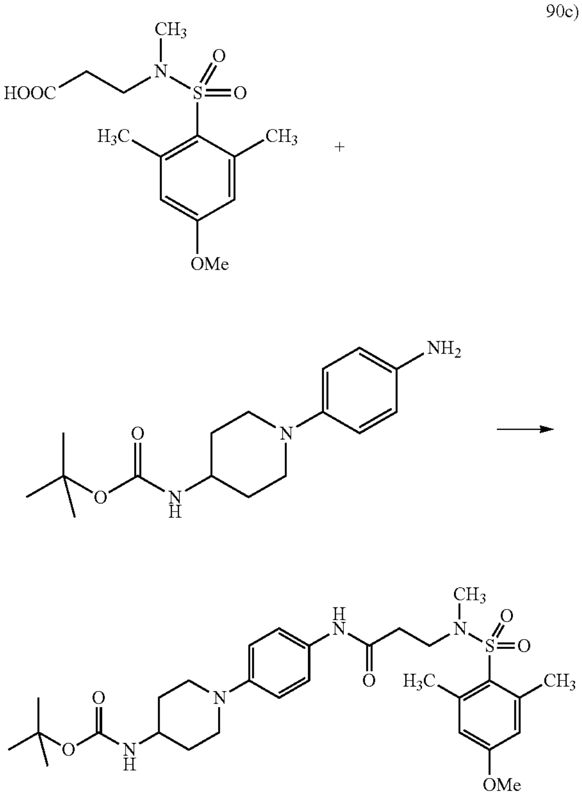
90c is prepared analogously to 1f from 0.10 g (0.33 mmol) of product from 22c, 0.097 g (0.33 mmol) of product from 90b, 0.14 ml (1.00 mmol) of triethylamine and 0.11 g (0.33 mmol) of TBTU in 2 ml THF.
$C_{29}H_{42}N_4O_6S$ (574.73)
[M+H]+=575
HPLC (Method 5): retention time=1.62 min
Example 90 is prepared analogously to 18b from 0.19 g (0.33 mmol) of product from 90c and 0.33 ml TFA in 0.5 ml dichloromethane.
$C_{24}H_{34}N_4O_4S \times C_2HF_3O_2$ (588.64)
[M+H]+=475
HPLC (Method 5): retention time=1.41 min
Example 91
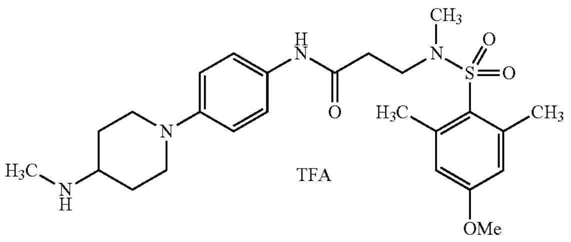
91a)
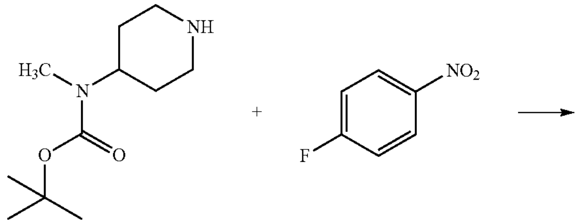
90d)
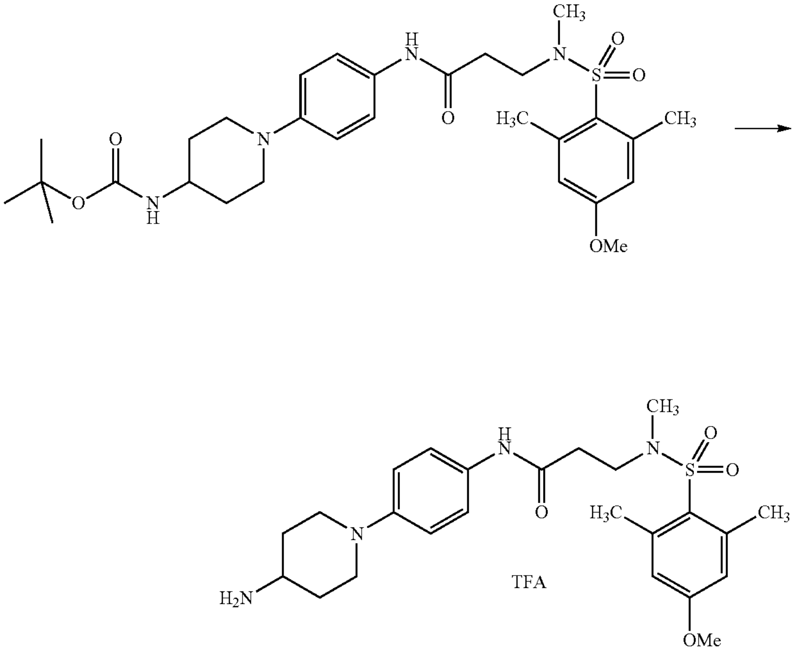

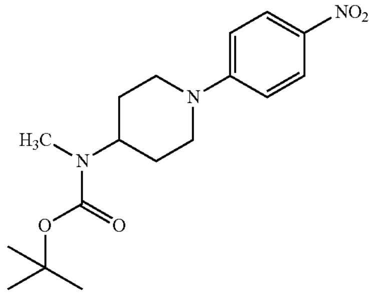

91a is prepared analogously to 8a from 0.90 g (4.18 mmol) of tert-butyl methyl-piperidin-4-yl-carbamate (Fluorochem), 0.44 ml (4.18 mmol) of 1-fluoro-4-nitrobenzene (Acros) and 1.33 ml (9.61 mmol) of triethylamine in 12 ml DMF.

$C_{17}H_{25}N_3O_4$ (335.40)

[M+H]+=336

TLC: silica gel, dichloromethane/methanol 30:1, Rf value=0.6

91b)

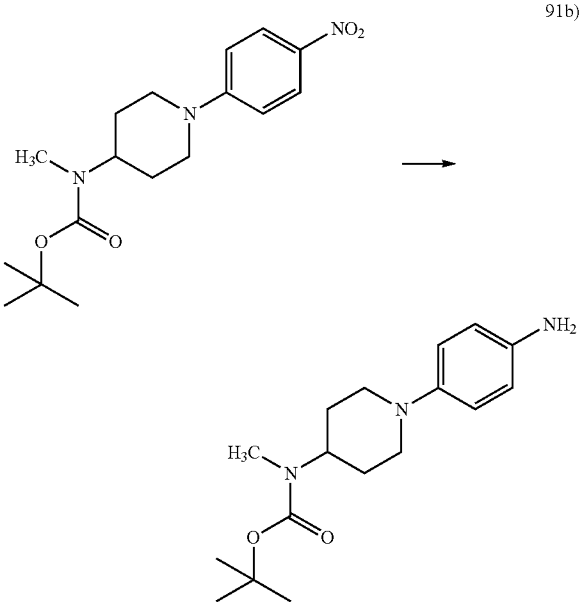

91b is prepared analogously to 8b from 1.08 g (3.22 mmol) of product from 91a and 0.11 g palladium on charcoal (5%) in 45 ml of ethanol.

$C_{17}H_{27}N_3O_2$ (305.42)

[M+H]+=306

TLC: silica gel, dichloromethane/methanol 30:1, Rf value=0.4

91c)

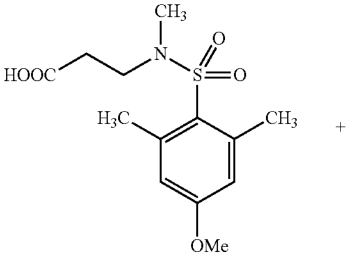

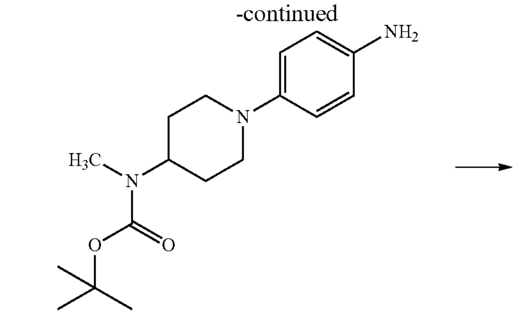

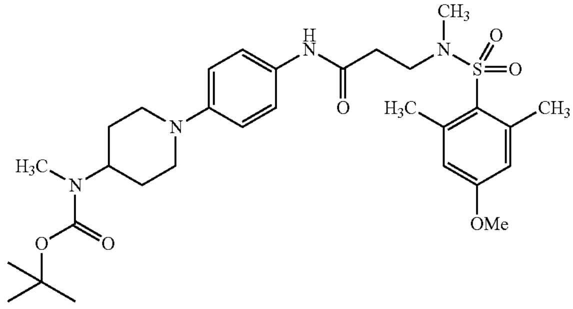

91c is prepared analogously to 1f from 0.10 g (0.33 mmol) of product from 22c, 0.10 g (0.33 mmol) of product from 91b, 0.14 ml (1.00 mmol) of triethylamine and 0.11 g (0.33 mmol) of TBTU in 2 ml THF.

$C_{30}H_{44}N_4O_6S$ (588.76)

[M+H]+=589

HPLC (Method 5): retention time=1.69 min

91d)

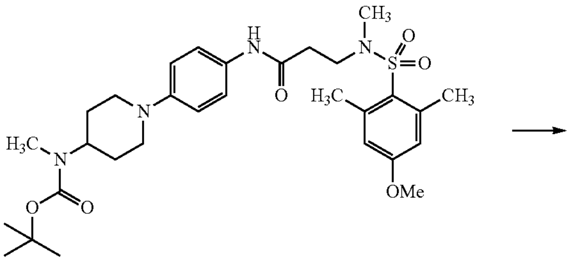

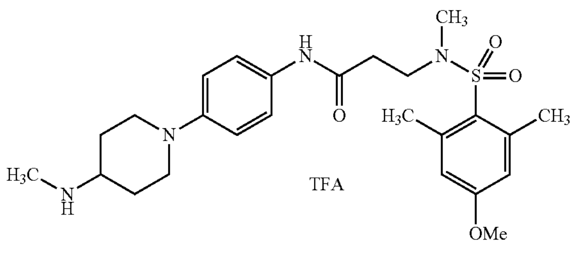

Example 91 is prepared analogously to 18b from 0.21 g (0.36 mmol) of product from 91c and 0.36 ml TFA in 0.6 ml dichloromethane.

$C_{25}H_{36}N_4O_4S \times C_2HF_3O_2$ (602.67)

[M+H]+=489

HPLC (Method 5): retention time=1.42 min

Example 92

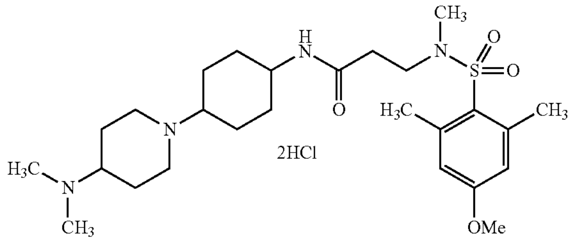

92a)

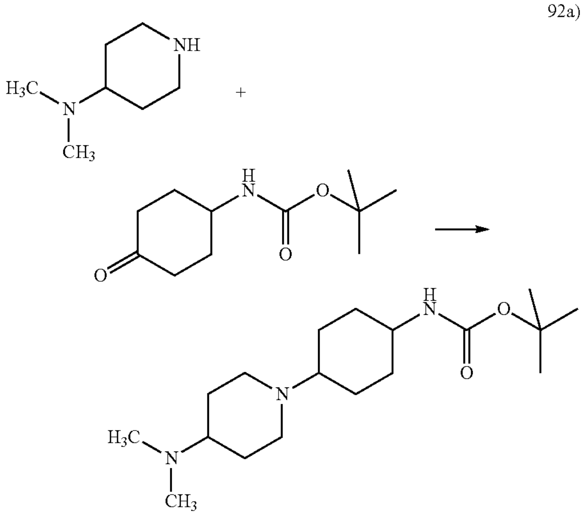

A mixture of 0.66 g (5.16 mmol) of 4-dimethylamino-piperidine (Alfa Aesar), 1.00 g (4.69 mmol) of tert-butyl (4-oxocyclohexyl)-carbamate (Fluorochem), 1.19 g (5.16 mmol) of sodium triacetoxyborohydride and 20 ml dichloromethane is stirred under nitrogen for four hours at ambient temperature. The reaction mixture is then diluted with dichloromethane, washed with saturated sodium hydrogen carbonate solution, dried on sodium sulphate and evaporated to dryness in vacuo.

$C_{18}H_{35}N_3O_2$ (325.49)

92b)

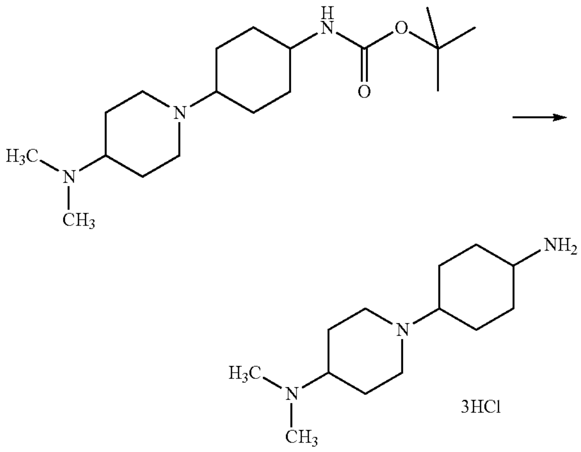

A mixture of 0.80 g (2.46 mmol) of product from 92a, 4 ml 6 M HCl, 3 ml 37% HCl and 3 ml of methanol is stirred for two hours at 50° C. The reaction mixture is then evaporated to dryness in vacuo.

$C_{13}H_{27}N_3$×3HCl (334.76)

92c)

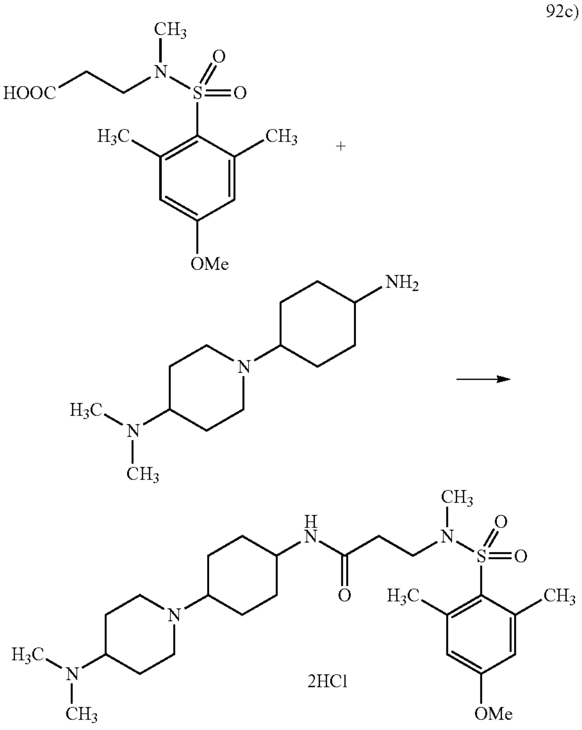

Example 92 is prepared analogously to 1f from 0.10 g (0.33 mmol) of product from 22c, 0.13 g (0.40 mmol) of product from 92b, 0.23 ml (1.66 mmol) of triethylamine and 0.13 g (0.40 mmol) of TBTU in 8 ml DMF.

$C_{26}H_{44}N_4O_4S$×2HCl (581.64)

[M+H]+=509

HPLC (Method 5): retention time=1.36 min

Example 93

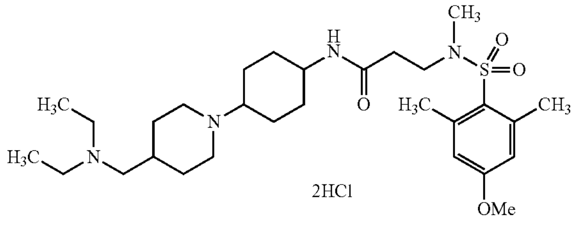

93a)

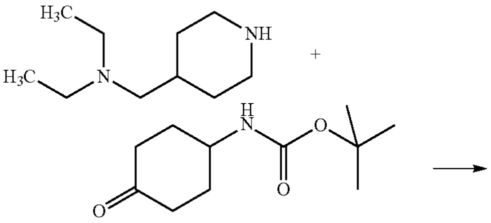

-continued

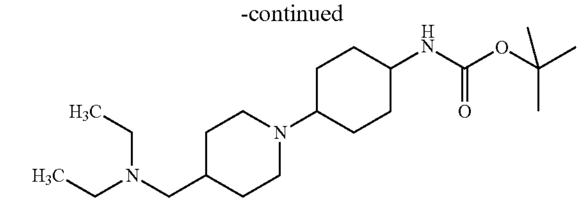

93a is carried out analogously to 92a from 0.63 g (3.70 mmol) of diethyl-piperidin-4-ylmethyl-amine (Chem. Pharm. Bull. 42, 1994, 74-84), 0.72 g (3.37 mmol) of tert-butyl (4-oxocyclohexyl)-carbamate (Fluorochem) and 0.86 g (4.04 mmol) of sodium triacetoxyborohydride in 20 ml dichloromethane.

$O_{21}H_{41}N_3O_2$ (367.57)

93b)

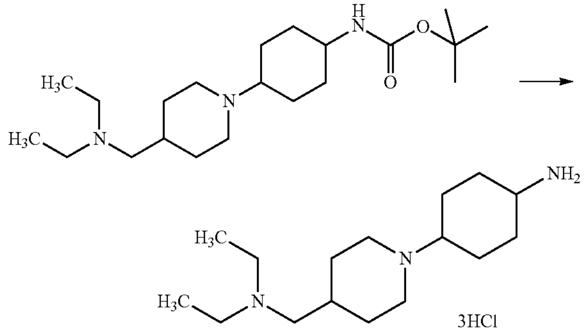

93b is prepared analogously to 92b from 0.90 g (2.45 mmol) of product from 93a, 4 ml 6 M HCl and 3 ml 37% HCl in 3 ml of methanol.

$C_{16}H_{33}N_3 \times 3HCl$ (376.84)

93c)

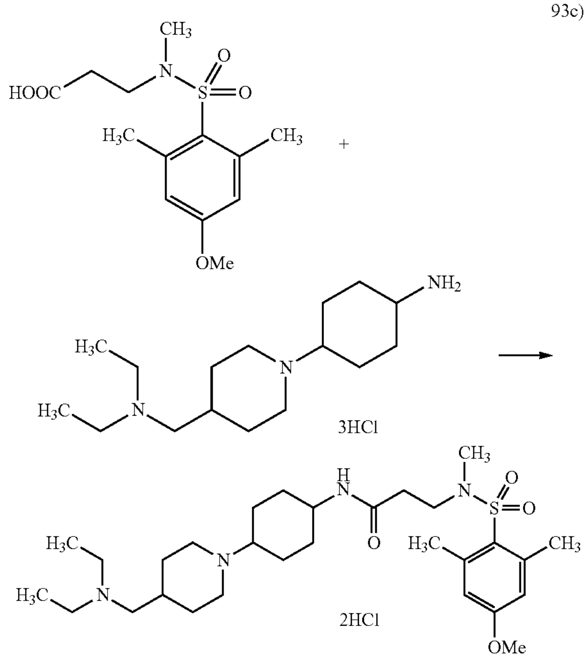

Example 93 is prepared analogously to 1f from 0.10 g (0.33 mmol) of product from 22c, 0.14 g (0.37 mmol) of product from 93b, 0.23 ml (1.66 mmol) of triethylamine and 0.13 g (0.40 mmol) of TBTU in 8 ml DMF.

$C_{29}H_{50}N_4O_4S \times 2HCl$ (623.72)

[M+H]+=551

HPLC (Method 5): retention time=1.39 min

Example 94

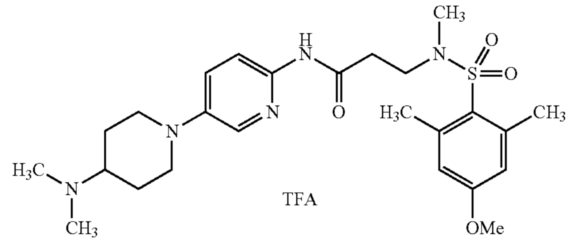

94a)

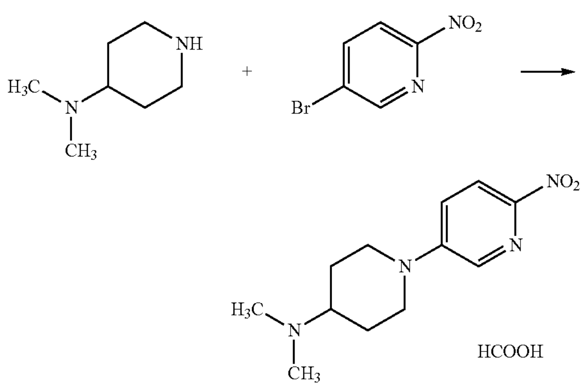

A mixture of 0.88 g (6.88 mmol) of 4-dimethylamino-piperidine (Alfa Aesar), 1.00 g (4.93 mmol) of 3-bromo-6-nitropyridine (Aldrich), 0.18 g (0.49 mmol) of tetrabutyl-ammonium iodide, 0.74 g (5.33 mmol) of potassium carbonate and 5 ml DMSO is stirred for two hours at 80° C. Then the reaction mixture is poured onto water and extracted with dichloromethane. The organic extracts are washed with saturated sodium hydrogen carbonate solution and saturated sodium chloride solution, dried on sodium sulphate and evaporated to dryness in vacuo. The crude product thus obtained is purified by preparative HPLC.

$C_{12}H_{18}N_4O_2 \times CH_2O_2$ (296.32)

HPLC (Method 1): retention time=1.49 min

94b)

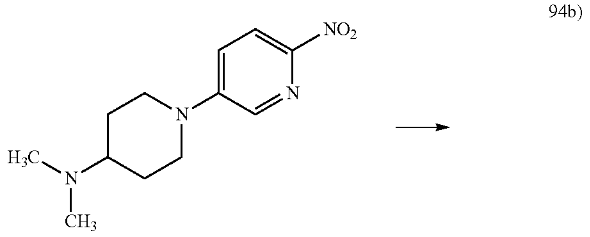

-continued

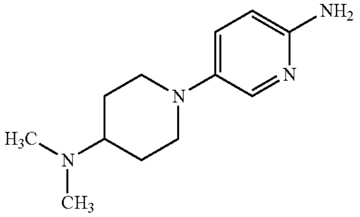

94b is prepared analogously to 8b from 0.50 g (2.00 mmol) of product from 94a and 0.08 g palladium on charcoal (10%) in 40 ml of methanol.

$C_{12}H_{20}N_4$ (220.31)

94c)

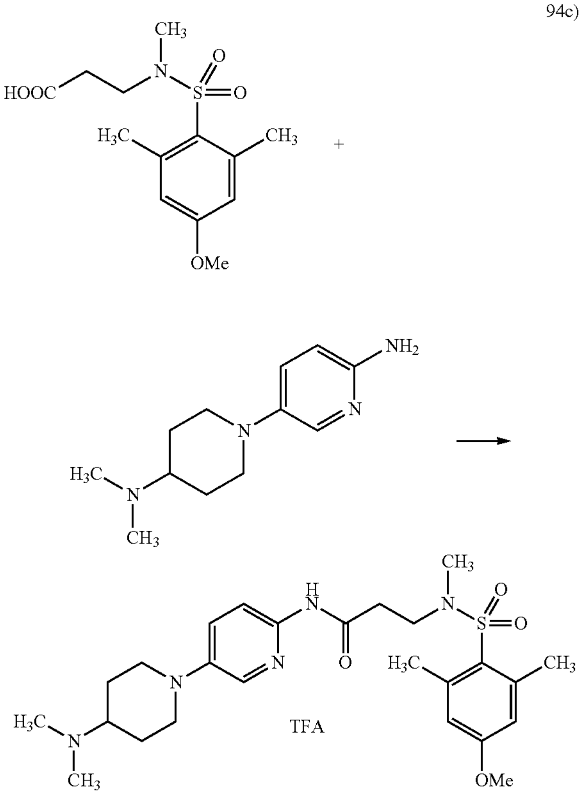

A mixture of 0.63 g (2.10 mmol) of product from 22c, 0.91 g (9.00 mmol) of N-methylmorpholine, 0.45 g (2.04 mmol) of product from 94b and 50 ml THF is stirred for 10 minutes at ambient temperature and then combined with 5.22 ml (9.00 mmol) of propylphosphonic anhydride 50% in ethyl acetate (Fluka). The reaction mixture is stirred overnight at ambient temperature and then evaporated to dryness in vacuo. The residue is combined with 2 N potassium carbonate solution and extracted with dichloromethane. The organic extracts are washed with water and saturated sodium chloride solution, dried on sodium sulphate and evaporated to dryness in vacuo. The crude product thus obtained is purified by preparative HPLC.

$C_{25}H_{37}N_5O_4S \times C_2HF_3O_2$ (617.68)

[M+H]+=504

HPLC (Method 5): retention time=1.38 min

Example 95

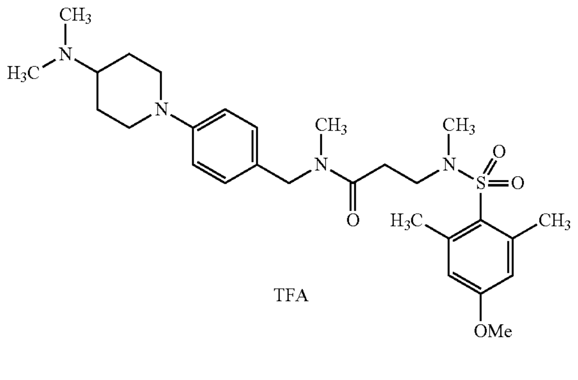

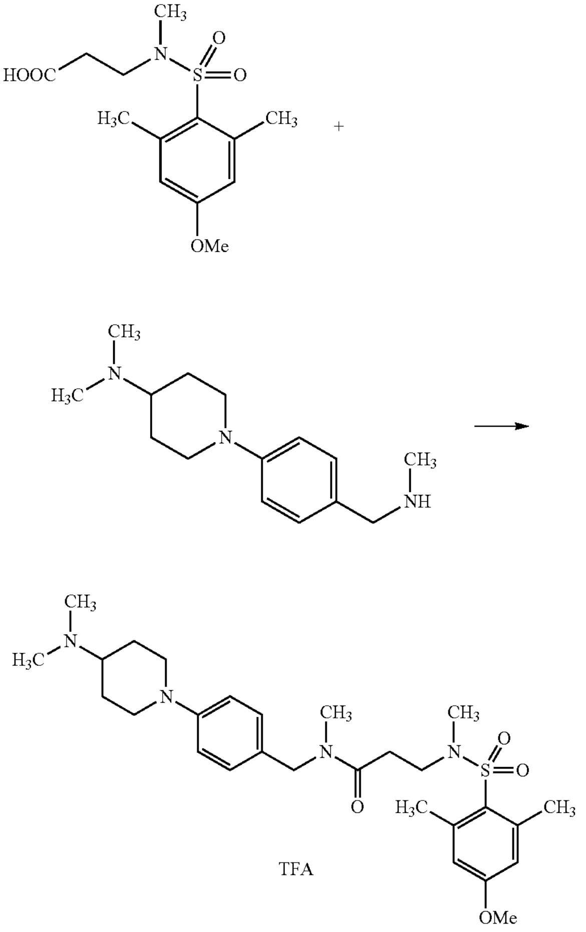

Example 95 is prepared analogously to 1f from 0.08 g (0.27 mmol) of product from 22c, 0.066 g (0.27 mmol) of product from 80a, 0.11 ml (0.80 mmol) of triethylamine and 0.085 g (0.27 mmol) of TBTU in 2 ml THF.

$C_{28}H_{42}N_4O_4S \times C_2HF_3O_2$ (644.75)

[M+H]+=531

HPLC (Method 5): retention time=1.50 min

Example 96

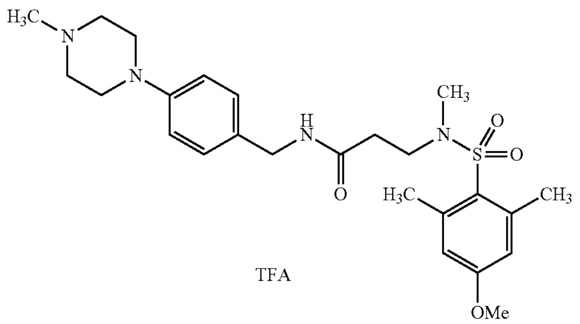

TFA

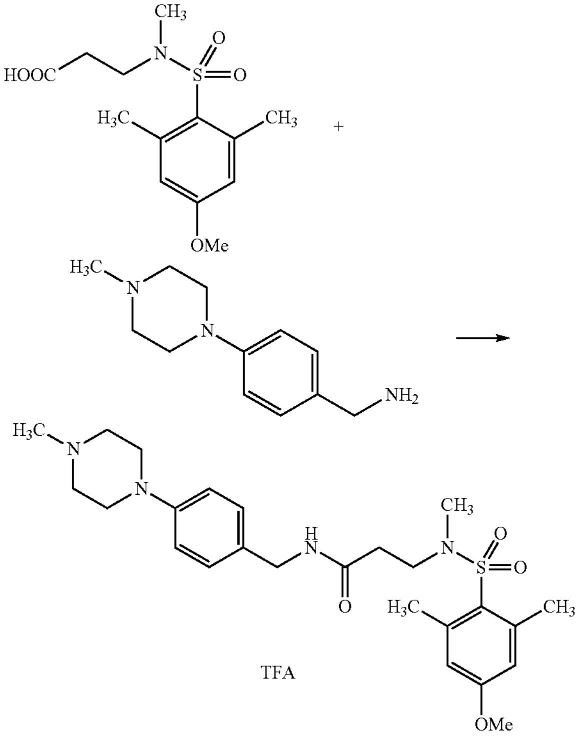

TFA

Example 96 is prepared analogously to 1f from 0.08 g (0.27 mmol) of product from 22c, 0.054 g (0.27 mmol) of product from 19b, 0.11 ml (0.80 mmol) of triethylamine and 0.085 g (0.27 mmol) of TBTU in 2 ml THF.

$C_{25}H_{36}N_4O_4S \times C_2HF_3O_2$ (602.67)

[M+H]+=489

HPLC (Method 5): retention time=1.49 min

Example 97

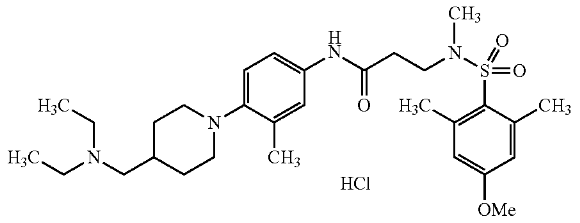

HCl

97a)

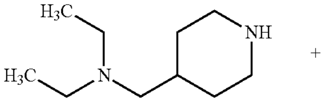

-continued

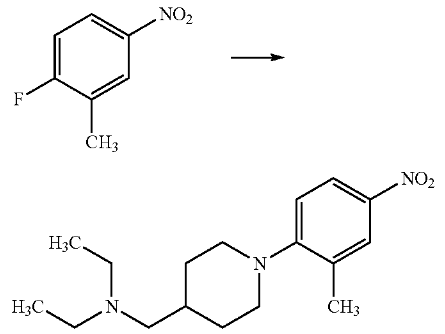

97a is prepared analogously to 8a from 1.00 g (5.87 mmol) of diethyl-piperidin-4-ylmethyl-amine (Chem. Pharm. Bull. 42, 1994, 74-84), 0.91 g (5.87 mmol) of 1-fluoro-2-methyl-4-nitrobenzene (ABCR) and 1.14 ml (8.20 mmol) of triethylamine in 12 ml DMF.

$C_{17}H_{27}N_3O_2$ (305.42)

[M+H]+=306

97b)

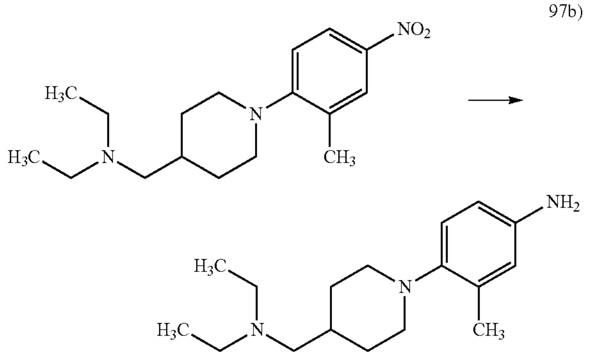

97b is prepared analogously to 8b from 0.91 g (2.98 mmol) of product from 97a and 0.20 g palladium on charcoal (10%) in 50 ml of methanol.

$C_{17}H_{29}N_3$ (275.43)

97c)

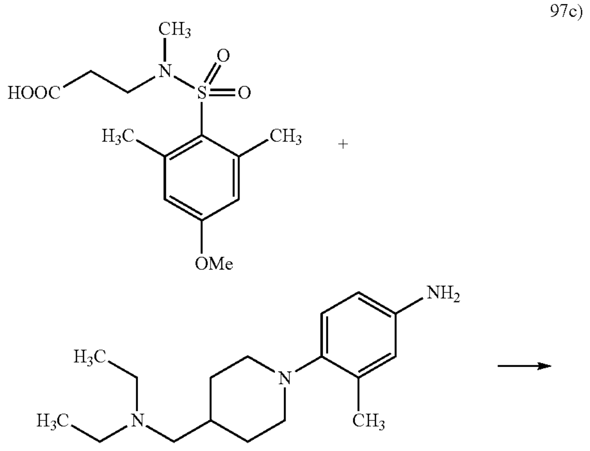

-continued

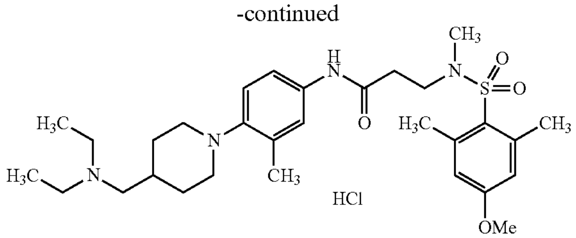

Example 97 is prepared analogously to 1f from 0.15 g (0.50 mmol) of product from 22c, 0.14 g (0.50 mmol) of product from 97b, 0.21 ml (1.50 mmol) of triethylamine and 0.16 g (0.50 mmol) of TBTU in 7 ml THF and 1 ml DMF.

$C_{30}H_{46}N_4O_4S \times HCl$ (595.24)

[M+H]+=559

HPLC (Method 5): retention time=1.44 min

Example 98

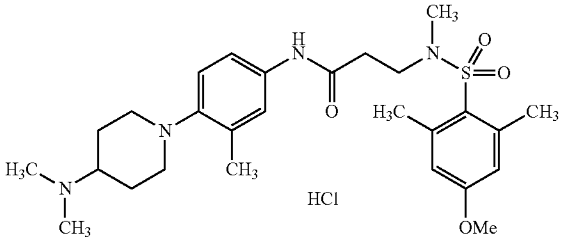

98a)

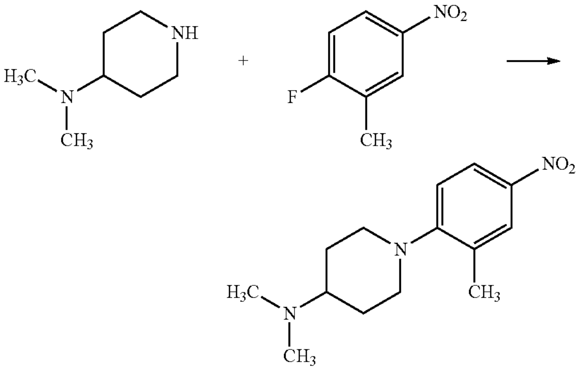

98a is prepared analogously to 8a from 0.75 g (5.87 mmol) of 4-dimethylamino-piperidine (Alfar Aesar), 0.91 g (5.87 mmol) of 1-fluoro-2-methyl-4-nitrobenzene (ABCR) and 1.14 ml (8.20 mmol) of triethylamine in 12 ml DMF.

$C_{14}H_{21}N_3O_2$ (263.34)

98b)

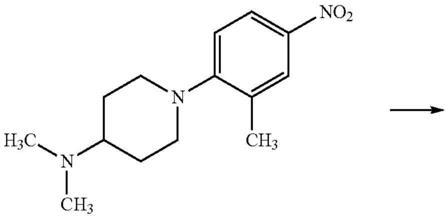

-continued

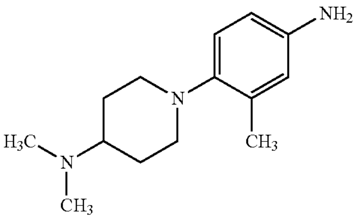

98b is prepared analogously to 8b from 0.30 g (1.14 mmol) of product from 98a and 0.10 g palladium on charcoal (10%) in 25 ml of methanol.

$C_{14}H_{23}N_3$ (233.35)

98c)

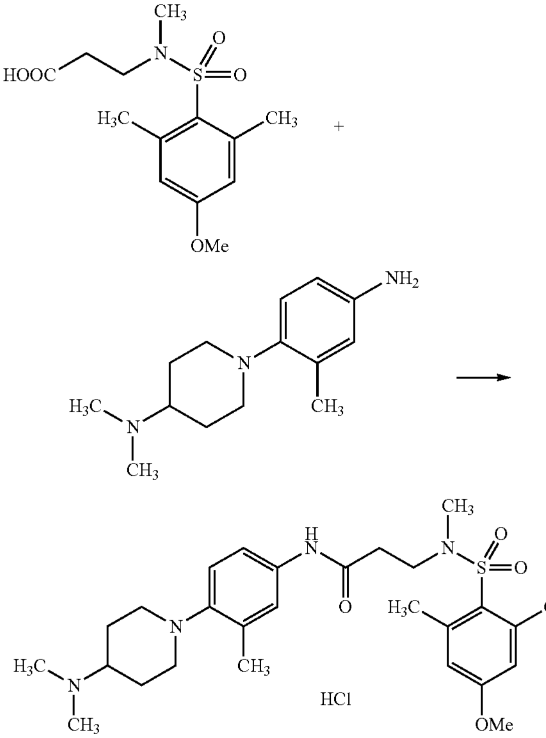

Example 98 is prepared analogously to 1f from 0.32 g (1.07 mmol) of product from 22c, 0.25 g (1.07 mmol) of product from 98b, 0.42 ml (3.00 mmol) of triethylamine and 0.34 g (1.07 mmol) of TBTU in 7 ml THF and 1 ml DMF.

$C_{27}H_{40}N_4O_4S \times HCl$ (553.16)

[M+H]+=517

HPLC (Method 5): retention time=1.52 min

Example 99

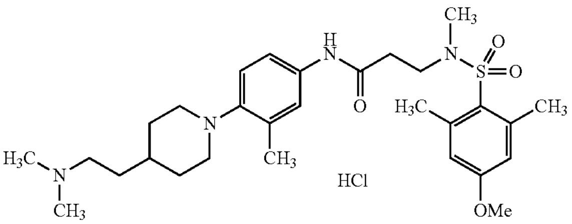

-continued

99a)

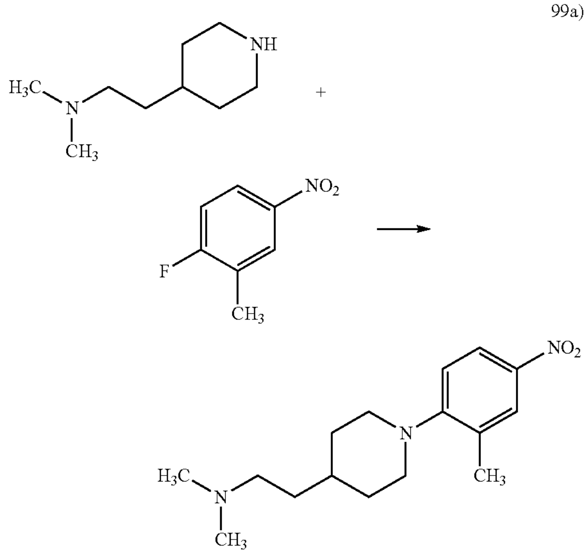

99a is prepared analogously to 8a from 0.92 g (5.87 mmol) of dimethyl-(2-piperidin-4-yl-ethyl)-amine (J. Med. Chem. 36, 1993, 162-165), 0.91 g (5.87 mmol) of 1-fluoro-2-methyl-4-nitrobenzene (ABCR) and 2.49 g (18.00 mmol) of potassium carbonate in 12 ml DMF.

$C_{16}H_{25}N_3O_2$ (291.39)

[M+H]+=292

99b)

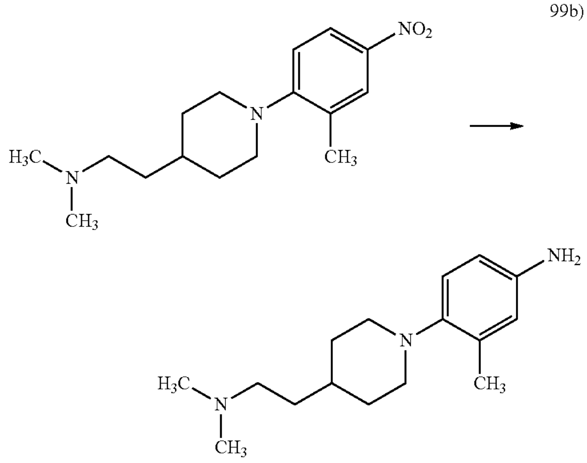

99b is prepared analogously to 8b from 0.60 g (1.14 mmol) of product from 99a and 0.20 g palladium on charcoal (10%) in 50 ml of methanol.

$C_{16}H_{27}N_3$ (261.41)

99c)

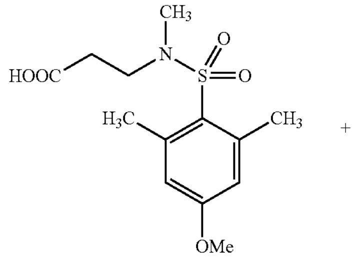

-continued

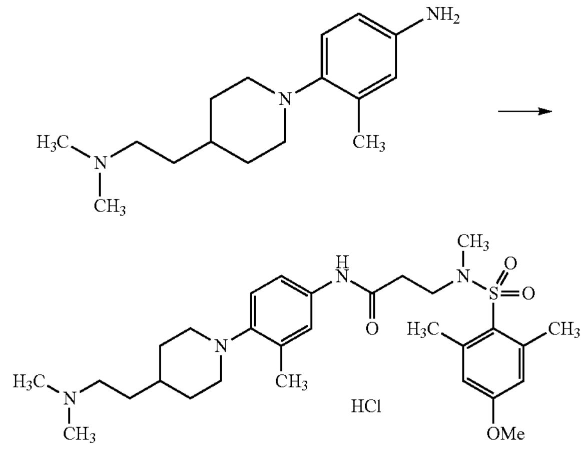

Example 99 is prepared analogously to 1f from 0.15 g (0.50 mmol) of product from 22c, 0.13 g (0.50 mmol) of product from 99b, 0.21 ml (1.50 mmol) of triethylamine and 0.16 g (0.50 mmol) of TBTU in 7 ml THF and 1 ml DMF.

$C_{29}H_{44}N_4O_4S \times HCl$ (581.21)

[M+H]+=545

HPLC (Method 5): retention time=1.42 min

Example 100

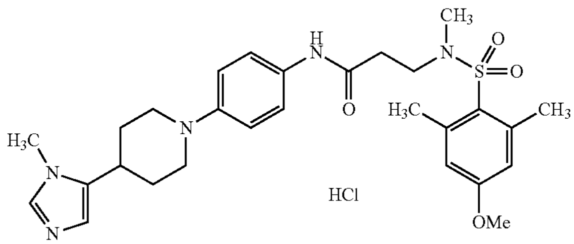

100a)

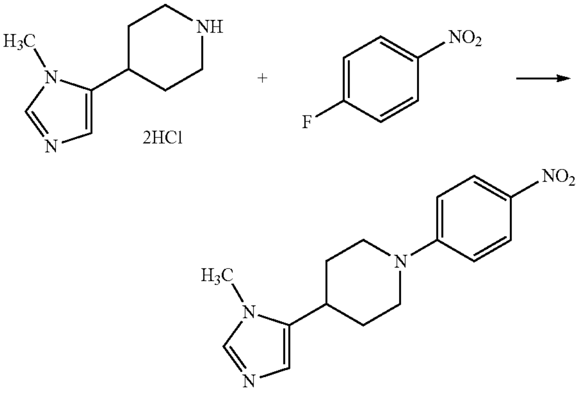

100a is prepared analogously to 8a from 1.00 g (4.47 mmol) of 4-(3-methyl-3H-imidazol-4-yl)-piperidine (J. Med. Chem. 46, 2003, 5445-5457), 0.63 g (4.47 mmol) of 4-fluoronitrobenzene (ABCR) and 2.10 g (15.20 mmol) of potassium carbonate in 50 ml DMF.

$C_{14}H_{16}N_4O_2$ (272.30)

[M+H]+=273

100b)

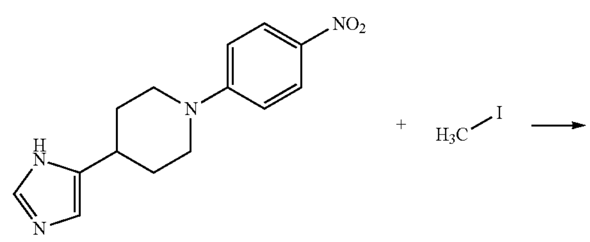

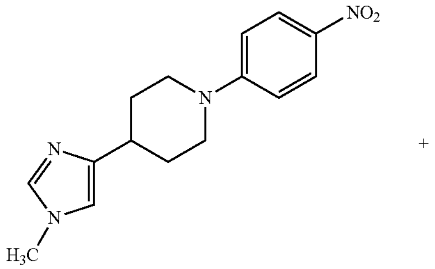

100b-1

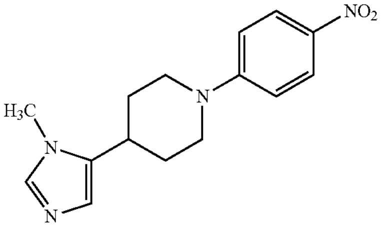

100b-2

100b-1 and 100b-2 are prepared analogously to 62a from 1.10 g (4.04 mmol) of product from 100a, 0.60 g (4.23 mmol) of methyl iodide and 0.46 g (4.10 mmol) of potassium-tert-butoxide in 50 ml DMSO. The resulting mixture of isomers is separated by column chromatography through silica gel (eluant: dichloromethane/methanol 100:1 to 30:1).

100b-1: $C_{15}H_{18}N_4O_2$ (286.33)

[M+H]+=287

TLC: silica gel, dichloromethane/methanol 9:1, Rf value=0.50

100b-2: $C_{15}H_{18}N_4O_2$ (286.33)

[M+H]+=287

TLC: silica gel, dichloromethane/methanol 9:1, Rf value=0.38

100c)

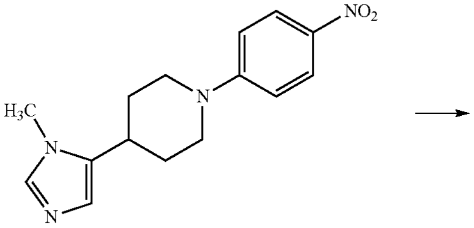

-continued

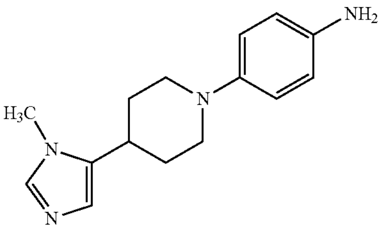

100c is prepared analogously to 8b from 0.10 g (0.35 mmol) of 100b-2 and 0.20 g palladium on charcoal (10%) in 30 ml of methanol.

$C_{15}H_{20}N_4$ (256.35)

TLC: silica gel, dichloromethane/methanol 9:1, Rf value=0.10

100d)

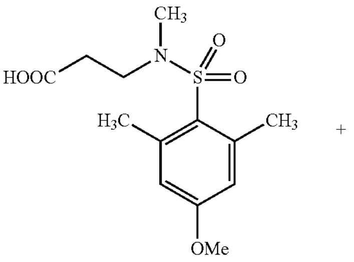

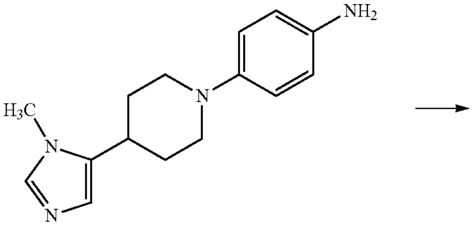

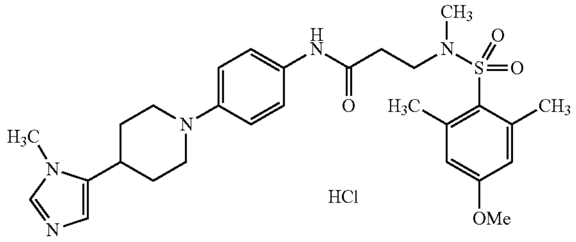

Example 100 is prepared analogously to 1f from 0.085 g (0.28 mmol) of product from 22c, 0.070 g (0.27 mmol) of product from 100c, 0.048 ml (0.35 mmol) of triethylamine and 0.095 g (0.30 mmol) of TBTU in 20 ml THF and 3 ml DMF.

$C_{28}H_{37}N_5O_4S \times HCl$ (576.15)

[M+H]+=540

HPLC (Method 5): retention time=1.41 mi

Example 101

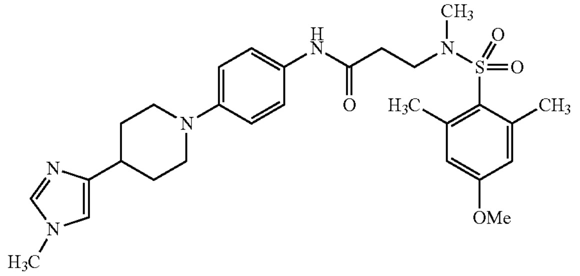

101a)

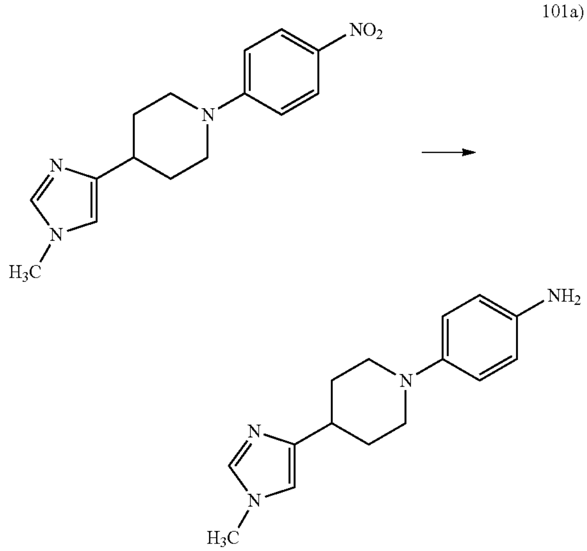

101a is prepared analogously to 8b from 0.35 g (1.22 mmol) of 100b-1 and 0.50 g palladium on charcoal (10%) in 50 ml of methanol.

$C_{15}H_{20}N_4$ (256.35)

TLC: silica gel, dichloromethane/methanol 9:1, Rf value=0.14

101b)

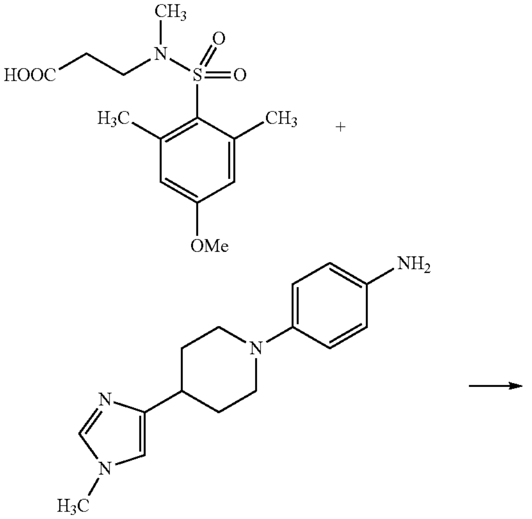

-continued

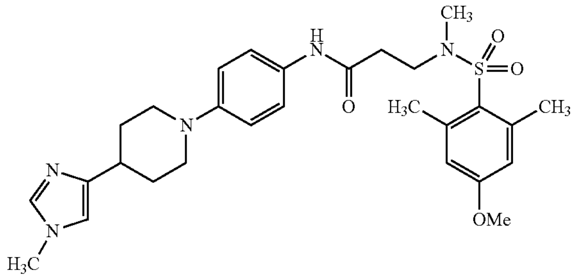

Example 101 is prepared analogously to 1f from 0.12 g (0.40 mmol) of product from 22c, 0.10 g (0.39 mmol) of product from 101a, 0.05 ml (0.50 mmol) of triethylamine and 0.14 g (0.42 mmol) of TBTU in 30 ml THF and 5 ml DMF.

$C_{28}H_{37}N_5O_4S$ (539.69)

[M+H]+=540

TLC: silica gel, dichloromethane/methanol 9:1, Rf value=0.47

Example 102

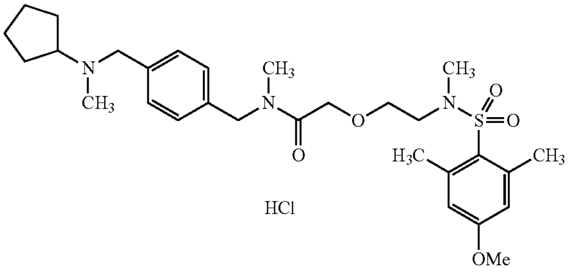

102a)

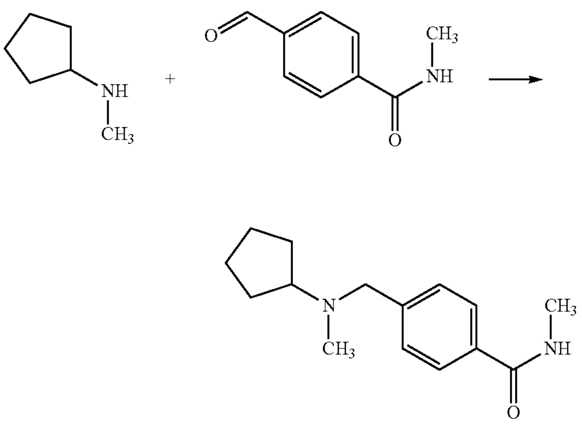

102a is prepared analogously to 60a from 0.50 g (5.00 mmol) of N-methylcyclohexylamine (CHESS), 0.82 g (5.00 mmol) of 4-formyl-benzoic acid methylamide (EMKA), 1.59 g (7.50 mmol) of sodium triacetoxyborohydride and 0.37 ml (6.50 mmol) of acetic acid in 30 ml THF.

$C_{15}H_{22}N_2$ (246.35)

102b)

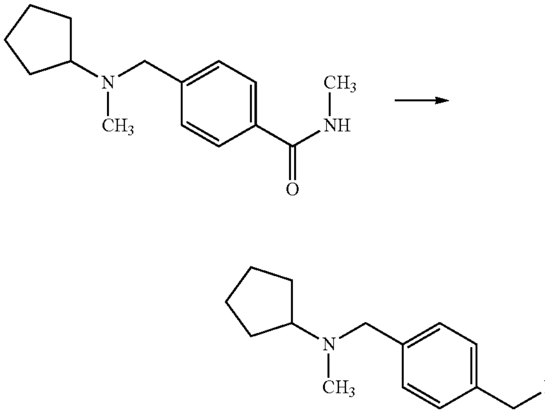

102b is prepared analogously to 38f from 1.06 g (4.30 mmol) of product from 102a and 8.60 ml (8.60 mmol) of lithium aluminium hydride 1 M in THF (Aldrich) in 40 ml THF.

$C_{15}H_{24}N_2$ (232.36)

102c)

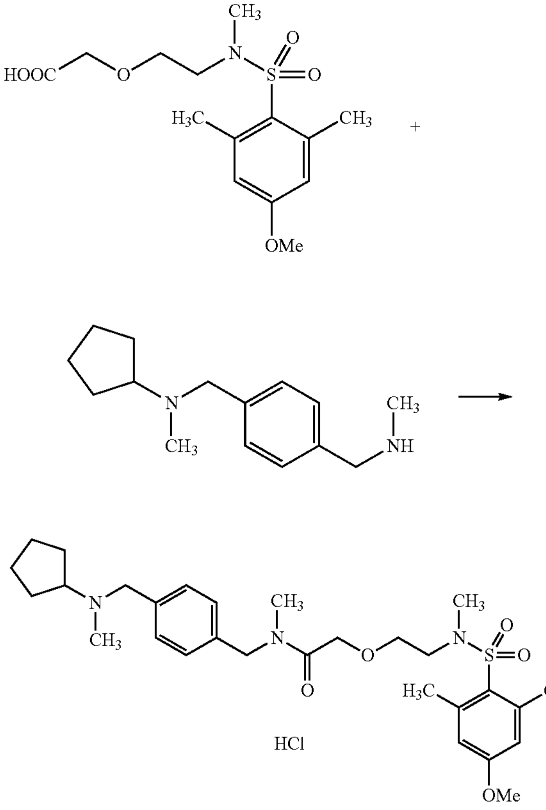

Example 102 is prepared analogously to 1f from 0.20 g (0.60 mmol) of product from 53c, 0.14 g (0.60 mmol) of product from 102b, 0.21 ml (1.50 mmol) of triethylamine and 0.23 g (0.72 mmol) of TBTU in 10 ml THF.

$C_{29}H_{43}N_3O_5S \times HCl$ (582.20)

[M+H]+=546

HPLC (Method 5): retention time=1.58 min

Example 103

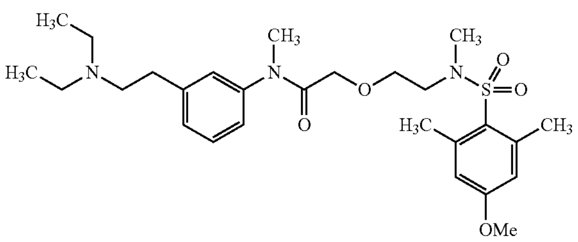

103a)

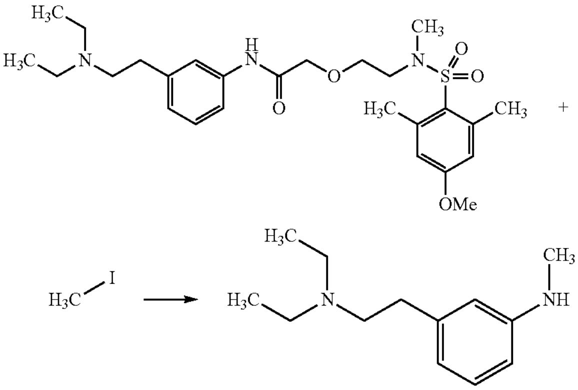

A mixture of 0.04 g (0.079 mmol) of 70, 4.8 mg (0.12 mmol) of sodium hydride 60%, 1 ml THF and 0.5 ml DMF is stirred for 30 minutes at ambient temperature. Then 4.9 μl (0.079 mmol) of methyl iodide are added and the mixture is stirred for a further two hours at ambient temperature. The reaction mixture is then evaporated to dryness in vacuo, the residue is mixed with water and extracted with ethyl acetate. The organic extracts are dried on sodium sulphate and evaporated to dryness in vacuo. The crude product thus obtained is purified by column chromatography (eluant: dichloromethane/methanol/ammonia 95:5:0.5).

$C_{13}H_{22}N_2$ (206.33)

[M+H]+=207

103b)

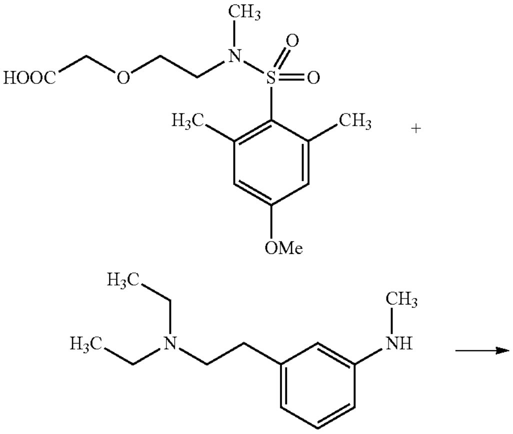

-continued

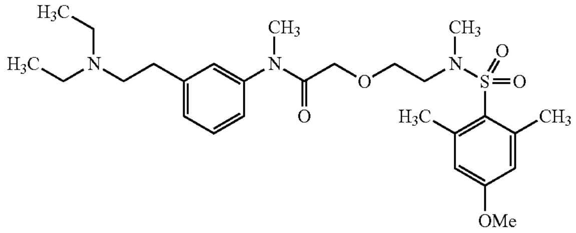

Example 103 is prepared analogously to 1f from 0.08 g (0.24 mmol) of product from 53c, 0.05 g (0.24 mmol) of product from 103a, 0.067 ml (0.48 mmol) of triethylamine and 0.093 g (0.29 mmol) of TBTU in 7 ml THF and 1 ml DMF.

$C_{27}H_{41}N_3O_5S$ (519.70)

[M+H]+=520

HPLC (Method 4): retention time=3.2 min

Example 104

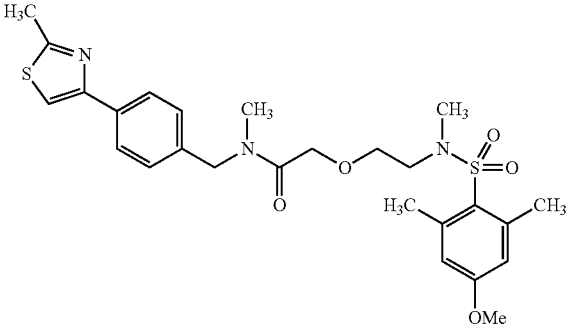

104a)

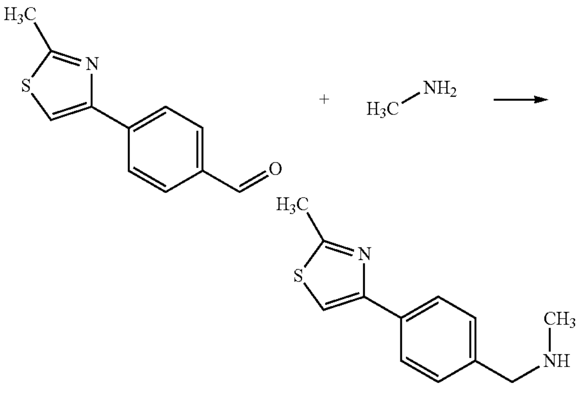

104a is prepared analogously to 60a from 0.35 g (1.72 mmol) of 4-(2-methyl-1.3-thiazol-4-yl)-benzaldehyde (Maybridge), 1.50 ml (3.00 mmol) of methylamine 2 M in THF (Acros), 0.70 g (3.30 mmol) of sodium triacetoxyborohydride and 0.23 ml (4.00 mmol) of acetic acid in 20 ml THF.

$C_{12}H_{14}N_2S$ (218.32)

[M+H]+=219

104b)

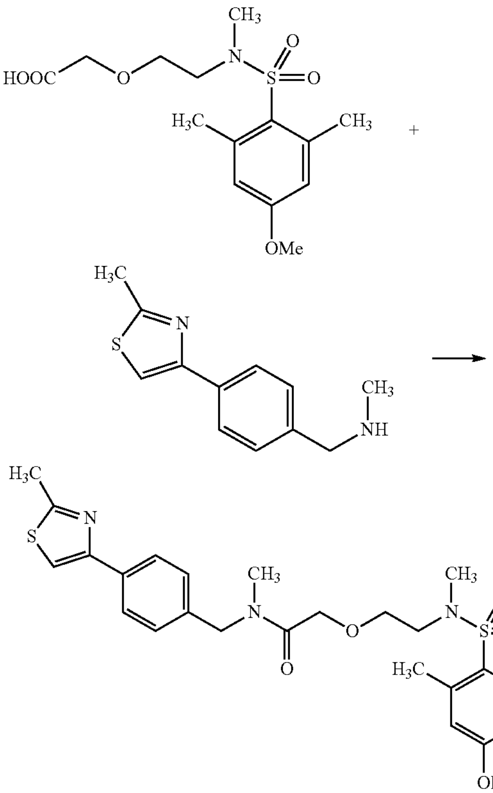

Example 104 is prepared analogously to 1f from 0.16 g (0.47 mmol) of product from 53c, 0.10 g (0.46 mmol) of product from 104a, 0.11 ml (1.09 mmol) of triethylamine and 0.16 g (0.48 mmol) of TBTU in 30 ml THF and 5 ml DMF.

$C_{26}H_{33}N_3O_5S_2$ (531.69)

[M+H]+=532

TLC: silica gel, dichloromethane/methanol 9:1, Rf value=0.66

Example 105

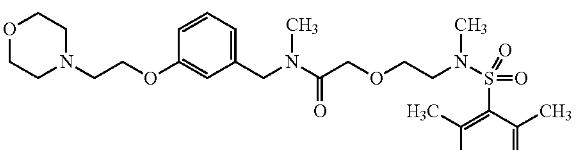

HCl

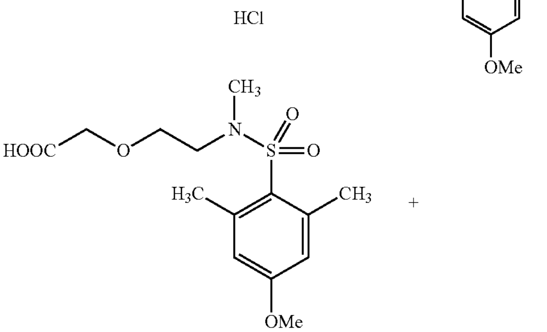

-continued

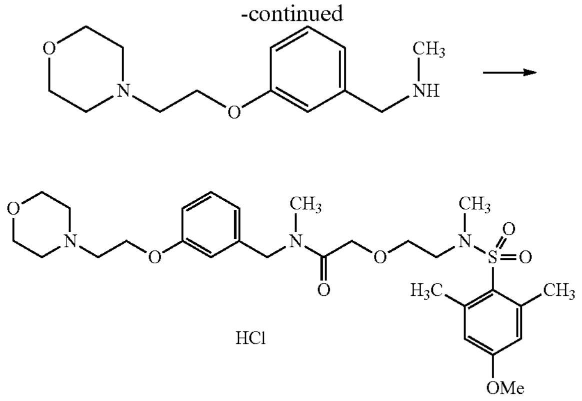

Example 105 is prepared analogously to 1f from 0.14 g (0.41 mmol) of product from 53c, 0.10 g (0.40 mmol) of methyl-[3-(2-morpholin-4-yl-ethoxy)-benzyl]-amine (Maybridge), 0.14 ml (0.99 mmol) of triethylamine and 0.14 g (0.44 mmol) of TBTU in 30 ml THF and 5 ml DMF.

$C_{28}H_{41}N_3O_7S$×HCl (600.17)

[M+H]+=564

TLC: silica gel, dichloromethane/methanol 9:1, Rf value=0.59

Example 106

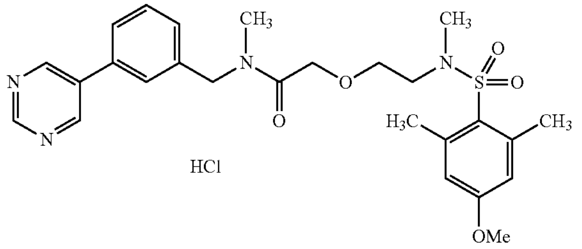

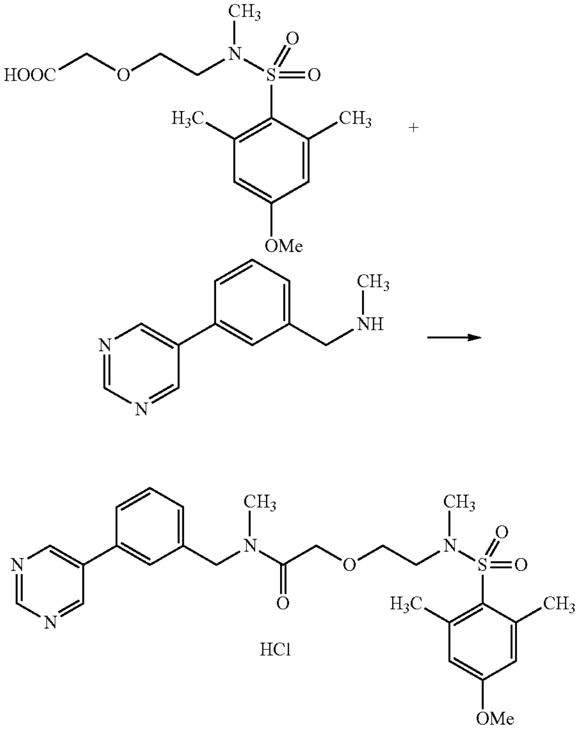

Example 106 is prepared analogously to 1f from 0.17 g (0.51 mmol) of product from 53c, 0.10 g (0.50 mmol) of methyl-(3-pyrimidin-5-yl-benzyl)-amine (Maybridge), 0.17 ml (1.19 mmol) of triethylamine and 0.17 g (0.53 mmol) of TBTU in 30 ml THF and 5 ml DMF.

$C_{26}H_{32}N_4O_5S$×HCl (549.08)

[M+H]+=513

HPLC (Method 5): retention time=1.78 min

Example 107

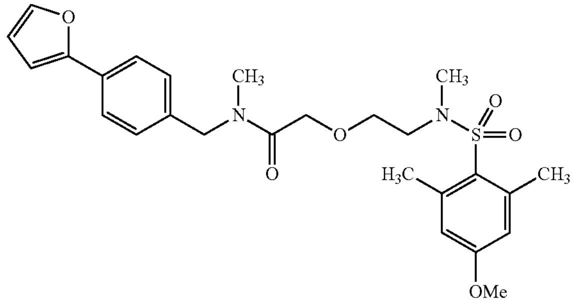

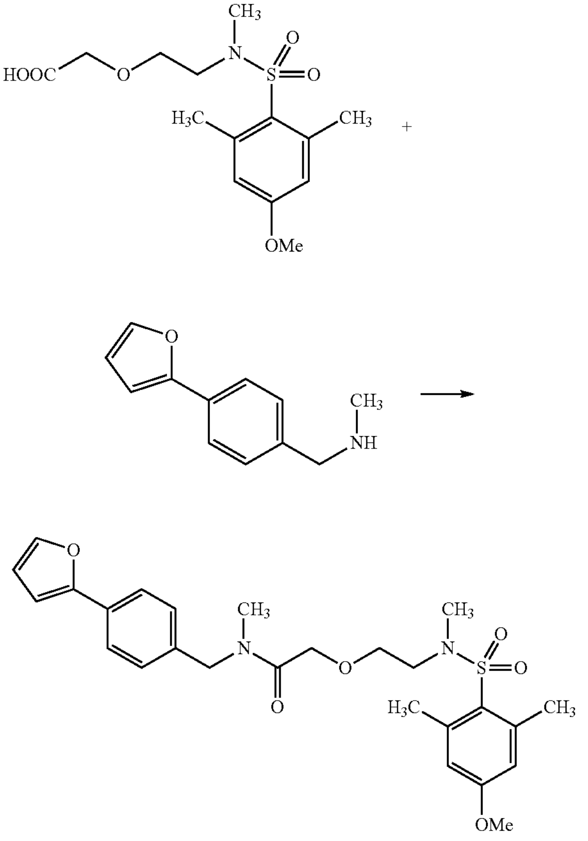

Example 107 is prepared analogously to 1f from 0.18 g (0.54 mmol) of product from 53c, 0.10 g (0.53 mmol) of (4-furan-2-yl-benzyl)-methyl-amine (Maybridge), 0.18 ml (1.29 mmol) of triethylamine and 0.18 g (0.56 mmol) of TBTU in 30 ml THF and 5 ml DMF.

$C_{26}H_{32}N_2O_6S$ (500.61)

[M+H]+=501

HPLC (Method 5): retention time=2.09 min

Example 108

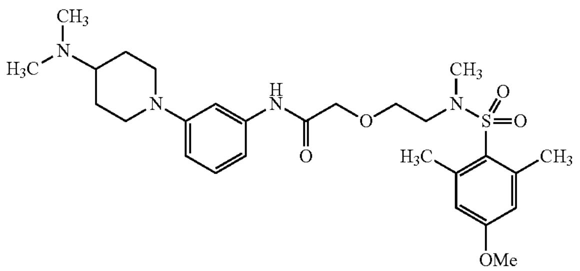

108a)

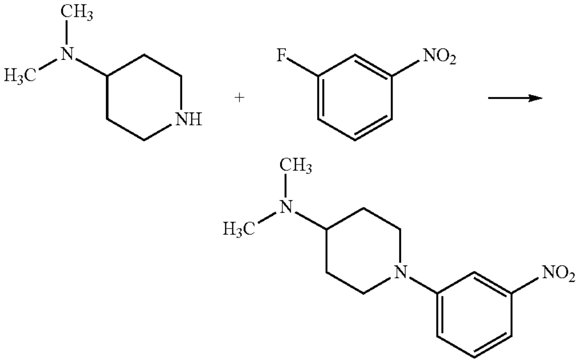

107a is prepared analogously to 79a from 2.41 g (18.78 mmol) of 4-dimethylamino-piperidine (Alfa Aesar), 1.00 ml (9.39 mmol) of 1-fluoro-3-nitrobenzene (Fluka) and 1.30 g (9.39 mmol) of potassium carbonate in 15 ml DMSO.

$C_{13}H_{19}N_3O_2$ (249.31)

[M+H]+=250

108b)

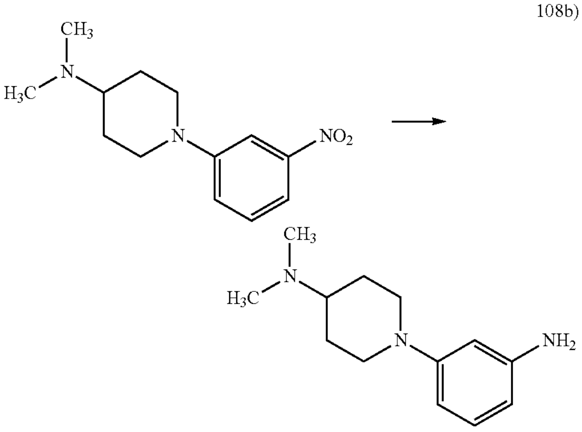

A mixture of 1.74 g (6.98 mmol) of product from 108a, 12.00 g (68.92 mmol) of sodium dithionite, 10.00 g (72.35 mmol) of potassium carbonate, 60 ml THF and 30 ml of water six hours is heated to 80° C. After cooling the organic phase is separated off, washed with saturated sodium chloride solution, dried on sodium sulphate and evaporated to dryness in vacuo.

$C_{13}H_{21}N_3$ (219.33)

108c)

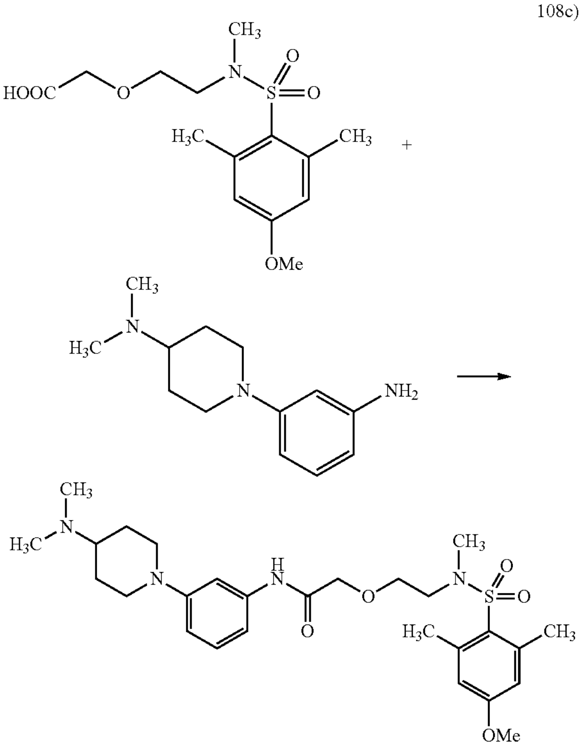

Example 108 is prepared analogously to 1f from 0.13 g (0.40 mmol) of product from 53c, 0.10 g (0.47 mmol) of product from 108b, 0.067 ml (0.48 mmol) of triethylamine and 0.15 g (0.48 mmol) of TBTU in 5 ml DMF.

$C_{27}H_{40}N_4O_5S$ (532.70)

[M+H]+=533

HPLC (Method 5): retention time=1.56 min

Example 109

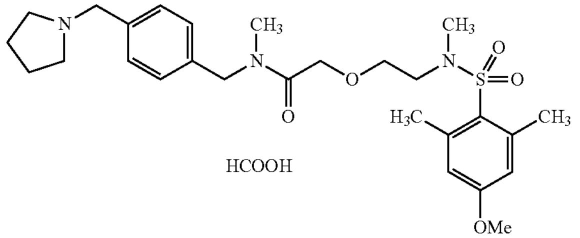

109a)

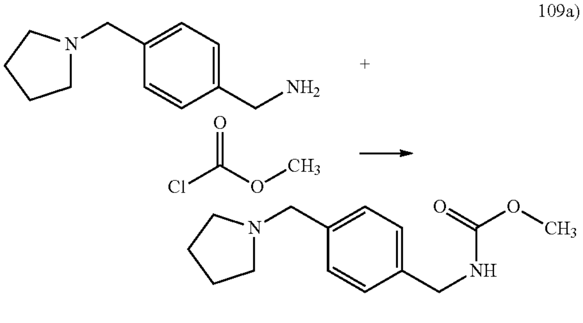

A mixture of 0.59 g (3.12 mmol) of 4-pyrrolidin-1-ylmethyl-benzylamine (Enamine-BB), 0.29 ml (3.75 mmol) of methyl chloroformate (Fluka), 0.52 ml (3.75 mmol) of triethylamine and 10 ml dichloromethane is stirred for two hours at ambient temperature. The reaction mixture is diluted with 10 ml dichloromethane, washed twice with water, dried on sodium sulphate and evaporated to dryness in vacuo.

$C_{14}H_{20}N_2O_2$ (248.32)

109b)

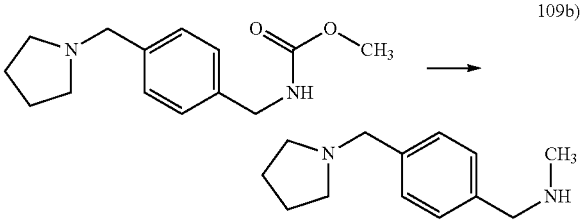

109b is prepared analogously to 51b from 0.61 g (2.44 mmol) of product from 109a and 5.00 ml (5.00 mmol) of lithium aluminium hydride 1 M in THF (Aldrich) in 5 ml THF.

$C_{13}H_{20}N_2$ (204.31)

109c)

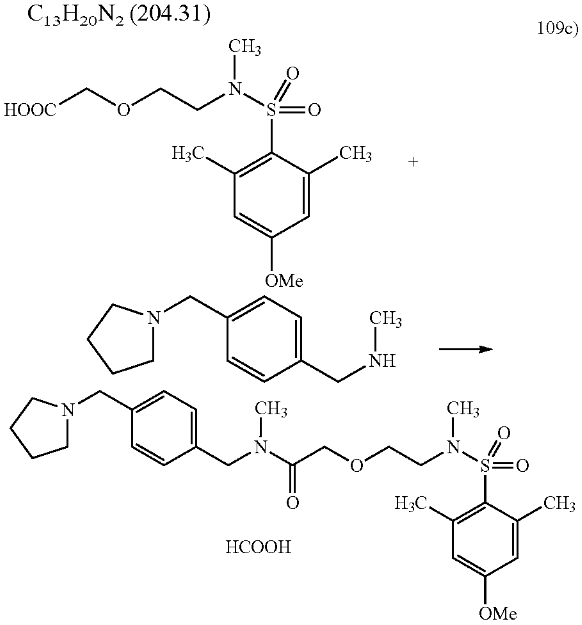

Example 109 is prepared analogously to 1f from 0.18 g (0.54 mmol) of product from 53c, 0.17 g (0.81 mmol) of product from 109b, 0.15 ml (1.07 mmol) of triethylamine and 0.21 g (0.65 mmol) of TBTU in 4 ml DMF.

$C_{27}H_{39}N_3O_5S \times CH_2O_2$ (631.71)

[M+H]+=518

HPLC (Method 5): retention time=1.56 min

Example 110

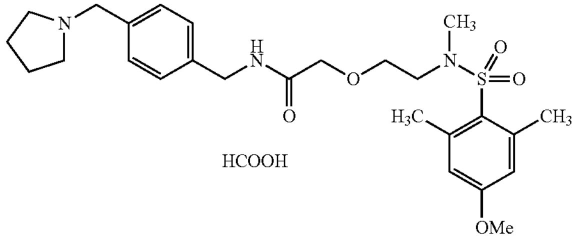

-continued

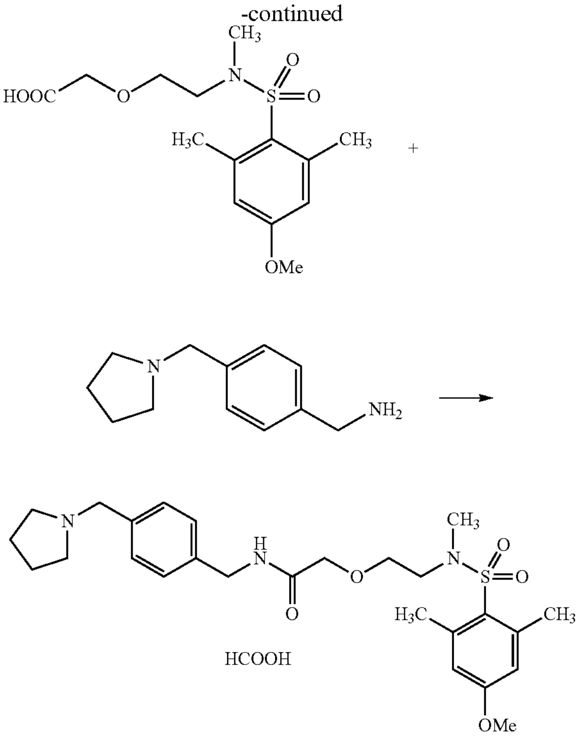

Example 110 is prepared analogously to 1f from 0.12 g (0.36 mmol) of product from 53c, 0.096 g (0.51 mmol) of 4-pyrrolidin-1-ylmethyl-benzylamine (Enamine-BB), 0.10 ml (0.72 mmol) of triethylamine and 0.14 g (0.44 mmol) of TBTU in 4 ml DMF.

$C_{26}H_{37}N_3O_5S \times CH_2O_2$ (617.68)

[M+H]+=504

HPLC (Method 5): retention time=1.56 min

Example 111

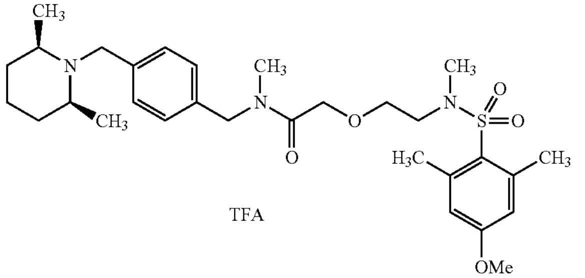

111a)

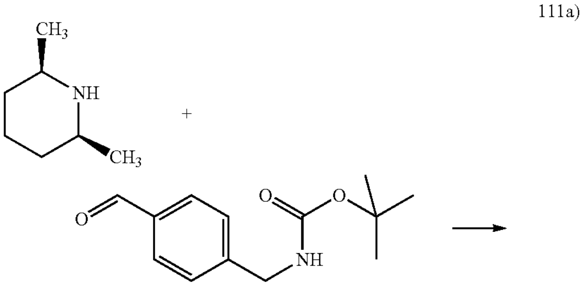

-continued

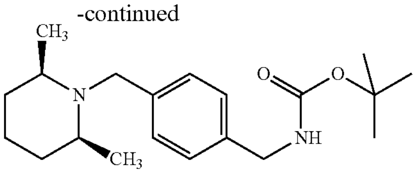

A mixture of 1.00 g (4.25 mmol) of tert-butyl (4-formyl-benzyl)-carbamate (Acros) and 10 ml dichloromethane is combined successively with 1.15 ml (8.50 mmol) of cis-2,6-dimethylpiperidine (Aldrich) and 1.80 g (8.50 mmol) of sodium triacetoxyborohydride while cooling with an ice bath. The reaction mixture is stirred for three days at ambient temperature, then slowly quenched with saturated sodium hydrogen carbonate solution and extracted with dichloromethane. The organic extracts are washed with water and saturated sodium chloride solution, dried on sodium sulphate and evaporated to dryness in vacuo. The crude product thus obtained is purified by column chromatography (eluant: dichloromethane/methanol 93:7).

$C_{20}H_{32}N_2O_2$ (332.48)

[M+H]+=333

HPLC (Method 5): retention time=1.47 min

111b)

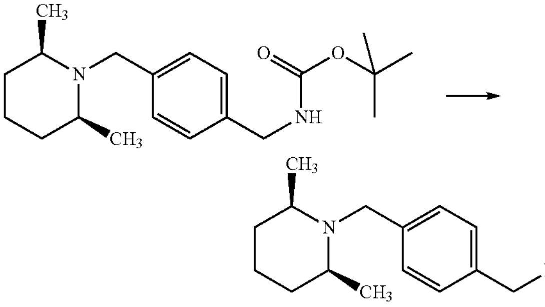

111b is prepared analogously to 51b from 0.92 g (2.76 mmol) of product from 111a and 8.27 ml (8.27 mmol) of lithium aluminium hydride 1 M in THF (Aldrich) in 30 ml THF.

$C_{16}H_{26}N_2$ (246.39)

[M+H]+=247

HPLC (Method 5): retention time=1.03 min

111c)

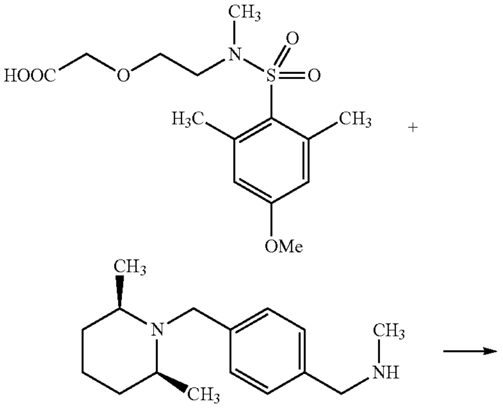

-continued

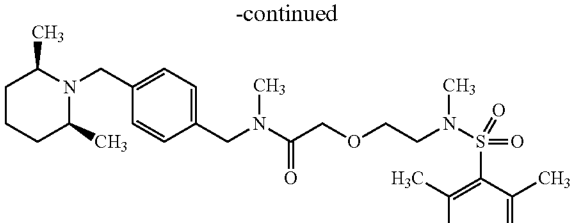

TFA

Example 111 is prepared analogously to 1f from 0.08 g (0.24 mmol) of product from 53c, 0.059 g (0.24 mmol) of product from 111b, 0.10 ml (0.72 mmol) of triethylamine and 0.078 g (0.24 mmol) of TBTU in 2 ml THF.

$C_{30}H_{45}N_3O_5S{\times}C_2HF_3O_2$ (673.78)

[M+H]+=560

HPLC (Method 5): retention time=1.59 min

Example 112

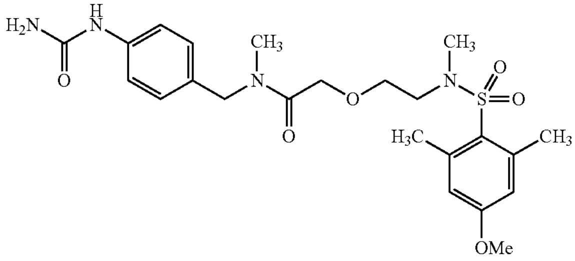

112a)

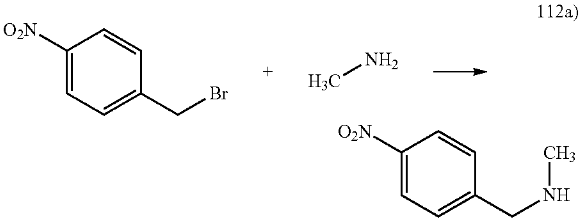

250.00 ml (500.00 mmol) of methylamine 2 M in methanol (Fluka) are slowly combined with 54.00 g (250.00 mmol) of 4-nitrobenzylbromide (Fluka) while cooling with an ice bath. The reaction mixture is stirred for one hour while cooling with an ice bath and for 30 minutes at ambient temperature and then evaporated to dryness in vacuo. The residue is stirred with diethyl ether and filtered off. The filtrate is evaporated to dryness in vacuo, combined with sodium carbonate solution and extracted with diethyl ether. The organic extracts are dried on sodium sulphate and evaporated to dryness in vacuo. The crude product thus obtained is purified by column chromatography (eluant: dichloromethane/methanol 5:0 to 5:1).

$C_8H_{10}N_2O_2$ (166.18)

[M+H]+=167

112b)

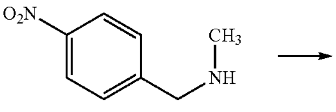

-continued

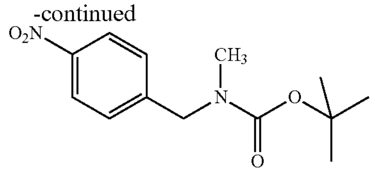

A mixture of 13.40 g (80.64 mmol) of product from 112a and 25 ml ethyl acetate is slowly combined with 17.68 g (81.00 mmol) of Boc-anhydride while cooling with an ice bath. The reaction mixture is stirred for three hours at ambient temperature, then washed with water, dried on sodium sulphate and evaporated to dryness in vacuo.

$C_{13}H_{18}N_2O_4$ (266.29)

112c)

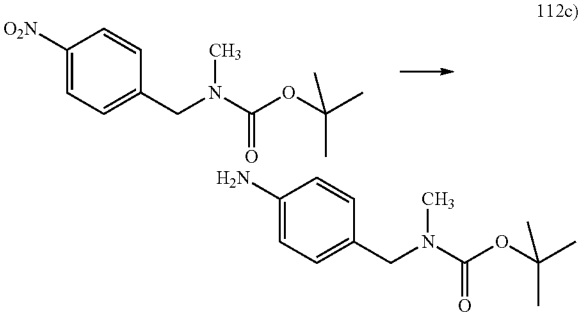

A mixture of 23.00 g (86.37 mmol) of product from 112b, 2.30 g Raney nickel, 230 ml of ethanol and 230 ml ethyl acetate is hydrogenated in the autoclave at ambient temperature. The catalyst is filtered off, the filtrate is evaporated to dryness in vacuo. The crude product thus obtained is purified by column chromatography (eluant: petroleum ether/ethyl acetate 1:1).

$C_{13}H_{20}N_2O_2$ (236.31)

[M+H]+=237

TLC: silica gel, petroleum ether/ethyl acetate 1:1, Rf value=0.55

112d)

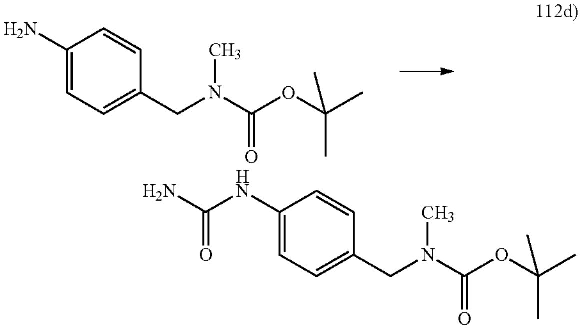

A mixture of 0.50 g (2.12 mmol) of product from 112c, 0.48 g (3.56 mmol) of trimethylsilyl isocyanate (Fluka) and 15 ml THF is refluxed over the weekend with stirring. Then the reaction mixture is evaporated to dryness in vacuo.

$C_{14}H_{21}N_3O_3$ (279.33)

[2M+H]+=559

112e)

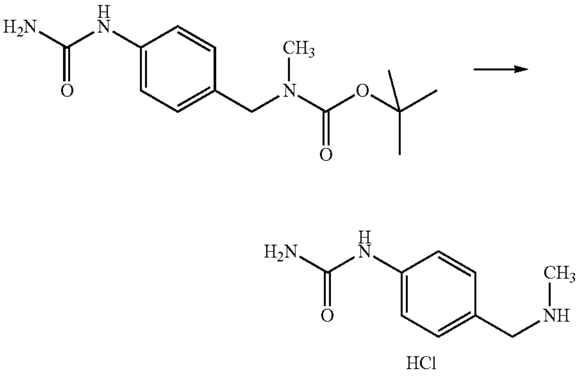

A mixture of 0.64 g (2.29 mmol) of product from 112d and 10 ml of methanolic HCl is stirred for three hours at ambient temperature and for two hours at 50° C. Then the reaction mixture is evaporated to dryness in vacuo. The residue is dried overnight in vacuo.

$C_9H_{13}N_3$×HCl (215.68)

[M+H]+=180

112f)

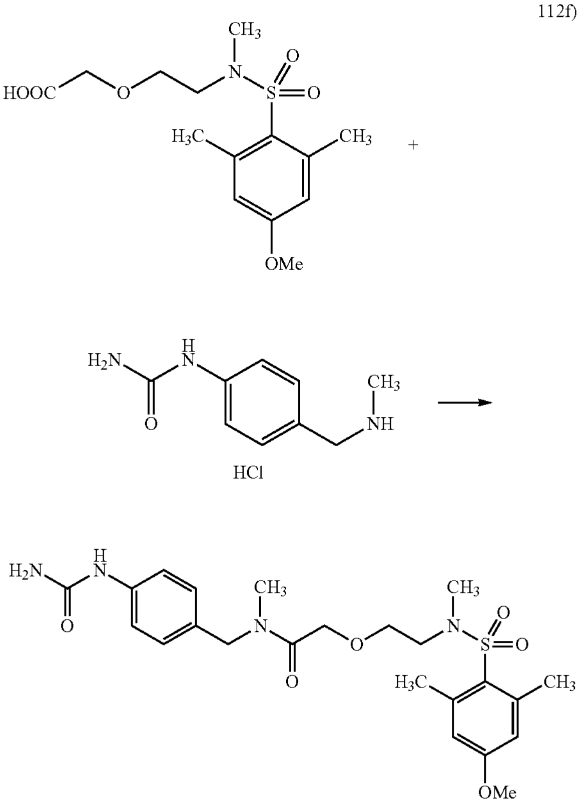

Example 112 is prepared analogously to 1f from 0.20 g (0.60 mmol) of product from 53c, 0.13 g (0.60 mmol) of product from 112e, 0.42 ml (3.02 mmol) of triethylamine and 0.22 g (0.66 mmol) of TBTU in 4 ml DMF.

$C_{23}H_{32}N_4O_6S$ (492.59)

[M+H]+=493

HPLC (Method 6): retention time=2.93 min

Example 113

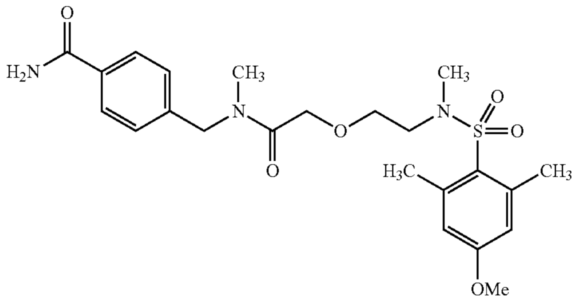

113a)

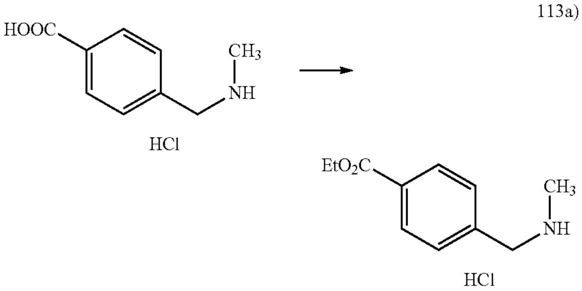

A mixture of 2.00 g (9.92 mmol) of 4-methylaminomethyl-benzoic acid hydrochloride (J. Med. Chem. 26, 1983, 309-312) and 25 ml of ethanolic HCl is stirred for 1.5 hours at reflux temperature. Then the reaction mixture is evaporated to dryness in vacuo.

$C_{11}H_{15}NO_2 \times HCl$ (229.70)

[M+H]+=194

HPLC (Method 6): retention time=1.39 min

113b)

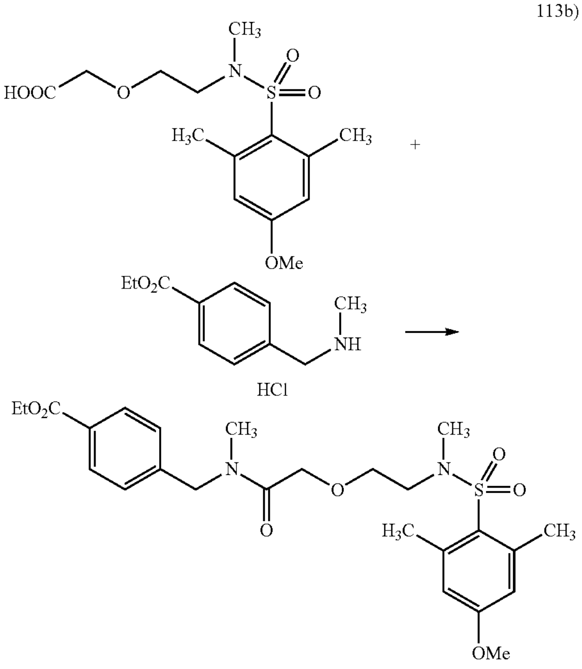

113b is prepared analogously to 1f from 0.70 g (2.11 mmol) of product from 53c, 0.49 g (2.11 mmol) of product from 113a, 0.88 ml (6.34 mmol) of triethylamine and 0.78 g (2.32 mmol) of TBTU in 12 ml DMF.

$C_{25}H_{34}N_2O_7S$ (506.61)

[M+H]+=507

HPLC (Method 6): retention time=3.95 min

113c)

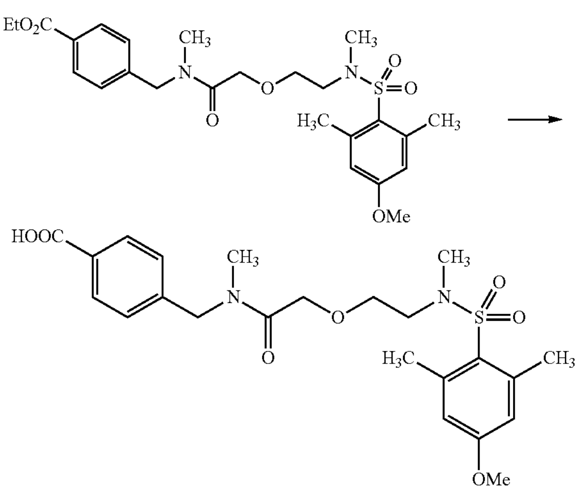

A mixture of 1.06 g (2.09 mmol) of product from 133b, 7.00 ml (7.00 mmol) of 1 M sodium hydroxide solution, 15 ml THF and 1.5 ml of ethanol is stirred for four hours at 50° C. The reaction mixture is then combined with 7 ml 1 M HCl and evaporated to dryness in vacuo. The residue is taken up in acetone, dried on magnesium sulphate and evaporated to dryness in vacuo.

$C_{23}H_{30}N_2O_7S$ (478.56)

[M+H]+=479

HPLC (Method 6): retention time=3.21 min

113d)

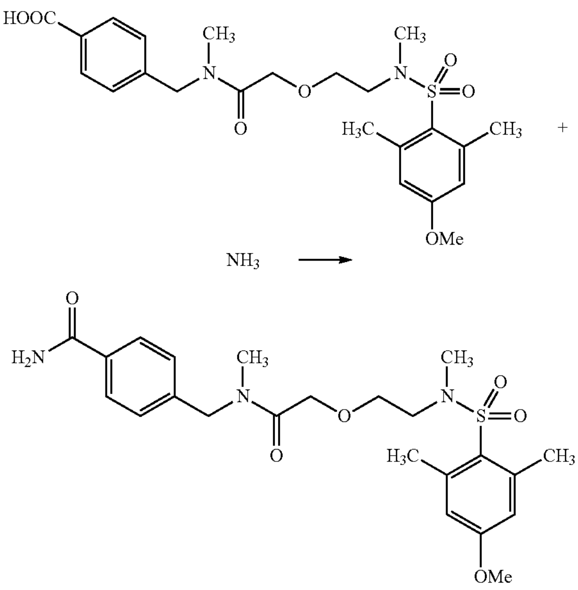

Example 113 is prepared analogously to 1f from 0.50 g (1.05 mmol) of product from 113c, 4.00 ml (2.00 mmol) of ammonia 0.5 M in dioxane, 0.44 ml (3.14 mmol) of triethylamine and 0.38 g (1.15 mmol) of TBTU in 4 ml DMF.

$C_{23}H_{31}N_3O_6S$ (477.57)

[M+H]+=478

HPLC (Method 6): retention time=2.92 min

Example 114

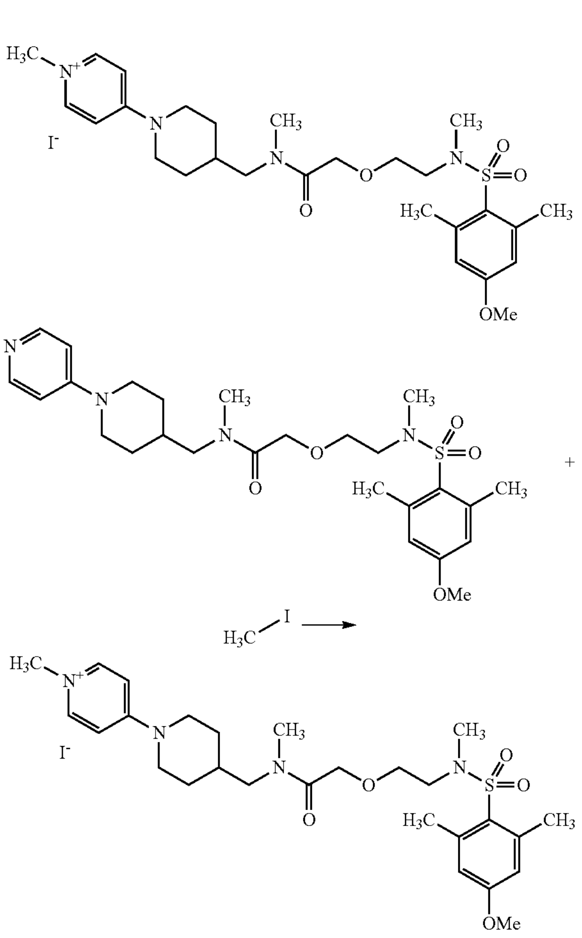

A mixture of 0.075 g (0.15 mmol) of 61, 0.1 g (0.71 mmol) of methyl iodide and 5 ml dichloromethane is stirred overnight at ambient temperature. The reaction mixture is then evaporated to dryness in vacuo.

$C_{27}H_{41}N_4O_5S{\times}I$ (660.61)

[M+H]+=533

HPLC (Method 5): retention time=1.55 min

Example 115

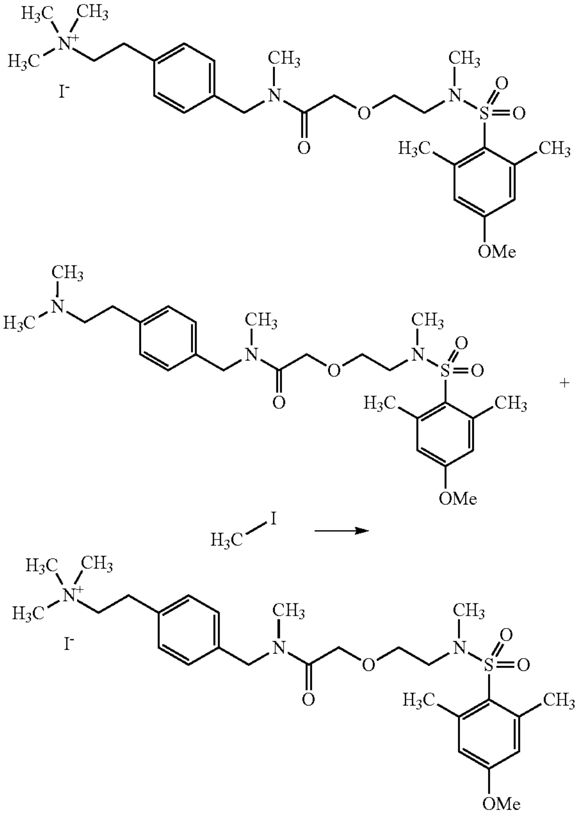

Example 115 is prepared analogously to 114 from 0.03 g (0.059 mmol) of 64 and 0.05 g (0.35 mmol) of methyl iodide in 5 ml dichloromethane.

$C_{27}H_{42}N_3O_5S{\times}I$ (647.61)

[M+H]+=520

HPLC (Method 5): retention time=1.55 min

Example 116

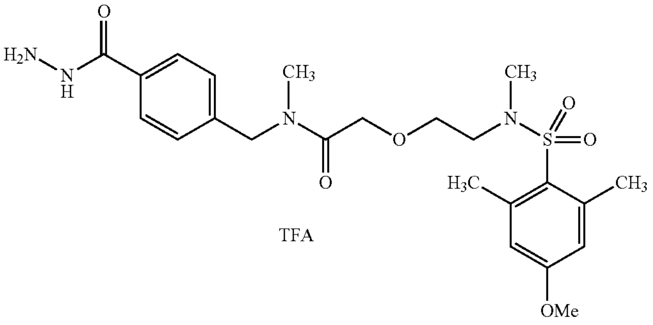

TFA

-continued

116a)

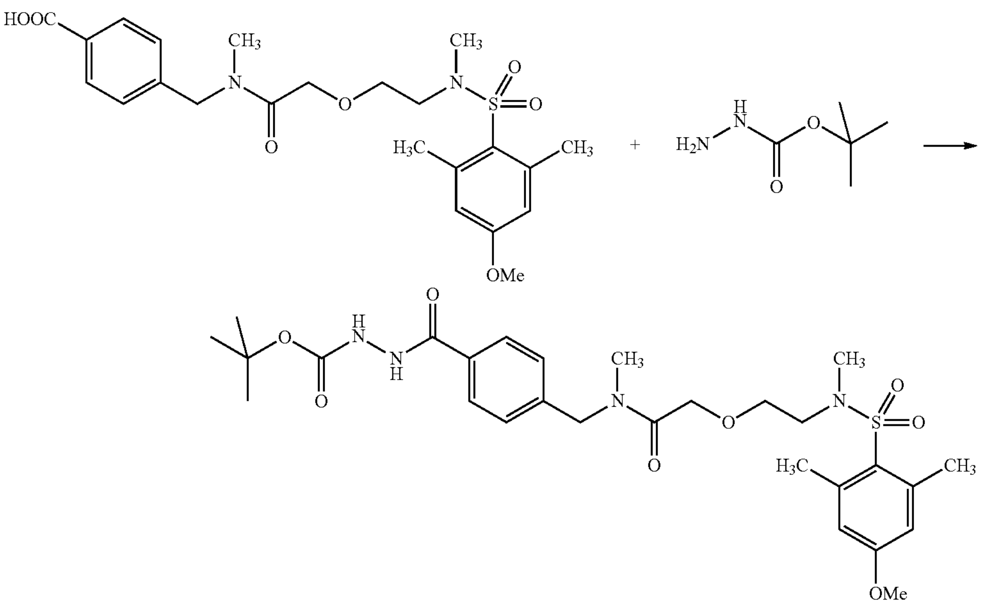

116a is prepared analogously to 1f from 0.50 g (1.05 mmol) of product from 113c, 0.14 g (1.05 mmol) of tert-butyl hydrazine carboxylate (Aldrich), 0.58 ml (4.18 mmol) of triethylamine and 0.38 g (1.15 mmol) of TBTU in 6 ml DMF.

$C_{28}H_{40}N_4O_8S$ (592.71)

[M+H]+=593

HPLC (Method 6): retention time=3.46 min

116b)

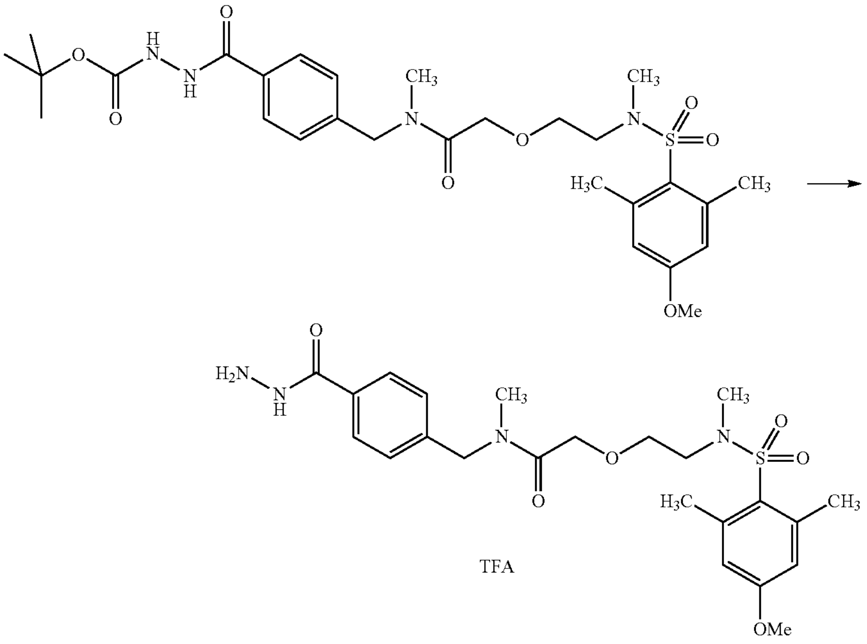

TFA

Example 116 is prepared analogously to 112e from 0.68 g (1.15 mmol) of product from 116a and 10 ml of methanolic HCl.

$C_{23}H_{32}N_4O_6S \times C_2HF_3O_2$ (606.61)

[M+H]+=493

HPLC (Method 6): retention time=3.46 min

Example 117

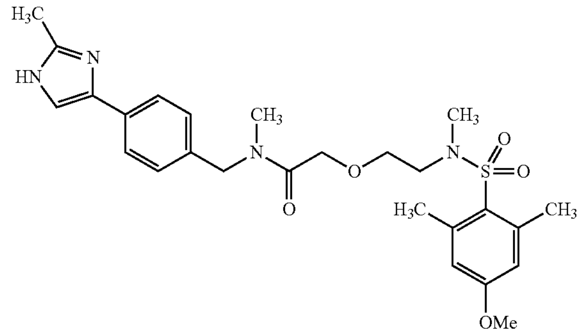

117a)

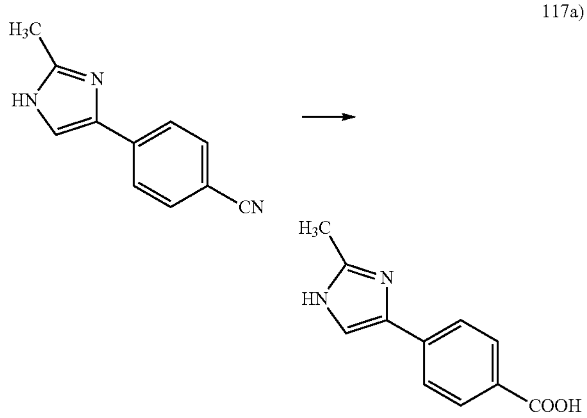

A mixture of 3.20 g (17.47 mmol) of product from 63a, 50 ml 20% sodium hydroxide solution and 50 ml of ethanol is refluxed overnight with stirring. Then the ethanol is eliminated in vacuo and the aqueous residue is neutralised with concentrated HCl. The precipitate formed is filtered off and dried.

$C_{11}H_{10}N_2O_2$ (202.21)

[M+H]+=203

117b)

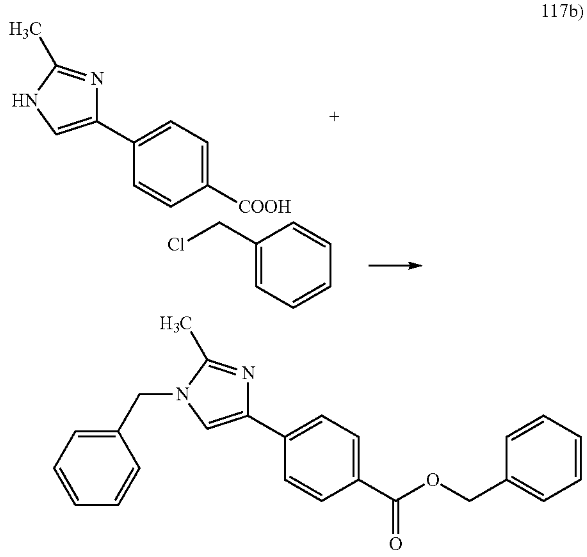

A mixture of 2.70 g (13.35 mmol) of product from 117a, 8.00 g (57.89 mmol) of potassium carbonate and 100 ml DMF is stirred for one hour at 60° C. After cooling the reaction mixture is combined with 3.50 g (27.65 mmol) of benzyl chloride (Aldrich) at ambient temperature and then stirred over the weekend at 60° C. The reaction mixture is poured onto water and stirred for one hour at ambient temperature. The precipitate formed is filtered off and dried.

$C_{25}H_{22}N_2O_2$ (382.45)

[M+H]+=383

TLC: silica gel, dichloromethane/methanol 9:1, Rf value=0.64

117c)

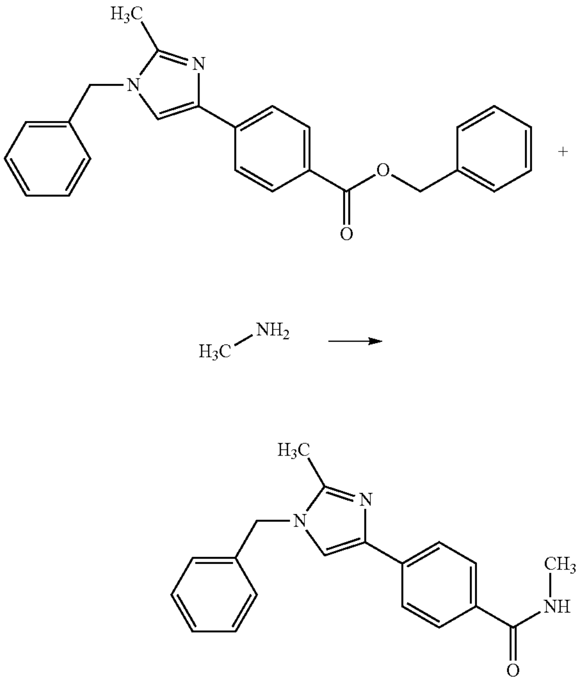

A mixture of 1.80 g (4.71 mmol) of product from 117b and 100 ml methylamine 33% in ethanol (Aldrich) is stirred for six hours at 180° C. and overnight at 160° C. in the autoclave. The reaction mixture is then evaporated to dryness in vacuo. The crude product thus obtained is purified by column chromatography (eluant: dichloromethane/methanol 19:1).

$C_{19}H_{19}N_3O$ (305.37)

[M+H]+=306

117d)

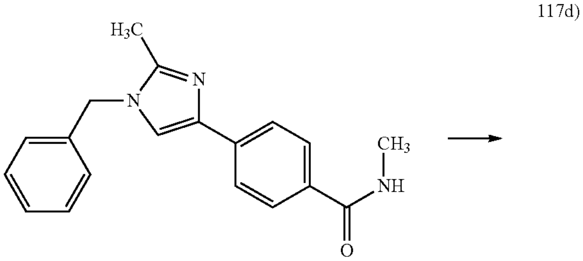

-continued

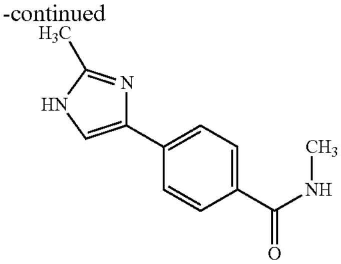

A mixture of 1.20 g (3.93 mmol) of product from 117c, 0.20 g palladium on charcoal (20%) and 50 ml of methanol is hydrogenated at 50° C. in the autoclave. The catalyst is filtered off, the filtrate is evaporated to dryness in vacuo.

$C_{12}H_{13}N_3O$ (215.25)

[M+H]+=216

117e)

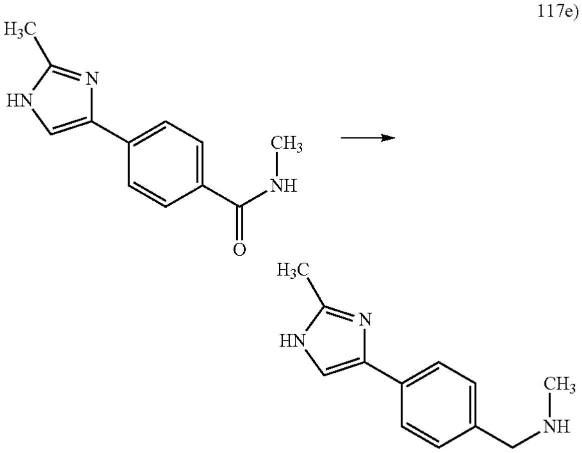

117e is prepared analogously to 38f from 0.70 g (3.25 mmol) of product from 117d and 10.00 ml (10.00 mmol) of lithium aluminium hydride 1 M in THF (Aldrich) in 200 ml THF.

$C_{12}H_{15}N_3$ (201.27)

[M+H]+=202

117f)

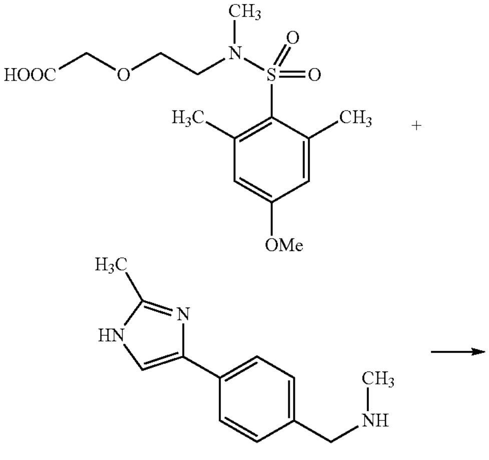

-continued

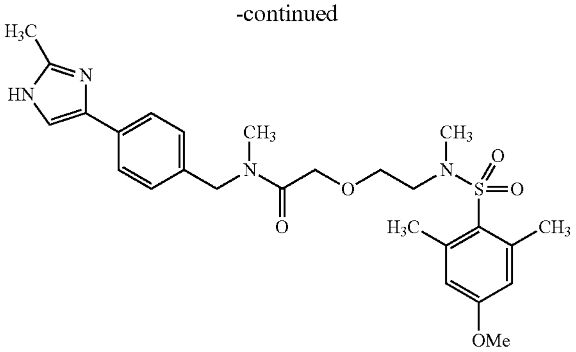

Example 117 is prepared analogously to 1f from 0.17 g (0.51 mmol) of product from 53c, 0.10 g (0.50 mmol) of product from 117e, 0.17 ml (1.19 mmol) of triethylamine and 0.17 g (0.53 mmol) of TBTU in 30 ml THF and 5 ml DMF.

$C_{26}H_{34}N_4O_5S$ (514.64)

[M+H]+=515

TLC: silica gel, dichloromethane/methanol 9:1, Rf value=0.28

Example 118

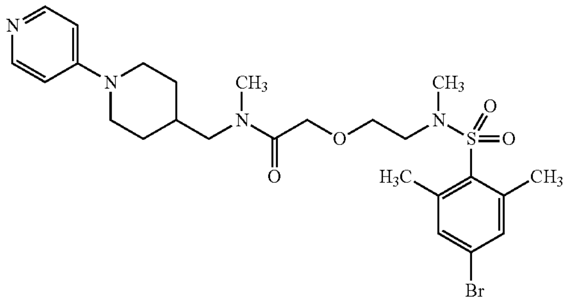

118a)

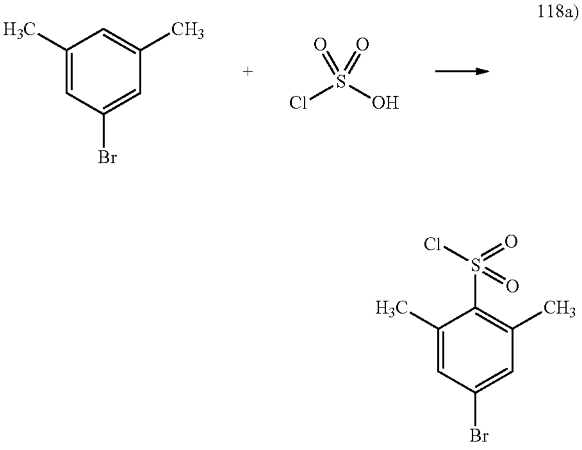

118a is prepared analogously to 13a from 0.75 g (4.05 mmol) of 5-bromo-m-xylene (Aldrich), 0.55 ml (8.30 mmol) of chlorosulphonic acid (Aldrich) and 10 ml dichloromethane.

$C_8H_8BrClO_2S$ (283.57)

HPLC (Method 6): retention time=4.76 min

118b)

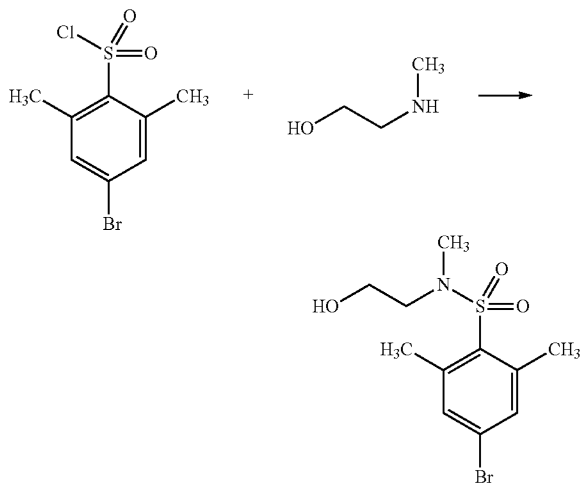

118b is prepared analogously to 3a from 0.65 g (2.29 mmol) of product from 118a and 0.28 ml (3.44 mmol) of N-methylaminoethanol (BASF) in 5 ml THF.

$C_{11}H_{16}BrNO_3S$ (322.22)

HPLC (Method 6): retention time=3.38 min

118c)

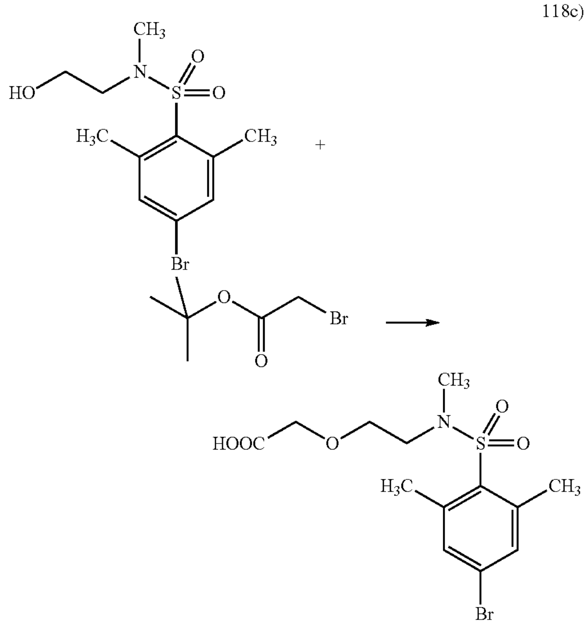

118c is first prepared analogously to 53b from 0.74 g (2.29 mmol) of product from 118b, 0.75 g (5.06 mmol) of tert-butyl 2-bromopropionate (Fluka), 0.42 g (1.14 mmol) of tetrabutylammonium iodide (Aldrich) and 8.67 g (75.90 mmol) of 35% sodium hydroxide solution in 40 ml of toluene. The tert-butyl ester is then stirred overnight together with 2 ml HCl 4 M in dioxane (Aldrich) in 4 ml dioxane at ambient temperature. The product is then obtained by evaporating the reaction mixture in vacuo.

$C_{13}H_{18}BrNO_5S$ (380.26)

HPLC (Method 6): retention time=3.48 min

118d)

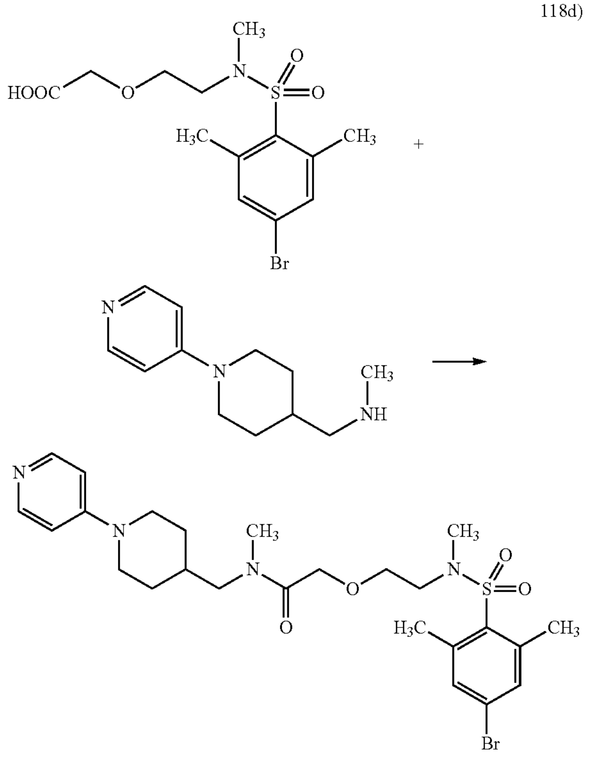

Example 118 is prepared analogously to 1f from 0.10 g (0.26 mmol) of product from 118c, 0.054 g (0.26 mmol) of product from 61b, 0.11 ml (0.79 mmol) of triethylamine and 0.084 g (0.26 mmol) of TBTU in 10 ml THF and 3 ml DMF.

$C_{25}H_{35}BrN_4O_4S$ (567.54)

[M+H]+=568/569/571

HPLC (Method 6): retention time=2.77 min

Example 119

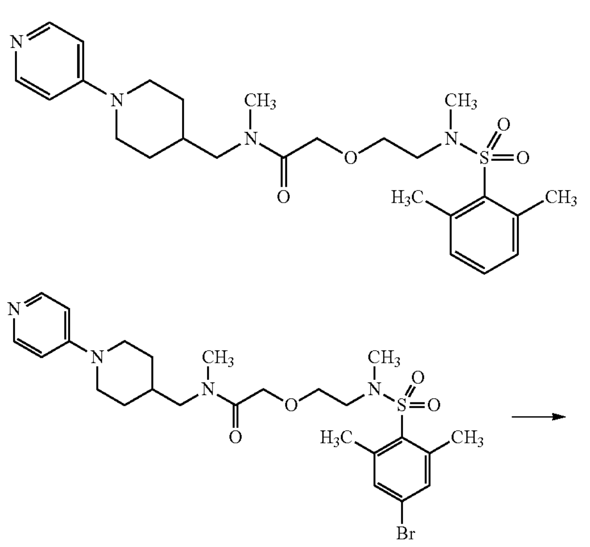

-continued

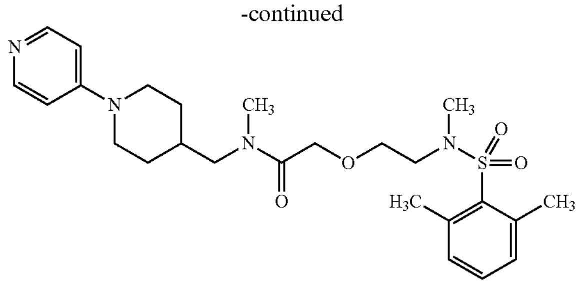

A mixture of 0.03 g (0.053 mmol) of 118 and 0.03 g palladium on charcoal in 5 ml of methanol is hydrogenated in the autoclave at ambient temperature. The catalyst is filtered off, the filtrate is evaporated to dryness in vacuo. The crude product thus obtained is purified by preparative HPLC.

$C_{25}H_{36}N_4O_4S$ (488.64)

[M+H]+=489

HPLC (Method 6): retention time=2.45 min

Example 120

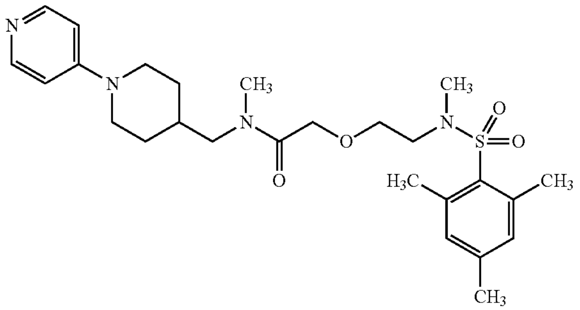

120a)

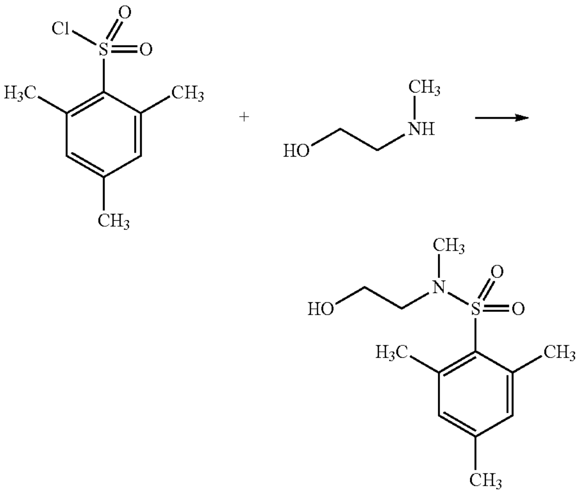

120a is prepared analogously to 3a from 0.50 g (2.29 mmol) of 2,4,6-trimethylbenzene-sulphonic acid chloride (Fluka) and 0.19 g (2.52 mmol) of N-methylaminoethanol (BASF) in 5 ml THF.

$C_{12}H_{19}NO_3S$ (257.35)

[M+H]+=258

120b)

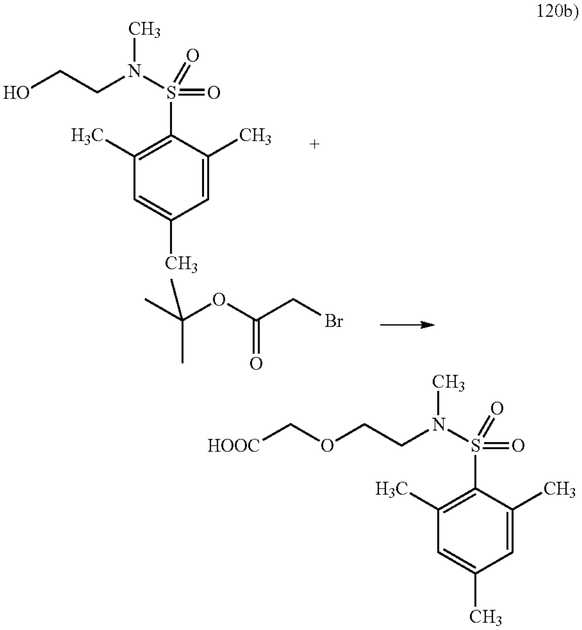

120b is prepared analogously to 118c from 0.56 g (2.18 mmol) of product from 120a, 0.48 ml (3.26 mmol) of tert-butyl 2-bromopropionate (Fluka), 0.18 g (0.65 mmol) of tetrabutylammonium chloride (Fluka) and 7.46 g (65.28 mmol) of 35% sodium hydroxide solution in 20 ml of toluene and subsequent stirring in 2 ml HCl 4 M in dioxane.

$C_{14}H_{21}NO_5S$ (315.39)

120c)

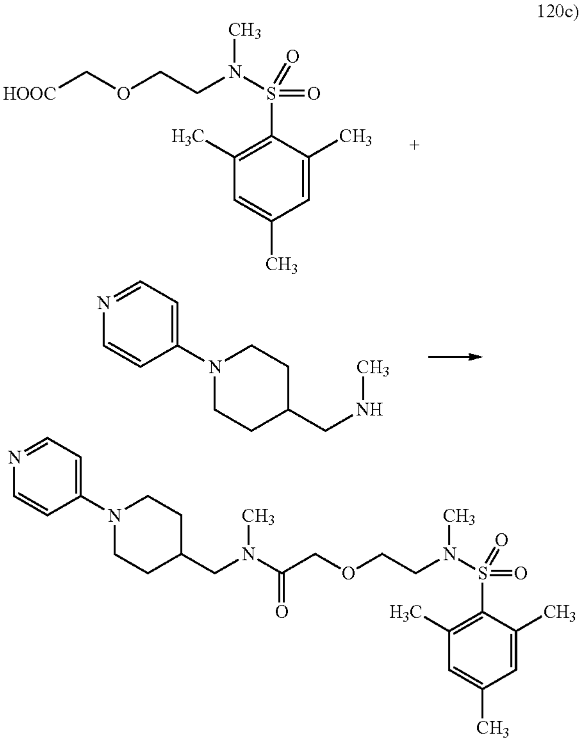

Example 120 is prepared analogously to 1f from 0.10 g (0.32 mmol) of product from 120b, 0.065 g (0.32 mmol) of product from 61b, 0.13 ml (0.95 mmol) of triethylamine and 0.20 g (0.63 mmol) of TBTU in 10 ml THF.

$C_{26}H_{38}N_4O_4S$ (502.67)

[M+H]+=503

HPLC (Method 5): retention time=1.57 min

Example 121

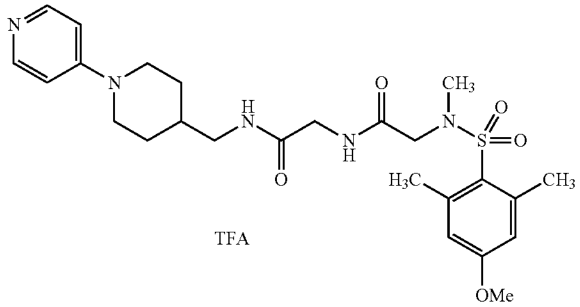

TFA

121a)

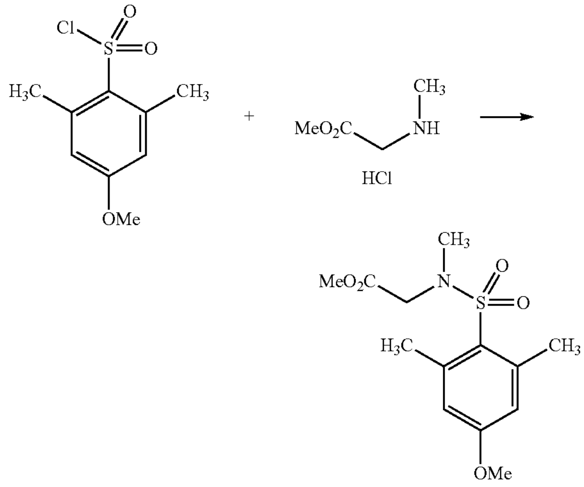

A mixture of 0.98 g (7.05 mmol) of sarcosine methylester hydrochloride (Fluka), 1.65 g (7.05 mmol) of product from 13a and 50 ml of pyridine is stirred for one hour at ambient temperature. The reaction mixture is then evaporated to dryness in vacuo. The residue is then taken up in 1 M HCl and extracted with ethyl acetate. The organic extracts are dried on sodium sulphate and evaporated to dryness in vacuo.

$C_{13}H_{19}NO_5S$ (301.36)

[M+H]+=302

121b)

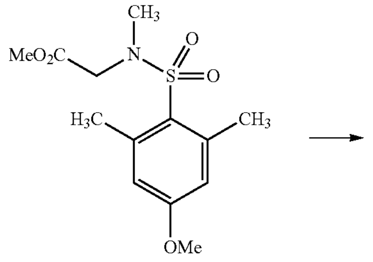

-continued

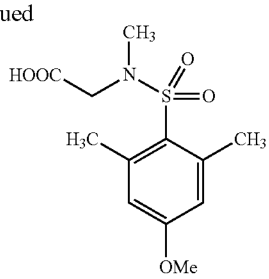

A mixture of 1.90 g (6.29 mmol) of product from 121a, 6.45 ml (12.90 mmol) of 2 M sodium hydroxide solution and 9 ml of methanol is stirred for three days at ambient temperature. The methanol is eliminated in vacuo, the aqueous residue is poured onto 1 M HCl. The precipitate formed is filtered off and dried overnight in the vacuum desiccator.

$C_{12}H_{17}NO_5S$ (287.33)

[M+H]+=288

121c)

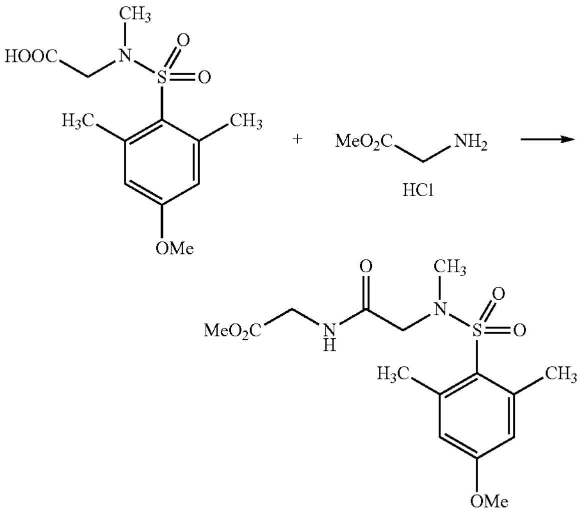

121c is prepared analogously to 1f from 0.20 g (0.70 mmol) of product from 121b, 0.087 g (0.70 mmol) of glycine methylester hydrochloride (Aldrich), 0.29 ml (2.09 mmol) of triethylamine and 0.22 g (0.70 mmol) of TBTU in 5 ml THF.

$C_{15}H_{22}N_2O_6S$ (358.41)

[M+H]+=359

HPLC (Method 5): retention time=1.72 min

121d)

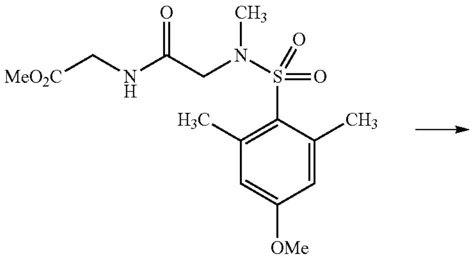

-continued

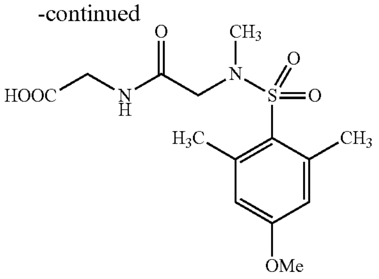

121d is prepared analogously to 121b from 0.23 g (0.63 mmol) of product from 121c and 0.64 ml (1.29 mmol) of 2 M sodium hydroxide solution in 1 ml of methanol.

$C_{14}H_{20}N_2O_6S$ (344.38)

[M+H]+=345

121e)

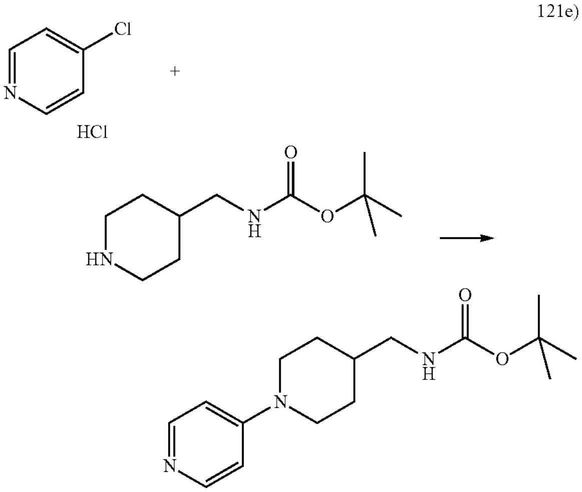

121e is prepared analogously to 28c from 3.00 g (14.00 mmol) of tert-butyl piperidine-4-ylmethyl-carbamate (EMKA), 2.10 g (14.00 mmol) of 4-chloropyridine hydrochloride (Aldrich) and 7.80 ml (56.32 mmol) of triethylamine in 15 ml isopropanol.

$C_{16}H_{25}N_3O_2$ (291.39)

[M+H]+=292

HPLC (Method 5): retention time=1.40 min

121f)

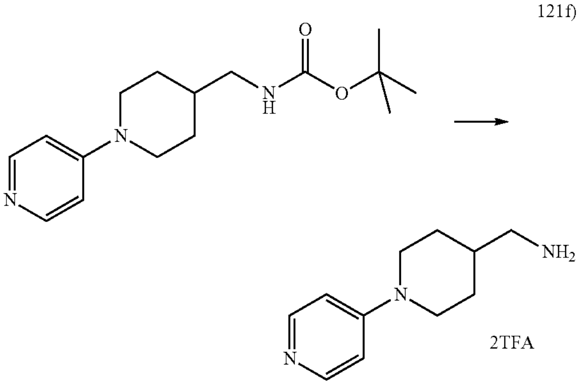

121f is prepared analogously to 18b from 1.44 g (4.95 mmol) of product from 121e and 4.95 ml TFA in 8 ml dichloromethane.

$C_{11}H_{17}N_3 \times 2C_2HF_3O_2$ (419.32)

[M+H]+=192

HPLC (Method 5): retention time=0.36 min

121g)

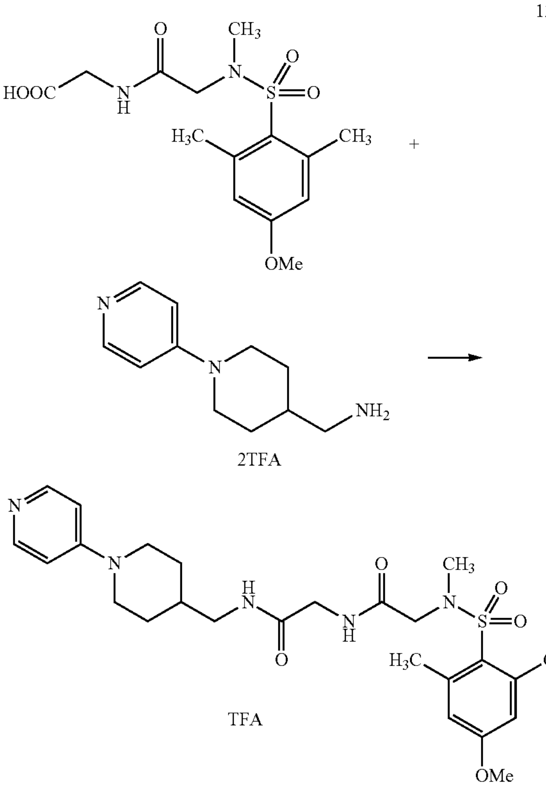

Example 121 is prepared analogously to 1f from 0.09 g (0.26 mmol) of product from 121d, 0.11 g (0.26 mmol) of product from 121f, 0.15 ml (1.05 mmol) of triethylamine and 0.084 g (0.26 mmol) of TBTU in 1.9 ml THF.

$C_{25}H_{35}N_5O_5S \times C_2HF_3O_2$ (631.67)

[M+H]+=518

HPLC (Method 5): retention time=1.46 min

Example 122

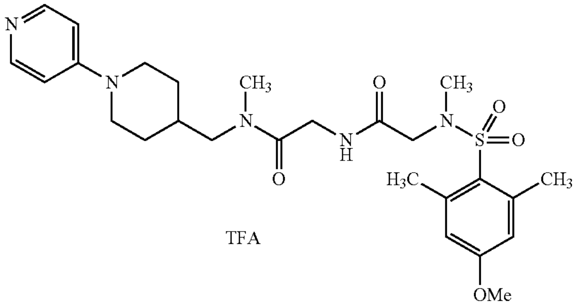

-continued

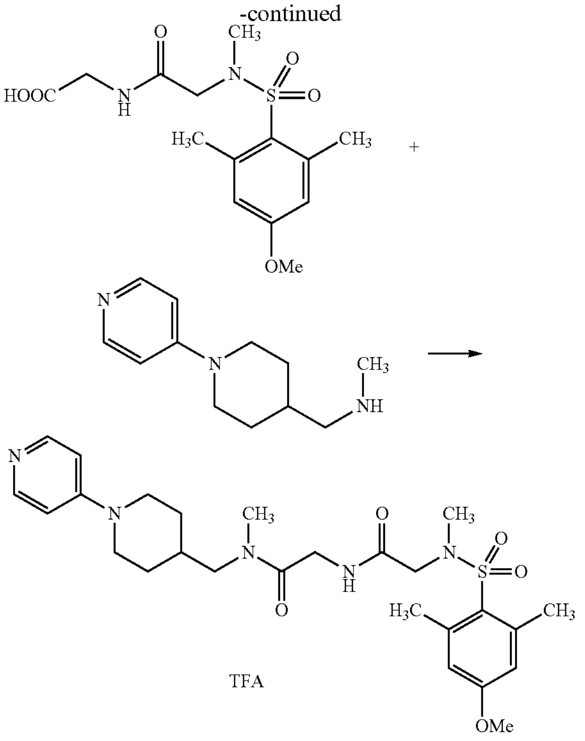

Example 122 is prepared analogously to 1f from 0.09 g (0.26 mmol) of product from 121d, 0.054 g (0.26 mmol) of product from 61b, 0.11 ml (0.78 mmol) of triethylamine and 0.084 g (0.26 mmol) of TBTU in 1.9 ml THF.

$C_{26}H_{37}N_5O_5S \times C_2HF_3O_2$ (645.69)

[M+H]+=532

HPLC (Method 5): retention time=1.50 min

Example 123

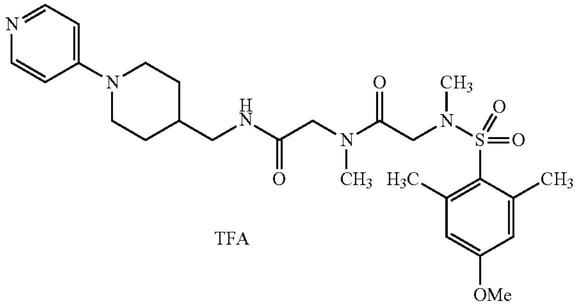

123a)

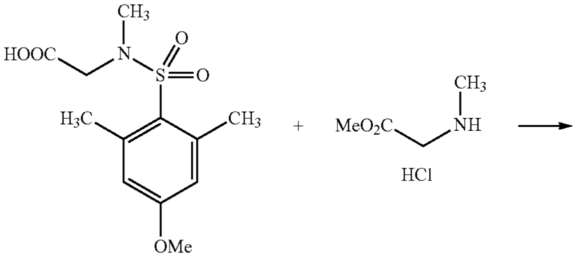

-continued

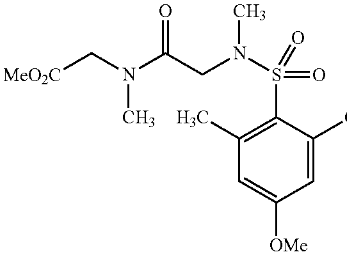

123a is prepared analogously to 1f from 0.20 g (0.70 mmol) of product from 121b, 0.097 g (0.70 mmol) of sarcosine methylester hydrochloride (Fluka), 0.29 ml (2.09 mmol) of triethylamine and 0.22 g (0.70 mmol) of TBTU in 5 ml THF.

$C_{16}H_{24}N_2O_6S$ (372.44)

[M+H]+=373

HPLC (Method 5): retention time=1.78 min

123b)

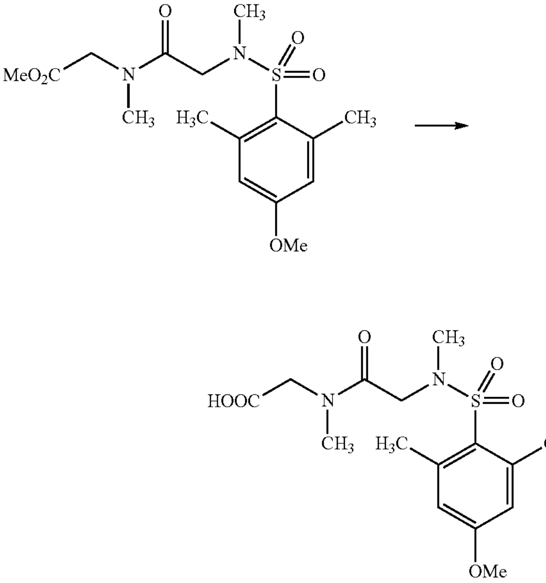

123b is prepared analogously to 121b from 0.23 g (0.60 mmol) of product from 123a and 0.62 ml (1.24 mmol) of 2 M sodium hydroxide solution in 1 ml of methanol.

$C_{15}H_{22}N_2O_6S$ (258.41)

[M+H]+=359

123c)

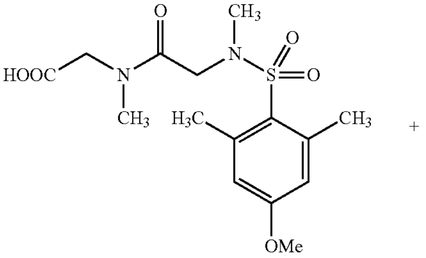

-continued

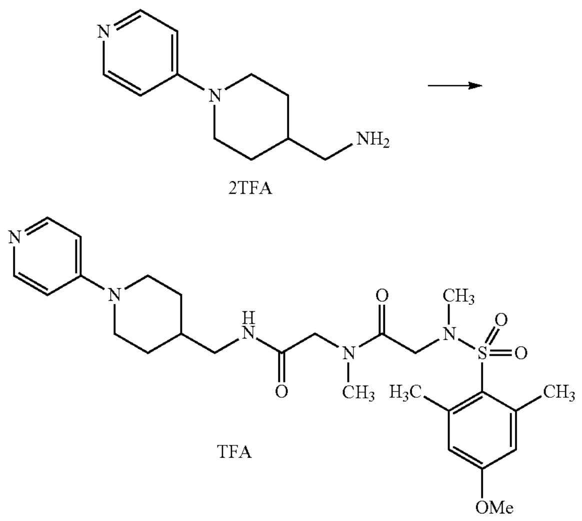

Example 123 is prepared analogously to 1f from 0.094 g (0.26 mmol) of product from 123b, 0.11 g (0.26 mmol) of product from 121f, 0.15 ml (1.05 mmol) of triethylamine and 0.084 g (0.26 mmol) of TBTU in 1.9 ml THF.

$C_{26}H_{37}N_5O_5S \times C_2HF_3O_2$ (645.69)

[M+H]+=532

HPLC (Method 5): retention time=1.47 min

Example 124

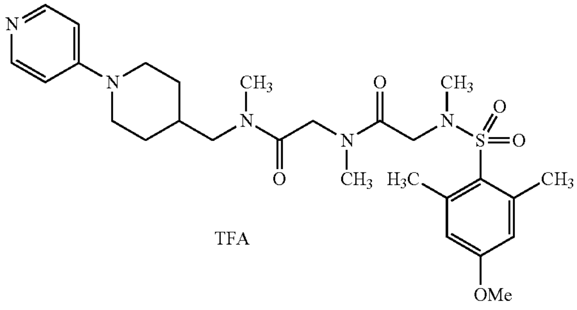

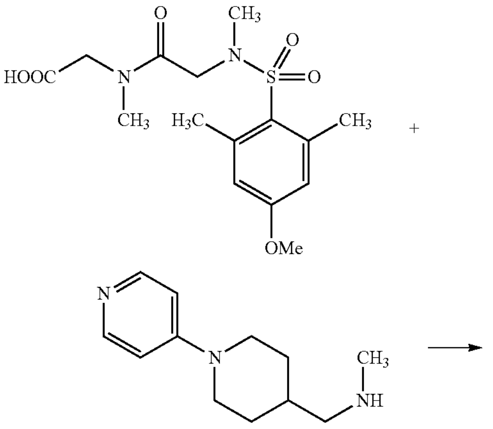

-continued

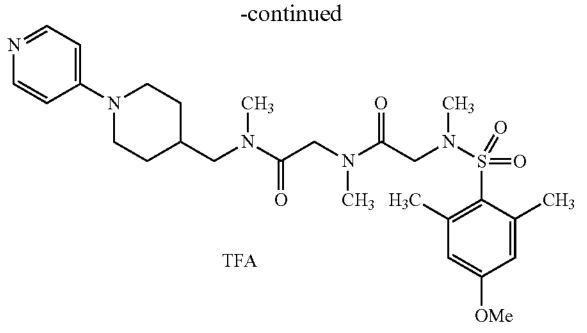

Example 124 is prepared analogously to 1f from 0.094 g (0.26 mmol) of product from 123b, 0.054 g (0.26 mmol) of product from 61b, 0.11 ml (0.78 mmol) of triethylamine and 0.084 g (0.26 mmol) of TBTU in 1.9 ml THF.

$C_{27}H_{39}N_5O_5S \times C_2HF_3O_2$ (659.72)

[M+H]+=548

HPLC (Method 5): retention time=1.49 min

Example 125

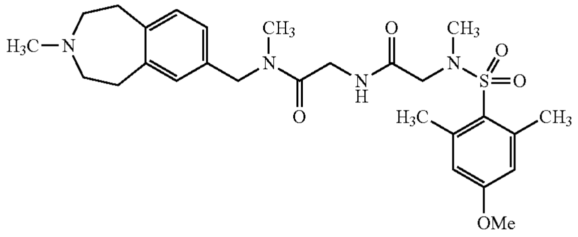

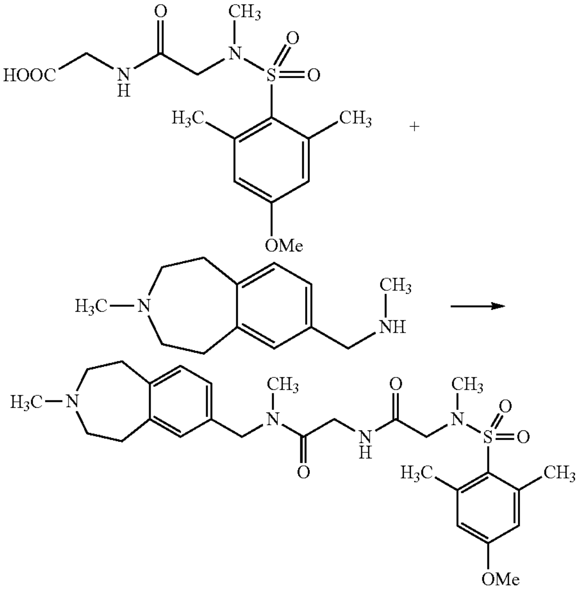

Example 125 is prepared analogously to 1f from 0.09 g (0.26 mmol) of product from 121d, 0.076 g (0.26 mmol) of product from 54b, 0.11 ml (0.78 mmol) of triethylamine and 0.084 g (0.26 mmol) of TBTU in 1.9 ml THF.

$C_{27}H_{38}N_4O_5S$ (530.68)

[M+H]+=531

HPLC (Method 1): retention time=2.43 min

Example 126

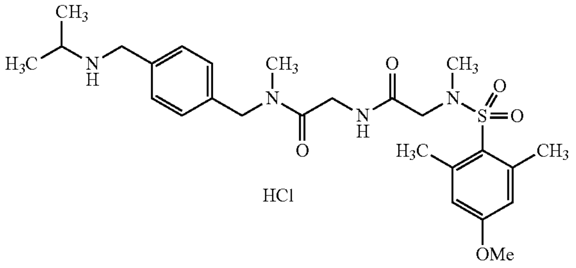

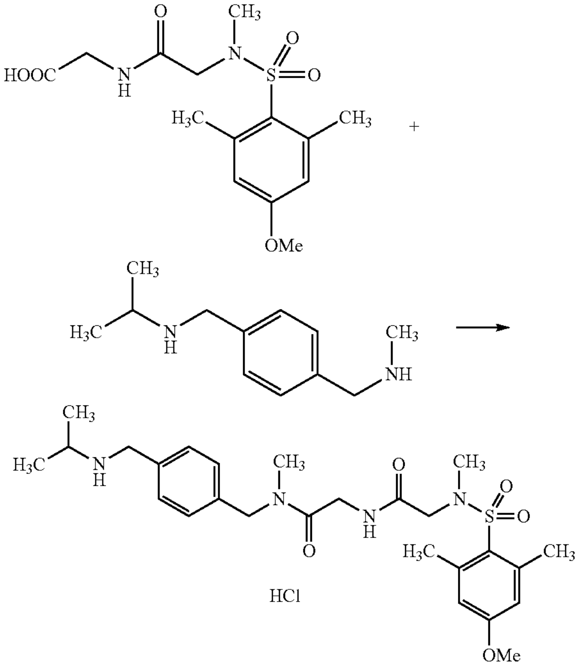

Example 126 is prepared analogously to 1f from 0.09 g (0.26 mmol) of product from 121d, 0.05 g (0.26 mmol) of product from 59b, 0.11 ml (0.78 mmol) of triethylamine and 0.084 g (0.26 mmol) of TBTU in 1.9 ml THF.

$C_{26}H_{38}N_4O_5S \times HCl$ (555.13)

[M+H]+=519

HPLC (Method 1): retention time=2.42 min

Example 127

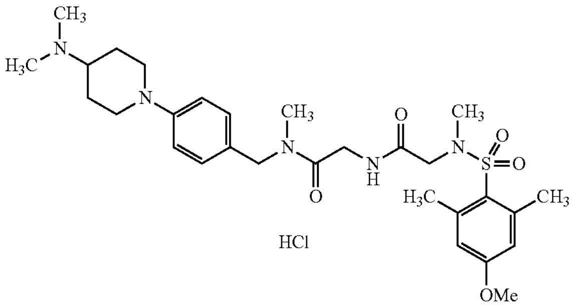

-continued

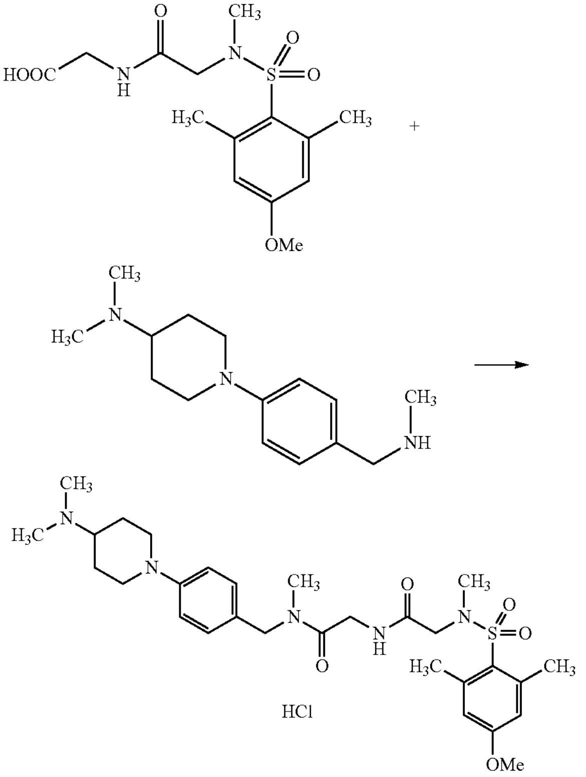

Example 127 is prepared analogously to 1f from 0.09 g (0.26 mmol) of product from 121d, 0.065 g (0.26 mmol) of product from 80a, 0.11 ml (0.78 mmol) of triethylamine and 0.084 g (0.26 mmol) of TBTU in 1.9 ml THF.

$C_{29}H_{43}N_5O_5S \times HCl$ (610.21)

[M+H]+=574

HPLC (Method 1): retention time=2.38 min

Example 128

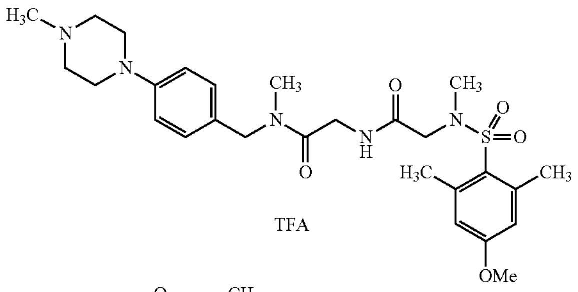

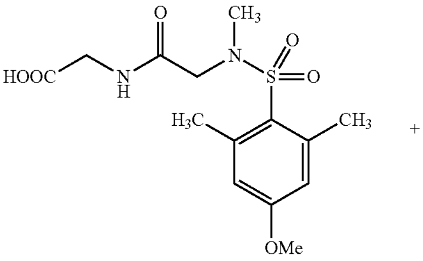

-continued

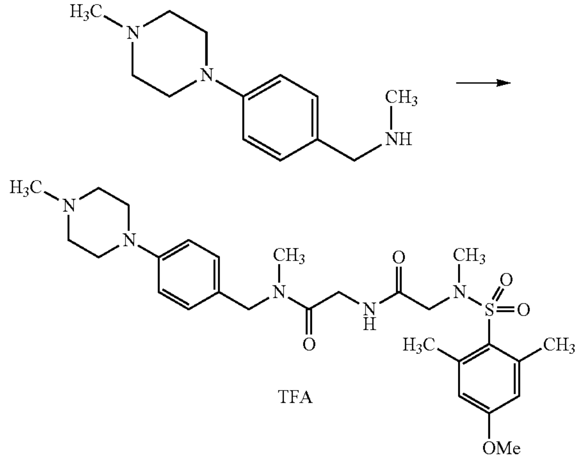

TFA

Example 128 is prepared analogously to 1f from 0.09 g (0.26 mmol) of product from 121d, 0.057 g (0.26 mmol) of product from 81a, 0.11 ml (0.78 mmol) of triethylamine and 0.084 g (0.26 mmol) of TBTU in 1.9 ml THF.

$C_{27}H_{39}N_5O_5S \times C_2HF_3O_2$ (610.21)

[M+H]+=546

HPLC (Method 5): retention time=1.51 min

Example 129

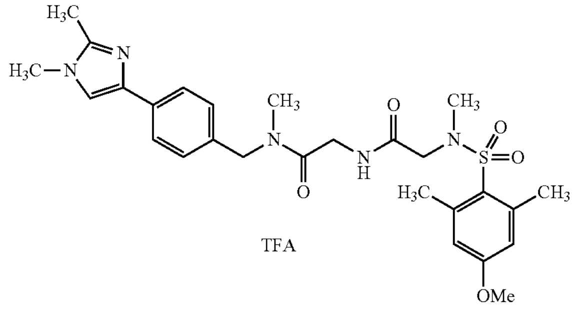

TFA

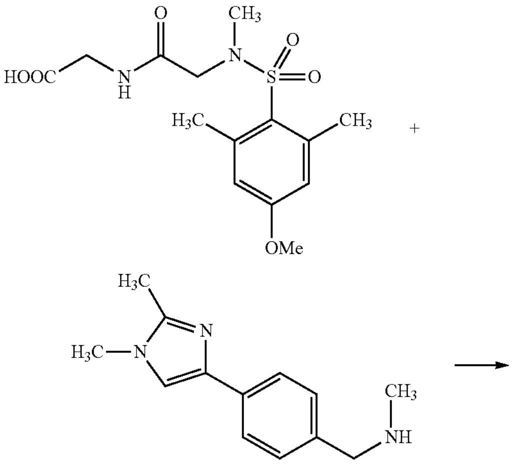

-continued

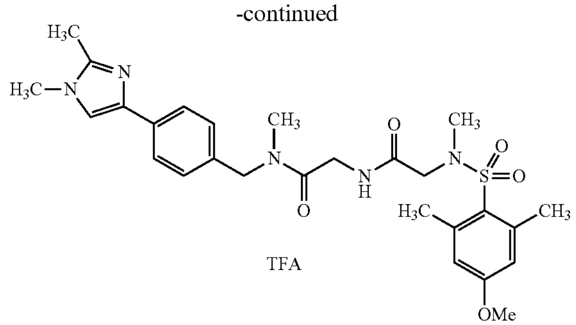

TFA

Example 129 is prepared analogously to 1f from 0.09 g (0.26 mmol) of product from 121d, 0.056 g (0.26 mmol) of product from 67c, 0.11 ml (0.78 mmol) of triethylamine and 0.084 g (0.26 mmol) of TBTU in 1.9 ml THF.

$C_{27}H_{35}N_5O_5S \times C_2HF_3O_2$ (655.69)

[M+H]+=542

HPLC (Method 5): retention time=1.52 min

Example 130

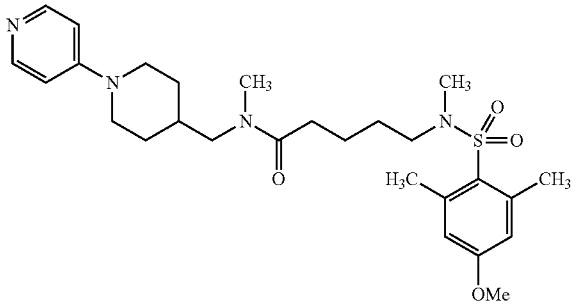

130a)

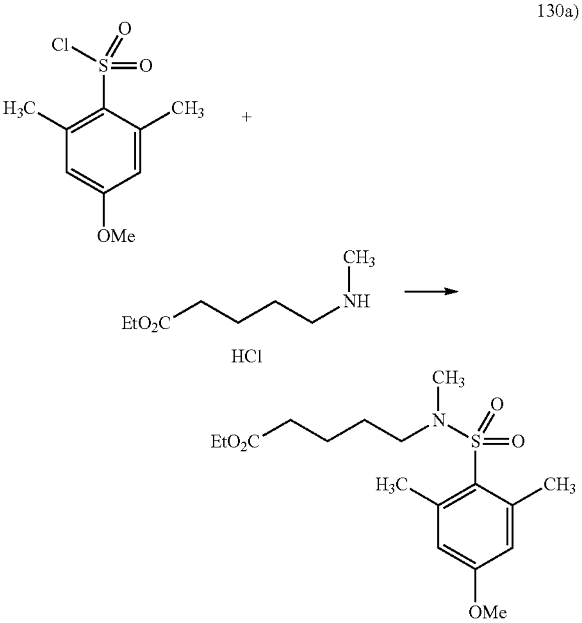

HCl 130a is prepared analogously to 10d from 0.50 g (2.13 mmol) of product from 13a, 0.42 g (2.13 mmol) of ethyl 5-methylaminovalerate (J. Am. Chem. Soc. 55, 1933, 1233-1241) and 1.18 ml (8.52 mmol) of triethylamine in 15 ml THF.

$C_{17}H_{27}NO_5S$ (357.47)
[M+H]+=358
HPLC (Method 6): retention time=4.10 min 130b)

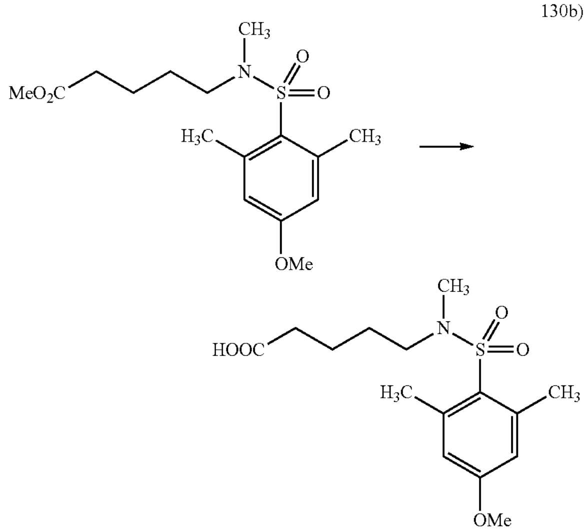

130b is prepared analogously to 121b from 0.62 g (1.73 mmol) of product from 130a and 7.00 ml (7.00 mmol) of 1 M sodium hydroxide solution in 1.5 ml of methanol and 15 ml THF.

$C_{15}H_{23}NO_5S$ (329.41)
[M+H]+=330
HPLC (Method 6): retention time=3.24 min 130c)

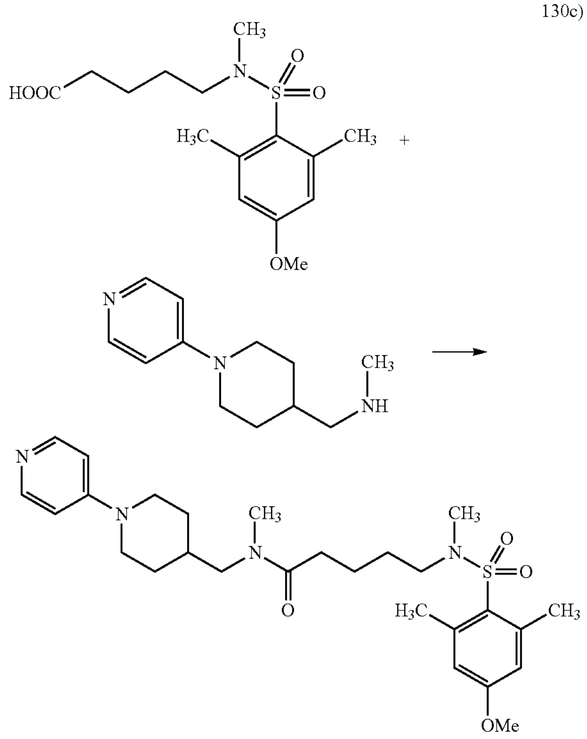

Example 130 is prepared analogously to 1f from 0.18 g (0.54 mmol) of product from 130b, 0.10 g (0.49 mmol) of product from 61b, 0.14 ml (0.97 mmol) of triethylamine and 0.18 g (0.54 mmol) of TBTU in 3 ml DMF.

$C_{27}H_{40}N_4O_4S$ (516.70)
[M+H]+=517
HPLC (Method 6): retention time=2.65 min

Example 131

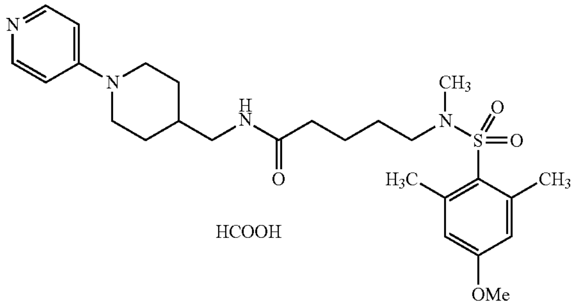

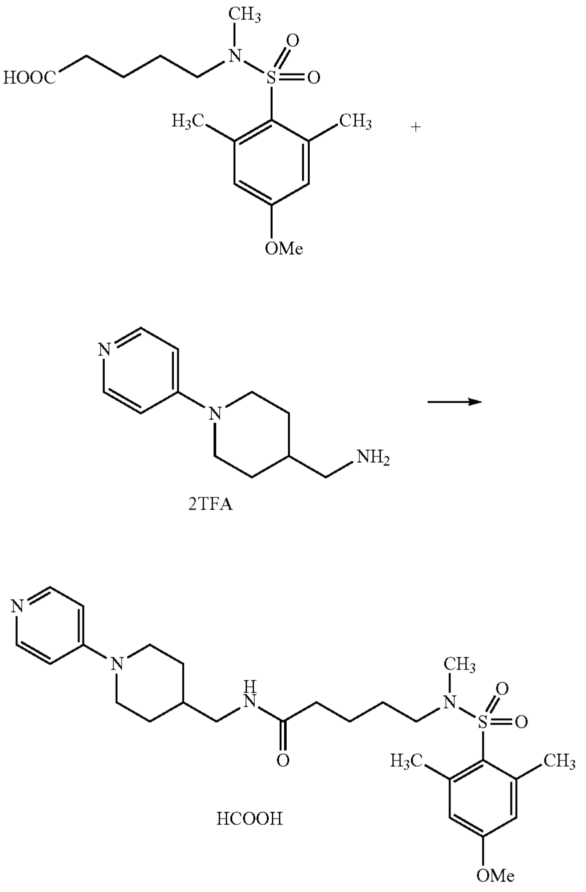

Example 131 is prepared analogously to 1f from 0.069 g (0.21 mmol) of product from 130b, 0.088 g (0.21 mmol) of product from 121f, 0.087 ml (0.63 mmol) of triethylamine and 0.077 g (0.23 mmol) of TBTU in 1 ml DMF.

$C_{26}H_{38}N_4O_4S \times CH_2O_2$ (548.71)
[M+H]+=503
HPLC (Method 6): retention time=2.52 min Example 132

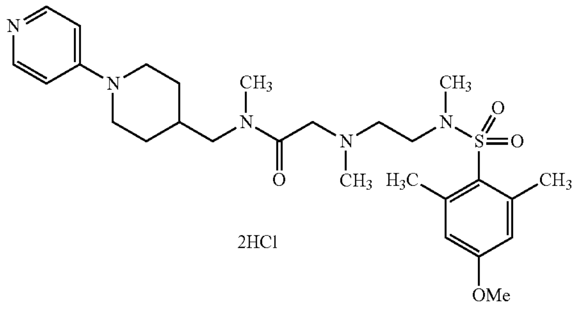

132a)

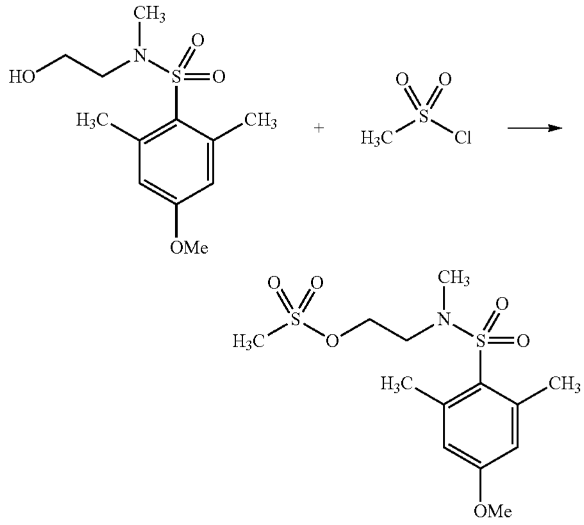

A mixture of 2.50 g (9.15 mmol) of product from 53a, 1.39 ml (10.00 mmol) of triethylamine and 50 ml THF is combined at ambient temperature with 0.77 ml (10.00 mmol) of methanesulphonic acid chloride (Aldrich). The reaction mixture is then stirred overnight at ambient temperature. The precipitate formed is filtered off. The filtrate is evaporated to dryness in vacuo. The residue is taken up in ethyl acetate and washed with water and saturated sodium chloride solution, dried on sodium sulphate and evaporated to dryness in vacuo.

$C_{13}H_{21}NO_6S_2$ (351.44)

[M+H]+=352

TLC: silica gel, dichloromethane/methanol 9.5:0.5, Rf value=0.95

132b)

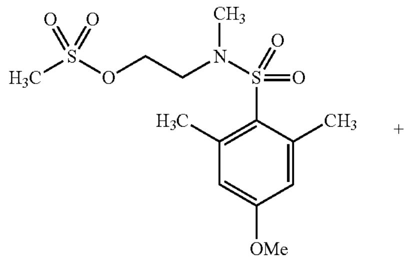

-continued

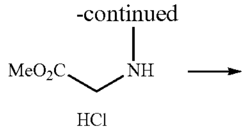

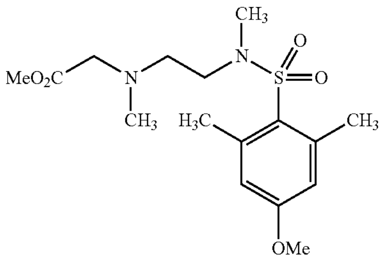

A mixture of 0.50 g (1.42 mmol) of product from 132a, 0.20 g (1.42 mmol) of sarcosine methylester hydrochloride (Aldrich), 0.52 ml (3.00 mmol) of DIPEA and 5 ml DMF is stirred for 24 hours at 80° C. The reaction mixture is evaporated down in vacuo. The residue is taken up in dichloromethane and washed with water and saturated sodium hydrogen carbonate solution, dried on sodium sulphate and evaporated to dryness in vacuo. The crude product thus obtained is purified by column chromatography (eluant: dichloromethane/0-3% methanol).

$C_{16}H_{26}N_2O_5S$ (358.45)

[M+H]+=359

132c)

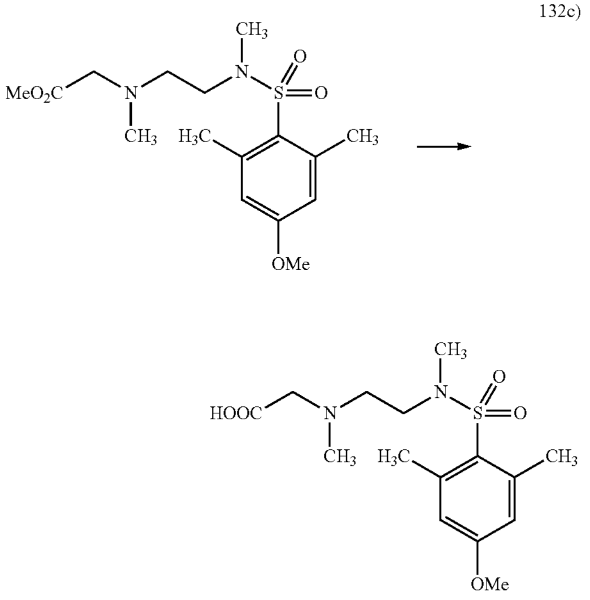 [SMILES: COC(=O)CN(C)CCN(C)S(=O)(=O)c1c(C)cc(OC)cc1C ; COc1cc(C)c(S(=O)(=O)N(C)CCN(C)CC(=O)O)c(C)c1]

132c is prepared analogously to 1c from 0.29 g (0.81 mmol) of product from 132b and 0.17 g (4.00 mmol) of lithium hydroxide monohydrate (Aldrich) in 5 ml THF and 4 ml of water.

$C_{15}H_{24}N_2O_5S$ (344.43)

HPLC (Method 1): retention time=2.32 min

132d)

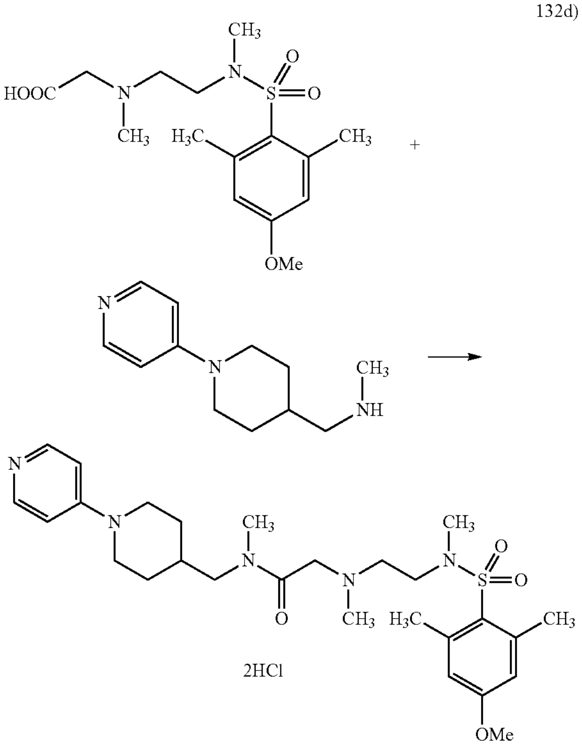

Example 132 is prepared analogously to 1f from 0.10 g (0.29 mmol) of product from 132c, 0.06 g (0.29 mmol) of product from 61b, 0.084 ml (0.60 mmol) of triethylamine and 0.096 g (0.30 mmol) of TBTU in 10 ml DMF.

$C_{27}H_{41}N_5O_4S \times 2HCl$ (604.63)

[M+H]+=532

HPLC (Method 5): retention time=1.39 min

Example 133

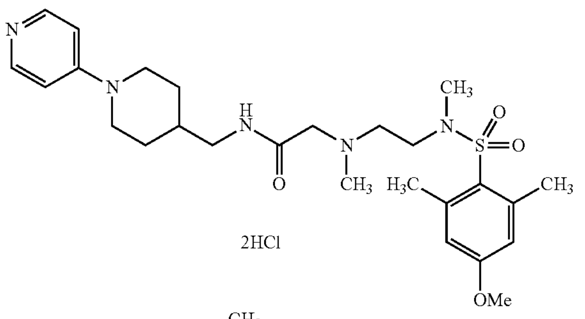

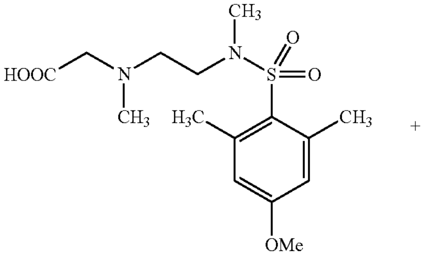

-continued

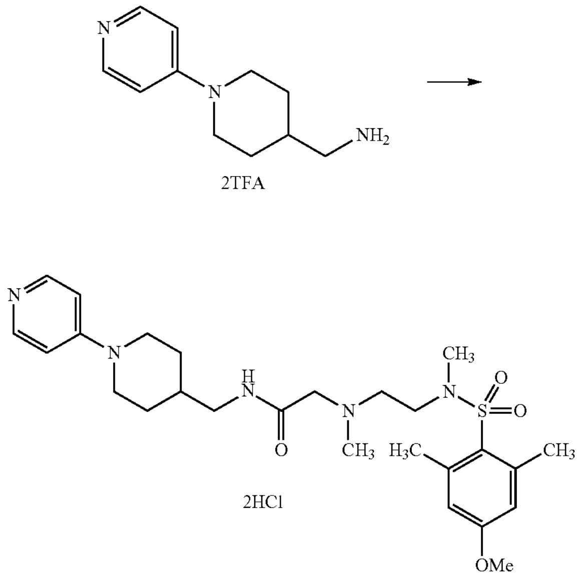

Example 133 is prepared analogously to 1f from 0.10 g (0.29 mmol) of product from 132c, 0.12 g (0.29 mmol) of product from 121f, 0.17 ml (1.20 mmol) of triethylamine and 0.096 g (0.30 mmol) of TBTU in 60 ml DMF.

$C_{26}H_{39}N_5O_4S \times 2HCl$ (590.61)

[M+H]+=518

HPLC (Method 5): retention time=1.37 min

Example 134

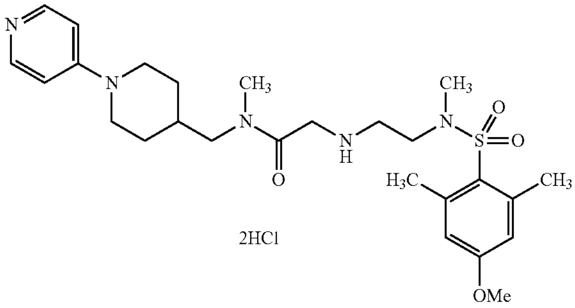

134a)

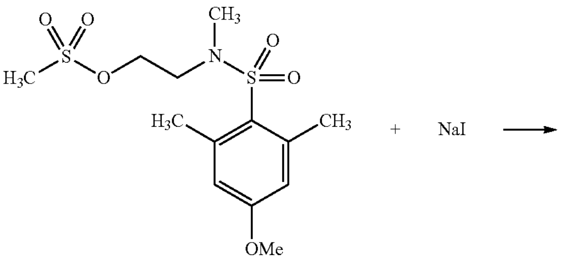

-continued

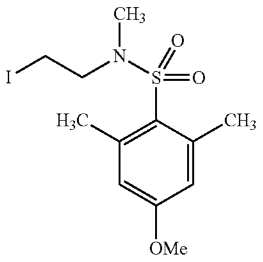

A mixture of 1.60 g (4.55 mmol) of product from 132a, 2.10 g (14.00 mmol) of sodium iodide and 30 ml acetone is stirred for eight hours at reflux temperature. The reaction mixture is then filtered through silica gel. The filtrate is evaporated to dryness in vacuo. The residue is taken up in ethyl acetate, washed with water, dried on sodium sulphate and evaporated to dryness in vacuo.

$C_{12}H_{18}INO_3S$ (383.25)

[M+H]+=384

HPLC (Method 1): retention time=3.75 min

134b)

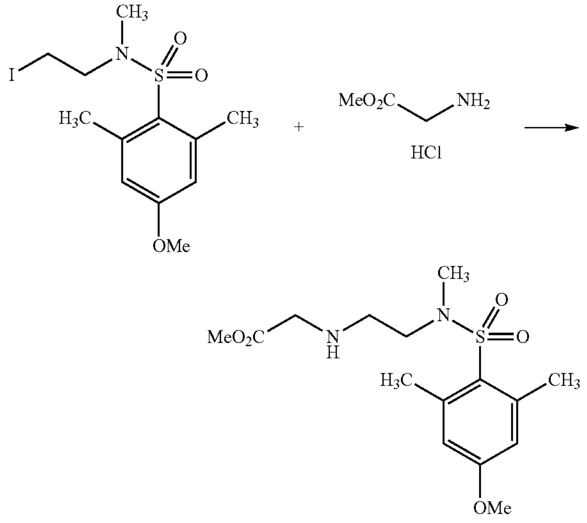

134b is prepared analogously to 132b from 1.30 g (3.39 mmol) of product from 134a, 1.28 g (10.20 mmol) of glycine methylester hydrochloride (Aldrich) and 3.48 ml (20.00 mmol) of DIPEA in 15 ml acetonitrile.

$C_{15}H_{24}N_2O_5S$ (344.43)

[M+H]+=345

TLC: silica gel, dichloromethane/methanol 9.5:0.5, Rf value=0.38

134c)

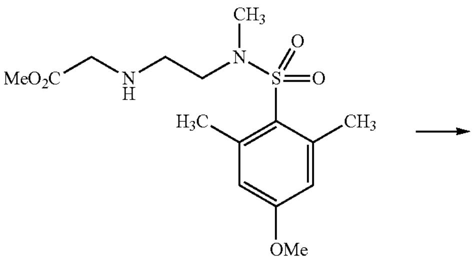

-continued

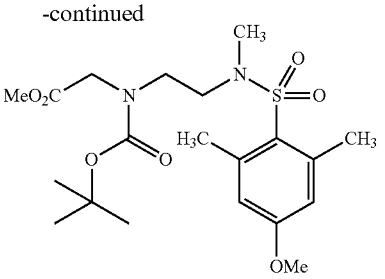

A mixture of 0.46 g (1.34 mmol) of product from 134b, 0.33 g (1.50 mmol) of Boc-anhydride, 0.21 ml (1.50 mmol) of triethylamine and 30 ml dichloromethane is stirred overnight at ambient temperature. The reaction mixture is then diluted with dichloromethane and washed with saturated sodium hydrogen carbonate solution and saturated sodium chloride solution, dried on sodium sulphate and evaporated to dryness in vacuo.

$C_{20}H_{32}N_2O_7S$ (444.54)

[M+H]+=445

TLC: silica gel, dichloromethane/methanol 9.5:0.5, Rf value=0.45

134d)

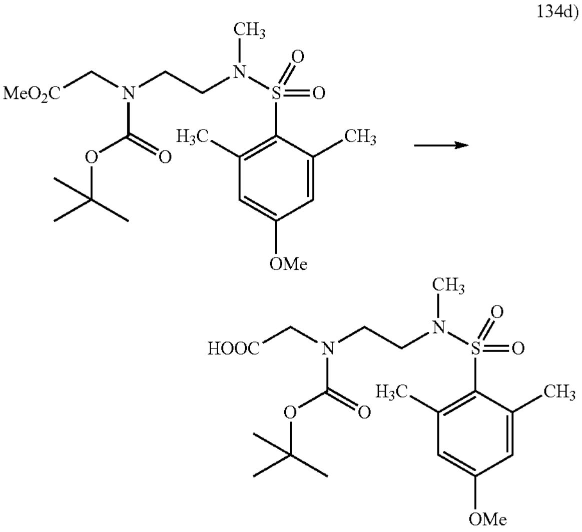

134d is prepared analogously to 1c from 0.59 g (1.33 mmol) of product from 134c and 0.28 g (6.60 mmol) of lithium hydroxide monohydrate (Aldrich) in 7 ml THF and 6.6 ml of water.

$C_{19}H_{30}N_2O_7S$ (430.52)

[M+H]+=431

134e)

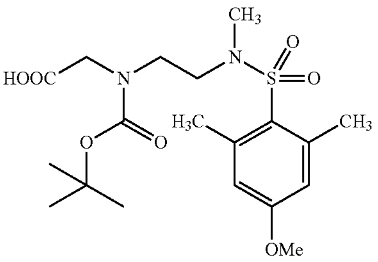
+

-continued

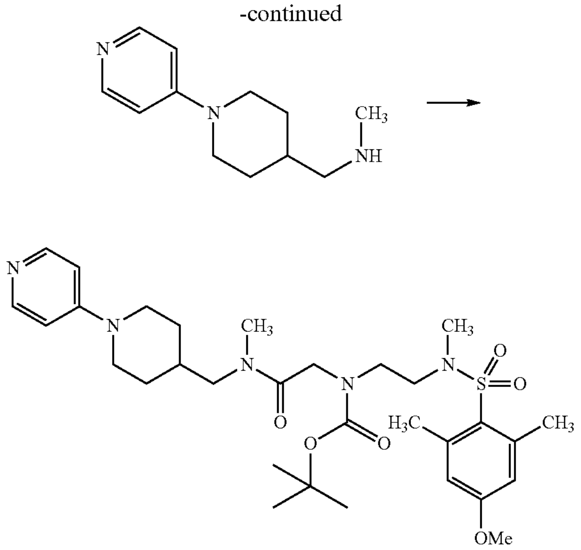

134e is prepared analogously to 1f from 0.15 g (0.35 mmol) of product from 134d, 0.072 g (0.35 mmol) of product from 61b, 0.098 ml (0.70 mmol) of triethylamine and 0.11 g (0.35 mmol) of TBTU in 7 ml DMF.

$C_{31}H_{47}N_5O_6S$ (617.80)

[M+H]+=618

HPLC (Method 1): retention time=2.62 min

134f)

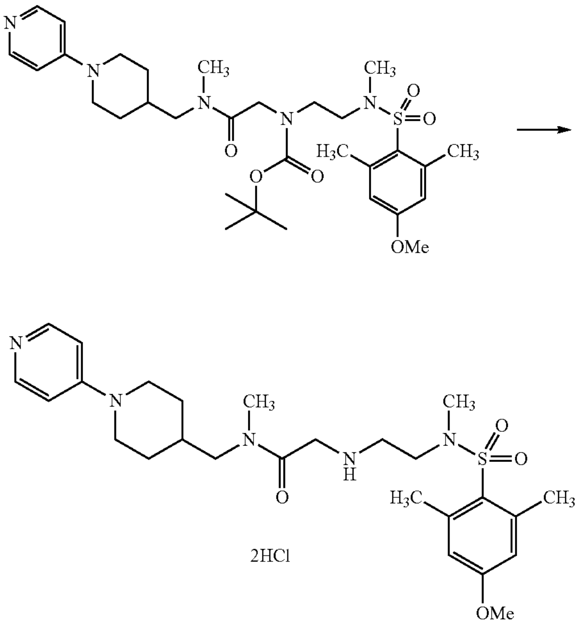

Example 134 is prepared analogously to 18b from 0.16 g (0.26 mmol) of product from 134e and 3 ml TFA in 3 ml dichloromethane.

$C_{26}H_{39}N_5O_4S \times 2HCl$ (590.61)

[M+H]+=518

HPLC (Method 5): retention time=1.40 min

Example 135

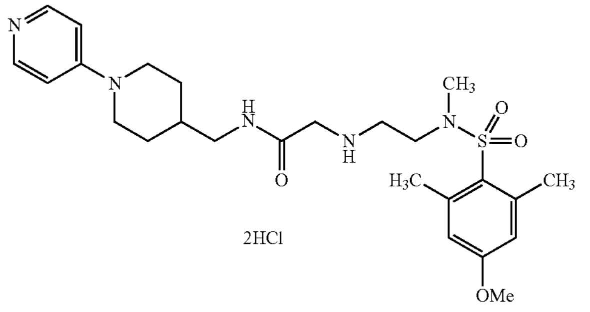

135a)

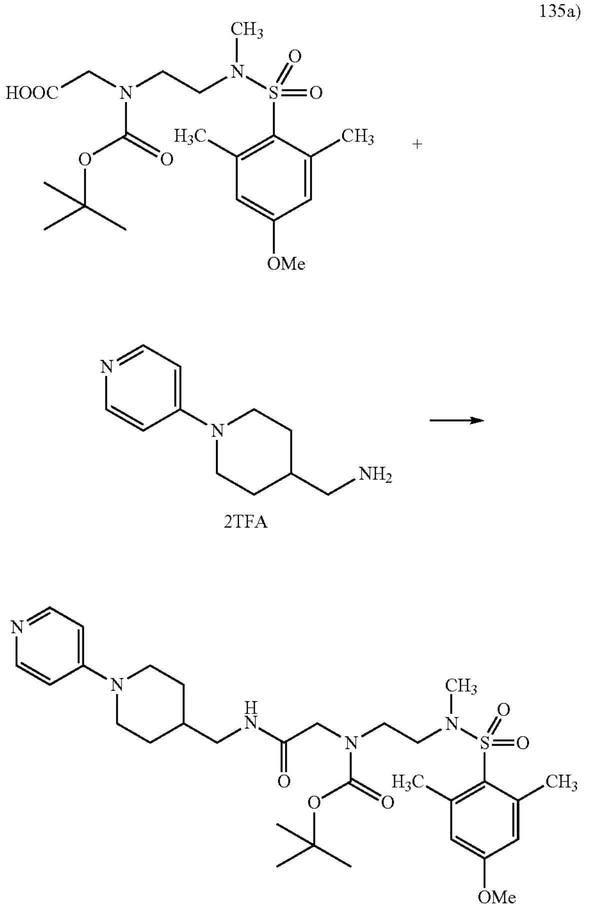

135a is prepared analogously to 1f from 0.15 g (0.35 mmol) of product from 134d, 0.15 g (0.35 mmol) of product from 121f, 0.20 ml (1.40 mmol) of triethylamine and 0.11 g (0.35 mmol) of TBTU in 7 ml DMF.

$C_{30}H_{45}N_5O_6S$ (603.77)

[M+H]+=604

TLC: silica gel, dichloromethane/methanol/ammonia 9:1:0.1, Rf value=0.48

135b)

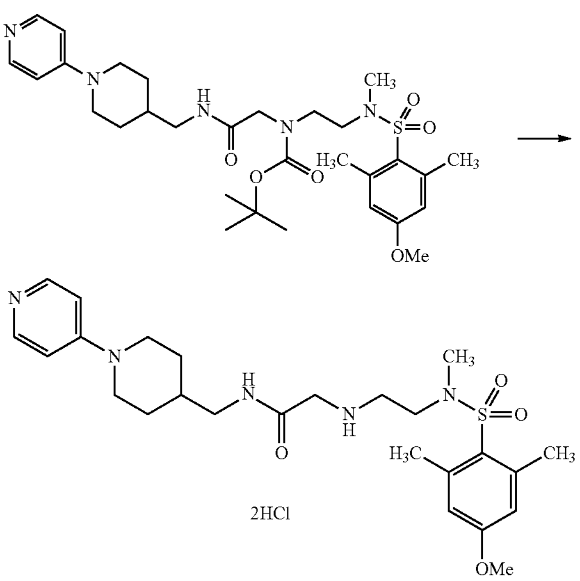

2HCl

Example 135 is prepared analogously to 18b from 0.16 g (0.27 mmol) of product from 135a and 5 ml TFA in 5 ml dichloromethane.

$C_{25}H_{37}N_5O_4S\times2HCl$ (576.58)

[M+H]+=504

HPLC (Method 1): retention time=2.17 min

Example 136

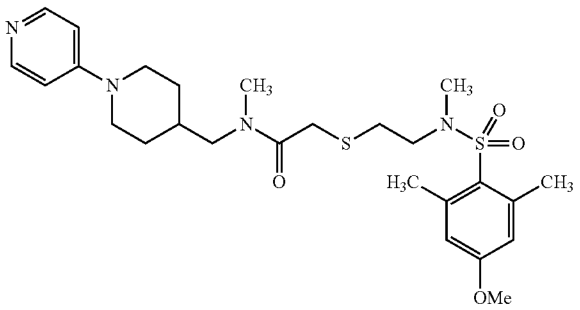

136a)

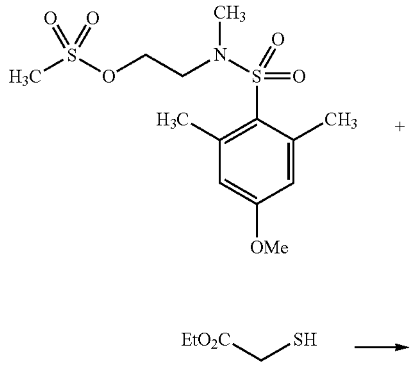

-continued

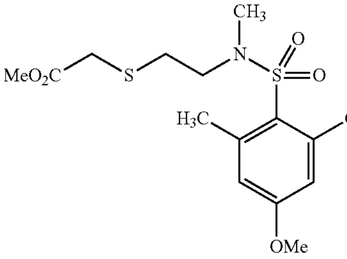

A mixture of 0.21 g (0.60 mmol) of product from 132a, 0.065 ml (0.60 mmol) of ethyl mercaptoacetate (Aldrich), 0.17 g (1.20 mmol) of potassium carbonate and 10 ml acetonitrile is stirred for 24 hours at ambient temperature. The precipitate is filtered off, the filtrate is evaporated down in vacuo. The crude product thus obtained is purified by preparative HPLC.

$C_{16}H_{25}NO_5S_2$ (375.51)

[M+H]+=376

136b)

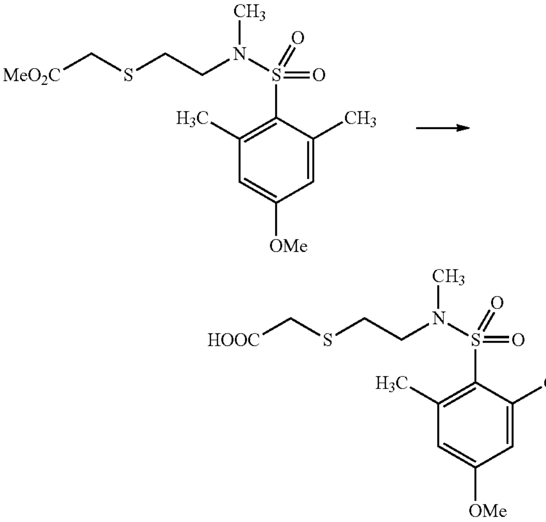

136b is prepared analogously to 121b from 0.070 g (0.19 mmol) of product from 136a and 2.00 ml (2.00 mmol) of 1 M sodium hydroxide solution in 5 ml THF.

$C_{14}H_{21}NO_5S_2$ (347.45)

[M+H]+=348

136c)

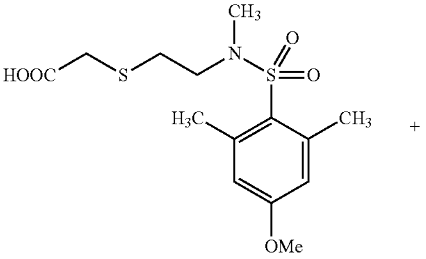

-continued

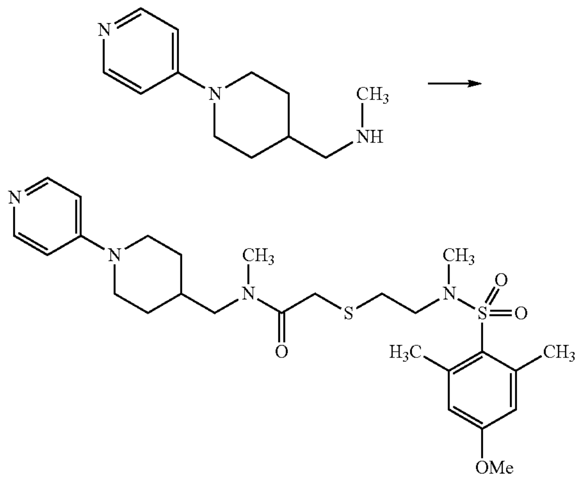

Example 136 is prepared analogously to 1f from 0.064 g (0.18 mmol) of product from 136b, 0.038 g (0.18 mmol) of product from 61b, 0.079 ml (0.46 mmol) of DIPEA and 0.059 g (0.18 mmol) of TBTU in 5 ml DMF.

$C_{26}H_{38}N_4O_4S_2$ (534.74)

[M+H]+=535

HPLC (Method 6): retention time=2.68 min

Example 137

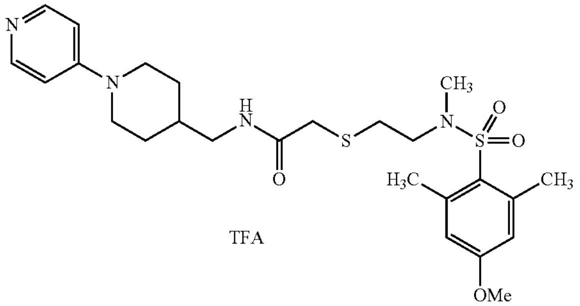

TFA

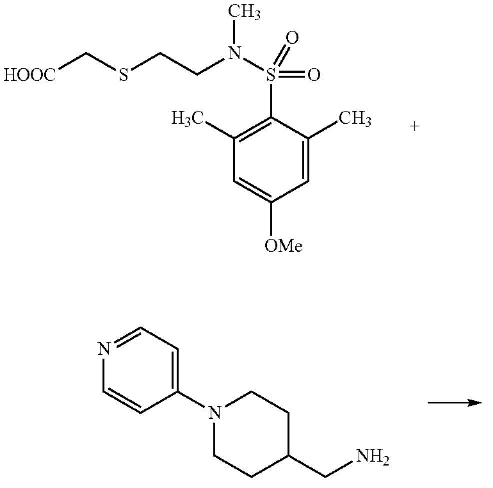

2TFA

-continued

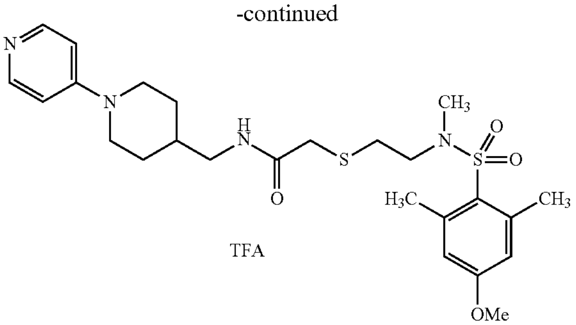

TFA

Example 137 is prepared analogously to 1f from 0.073 g (0.21 mmol) of product from 136b, 0.088 g (0.21 mmol) of product from 121f, 0.11 ml (0.63 mmol) of DIPEA and 0.087 g (0.27 mmol) of TBTU in 5 ml DMF.

$C_{25}H_{36}N_4O_4S_2 \times C_2HF_3O_2$ (634.73)

[M+H]+=521

HPLC (Method 6): retention time=2.57 min

Example 138

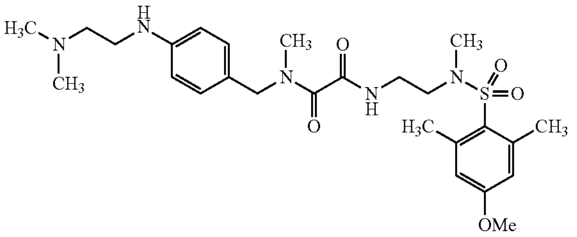

138a)

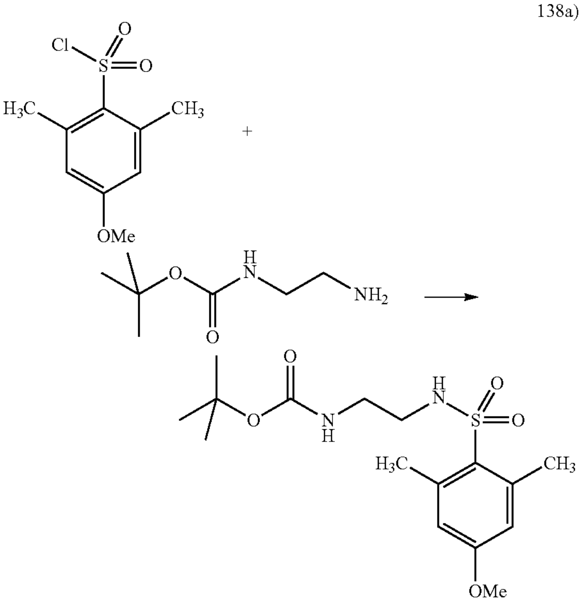

138a is prepared analogously to 3a from 2.0 g (8.52 mmol) of product of 13a, 1.37 g (8.55 mmol) of N-Boc-ethylenediamine (Fluka) and 1.0 g (9.89 mmol) of triethylamine in 50 ml THF.

$C_{16}H_{26}N_2O_5S$ (358.45)

[M−H]−=357

HPLC (Method 6): retention time=3.63 min

138b)

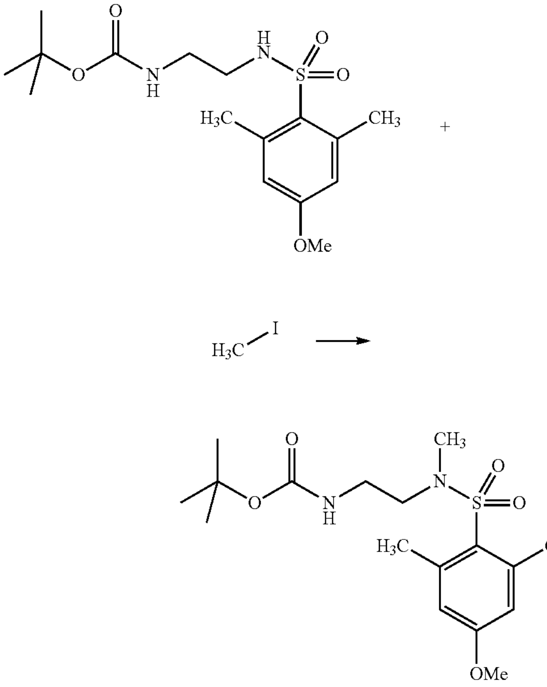

138b is prepared analogously to 3b from 3.38 g (9.43 mmol) of the product of 138a, 0.53 ml (8.55 mmol) of methyl iodide, 1.77 g (12.83 mmol) of potassium carbonate under anhydrous conditions in 30 ml DMSO.

$C_{17}H_{28}N_2O_5S$ (372.48)

[M+H]+=373

HPLC (Method 6): retention time=3.89 min

138c)

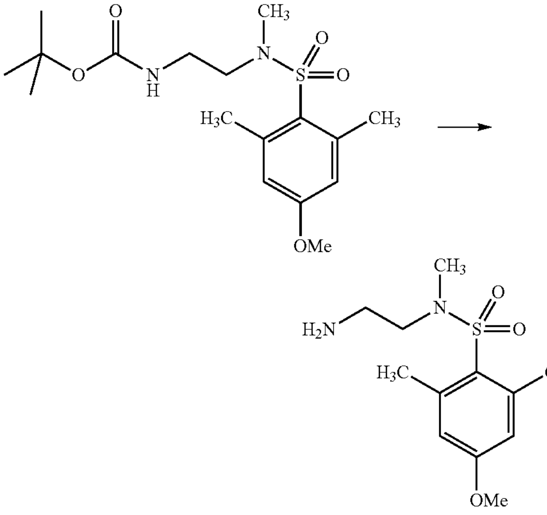

138b is prepared analogously to 28d from 3.61 g (9.69 mmol) of the product of 138b and 10 ml TFA in 50 ml dichloromethane.

$C_{127}H_{20}N_2O_3S$ (272.36)

[M+H]+=273

HPLC (Method 6): retention time=1.95 min

138d)

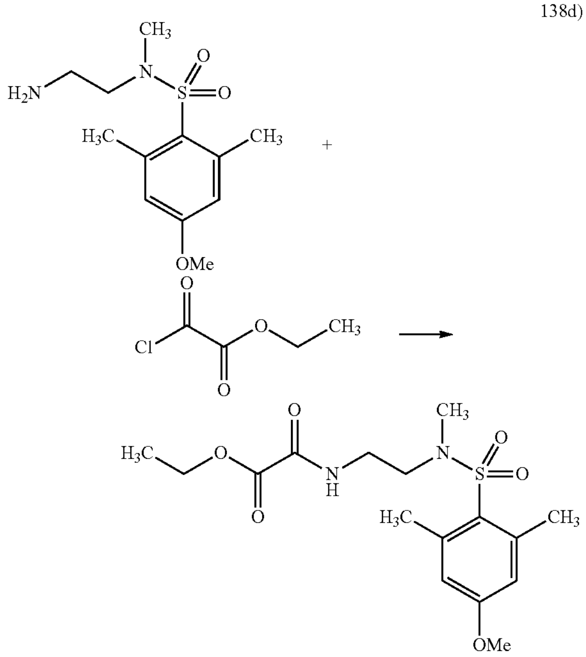

A mixture of 0.50 g (1.84 mmol) of the product of 138c, 0.56 ml (5.51 mmol) of triethylamine and 25 ml dichloromethane is combined with 0.38 ml (2.75 mmol) of monoethyl oxalate chloride (Fluka) in 5 ml dichloromethane while cooling with an ice bath and the mixture is stirred for two hours at ambient temperature. The reaction mixture is then diluted with dichloromethane, washed with 10% aqueous citric acid solution, saturated sodium sulphate solution and with water, dried on sodium sulphate and evaporated to dryness in vacuo.

$C_{16}H_{24}N_2O_6S$ (372.44)

[M+H]+=373

138e)

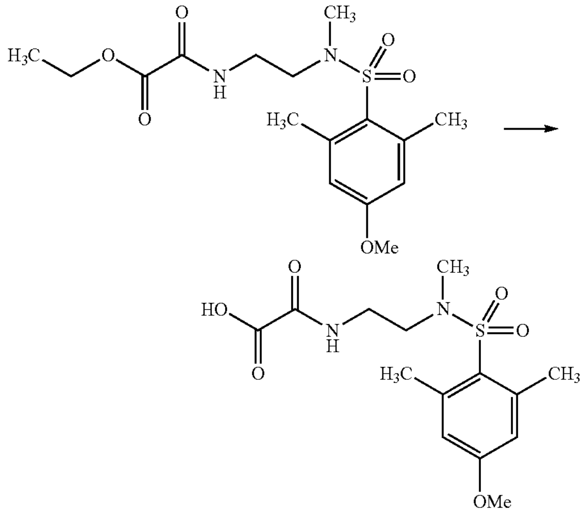

A mixture of 0.60 g (1.60 mmol) of the product of 138d, 5.6 ml 1 M sodium hydroxide solution and 6 ml of ethanol is stirred for four hours at ambient temperature and then evaporated to dryness in vacuo. The residue is combined with 8 ml 1 M hydrochloric acid and extracted with ethyl acetate. The combined organic extracts are washed with water and saturated sodium chloride solution, dried on sodium sulphate and evaporated to dryness in vacuo.

$C_{14}H_{20}N_2O_6S$ (344.38)

[M+H]+=345

138f)

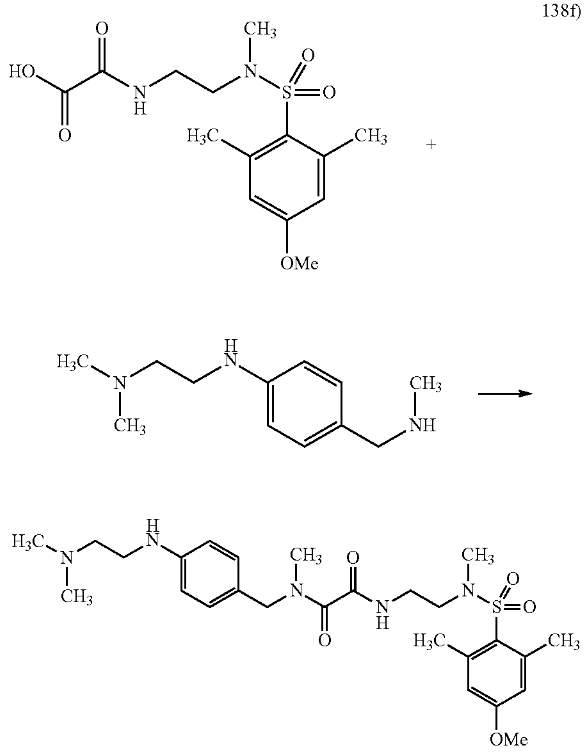

Example 138 is prepared analogously to 1f from 40.0 mg (0.12 mmol) of the product of 138e, 48.2 mg (0.12 mmol) of N,N-dimethyl-N'-(4-methylaminomethyl-phenyl)-ethan-1, 2-diamine (analogously to J. Chem. Soc 1960, 3163-3165), 0.038 ml (0.29 mmol) of DIPEA and 38.9 mg (0.12 mmol) of TBTU in 1.5 ml DMF.

$C_{26}H_{39}N_5O_5S$ (533.68)

[M+H]+=534

HPLC (Method 6): retention time=1.61 min

Example 139

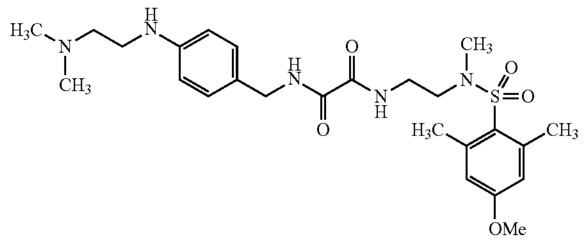

-continued

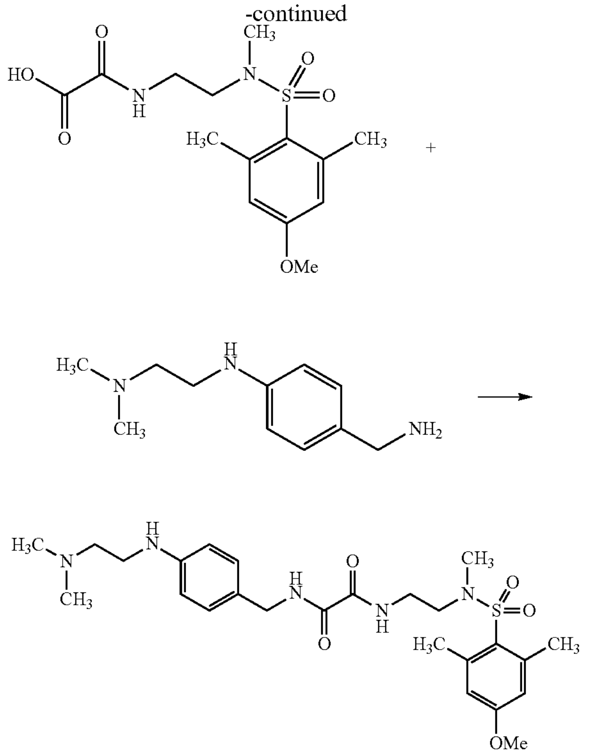

Example 139 is prepared analogously to 1f from 40.0 mg (0.12 mmol) of the product of 138e, 22.5 mg (0.12 mmol) of N-(4-aminomethyl-phenyl)-N',N'-dimethylethan-1,2-diamine (analogously to J. Chem. Soc 1960, 3163-3165), 0.038 ml (0.29 mmol) of DIPEA and 38.9 mg (0.12 mmol) of TBTU in 1.5 ml DMF.

$C_{25}H_{37}N_5O_5S$ (519.66)

[M+H]+=520

HPLC (Method 6): retention time=1.53 min

The following compounds were prepared analogously to Example 22:

Example 140

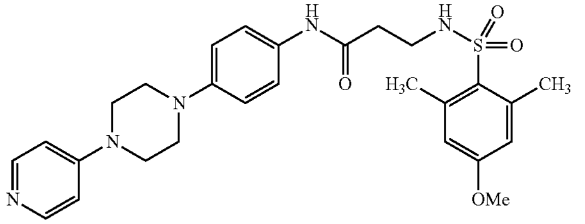 [SMILES: COc1cc(C)c(S(=O)(=O)NCCC(=O)Nc2ccc(N3CCN(c4ccncc4)CC3)cc2)c(C)c1]

$C_{27}H_{33}N_5O_4S \times C_2HF_3O_2$ (637.67)

[M+H]+=524

HPLC (Method 6): retention time=2.43 min

Example 141

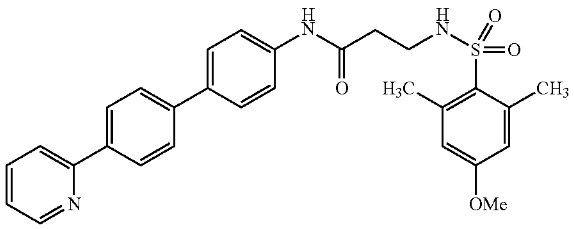 [SMILES: COc1cc(C)c(S(=O)(=O)NCCC(=O)Nc2ccc(-c3ccc(-c4ccccn4)cc3)cc2)c(C)c1]

$C_{29}H_{29}N_3O_4S \times C_2HF_3O_2$ (629.65)

[M+H]+=516

HPLC (Method 6): retention time=3.39 min

Example 142

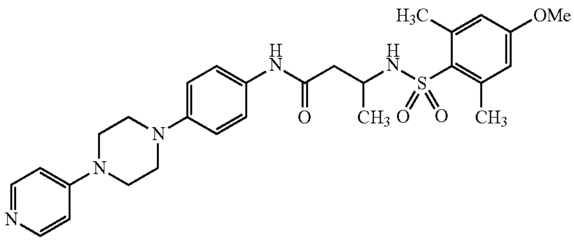 [SMILES: COc1cc(C)c(S(=O)(=O)NC(C)CC(=O)Nc2ccc(N3CCN(c4ccncc4)CC3)cc2)c(C)c1]

$C_{28}H_{35}N_5O_4S$ (537.67)

[M+H]+=538

HPLC (Method 6): retention time=2.45 min

Example 143

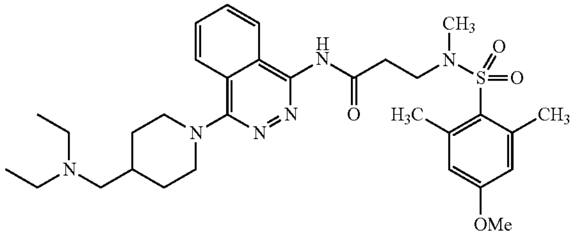 [SMILES: CCN(CC)CC1CCN(c2nnc(NC(=O)CCN(C)S(=O)(=O)c3c(C)cc(OC)cc3C)c3ccccc23)CC1]

$C_{31}H_{44}N_6O_4S \times C_2HF_3O_2$ (710.81)

[M+H]+=597

HPLC (Method 6): retention time=2.30 min

Example 144

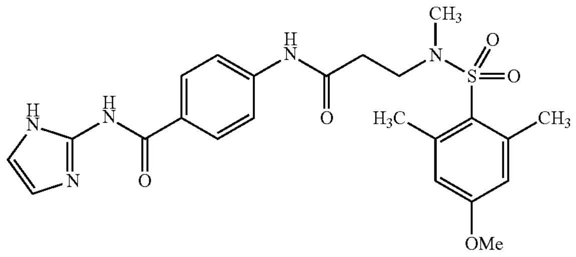 [SMILES: COc1cc(C)c(S(=O)(=O)N(C)CCC(=O)Nc2ccc(C(=O)Nc3ncc[nH]3)cc2)c(C)c1]

$C_{23}H_{27}N_5O_5S \times C_2HF_3O_2$ (599.58)

[M+H]+=486

HPLC (Method 6): retention time=2.46 min

Example 145

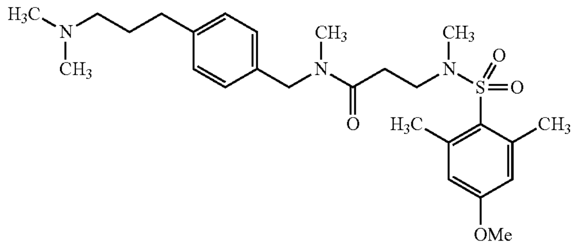

$C_{26}H_{39}N_3O_4S$ (489.67)

[M+H]+=490

HPLC (Method 6): retention time=2.66 min

Example 146

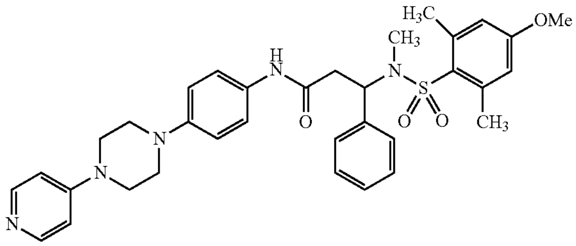 [SMILES: COc1cc(C)c(S(=O)(=O)N(C)C(CC(=O)Nc2ccc(N3CCN(c4ccncc4)CC3)cc2)c2ccccc2)c(C)c1]

$C_{34}H_{39}N_5O_4S$ (613.77)

[M+H]+=614

HPLC (Method 6): retention time=3.07 min

Example 147

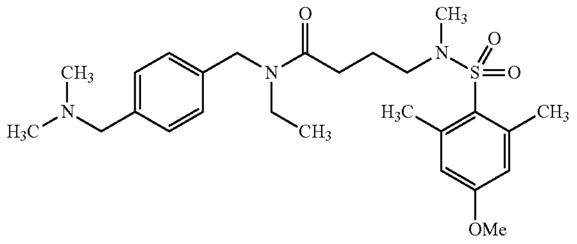

$C_{26}H_{39}N_3O_4S{\times}C_2HF_3O_2$ (603.70)

[M+H]+=490

HPLC (Method 6): retention time=2.60 min

Example 148

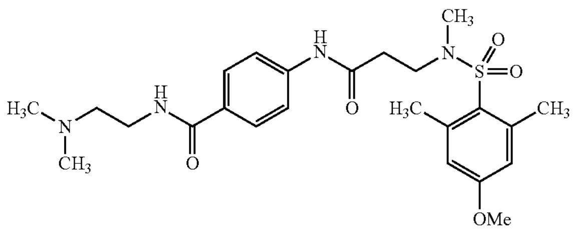

$C_{24}H_{34}N_4O_5S{\times}CH_2O_2$ (536.64)

[M+H]+=491

HPLC (Method 6): retention time=2.29 min

Example 149

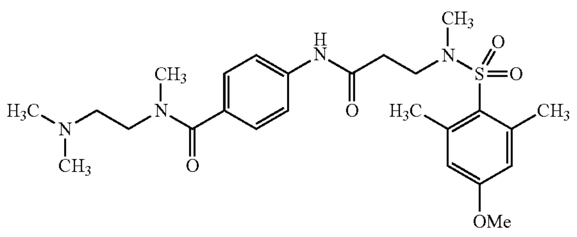

$C_{25}H_{36}N_4O_5S{\times}CH_2O_2$ (550.67)

[M+H]+=505

HPLC (Method 6): retention time=2.32 min

Example 150

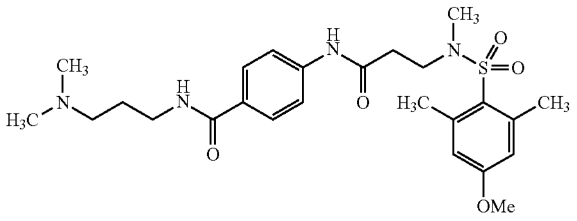

$C_{25}H_{36}N_4O_5S$ (504.64)

[M+H]+=505

HPLC (Method 6): retention time=2.31 min

Example 151

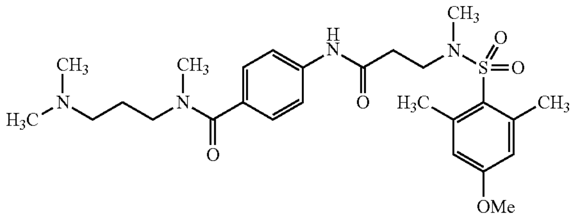

$C_{26}H_{38}N_4O_5S{\times}CH_2O_2$ (564.70)

[M+H]+=519

HPLC (Method 6): retention time=2.34 min

Example 152

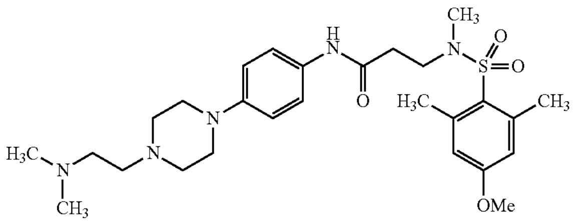

$C_{27}H_{41}N_5O_4S{\times}2C_2HF_3O_2$ (759.76)

[M+H]+=532

HPLC (Method 5): retention time=1.40 min

Example 153

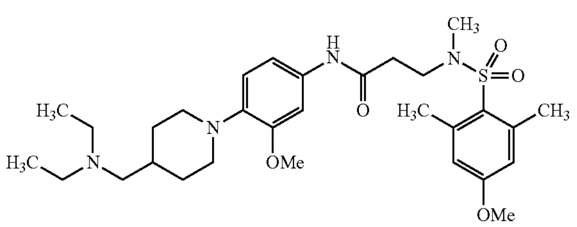 [SMILES: CCN(CC)CC1CCN(c2ccc(NC(=O)CCN(C)S(=O)(=O)c3c(C)cc(OC)cc3C)cc2OC)CC1]

$C_{30}H_{46}N_4O_5S{\times}HCl$ (611.24)

[M+H]+=575

HPLC (Method 1): retention time=2.12 min

Example 154

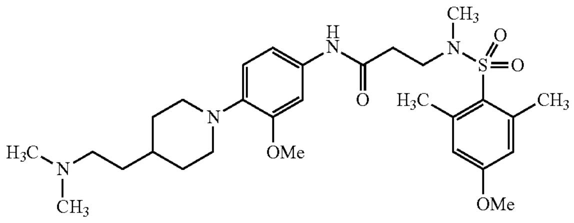

$C_{29}H_{44}N_4O_5S \times HCl$ (597.21)
[M+H]+=561
HPLC (Method 8): retention time=3.12 min Example 155

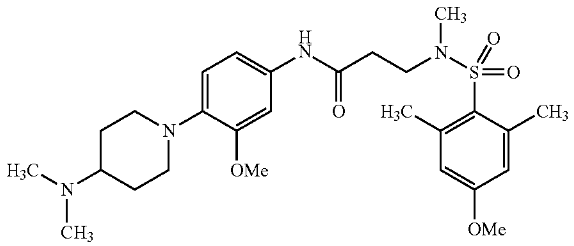

$C_{27}H_{40}N_4O_5S \times HCl$ (569.16)
[M+H]+=533
HPLC (Method 11): retention time=1.67 min Example 156

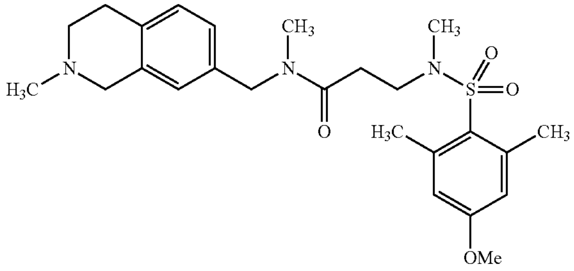

$C_{25}H_{35}N_3O_4S \times HCl$ (510.09)
[M+H]+=474
HPLC (Method 7): retention time=1.90 min Example 157

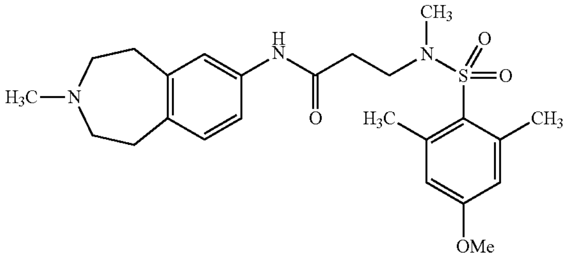

$C_{24}H_{33}N_3O_4S \times C_2HF_3O_2$ (573.63)
[M+H]+=460
HPLC (Method 5): retention time=1.52 min Example 158

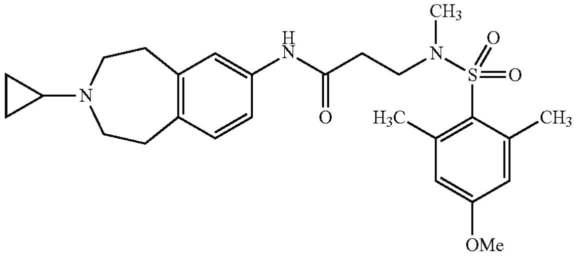 [SMILES: COc1cc(C)c(S(=O)(=O)N(C)CCC(=O)Nc2ccc3c(c2)CCN(C2CC2)CC3)c(C)c1]

$C_{26}H_{35}N_3O_4S \times C_2HF_3O_2$ (599.66)
[M+H]+=486
HPLC (Method 5): retention time=1.55 min Example 159

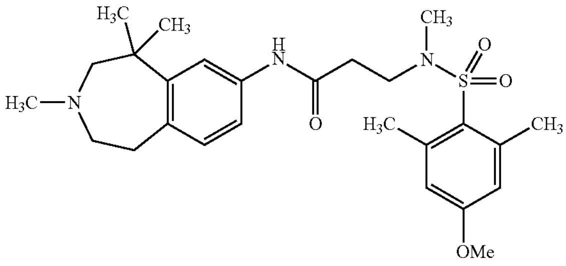

$C_{26}H_{37}N_3O_4S \times C_2HF_3O_2$ (601.68)
[M+H]+=488
HPLC (Method 5): retention time=1.54 min Example 160

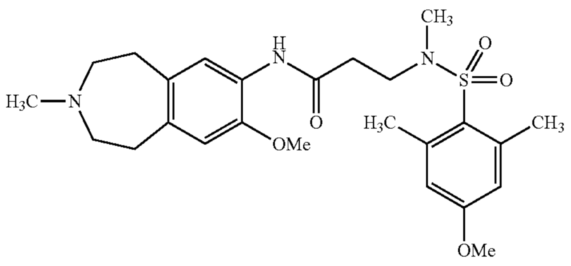

$C_{25}H_{35}N_3O_5S \times C_2HF_3O_2$ (603.65)

[M+H]+=490

HPLC (Method 5): retention time=1.54 min

Example 161

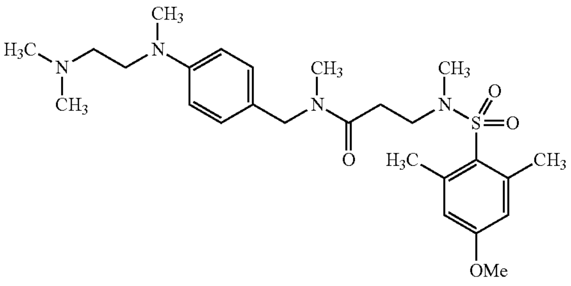

$C_{26}H_{40}N_4O_4S \times HCl$ (541.15)

[M+H]+=505

HPLC (Method 5): retention time=1.59 min

Example 162

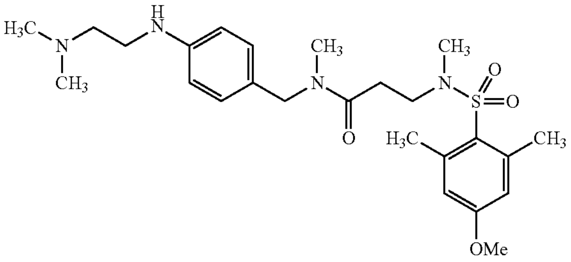

$C_{25}H_{38}N_4O_4S \times HCl$ (527.12)

[M+H]+=491

HPLC (Method 5): retention time=1.55 min

Example 163

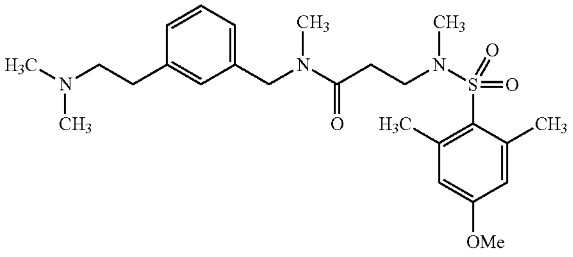

$C_{25}H_{37}N_{13}O_4S \times HCl$ (512.11)

[M+H]+=476

HPLC (Method 5): retention time=1.56 min

Example 164

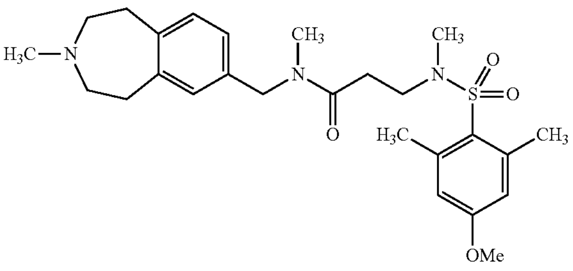

$C_{26}H_{37}N_3O_4S \times HCl$ (524.12)

[M+H]+=488

HPLC (Method 5): retention time=1.54 min

Example 165

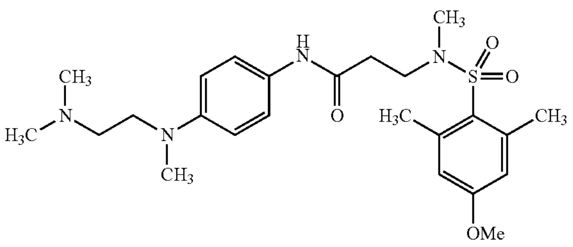

$C_{24}H_{36}N_4O_4S \times HCl$ (513.09)

[M+H]+=477

HPLC (Method 7): retention time=1.88 min

Example 166

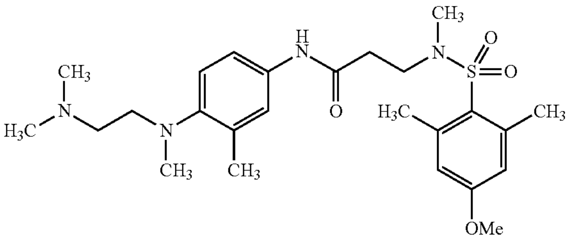

$C_{25}H_{38}N_4O_4S \times HCl$ (527.12)
[M+H]+=491
HPLC (Method 7): retention time=1.92 min Example 167

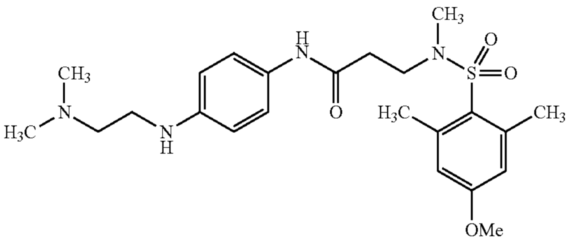

$C_{23}H_{34}N_4O_4S \times HCl$ (499.07)
[M+H]+=463
HPLC (Method 7): retention time=1.79 min Example 168

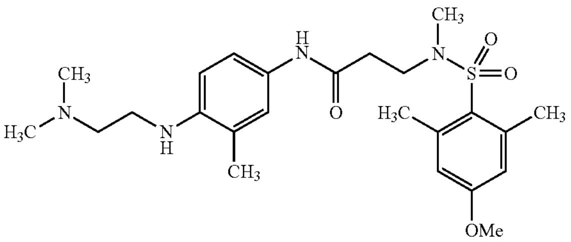

$C_{24}H_{36}N_4O_4S \times HCl$ (513.09)
[M+H]+=477
HPLC (Method 7): retention time=1.86 min Example 169

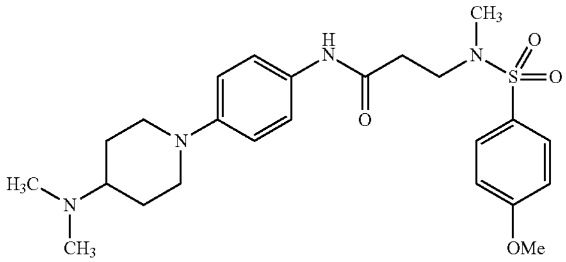 [SMILES: COc1ccc(S(=O)(=O)N(C)CCC(=O)Nc2ccc(N3CCC(N(C)C)CC3)cc2)cc1]

$C_{24}H_{34}N_4O_4S \times C_2HF_3O_2$ (588.64)
[M+H]+=475
HPLC (Method 5): retention time=1.39 min Example 170

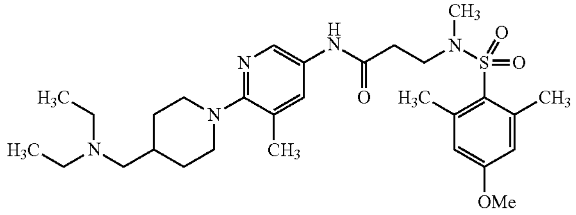 [SMILES: CCN(CC)CC1CCN(c2ncc(NC(=O)CCN(C)S(=O)(=O)c3c(C)cc(OC)cc3C)cc2C)CC1]

$C_{29}H_{45}N_5O_4S \times 2HCl$ (632.69)
[M+H]+=560
TLC: silica gel, dichloromethane/ethanol 9:1, Rf value=0.22

Example 171

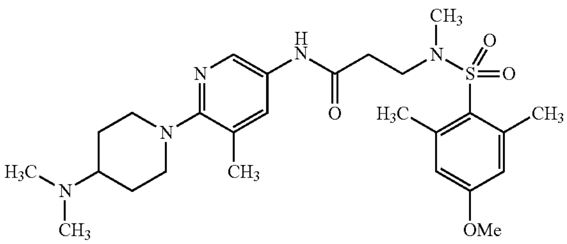

$C_{26}H_{39}N_5O_4S \times 2HCl$ (590.61)
[M+H]+=518
TLC: silica gel, dichloromethane/ethanol 4:1, Rf value=0.68

Example 172

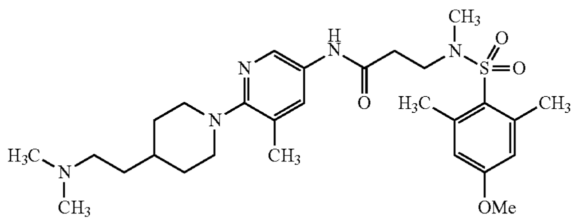

$C_{28}H_{43}N_5O_4S \times 2HCl$ (618.66)

[M+H]+=546

HPLC (Method 5): retention time=1.26 min

Example 173

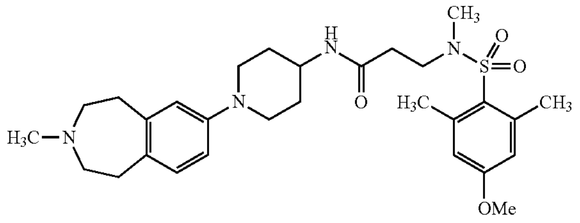

$C_{29}H_{42}N_4O_4S$ (542.73)

[M+H]+=543

HPLC (Method 4): retention time=2.8 min

Example 174

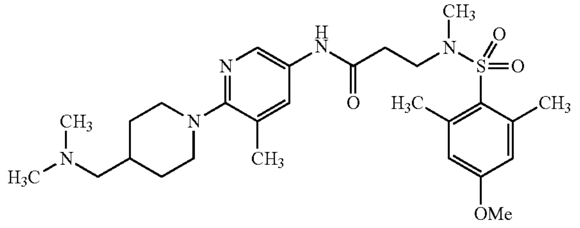

$C_{27}H_{41}N_5O_4S \times 2HCl$ (604.63)

[M+H]+=532

HPLC (Method 5): retention time=1.39 min

Example 175

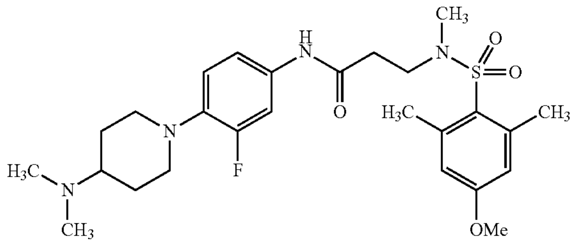

$C_{26}H_{37}FN_4O_4S \times HCl$ (557.12)

[M+H]+=521

TLC: silica gel, dichloromethane/ethanol 9:1, Rf value=0.25

Example 176

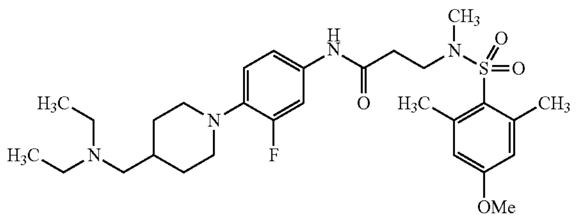 [SMILES: CCN(CC)CC1CCN(c2ccc(NC(=O)CCN(C)S(=O)(=O)c3c(C)cc(OC)cc3C)cc2F)CC1]

$C_{29}H_{43}FN_4O_4S \times HCl$ (599.20)

[M+H]+=563

TLC: silica gel, dichloromethane/ethanol 9:1, Rf value=0.40

Example 177

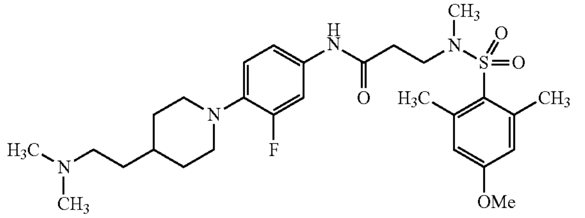

$C_{28}H_{41}FN_4O_4S \times HCl$ (585.17)

[M+H]+=549

TLC: silica gel, dichloromethane/ethanol 9:1, Rf value=0.35

Example 178

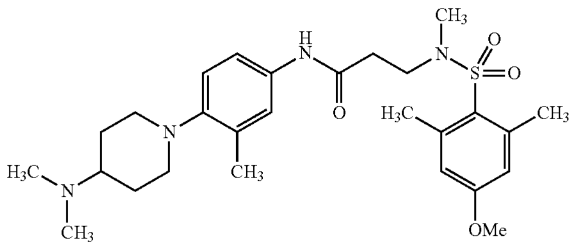

$C_{27}H_{40}N_4O_4S$ (516.70)

[M+H]+=517

TLC: silica gel, dichloromethane/ethanol/ammonia 8:2:0.01, Rf value=0.41

Example 179

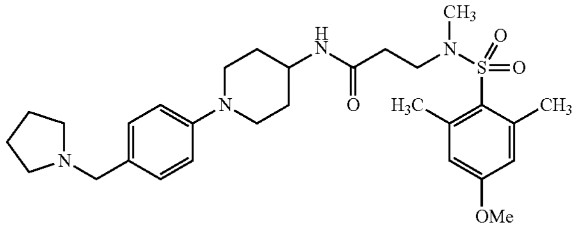 [SMILES: COc1cc(C)c(S(=O)(=O)N(C)CCC(=O)NC2CCN(c3ccc(CN4CCCC4)cc3)CC2)c(C)c1]

$C_{29}H_{42}N_4O_4S \times HCl$ (579.19)

[M+H]+=543

TLC: silica gel, dichloromethane/ethanol/ammonia 8:2:0.01, Rf value=0.47

Example 180

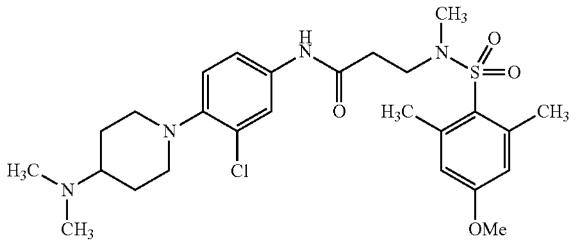

$C_{26}H_{37}ClN_4O_4S \times HCl$ (573.58)

[M+H]+=537/539

TLC: silica gel, dichloromethane/ethanol 9:1, Rf value=0.26

Example 181

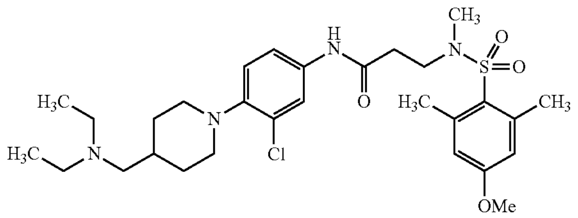 [SMILES: CCN(CC)CC1CCN(c2ccc(NC(=O)CCN(C)S(=O)(=O)c3c(C)cc(OC)cc3C)cc2Cl)CC1]

$C_{29}H_{43}ClN_4O_4S \times HCl$ (615.66)

[M+H]+=579/581

TLC: silica gel, dichloromethane/ethanol 9:1, Rf value=0.45

Example 182

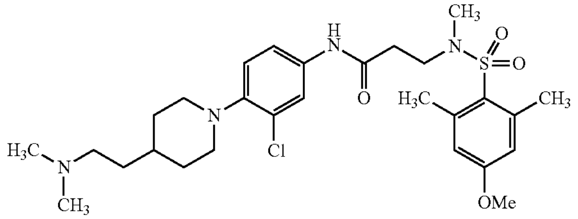

$C_{28}H_{41}ClN_4O_4S \times HCl$ (601.63)

[M+H]+=565/567

TLC: silica gel, dichloromethane/ethanol 9:1, Rf value=0.30

Example 183

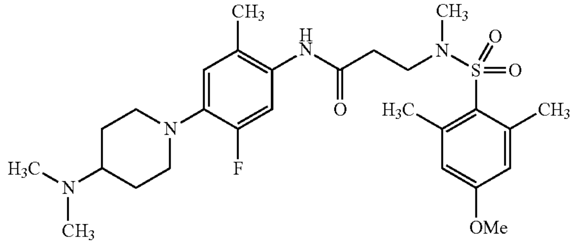

$C_{27}H_{39}FN_4O_4S \times HCl$ (571.15)

[M+H]+=535

Example 184

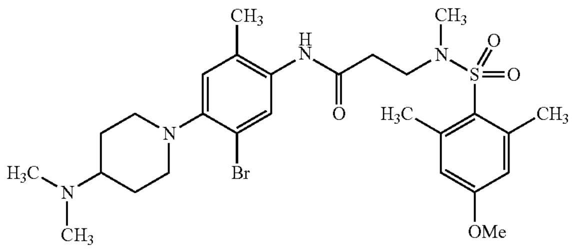

$C_{27}H_{39}BrN_4O_4S \times HCl$ (632.05)

[M+H]+=595/597

TLC: silica gel, dichloromethane/ethanol/ammonia 8:2:0.01, Rf value=0.51

Example 185

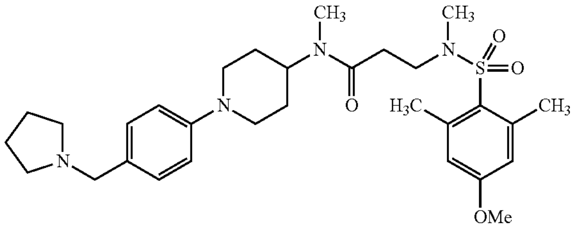 [SMILES: COc1cc(C)c(S(=O)(=O)N(C)CCC(=O)N(C)C2CCN(c3ccc(CN4CCCC4)cc3)CC2)c(C)c1]

$C_{30}H_{44}N_4O_4S \times HCl$ (593.22)

[M+H]+=557

TLC: silica gel, dichloromethane/ethanol/ammonia 8:2:0.01, Rf value=0.63

Example 186

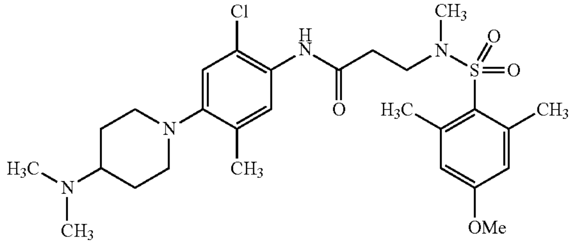

$C_{27}H_{39}ClN_4O_4S \times HCl$ (587.60)

[M+H]+=551

TLC: silica gel, dichloromethane/ethanol/ammonia 8:2:0.01, Rf value=0.58

Example 187

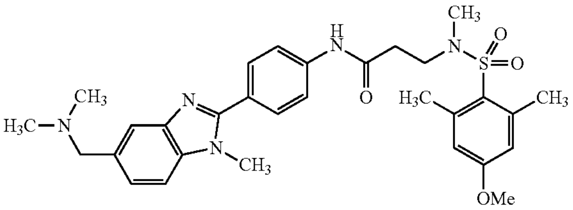

$C_{30}H_{37}N_5O_4S \times HCl$ (600.17)

[M+H]+=564

HPLC (Method 4): retention time=3.0 min

Example 188

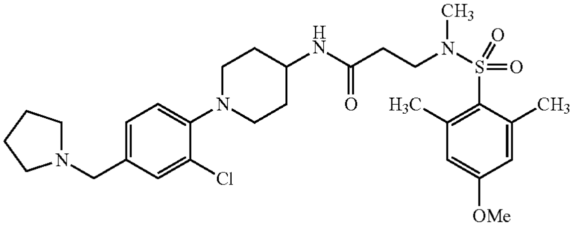 [SMILES: COc1cc(C)c(S(=O)(=O)N(C)CCC(=O)NC2CCN(c3ccc(CN4CCCC4)cc3Cl)CC2)c(C)c1]

$C_{29}H_{41}ClN_4O_4S \times HCl$ (613.64)

[M+H]+=577/579

TLC: silica gel, dichloromethane/methanol 9:1, Rf value=0.24

Example 189

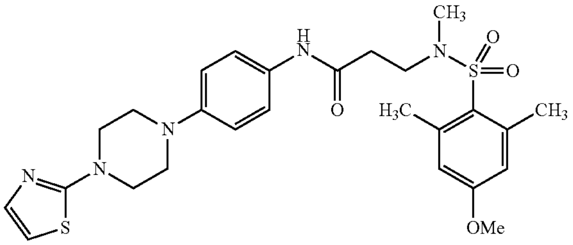 [SMILES: COc1cc(C)c(S(=O)(=O)N(C)CCC(=O)Nc2ccc(N3CCN(c4nccs4)CC3)cc2)c(C)c1]

$C_{26}H_{33}N_5O_4S_2$ (543.70)

[M+H]+=544

HPLC (Method 6): retention time=3.11 min

Example 190
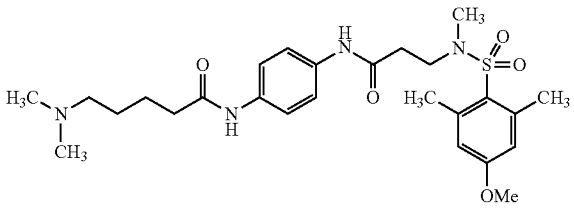
$C_{26}H_{38}N_4O_5S$ (518.67)
[M+H]+=519
HPLC (Method 6): retention time=2.44 min
Example 191
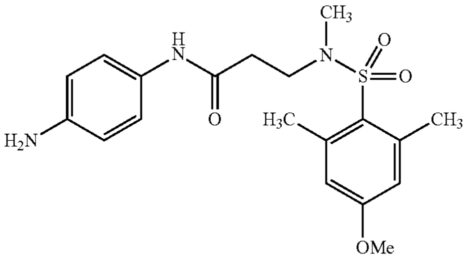 [SMILES: COc1cc(C)c(S(=O)(=O)N(C)CCC(=O)Nc2ccc(N)cc2)c(C)c1]
$C_{19}H_{25}N_3O_4S\times C_2HF_3O_2$ (505.51)
[M+H]+=392
HPLC (Method 6): retention time=2.04 min
Example 192
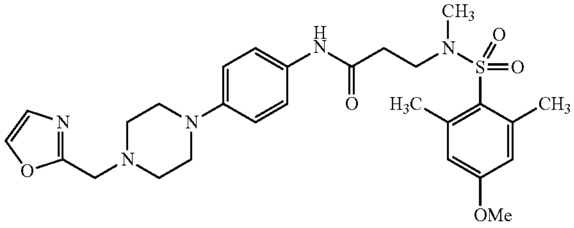 [SMILES: COc1cc(C)c(S(=O)(=O)N(C)CCC(=O)Nc2ccc(N3CCN(Cc4ncco4)CC3)cc2)c(C)c1]
$C_{27}H_{35}N_5O_5S$ (541.66)
[M+H]+=542
HPLC (Method 6): retention time=2.51 min
Example 193
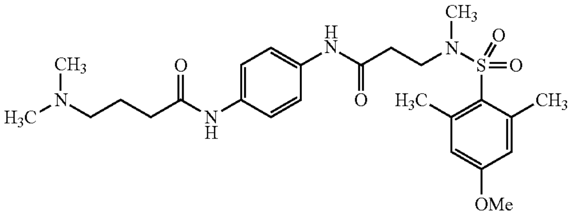
$C_{25}H_{36}N_4O_5S$ (504.64)
[M+H]+=505
HPLC (Method 6): retention time=2.43 min
Example 194
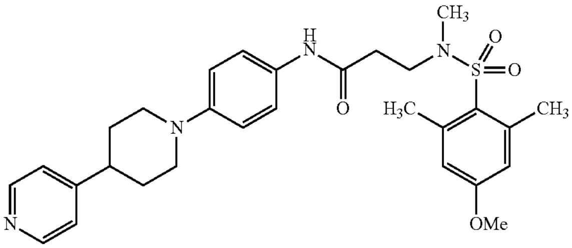 [SMILES: COc1cc(C)c(S(=O)(=O)N(C)CCC(=O)Nc2ccc(N3CCC(c4ccncc4)CC3)cc2)c(C)c1]
$C_{29}H_{36}N_4O_4S$ (536.69)
[M+H]+=537
HPLC (Method 6): retention time=2.19 min
Example 195
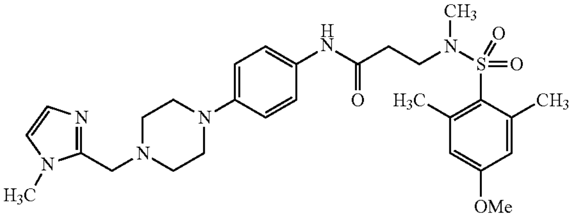 [SMILES: COc1cc(C)c(S(=O)(=O)N(C)CCC(=O)Nc2ccc(N3CCN(Cc4nccn4C)CC3)cc2)c(C)c1]
$C_{28}H_{38}N_6O_4S$ (554.71)
[M+H]+=555
HPLC (Method 6): retention time=2.37 min Example 196
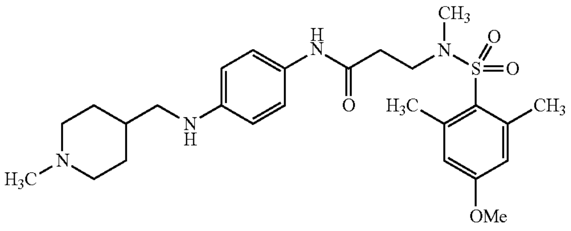
$C_{26}H_{38}N_4O_4S$ (502.67)
[M+H]+=503
HPLC (Method 6): retention time=2.35 min
Example 197
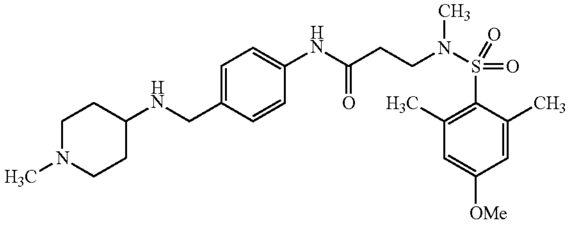
$C_{26}H_{38}N_4O_4S$ (502.67)
[M+H]+=503
HPLC (Method 6): retention time=2.00 min
Example 198
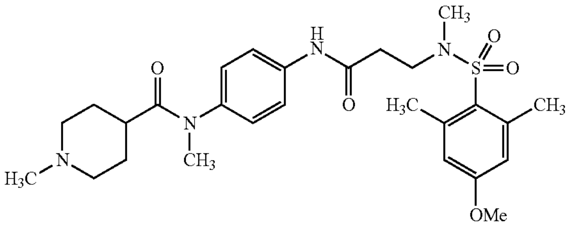
$C_{27}H_{38}N_4O_5S{\times}C_2HF_3O_2$ (644.70)
[M+H]+=531
HPLC (Method 6): retention time=2.45 min
Example 199
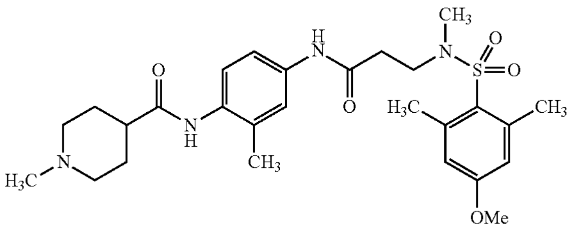
$C_{27}H_{38}N_4O_5S$ (530.68)
[M+H]+=531
HPLC (Method 6): retention time=2.53 min
Example 200
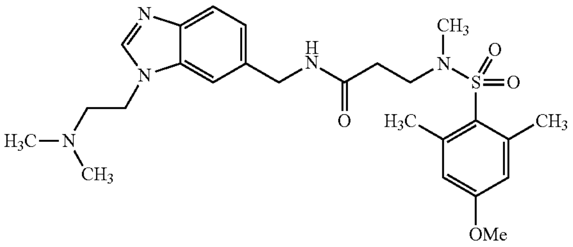
$C_{25}H_{35}N_5O_4S$ (501.64)
[M+H]+=502
HPLC (Method 6): retention time=2.05 min
Example 201
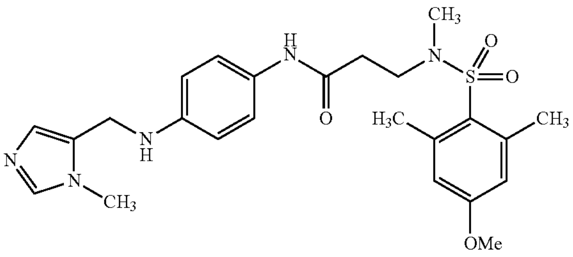 [SMILES: COc1cc(C)c(S(=O)(=O)N(C)CCC(=O)Nc2ccc(NCc3cncn3C)cc2)c(C)c1]
$C_{24}H_{31}N_5O_4S$ (485.60)
[M+H]+=486
HPLC (Method 6): retention time=2.41 min Example 202
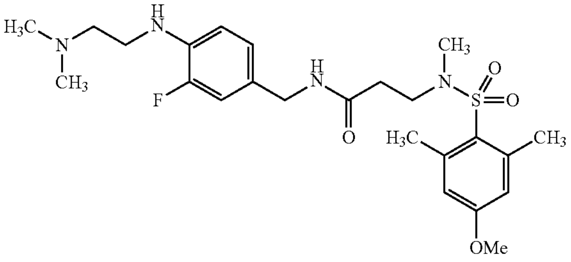
$C_{24}H_{35}FN_4O_4S \times CH_2O_2$ (540.65)
[M+H]+=495
HPLC (Method 6): retention time=2.50 min
Example 203
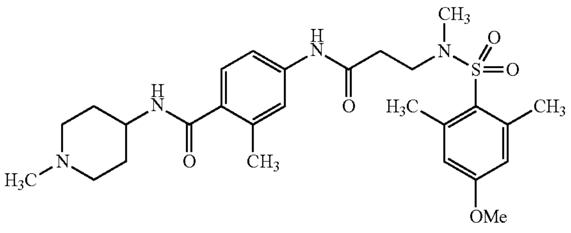
$C_{27}H_{38}N_4O_5S$ (530.68)
[M+H]+=531
HPLC (Method 6): retention time=2.36 min
Example 204
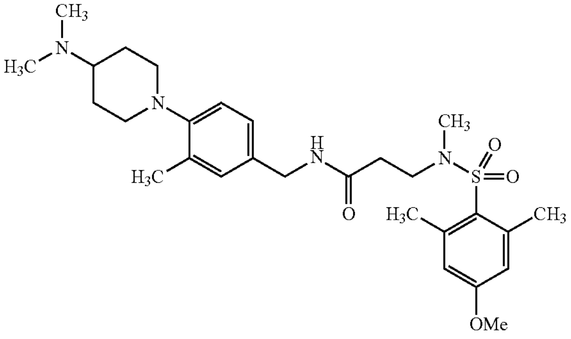
$C_{28}H_{42}N_4O_4S$ (530.72)
[M+H]+=531
HPLC (Method 6): retention time=2.60 min
Example 205
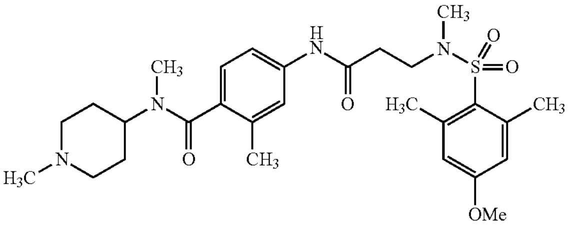
$C_{28}H_{40}N_4O_5S$ (544.71)
[M+H]+=545
HPLC (Method 6): retention time=2.21 min
Example 206
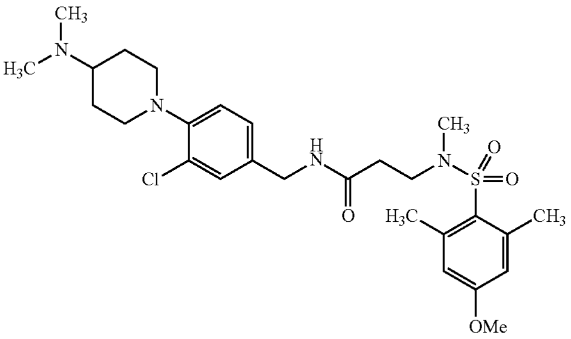
$C_{27}H_{39}ClN_4O_4S$ (551.14)
[M+H]+=551/553
HPLC (Method 6): retention time=2.65 min
Example 207
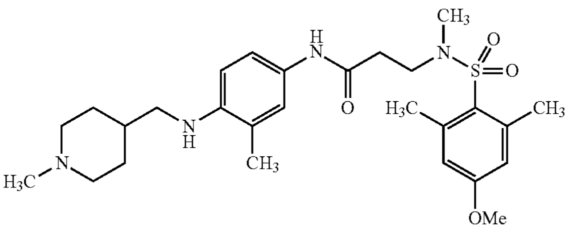
$C_{27}H_{40}N_4O_4S \times C_2HF_3O_2$ (630.72)
[M+H]+=517
HPLC (Method 6): retention time=2.51 min Example 208

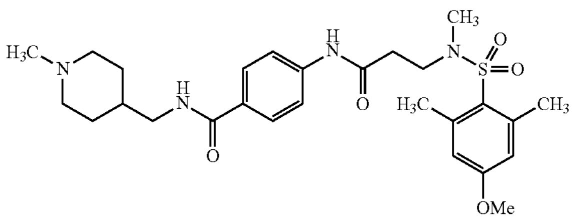

$C_{27}H_{38}N_4O_5S \times CH_2O_2$ (576.71)
[M+H]+=531
HPLC (Method 6): retention time=2.33 min Example 209

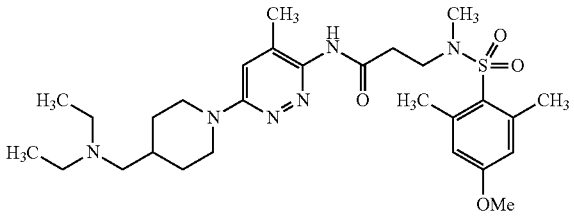 [SMILES: CCN(CC)CC1CCN(c2cc(C)c(NC(=O)CCN(C)S(=O)(=O)c3c(C)cc(OC)cc3C)nn2)CC1]

$C_{28}H_{44}N_6O_4S \times C_2HF_3O_2$ (674.78)
[M+H]+=561
HPLC (Method 6): retention time=2.14 min Example 210

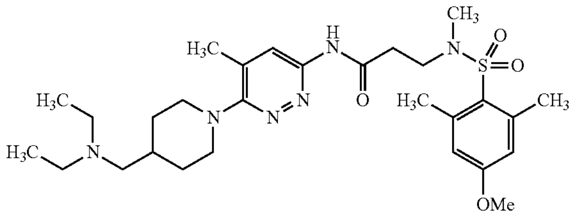 [SMILES: CCN(CC)CC1CCN(c2nnc(NC(=O)CCN(C)S(=O)(=O)c3c(C)cc(OC)cc3C)cc2C)CC1]

$C_{28}H_{44}N_6O_4S \times C_2HF_3O_2$ (674.78)
[M+H]+=561
HPLC (Method 6): retention time=2.43 min Example 211

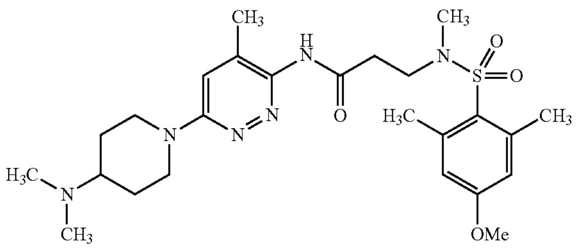

$C_{25}H_{38}N_6O_4S \times C_2HF_3O_2$ (632.70)
[M+H]+=519
HPLC (Method 6): retention time=2.11 min Example 212

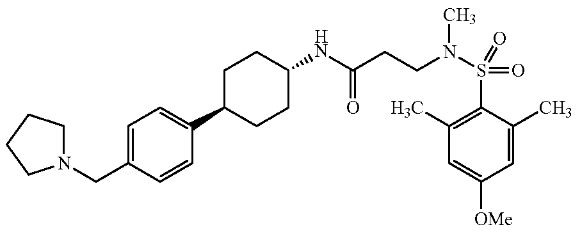 [SMILES: COc1cc(C)c(S(=O)(=O)N(C)CCC(=O)N[C@H]2CC[C@H](c3ccc(CN4CCCC4)cc3)CC2)c(C)c1]

$C_{30}H_{43}N_3O_4S \times C_2HF_3O_2$ (655.77)
[M+H]+=542
HPLC (Method 6): retention time=2.75 min Example 213

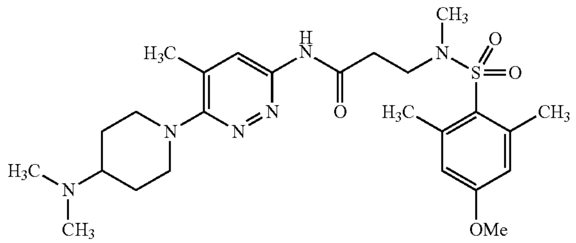

$C_{25}H_{38}N_6O_4S \times C_2HF_3O_2$ (632.70)
[M+H]+=519
HPLC (Method 6): retention time=2.30 min Example 214

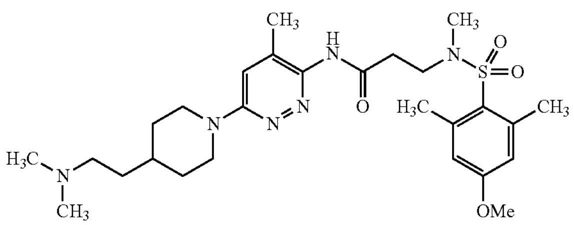

$C_{27}H_{42}N_6O_4S \times C_2HF_3O_2$ (660.75)
[M+H]+=547
HPLC (Method 6): retention time=2.08 min Example 215

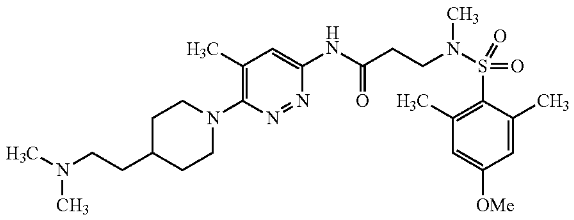

$C_{27}H_{42}N_6O_4S \times C_2HF_3O_2$ (660.75)
[M+H]+=547
HPLC (Method 6): retention time=2.34 min Example 216

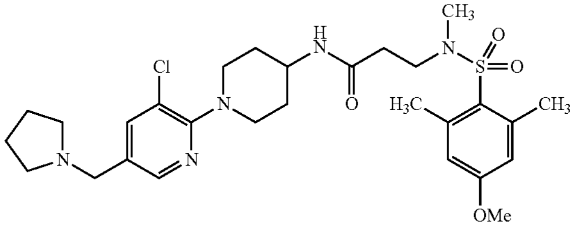 [SMILES: COc1cc(C)c(S(=O)(=O)N(C)CCC(=O)NC2CCN(c3ncc(CN4CCCC4)cc3Cl)CC2)c(C)c1]

$C_{28}H_{40}ClN_5O_4S \times CH_2O_2$ (624.19)
[M+H]+=578/580
HPLC (Method 6): retention time=2.64 min Example 217

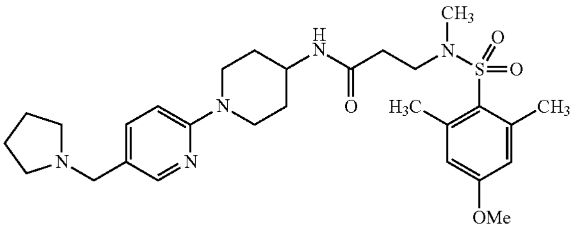

$C_{28}H_{41}N_5O_4S \times CH_2O_2$ (589.75)
[M+H]+=544
HPLC (Method 6): retention time=2.09 min Example 218

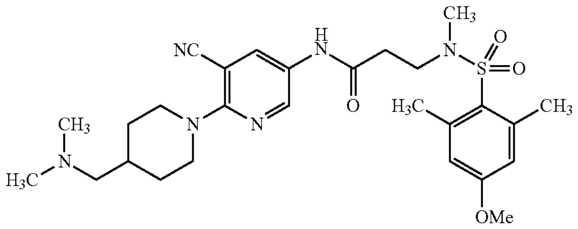

$C_{27}H_{38}N_6O_4S \times CH_2O_2$ (588.72)
[M+H]+=543
HPLC (Method 9): retention time=1.67 min Example 219

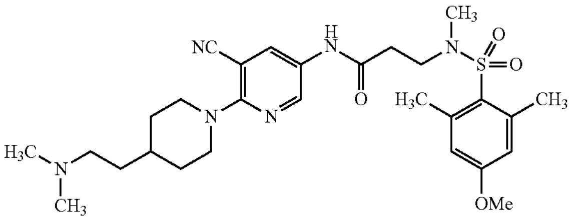

$C_{28}H_{40}N_6O_4S$ (556.72)
[M+H]+=557
HPLC (Method 9): retention time=1.71 min Example 220

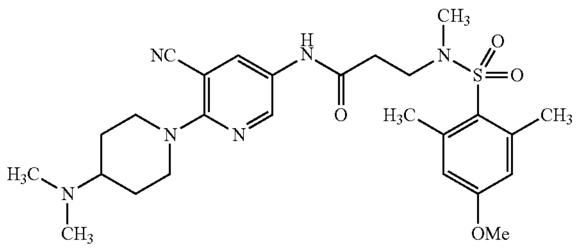

$C_{26}H_{36}N_6O_4S \times CH_2O_2$ (574.69)
[M+H]+=529
HPLC (Method 9): retention time=1.61 min Example 221

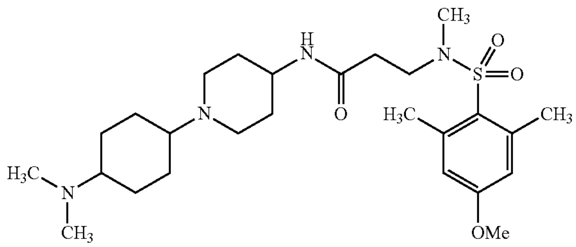

$C_{26}H_{44}N_4O_4S$ (508.72)
[M+H]+=509
HPLC (Method 9): retention time=1.23 min Example 222

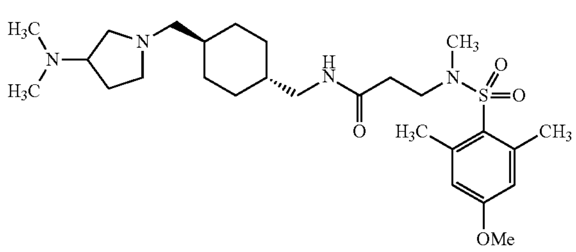

$C_{27}H_{46}N_4O_4S \times 2C_2HF_3O_2$ (750.79)
[M+H]+=523
HPLC (Method 9): retention time=1.30 min Example 223

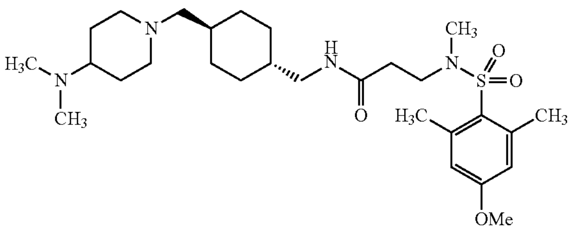

$C_{28}H_{48}N_4O_4S \times 2C_2HF_3O_2$ (764.82)
[M+H]+=537
HPLC (Method 9): retention time=1.31 min Example 224

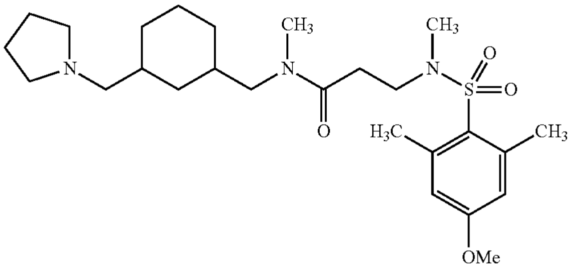 [SMILES: COc1cc(C)c(S(=O)(=O)N(C)CCC(=O)N(C)CC2CCCC(CN3CCCC3)C2)c(C)c1]

$C_{26}H_{43}N_3O_4S$ (493.70)
[M+H]+=494
HPLC (Method 9): retention time=1.72 min Example 225

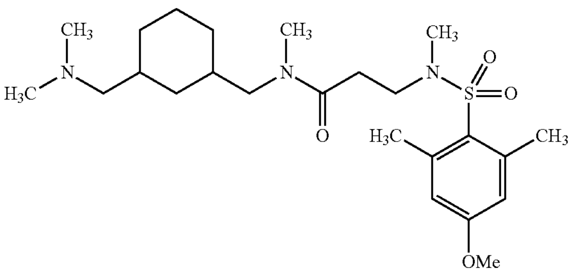

$C_{24}H_{41}N_3O_4S \times C_2HF_3O_2$ (581.69)
[M+H]+=468
HPLC (Method 9): retention time=1.69 min Example 226

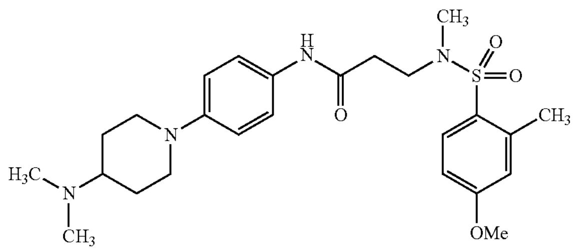

$C_{25}H_{36}N_4O_4S \times C_2HF_3O_2$ (602.67)
[M+H]+=489
HPLC (Method 5): retention time=1.39 min Example 227

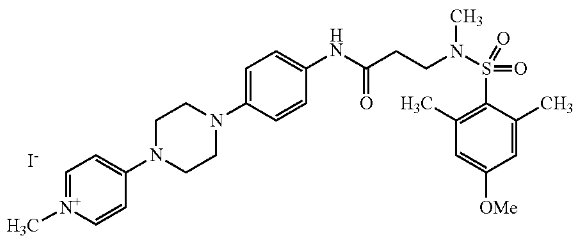

$C_{29}H_{38}N_5O_4S \times I$ (679.61)
[M+H]+=552
HPLC (Method 5): retention time=1.55 min Example 228

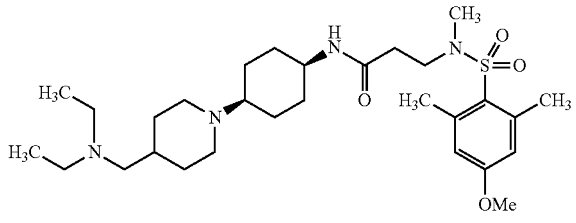 [SMILES: CCN(CC)CC1CCN([C@H]2CC[C@@H](NC(=O)CCN(C)S(=O)(=O)c3c(C)cc(OC)cc3C)CC2)CC1]

$C_{29}H_{50}N_4O_4S$ (550.80)
[M+H]+=551
HPLC (Method 5): retention time=1.38 min Example 229

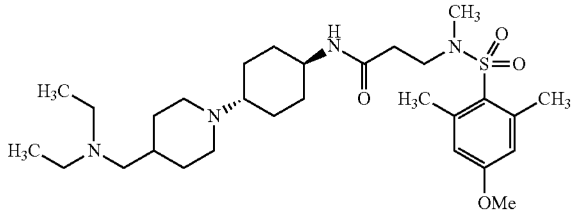 [SMILES: CCN(CC)CC1CCN([C@H]2CC[C@H](NC(=O)CCN(C)S(=O)(=O)c3c(C)cc(OC)cc3C)CC2)CC1]

$C_{29}H_{50}N_4O_4S$ (550.80)
[M+H]+=551
HPLC (Method 5): retention time=1.40 min Example 230

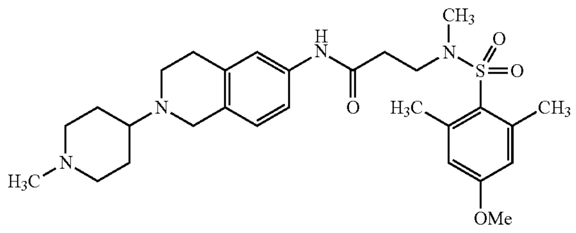

$C_{28}H_{40}N_4O_4S \times 2HCl$ (601.63)
[M+H]+=529
HPLC (Method 5): retention time=1.41 min Example 231

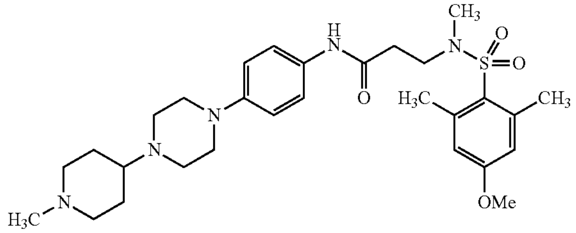

$C_{29}H_{43}N_5O_4S$ (557.75)
[M+H]+=558
HPLC (Method 1): retention time=1.90 min Example 232

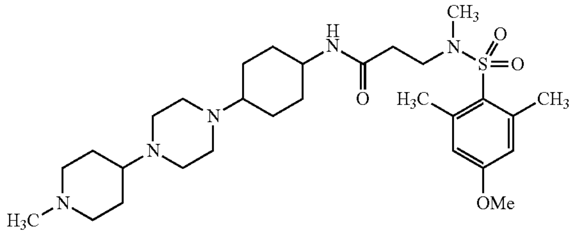

$C_{29}H_{49}N_5O_4S$ (563.80)
[M+H]+=564
HPLC (Method 5): retention time=1.33 min Example 233

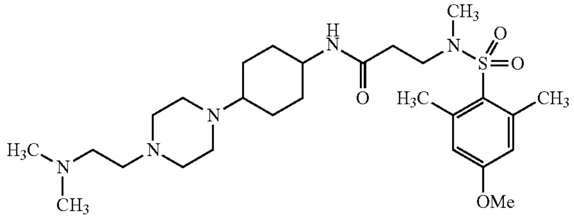

$C_{27}H_{47}N_5O_4S \times 2HCl$ (610.68)
[M+H]+=538
HPLC (Method 7): retention time=1.74 min Example 234

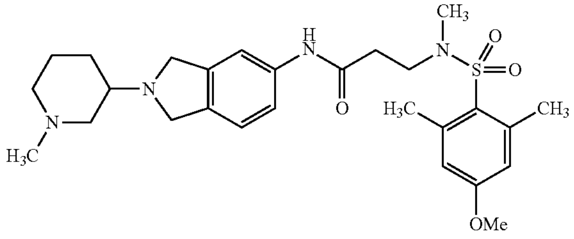 [SMILES: COc1cc(C)c(S(=O)(=O)N(C)CCC(=O)Nc2ccc3c(c2)CN(C2CCCN(C)C2)C3)c(C)c1]

$C_{27}H_{38}N_4O_4S$ (610.68)
[M+H]+=515
HPLC (Method 5): retention time=1.41 min Example 235

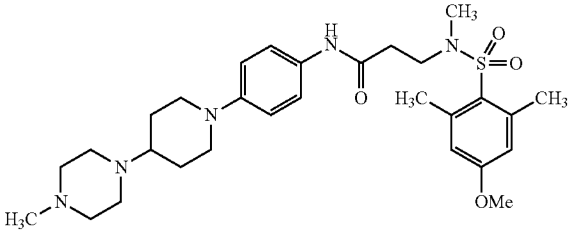

$C_{29}H_{43}N_5O_4S$ (557.75)
[M+H]+=558
HPLC (Method 5): retention time=1.43 min Example 236

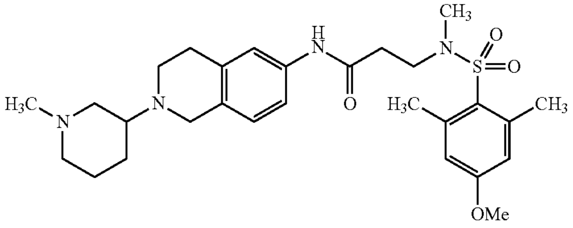

$C_{28}H_{40}N_4O_4S \times 2C_2HF_3O_2$ (756.75)
[M+H]+=529
HPLC (Method 5): retention time=1.42 min Example 237

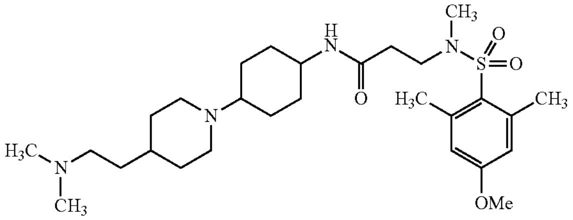

$C_{28}H_{48}N_4O_4S \times 2HCl$ (609.69)
[M+H]+=537
HPLC (Method 7): retention time=1.70 min Example 238

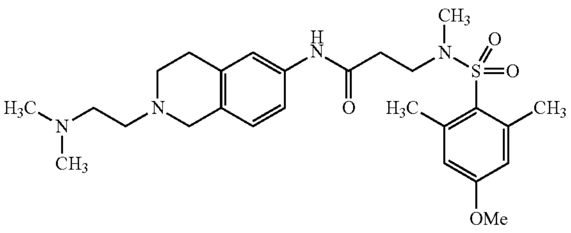

$C_{26}H_{38}N_4O_4S \times 2C_2HF_3O_2$ (730.72)

[M+H]+=503

HPLC (Method 5): retention time=1.40 min

Example 239

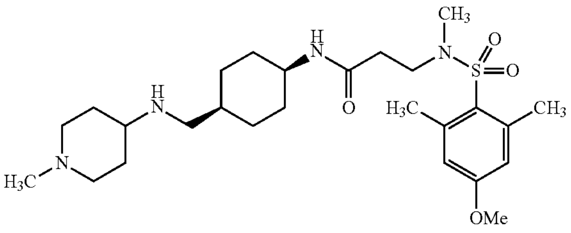

$C_{26}H_{44}N_4O_4S \times 2HCl$ (581.64)

[M+H]+=509

HPLC (Method 5): retention time=1.38 min

Example 240

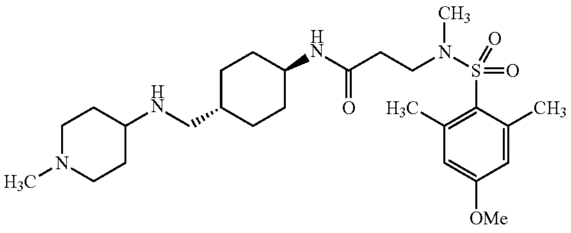

$C_{26}H_{44}N_4O_4S \times 2HCl$ (581.64)

[M+H]+=509

HPLC (Method 5): retention time=1.40 min

Example 241

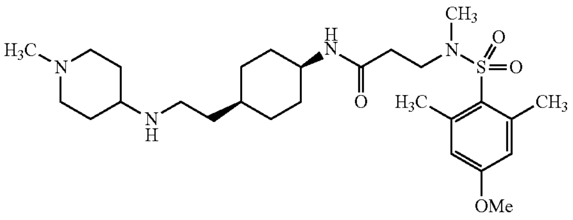

$C_{27}H_{46}N_4O_4S \times 2HCl$ (595.67)

[M+H]+=523

TLC: silica gel, dichloromethane/methanol/ammonia 9:1:0.1, Rf value=0.13

Example 242

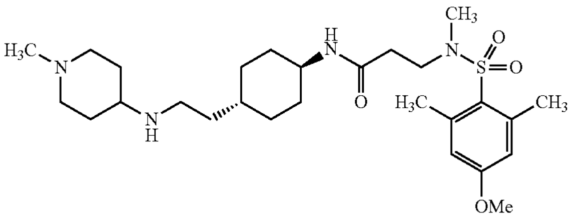

$C_{27}H_{46}N_4O_4S \times 2HCl$ (595.67)

[M+H]+=523

TLC: silica gel, dichloromethane/methanol/ammonia 9:1:0.1, Rf value=0.13

Example 243

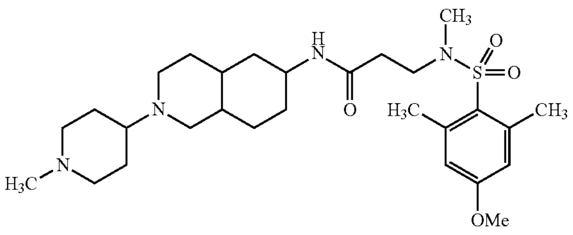

$C_{28}H_{46}N_4O_4S \times 2HCl$ (607.68)

[M+H]+=535

HPLC (Method 5): retention time=1.10 min

Example 244

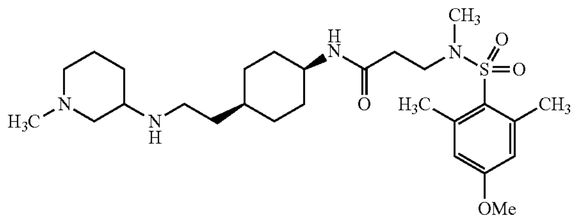

$C_{27}H_{46}N_4O_4S \times 2HCl$ (595.67)

[M+H]+=523

TLC: silica gel, dichloromethane/methanol/ammonia 9:1:0.1, Rf value=0.25

Example 245

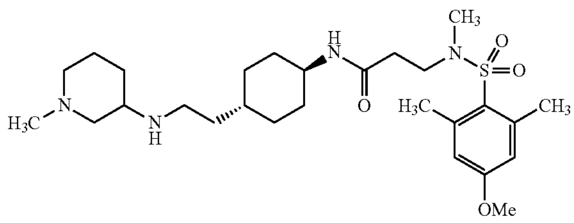

$C_{27}H_{46}N_4O_4S \times 2HCl$ (595.67)

[M+H]+=523

TLC: silica gel, dichloromethane/methanol/ammonia 9:1:0.1, Rf value=0.25

Example 246

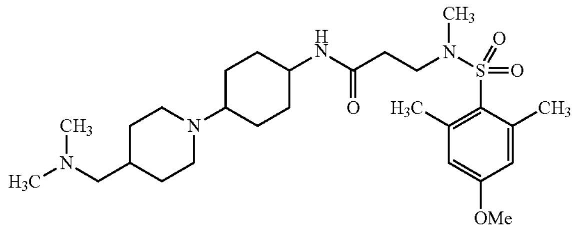

$C_{27}H_{46}N_4O_4S \times 2C_2HF_3O_2$ (750.79)

[M+H]+=523

HPLC (Method 5): retention time=1.38 min

Example 247

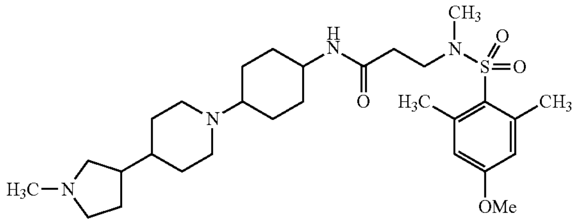

$C_{29}H_{48}N_4O_4S \times 2C_2HF_3O_2$ (776.83)

[M+H]+=549

HPLC (Method 5): retention time=1.39 min

Example 248

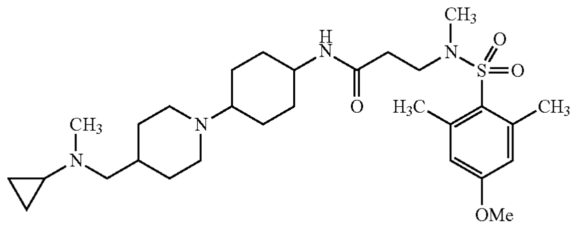 [SMILES: COc1cc(C)c(S(=O)(=O)N(C)CCC(=O)NC2CCC(N3CCC(CN(C)C4CC4)CC3)CC2)c(C)c1]

$C_{29}H_{48}N_4O_4S \times 2C_2HF_3O_2$ (776.83)

[M+H]+=549

HPLC (Method 5): retention time=1.39 min

Example 249

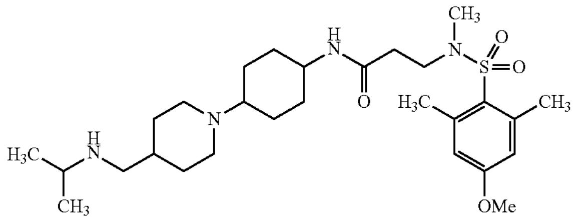 [SMILES: COc1cc(C)c(S(=O)(=O)N(C)CCC(=O)NC2CCC(N3CCC(CNC(C)C)CC3)CC2)c(C)c1]

$C_{28}H_{48}N_4O_4S \times 2HCl$ (609.69)

[M+H]+=537

HPLC (Method 5): retention time=1.38 min

Example 250

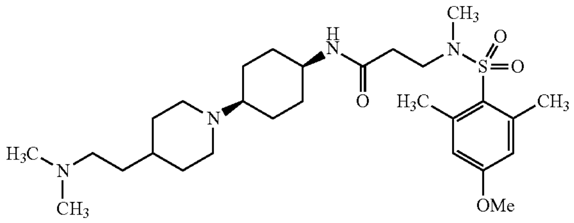

$C_{28}H_{48}N_4O_4S$×2HCl (609.69)

[M+H]+=537

HPLC (Method 11): retention time=1.60 min

Example 251

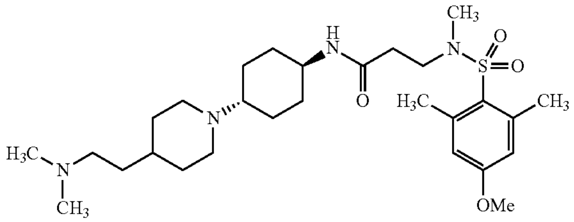

$C_{28}H_{48}N_4O_4S$×2HCl (609.69)

[M+H]+=537

HPLC (Method 7): retention time=1.71 min

Example 252

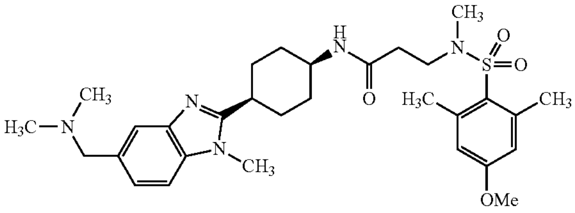

$C_{30}H_{43}N_5O_4S$×HCl (606.22)

[M+H]+=570

TLC: silica gel, dichloromethane/methanol/ammonia 9:1:0.1, Rf value=0.29

Example 253

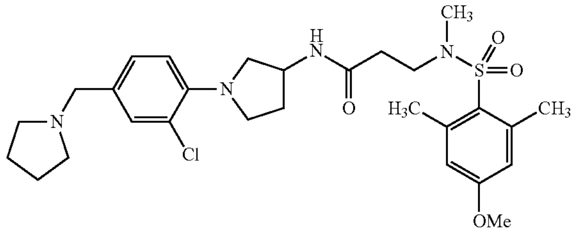 [SMILES: COc1cc(C)c(S(=O)(=O)N(C)CCC(=O)NC2CCN(c3ccc(CN4CCCC4)cc3Cl)C2)c(C)c1]

$C_{28}H_{39}ClN_4O_4S$×HCl (599.61)

[M+H]+=563/565

HPLC (Method 5): retention time=1.59 min

Example 254

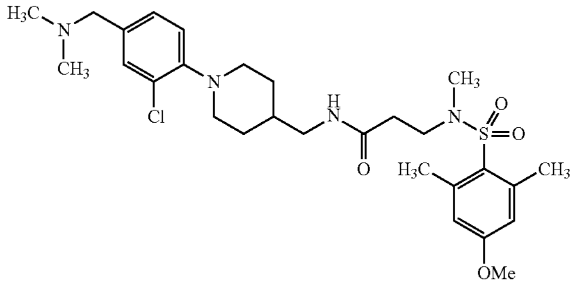

$C_{28}H_{41}ClN_4O_4S$×HCl (601.63)

[M+H]+=565/567

TLC: silica gel, dichloromethane/methanol/ammonia 9:1:0.1, Rf value=0.46

Example 255

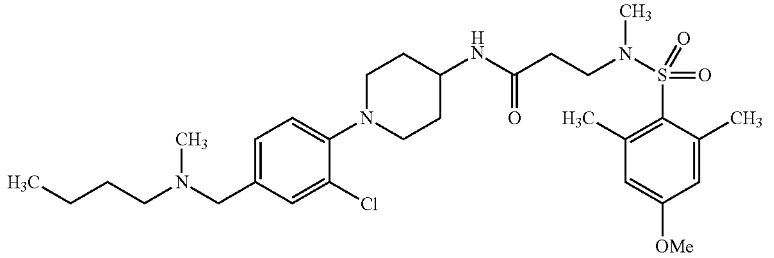 [SMILES: CCCCN(C)Cc1ccc(N2CCC(NC(=O)CCN(C)S(=O)(=O)c3c(C)cc(OC)cc3C)CC2)c(Cl)c1]

$C_{30}H_{45}ClN_4O_4S$×HCl (629.68)

[M+H]+=593/595

TLC: silica gel, dichloromethane/methanol 9:1, Rf value=0.42

Example 256

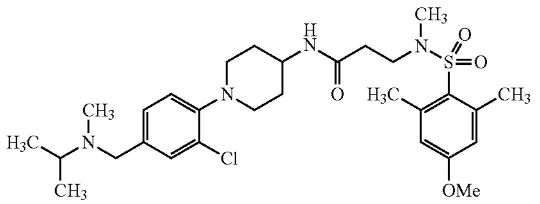 [SMILES: COc1cc(C)c(S(=O)(=O)N(C)CCC(=O)NC2CCN(c3ccc(CN(C)C(C)C)cc3Cl)CC2)c(C)c1]

$C_{29}H_{43}ClN_4O_4S \times HCl$ (615.66)

[M+H]+=579/581

TLC: silica gel, dichloromethane/methanol 9:1, Rf value=0.23

Example 257

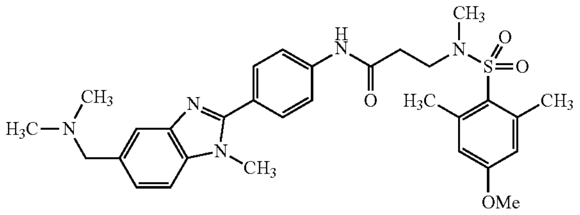

$C_{30}H_{37}N_5O_4S \times HCl$ (600.17)

[M+H]+=564

TLC: silica gel, dichloromethane/methanol/ammonia 8:2:0.1, Rf value=0.67

Example 258

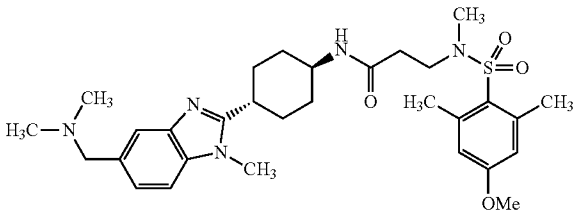

$C_{30}H_{43}N_5O_4S$ (569.76)

[M+H]+=570

TLC: silica gel, dichloromethane/methanol/ammonia 8:2:0.2, Rf value=0.65

Example 259

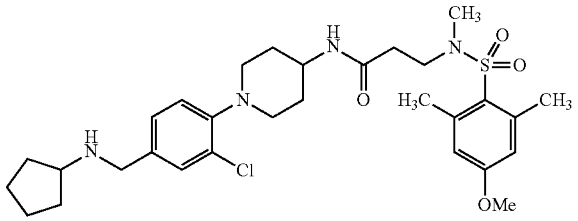 [SMILES: COc1cc(C)c(S(=O)(=O)N(C)CCC(=O)NC2CCN(c3ccc(CNC4CCCC4)cc3Cl)CC2)c(C)c1]

$C_{30}H_{43}ClN_4O_4S \times HCl$ (627.67)

[M+H]+=591/593

TLC: silica gel, dichloromethane/methanol 9:1, Rf value=0.20

Example 260

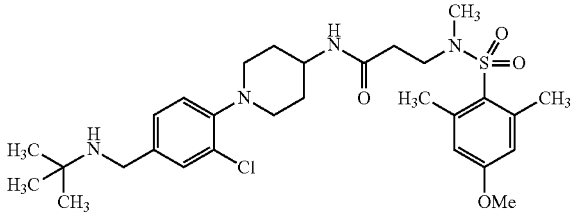 [SMILES: COc1cc(C)c(S(=O)(=O)N(C)CCC(=O)NC2CCN(c3ccc(CNC(C)(C)C)cc3Cl)CC2)c(C)c1]

$C_{29}H_{43}ClN_4O_4S \times HCl$ (615.66)

[M+H]+=579/581

TLC: silica gel, dichloromethane/methanol 9:1, Rf value=0.17

Example 261

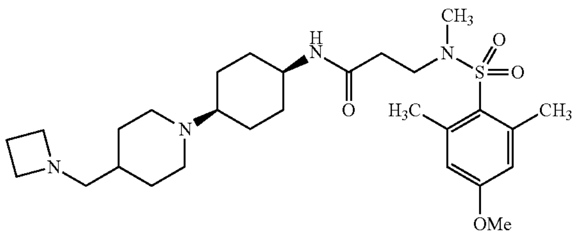 [SMILES: COc1cc(C)c(S(=O)(=O)N(C)CCC(=O)N[C@H]2CC[C@@H](N3CCC(CN4CCC4)CC3)CC2)c(C)c1]

$C_{28}H_{46}N_4O_4S \times 2HCl$ (607.68)

[M+H]+=535

TLC: silica gel, dichloromethane/methanol/ammonia 8:2:0.2, Rf value=0.23

Example 262

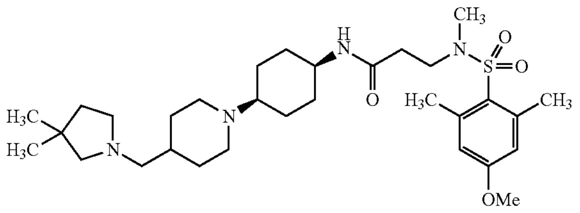

$C_{31}H_{52}N_4O_4S$×2HCl (649.76)

[M+H]+=577

TLC: silica gel, dichloromethane/methanol/ammonia 8:2:0.2, Rf value=0.69

Example 263

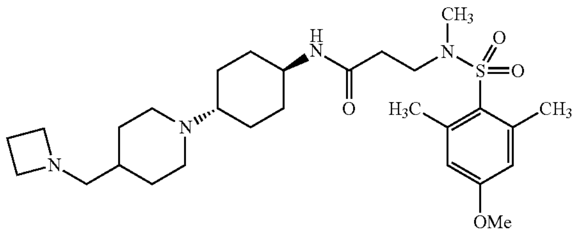 [SMILES: COc1cc(C)c(S(=O)(=O)N(C)CCC(=O)N[C@H]2CC[C@H](N3CCC(CN4CCC4)CC3)CC2)c(C)c1]

$C_{28}H_{46}N_4O_4S$ (534.76)

[M+H]+=535

TLC: silica gel, dichloromethane/methanol/ammonia 8:2:0.2, Rf value=0.58

Example 264

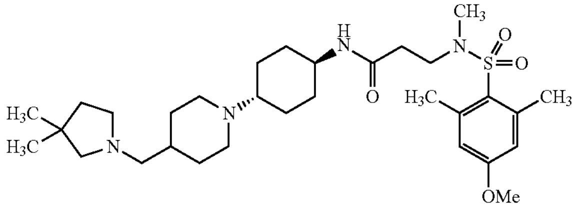

$C_{31}H_{52}N_4O_4S$ (576.84)

[M+H]+=577

TLC: silica gel, dichloromethane/methanol/ammonia 8:2:0.2, Rf value=0.56

Example 265

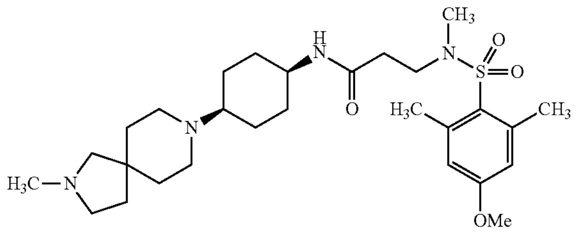

$C_{28}H_{46}N_4O_4S$×2HCl (607.68)

[M+H]+=535

TLC: silica gel, dichloromethane/methanol/ammonia 8:2:0.2, Rf value=0.58

Example 266

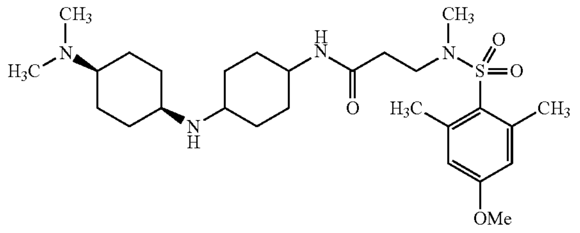

$C_{27}H_{46}N_4O_4S$ (522.74)

[M+H]+=523

HPLC (Method 9): retention time=1.30 min

Example 267

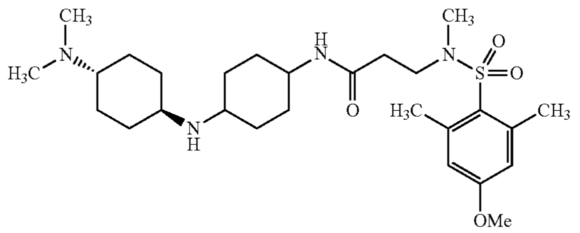

$C_{27}H_{46}N_4O_4S$ (522.74)

[M+H]+=523

HPLC (Method 9): retention time=1.28 min

Example 268

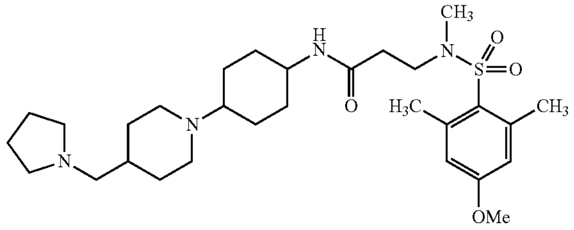 [SMILES: COc1cc(C)c(S(=O)(=O)N(C)CCC(=O)NC2CCC(N3CCC(CN4CCCC4)CC3)CC2)c(C)c1]

$C_{29}H_{48}N_4O_4S{\times}CH_2O_2$ (594.81)
[M+H]+=549
HPLC (Method 6): retention time=1.96 min Example 269

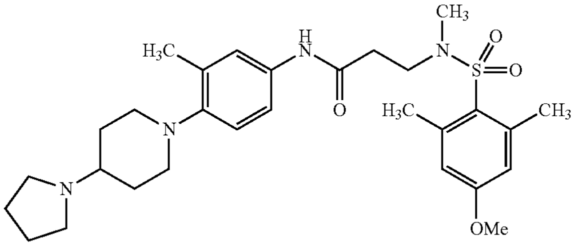 [SMILES: COc1cc(C)c(S(=O)(=O)N(C)CCC(=O)Nc2ccc(N3CCC(N4CCCC4)CC3)c(C)c2)c(C)c1]

$C_{309}H_{44}N_4O_4S$ (556.76)
[M+H]+=557
HPLC (Method 9): retention time=1.71 min Example 270

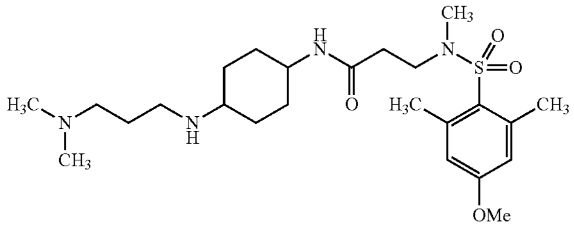

$C_{24}H_{42}N_4O_4S{\times}C_2HF_3O_2$ (596.70)
[M+H]+=483
HPLC (Method 9): retention time=1.23 min Example 271

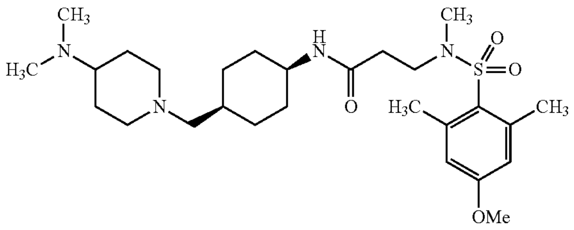

$C_{27}H_{46}N_4O_4S$ (522.74)
[M+H]+=523
HPLC (Method 9): retention time=1.23 min Example 272

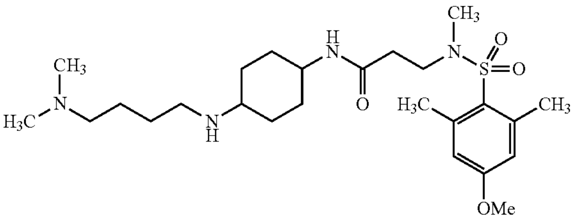

$C_{25}H_{44}N_4O_4S$ (496.71)
[M+H]+=497
HPLC (Method 9): retention time=1.25 min Example 273

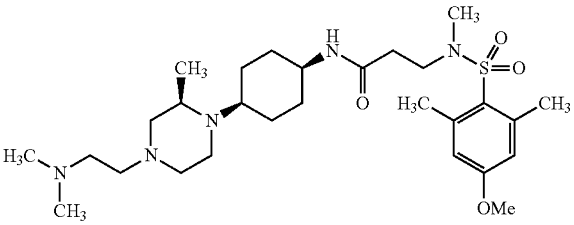

$C_{28}H_{49}N_5O_4S{\times}2HCl$ (624.71)
[M+H]+=552
HPLC (Method 10): retention time=1.06 min Example 274

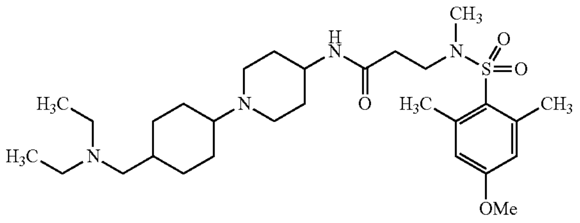 [SMILES: CCN(CC)CC1CCC(N2CCC(NC(=O)CCN(C)S(=O)(=O)c3c(C)cc(OC)cc3C)CC2)CC1]

$C_{29}H_{50}N_4O_4S \times CH_2O_2$ (596.82)
[M+H]+=551
HPLC (Method 9): retention time=1.31 min Example 275

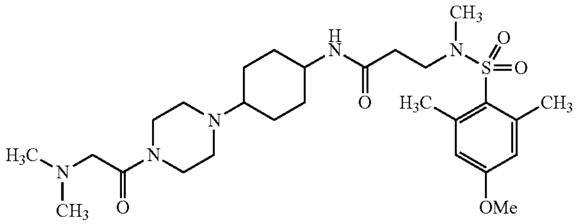

$C_{27}H_{45}N_5O_5S \times CH_2O_2$ (597.77)
[M+H]+=552
HPLC (Method 9): retention time=1.20 min Example 276

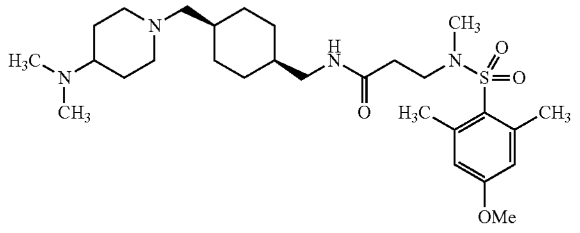

$C_{28}H_{48}N_4O_4S$ (536.77)
[M+H]+=537
HPLC (Method 6): retention time=1.32 min Example 277

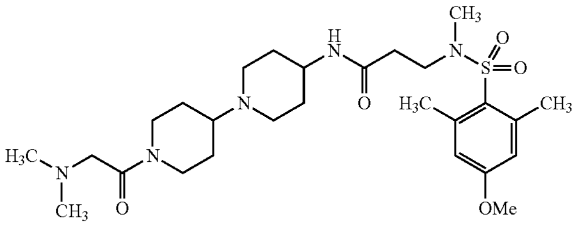

$C_{27}H_{45}N_5O_5S \times C_2HF_3O_2$ (665.77)
[M+H]+=552
HPLC (Method 9): retention time=1.18 min Example 278

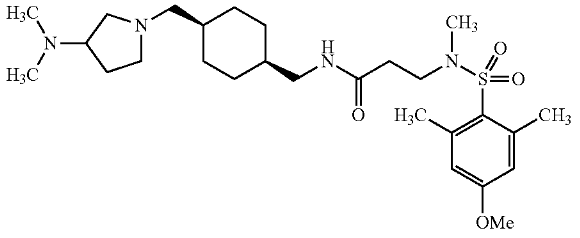

$C_{27}H_{46}N_4O_4S \times 2\ C_2HF_3O_2$ (750.79)
[M+H]+=523
HPLC (Method 9): retention time=1.29 min Example 279

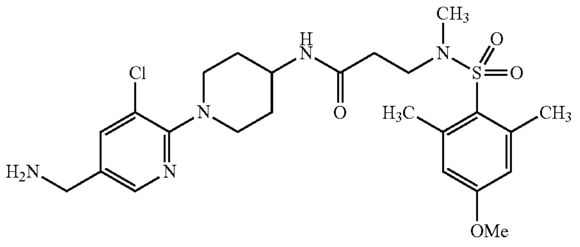 [SMILES: COc1cc(C)c(S(=O)(=O)N(C)CCC(=O)NC2CCN(c3ncc(CN)cc3Cl)CC2)c(C)c1]

$C_{24}H_{34}ClN_5O_4S$ (524.08)
[M+H]+=524/526
HPLC (Method 9): retention time=1.60 min Example 280

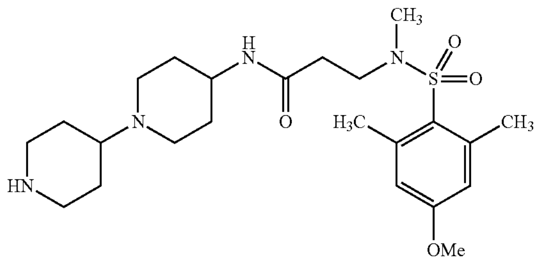 [SMILES: COc1cc(C)c(S(=O)(=O)N(C)CCC(=O)NC2CCN(C3CCNCC3)CC2)c(C)c1]

$C_{23}H_{38}N_4O_4S{\times}2C_2HF_3O_2$ (694.69)

[M+H]+=467

HPLC (Method 9): retention time=1.16 min

Example 281

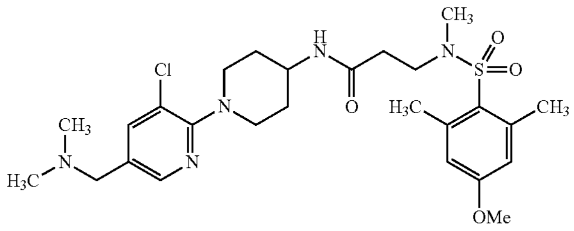

$C_{26}H_{38}ClN_5O_4S{\times}C_2HF_3O_2$ (666.15)

[M+H]+=552/554

HPLC (Method 9): retention time=1.68 min

Example 282

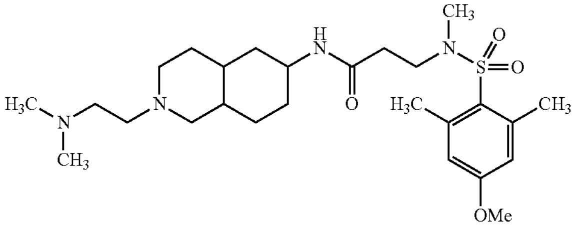

$C_{26}H_{44}N_4O_4S{\times}2HCl$ (581.64)

[M+H]+=509

HPLC (Method 5): retention time=1.36 min

Example 283

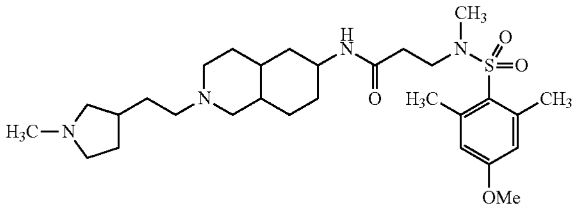

$C_{29}H_{48}N_4O_4S{\times}2HCl$ (621.70)

[M+H]+=549

HPLC (Method 5): retention time=1.38 min

Example 284

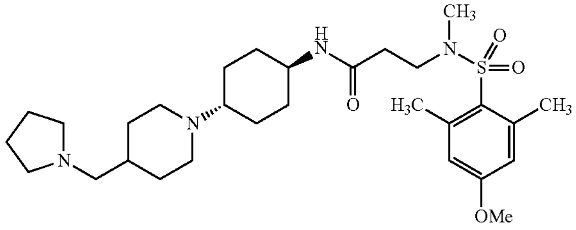 [SMILES: COc1cc(C)c(S(=O)(=O)N(C)CCC(=O)N[C@H]2CC[C@H](N3CCC(CN4CCCC4)CC3)CC2)c(C)c1]

$C_{29}H_{48}N_4O_4S$ (548.78)

[M+H]+=549

HPLC (Method 5): retention time=1.38 min

Example 285

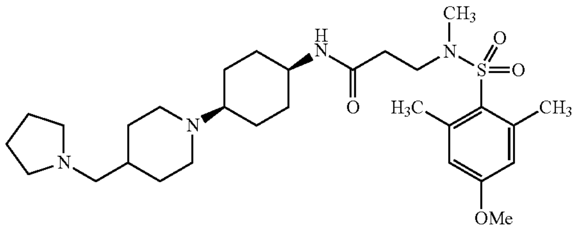 [SMILES: COc1cc(C)c(S(=O)(=O)N(C)CCC(=O)N[C@H]2CC[C@@H](N3CCC(CN4CCCC4)CC3)CC2)c(C)c1]

$C_{29}H_{48}N_4O_4S$ (548.78)

[M+H]+=549

HPLC (Method 5): retention time=1.36 min

Example 286
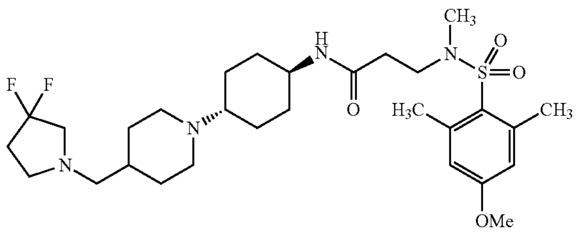 [SMILES: COc1cc(C)c(S(=O)(=O)N(C)CCC(=O)N[C@H]2CC[C@H](N3CCC(CN4CCC(F)(F)C4)CC3)CC2)c(C)c1]
$C_{29}H_{46}F_2N_4O_4S$ (584.76)
[M+H]+=585
HPLC (Method 5): retention time=1.38 min
Example 287
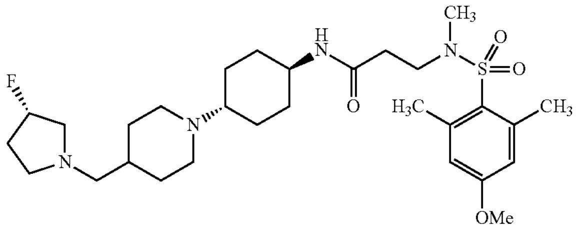 [SMILES: COc1cc(C)c(S(=O)(=O)N(C)CCC(=O)N[C@H]2CC[C@H](N3CCC(CN4CC[C@H](F)C4)CC3)CC2)c(C)c1]
$C_{29}H_{47}FN_4O_4S$ (566.77)
[M+H]+=567
HPLC (Method 5): retention time=1.38 min
Example 288
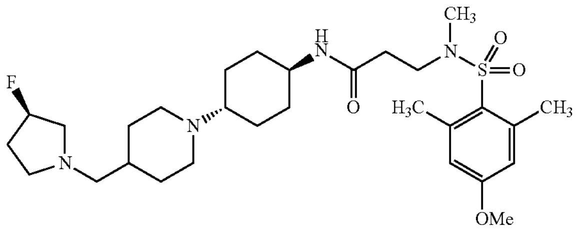 [SMILES: COc1cc(C)c(S(=O)(=O)N(C)CCC(=O)N[C@H]2CC[C@H](N3CCC(CN4CC[C@@H](F)C4)CC3)CC2)c(C)c1]
$C_{29}H_{47}FN_4O_4S$ (566.77)
[M+H]+=567
HPLC (Method 5): retention time=1.36 min
Example 289
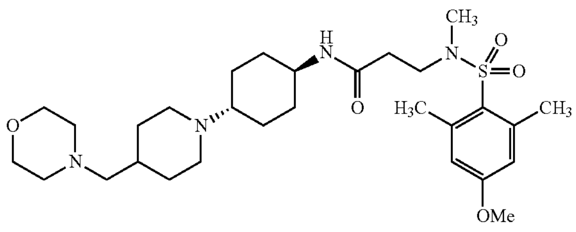 [SMILES: COc1cc(C)c(S(=O)(=O)N(C)CCC(=O)N[C@H]2CC[C@H](N3CCC(CN4CCOCC4)CC3)CC2)c(C)c1]
$C_{29}H_{48}N_4O_5S$ (564.78)
[M+H]+=565
HPLC (Method 5): retention time=1.37 min
Example 290
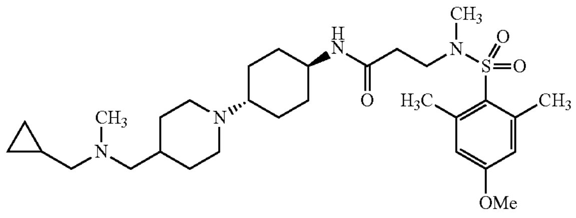 [SMILES: COc1cc(C)c(S(=O)(=O)N(C)CCC(=O)N[C@H]2CC[C@H](N3CCC(CN(C)CC4CC4)CC3)CC2)c(C)c1]
$C_{30}H_{50}N_4O_4S$ (562.81)
[M+H]+=563
HPLC (Method 5): retention time=1.39 min
Example 291
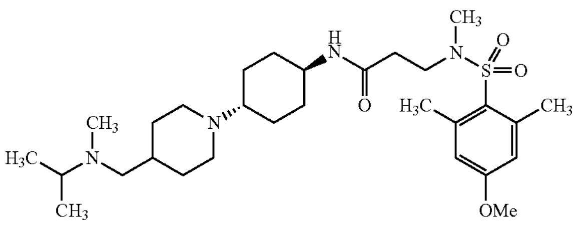 [SMILES: COc1cc(C)c(S(=O)(=O)N(C)CCC(=O)N[C@H]2CC[C@H](N3CCC(CN(C)C(C)C)CC3)CC2)c(C)c1]
$C_{29}H_{50}N_4O_4S$ (550.80)
[M+H]+=551
HPLC (Method 5): retention time=1.36 min Example 292

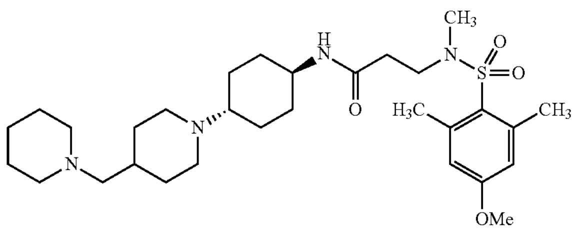 [SMILES: COc1cc(C)c(S(=O)(=O)N(C)CCC(=O)N[C@H]2CC[C@H](N3CCC(CN4CCCCC4)CC3)CC2)c(C)c1]

$C_{30}H_{50}N_4O_4S$ (562.81)
[M+H]+=563
HPLC (Method 5): retention time=1.28 min Example 293

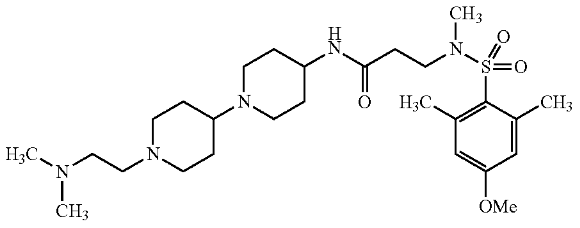

$C_{27}H_{47}N_5O_4S \times 3C_2HF_3O_2$ (879.83)
[M+H]+=538
HPLC (Method 5): retention time=1.33 min Example 294

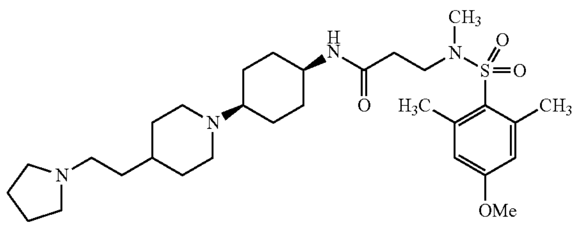 [SMILES: COc1cc(C)c(S(=O)(=O)N(C)CCC(=O)N[C@H]2CC[C@@H](N3CCC(CCN4CCCC4)CC3)CC2)c(C)c1]

$C_{30}H_{50}N_4O_4S \times 2HCl$ (635.73)
[M+H]+=563
HPLC (Method 5): retention time=1.37 min Example 295

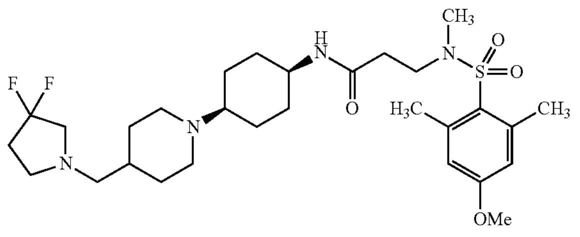 [SMILES: COc1cc(C)c(S(=O)(=O)N(C)CCC(=O)N[C@H]2CC[C@@H](N3CCC(CN4CCC(F)(F)C4)CC3)CC2)c(C)c1]

$C_{29}H_{46}F_2N_4O_4S \times 2C_2HF_3O_2$ (584.76)
[M+H]+=585
HPLC (Method 5): retention time=1.38 min Example 296

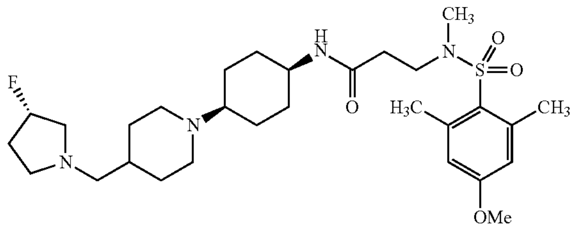 [SMILES: COc1cc(C)c(S(=O)(=O)N(C)CCC(=O)N[C@H]2CC[C@@H](N3CCC(CN4CC[C@H](F)C4)CC3)CC2)c(C)c1]

$C_{29}H_{47}FN_4O_4S \times 2C_2HF_3O_2$ (794.82)
[M+H]+=567
HPLC (Method 5): retention time=1.35 min Example 297

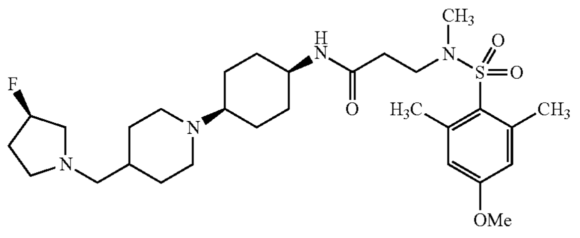 [SMILES: COc1cc(C)c(S(=O)(=O)N(C)CCC(=O)N[C@H]2CC[C@@H](N3CCC(CN4CC[C@@H](F)C4)CC3)CC2)c(C)c1]

$C_{29}H_{47}FN_4O_4S \times 2C_2HF_3O_2$ (794.82)
[M+H]+=567
HPLC (Method 5): retention time=1.36 min Example 298
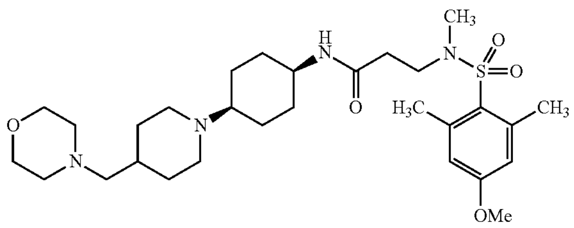 [SMILES: COc1cc(C)c(S(=O)(=O)N(C)CCC(=O)N[C@H]2CC[C@@H](N3CCC(CN4CCOCC4)CC3)CC2)c(C)c1]
$C_{29}H_{48}N_4O_5S$ (564.78)
[M+H]+=565
HPLC (Method 5): retention time=1.36 min
Example 299
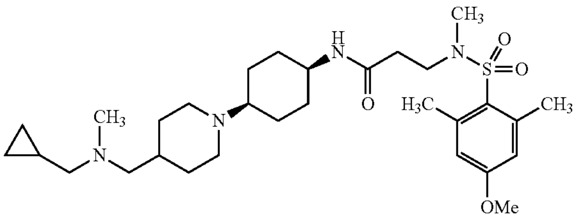 [SMILES: COc1cc(C)c(S(=O)(=O)N(C)CCC(=O)N[C@H]2CC[C@@H](N3CCC(CN(C)CC4CC4)CC3)CC2)c(C)c1]
$C_{30}H_{50}N_4O_4S$ (562.81)
[M+H]+=563
HPLC (Method 5): retention time=1.37 min
Example 300
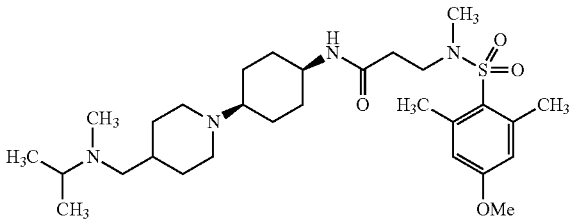 [SMILES: COc1cc(C)c(S(=O)(=O)N(C)CCC(=O)N[C@H]2CC[C@@H](N3CCC(CN(C)C(C)C)CC3)CC2)c(C)c1]
$C_{29}H_{50}N_4O_4S$ (550.80)
[M+H]+=551
HPLC (Method 5): retention time=1.37 min
Example 301
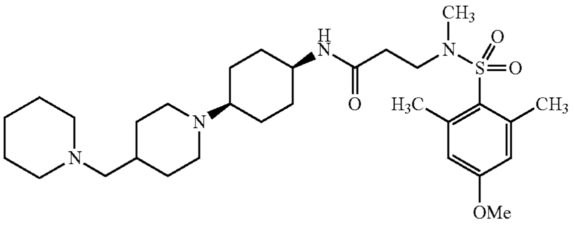 [SMILES: COc1cc(C)c(S(=O)(=O)N(C)CCC(=O)N[C@H]2CC[C@@H](N3CCC(CN4CCCCC4)CC3)CC2)c(C)c1]
$C_{30}H_{50}N_4O_4S$ (562.81)
[M+H]+=563
HPLC (Method 5): retention time=1.37 min
Example 302
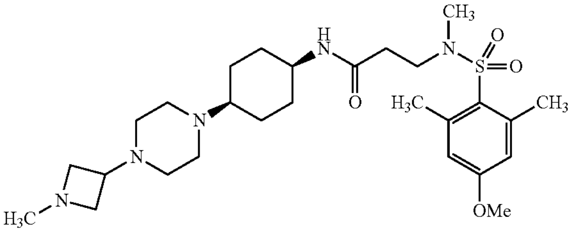
$C_{30}H_{50}N_4O_4S \times 3C_2HF_3O_2$ (877.81)
[M+H]+=536
HPLC (Method 5): retention time=1.34 min
Example 303
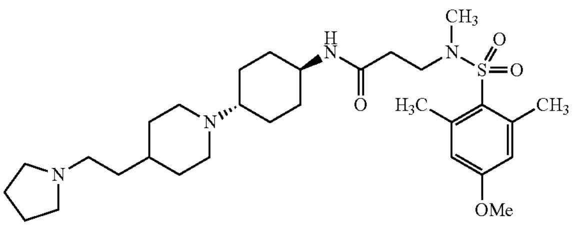 [SMILES: COc1cc(C)c(S(=O)(=O)N(C)CCC(=O)N[C@H]2CC[C@H](N3CCC(CCN4CCCC4)CC3)CC2)c(C)c1]
$C_{30}H_{50}N_4O_4S$ (562.81)
[M+H]+=563
HPLC (Method 5): retention time=1.37 min Example 304

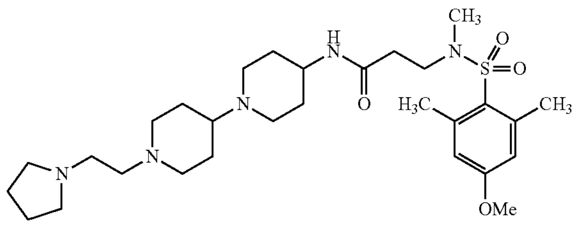 [SMILES: COc1cc(C)c(S(=O)(=O)N(C)CCC(=O)NC2CCN(C3CCN(CCN4CCCC4)CC3)CC2)c(C)c1]

$C_{29}H_{49}N_5O_4S \times 3C_2HF_3O_2$ (905.87)
[M+H]+=564
HPLC (Method 5): retention time=1.08 min Example 305

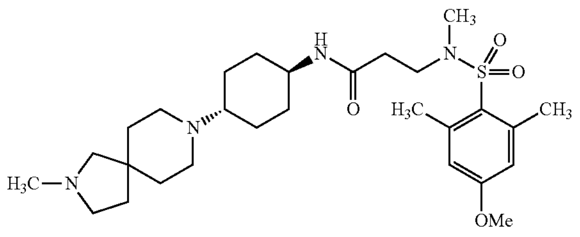

$C_{28}H_{46}N_4O_4S \times 2HCl$ (607.68)
[M+H]+=535
TLC: silica gel, dichloromethane/methanol/ammonia 8:2:0.2, Rf value=0.19

Example 306

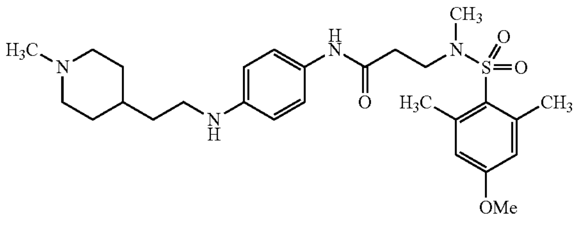

$C_{27}H_{40}N_4O_4S \times C_2HF_3O_4$ (630.72)
[M+H]+=517
HPLC (Method 9): retention time=1.40 min Example 307

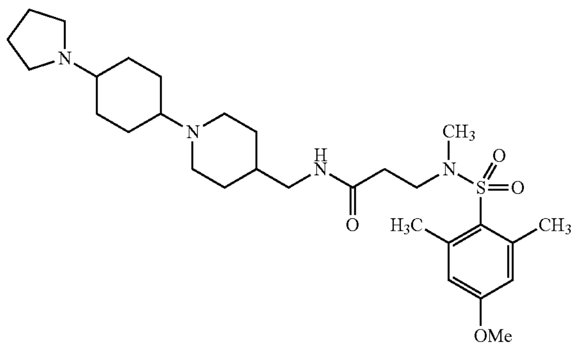 [SMILES: COc1cc(C)c(S(=O)(=O)N(C)CCC(=O)NCC2CCN(C3CCC(N4CCCC4)CC3)CC2)c(C)c1]

$C_{29}H_{48}N_4O_4S$ (548.78)
[M+H]+=549
HPLC (Method 6): retention time=1.24 min Example 308

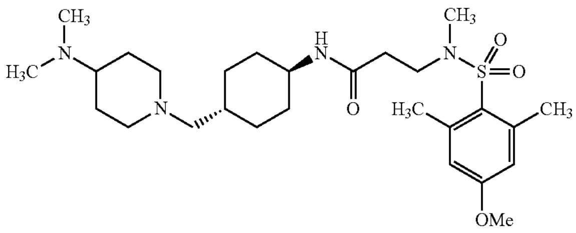

$C_{27}H_{46}N_4O_4S$ (522.74)
[M+H]+=523
HPLC (Method 9): retention time=1.29 min Example 309

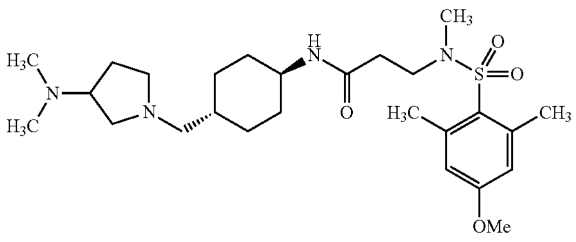

$C_{26}H_{44}N_4O_4S$ (508.72)
[M+H]+=509
HPLC (Method 9): retention time=1.30 min Example 310

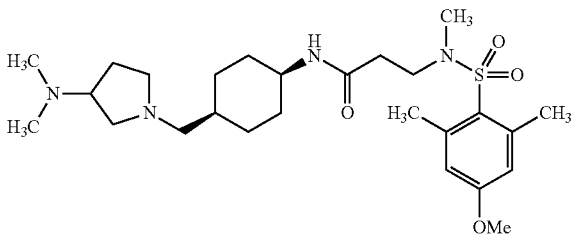

$C_{26}H_{44}N_4O_4S$ (508.72)
[M+H]+=509
HPLC (Method 9): retention time=1.23 min Example 311

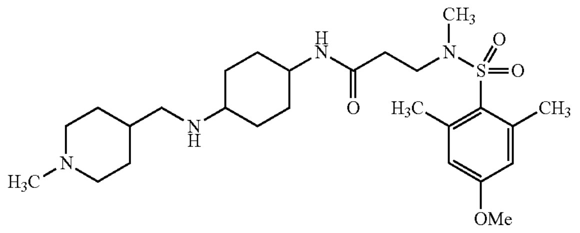

$C_{26}H_{44}N_4O_4S$ (508.72)
[M+H]+=509
HPLC (Method 6): retention time=1.20 min Example 312

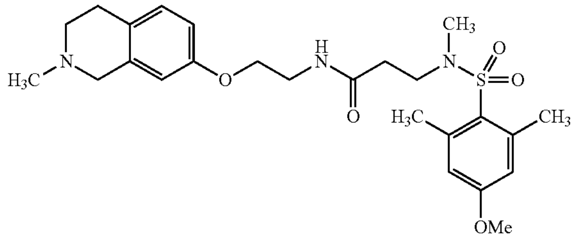

$C_{25}H_{35}N_3O_5S \times HCl$ (526.09)
[M+H]+=490
HPLC (Method 10): retention time=1.16 min Example 313

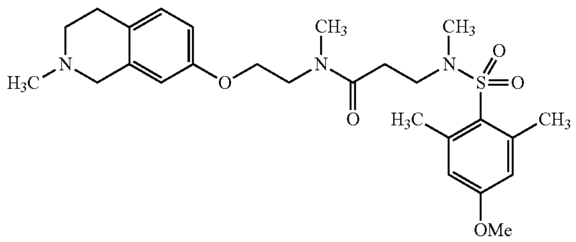

$C_{26}H_{37}N_3O_5S \times HCl$ (540.12)
[M+H]+=504
HPLC (Method 10): retention time=1.22 min Example 314

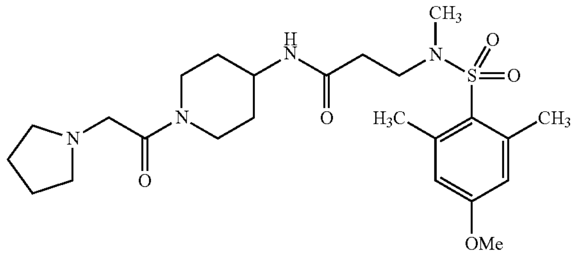 [SMILES: COc1cc(C)c(S(=O)(=O)N(C)CCC(=O)NC2CCN(C(=O)CN3CCCC3)CC2)c(C)c1]

$C_{24}H_{38}N_4O_5S \times C_2HF_3O_2$ (608.67)
[M+H]+=495
HPLC (Method 9): retention time=1.47 min Example 315

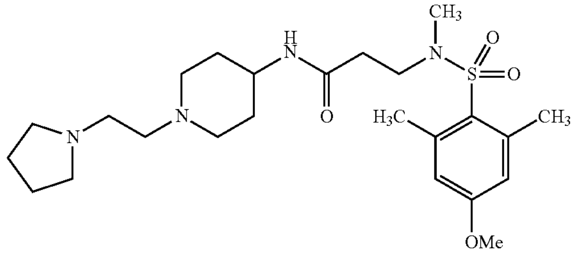 [SMILES: COc1cc(C)c(S(=O)(=O)N(C)CCC(=O)NC2CCN(CCN3CCCC3)CC2)c(C)c1]

$C_{24}H_{40}N_4O_4S$ (480.66)
[M+H]+=481
HPLC (Method 9): retention time=1.21 min Example 316

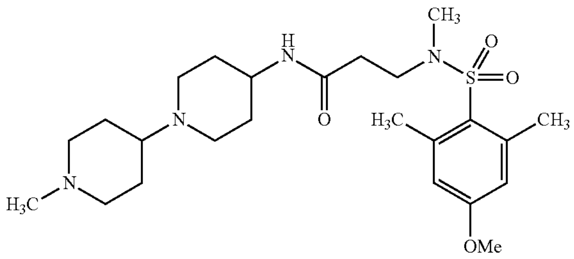

$C_{24}H_{40}N_4O_4S \times C_2HF_3O_2$ (594.69)
[M+H]+=481
HPLC (Method 9): retention time=1.19 min Example 317

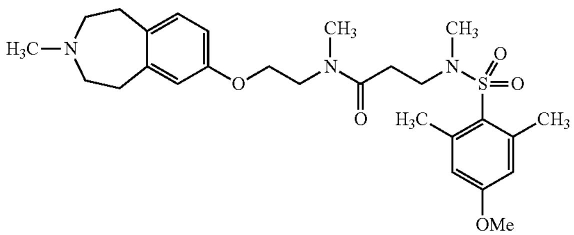

$C_{27}H_{39}N_3O_5S \times HCl$ (554.14)
[M+H]+=518
HPLC (Method 5): retention time=1.36 min Example 593

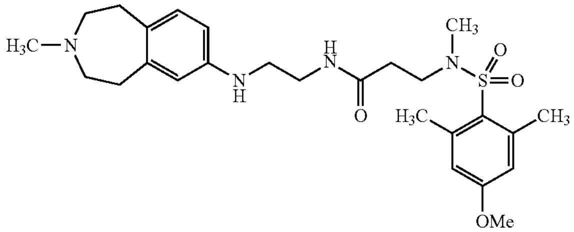

$C_{26}H_{38}N_4O_4S \times HCl$ (539.13)
[M+H]+=503
HPLC (Method 5): retention time=1.29 min Example 594

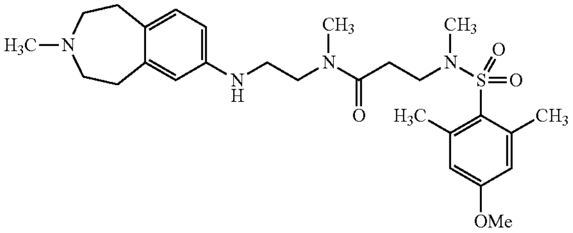

$C_{27}H_{40}N_4O_4S \times HCl$ (553.16)
[M+H]+=517
HPLC (Method 5): retention time=1.35 min Example 595

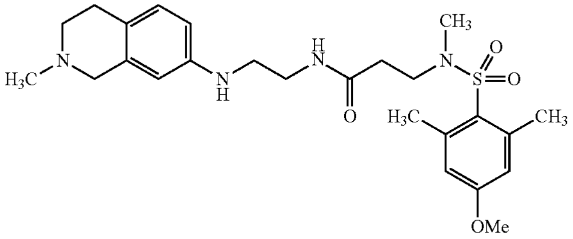

$C_{25}H_{36}N_4O_4S \times HCl$ (525.10)
[M+H]+=489
HPLC (Method 5): retention time=1.31 min Example 596

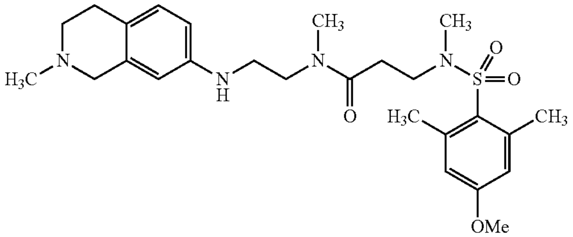

$C_{26}H_{38}N_4O_4S \times HCl$ (539.13)
[M+H]+=503
HPLC (Method 5): retention time=1.35 min Example 597

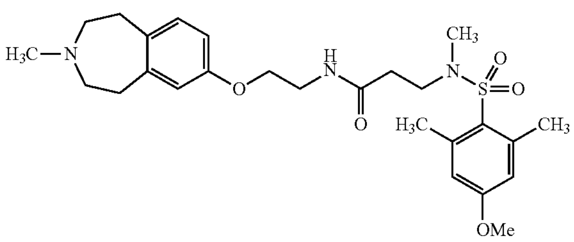

$C_{26}H_{37}N_3O_5S$×HCl (540.12)
[M+H]+=504
HPLC (Method 10): retention time=1.18 min Example 598

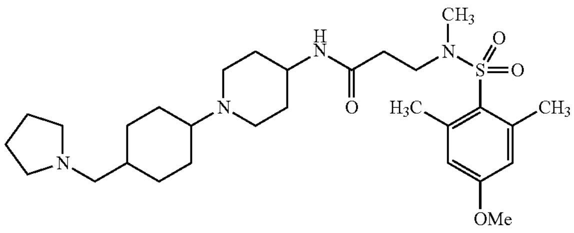 [SMILES: COc1cc(C)c(S(=O)(=O)N(C)CCC(=O)NC2CCN(C3CCC(CN4CCCC4)CC3)CC2)c(C)c1]

$C_{29}H_{48}N_4O_4S$×$C_2HF_3O_2$ (662.81)
[M+H]+=549
HPLC (Method 9): retention time=1.27 min Example 599

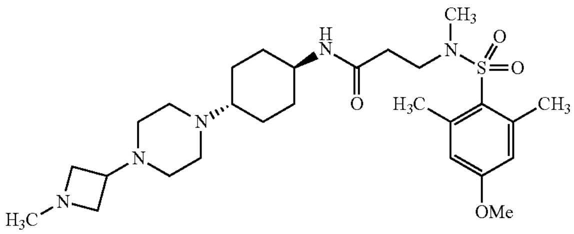

$C_{27}H_{45}N_5O_4S$×3HCl (645.13)
[M+H]+=536
HPLC (Method 5): retention time=1.14 min Example 600

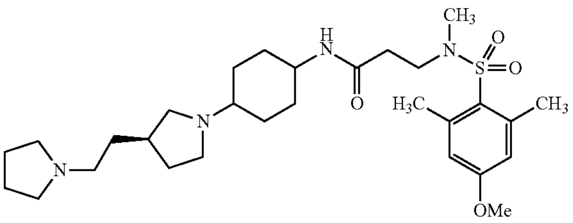 [SMILES: COc1cc(C)c(S(=O)(=O)N(C)CCC(=O)NC2CCC(N3CC[C@@H](CCN4CCCC4)C3)CC2)c(C)c1]

$C_{29}H_{48}N_4O_4S$×2HCl (621.70)
[M+H]+=549
HPLC (Method 5): retention time=1.16 min Example 601

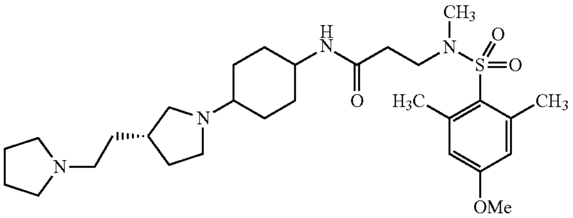 [SMILES: COc1cc(C)c(S(=O)(=O)N(C)CCC(=O)NC2CCC(N3CC[C@H](CCN4CCCC4)C3)CC2)c(C)c1]

$C_{29}H_{48}N_4O_4S$ (548.78)
[M+H]+=549
HPLC (Method 5): retention time=1.16 min Example 602

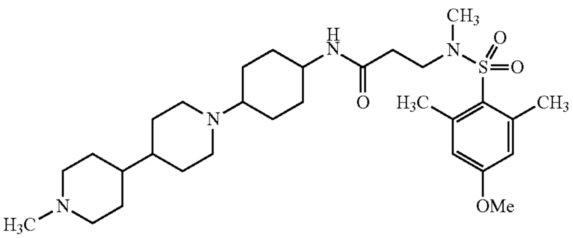

$C_{30}H_{50}N_4O_4S$×$C_2HF_3O_2$ (676.83)
[M+H]+=563
HPLC (Method 9): retention time=1.14 min Example 608

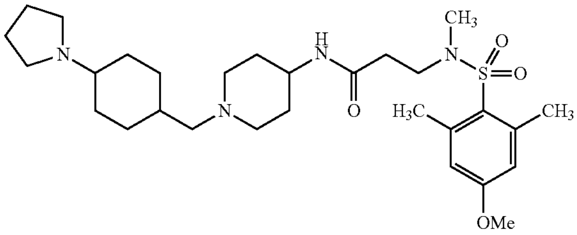 [SMILES: COc1cc(C)c(S(=O)(=O)N(C)CCC(=O)NC2CCN(CC3CCC(N4CCCC4)CC3)CC2)c(C)c1]

$C_{29}H_{48}N_4O_4S{\times}C_2HF_3O_2$ (662.81)
[M+H]+=549
HPLC (Method 9): retention time=1.30 min Example 609

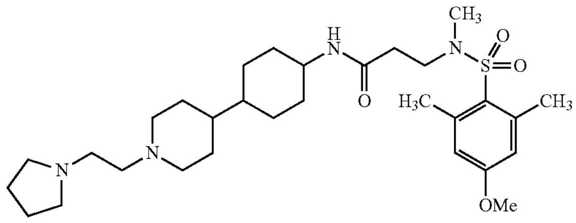 [SMILES: COc1cc(C)c(S(=O)(=O)N(C)CCC(=O)NC2CCC(C3CCN(CCN4CCCC4)CC3)CC2)c(C)c1]

$C_{30}H_{50}N_4O_4S{\times}2HCl$ (635.73)
[M+H]+=563
HPLC (Method 11): retention time=1.70 min Example 610

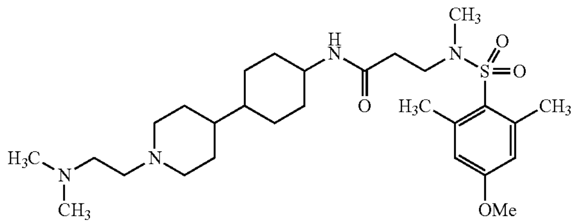

$C_{28}H_{48}N_4O_4S{\times}2HCl$ (609.69)
[M+H]+=537
HPLC (Method 11): retention time=1.67 min Example 611

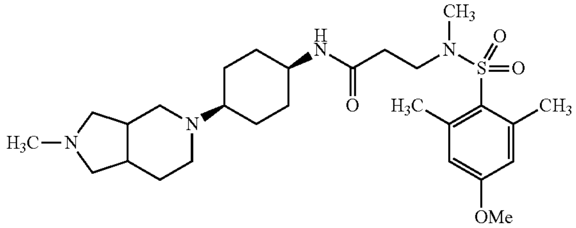

$C_{27}H_{44}N_4O_4S{\times}2HCl$ (593.65)
[M+H]+=521
HPLC (Method 11): retention time=1.61 min Example 636

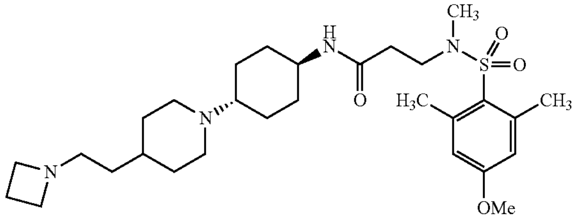 [SMILES: COc1cc(C)c(S(=O)(=O)N(C)CCC(=O)N[C@H]2CC[C@H](N3CCC(CCN4CCC4)CC3)CC2)c(C)c1]

$C_{29}H_{48}N_4O_4S{\times}2HCl$ (621.70)
[M+H]+=549
HPLC (Method 4): retention time=2.39 min Example 637

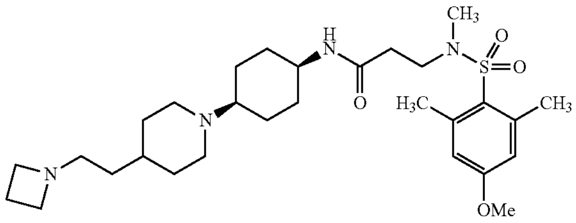 [SMILES: COc1cc(C)c(S(=O)(=O)N(C)CCC(=O)N[C@H]2CC[C@@H](N3CCC(CCN4CCC4)CC3)CC2)c(C)c1]

$C_{29}H_{48}N_4O_4S{\times}2HCl$ (621.70)
[M+H]+=549
HPLC (Method 4): retention time=2.34 min The following compounds were prepared analogously to Example 53:
Example 318
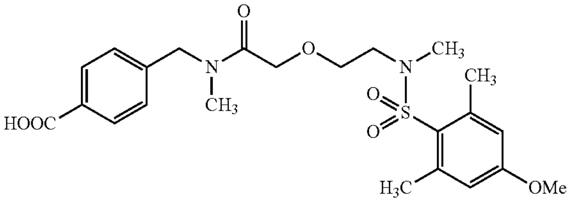 [SMILES: COc1cc(C)c(S(=O)(=O)N(C)CCOCC(=O)N(C)Cc2ccc(C(=O)O)cc2)c(C)c1]
$C_{23}H_{30}N_2O_7S$ (478.56)
[M+H]+=479
HPLC (Method 6): retention time=3.21 min
Example 319
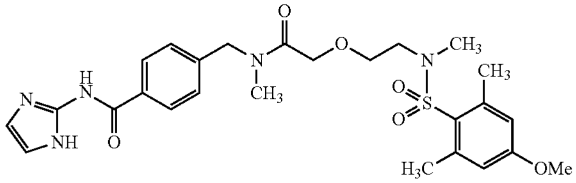 [SMILES: COc1cc(C)c(S(=O)(=O)N(C)CCOCC(=O)N(C)Cc2ccc(C(=O)Nc3ncc[nH]3)cc2)c(C)c1]
$C_{26}H_{33}N_5O_6S$ (543.64)
[M+H]+=544
HPLC (Method 6): retention time=2.51 min
Example 320
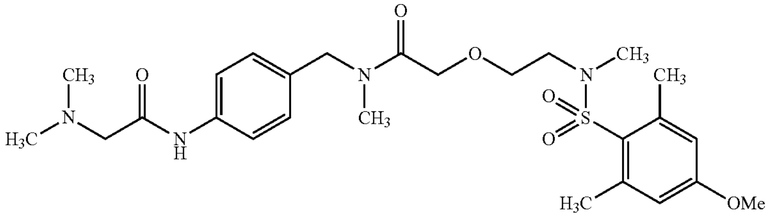 [SMILES: COc1cc(C)c(S(=O)(=O)N(C)CCOCC(=O)N(C)Cc2ccc(NC(=O)CN(C)C)cc2)c(C)c1]
$C_{26}H_{38}N_4O_6S$ (534.67)
[M+H]+=535
HPLC (Method 6): retention time=2.48 min
Example 321
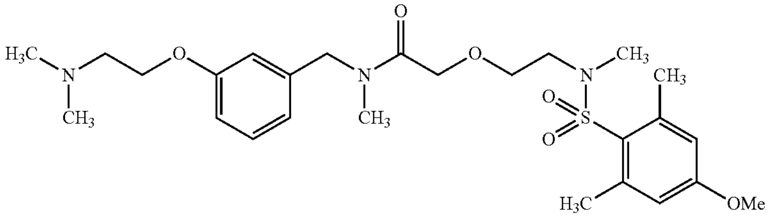 [SMILES: COc1cc(C)c(S(=O)(=O)N(C)CCOCC(=O)N(C)Cc2cccc(OCCN(C)C)c2)c(C)c1]
$C_{26}H_{398}N_3O_6S$ (521.67)
[M+H]+=522
HPLC (Method 6): retention time=2.60 min
Example 322
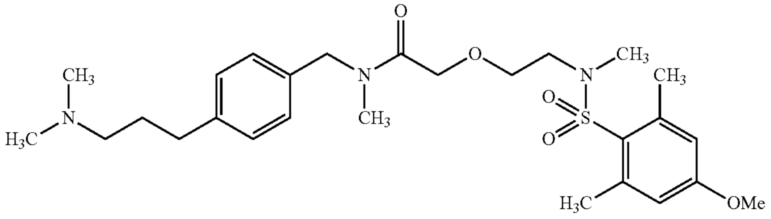 [SMILES: COc1cc(C)c(S(=O)(=O)N(C)CCOCC(=O)N(C)Cc2ccc(CCCN(C)C)cc2)c(C)c1]
$C_{27}H_{41}N_3O_5S$ (519.70)
[M+H]+=520
HPLC (Method 6): retention time=2.61 min Example 323
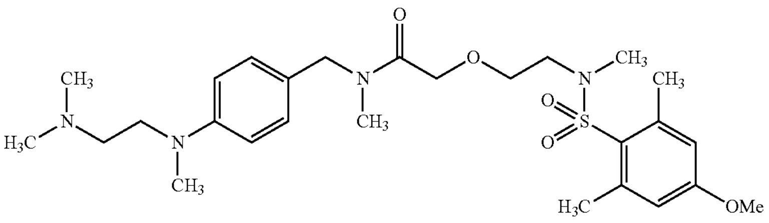 [SMILES: COc1cc(C)c(S(=O)(=O)N(C)CCOCC(=O)N(C)Cc2ccc(N(C)CCN(C)C)cc2)c(C)c1]
$C_{27}H_{42}N_4O_5S×HCl$ (571.17)
[M+H]+=535
HPLC (Method 5): retention time=1.57 min
Example 324
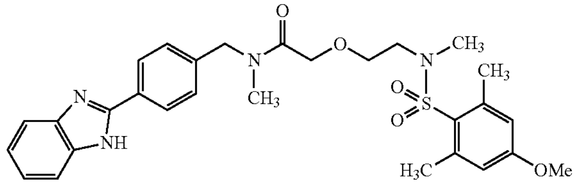 [SMILES: COc1cc(C)c(S(=O)(=O)N(C)CCOCC(=O)N(C)Cc2ccc(-c3nc4ccccc4[nH]3)cc2)c(C)c1]
$C_{29}H_{34}N_4O_5S×C_2HF_3O_2$ (664.69)
[M+H]+=551
HPLC (Method 5): retention time=1.60 min
Example 325
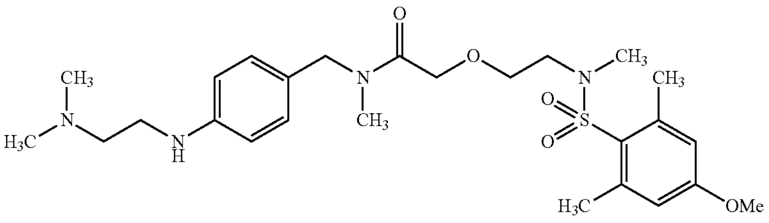 [SMILES: COc1cc(C)c(S(=O)(=O)N(C)CCOCC(=O)N(C)Cc2ccc(NCCN(C)C)cc2)c(C)c1]
$C_{26}H_{40}N_4O_5S×HCl$ (557.15)
[M+H]+=521
HPLC (Method 5): retention time=1.53 min
Example 326
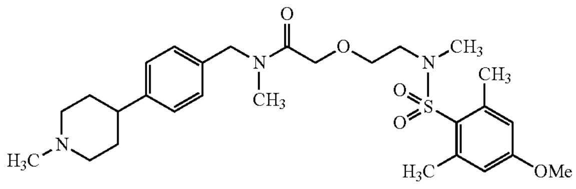 [SMILES: COc1cc(C)c(S(=O)(=O)N(C)CCOCC(=O)N(C)Cc2ccc(C3CCN(C)CC3)cc2)c(C)c1]
$C_{28}H_{41}N_3O_5S×C_2HF_3O_2$ (645.73)
[M+H]+=532
HPLC (Method 5): retention time=1.54 min
Example 327
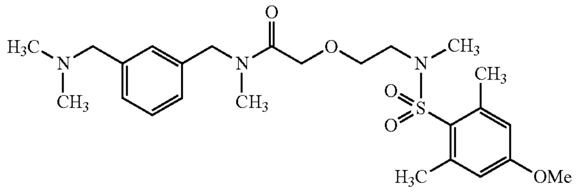 [SMILES: COc1cc(C)c(S(=O)(=O)N(C)CCOCC(=O)N(C)Cc2cccc(CN(C)C)c2)c(C)c1]
$C_{25}H_{37}N_3O_5S×HCl$ (528.11)
[M+H]+=492
HPLC (Method 5): retention time=1.53 min Example 328

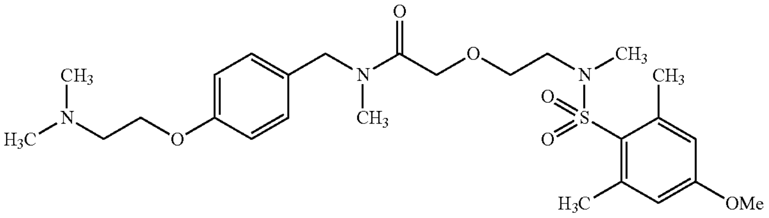

$C_{26}H_{39}N_3O_6S \times C_2HF_3O_2$ (635.69)
[M+H]+=522
HPLC (Method 5): retention time=1.53 min Example 329

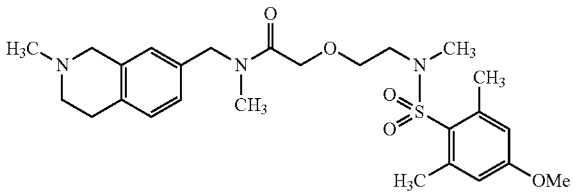 [SMILES: COc1cc(C)c(S(=O)(=O)N(C)CCOCC(=O)N(C)Cc2ccc3c(c2)CN(C)CC3)c(C)c1]

$C_{26}H_{37}N_3O_5S \times HCl$ (540.12)
[M+H]+=504
HPLC (Method 7): retention time=1.93 min Example 330

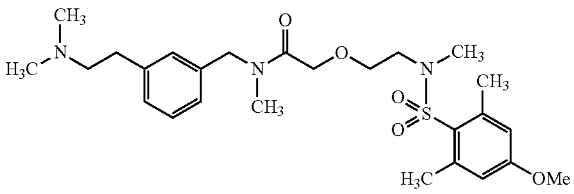 [SMILES: COc1cc(C)c(S(=O)(=O)N(C)CCOCC(=O)N(C)Cc2cccc(CCN(C)C)c2)c(C)c1]

$C_{26}H_{39}N_3O_5S \times HCl$ (542.13)
[M+H]+=506
HPLC (Method 5): retention time=1.54 min Example 331

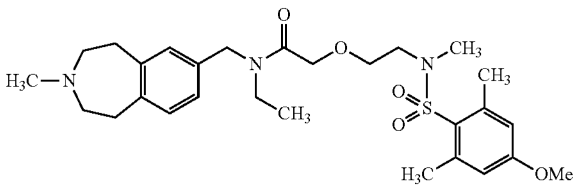 [SMILES: CCN(Cc1ccc2c(c1)CCN(C)CC2)C(=O)COCCN(C)S(=O)(=O)c1c(C)cc(OC)cc1C]

$C_{28}H_{41}N_3O_5S \times HCl$ (568.17)
[M+H]+=532
TLC: silica gel, dichloromethane/methanol/ammonia 9:1:0.1, Rf value=0.30

Example 332

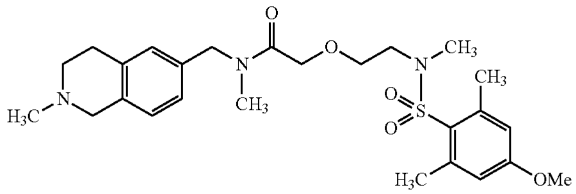 [SMILES: COc1cc(C)c(S(=O)(=O)N(C)CCOCC(=O)N(C)Cc2ccc3c(c2)CCN(C)C3)c(C)c1]

$C_{26}H_{37}N_3O_5S \times HCl$ (540.12)
[M+H]+=504
HPLC (Method 5): retention time=1.51 min Example 333

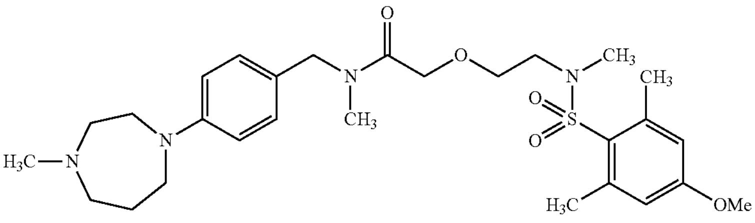 [SMILES: COc1cc(C)c(S(=O)(=O)N(C)CCOCC(=O)N(C)Cc2ccc(N3CCCN(C)CC3)cc2)c(C)c1]

$C_{28}H_{42}N_4O_5S \times HCl$ (583.18)

[M+H]+=547

HPLC (Method 5): retention time=1.54 min

Example 334

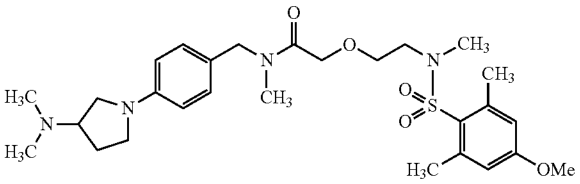 [SMILES: COc1cc(C)c(S(=O)(=O)N(C)CCOCC(=O)N(C)Cc2ccc(N3CCC(N(C)C)C3)cc2)c(C)c1]

$C_{28}H_{42}N_4O_5S{\times}HCl$ (583.18)
[M+H]+=547
HPLC (Method 10): retention time=1.24 min Example 335

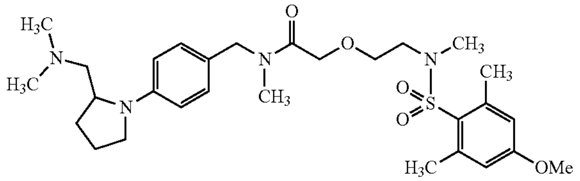 [SMILES: COc1cc(C)c(S(=O)(=O)N(C)CCOCC(=O)N(C)Cc2ccc(N3CCCC3CN(C)C)cc2)c(C)c1]

$C_{29}H_{44}N_4O_5S{\times}HCl$ (597.21)
[M+H]+=561
HPLC (Method 5): retention time=1.55 min Example 336

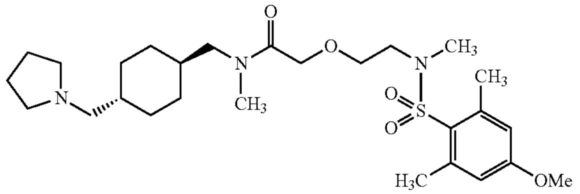 [SMILES: COc1cc(C)c(S(=O)(=O)N(C)CCOCC(=O)N(C)C[C@H]2CC[C@H](CN3CCCC3)CC2)c(C)c1]

$C_{27}H_{45}N_3O_5S{\times}HCl$ (560.19)
[M+H]+=524
TLC: silica gel, dichloromethane/methanol/ammonia 8:2:0.01, Rf value=0.39

Example 337

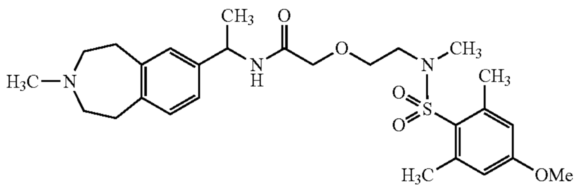 [SMILES: COc1cc(C)c(S(=O)(=O)N(C)CCOCC(=O)NC(C)c2ccc3c(c2)CCN(C)CC3)c(C)c1]

$C_{27}H_{39}N_3O_5S{\times}HCl$ (554.14)
[M+H]+=518
HPLC (Method 4): retention time=3.4 min Example 338

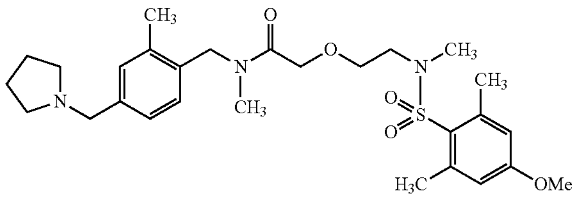 [SMILES: COc1cc(C)c(S(=O)(=O)N(C)CCOCC(=O)N(C)Cc2ccc(CN3CCCC3)cc2C)c(C)c1]

$C_{28}H_{41}N_3O_5S{\times}HCl$ (568.17)
[M+H]+=532
TLC: silica gel, dichloromethane/methanol 9:1, Rf value=0.14

Example 339

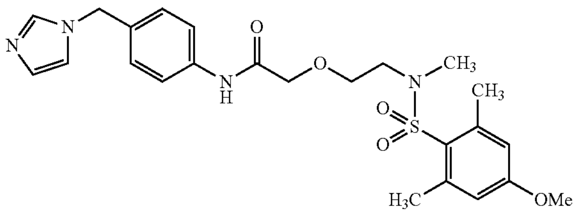 [SMILES: COc1cc(C)c(S(=O)(=O)N(C)CCOCC(=O)Nc2ccc(Cn3ccnc3)cc2)c(C)c1]

$C_{24}H_{30}N_4O_5S{\times}C_2HF_3O_2$ (600.61)
[M+H]+=487
HPLC (Method 6): retention time=2.58 min Example 340

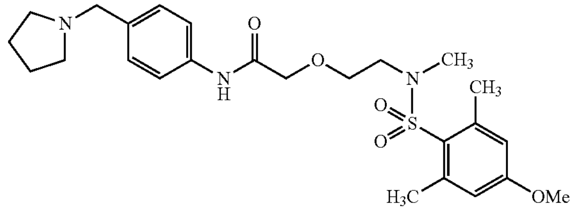 [SMILES: COc1cc(C)c(S(=O)(=O)N(C)CCOCC(=O)Nc2ccc(CN3CCCC3)cc2)c(C)c1]

$C_{25}H_{35}N_3O_5S{\times}C_2HF_3O_2$ (603.65)
[M+H]+=490
HPLC (Method 6): retention time=2.61 min Example 341
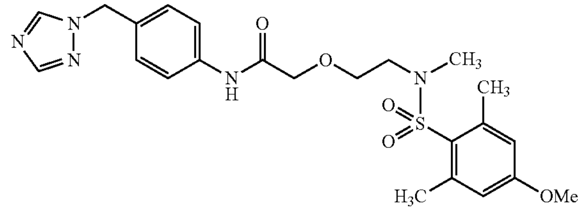 [SMILES: COc1cc(C)c(S(=O)(=O)N(C)CCOCC(=O)Nc2ccc(Cn3cncn3)cc2)c(C)c1]
$C_{23}H_{29}N_5O_5S \times C_2HF_3O_2$ (601.60)
[M+H]+=488
HPLC (Method 6): retention time=3.28 min
Example 342
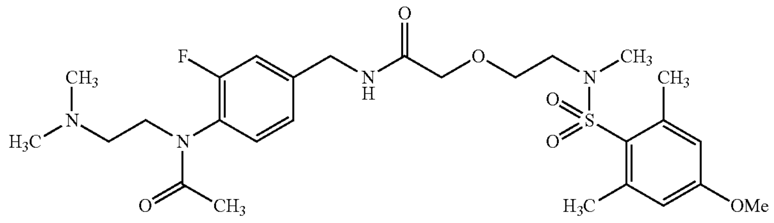 [SMILES: COc1cc(C)c(S(=O)(=O)N(C)CCOCC(=O)NCc2ccc(N(CCN(C)C)C(C)=O)c(F)c2)c(C)c1]
$C_{27}H_{39}FN_4O_6S$ (566.69)
[M+H]+=567
HPLC (Method 6): retention time=2.59 min
Example 343
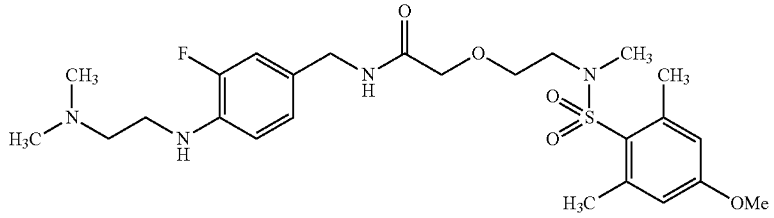 [SMILES: COc1cc(C)c(S(=O)(=O)N(C)CCOCC(=O)NCc2ccc(NCCN(C)C)c(F)c2)c(C)c1]
$C_{25}H_{37}FN_4O_5S$ (524.65)
[M+H]+=525
HPLC (Method 6): retention time=2.59 min
Example 344
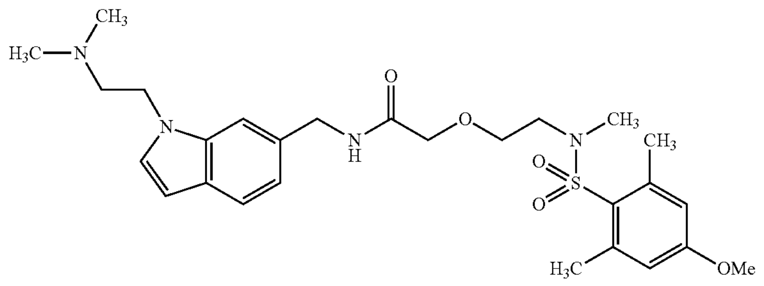 [SMILES: COc1cc(C)c(S(=O)(=O)N(C)CCOCC(=O)NCc2ccc3ccn(CCN(C)C)c3c2)c(C)c1]
$C_{27}H_{38}N_4O_5S$ (530.68)
[M+H]+=531
HPLC (Method 6): retention time=2.65 min Example 345
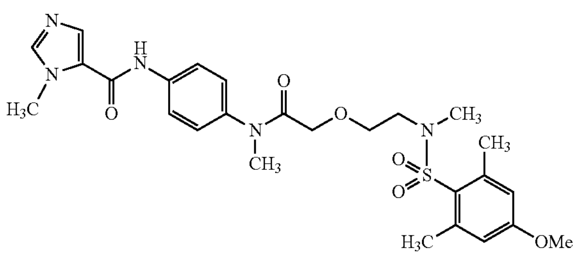 [SMILES: COc1cc(C)c(S(=O)(=O)N(C)CCOCC(=O)N(C)c2ccc(NC(=O)c3cncn3C)cc2)c(C)c1]
$C_{26}H_{33}N_5O_6S$ (543.64)
[M+H]+=544
HPLC (Method 6): retention time=2.39 min
Example 346
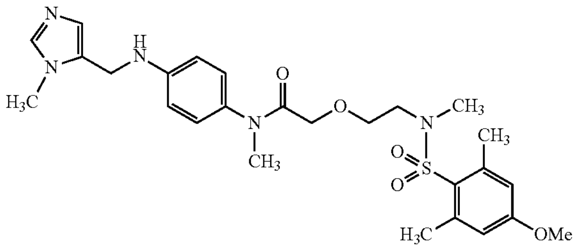 [SMILES: COc1cc(C)c(S(=O)(=O)N(C)CCOCC(=O)N(C)c2ccc(NCc3cncn3C)cc2)c(C)c1]
$C_{26}H_{35}N_5O_5S$ (529.65)
[M+H]+=530
HPLC (Method 6): retention time=2.43 min
Example 347
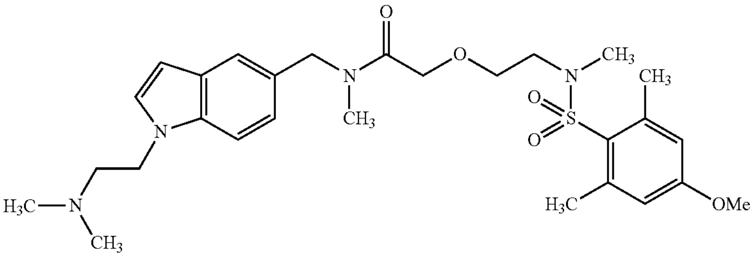 [SMILES: COc1cc(C)c(S(=O)(=O)N(C)CCOCC(=O)N(C)Cc2ccc3c(ccn3CCN(C)C)c2)c(C)c1]
$C_{28}H_{40}N_4O_5S$ (544.71)
[M+H]+=545
HPLC (Method 6): retention time=2.65 min
Example 348
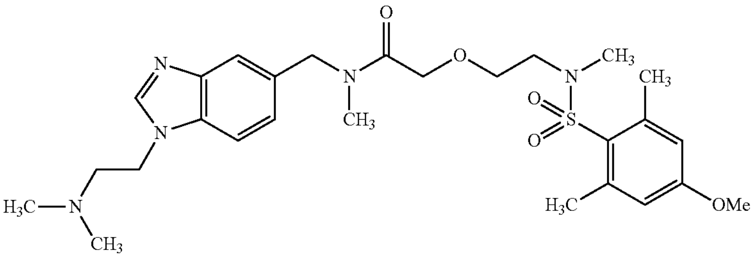 [SMILES: COc1cc(C)c(S(=O)(=O)N(C)CCOCC(=O)N(C)Cc2ccc3c(c2)ncn3CCN(C)C)c(C)c1]
$C_{27}H_{39}N_5O_5S$ (545.70)
[M+H]+=546
HPLC (Method 6): retention time=2.19 min
Example 349
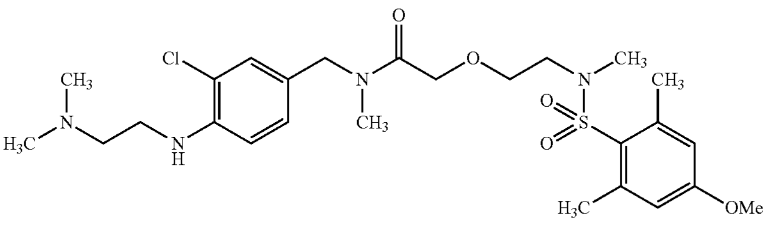 [SMILES: COc1cc(C)c(S(=O)(=O)N(C)CCOCC(=O)N(C)Cc2ccc(NCCN(C)C)c(Cl)c2)c(C)c1]
$C_{26}H_{39}ClN_4O_5S$ (555.13)
[M+H]+=555/557
HPLC (Method 6): retention time=2.63 min Example 350
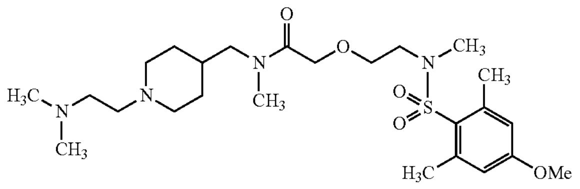 [SMILES: COc1cc(C)c(S(=O)(=O)N(C)CCOCC(=O)N(C)CC2CCN(CCN(C)C)CC2)c(C)c1]
$C_{25}H_{44}N_4O_5S$ (512.71)
[M+H]+=513
HPLC (Method 6): retention time=1.94 min
Example 351
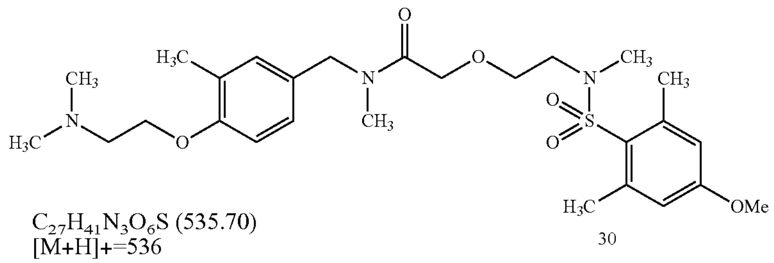
$C_{27}H_{41}N_3O_6S$ (535.70)
[M+H]+=536
HPLC (Method 6): retention time=2.56 min
Example 352
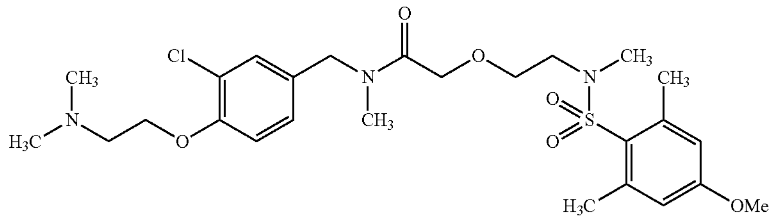 [SMILES: COc1cc(C)c(S(=O)(=O)N(C)CCOCC(=O)N(C)Cc2ccc(OCCN(C)C)c(Cl)c2)c(C)c1]
$C_{26}H_{38}ClN_3O_6S \times CH_2O_2$ (602.14)
[M+H]+=556/558
HPLC (Method 6): retention time=2.65 min
Example 353
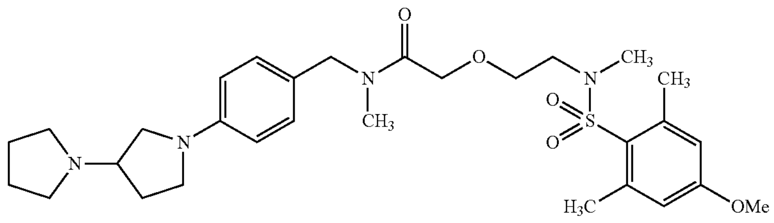 [SMILES: COc1cc(C)c(S(=O)(=O)N(C)CCOCC(=O)N(C)Cc2ccc(N3CCC(N4CCCC4)C3)cc2)c(C)c1]
$C_{30}H_{44}N_4O_6S$ (572.76)
[M+H]+=573
HPLC (Method 6): retention time=2.69 min Example 354
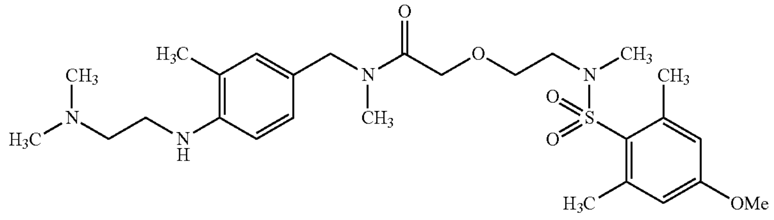 [SMILES: COc1cc(C)c(S(=O)(=O)N(C)CCOCC(=O)N(C)Cc2ccc(NCCN(C)C)c(C)c2)c(C)c1]
$C_{27}H_{42}N_4O_6S$ (534.71)
[M+H]+=535
HPLC (Method 6): retention time=2.54 min
Example 355
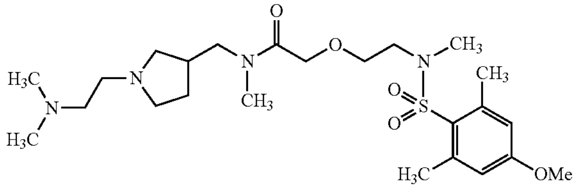 [SMILES: COc1cc(C)c(S(=O)(=O)N(C)CCOCC(=O)N(C)CC2CCN(CCN(C)C)C2)c(C)c1]
$C_{24}H_{42}N_4O_5S$ (498.68)
[M+H]+=499
HPLC (Method 6): retention time=1.95 min
Example 356
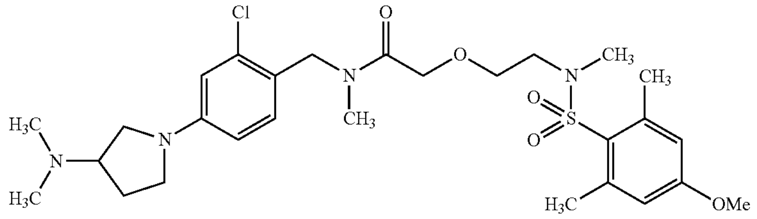 [SMILES: COc1cc(C)c(S(=O)(=O)N(C)CCOCC(=O)N(C)Cc2ccc(N3CCC(N(C)C)C3)cc2Cl)c(C)c1]
$C_{28}H_{41}ClN_4O_5S$ (581.17)
[M+H]+=581/583
HPLC (Method 6): retention time=2.77 min
Example 357
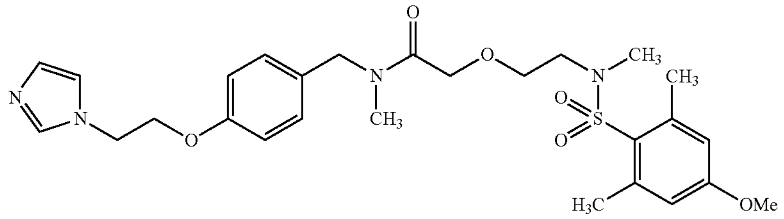 [SMILES: COc1cc(C)c(S(=O)(=O)N(C)CCOCC(=O)N(C)Cc2ccc(OCCn3ccnc3)cc2)c(C)c1]
$C_{27}H_{36}N_4O_6S$ (544.66)
[M+H]+=545
HPLC (Method 6): retention time=2.59 min Example 358
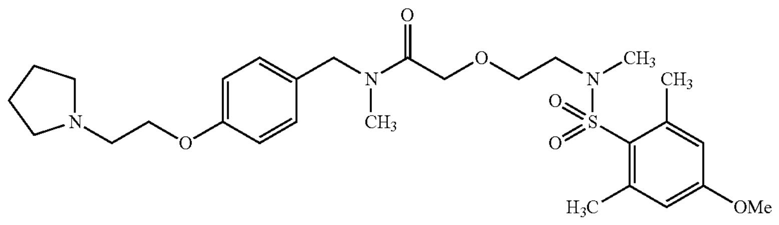 [SMILES: COc1cc(C)c(S(=O)(=O)N(C)CCOCC(=O)N(C)Cc2ccc(OCCN3CCCC3)cc2)c(C)c1]
$C_{28}H_{41}N_3O_6S$ (547.71)
[M+H]+=548
HPLC (Method 6): retention time=2.59 min
Example 359
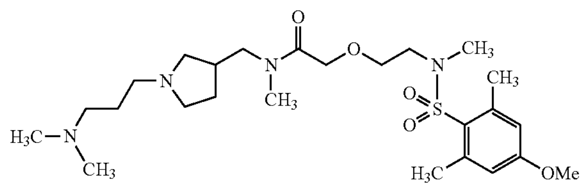
$C_{25}H_{44}N_4O_5S$ (512.71)
[M+H]+=513
HPLC (Method 6): retention time=1.94 min
Example 360
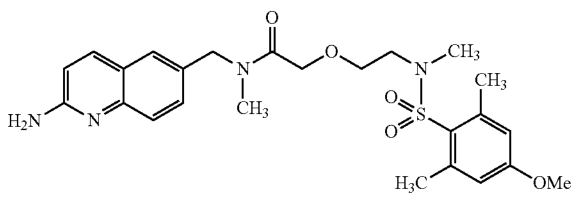 [SMILES: COc1cc(C)c(S(=O)(=O)N(C)CCOCC(=O)N(C)Cc2ccc3nc(N)ccc3c2)c(C)c1]
$C_{25}H_{32}N_4O_5S$ (500.61)
[M+H]+=501
HPLC (Method 6): retention time=2.41 min
Example 361
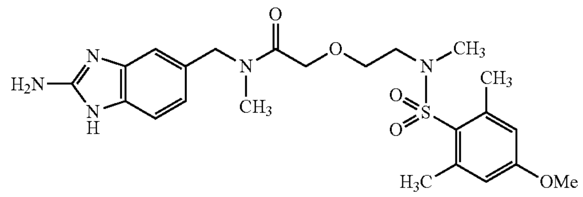 [SMILES: COc1cc(C)c(S(=O)(=O)N(C)CCOCC(=O)N(C)Cc2ccc3[nH]c(N)nc3c2)c(C)c1]
$C_{23}H_{31}N_5O_5S$ (489.59)
[M+H]+=490
HPLC (Method 6): retention time=2.46 min
Example 362
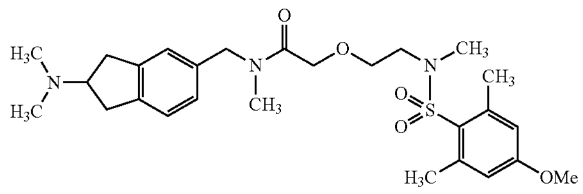 [SMILES: COc1cc(C)c(S(=O)(=O)N(C)CCOCC(=O)N(C)Cc2ccc3c(c2)CC(N(C)C)C3)c(C)c1]
$C_{27}H_{39}N_3O_5S \times C_2HF_3O_2$ (631.71)
[M+H]+=518
HPLC (Method 6): retention time=2.54 min
Example 363
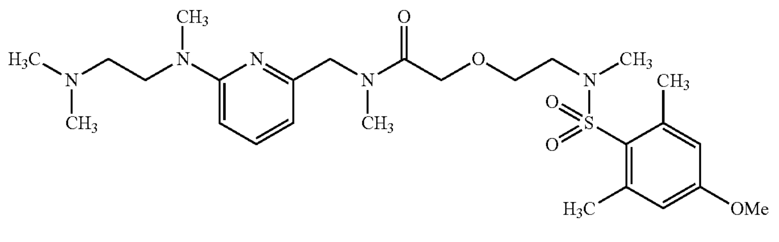 [SMILES: COc1cc(C)c(S(=O)(=O)N(C)CCOCC(=O)N(C)Cc2cccc(N(C)CCN(C)C)n2)c(C)c1]
$C_{26}H_{41}N_5O_5S \times CH_2O_2$ (581.73)
[M+H]+=536
HPLC (Method 6): retention time=2.58 min Example 364
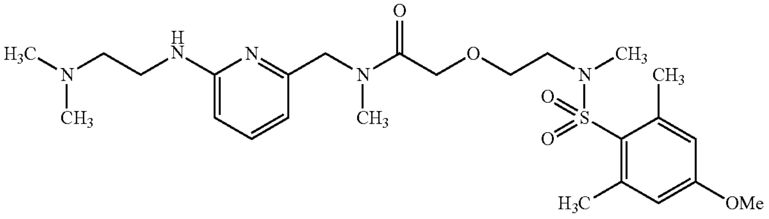 [SMILES: COc1cc(C)c(S(=O)(=O)N(C)CCOCC(=O)N(C)Cc2cccc(NCCN(C)C)n2)c(C)c1]
$C_{25}H_{39}N_5O_5S \times CH_2O_2$ (567.70)
[M+H]+=522
HPLC (Method 6): retention time=2.31 min
Example 365
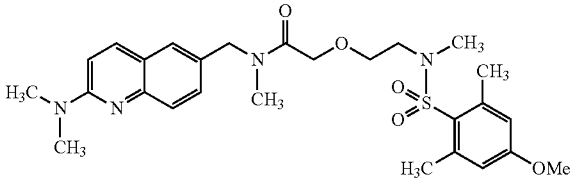 [SMILES: COc1cc(C)c(S(=O)(=O)N(C)CCOCC(=O)N(C)Cc2ccc3nc(N(C)C)ccc3c2)c(C)c1]
$C_{27}H_{36}N_4O_5S \times C_2HF_3O_2$ (642.69)
[M+H]+=529
HPLC (Method 6): retention time=2.56 min
Example 366
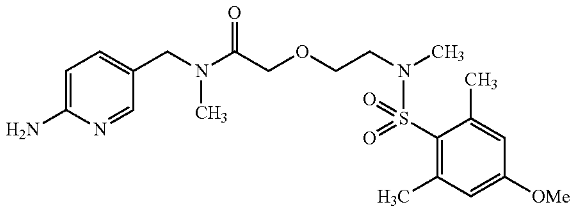 [SMILES: COc1cc(C)c(S(=O)(=O)N(C)CCOCC(=O)N(C)Cc2ccc(N)nc2)c(C)c1]
$O_{21}H_{30}N_4O_5S$ (450.55)
[M+H]+=451
HPLC (Method 6): retention time=2.31 min
Example 367
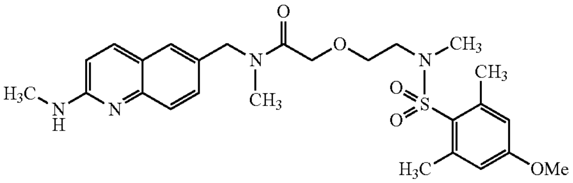 [SMILES: CNc1ccc2cc(CN(C)C(=O)COCCN(C)S(=O)(=O)c3c(C)cc(OC)cc3C)ccc2n1]
$C_{26}H_{34}N_4O_5S$ (514.64)
[M+H]+=515
HPLC (Method 6): retention time=2.51 min
Example 368
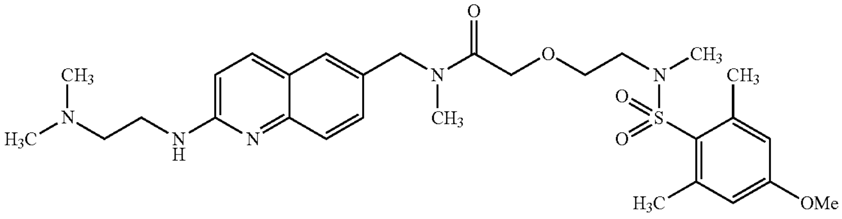 [SMILES: COc1cc(C)c(S(=O)(=O)N(C)CCOCC(=O)N(C)Cc2ccc3nc(NCCN(C)C)ccc3c2)c(C)c1]
$C_{29}H_{41}N_5O_5S \times C_2HF_3O_2$ (685.76)
[M+H]+=572
HPLC (Method 6): retention time=2.14 min Example 369
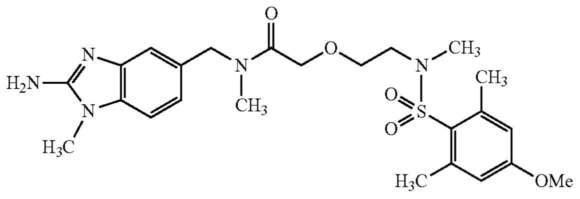 [SMILES: COc1cc(C)c(S(=O)(=O)N(C)CCOCC(=O)N(C)Cc2ccc3c(c2)nc(N)n3C)c(C)c1]
$C_{24}H_{33}N_5O_5S \times C_2HF_3O_2$ (617.64)
[M+H]+=504
HPLC (Method 9): retention time=1.61 min
Example 370
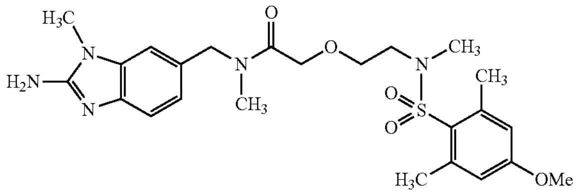 [SMILES: COc1cc(C)c(S(=O)(=O)N(C)CCOCC(=O)N(C)Cc2ccc3nc(N)n(C)c3c2)c(C)c1]
$C_{24}H_{33}N_5O_5S \times C_2HF_3O_2$ (617.64)
[M+H]+=504
HPLC (Method 9): retention time=1.59 min
Example 371
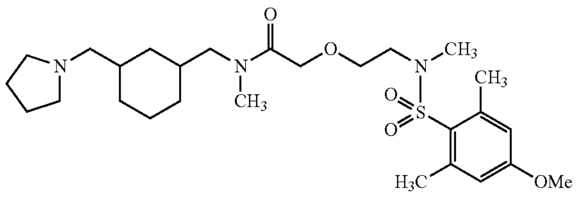 [SMILES: COc1cc(C)c(S(=O)(=O)N(C)CCOCC(=O)N(C)CC2CCCC(CN3CCCC3)C2)c(C)c1]
$C_{27}H_{45}N_3O_5S \times C_2HF_3O_2$ (637.75)
[M+H]+=524
HPLC (Method 9): retention time=1.70 min
Example 372
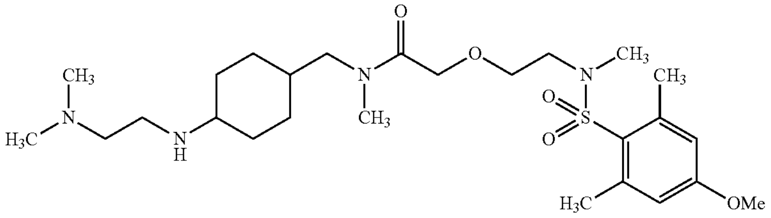 [SMILES: COc1cc(C)c(S(=O)(=O)N(C)CCOCC(=O)N(C)CC2CCC(NCCN(C)C)CC2)c(C)c1]
$C_{26}H_{46}N_4O_5S$ (526.73)
[M+H]+=527
HPLC (Method 5): retention time=1.43 min
Example 373
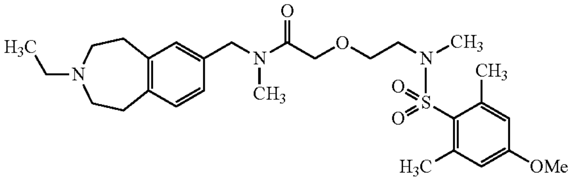 [SMILES: CCN1CCc2ccc(CN(C)C(=O)COCCN(C)S(=O)(=O)c3c(C)cc(OC)cc3C)cc2CC1]
$C_{28}H_{41}N_3O_5S \times C_2HF_3O_2$ (645.73)
[M+H]+=532
HPLC (Method 5): retention time=1.56 min Example 374
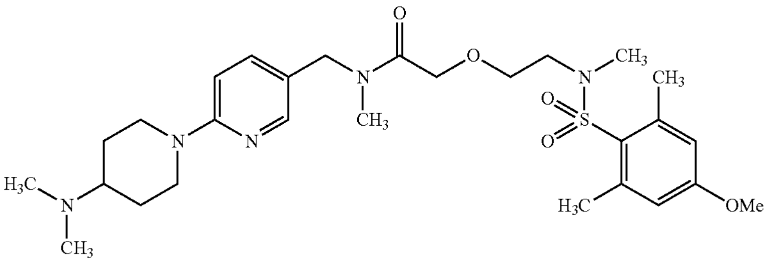 [SMILES: COc1cc(C)c(S(=O)(=O)N(C)CCOCC(=O)N(C)Cc2ccc(N3CCC(N(C)C)CC3)nc2)c(C)c1]
$C_{28}H_{43}N_5O_5S \times C_2HF_3O_2$ (675.76)
[M+H]+=562
HPLC (Method 5): retention time=1.41 min
Example 375
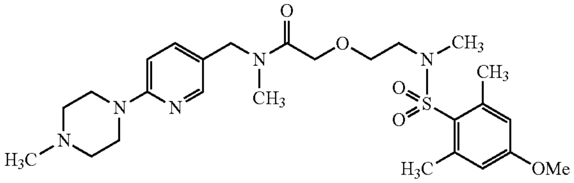 [SMILES: COc1cc(C)c(S(=O)(=O)N(C)CCOCC(=O)N(C)Cc2ccc(N3CCN(C)CC3)nc2)c(C)c1]
$C_{26}H_{39}N_5O_5S \times C_2HF_3O_2$ (647.71)
[M+H]+=534
HPLC (Method 5): retention time=1.42 min
Example 376
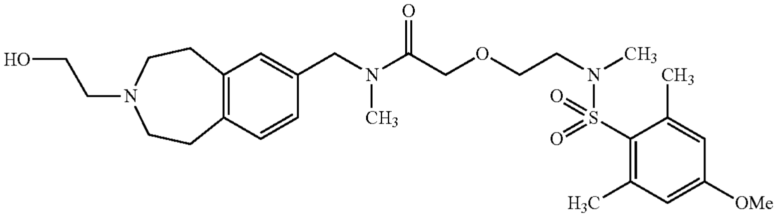 [SMILES: COc1cc(C)c(S(=O)(=O)N(C)CCOCC(=O)N(C)Cc2ccc3c(c2)CCN(CCO)CC3)c(C)c1]
$C_{28}H_{41}N_3O_6S$ (547.71)
[M+H]+=548
HPLC (Method 5): retention time=1.53 min
Example 377
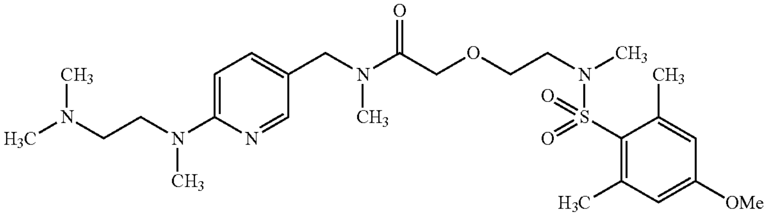 [SMILES: COc1cc(C)c(S(=O)(=O)N(C)CCOCC(=O)N(C)Cc2ccc(N(C)CCN(C)C)nc2)c(C)c1]
$C_{26}H_{41}N_5O_5S$ (535.70)
[M+H]+=536
HPLC (Method 5): retention time=1.42 min Example 378
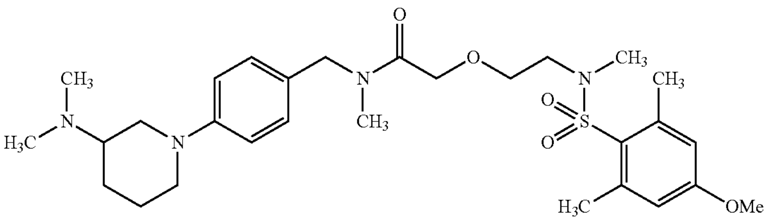 [SMILES: COc1cc(C)c(S(=O)(=O)N(C)CCOCC(=O)N(C)Cc2ccc(N3CCCC(N(C)C)C3)cc2)c(C)c1]
$C_{29}H_{44}N_4O_5S{\times}HCl$ (597.21)
[M+H]+=561
HPLC (Method 7): retention time=1.91 min
Example 379
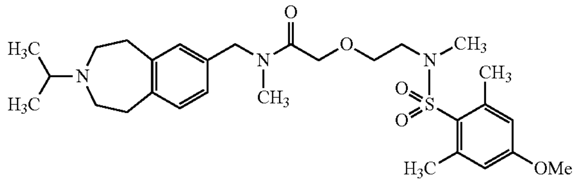 [SMILES: COc1cc(C)c(S(=O)(=O)N(C)CCOCC(=O)N(C)Cc2ccc3c(c2)CCN(C(C)C)CC3)c(C)c1]
$C_{29}H_{43}N_3O_5S{\times}C_2HF_3O_2$ (659.76)
[M+H]+=546
HPLC (Method 5): retention time=1.59 min
Example 380
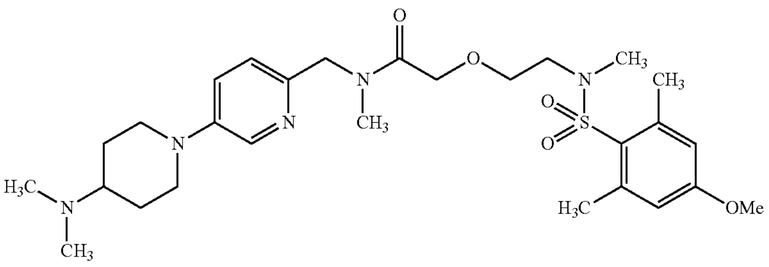
$C_{28}H_{43}N_5O_5S{\times}2C_2HF_3O_2$ (789.78)
[M+H]+=562
HPLC (Method 5): retention time=1.40 min
Example 381
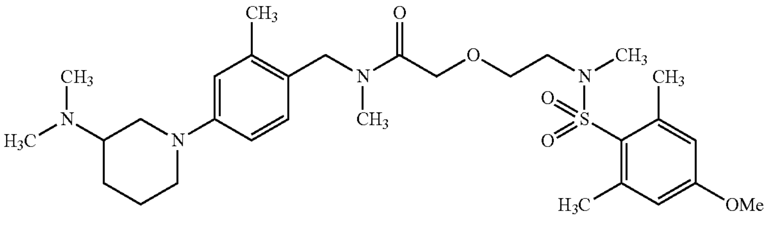 [SMILES: COc1cc(C)c(S(=O)(=O)N(C)CCOCC(=O)N(C)Cc2ccc(N3CCCC(N(C)C)C3)cc2C)c(C)c1]
$C_{30}H_{46}N_4O_5S{\times}C_2HF_3O_2$ (688.80)
[M+H]+=575
HPLC (Method 5): retention time=1.56 min Example 382

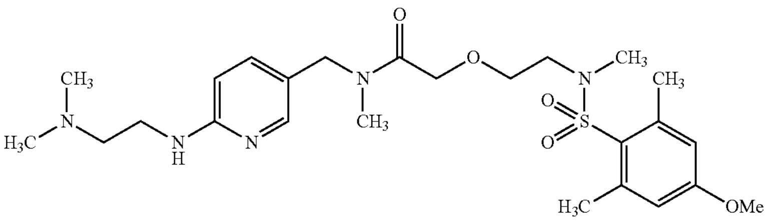 [SMILES: COc1cc(C)c(S(=O)(=O)N(C)CCOCC(=O)N(C)Cc2ccc(NCCN(C)C)nc2)c(C)c1]

$C_{25}H_{39}N_5O_5S \times 2HCl$ (594.60)
[M+H]+=522
HPLC (Method 5): retention time=1.40 min Example 383

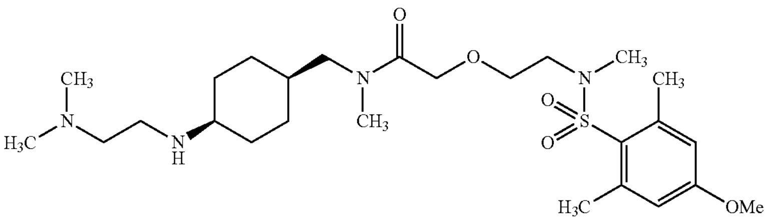 [SMILES: COc1cc(C)c(S(=O)(=O)N(C)CCOCC(=O)N(C)C[C@H]2CC[C@@H](NCCN(C)C)CC2)c(C)c1]

$C_{26}H_{46}N_4O_5S \times 2HCl$ (599.65)
[M+H]+=527
HPLC (Method 5): retention time=1.41 min Example 384

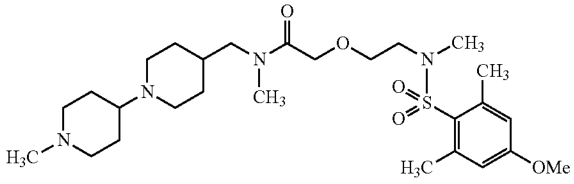 [SMILES: COc1cc(C)c(S(=O)(=O)N(C)CCOCC(=O)N(C)CC2CCN(C3CCN(C)CC3)CC2)c(C)c1]

$C_{27}H_{46}N_4O_5S \times HCl$ (575.20)
[M+H]+=539
TLC: silica gel, dichloromethane/methanol/ammonia 8:2:0.01, Rf value=0.35

Example 385

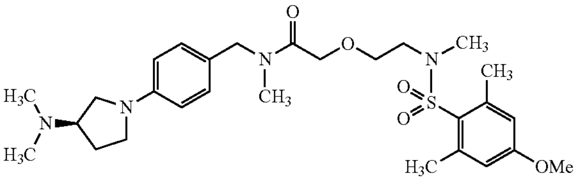 [SMILES: COc1cc(C)c(S(=O)(=O)N(C)CCOCC(=O)N(C)Cc2ccc(N3CC[C@@H](N(C)C)C3)cc2)c(C)c1]

$C_{28}H_{42}N_4O_5S \times HCl$ (583.18)
[M+H]+=547
TLC: silica gel, dichloromethane/methanol/ammonia 9:1:0.1, Rf value=0.32

Example 386

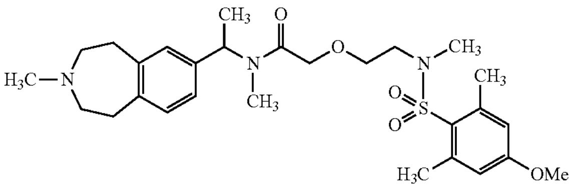 [SMILES: COc1cc(C)c(S(=O)(=O)N(C)CCOCC(=O)N(C)C(C)c2ccc3c(c2)CCN(C)CC3)c(C)c1]

$C_{28}H_{41}N_3O_5S \times HCl$ (568.17)
[M+H]+=532
TLC: silica gel, dichloromethane/methanol/ammonia 9:1:0.1, Rf value=0.35

Example 387

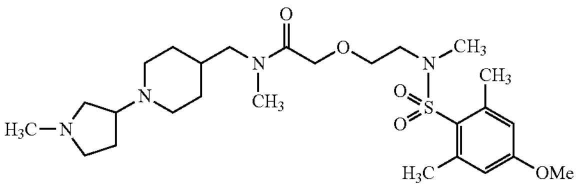 [SMILES: COc1cc(C)c(S(=O)(=O)N(C)CCOCC(=O)N(C)CC2CCN(C3CCN(C)C3)CC2)c(C)c1]

$C_{26}H_{44}N_4O_5S \times HCl$ (561.18)
[M+H]+=525
TLC: silica gel, dichloromethane/methanol/ammonia 8:2:0.01, Rf value=0.12

Example 388

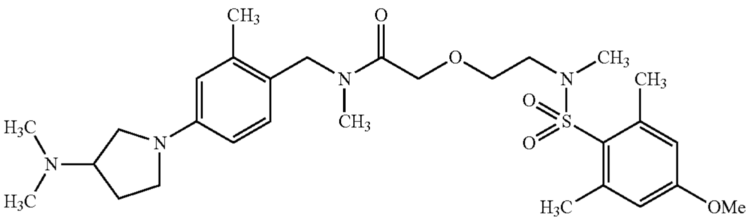 [SMILES: COc1cc(C)c(S(=O)(=O)N(C)CCOCC(=O)N(C)Cc2ccc(N3CCC(N(C)C)C3)cc2C)c(C)c1]

$C_{29}H_{44}N_4O_5S$×HCl (597.21)
[M+H]+=561
TLC: silica gel, dichloromethane/methanol 9:1, Rf value=0.30

Example 389

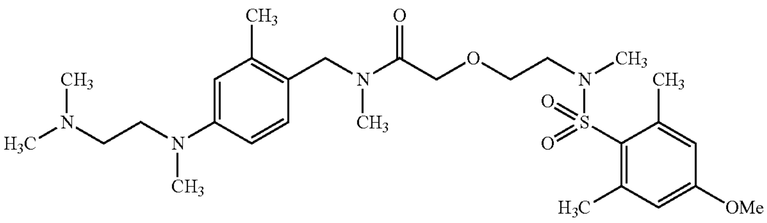 [SMILES: COc1cc(C)c(S(=O)(=O)N(C)CCOCC(=O)N(C)Cc2ccc(N(C)CCN(C)C)cc2C)c(C)c1]

$C_{28}H_{44}N_4O_5S$×HCl (585.20)
[M+H]+=549
TLC: silica gel, dichloromethane/methanol 9:1, Rf value=0.15

Example 390

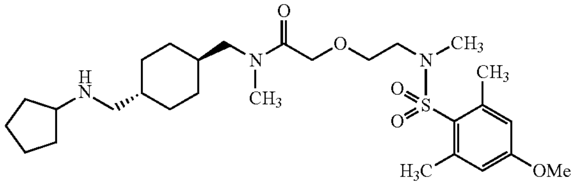 [SMILES: COc1cc(C)c(S(=O)(=O)N(C)CCOCC(=O)N(C)C[C@H]2CC[C@H](CNC3CCCC3)CC2)c(C)c1]

$C_{28}H_{47}N_3O_5S$×HCl (574.22)
[M+H]+=538
TLC: silica gel, dichloromethane/methanol 9:1, Rf value=0.05

Example 391

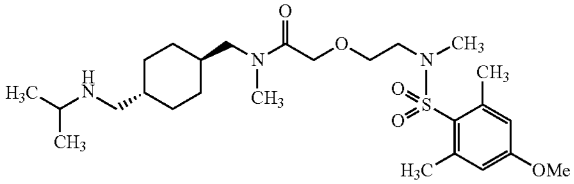 [SMILES: COc1cc(C)c(S(=O)(=O)N(C)CCOCC(=O)N(C)C[C@H]2CC[C@H](CNC(C)C)CC2)c(C)c1]

$C_{26}H_{45}N_3O_5S$×HCl (548.18)
[M+H]+=512
HPLC (Method 5): retention time=1.56 min Example 392

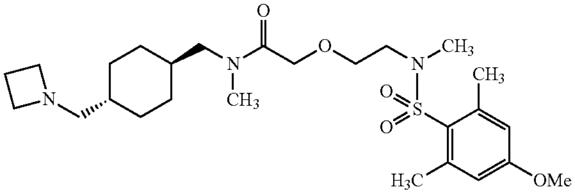 [SMILES: COc1cc(C)c(S(=O)(=O)N(C)CCOCC(=O)N(C)C[C@H]2CC[C@H](CN3CCC3)CC2)c(C)c1]

$C_{26}H_{43}N_3O_5S$×HCl (546.16)
[M+H]+=510
TLC: silica gel, dichloromethane/methanol 9:1, Rf value=0.05

Example 393

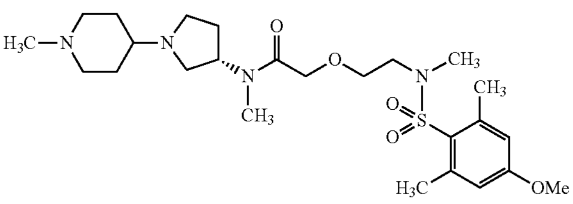 [SMILES: COc1cc(C)c(S(=O)(=O)N(C)CCOCC(=O)N(C)[C@H]2CCN(C3CCN(C)CC3)C2)c(C)c1]

$C_{25}H_{42}N_4O_5S$×2HCl (583.61)
[M+H]+=511

TLC: silica gel, dichloromethane/ethanol/ammonia 9:1:0.1, Rf value=0.22

Example 394

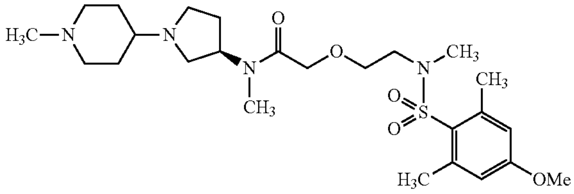 [SMILES: COc1cc(C)c(S(=O)(=O)N(C)CCOCC(=O)N(C)[C@@H]2CCN(C3CCN(C)CC3)C2)c(C)c1]

$C_{25}H_{42}N_4O_5S \times 2HCl$ (583.61)

[M+H]+=511

HPLC (Method 5): retention time=1.37 min

Example 395

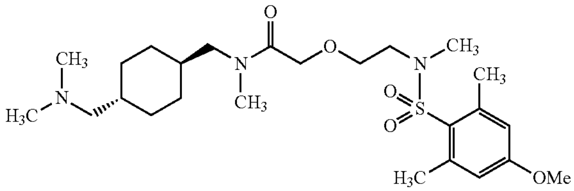 [SMILES: COc1cc(C)c(S(=O)(=O)N(C)CCOCC(=O)N(C)C[C@H]2CC[C@H](CN(C)C)CC2)c(C)c1]

$C_{25}H_{43}N_3O_5S \times HCl$ (534.15)

[M+H]+=498

TLC: silica gel, dichloromethane/methanol/ammonia 8:2:0.01, Rf value=0.58

Example 396

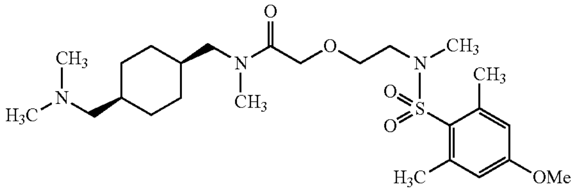 [SMILES: COc1cc(C)c(S(=O)(=O)N(C)CCOCC(=O)N(C)C[C@H]2CC[C@@H](CN(C)C)CC2)c(C)c1]

$C_{25}H_{43}N_3O_5S \times HCl$ (534.15)

[M+H]+=498

TLC: silica gel, dichloromethane/methanol/ammonia 8:2:0.01, Rf value=0.57

Example 397

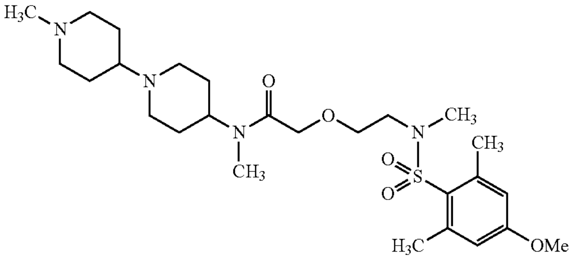 [SMILES: COc1cc(C)c(S(=O)(=O)N(C)CCOCC(=O)N(C)C2CCN(C3CCN(C)CC3)CC2)c(C)c1]

$C_{26}H_{44}N_4O_5S \times 2HCl$ (597.64)

[M+H]+=525

TLC: silica gel, dichloromethane/methanol/ammonia 8:2:0.2, Rf value=0.52

Example 398

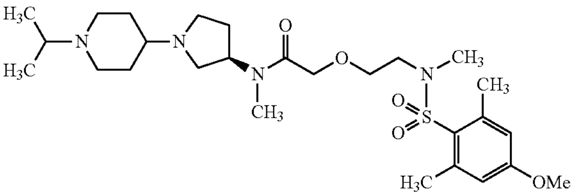 [SMILES: COc1cc(C)c(S(=O)(=O)N(C)CCOCC(=O)N(C)[C@@H]2CCN(C3CCN(C(C)C)CC3)C2)c(C)c1]

$C_{27}H_{46}N_4O_5S \times 2HCl$ (611.67)

[M+H]+=539

HPLC (Method 12): retention time=2.45 min

Example 399

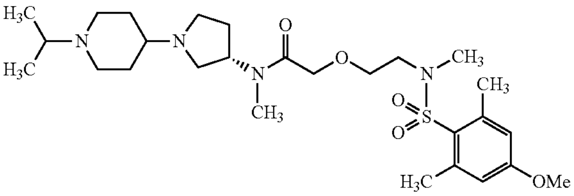 [SMILES: COc1cc(C)c(S(=O)(=O)N(C)CCOCC(=O)N(C)[C@H]2CCN(C3CCN(C(C)C)CC3)C2)c(C)c1]

$C_{27}H_{46}N_4O_5S \times 2HCl$ (611.67)

[M+H]+=539

HPLC (Method 12): retention time=2.35 min

Example 400
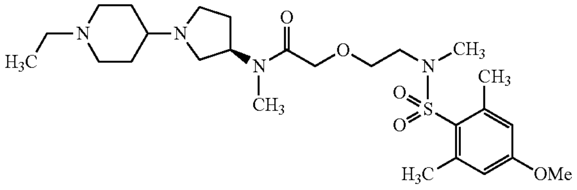 [SMILES: CCN1CCC(N2CC[C@@H](N(C)C(=O)COCCN(C)S(=O)(=O)c3c(C)cc(OC)cc3C)C2)CC1]
$C_{26}H_{44}N_4O_6S$×2HCl (597.64)
[M+H]+=525
HPLC (Method 12): retention time=2.3 min
Example 401
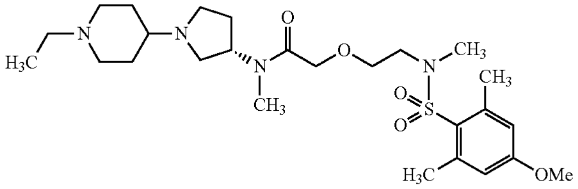 [SMILES: CCN1CCC(N2CC[C@H](N(C)C(=O)COCCN(C)S(=O)(=O)c3c(C)cc(OC)cc3C)C2)CC1]
$C_{26}H_{44}N_4O_6S$×2HCl (597.64)
[M+H]+=525
HPLC (Method 12): retention time=2.3 min
Example 402
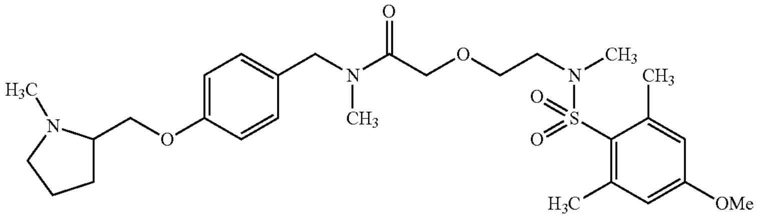 [SMILES: COc1cc(C)c(S(=O)(=O)N(C)CCOCC(=O)N(C)Cc2ccc(OCC3CCCN3C)cc2)c(C)c1]
$C_{28}H_{41}N_3O_6S$ (547.71)
[M+H]+=548
HPLC (Method 9): retention time=1.7 min
Example 403
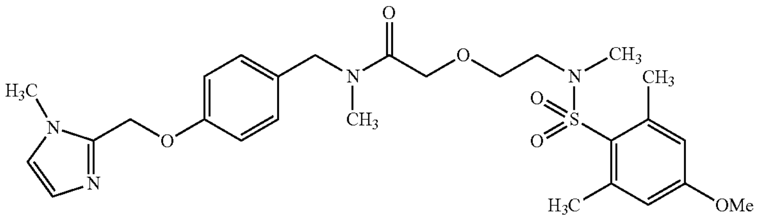 [SMILES: COc1cc(C)c(S(=O)(=O)N(C)CCOCC(=O)N(C)Cc2ccc(OCc3nccn3C)cc2)c(C)c1]
$C_{27}H_{36}N_4O_6S$ (544.66)
[M+H]+=545
HPLC (Method 9): retention time=1.69 min
Example 404
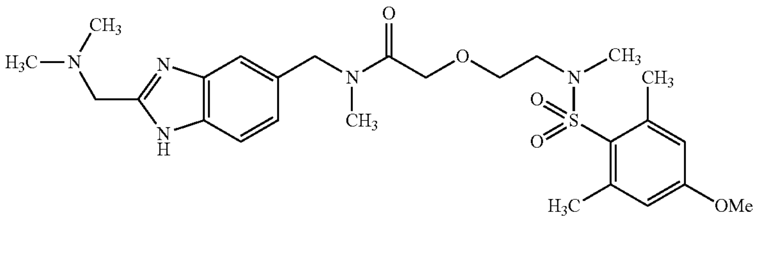 [SMILES: COc1cc(C)c(S(=O)(=O)N(C)CCOCC(=O)N(C)Cc2ccc3[nH]c(CN(C)C)nc3c2)c(C)c1]
$C_{26}H_{37}N_5O_5S$ (531.67)
[M+H]+=532
HPLC (Method 6): retention time=1.56 min Example 405
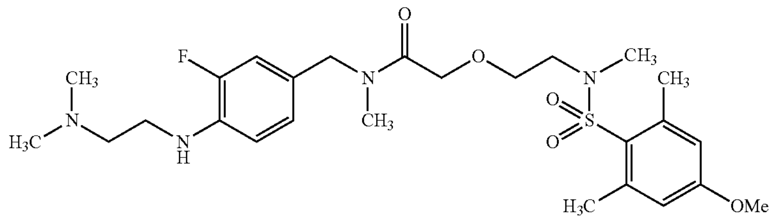 [SMILES: COc1cc(C)c(S(=O)(=O)N(C)CCOCC(=O)N(C)Cc2ccc(NCCN(C)C)c(F)c2)c(C)c1]
$C_{26}H_{39}FN_4O_5S$ (538.68)
[M+H]+=539
HPLC (Method 6): retention time=2.60 min
Example 406
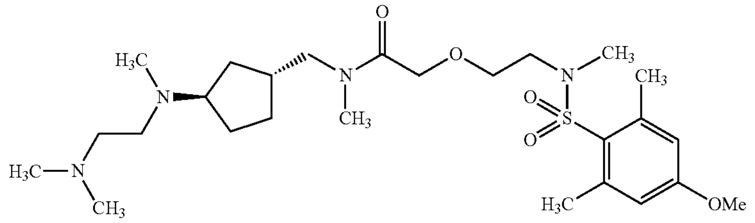 [SMILES: COc1cc(C)c(S(=O)(=O)N(C)CCOCC(=O)N(C)C[C@@H]2CC[C@@H](N(C)CCN(C)C)C2)c(C)c1]
$C_{26}H_{46}N_4O_5S\times2HCl$ (599.65)
[M+H]+=527
HPLC (Method 7): retention time=1.78 min
Example 407
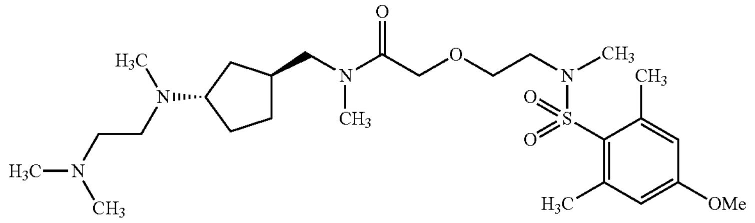 [SMILES: COc1cc(C)c(S(=O)(=O)N(C)CCOCC(=O)N(C)C[C@H]2CC[C@H](N(C)CCN(C)C)C2)c(C)c1]
$C_{26}H_{46}N_4O_5S\times2HCl$ (599.65)
[M+H]+=527
HPLC (Method 7): retention time=1.77 min
Example 408
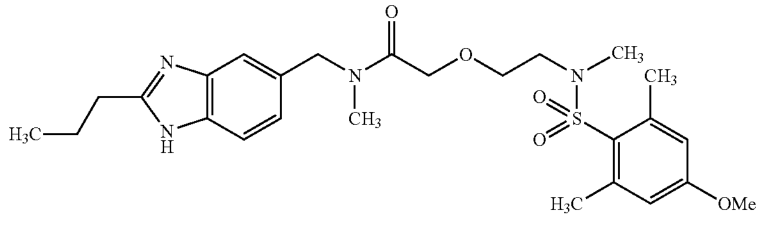 [SMILES: CCCc1nc2cc(CN(C)C(=O)COCCN(C)S(=O)(=O)c3c(C)cc(OC)cc3C)ccc2[nH]1]
$C_{26}H_{36}N_4O_5S$ (516.65)
[M+H]+=517
HPLC (Method 9): retention time=1.65 min Example 409

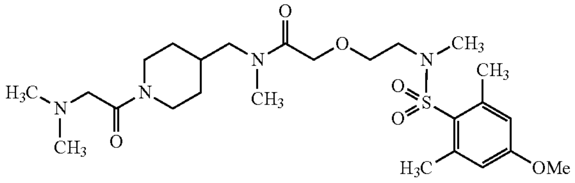 [SMILES: COc1cc(C)c(S(=O)(=O)N(C)CCOCC(=O)N(C)CC2CCN(C(=O)CN(C)C)CC2)c(C)c1]

$C_{25}H_{42}N_4O_6S \times C_2HF_3O_2$ (640.71)
[M+H]+=527
HPLC (Method 9): retention time=1.55 min Example 410

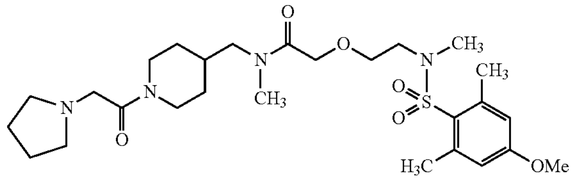 [SMILES: COc1cc(C)c(S(=O)(=O)N(C)CCOCC(=O)N(C)CC2CCN(C(=O)CN3CCCC3)CC2)c(C)c1]

$C_{27}H_{44}N_4O_6S \times C_2HF_3O_2$ (666.75)
[M+H]+=553
HPLC (Method 9): retention time=1.57 min Example 411

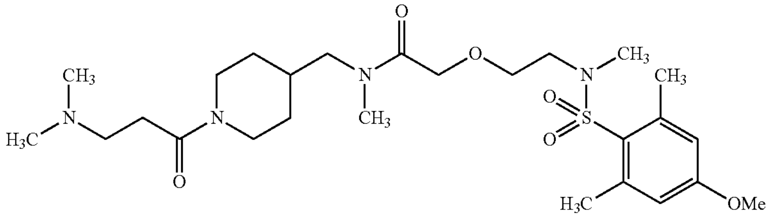 [SMILES: COc1cc(C)c(S(=O)(=O)N(C)CCOCC(=O)N(C)CC2CCN(C(=O)CCN(C)C)CC2)c(C)c1]

$C_{26}H_{44}N_4O_6S \times C_2HF_3O_2$ (654.74)
[M+H]+=541
HPLC (Method 9): retention time=1.57 min Example 412

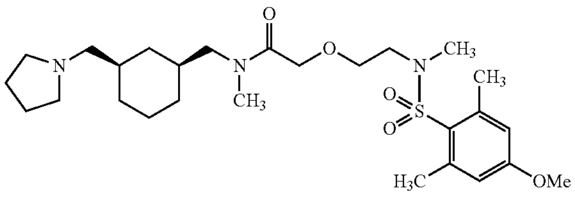 [SMILES: COc1cc(C)c(S(=O)(=O)N(C)CCOCC(=O)N(C)C[C@H]2CCC[C@@H](CN3CCCC3)C2)c(C)c1]

$C_{27}H_{45}N_3O_5S \times C_2HF_3O_2$ (637.75)
[M+H]+=524
HPLC (Method 6): retention time=1.71 min Example 413

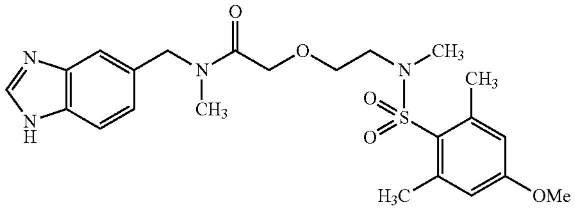 [SMILES: COc1cc(C)c(S(=O)(=O)N(C)CCOCC(=O)N(C)Cc2ccc3[nH]cnc3c2)c(C)c1]

$C_{23}H_{30}N_4O_5S$ (474.57)
[M+H]+=475
HPLC (Method 9): retention time=1.53 min Example 414

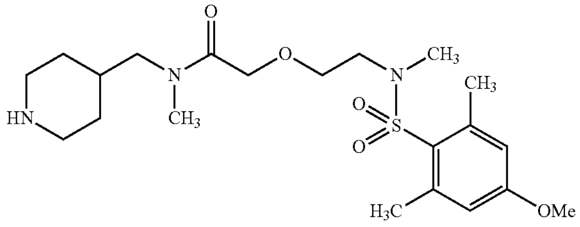 [SMILES: COc1cc(C)c(S(=O)(=O)N(C)CCOCC(=O)N(C)CC2CCNCC2)c(C)c1]

$O_{21}H_{35}N_3O_5S$ (441.59)
[M+H]+=442
HPLC (Method 9): retention time=1.48 min Example 415

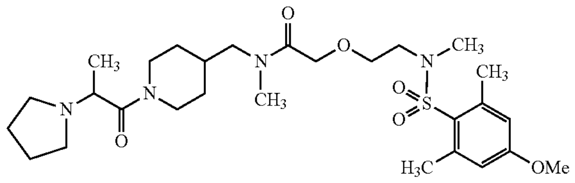 [SMILES: COc1cc(C)c(S(=O)(=O)N(C)CCOCC(=O)N(C)CC2CCN(C(=O)C(C)N3CCCC3)CC2)c(C)c1]

$C_{28}H_{46}N_4O_6S \times C_2HF_3O_2$ (680.78)
[M+H]+=567
HPLC (Method 9): retention time=1.60 min Example 416

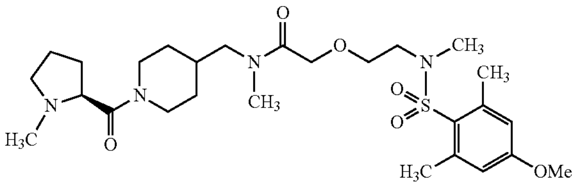 [SMILES: COc1cc(C)c(S(=O)(=O)N(C)CCOCC(=O)N(C)CC2CCN(C(=O)[C@@H]3CCCN3C)CC2)c(C)c1]

$C_{27}H_{44}N_4O_6S \times C_2HF_3O_2$ (666.75)
[M+H]+=553
HPLC (Method 9): retention time=1.57 min Example 417

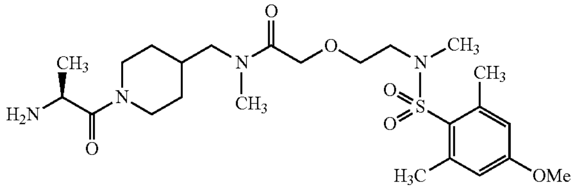 [SMILES: COc1cc(C)c(S(=O)(=O)N(C)CCOCC(=O)N(C)CC2CCN(C(=O)[C@H](C)N)CC2)c(C)c1]

$C_{24}H_{40}N_4O_6S \times C_2HF_3O_2$ (626.69)
[M+H]+=513
HPLC (Method 9): retention time=1.53 min Example 418

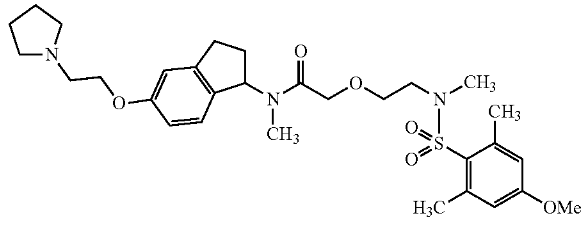 [SMILES: COc1cc(C)c(S(=O)(=O)N(C)CCOCC(=O)N(C)C2CCc3cc(OCCN4CCCC4)ccc32)c(C)c1]

$C_{30}H_{43}N_3O_6S \times CH_2O_2$ (619.77)
[M+H]+=574
HPLC (Method 9): retention time=1.73 min Example 419

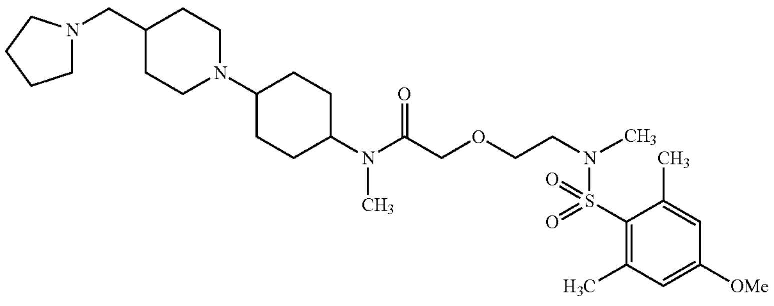 [SMILES: COc1cc(C)c(S(=O)(=O)N(C)CCOCC(=O)N(C)C2CCC(N3CCC(CN4CCCC4)CC3)CC2)c(C)c1]

$O_{31}H_{52}N_4O_5S \times C_2HF_3O_2$ (706.86)
[M+H]+=593
HPLC (Method 9): retention time=1.34 min Example 420

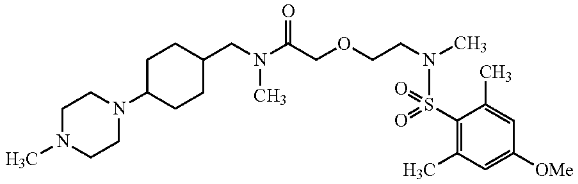

$C_{27}H_{46}N_4O_5S$ (538.74)
[M+H]+=539
HPLC (Method 9): retention time=1.43 min Example 421

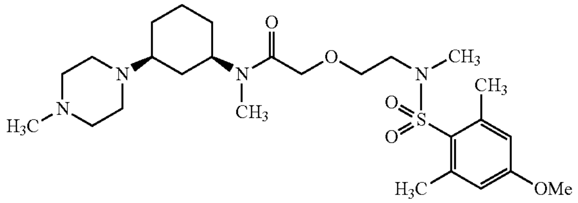 [SMILES: COc1cc(C)c(S(=O)(=O)N(C)CCOCC(=O)N(C)[C@@H]2CCC[C@H](N3CCN(C)CC3)C2)c(C)c1]

$C_{26}H_{44}N_4O_5S \times C_2HF_3O_2$ (638.74)
[M+H]+=525
HPLC (Method 6): retention time=1.53 min Example 422

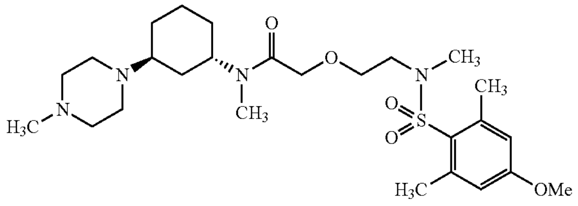 [SMILES: COc1cc(C)c(S(=O)(=O)N(C)CCOCC(=O)N(C)[C@H]2CCC[C@H](N3CCN(C)CC3)C2)c(C)c1]

$C_{26}H_{44}N_4O_5S \times C_2HF_3O_2$ (638.74)
[M+H]+=525
HPLC (Method 6): retention time=1.41 min Example 423

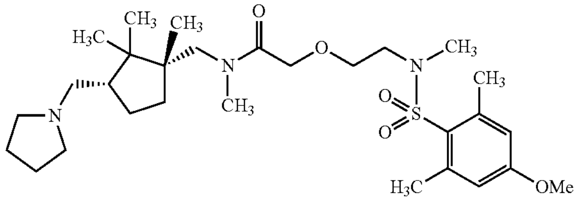 [SMILES: COc1cc(C)c(S(=O)(=O)N(C)CCOCC(=O)N(C)C[C@]2(C)CC[C@H](CN3CCCC3)C2(C)C)c(C)c1]

$C_{29}H_{49}N_3O_5S \times C_2HF_3O_2$ (665.81)
[M+H]+=552
HPLC (Method 9): retention time=1.74 min Example 424

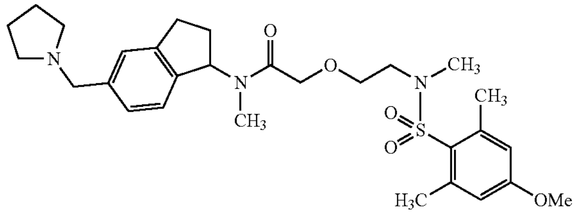 [SMILES: COc1cc(C)c(S(=O)(=O)N(C)CCOCC(=O)N(C)C2CCc3cc(CN4CCCC4)ccc32)c(C)c1]

$C_{29}H_{41}N_3O_5S$ (543.72)
[M+H]+=544
HPLC (Method 6): retention time=1.73 min Example 425

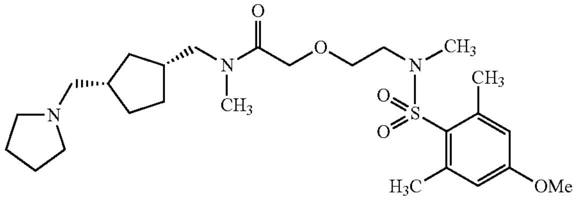 [SMILES: COc1cc(C)c(S(=O)(=O)N(C)CCOCC(=O)N(C)C[C@@H]2CC[C@H](CN3CCCC3)C2)c(C)c1]

$C_{26}H_{43}N_3O_5S \times C_2HF_3O_2$ (623.73)
[M+H]+=510
HPLC (Method 9): retention time=1.63 min Example 426

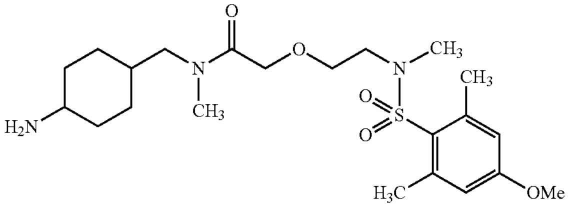 [SMILES: COc1cc(C)c(S(=O)(=O)N(C)CCOCC(=O)N(C)CC2CCC(N)CC2)c(C)c1]

$C_{22}H_{37}N_3O_5S$ (455.61)
[M+H]+=456
HPLC (Method 6): retention time=1.55 min Example 427

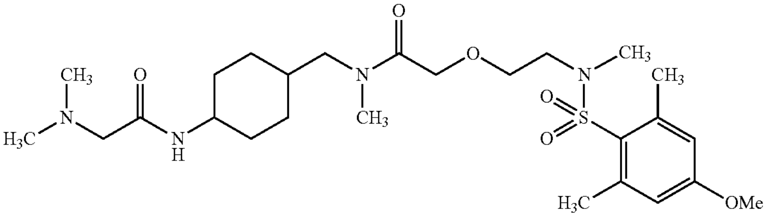 [SMILES: COc1cc(C)c(S(=O)(=O)N(C)CCOCC(=O)N(C)CC2CCC(NC(=O)CN(C)C)CC2)c(C)c1]

$C_{26}H_{44}N_4O_6S$ (540.72)
[M+H]+=541
HPLC (Method 6): retention time=1.59 min Example 428

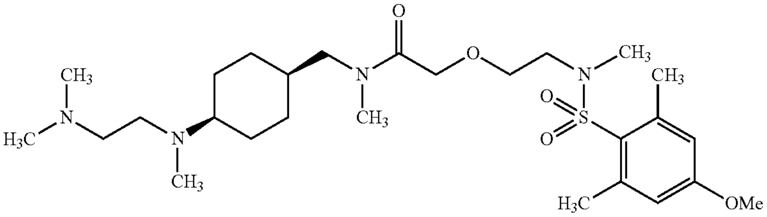 [SMILES: COc1cc(C)c(S(=O)(=O)N(C)CCOCC(=O)N(C)C[C@H]2CC[C@@H](N(C)CCN(C)C)CC2)c(C)c1]

$C_{27}H_{48}N_4O_5S \times 2HCl$ (613.68)
[M+H]+=541
HPLC (Method 7): retention time=1.65 min Example 429

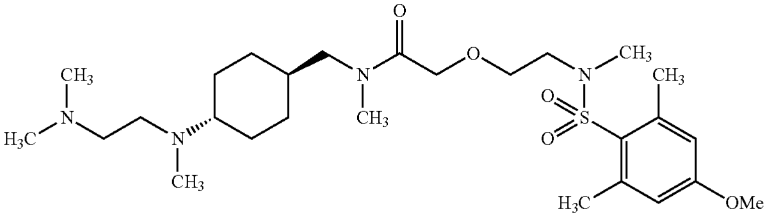 [SMILES: COc1cc(C)c(S(=O)(=O)N(C)CCOCC(=O)N(C)C[C@H]2CC[C@H](N(C)CCN(C)C)CC2)c(C)c1]

$C_{27}H_{48}N_4O_5S \times 2HCl$ (613.68)
[M+H]+=541
HPLC (Method 11): retention time=1.64 min Example 430

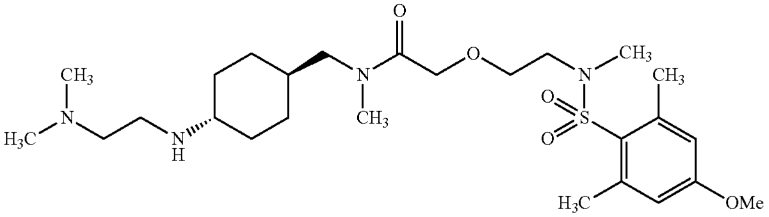 [SMILES: COc1cc(C)c(S(=O)(=O)N(C)CCOCC(=O)N(C)C[C@H]2CC[C@H](NCCN(C)C)CC2)c(C)c1]

$C_{26}H_{46}N_4O_5S \times 2C_2HF_3O_2$ (754.78)
[M+H]+=527
HPLC (Method 5): retention time=1.16 min Example 431

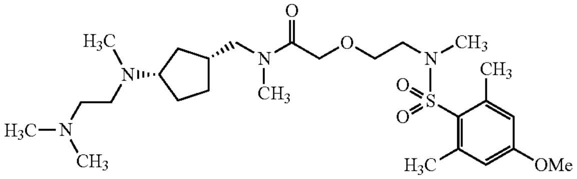 [SMILES: COc1cc(C)c(S(=O)(=O)N(C)CCOCC(=O)N(C)C[C@@H]2CC[C@H](N(C)CCN(C)C)C2)c(C)c1]

$C_{26}H_{46}N_4O_5S \times 2HCl$ (599.65)
[M+H]+=527
HPLC (Method 7): retention time=1.82 min Example 432

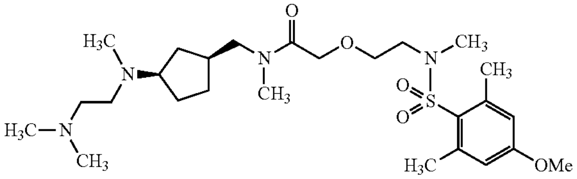 [SMILES: COc1cc(C)c(S(=O)(=O)N(C)CCOCC(=O)N(C)C[C@H]2CC[C@@H](N(C)CCN(C)C)C2)c(C)c1]

$C_{26}H_{46}N_4O_5S \times 2HCl$ (599.65)
[M+H]+=527
HPLC (Method 7): retention time=1.82 min Example 433

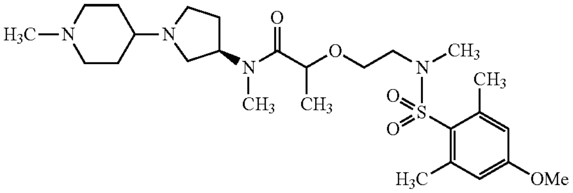 [SMILES: COc1cc(C)c(S(=O)(=O)N(C)CCOC(C)C(=O)N(C)[C@@H]2CCN(C3CCN(C)CC3)C2)c(C)c1]

$C_{26}H_{44}N_4O_5S \times 2HCl$ (597.64)
[M+H]+=525
HPLC (Method 12): retention time=2.3 min Example 434

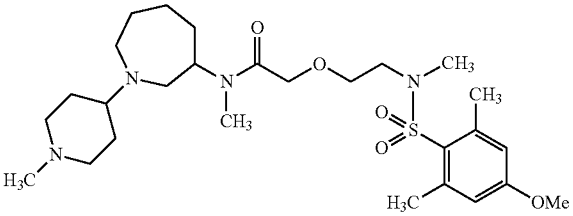 [SMILES: COc1cc(C)c(S(=O)(=O)N(C)CCOCC(=O)N(C)C2CCCCN(C3CCN(C)CC3)C2)c(C)c1]

$C_{27}H_{46}N_4O_5S \times 2HCl$ (611.67)
[M+H]+=539
TLC: silica gel, dichloromethane/methanol/ammonia 8:2:0.2, Rf value=0.65

Example 435

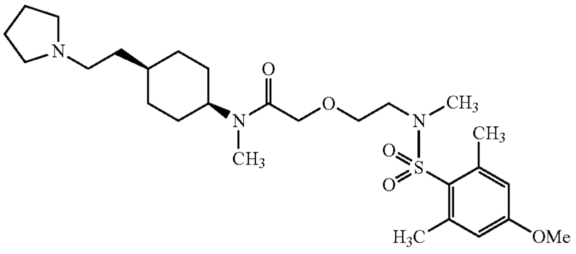 [SMILES: COc1cc(C)c(S(=O)(=O)N(C)CCOCC(=O)N(C)[C@H]2CC[C@@H](CCN3CCCC3)CC2)c(C)c1]

$C_{27}H_{45}N_3O_5S$ (523.73)
[M+H]+=524
HPLC (Method 6): retention time=1.29 min Example 436

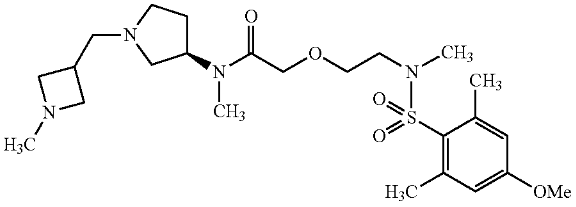 [SMILES: COc1cc(C)c(S(=O)(=O)N(C)CCOCC(=O)N(C)[C@@H]2CCN(CC3CN(C)C3)C2)c(C)c1]

$C_{24}H_{40}N_4O_5S \times CH_2O_2$ (542.69)
[M+H]+=497
HPLC (Method 9): retention time=1.25 min Example 437

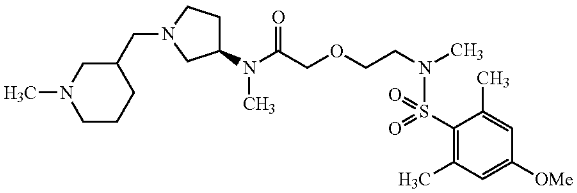 [SMILES: COc1cc(C)c(S(=O)(=O)N(C)CCOCC(=O)N(C)[C@@H]2CCN(CC3CCCN(C)C3)C2)c(C)c1]

$C_{26}H_{44}N_4O_5S \times CH_2O_2$ (570.74)
[M+H]+=525
HPLC (Method 9): retention time=1.31 min Example 438

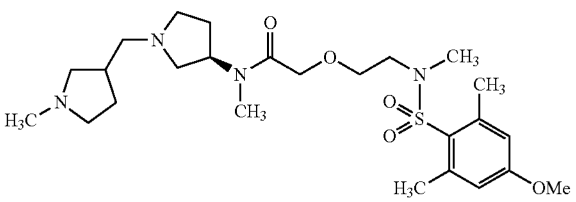 [SMILES: COc1cc(C)c(S(=O)(=O)N(C)CCOCC(=O)N(C)[C@@H]2CCN(CC3CCN(C)C3)C2)c(C)c1]

$C_{25}H_{42}N_4O_5S \times CH_2O_2$ (556.72)
[M+H]+=511
HPLC (Method 9): retention time=1.31 min Example 439

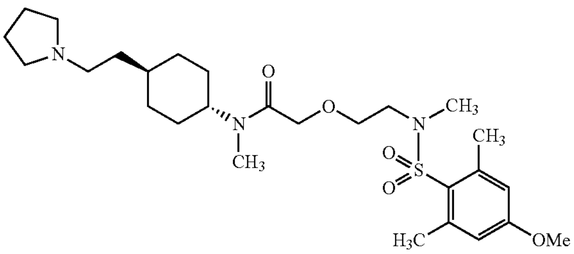 [SMILES: COc1cc(C)c(S(=O)(=O)N(C)CCOCC(=O)N(C)[C@H]2CC[C@H](CCN3CCCC3)CC2)c(C)c1]

$C_{27}H_{45}N_3O_5S$ (523.73)
[M+H]+=524
HPLC (Method 6): retention time=1.67 min Example 440

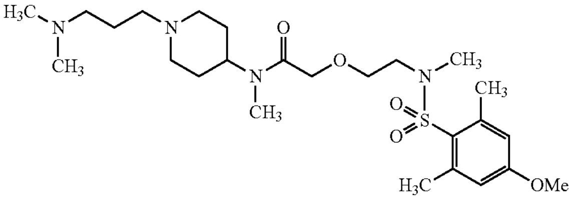 [SMILES: COc1cc(C)c(S(=O)(=O)N(C)CCOCC(=O)N(C)C2CCN(CCCN(C)C)CC2)c(C)c1]

$C_{25}H_{44}N_4O_5S \times C_2HF_3O_2$ (626.73)
[M+H]+=513
HPLC (Method 9): retention time=1.29 min Example 441

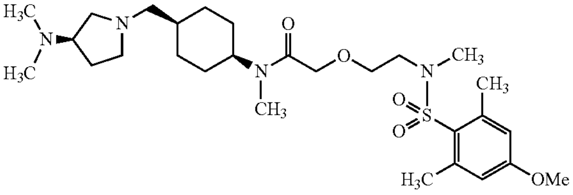 [SMILES: COc1cc(C)c(S(=O)(=O)N(C)CCOCC(=O)N(C)[C@H]2CC[C@@H](CN3CC[C@@H](N(C)C)C3)CC2)c(C)c1]

$C_{28}H_{48}N_4O_5S \times 2HCl$ (625.69)
[M+H]+=553
HPLC (Method 9): retention time=1.35 min Example 442

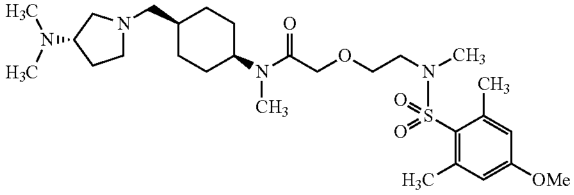 [SMILES: COc1cc(C)c(S(=O)(=O)N(C)CCOCC(=O)N(C)[C@H]2CC[C@@H](CN3CC[C@H](N(C)C)C3)CC2)c(C)c1]

$C_{28}H_{48}N_4O_5S \times 2HCl$ (625.69)
[M+H]+=553
HPLC (Method 9): retention time=1.32 min Example 443

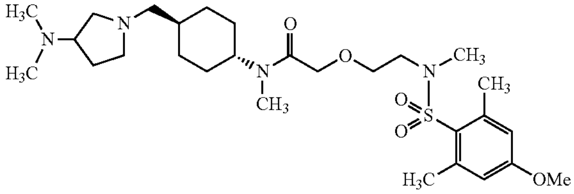 [SMILES: COc1cc(C)c(S(=O)(=O)N(C)CCOCC(=O)N(C)[C@H]2CC[C@H](CN3CCC(N(C)C)C3)CC2)c(C)c1]

$C_{28}H_{48}N_4O_5S$ (552.77)
[M+H]+=553
HPLC (Method 9): retention time=1.37 min Example 444

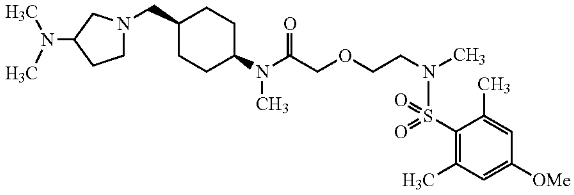

$C_{28}H_{48}N_4O_5S \times CH_2O_2$ (598.80)
[M+H]+=553
HPLC (Method 9): retention time=1.35 min Example 445

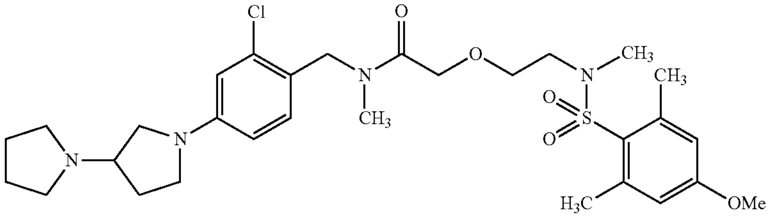 [SMILES: COc1cc(C)c(S(=O)(=O)N(C)CCOCC(=O)N(C)Cc2ccc(N3CCC(N4CCCC4)C3)cc2Cl)c(C)c1]

$C_{30}H_{43}ClN_4O_5S$ (607.21)
[M+H]+=608
HPLC (Method 6): retention time=1.80 min Example 446

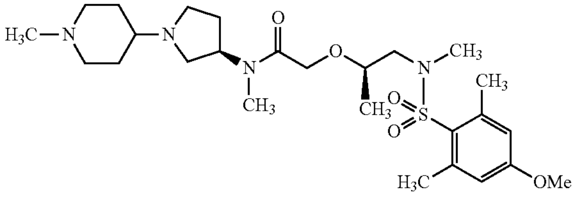 [SMILES: COc1cc(C)c(S(=O)(=O)N(C)C[C@@H](C)OCC(=O)N(C)[C@@H]2CCN(C3CCN(C)CC3)C2)c(C)c1]

$C_{26}H_{44}N_4O_5S \times 2HCl$ (597.64)
[M+H]+=525
HPLC (Method 12): retention time=2.4 min Example 447

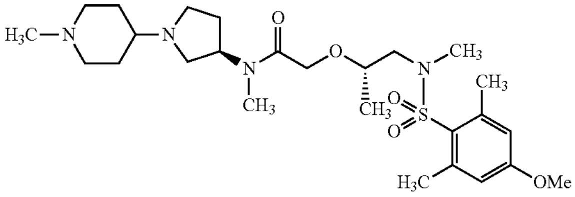 [SMILES: COc1cc(C)c(S(=O)(=O)N(C)C[C@H](C)OCC(=O)N(C)[C@@H]2CCN(C3CCN(C)CC3)C2)c(C)c1]

$C_{26}H_{44}N_4O_5S \times 2HCl$ (597.64)
[M+H]+=525
HPLC (Method 12): retention time=2.4 min Example 448

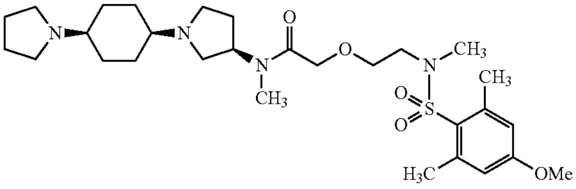 [SMILES: COc1cc(C)c(S(=O)(=O)N(C)CCOCC(=O)N(C)[C@@H]2CCN([C@H]3CC[C@@H](N4CCCC4)CC3)C2)c(C)c1]

$C_{29}H_{48}N_4O_5S \times 2HCl$ (637.70)
[M+H]+=565
HPLC (Method 12): retention time=2.3 min Example 449

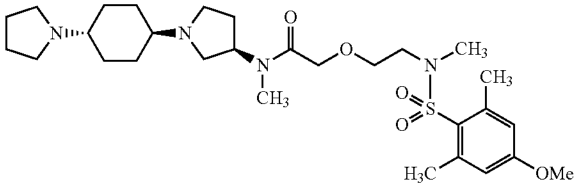 [SMILES: COc1cc(C)c(S(=O)(=O)N(C)CCOCC(=O)N(C)[C@@H]2CCN([C@H]3CC[C@H](N4CCCC4)CC3)C2)c(C)c1]

$C_{29}H_{48}N_4O_5S×2HCl$ (637.70)
[M+H]+=565
HPLC (Method 12): retention time=2.92 min Example 450

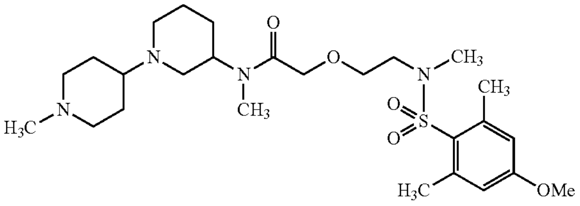 [SMILES: COc1cc(C)c(S(=O)(=O)N(C)CCOCC(=O)N(C)C2CCCN(C3CCN(C)CC3)C2)c(C)c1]

$C_{26}H_{44}N_4O_5S×2HCl$ (597.64)
[M+H]+=525
TLC: silica gel, dichloromethane/methanol/ammonia 8:2:0.2, Rf value=0.60

Example 451

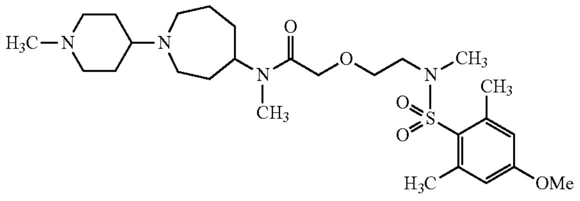 [SMILES: COc1cc(C)c(S(=O)(=O)N(C)CCOCC(=O)N(C)C2CCCN(C3CCN(C)CC3)CC2)c(C)c1]

$C_{27}H_{46}N_4O_5S×2HCl$ (611.67)
[M+H]+=539
TLC: silica gel, dichloromethane/methanol/ammonia 8:2:0.2, Rf value=0.62

Example 452

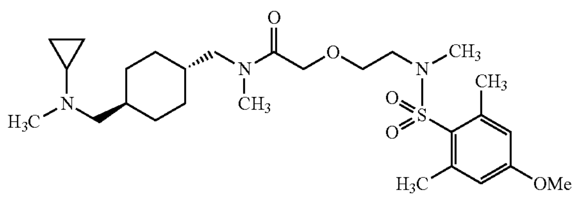 [SMILES: COc1cc(C)c(S(=O)(=O)N(C)CCOCC(=O)N(C)C[C@H]2CC[C@H](CN(C)C3CC3)CC2)c(C)c1]

$C_{27}H_{45}N_3O_5S×HCl$ (560.19)
[M+H]+=524
HPLC (Method 12): retention time=3.01 min Example 453

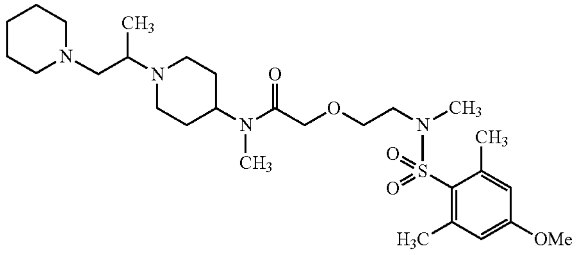 [SMILES: COc1cc(C)c(S(=O)(=O)N(C)CCOCC(=O)N(C)C2CCN(C(C)CN3CCCCC3)CC2)c(C)c1]

$C_{28}H_{48}N_4O_5S×2HCl$ (625.69)
[M+H]+=553
HPLC (Method 12): retention time=2.45 min Example 454

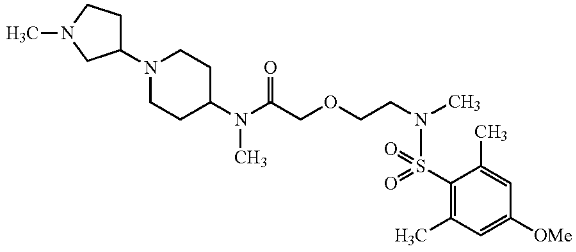 [SMILES: COc1cc(C)c(S(=O)(=O)N(C)CCOCC(=O)N(C)C2CCN(C3CCN(C)C3)CC2)c(C)c1]

$C_{25}H_{42}N_4O_5S×2HCl$ (583.61)
[M+H]+=511

HPLC (Method 12): retention time=2.33 min xample 455

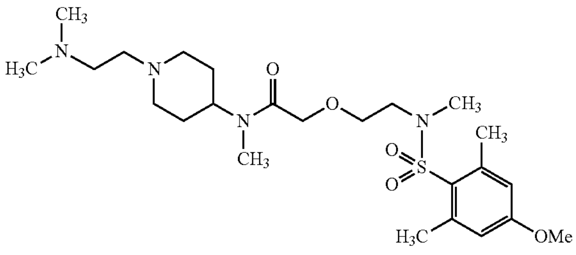 [SMILES: COc1cc(C)c(S(=O)(=O)N(C)CCOCC(=O)N(C)C2CCN(CCN(C)C)CC2)c(C)c1]

$C_{24}H_{42}N_4O_5S×C_2HF_3O_2$ (612.70)
[M+H]+=499
HPLC (Method 9): retention time=1.32 min Example 456

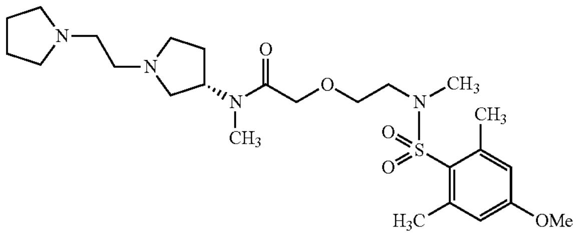 [SMILES: COc1cc(C)c(S(=O)(=O)N(C)CCOCC(=O)N(C)[C@H]2CCN(CCN3CCCC3)C2)c(C)c1]

$C_{25}H_{42}N_4O_5S \times 2C_2HF_3O_2$ (738.74)
[M+H]+=511
HPLC (Method 9): retention time=1.24 min Example 457

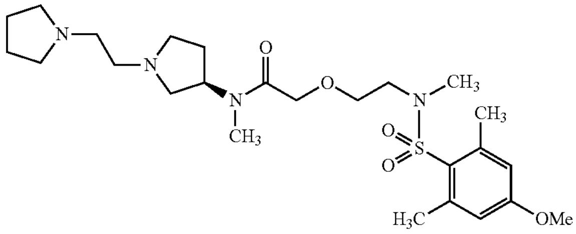 [SMILES: COc1cc(C)c(S(=O)(=O)N(C)CCOCC(=O)N(C)[C@@H]2CCN(CCN3CCCC3)C2)c(C)c1]

$C_{25}H_{42}N_4O_5S \times 2C_2HF_3O_2$ (738.74)
[M+H]+=511
HPLC (Method 9): retention time=1.27 min Example 458

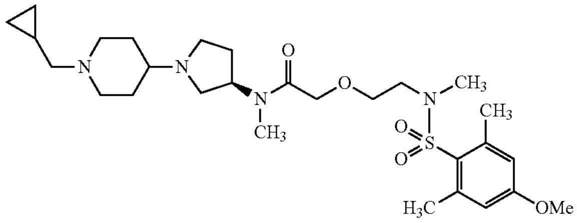 [SMILES: COc1cc(C)c(S(=O)(=O)N(C)CCOCC(=O)N(C)[C@@H]2CCN(C3CCN(CC4CC4)CC3)C2)c(C)c1]

$C_{28}H_{46}N_4O_5S \times CH_2O_2$ (596.78)
[M+H]+=551
HPLC (Method 6): retention time=1.31 min Example 459

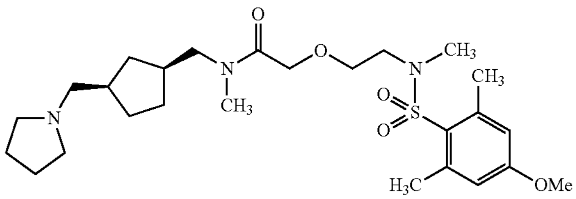 [SMILES: COc1cc(C)c(S(=O)(=O)N(C)CCOCC(=O)N(C)C[C@H]2CC[C@@H](CN3CCCC3)C2)c(C)c1]

$C_{26}H_{43}N_3O_5S \times C_2HF_3O_2$ (623.73)
[M+H]+=510
HPLC (Method 9): retention time=1.62 min Example 460

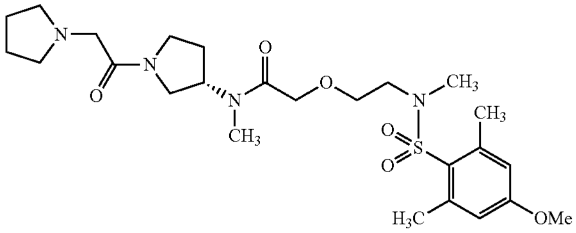 [SMILES: COc1cc(C)c(S(=O)(=O)N(C)CCOCC(=O)N(C)[C@H]2CCN(C(=O)CN3CCCC3)C2)c(C)c1]

$C_{25}H_{40}N_4O_6S \times C_2HF_3O_2$ (638.70)
[M+H]+=525
HPLC (Method 9): retention time=1.49 min Example 461

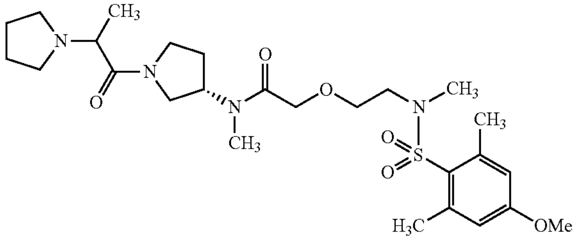 [SMILES: COc1cc(C)c(S(=O)(=O)N(C)CCOCC(=O)N(C)[C@H]2CCN(C(=O)C(C)N3CCCC3)C2)c(C)c1]

$C_{26}H_{42}N_4O_6S \times C_2HF_3O_2$ (652.72)
[M+H]+=539
HPLC (Method 9): retention time=1.51 min Example 462
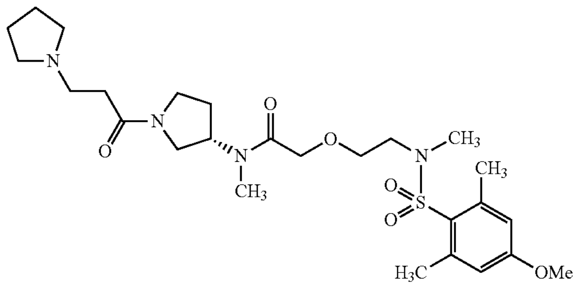 [SMILES: COc1cc(C)c(S(=O)(=O)N(C)CCOCC(=O)N(C)[C@H]2CCN(C(=O)CCN3CCCC3)C2)c(C)c1]
$C_{26}H_{42}N_4O_6S \times C_2HF_3O_2$ (652.72)
[M+H]+=539
HPLC (Method 9): retention time=1.52 min
Example 463
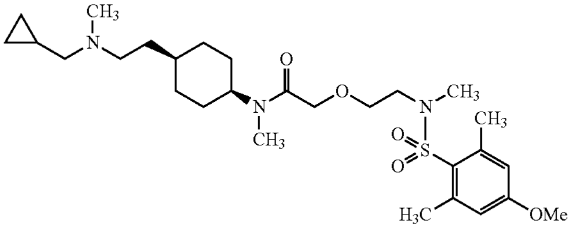 [SMILES: COc1cc(C)c(S(=O)(=O)N(C)CCOCC(=O)N(C)[C@H]2CC[C@@H](CCN(C)CC3CC3)CC2)c(C)c1]
$C_{28}H_{47}N_3O_5S$ (537.76)
[M+H]+=538
HPLC (Method 9): retention time=1.71 min
Example 464
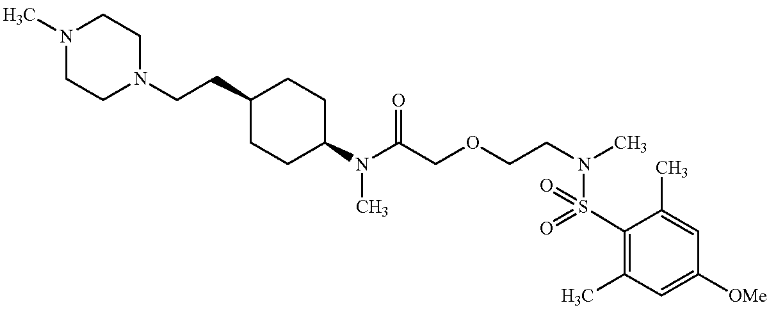 [SMILES: COc1cc(C)c(S(=O)(=O)N(C)CCOCC(=O)N(C)[C@H]2CC[C@@H](CCN3CCN(C)CC3)CC2)c(C)c1]
$C_{28}H_{48}N_4O_5S$ (552.77)
[M+H]+=553
HPLC (Method 9): retention time=1.39 min
Example 465
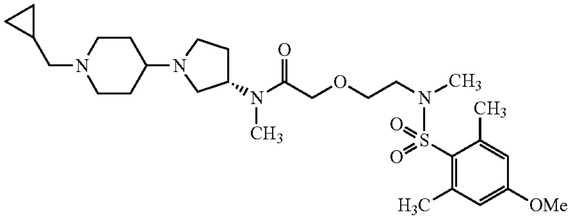 [SMILES: COc1cc(C)c(S(=O)(=O)N(C)CCOCC(=O)N(C)[C@H]2CCN(C3CCN(CC4CC4)CC3)C2)c(C)c1]
$C_{28}H_{46}N_4O_5S \times CH_2O_2$ (596.78)
[M+H]+=551
HPLC (Method 6): retention time=1.32 min
Example 466
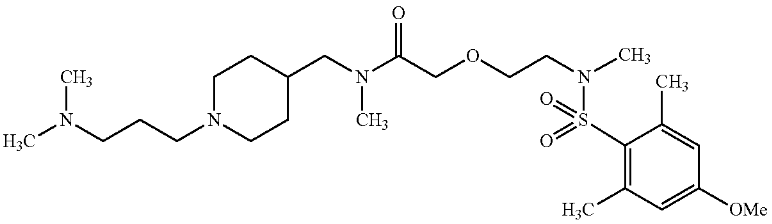 [SMILES: COc1cc(C)c(S(=O)(=O)N(C)CCOCC(=O)N(C)CC2CCN(CCCN(C)C)CC2)c(C)c1]

$C_{26}H_{46}N_4O_5S$ (526.73)
[M+H]+=527
HPLC (Method 9): retention time=1.27 min
Example 467
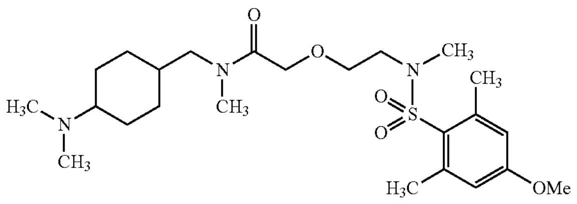 [SMILES: COc1cc(C)c(S(=O)(=O)N(C)CCOCC(=O)N(C)CC2CCC(N(C)C)CC2)c(C)c1]
$C_{24}H_{41}N_3O_5S$ (483.67)
[M+H]+=484
HPLC (Method 6): retention time=1.60 min
Example 468
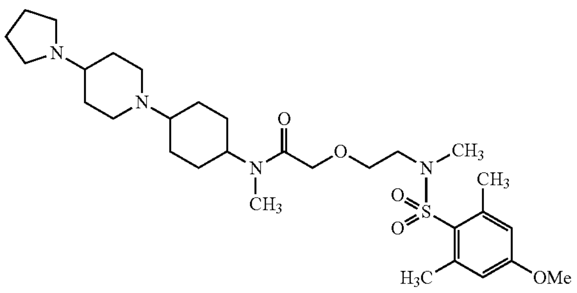 [SMILES: COc1cc(C)c(S(=O)(=O)N(C)CCOCC(=O)N(C)C2CCC(N3CCC(N4CCCC4)CC3)CC2)c(C)c1]
$C_{30}H_{50}N_4O_5S \times CH_2O_2$ (624.83)
[M+H]+=579
HPLC (Method 6): retention time=1.31 min
Example 469
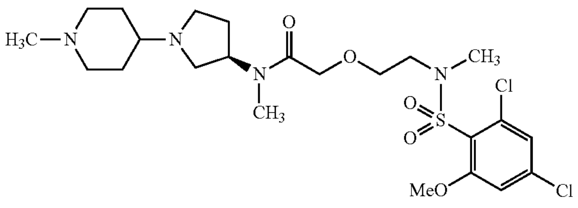 [SMILES: COc1cc(Cl)cc(Cl)c1S(=O)(=O)N(C)CCOCC(=O)N(C)[C@@H]1CCN(C2CCN(C)CC2)C1]
$C_{23}H_{36}Cl_2N_4O_5S$ (551.53)
[M+H]+=551/553/555
HPLC (Method 9): retention time=1.30 min
Example 470
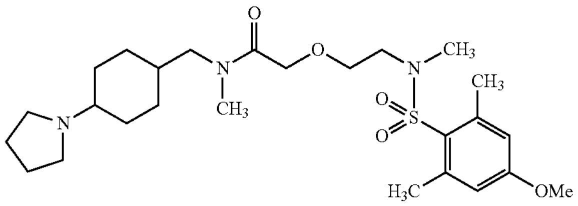 [SMILES: COc1cc(C)c(S(=O)(=O)N(C)CCOCC(=O)N(C)CC2CCC(N3CCCC3)CC2)c(C)c1]
$C_{26}H_{43}N_3O_5S$ (509.70)
[M+H]+=510
HPLC (Method 6): retention time=1.67 min
Example 471
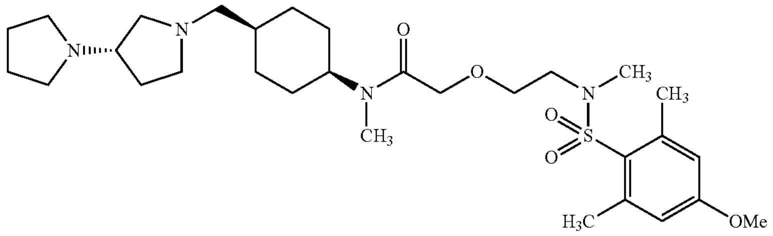 [SMILES: COc1cc(C)c(S(=O)(=O)N(C)CCOCC(=O)N(C)[C@H]2CC[C@@H](CN3CC[C@H](N4CCCC4)C3)CC2)c(C)c1]
$C_{30}H_{50}N_4O_5S \times C_2HF_3O_2$ (692.83)
[M+H]+=579
HPLC (Method 9): retention time=1.39 min
Example 472
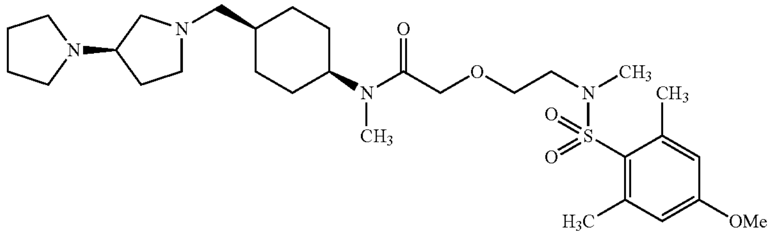 [SMILES: COc1cc(C)c(S(=O)(=O)N(C)CCOCC(=O)N(C)[C@H]2CC[C@@H](CN3CC[C@@H](N4CCCC4)C3)CC2)c(C)c1]

$C_{30}H_{50}N_4O_5S \times C_2HF_3O_2$ (692.83)
[M+H]+=579
HPLC (Method 9): retention time=1.39 min
Example 473
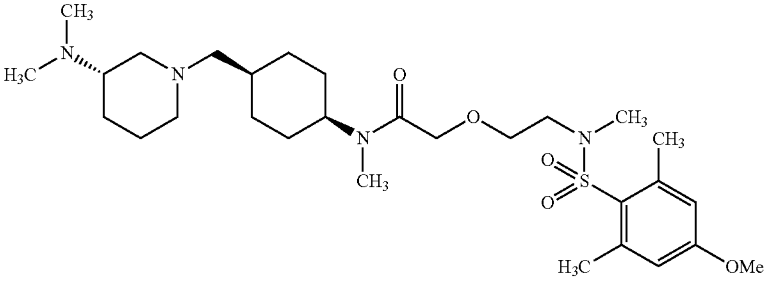 [SMILES: COc1cc(C)c(S(=O)(=O)N(C)CCOCC(=O)N(C)[C@H]2CC[C@@H](CN3CCC[C@H](N(C)C)C3)CC2)c(C)c1]
$C_{29}H_{50}N_4O_5S \times C_2HF_3O_2$ (680.82)
[M+H]+=567
HPLC (Method 9): retention time=1.40 min
Example 474
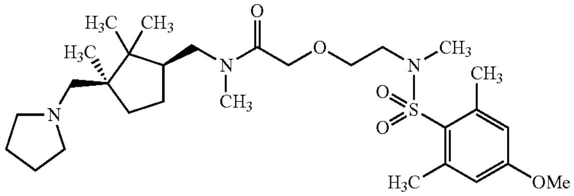 [SMILES: COc1cc(C)c(S(=O)(=O)N(C)CCOCC(=O)N(C)C[C@H]2CC[C@@](C)(CN3CCCC3)C2(C)C)c(C)c1]
$C_{29}H_{49}N_3O_5S$ (551.78)
[M+H]+=552
HPLC (Method 9): retention time=1.72 min
Example 475
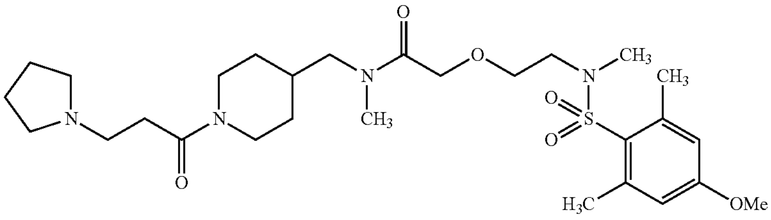 [SMILES: COc1cc(C)c(S(=O)(=O)N(C)CCOCC(=O)N(C)CC2CCN(C(=O)CCN3CCCC3)CC2)c(C)c1]
$C_{28}H_{46}N_4O_6S \times C_2HF_3O_2$ (680.78)
[M+H]+=567
HPLC (Method 9): retention time=1.60 min Example 476

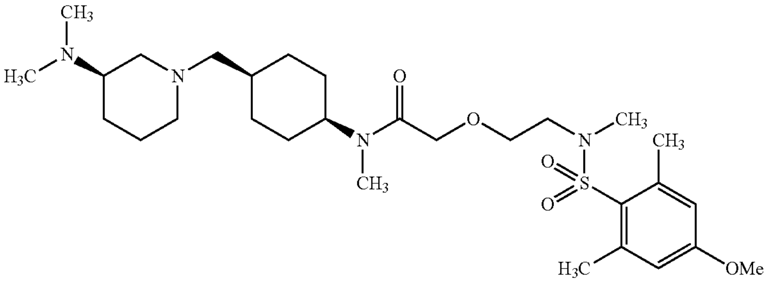 [SMILES: COc1cc(C)c(S(=O)(=O)N(C)CCOCC(=O)N(C)[C@H]2CC[C@@H](CN3CCC[C@@H](N(C)C)C3)CC2)c(C)c1]

$C_{29}H_{50}N_4O_5S \times C_2HF_3O_2$ (680.82)
[M+H]+=567
HPLC (Method 9): retention time=1.41 min Example 477

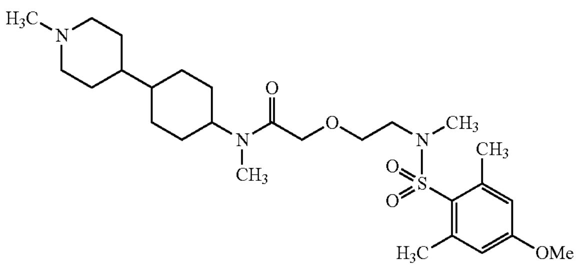 [SMILES: COc1cc(C)c(S(=O)(=O)N(C)CCOCC(=O)N(C)C2CCC(C3CCN(C)CC3)CC2)c(C)c1]

$C_{27}H_{45}N_3O_5S \times C_2HF_3O_2$ (637.75)
[M+H]+=524
HPLC (Method 9): retention time=1.69 min Example 478

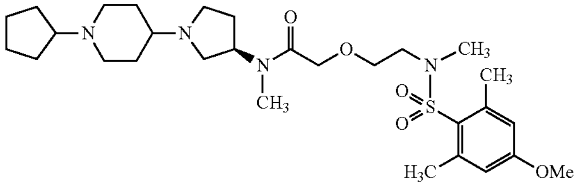 [SMILES: COc1cc(C)c(S(=O)(=O)N(C)CCOCC(=O)N(C)[C@@H]2CCN(C3CCN(C4CCCC4)CC3)C2)c(C)c1]

$C_{29}H_{48}N_4O_5S \times 2HCl$ (637.70)
[M+H]+=565
HPLC (Method 12): retention time=2.4 min Example 479

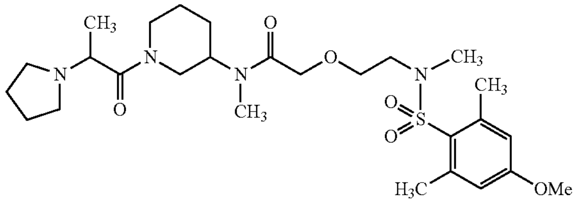 [SMILES: COc1cc(C)c(S(=O)(=O)N(C)CCOCC(=O)N(C)C2CCCN(C(=O)C(C)N3CCCC3)C2)c(C)c1]

$C_{27}H_{44}N_4O_6S \times C_2HF_3O_2$ (666.75)
[M+H]+=553
HPLC (Method 9): retention time=1.61 min Example 480

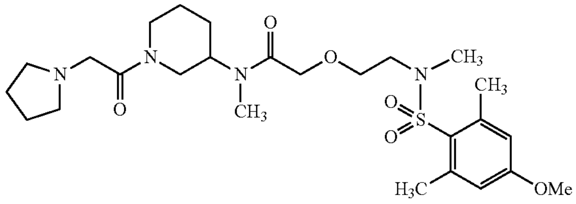 [SMILES: COc1cc(C)c(S(=O)(=O)N(C)CCOCC(=O)N(C)C2CCCN(C(=O)CN3CCCC3)C2)c(C)c1]

$C_{26}H_{42}N_4O_6S \times C_2HF_3O_2$ (652.72)
[M+H]+=539
HPLC (Method 9): retention time=1.60 min Example 481

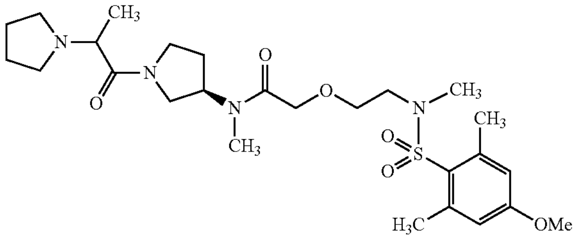 [SMILES: COc1cc(C)c(S(=O)(=O)N(C)CCOCC(=O)N(C)[C@@H]2CCN(C(=O)C(C)N3CCCC3)C2)c(C)c1]

$C_{26}H_{42}N_4O_6S$ (538.70)
[M+H]+=539
HPLC (Method 9): retention time=1.47 min Example 482

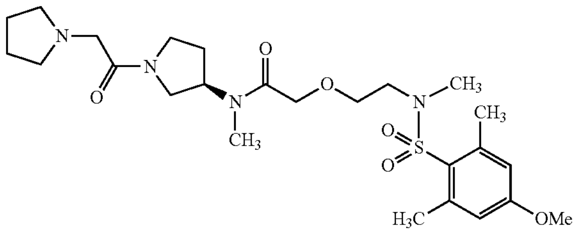 [SMILES: COc1cc(C)c(S(=O)(=O)N(C)CCOCC(=O)N(C)[C@@H]2CCN(C(=O)CN3CCCC3)C2)c(C)c1]

$C_{25}H_{40}N_4O_6S$ (524.67)
[M+H]+=525
HPLC (Method 9): retention time=1.48 min Example 575

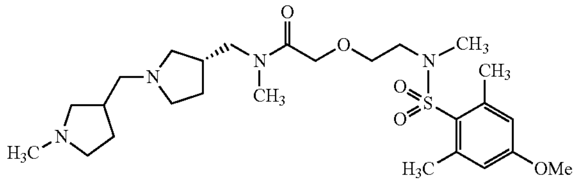 [SMILES: COc1cc(C)c(S(=O)(=O)N(C)CCOCC(=O)N(C)C[C@@H]2CCN(CC3CCN(C)C3)C2)c(C)c1]

$C_{26}H_{44}N_4O_5S$ (524.72)
[M+H]+=525
HPLC (Method 9): retention time=1.30 min Example 576

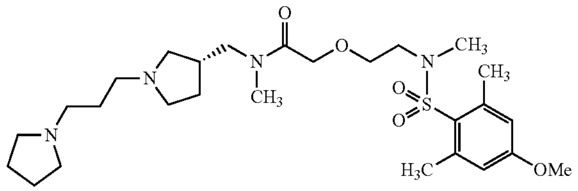 [SMILES: COc1cc(C)c(S(=O)(=O)N(C)CCOCC(=O)N(C)C[C@@H]2CCN(CCCN3CCCC3)C2)c(C)c1]

$C_{27}H_{46}N_4O_5S$ (538.74)
[M+H]+=539
HPLC (Method 9): retention time=1.34 min Example 577

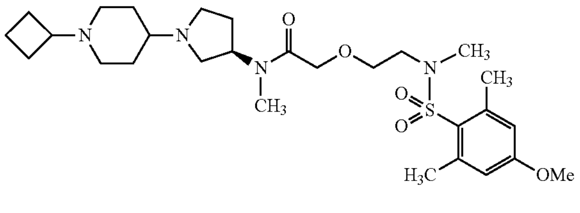 [SMILES: COc1cc(C)c(S(=O)(=O)N(C)CCOCC(=O)N(C)[C@@H]2CCN(C3CCN(C4CCC4)CC3)C2)c(C)c1]

$C_{28}H_{46}N_4O_5S \times 2HCl$ (623.68)
[M+H]+=551

TLC: silica gel, dichloromethane/methanol/ammonia 8:2:0.2, Rf value=0.71

Example 578

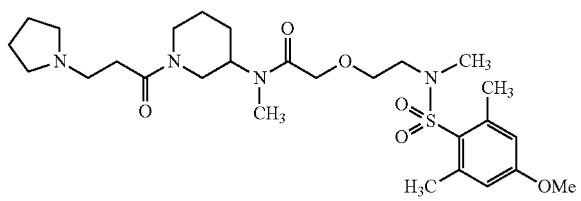 [SMILES: COc1cc(C)c(S(=O)(=O)N(C)CCOCC(=O)N(C)C2CCCN(C(=O)CCN3CCCC3)C2)c(C)c1]

$C_{27}H_{44}N_4O_6S \times C_2HF_3O_2$ (666.75)
[M+H]+=553
HPLC (Method 9): retention time=1.62 min Example 579

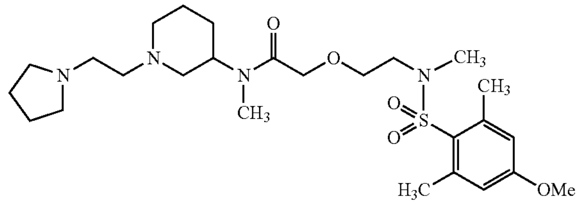 [SMILES: COc1cc(C)c(S(=O)(=O)N(C)CCOCC(=O)N(C)C2CCCN(CCN3CCCC3)C2)c(C)c1]

$C_{26}H_{44}N_4O_5S \times 2C_2HF_3O_2$ (752.76)
[M+H]+=525
HPLC (Method 9): retention time=1.33 min Example 580

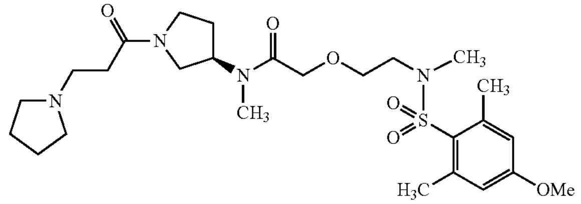 [SMILES: COc1cc(C)c(S(=O)(=O)N(C)CCOCC(=O)N(C)[C@@H]2CCN(C(=O)CCN3CCCC3)C2)c(C)c1]

$C_{26}H_{42}N_4O_6S \times C_2HF_3O_2$ (652.72)
[M+H]+=539
HPLC (Method 9): retention time=1.50 min Example 581

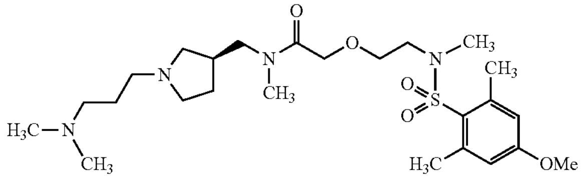 [SMILES: COc1cc(C)c(S(=O)(=O)N(C)CCOCC(=O)N(C)C[C@H]2CCN(CCCN(C)C)C2)c(C)c1]

$C_{25}H_{44}N_4O_5S$ (512.71)
[M+H]+=513
HPLC (Method 9): retention time=1.27 min Example 582

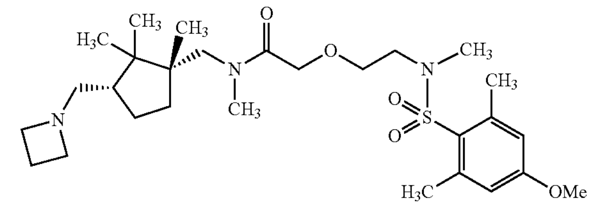 [SMILES: COc1cc(C)c(S(=O)(=O)N(C)CCOCC(=O)N(C)C[C@]2(C)CC[C@H](CN3CCC3)C2(C)C)c(C)c1]

$C_{28}H_{47}N_3O_5S \times C_2HF_3O_2$ (651.78)
[M+H]+=538
HPLC (Method 9): retention time=1.71 min Example 583

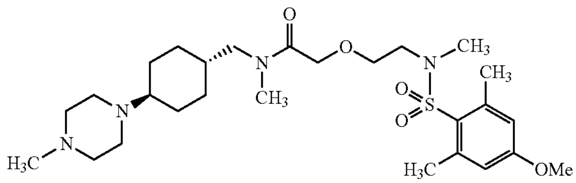 [SMILES: COc1cc(C)c(S(=O)(=O)N(C)CCOCC(=O)N(C)C[C@H]2CC[C@H](N3CCN(C)CC3)CC2)c(C)c1]

$C_{27}H_{46}N_4O_5S$ (538.74)
[M+H]+=539
HPLC (Method 9): retention time=1.37 min Example 584

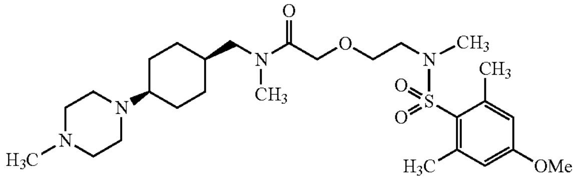 [SMILES: COc1cc(C)c(S(=O)(=O)N(C)CCOCC(=O)N(C)C[C@H]2CC[C@@H](N3CCN(C)CC3)CC2)c(C)c1]

$C_{27}H_{46}N_4O_5S$ (538.74)
[M+H]+=539
HPLC (Method 9): retention time=1.44 min Example 585

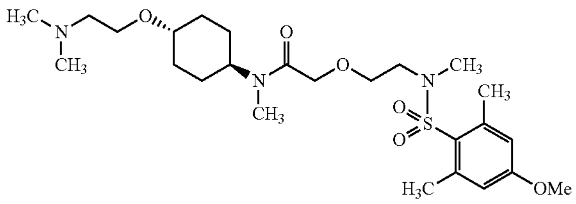 [SMILES: COc1cc(C)c(S(=O)(=O)N(C)CCOCC(=O)N(C)[C@H]2CC[C@H](OCCN(C)C)CC2)c(C)c1]

$C_{25}H_{43}N_3O_6S \times HCl$ (550.15)
[M+H]+=514
HPLC (Method 5): retention time=1.34 min Example 586

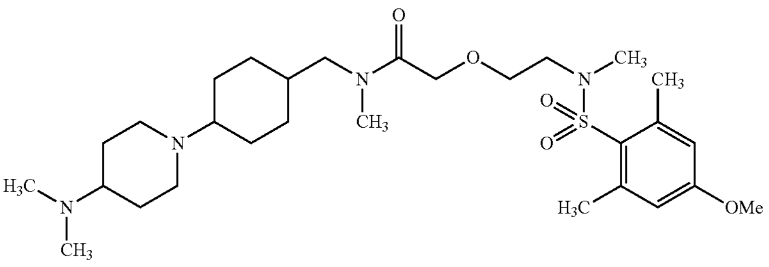 [SMILES: COc1cc(C)c(S(=O)(=O)N(C)CCOCC(=O)N(C)CC2CCC(N3CCC(N(C)C)CC3)CC2)c(C)c1]

$C_{29}H_{50}N_4O_5S \times 2HCl$ (639.72)
[M+H]+=567
HPLC (Method 5): retention time=1.21 min Example 587

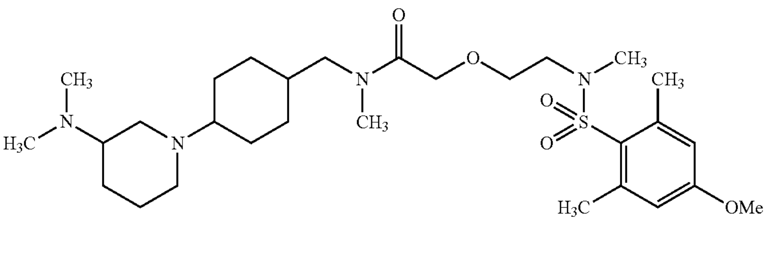 [SMILES: COc1cc(C)c(S(=O)(=O)N(C)CCOCC(=O)N(C)CC2CCC(N3CCCC(N(C)C)C3)CC2)c(C)c1]

$C_{29}H_{50}N_4O_5S \times 2HCl$ (639.72)
[M+H]+=567
HPLC (Method 5): retention time=1.20 min Example 588
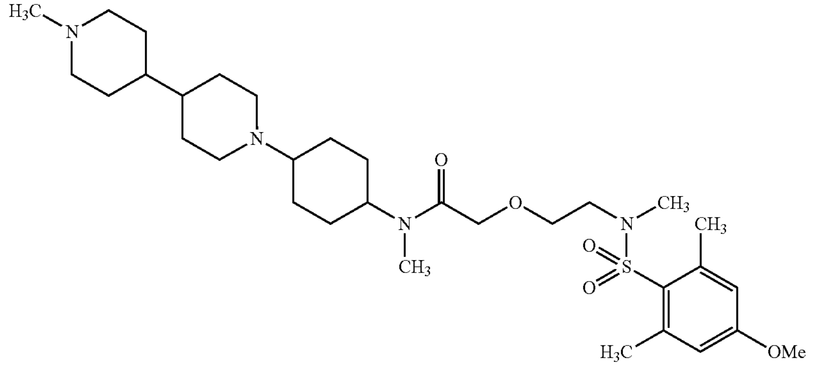 [SMILES: COc1cc(C)c(S(=O)(=O)N(C)CCOCC(=O)N(C)C2CCC(N3CCC(C4CCN(C)CC4)CC3)CC2)c(C)c1]
$C_{32}H_{54}N_4O_5S \times C_2HF_3O_2$ (720.88)
[M+H]+=607
HPLC (Method 9): retention time=1.37 min
Example 589
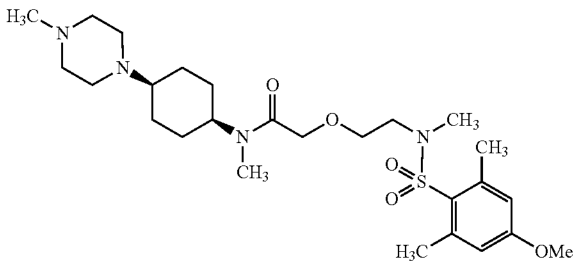 [SMILES: COc1cc(C)c(S(=O)(=O)N(C)CCOCC(=O)N(C)[C@H]2CC[C@@H](N3CCN(C)CC3)CC2)c(C)c1]
$C_{26}H_{44}N_4O_5S \times 2C_2HF_3O_2$ (752.76)
[M+H]+=525
HPLC (Method 9): retention time=1.41 min
Example 590
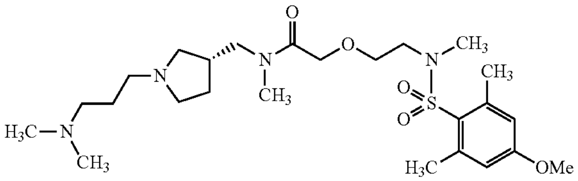 [SMILES: COc1cc(C)c(S(=O)(=O)N(C)CCOCC(=O)N(C)C[C@@H]2CCN(CCCN(C)C)C2)c(C)c1]
$C_{25}H_{44}N_4O_5S$ (512.71)
[M+H]+=513
HPLC (Method 9): retention time=1.35 min
Example 591
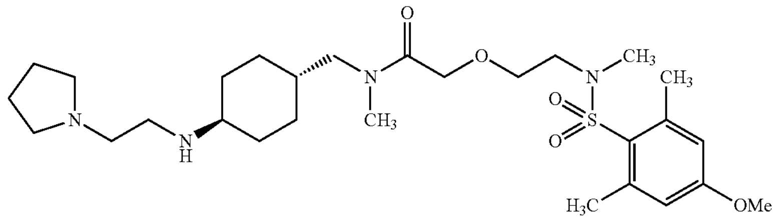 [SMILES: COc1cc(C)c(S(=O)(=O)N(C)CCOCC(=O)N(C)C[C@H]2CC[C@H](NCCN3CCCC3)CC2)c(C)c1]
$C_{28}H_{48}N_4O_5S \times 2C_2HF_3O_2$ (780.82)
[M+H]+=553
HPLC (Method 9): retention time=1.40 min Example 592

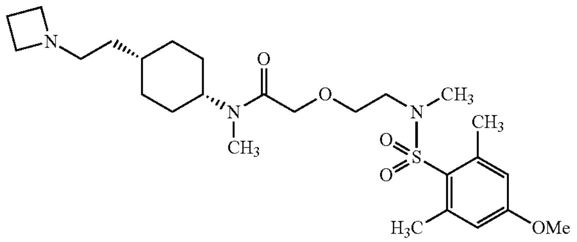 [SMILES: COc1cc(C)c(S(=O)(=O)N(C)CCOCC(=O)N(C)[C@H]2CC[C@@H](CCN3CCC3)CC2)c(C)c1]

$C_{26}H_{43}N_3O_5S$ (509.70)
[M+H]+=510
HPLC (Method 9): retention time=1.70 min Example 612

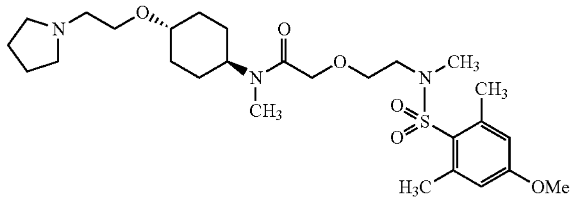 [SMILES: COc1cc(C)c(S(=O)(=O)N(C)CCOCC(=O)N(C)[C@H]2CC[C@H](OCCN3CCCC3)CC2)c(C)c1]

$C_{27}H_{45}N_3O_6S \times HCl$ (576.19)
[M+H]+=540
HPLC (Method 5): retention time=1.37 min Example 613

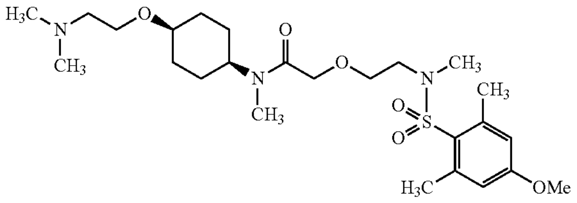 [SMILES: COc1cc(C)c(S(=O)(=O)N(C)CCOCC(=O)N(C)[C@H]2CC[C@@H](OCCN(C)C)CC2)c(C)c1]

$C_{25}H_{43}N_3O_6S \times HCl$ (550.15)
[M+H]+=514
HPLC (Method 5): retention time=1.36 min Example 614

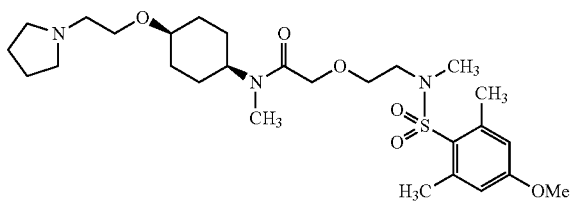 [SMILES: COc1cc(C)c(S(=O)(=O)N(C)CCOCC(=O)N(C)[C@H]2CC[C@@H](OCCN3CCCC3)CC2)c(C)c1]

$C_{27}H_{45}N_3O_6S \times HCl$ (576.19)
[M+H]+=540
HPLC (Method 5): retention time=1.38 min Example 615

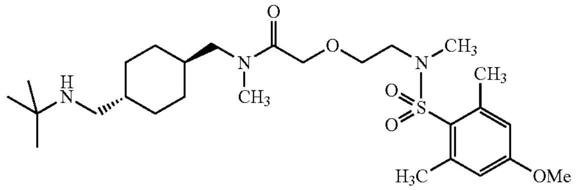 [SMILES: COc1cc(C)c(S(=O)(=O)N(C)CCOCC(=O)N(C)C[C@H]2CC[C@H](CNC(C)(C)C)CC2)c(C)c1]

$C_{27}H_{47}N_3O_5S \times HCl$ (562.21)
[M+H]+=526
HPLC (Method 4): retention time=3.0 min Example 616

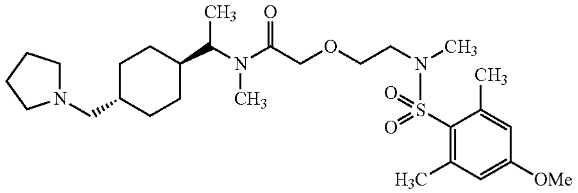 [SMILES: COc1cc(C)c(S(=O)(=O)N(C)CCOCC(=O)N(C)C(C)[C@H]2CC[C@H](CN3CCCC3)CC2)c(C)c1]

$C_{28}H_{47}N_3O_5S \times HCl$ (574.22)
[M+H]+=538
HPLC (Method 4): retention time=3.1 min Example 617

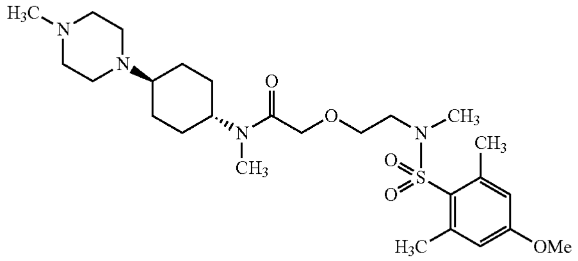 [SMILES: COc1cc(C)c(S(=O)(=O)N(C)CCOCC(=O)N(C)[C@H]2CC[C@H](N3CCN(C)CC3)CC2)c(C)c1]

$C_{26}H_{44}N_4O_5S$ (524.72)
[M+H]+=525
HPLC (Method 9): retention time=1.32 min Example 618

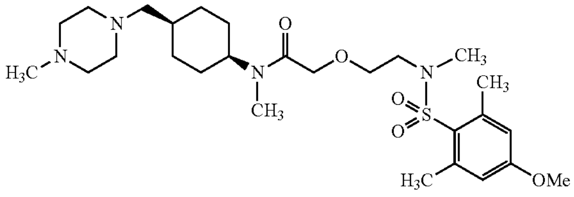 [SMILES: COc1cc(C)c(S(=O)(=O)N(C)CCOCC(=O)N(C)[C@H]2CC[C@@H](CN3CCN(C)CC3)CC2)c(C)c1]

$C_{27}H_{46}N_4O_5S$ (538.74)
[M+H]+=539
HPLC (Method 9): retention time=1.57 min Example 619

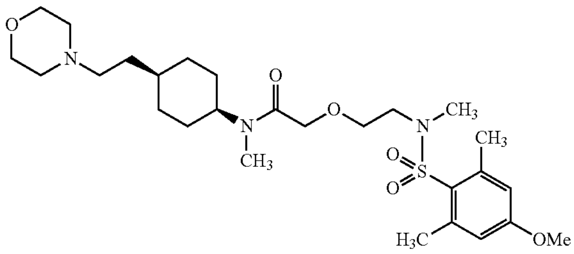 [SMILES: COc1cc(C)c(S(=O)(=O)N(C)CCOCC(=O)N(C)[C@H]2CC[C@@H](CCN3CCOCC3)CC2)c(C)c1]

$C_{27}H_{45}N_3O_6S$ (539.73)
[M+H]+=540
HPLC (Method 9): retention time=1.65 min Example 620

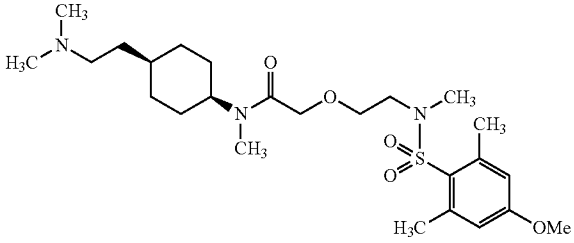 [SMILES: COc1cc(C)c(S(=O)(=O)N(C)CCOCC(=O)N(C)[C@H]2CC[C@@H](CCN(C)C)CC2)c(C)c1]

$C_{25}H_{43}N_3O_5S$ (497.69)
[M+H]+=498
HPLC (Method 9): retention time=1.65 min Example 621

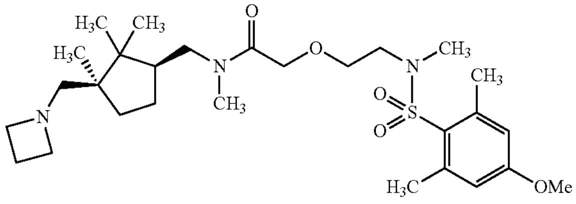 [SMILES: COc1cc(C)c(S(=O)(=O)N(C)CCOCC(=O)N(C)C[C@H]2CC[C@@](C)(CN3CCC3)C2(C)C)c(C)c1]

$C_{28}H_{47}N_3O_5S \times HCl$ (574.22)
[M+H]+=538
HPLC (Method 9): retention time=1.68 min Example 622

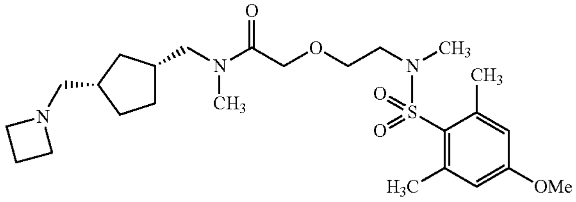 [SMILES: COc1cc(C)c(S(=O)(=O)N(C)CCOCC(=O)N(C)C[C@@H]2CC[C@H](CN3CCC3)C2)c(C)c1]

$C_{26}H_{41}N_3O_6S \times C_2HF_3O_2$ (609.70)
[M+H]+=496
HPLC (Method 9): retention time=1.62 min Example 623

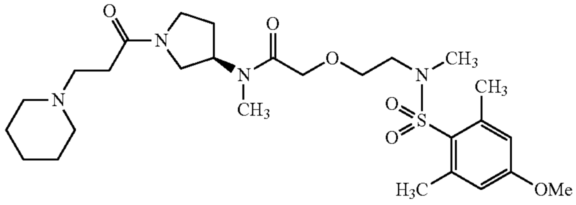 [SMILES: COc1cc(C)c(S(=O)(=O)N(C)CCOCC(=O)N(C)[C@@H]2CCN(C(=O)CCN3CCCCC3)C2)c(C)c1]

$C_{27}H_{44}N_4O_6S \times C_2HF_3O_2$ (666.76)
[M+H]+=553
HPLC (Method 9): retention time=1.57 min Example 624

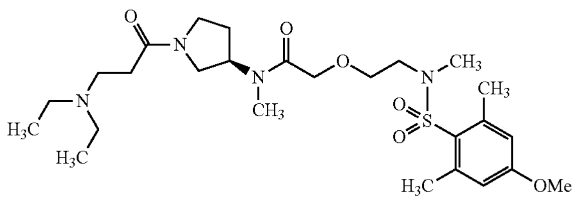 [SMILES: CCN(CC)CCC(=O)N1CC[C@@H](N(C)C(=O)COCCN(C)S(=O)(=O)c2c(C)cc(OC)cc2C)C1]

$C_{26}H_{44}N_4O_6S \times C_2HF_3O_2$ (654.75)
[M+H]+=541
HPLC (Method 9): retention time=1.56 min Example 625
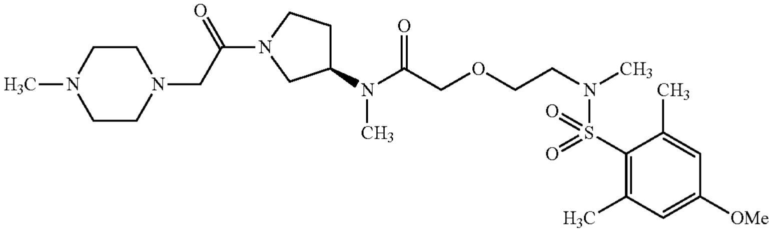 [SMILES: COc1cc(C)c(S(=O)(=O)N(C)CCOCC(=O)N(C)[C@@H]2CCN(C(=O)CN3CCN(C)CC3)C2)c(C)c1]
$C_{26}H_{43}N_5O_6S \times C_2HF_3O_2$ (667.74)
[M+H]+=554
HPLC (Method 9): retention time=1.00 min
Example 626
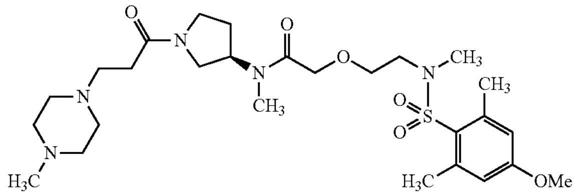 [SMILES: COc1cc(C)c(S(=O)(=O)N(C)CCOCC(=O)N(C)[C@@H]2CCN(C(=O)CCN3CCN(C)CC3)C2)c(C)c1]
$C_{27}H_{45}N_5O_6S \times C_2HF_3O_2$ (681.77)
[M+H]+=568
HPLC (Method 9): retention time=1.03 min
Example 627
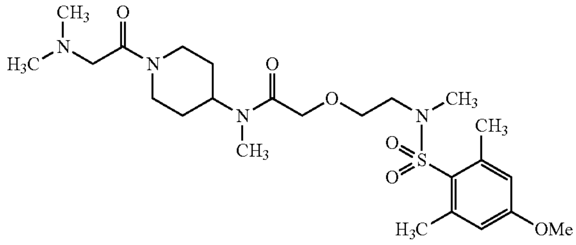 [SMILES: COc1cc(C)c(S(=O)(=O)N(C)CCOCC(=O)N(C)C2CCN(C(=O)CN(C)C)CC2)c(C)c1]
$C_{24}H_{40}N_4O_6S \times C_2HF_3O_2$ (626.69)
[M+H]+=513
HPLC (Method 9): retention time=1.50 min
Example 628
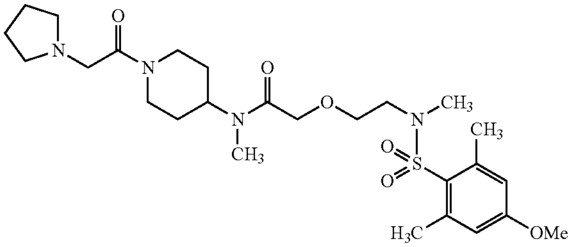 [SMILES: COc1cc(C)c(S(=O)(=O)N(C)CCOCC(=O)N(C)C2CCN(C(=O)CN3CCCC3)CC2)c(C)c1]
$C_{26}H_{42}N_4O_6S \times C_2HF_3O_2$ (654.72)
[M+H]+=539
HPLC (Method 9): retention time=1.55 min
Example 629
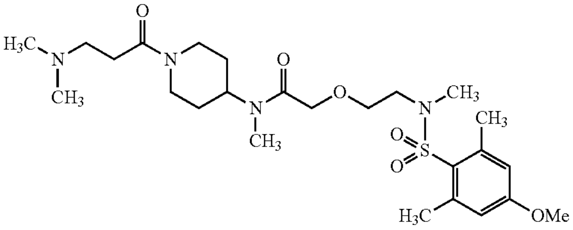 [SMILES: COc1cc(C)c(S(=O)(=O)N(C)CCOCC(=O)N(C)C2CCN(C(=O)CCN(C)C)CC2)c(C)c1]
$C_{25}H_{42}N_4O_6S \times C_2HF_3O_2$ (640.71)
[M+H]+=527
HPLC (Method 9): retention time=1.63 min Example 630
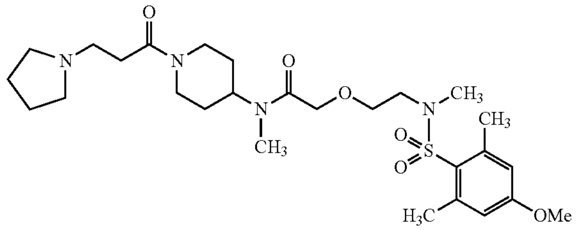 [SMILES: COc1cc(C)c(S(=O)(=O)N(C)CCOCC(=O)N(C)C2CCN(C(=O)CCN3CCCC3)CC2)c(C)c1]
$C_{27}H_{44}N_4O_6S$ (552.73)
[M+H]+=553
HPLC (Method 9): retention time=1.65 min
Example 638
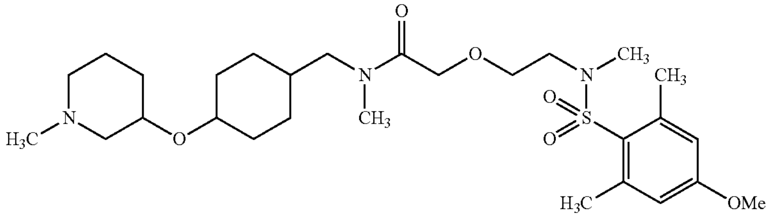 [SMILES: COc1cc(C)c(S(=O)(=O)N(C)CCOCC(=O)N(C)CC2CCC(OC3CCCN(C)C3)CC2)c(C)c1]
$C_{28}H_{47}N_3O_6S \times HCl$ (590.22)
[M+H]+=554
HPLC (Method 5): retention time=1.44 min
Example 639
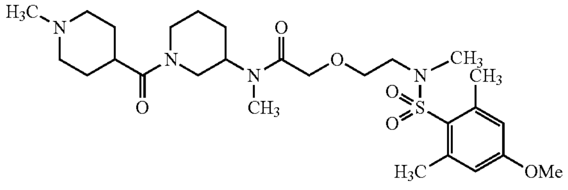 [SMILES: COc1cc(C)c(S(=O)(=O)N(C)CCOCC(=O)N(C)C2CCCN(C(=O)C3CCN(C)CC3)C2)c(C)c1]
$C_{27}H_{44}N_4O_6S \times C_2HF_3O_2$ (666.75)
[M+H]+=553
HPLC (Method 9): retention time=1.59 min
Example 640
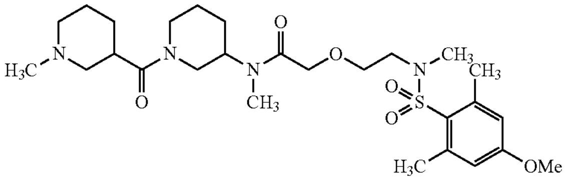 [SMILES: COc1cc(C)c(S(=O)(=O)N(C)CCOCC(=O)N(C)C2CCCN(C(=O)C3CCCN(C)C3)C2)c(C)c1]
$C_{27}H_{44}N_4O_6S \times C_2HF_3O_2$ (666.75)
[M+H]+=553
HPLC (Method 9): retention time=1.61 min
Example 641
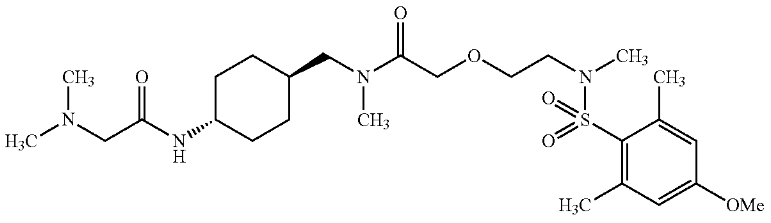 [SMILES: COc1cc(C)c(S(=O)(=O)N(C)CCOCC(=O)N(C)C[C@H]2CC[C@H](NC(=O)CN(C)C)CC2)c(C)c1]
$C_{26}H_{44}N_4O_6S \times C_2HF_3O_2$ (590.22)
[M+H]+=541
PLC (Method 9): retention time=1.56 min Example 642 1

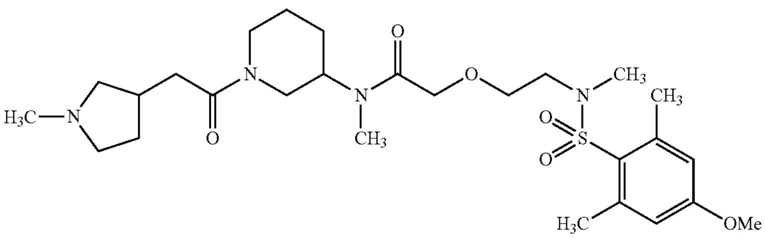 [SMILES: COc1cc(C)c(S(=O)(=O)N(C)CCOCC(=O)N(C)C2CCCN(C(=O)CC3CCN(C)C3)C2)c(C)c1]

$C_{27}H_{44}N_4O_6S \times C_2HF_3O_2$ (666.75)
[M+H]+=553
HPLC (Method 9): retention time=1.55 min Example 643

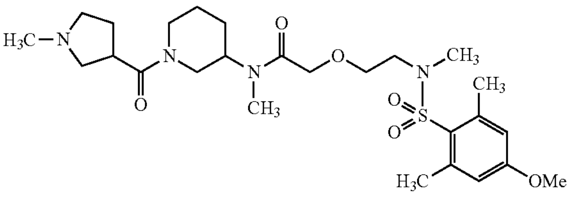 [SMILES: COc1cc(C)c(S(=O)(=O)N(C)CCOCC(=O)N(C)C2CCCN(C(=O)C3CCN(C)C3)C2)c(C)c1]

$C_{26}H_{42}N_4O_6S \times C_2HF_3O_2$ (652.72)
[M+H]+=539
HPLC (Method 9): retention time=1.55 min Example 644

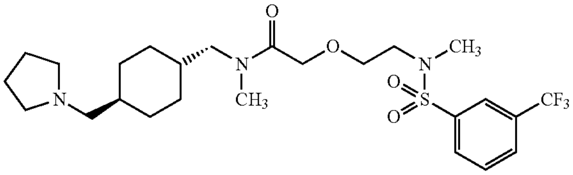

$C_{25}H_{38}F_3N_3O_4S$ (533.66)
[M+H]+=534

Example 645

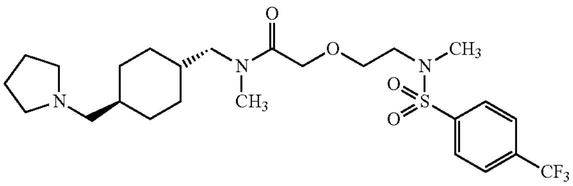

$C_{25}H_{38}F_3N_3O_4S$ (533.66)
[M+H]+=534

Example 646

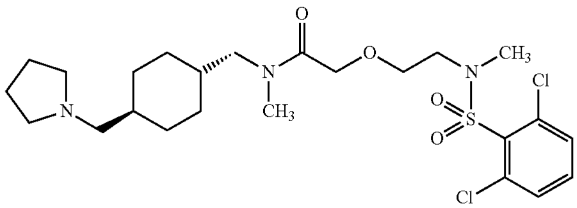

$C_{24}H_{37}Cl_2N_3O_4S$ (534.55)
[M+H]+=535

Example 647

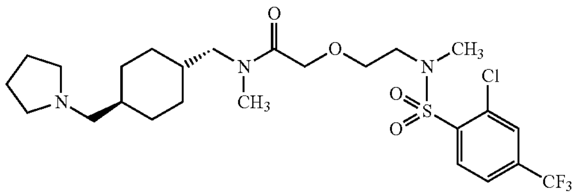

$C_{25}H_{37}ClF_3N_3O_4S$ (568.10)
[M+H]+=569

The following compounds were prepared analogously to Example 121:

Example 483

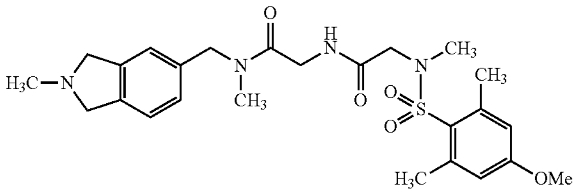 [SMILES: COc1cc(C)c(S(=O)(=O)N(C)CC(=O)NCC(=O)N(C)Cc2ccc3c(c2)CN(C)C3)c(C)c1]

$C_{25}H_{34}N_4O_5S \times C_2HF_3O_2$ (616.65)
[M+H]+=503
HPLC (Method 6): retention time=2.30 min Example 484

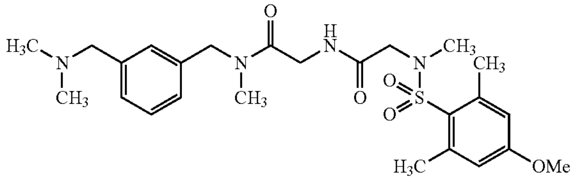 [SMILES: COc1cc(C)c(S(=O)(=O)N(C)CC(=O)NCC(=O)N(C)Cc2cccc(CN(C)C)c2)c(C)c1]

$C_{25}H_{36}N_4O_5S \times HCl$ (541.10)
[M+H]+=505
HPLC (Method 5): retention time=1.49 min Example 485

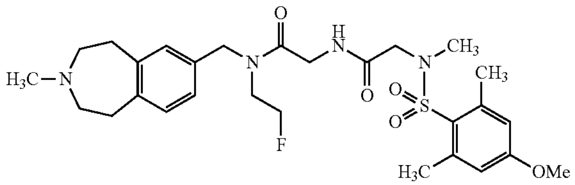 [SMILES: COc1cc(C)c(S(=O)(=O)N(C)CC(=O)NCC(=O)N(CCF)Cc2ccc3c(c2)CCN(C)CC3)c(C)c1]

$C_{28}H_{39}FN_4O_5S \times C_2HF_3O_2$ (676.72)
[M+H]+=563
HPLC (Method 5): retention time=1.55 min Example 486

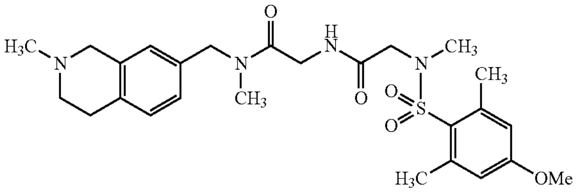 [SMILES: COc1cc(C)c(S(=O)(=O)N(C)CC(=O)NCC(=O)N(C)Cc2ccc3c(c2)CN(C)CC3)c(C)c1]

$C_{26}H_{36}N_4O_5S \times HCl$ (553.11)
[M+H]+=517
HPLC (Method 11): retention time=1.73 min Example 487

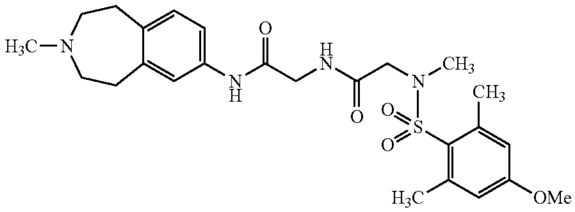 [SMILES: COc1cc(C)c(S(=O)(=O)N(C)CC(=O)NCC(=O)Nc2ccc3c(c2)CCN(C)CC3)c(C)c1]

$C_{25}H_{34}N_4O_5S \times C_2HF_3O_2$ (616.65)
[M+H]+=503
HPLC (Method 5): retention time=1.49 min Example 488

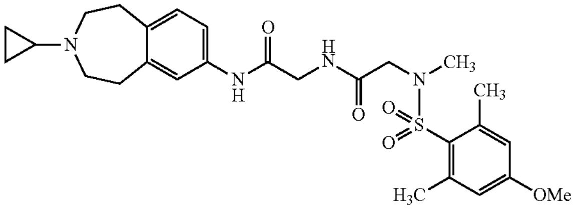 [SMILES: COc1cc(C)c(S(=O)(=O)N(C)CC(=O)NCC(=O)Nc2ccc3c(c2)CCN(C2CC2)CC3)c(C)c1]

$C_{27}H_{36}N_4O_5S \times C_2HF_3O_2$ (642.69)
[M+H]+=529
HPLC (Method 5): retention time=1.50 min Example 489

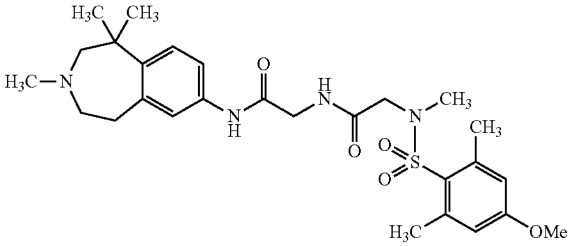 [SMILES: COc1cc(C)c(S(=O)(=O)N(C)CC(=O)NCC(=O)Nc2ccc3c(c2)CCN(C)CC3(C)C)c(C)c1]

$C_{27}H_{38}N_4O_5S \times C_2HF_3O_2$ (644.70)
[M+H]+=531
HPLC (Method 5): retention time=1.54 min Example 490

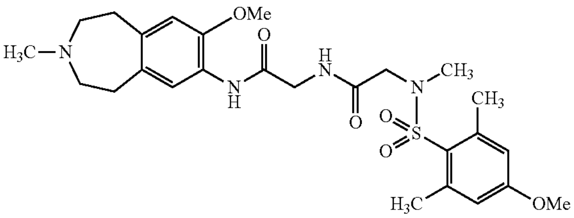 [SMILES: COc1cc(C)c(S(=O)(=O)N(C)CC(=O)NCC(=O)Nc2cc3c(cc2OC)CCN(C)CC3)c(C)c1]

$C_{26}H_{36}N_4O_6S \times C_2HF_3O_2$ (646.68)
[M+H]+=533
HPLC (Method 5): retention time=1.51 min Example 491

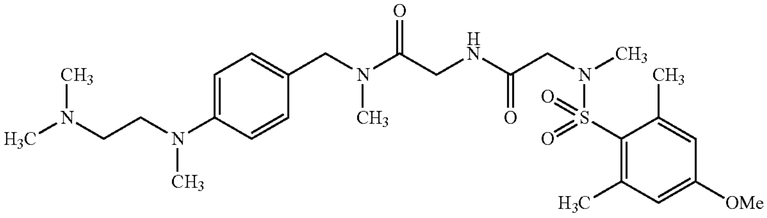 [SMILES: COc1cc(C)c(S(=O)(=O)N(C)CC(=O)NCC(=O)N(C)Cc2ccc(N(C)CCN(C)C)cc2)c(C)c1]

$C_{27}H_{41}N_5O_5S \times HCl$ (584.17)
[M+H]+=548
HPLC (Method 5): retention time=1.53 min Example 492

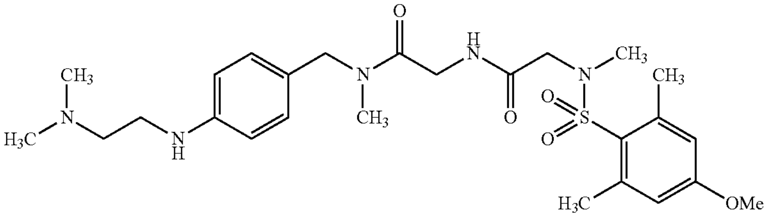 [SMILES: COc1cc(C)c(S(=O)(=O)N(C)CC(=O)NCC(=O)N(C)Cc2ccc(NCCN(C)C)cc2)c(C)c1]

$C_{26}H_{39}N_5O_5S \times HCl$ (570.15)
[M+H]+=534
HPLC (Method 5): retention time=1.52 min Example 493

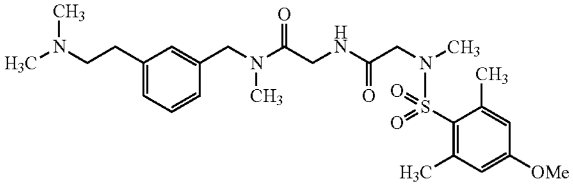 [SMILES: COc1cc(C)c(S(=O)(=O)N(C)CC(=O)NCC(=O)N(C)Cc2cccc(CCN(C)C)c2)c(C)c1]

$C_{26}H_{38}N_4O_5S \times HCl$ (555.13)
[M+H]+=519
HPLC (Method 5): retention time=1.51 min Example 494

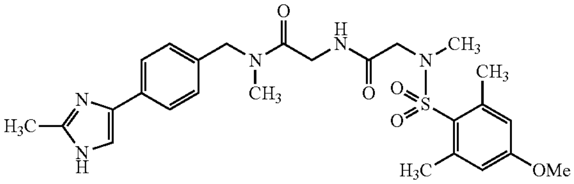 [SMILES: COc1cc(C)c(S(=O)(=O)N(C)CC(=O)NCC(=O)N(C)Cc2ccc(-c3c[nH]c(C)n3)cc2)c(C)c1]

$C_{26}H_{33}N_5O_5S$ (527.64)
[M+H]+=528
HPLC (Method 4): retention time=3.0 min Example 495

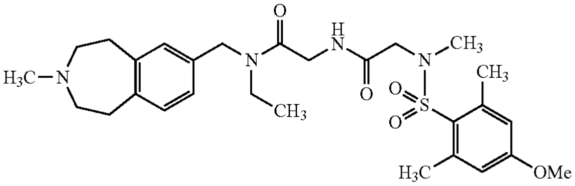 [SMILES: CCN(Cc1ccc2c(c1)CCN(C)CC2)C(=O)CNC(=O)CN(C)S(=O)(=O)c1c(C)cc(OC)cc1C]

$C_{28}H_{40}N_4O_5S \times HCl$ (581.17)
[M+H]+=545
HPLC (Method 4): retention time=3.1 min Example 496

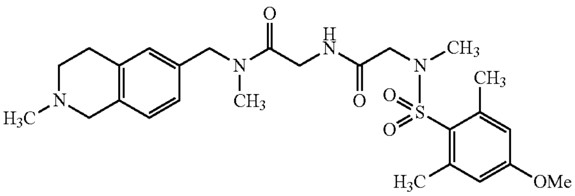 [SMILES: COc1cc(C)c(S(=O)(=O)N(C)CC(=O)NCC(=O)N(C)Cc2ccc3c(c2)CCN(C)C3)c(C)c1]

$C_{26}H_{36}N_4O_5S \times HCl$ (553.11)
[M+H]+=517
HPLC (Method 5): retention time=1.48 min Example 497

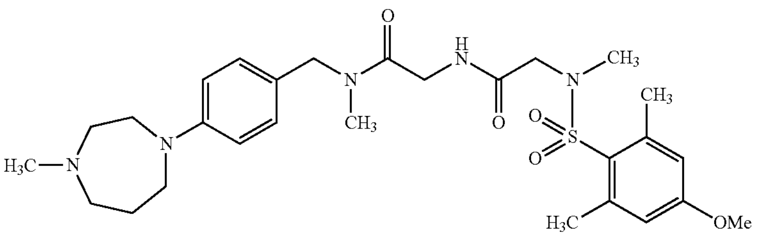 [SMILES: COc1cc(C)c(S(=O)(=O)N(C)CC(=O)NCC(=O)N(C)Cc2ccc(N3CCCN(C)CC3)cc2)c(C)c1]

$C_{28}H_{41}N_5O_5S \times HCl$ (596.18)
[M+H]+=560
HPLC (Method 5): retention time=1.52 min Example 498

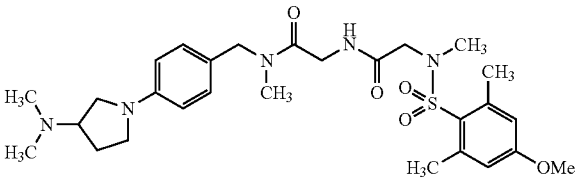 [SMILES: COc1cc(C)c(S(=O)(=O)N(C)CC(=O)NCC(=O)N(C)Cc2ccc(N3CCC(N(C)C)C3)cc2)c(C)c1]

$C_{28}H_{41}N_5O_5S \times HCl$ (596.18)
[M+H]+=560
HPLC (Method 5): retention time=1.52 min Example 499

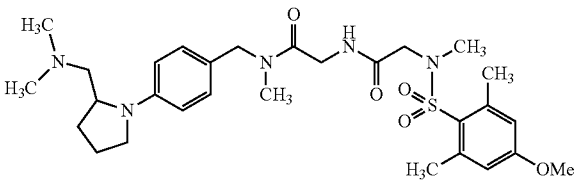 [SMILES: COc1cc(C)c(S(=O)(=O)N(C)CC(=O)NCC(=O)N(C)Cc2ccc(N3CCCC3CN(C)C)cc2)c(C)c1]

$C_{29}H_{43}N_5O_5S \times HCl$ (610.21)
[M+H]+=574
HPLC (Method 5): retention time=1.57 min Example 500

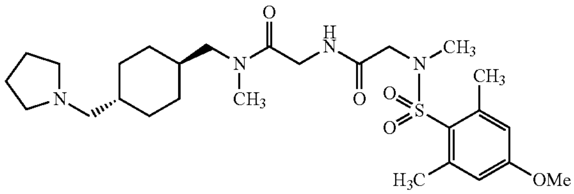 [SMILES: COc1cc(C)c(S(=O)(=O)N(C)CC(=O)NCC(=O)N(C)C[C@H]2CC[C@H](CN3CCCC3)CC2)c(C)c1]

$C_{27}H_{44}N_4O_5S \times HCl$ (573.19)
[M+H]+=537

TLC: silica gel, dichloromethane/methanol/ammonia 8:2:0.01, Rf value=0.66

Example 501

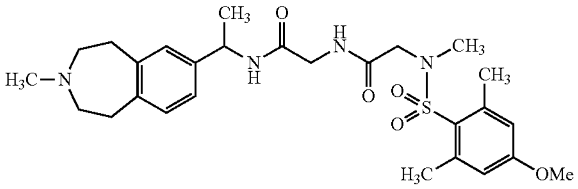 [SMILES: COc1cc(C)c(S(=O)(=O)N(C)CC(=O)NCC(=O)NC(C)c2ccc3c(c2)CCN(C)CC3)c(C)c1]

$C_{27}H_{38}N_4O_5S \times HCl$ (567.14)
[M+H]+=531
HPLC (Method 4): retention time=3.0 min Example 502

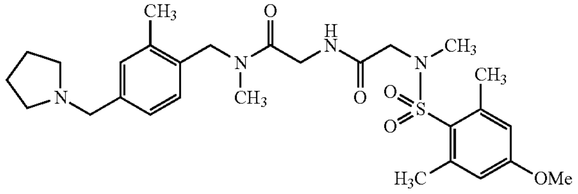 [SMILES: COc1cc(C)c(S(=O)(=O)N(C)CC(=O)NCC(=O)N(C)Cc2ccc(CN3CCCC3)cc2C)c(C)c1]

$C_{28}H_{40}N_4O_5S \times HCl$ (581.17)
[M+H]+=545
TLC: silica gel, dichloromethane/methanol 9:1, Rf value=0.18

Example 503

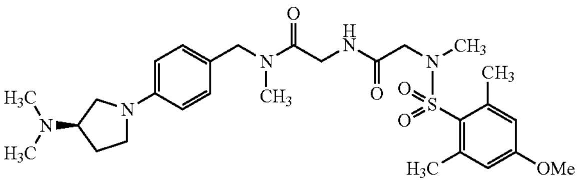 [SMILES: COc1cc(C)c(S(=O)(=O)N(C)CC(=O)NCC(=O)N(C)Cc2ccc(N3CC[C@@H](N(C)C)C3)cc2)c(C)c1]

$C_{28}H_{41}N_5O_5S \times HCl$ (596.18)
[M+H]+=560

TLC: silica gel, ethyl acetate/methanol/ammonia 9:1:0.1, Rf value=0.42
Example 504
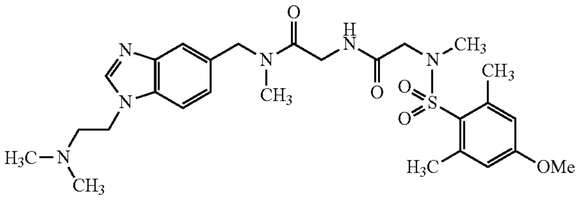
$C_{27}H_{38}N_8O_5S$ (558.69)
[M+H]+=559
HPLC (Method 6): retention time=2.23 min
Example 505
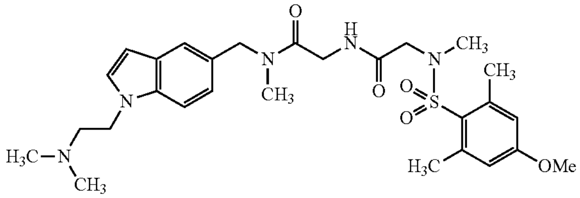 [SMILES: COc1cc(C)c(S(=O)(=O)N(C)CC(=O)NCC(=O)N(C)Cc2ccc3c(ccn3CCN(C)C)c2)c(C)c1]
$C_{28}H_{39}N_5O_5S$ (557.71)
[M+H]+=558
HPLC (Method 6): retention time=2.35 min
Example 506
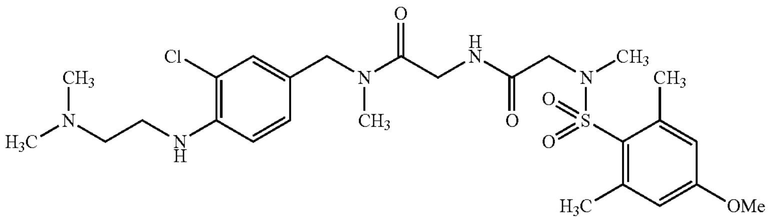 [SMILES: COc1cc(C)c(S(=O)(=O)N(C)CC(=O)NCC(=O)N(C)Cc2ccc(NCCN(C)C)c(Cl)c2)c(C)c1]
$C_{26}H_{38}ClN_5O_5S \times CH_2O_2$ (614.16)
[M+H]+=568/570
HPLC (Method 6): retention time=2.55 min
Example 507
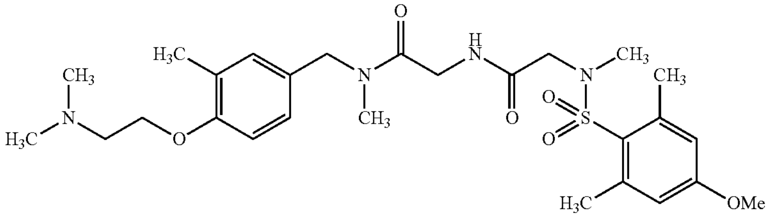 [SMILES: COc1cc(C)c(S(=O)(=O)N(C)CC(=O)NCC(=O)N(C)Cc2ccc(OCCN(C)C)c(C)c2)c(C)c1]
$C_{27}H_{40}N_4O_6S$ (548.70)
[M+H]+=549
HPLC (Method 6): retention time=2.49 min
Example 508
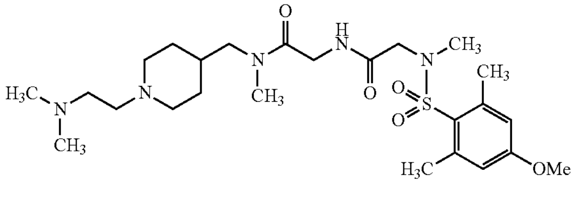 [SMILES: COc1cc(C)c(S(=O)(=O)N(C)CC(=O)NCC(=O)N(C)CC2CCN(CCN(C)C)CC2)c(C)c1]
$C_{25}H_{43}N_5O_5S$ (525.71)
[M+H]+=526
HPLC (Method 6): retention time=1.85 min Example 509
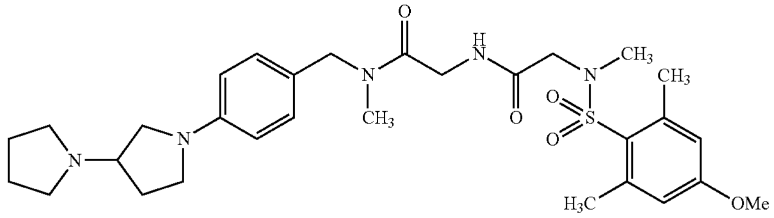 [SMILES: COc1cc(C)c(S(=O)(=O)N(C)CC(=O)NCC(=O)N(C)Cc2ccc(N3CCC(N4CCCC4)C3)cc2)c(C)c1]
$C_{30}H_{43}N_5O_5S$ (585.76)
[M+H]+=586
HPLC (Method 6): retention time=2.66 min
Example 510
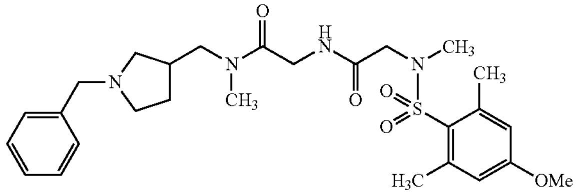 [SMILES: COc1cc(C)c(S(=O)(=O)N(C)CC(=O)NCC(=O)N(C)CC2CCN(Cc3ccccc3)C2)c(C)c1]
$C_{27}H_{38}N_4O_5S$ (530.68)
[M+H]+=531
HPLC (Method 6): retention time=2.52 min
Example 511
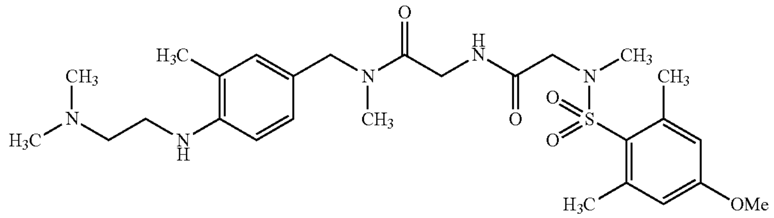 [SMILES: COc1cc(C)c(S(=O)(=O)N(C)CC(=O)NCC(=O)N(C)Cc2ccc(NCCN(C)C)c(C)c2)c(C)c1]
$C_{27}H_{41}N_5O_5S$ (547.71)
[M+H]+=548
HPLC (Method 6): retention time=2.44 min
Example 512
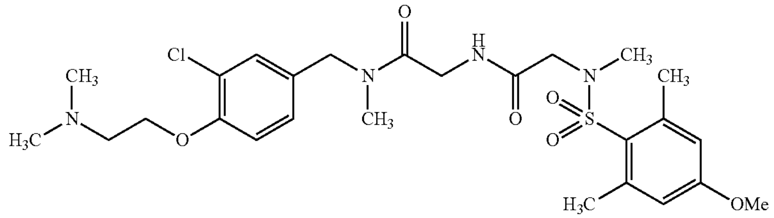 [SMILES: COc1cc(C)c(S(=O)(=O)N(C)CC(=O)NCC(=O)N(C)Cc2ccc(OCCN(C)C)c(Cl)c2)c(C)c1]
$C_{26}H_{37}ClN_4O_6S$ (569.11)
[M+H]+=570
HPLC (Method 6): retention time=2.56 min Example 513
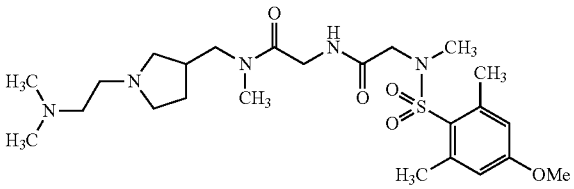 [SMILES: COc1cc(C)c(S(=O)(=O)N(C)CC(=O)NCC(=O)N(C)CC2CCN(CCN(C)C)C2)c(C)c1]
$C_{24}H_{41}N_5O_5S$ (511.68)
[M+H]+=512
HPLC (Method 6): retention time=1.80 min
Example 514
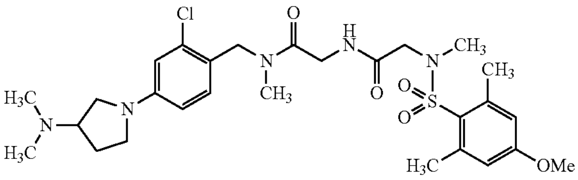 [SMILES: COc1cc(C)c(S(=O)(=O)N(C)CC(=O)NCC(=O)N(C)Cc2ccc(N3CCC(N(C)C)C3)cc2Cl)c(C)c1]
$C_{28}H_{40}ClN_5O_5S$ (594.17)
[M+H]+=594/596
HPLC (Method 6): retention time=2.68 min
Example 515
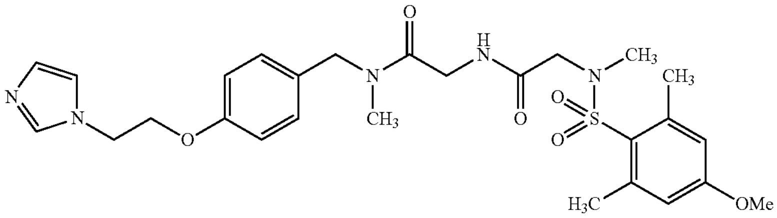 [SMILES: COc1cc(C)c(S(=O)(=O)N(C)CC(=O)NCC(=O)N(C)Cc2ccc(OCCn3ccnc3)cc2)c(C)c1]
$C_{27}H_{35}N_5O_6S$ (557.66)
[M+H]+=558
HPLC (Method 6): retention time=2.51 min
Example 516
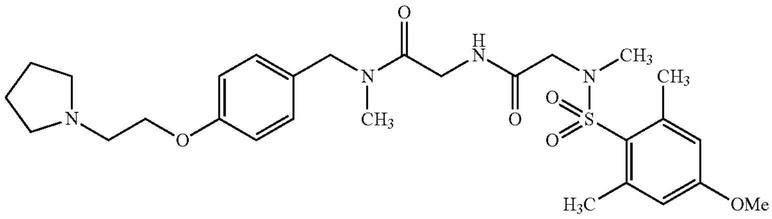 [SMILES: COc1cc(C)c(S(=O)(=O)N(C)CC(=O)NCC(=O)N(C)Cc2ccc(OCCN3CCCC3)cc2)c(C)c1]
$C_{28}H_{40}N_4O_6S$ (560.71)
[M+H]+=561
HPLC (Method 6): retention time=2.51 min
Example 517
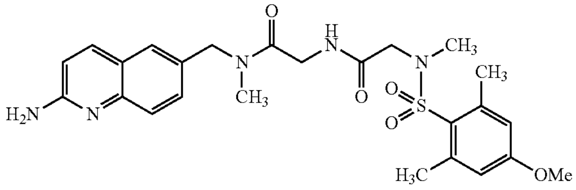 [SMILES: COc1cc(C)c(S(=O)(=O)N(C)CC(=O)NCC(=O)N(C)Cc2ccc3nc(N)ccc3c2)c(C)c1]
$C_{25}H_{31}N_5O_5S$ (513.61)
[M+H]+=514
HPLC (Method 6): retention time=2.35 min Example 518

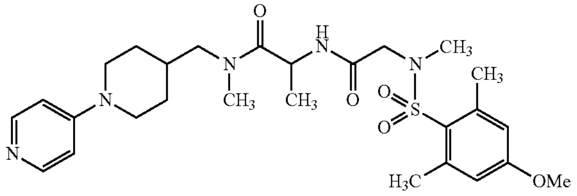 [SMILES: COc1cc(C)c(S(=O)(=O)N(C)CC(=O)NC(C)C(=O)N(C)CC2CCN(c3ccncc3)CC2)c(C)c1]

$C_{27}H_{39}N_5O_5S \times C_2HF_3O_2$ (659.72)
[M+H]+=546
HPLC (Method 6): retention time=2.44 min Example 519

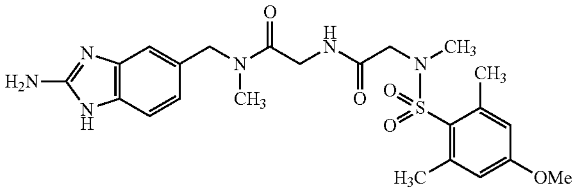 [SMILES: COc1cc(C)c(S(=O)(=O)N(C)CC(=O)NCC(=O)N(C)Cc2ccc3[nH]c(N)nc3c2)c(C)c1]

$C_{23}H_{30}N_6O_5S$ (502.59)
[M+H]+=503
HPLC (Method 6): retention time=2.37 min Example 520

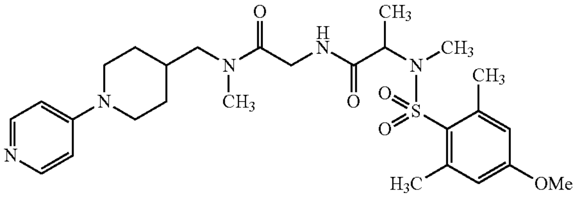 [SMILES: COc1cc(C)c(S(=O)(=O)N(C)C(C)C(=O)NCC(=O)N(C)CC2CCN(c3ccncc3)CC2)c(C)c1]

$C_{27}H_{39}N_5O_5S \times C_2HF_3O_2$ (659.72)
[M+H]+=546
HPLC (Method 6): retention time=2.52 min Example 521

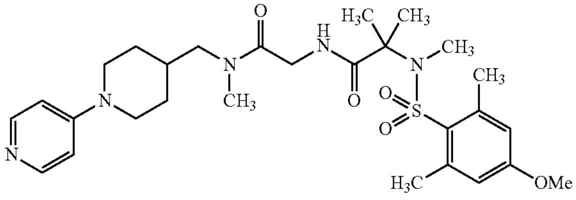 [SMILES: COc1cc(C)c(S(=O)(=O)N(C)C(C)(C)C(=O)NCC(=O)N(C)CC2CCN(c3ccncc3)CC2)c(C)c1]

$C_{28}H_{41}N_5O_5S \times C_2HF_3O_2$ (673.75)
[M+H]+=560
HPLC (Method 6): retention time=2.58 min Example 522

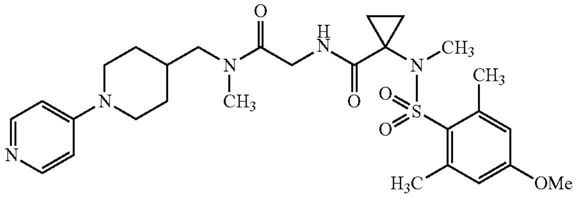 [SMILES: COc1cc(C)c(S(=O)(=O)N(C)C2(C(=O)NCC(=O)N(C)CC3CCN(c4ccncc4)CC3)CC2)c(C)c1]

$C_{28}H_{39}N_5O_5S \times C_2HF_3O_2$ (671.73)
[M+H]+=558
HPLC (Method 6): retention time=2.57 min Example 523

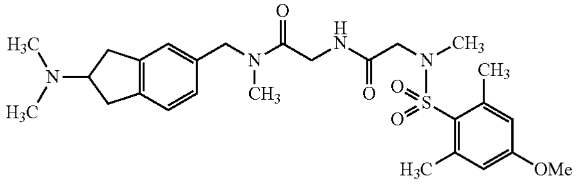 [SMILES: COc1cc(C)c(S(=O)(=O)N(C)CC(=O)NCC(=O)N(C)Cc2ccc3c(c2)CC(N(C)C)C3)c(C)c1]

$C_{27}H_{38}N_4O_5S \times C_2HF_3O_2$ (644.70)
[M+H]+=531
HPLC (Method 6): retention time=2.45 min Example 524

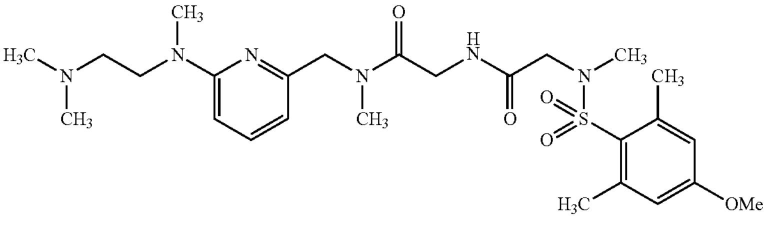 [SMILES: COc1cc(C)c(S(=O)(=O)N(C)CC(=O)NCC(=O)N(C)Cc2cccc(N(C)CCN(C)C)n2)c(C)c1]

$C_{26}H_{40}N_6O_5S$ (548.70)

[M+H]+=549

HPLC (Method 6): retention time=2.52 min

Example 525
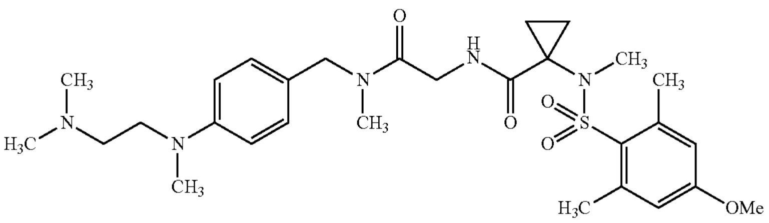 [SMILES: COc1cc(C)c(S(=O)(=O)N(C)C2(C(=O)NCC(=O)N(C)Cc3ccc(N(C)CCN(C)C)cc3)CC2)c(C)c1]
$C_{29}H_{43}N_5O_5S \times C_2HF_3O_2$ (687.77)
[M+H]+=574
HPLC (Method 6): retention time=2.72 min
Example 526
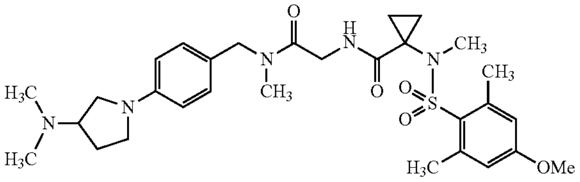 [SMILES: COc1cc(C)c(S(=O)(=O)N(C)C2(C(=O)NCC(=O)N(C)Cc3ccc(N4CCC(N(C)C)C4)cc3)CC2)c(C)c1]
$C_{30}H_{43}N_5O_5S$ (585.76)
[M+H]+=586
HPLC (Method 6): retention time=2.70 min
Example 527
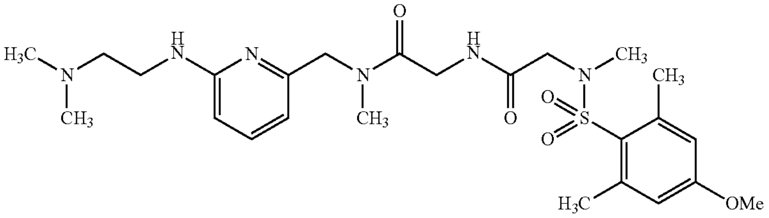 [SMILES: COc1cc(C)c(S(=O)(=O)N(C)CC(=O)NCC(=O)N(C)Cc2cccc(NCCN(C)C)n2)c(C)c1]
$C_{25}H_{38}N_6O_5S \times CH_2O_2$ (580.70)
[M+H]+=535
HPLC (Method 6): retention time=2.16 min
Example 528
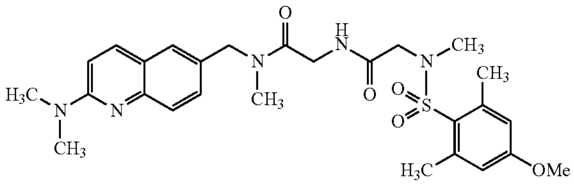 [SMILES: COc1cc(C)c(S(=O)(=O)N(C)CC(=O)NCC(=O)N(C)Cc2ccc3nc(N(C)C)ccc3c2)c(C)c1]
$C_{27}H_{35}N_5O_5S \times C_2HF_3O_2$ (655.69)
[M+H]+=542
HPLC (Method 6): retention time=2.48 min Example 529
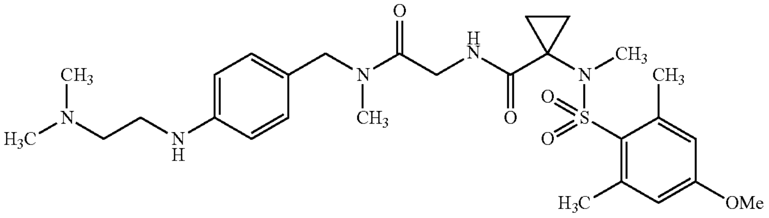 [SMILES: COc1cc(C)c(S(=O)(=O)N(C)C2(C(=O)NCC(=O)N(C)Cc3ccc(NCCN(C)C)cc3)CC2)c(C)c1]
$C_{28}H_{41}N_5O_5S \times C_2HF_3O_2$ (673.75)
[M+H]+=560
HPLC (Method 6): retention time=2.61 min
Example 530
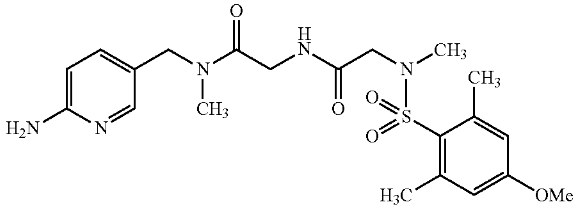 [SMILES: COc1cc(C)c(S(=O)(=O)N(C)CC(=O)NCC(=O)N(C)Cc2ccc(N)nc2)c(C)c1]
$O_{21}H_{29}N_5O_5S$ (463.55)
[M+H]+=464
HPLC (Method 9): retention time=1.47 min
Example 531
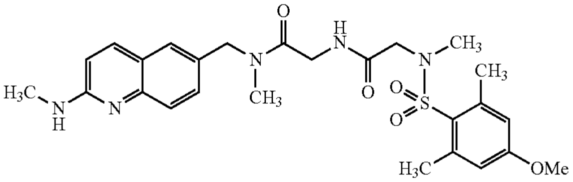 [SMILES: CNc1ccc2cc(CN(C)C(=O)CNC(=O)CN(C)S(=O)(=O)c3c(C)cc(OC)cc3C)ccc2n1]
$C_{26}H_{33}N_5O_5S$ (527.64)
[M+H]+=528
HPLC (Method 9): retention time=1.60 min
Example 532
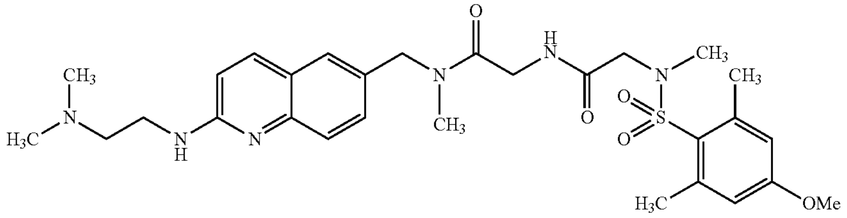 [SMILES: COc1cc(C)c(S(=O)(=O)N(C)CC(=O)NCC(=O)N(C)Cc2ccc3nc(NCCN(C)C)ccc3c2)c(C)c1]
$C_{29}H_{40}N_6O_5S$ (584.73)
[M+H]+=585
HPLC (Method 9): retention time=1.37 min
Example 533
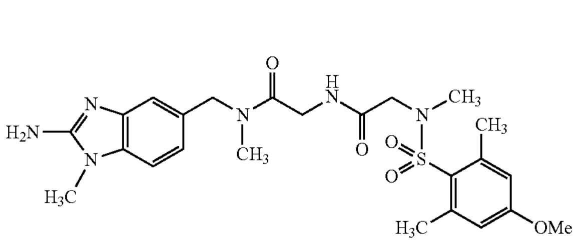 [SMILES: COc1cc(C)c(S(=O)(=O)N(C)CC(=O)NCC(=O)N(C)Cc2ccc3c(c2)nc(N)n3C)c(C)c1]
$C_{24}H_{32}N_6O_5S \times C_2HF_3O_2$ (630.64)
[M+H]+=517
HPLC (Method 9): retention time=1.58 min Example 534
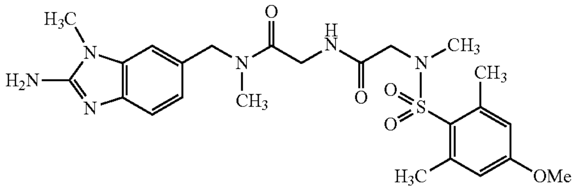 [SMILES: COc1cc(C)c(S(=O)(=O)N(C)CC(=O)NCC(=O)N(C)Cc2ccc3nc(N)n(C)c3c2)c(C)c1]
$C_{24}H_{32}N_6O_5S \times C_2HF_3O_2$ (630.64)
[M+H]+=517
HPLC (Method 9): retention time=1.57 min
Example 535
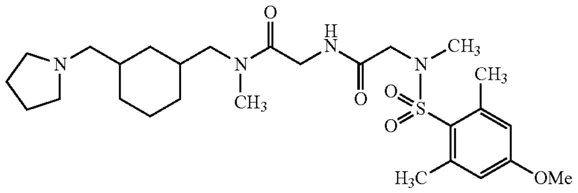 [SMILES: COc1cc(C)c(S(=O)(=O)N(C)CC(=O)NCC(=O)N(C)CC2CCCC(CN3CCCC3)C2)c(C)c1]
$C_{27}H_{44}N_4O_5S \times C_2HF_3O_2$ (650.75)
[M+H]+=537
HPLC (Method 9): retention time=1.68 min
Example 536
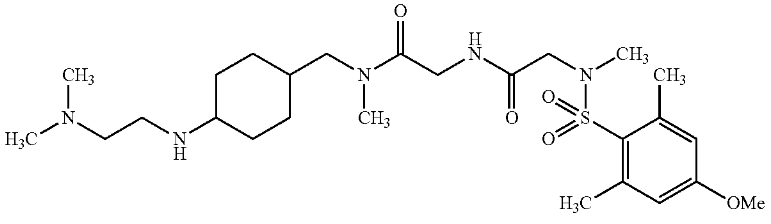 [SMILES: COc1cc(C)c(S(=O)(=O)N(C)CC(=O)NCC(=O)N(C)CC2CCC(NCCN(C)C)CC2)c(C)c1]
$C_{26}H_{45}N_5O_5S \times 2HCl$ (612.65)
[M+H]+=540
HPLC (Method 5): retention time=1.39 min
Example 537
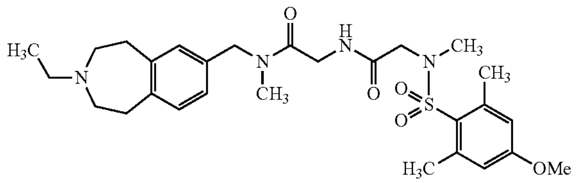 [SMILES: CCN1CCc2ccc(CN(C)C(=O)CNC(=O)CN(C)S(=O)(=O)c3c(C)cc(OC)cc3C)cc2CC1]
$C_{28}H_{40}N_4O_5S \times C_2HF_3O_2$ (658.73)
[M+H]+=545
HPLC (Method 5): retention time=1.53 min
Example 538
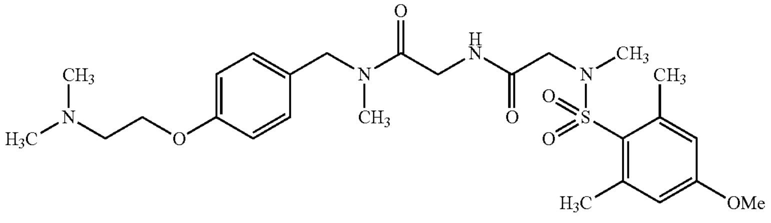 [SMILES: COc1cc(C)c(S(=O)(=O)N(C)CC(=O)NCC(=O)N(C)Cc2ccc(OCCN(C)C)cc2)c(C)c1]
$C_{26}H_{38}N_4O_6S \times C_2HF_3O_2$ (648.69)
[M+H]+=535
HPLC (Method 5): retention time=1.43 min Example 539
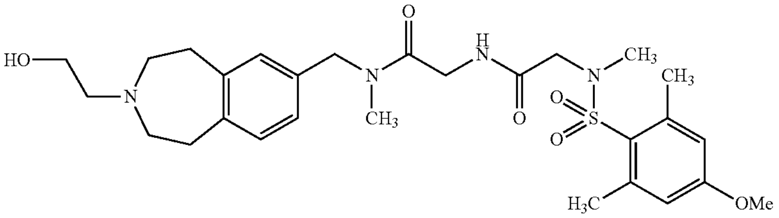 [SMILES: COc1cc(C)c(S(=O)(=O)N(C)CC(=O)NCC(=O)N(C)Cc2ccc3c(c2)CCN(CCO)CC3)c(C)c1]
$C_{28}H_{40}N_4O_6S$ (560.71)
[M+H]+=561
HPLC (Method 5): retention time=1.50 min
Example 540
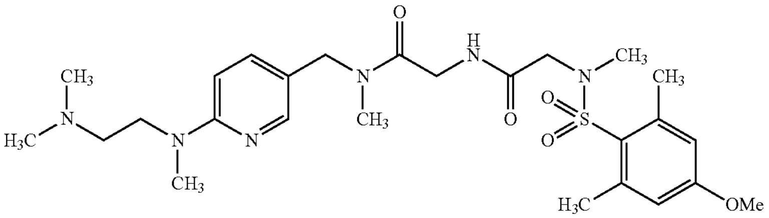 [SMILES: COc1cc(C)c(S(=O)(=O)N(C)CC(=O)NCC(=O)N(C)Cc2ccc(N(C)CCN(C)C)nc2)c(C)c1]
$C_{26}H_{40}N_6O_5S$ (548.70)
[M+H]+=549
HPLC (Method 5): retention time=1.39 min
Example 541
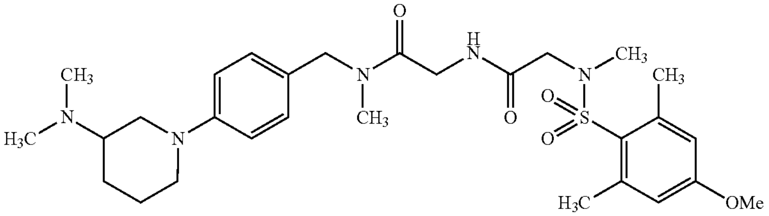 [SMILES: COc1cc(C)c(S(=O)(=O)N(C)CC(=O)NCC(=O)N(C)Cc2ccc(N3CCCC(N(C)C)C3)cc2)c(C)c1]
$C_{29}H_{43}N_5O_5S \times HCl$ (610.21)
[M+H]+=574
HPLC (Method 7): retention time=1.88 min
Example 542
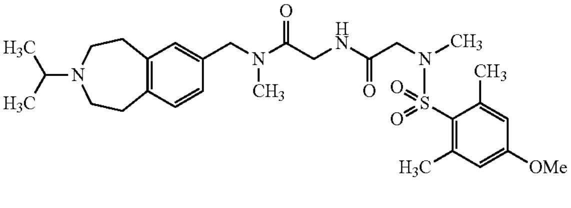
$C_{29}H_{42}N_4O_5S \times C_2HF_3O_2$ (672.76)
[M+H]+=559
HPLC (Method 5): retention time=1.55 min Example 543

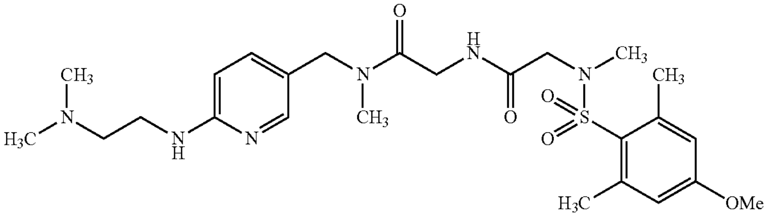 [SMILES: COc1cc(C)c(S(=O)(=O)N(C)CC(=O)NCC(=O)N(C)Cc2ccc(NCCN(C)C)nc2)c(C)c1]

$C_{25}H_{38}N_6O_5S \times 2HCl$ (607.59)
[M+H]+=535
HPLC (Method 5): retention time=1.39 min Example 544

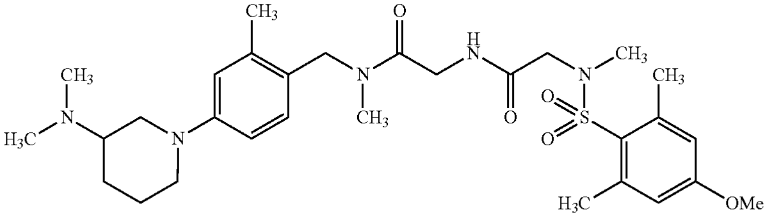 [SMILES: COc1cc(C)c(S(=O)(=O)N(C)CC(=O)NCC(=O)N(C)Cc2ccc(N3CCCC(N(C)C)C3)cc2C)c(C)c1]

$C_{30}H_{45}N_5O_5S \times C_2HF_3O_2$ (701.80)
[M+H]+=588
HPLC (Method 5): retention time=1.55 min Example 545

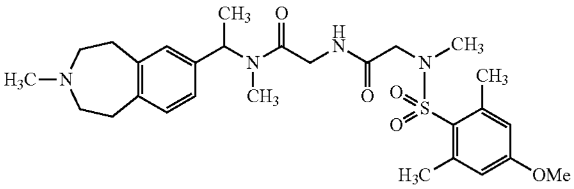 [SMILES: COc1cc(C)c(S(=O)(=O)N(C)CC(=O)NCC(=O)N(C)C(C)c2ccc3c(c2)CCN(C)CC3)c(C)c1]

$C_{28}H_{40}N_4O_5S \times HCl$ (581.17)
[M+H]+=545
HPLC (Method 4): retention time=3.3 min Example 546

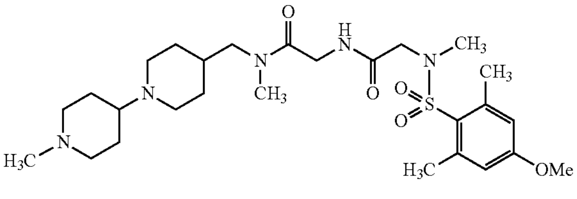 [SMILES: COc1cc(C)c(S(=O)(=O)N(C)CC(=O)NCC(=O)N(C)CC2CCN(C3CCN(C)CC3)CC2)c(C)c1]

$C_{27}H_{45}N_5O_5S \times 2HCl$ (624.66)
[M+H]+=552

TLC: silica gel, dichloromethane/methanol/ammonia 8:2: 0.01, Rf value=0.25

Example 547

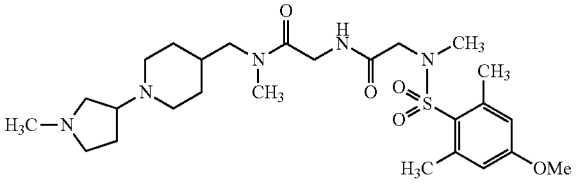 [SMILES: COc1cc(C)c(S(=O)(=O)N(C)CC(=O)NCC(=O)N(C)CC2CCN(C3CCN(C)C3)CC2)c(C)c1]

$C_{26}H_{43}N_5O_5S \times HCl$ (574.18)
[M+H]+=538
TLC: silica gel, dichloromethane/methanol/ammonia 8:2: 0.01, Rf value=0.10

Example 548

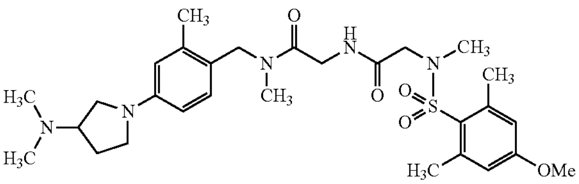 [SMILES: COc1cc(C)c(S(=O)(=O)N(C)CC(=O)NCC(=O)N(C)Cc2ccc(N3CCC(N(C)C)C3)cc2C)c(C)c1]

$C_{29}H_{43}N_5O_5S \times HCl$ (610.21)
[M+H]+=574

TLC: silica gel, dichloromethane/methanol 9:1, Rf value=0.25
Example 549
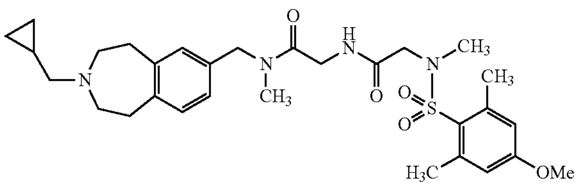 [SMILES: COc1cc(C)c(S(=O)(=O)N(C)CC(=O)NCC(=O)N(C)Cc2ccc3c(c2)CCN(CC2CC2)CC3)c(C)c1]
$O_{31}H_{44}N_4O_5S$×HCl (621.23)
[M+H]+=585
HPLC (Method 12): retention time=3.0 min
Example 550
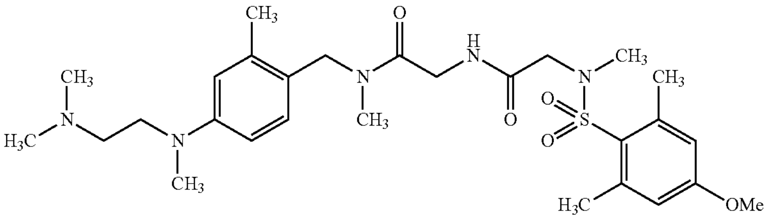 [SMILES: COc1cc(C)c(S(=O)(=O)N(C)CC(=O)NCC(=O)N(C)Cc2ccc(N(C)CCN(C)C)cc2C)c(C)c1]
$C_{28}H_{43}N_5O_5S$×HCl (598.20)
[M+H]+=562
TLC: silica gel, dichloromethane/methanol 9:1, Rf value=0.14
Example 551
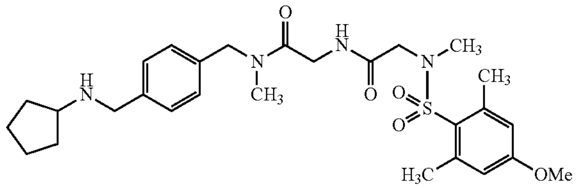 [SMILES: COc1cc(C)c(S(=O)(=O)N(C)CC(=O)NCC(=O)N(C)Cc2ccc(CNC3CCCC3)cc2)c(C)c1]
$C_{29}H_{42}N_4O_5S$×HCl (595.19)
[M+H]+=559
TLC: silica gel, dichloromethane/methanol/ammonia 9:1:0.1, Rf value=0.32
Example 552
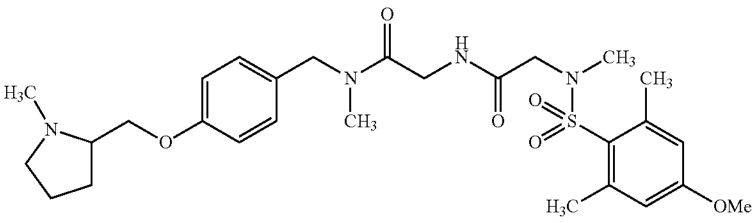 [SMILES: COc1cc(C)c(S(=O)(=O)N(C)CC(=O)NCC(=O)N(C)Cc2ccc(OCC3CCCN3C)cc2)c(C)c1]
$C_{28}H_{40}N_4O_6S$ (560.71)
[M+H]+=561
HPLC (Method 9): retention time=1.66 min Example 553
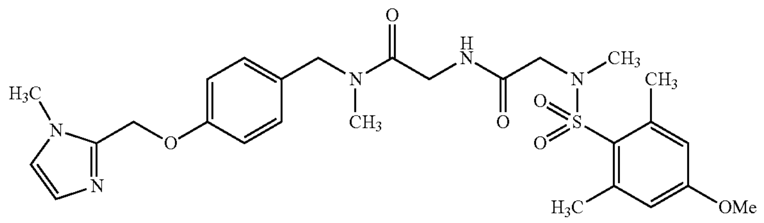 [SMILES: COc1cc(C)c(S(=O)(=O)N(C)CC(=O)NCC(=O)N(C)Cc2ccc(OCc3nccn3C)cc2)c(C)c1]
$C_{27}H_{35}N_5O_6S$ (557.66)
[M+H]+=558
HPLC (Method 9): retention time=1.64 min
Example 554
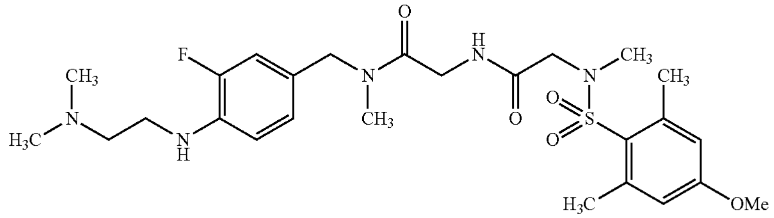
$C_{26}H_{38}FN_5O_5S$ (551.68)
[M+H]+=552
HPLC (Method 6): retention time=2.30 min
Example 555
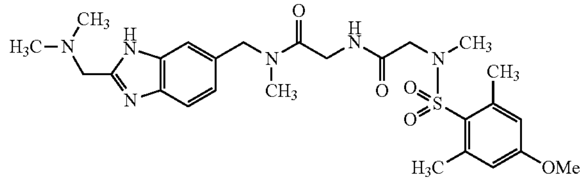 [SMILES: COc1cc(C)c(S(=O)(=O)N(C)CC(=O)NCC(=O)N(C)Cc2ccc3nc(CN(C)C)[nH]c3c2)c(C)c1]
$C_{26}H_{36}N_6O_5S$ (544.67)
[M+H]+=545
HPLC (Method 6): retention time=1.48 min
Example 556
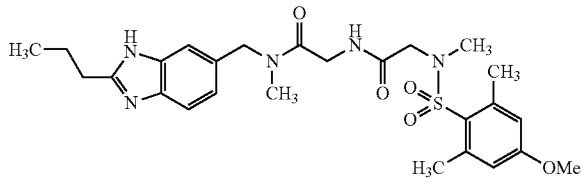 [SMILES: CCCc1nc2ccc(CN(C)C(=O)CNC(=O)CN(C)S(=O)(=O)c3c(C)cc(OC)cc3C)cc2[nH]1]
$C_{26}H_{35}N_5O_5S$ (529.65)
[M+H]+=530
HPLC (Method 9): retention time=1.61 min
Example 557
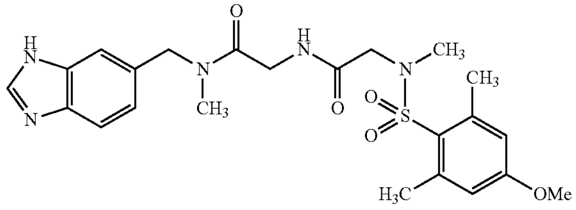 [SMILES: COc1cc(C)c(S(=O)(=O)N(C)CC(=O)NCC(=O)N(C)Cc2ccc3nc[nH]c3c2)c(C)c1]
$C_{23}H_{29}N_5O_5S$ (487.57)
[M+H]+=488
HPLC (Method 9): retention time=1.53 min Example 558

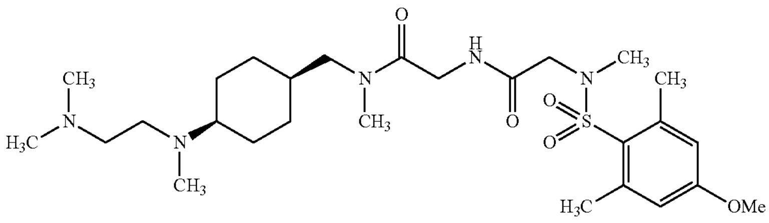 [SMILES: COc1cc(C)c(S(=O)(=O)N(C)CC(=O)NCC(=O)N(C)C[C@H]2CC[C@@H](N(C)CCN(C)C)CC2)c(C)c1]

$_{27}H_{47}N_5O_5S$×2HCl (626.68)
[M+H]+=554
HPLC (Method 7): retention time=1.61 min Example 559

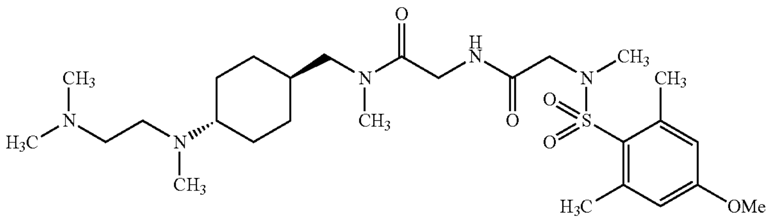 [SMILES: COc1cc(C)c(S(=O)(=O)N(C)CC(=O)NCC(=O)N(C)C[C@H]2CC[C@H](N(C)CCN(C)C)CC2)c(C)c1]

$C_{27}H_{47}N_5O_5S$×2HCl (626.68)
[M+H]+=554
HPLC (Method 7): retention time=1.61 min Example 560

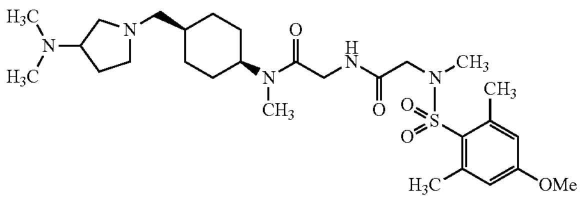 [SMILES: COc1cc(C)c(S(=O)(=O)N(C)CC(=O)NCC(=O)N(C)[C@H]2CC[C@@H](CN3CCC(N(C)C)C3)CC2)c(C)c1]

$C_{28}H_{47}N_5O_5S$×$CH_2O_2$ (611.80)
[M+H]+=566
HPLC (Method 9): retention time=1.33 min Example 561

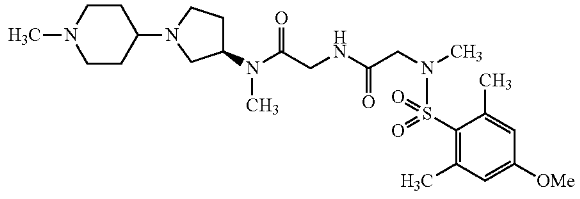 [SMILES: COc1cc(C)c(S(=O)(=O)N(C)CC(=O)NCC(=O)N(C)[C@@H]2CCN(C3CCN(C)CC3)C2)c(C)c1]

$C_{25}H_{41}N_5O_5S$×2HCl (596.61)
[M+H]+=524
HPLC (Method 12): retention time=2.3 min Example 562

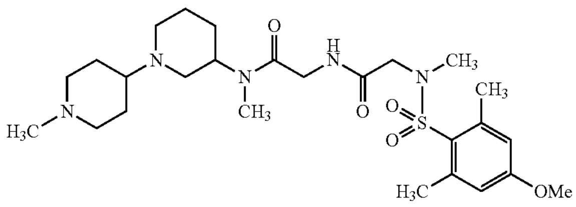 [SMILES: COc1cc(C)c(S(=O)(=O)N(C)CC(=O)NCC(=O)N(C)C2CCCN(C3CCN(C)CC3)C2)c(C)c1]

$C_{26}H_{43}N_5O_5S$×2HCl (610.64)

[M+H]+=538

TLC: silica gel, dichloromethane/methanol/ammonia 8:2:0.2, Rf value=0.53

Example 563

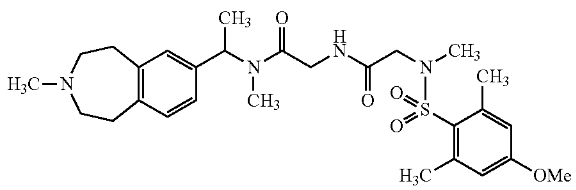 [SMILES: COc1cc(C)c(S(=O)(=O)N(C)CC(=O)NCC(=O)N(C)C(C)c2ccc3c(c2)CCN(C)CC3)c(C)c1]

$C_{29}H_{42}N_4O_5S$×HCl (595.19)

[M+H]+=559

HPLC (Method 12): retention time=2.8 min

Example 564
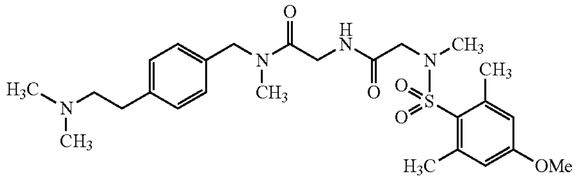 [SMILES: COc1cc(C)c(S(=O)(=O)N(C)CC(=O)NCC(=O)N(C)Cc2ccc(CCN(C)C)cc2)c(C)c1]
$C_{26}H_{38}N_4O_5S \times C_2HF_3O_2$ (632.69)
[M+H]+=519
HPLC (Method 9): retention time=1.61 min
Example 565
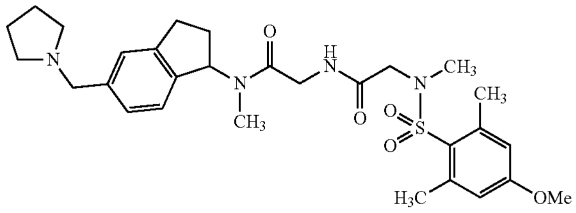 [SMILES: COc1cc(C)c(S(=O)(=O)N(C)CC(=O)NCC(=O)N(C)C2CCc3cc(CN4CCCC4)ccc32)c(C)c1]
$C_{29}H_{40}N_4O_5S$ (556.72)
[M+H]+=557
HPLC (Method 9): retention time=1.69 min
Example 566
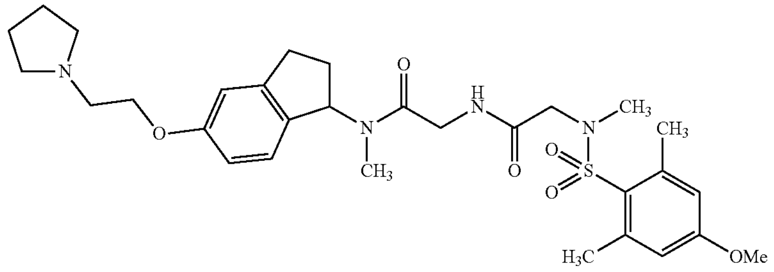 [SMILES: COc1cc(C)c(S(=O)(=O)N(C)CC(=O)NCC(=O)N(C)C2CCc3cc(OCCN4CCCC4)ccc32)c(C)c1]
$C_{30}H_{42}N_4O_6S$ (586.74)
[M+H]+=587
HPLC (Method 9): retention time=1.74 min
Example 60
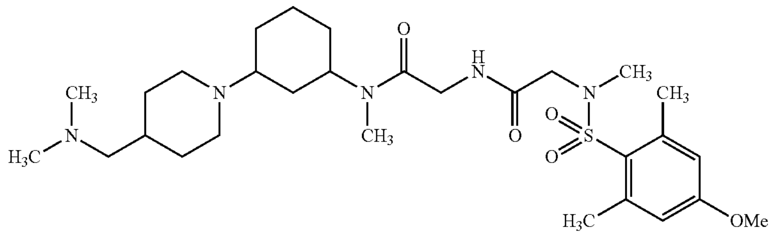 [SMILES: COc1cc(C)c(S(=O)(=O)N(C)CC(=O)NCC(=O)N(C)C2CCCC(N3CCC(CN(C)C)CC3)C2)c(C)c1]
$C_{29}H_{49}N_5O_5S \times 2HCl$ (652.72)
[M+H]+=580
HPLC (Method 10): retention time=1.11 min
Example 604
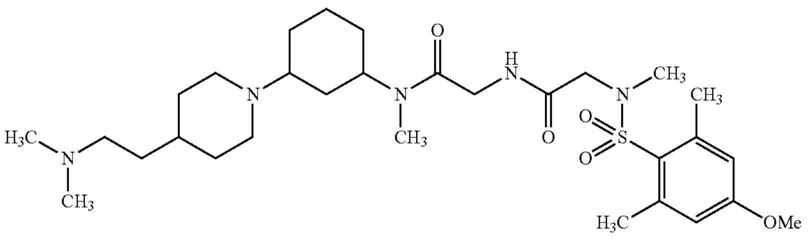 [SMILES: COc1cc(C)c(S(=O)(=O)N(C)CC(=O)NCC(=O)N(C)C2CCCC(N3CCC(CCN(C)C)CC3)C2)c(C)c1]
$C_{30}H_{51}N_5O_5S \times 2HCl$ (666.74)
[M+H]+=594
HPLC (Method 10): retention time=1.11 min Example 605

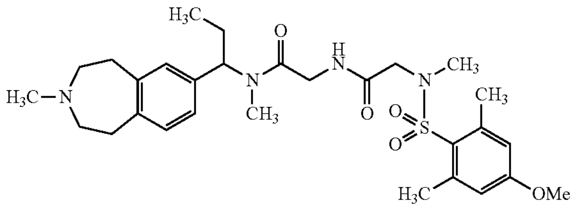 [SMILES: CCC(c1ccc2c(c1)CCN(C)CC2)N(C)C(=O)CNC(=O)CN(C)S(=O)(=O)c1c(C)cc(OC)cc1C]

$C_{29}H_{42}N_4O_5S$×HCl (595.19)
[M+H]+=559
HPLC (Method 12): retention time=3.1 min Example 606

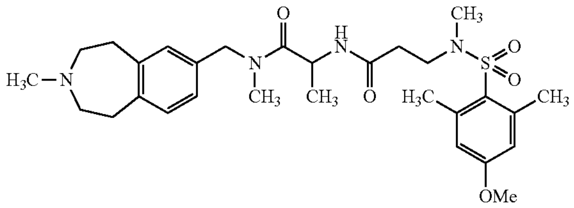

$C_{29}H_{42}N_4O_5S$×HCl (595.19)
[M+H]+=559
TLC: silica gel, dichloromethane/methanol/ammonia 8:2:0.01, Rf value=0.68

Example 631

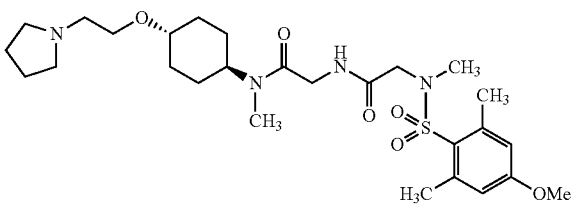 [SMILES: COc1cc(C)c(S(=O)(=O)N(C)CC(=O)NCC(=O)N(C)[C@H]2CC[C@H](OCCN3CCCC3)CC2)c(C)c1]

$C_{27}H_{44}N_4O_6S$×HCl (589.19)
[M+H]+=553
HPLC (Method 5): retention time=1.35 min Example 632

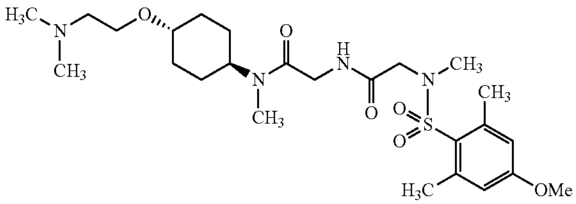 [SMILES: COc1cc(C)c(S(=O)(=O)N(C)CC(=O)NCC(=O)N(C)[C@H]2CC[C@H](OCCN(C)C)CC2)c(C)c1]

$C_{25}H_{42}N_4O_6S$×HCl (563.15)
[M+H]+=527
HPLC (Method 5): retention time=1.38 min Example 633

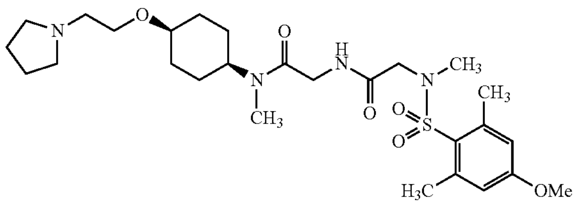 [SMILES: COc1cc(C)c(S(=O)(=O)N(C)CC(=O)NCC(=O)N(C)[C@H]2CC[C@@H](OCCN3CCCC3)CC2)c(C)c1]

$C_{27}H_{44}N_4O_6S$×HCl (589.19)
[M+H]+=553
HPLC (Method 5): retention time=1.35 min Example 634

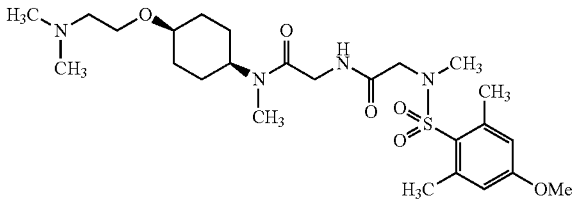 [SMILES: COc1cc(C)c(S(=O)(=O)N(C)CC(=O)NCC(=O)N(C)[C@H]2CC[C@@H](OCCN(C)C)CC2)c(C)c1]

$C_{25}H_{42}N_4O_6S$×HCl (563.15)
[M+H]+=527
HPLC (Method 5): retention time=1.32 min The following compounds were prepared analogously to Example 130:

Example 567

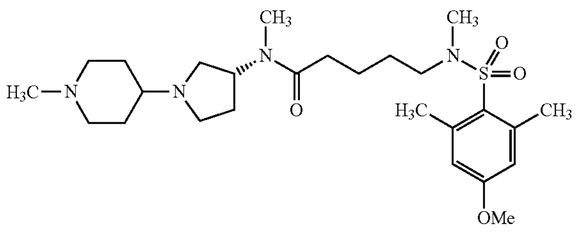

$C_{26}H_{44}N_4O_4S \times 2C_2HF_3O_2$ (736.76)
[M+H]+=509
HPLC (Method 6): retention time=1.36 min Example 568

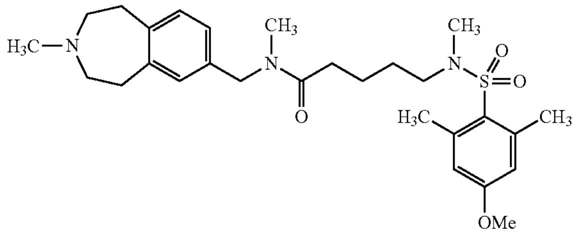

$C_{28}H_{41}N_3O_4S \times C_2HF_3O_2$ (629.73)
[M+H]+=516
HPLC (Method 6): retention time=1.77 min The following compounds were prepared analogously to Example 136:

Example 569

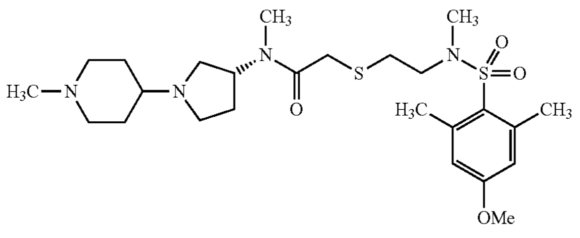

$C_{25}H_{42}N_4O_4S_2 \times C_2HF_3O_2$ (640.78)
[M+H]+=527
HPLC (Method 6): retention time=1.35 min Example 570

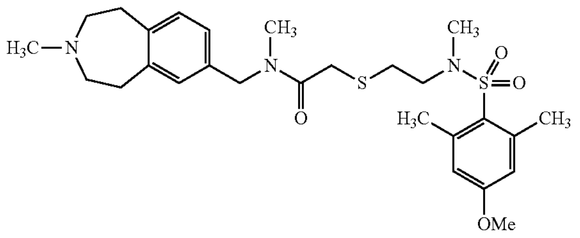

$C_{27}H_{39}N_3O_4S_2$ (533.75)
[M+H]+=534
HPLC (Method 6): retention time=1.74 min The following compound was prepared analogously to Example 138:

Example 571

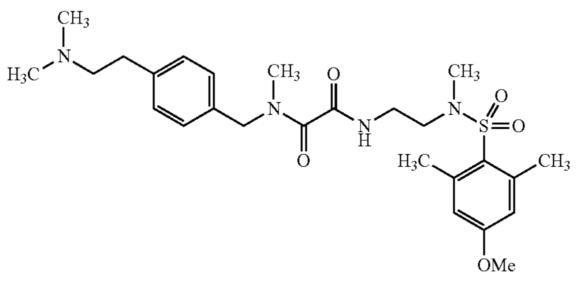

$C_{26}H_{38}N_4O_5S \times CH_2O_2$ (564.70)
[M+H]+=519
HPLC (Method 6): retention time=2.33 min Example 572

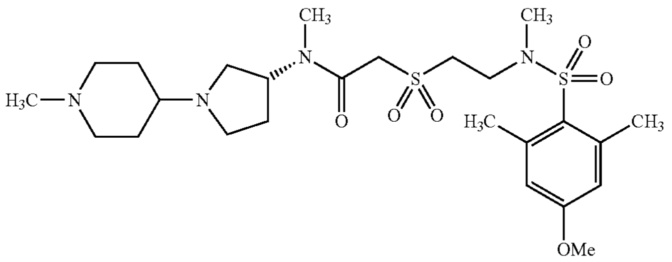

-continued

572a)

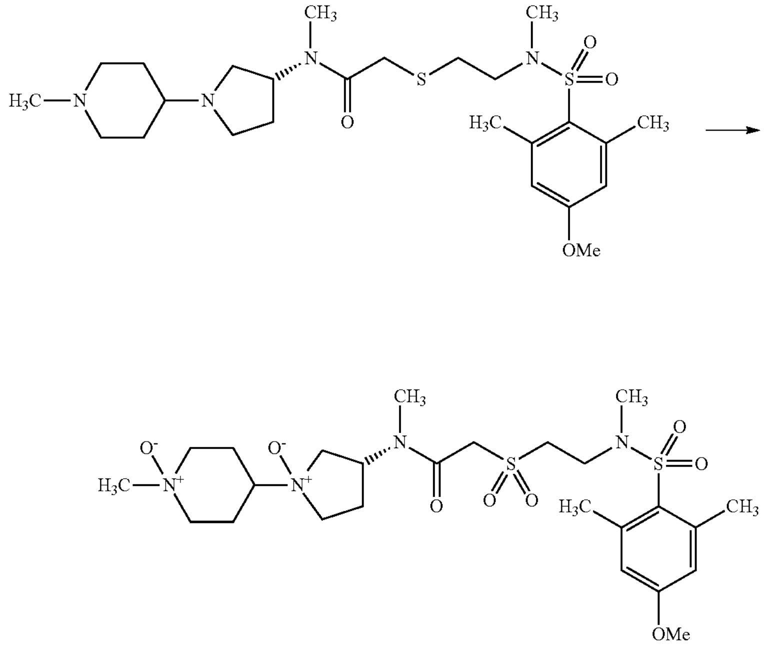

A mixture of 88.0 mg (0.167 mmol) of 569, 0.15 g (0.61 mmol) of 70% m-chloroper-benzoic acid (Fluka) and 3 ml dichloromethane is stirred for 30 minutes at ambient temperature and then evaporated to dryness in vacuo. The residue is dissolved in methanol and membrane-filtered. The product is then obtained by preparative HPLC from the filtrate.

$C_{25}H_{42}N_4O_8S_2$ (590.76)

[M+H]+=591

572b)

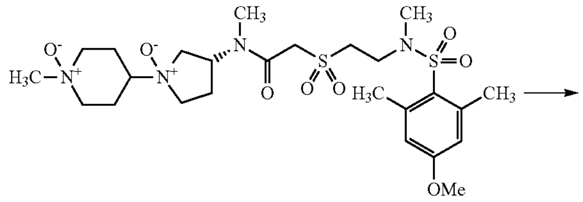

-continued

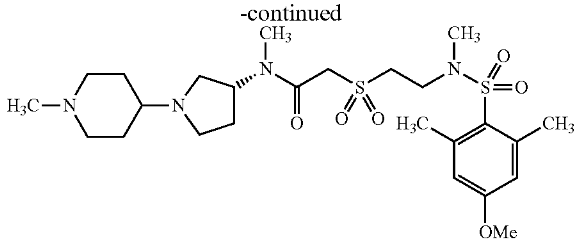

A mixture of 90.0 mg (0.15 mmol) of the product of 572a, 20.0 mg Raney nickel and 10 ml THF is stirred for one hour in the autoclave at ambient temperature. Then the catalyst is filtered off and the filtrate is evaporated to dryness in vacuo. The crude product thus obtained is purified by preparative HPLC.

$C_{25}H_{42}N_4O_6S_2 \times CH_2O_2$ (604.78)

[M+H]+=559

HPLC (Method 6): retention time=1.33 min

Example 573

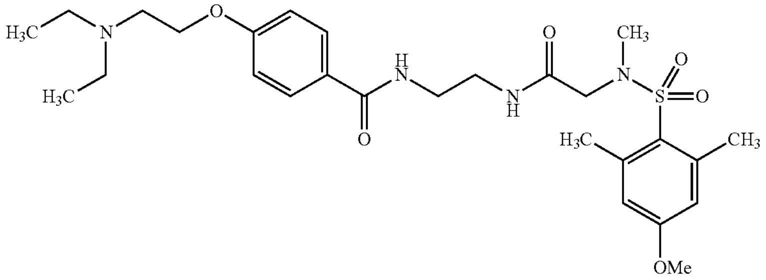

-continued

573a)

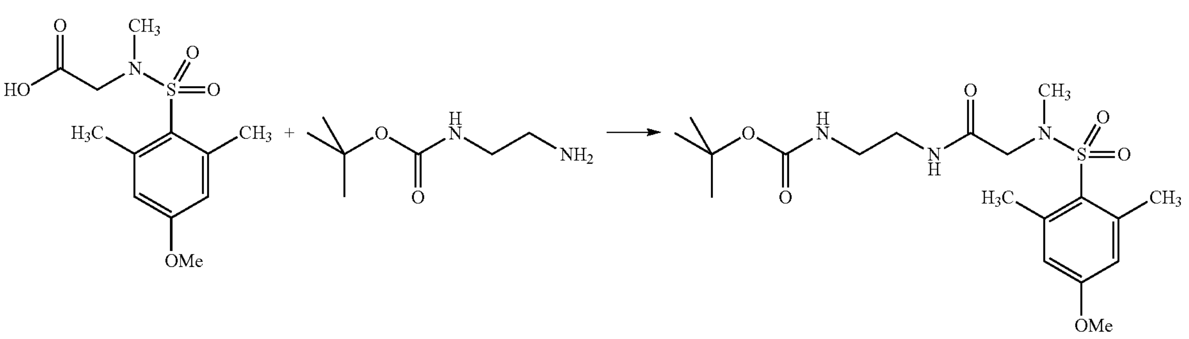

573a is prepared analogously to 1f from 2.16 g (7.50 mmol) of the product of 121b, 1.20 g (7.50 mmol) of N-Boc-ethylenediamine (Fluka), 3.14 ml (22.50 mmol) of triethylamine and 2.41 g (7.50 mmol) of TBTU in 28 ml THF and 4 ml DMF.

$C_{19}H_{31}N_3O_6S$ (429.53)

TLC: silica gel, dichloromethane/ethanol 19:1, Rf value=0.35

-continued

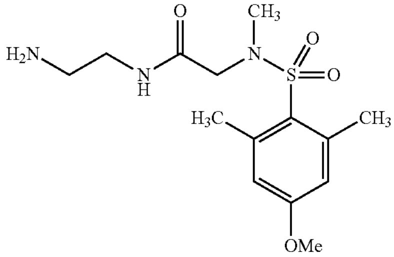

573b)

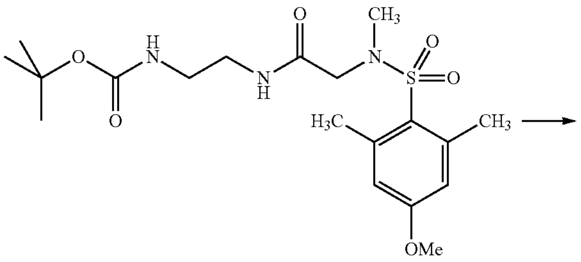

573b is prepared analogously to 28d from 2.70 g (6.29 mmol) of the product of 573a and 7 ml TFA in 50 ml dichloromethane.

$C_{14}H_{23}N_3O_4S$ (329.42)

TLC: silica gel, dichloromethane/ethanol 9:1, Rf value=0.15

573c)

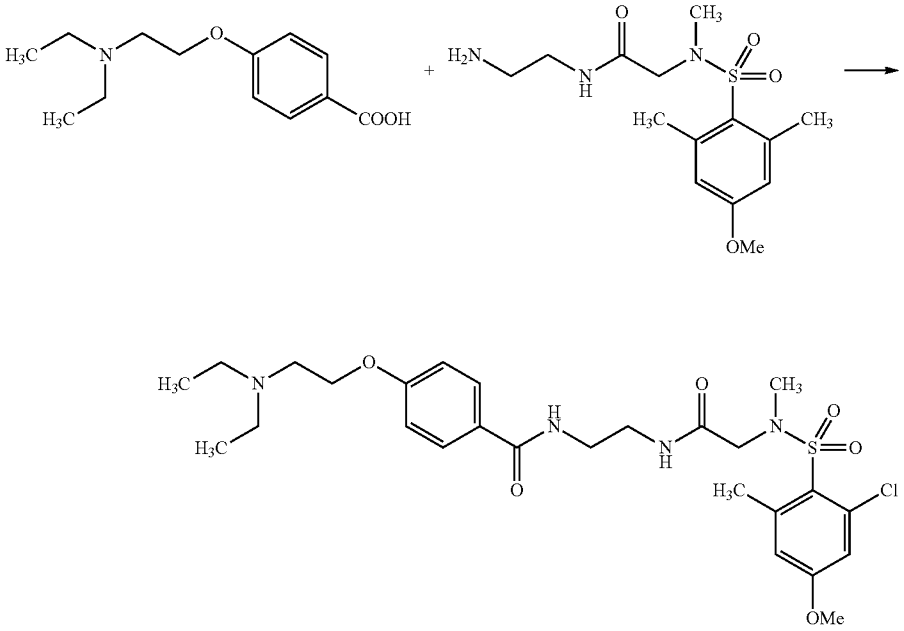

Example 573 is prepared analogously to 1f from 0.119 g (0.50 mmol) of 4-(2-diethylaminoethoxy)-benzoic acid (J. Med. Chem. 14, 1971, 836-842), 0.165 g (0.50 mmol) of the product of 573b, 0.21 ml (1.50 mmol) of triethylamine and 0.16 g (0.50 mmol) of TBTU in 7 ml THF and 1 ml DMF.

$C_{27}H_{40}N_4O_6S \times HCl$ (585.16)

HPLC (Method 5): retention time=1.44 min

The following compounds were prepared analogously to Example 573:

Example 574

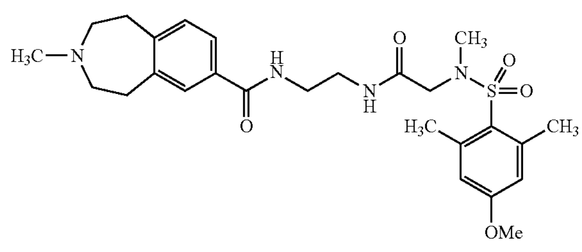

$C_{26}H_{36}N_4O_5S \times HCl$ (553.11)

[M+H]+=517

HPLC (Method 5): retention time=1.40 min

Example 607

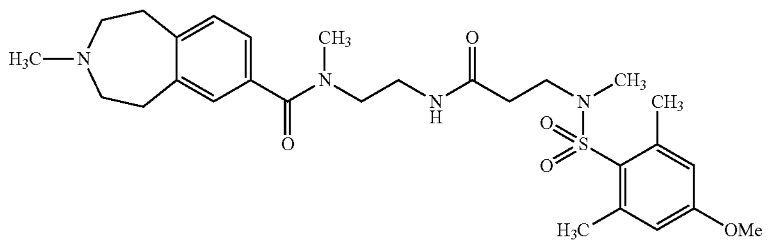 [SMILES: COc1cc(C)c(S(=O)(=O)N(C)CCC(=O)NCCN(C)C(=O)c2ccc3c(c2)CCN(C)CC3)c(C)c1]

$C_{28}H_{40}N_4O_5S \times HCl$ (581.17)

[M+H]+=545

HPLC (Method 12): retention time=3.51 min

Example 635

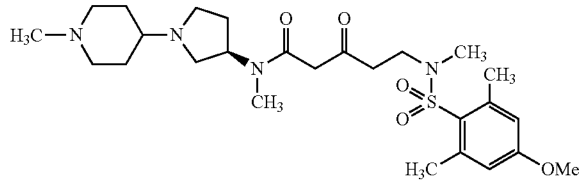

635a)

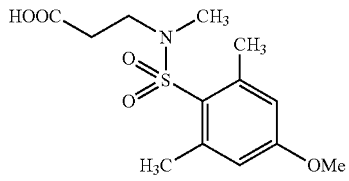

+

-continued

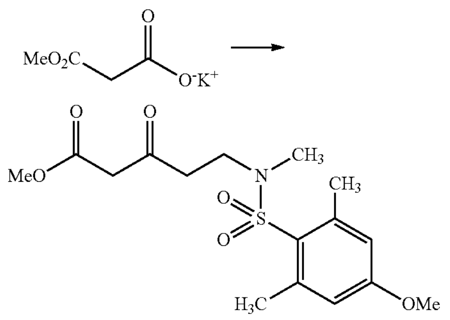

A mixture of 0.78 g (4.98 mmol) of monomethylmalonate potassium salt (Fluka), 0.52 g (5.47 mmol) of magnesium chloride and 30 ml THF is stirred for four hours at 50° C. A second mixture of 1.00 g (3.32 mmol) of the product of 22c, 0.65 g (3.98 mmol) of CU and 20 ml THF is stirred first for one hour at RT and then added to the first mixture. The mixture is stirred overnight at RT and then the precipitate formed is filtered off. The filtrate is evaporated to dryness in vacuo. The crude product thus obtained is triturated with water, filtered off and dried at 45° C. in the vacuum dryer.

$C_{16}H_{23}NO_6S$ (357.42)

[M+H]+=358

HPLC (Method 9): retention time=2.19 min

635b)

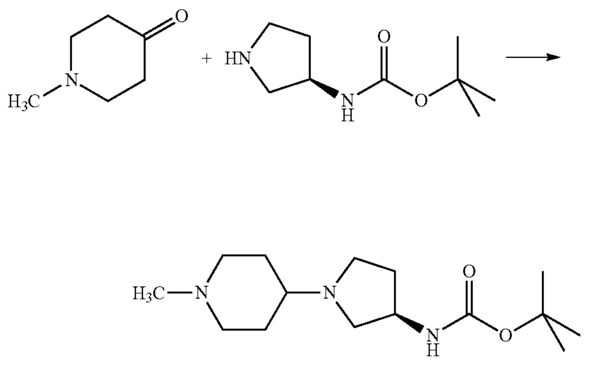

635b is prepared analogously to 60a from 0.47 ml (4.07 mmol) of 1-methyl-4-piperidone (Fluka), 0.76 g. (4.07 mmol) of (R)-3-(Boc-amino)-pyrrolidine (Fluka), 1.72 g (8.13 mmol) of sodium triacetoxyborohydride and 0.23 ml (4.07 mmol) of acetic acid in 10 ml dichloromethane.

$C_{15}H_{29}N_3O_2$ (283.41)

[M+H]+=284

635c)

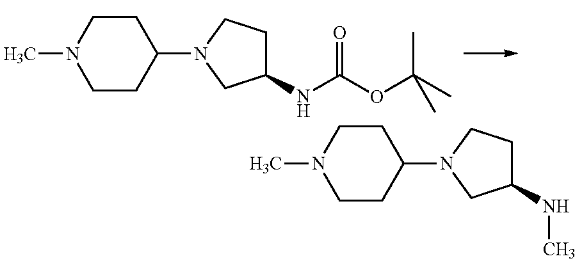

635c is prepared analogously to 38f from 0.90 g (3.18 mmol) of the product of 635b and 5.0 ml (10.00 mmol) of lithium aluminium hydride (2M in THF) in 15 ml THF.

$C_{11}H_{23}N_3$ (197.32)

[M+H]+=198

635d)

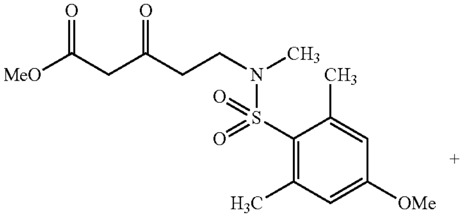

-continued

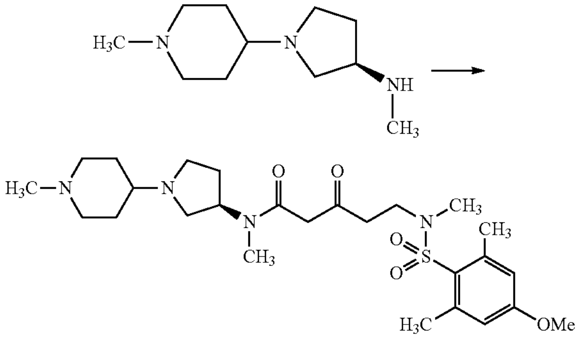

A mixture of 0.56 g (1.58 mmol) of the product of 635a, 0.54 g (2.73 mmol) of the product of 635c and 5 ml of toluene is heated to 120° C. for 24 hours. Then the reaction mixture is evaporated to dryness in vacuo. The crude product thus obtained is purified by preparative HPLC.

$C_{26}H_{42}N_4O_5S$ (522.70)

[M+H]+=523

HPLC (Method 9): retention time=1.33 min

The following were obtained analogously to the Examples described hereinbefore:

Example 651

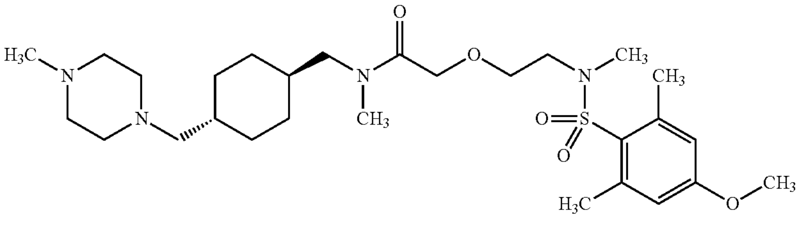

$C_{28}H_{48}N_4O_5S$ (552.78)

[M+H]+=553

HPLC (Method 5): Retention time=1.45 min

Example 652

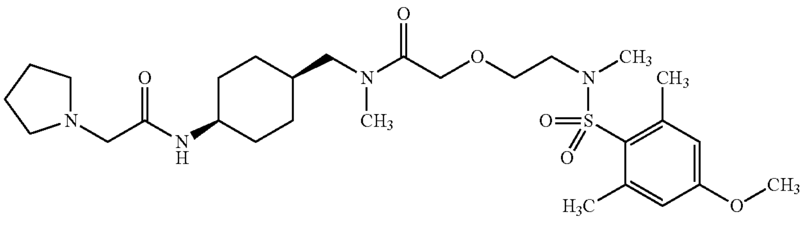 [SMILES: COc1cc(C)c(S(=O)(=O)N(C)CCOCC(=O)N(C)C[C@H]2CC[C@@H](NC(=O)CN3CCCC3)CC2)c(C)c1]

$C_{28}H_{46}N_4O_6S$ (566.76)

[M+H]+=5567

HPLC (Method 5): Retention time=1.65 min

Example 653
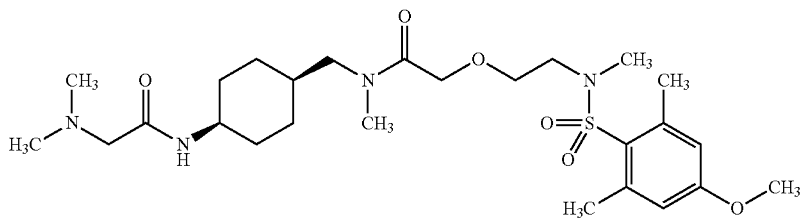
$C_{26}H_{44}N_4O_6S$ (540.72)
[M+H]+=567
HPLC (Method 5): Retention time=1.64 min
Example 654
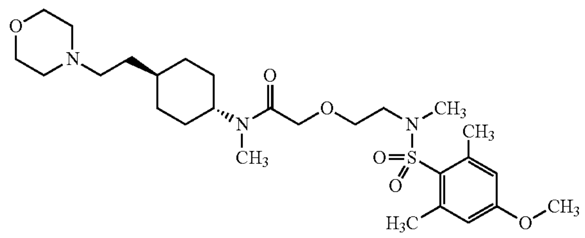 [SMILES: COc1cc(C)c(S(=O)(=O)N(C)CCOCC(=O)N(C)[C@H]2CC[C@H](CCN3CCOCC3)CC2)c(C)c1]
$C_{27}H_{45}N_3O_6S$ (539.73)
[M+H]+=540
HPLC (Method 5): Retention time=1.67 min
Example 655
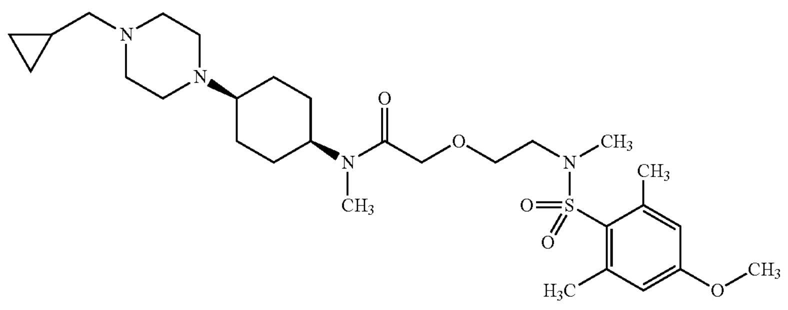 [SMILES: COc1cc(C)c(S(=O)(=O)N(C)CCOCC(=O)N(C)[C@H]2CC[C@@H](N3CCN(CC4CC4)CC3)CC2)c(C)c1]
$C_{29}H_{48}N_4O_5S$ (564.79)
[M+H]+=565
HPLC (Method 5): Retention time=1.47 min
Example 656
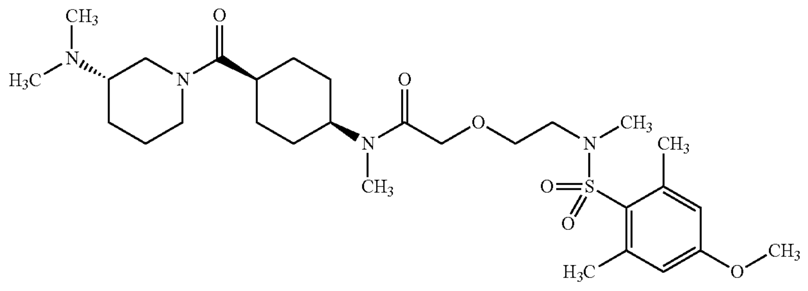

$C_{29}H_{48}N_4O_6S$ (580.79)
[M+H]+=581
HPLC (Method 5): Retention time=1.65 min
Example 657
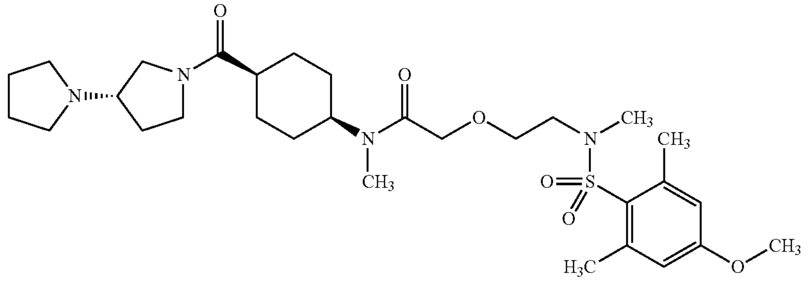 [SMILES: COc1cc(C)c(S(=O)(=O)N(C)CCOCC(=O)N(C)[C@H]2CC[C@@H](C(=O)N3CC[C@H](N4CCCC4)C3)CC2)c(C)c1]
$C_{30}H_{48}N_4O_6S$ (592.80)
[M+H]+=593
HPLC (Method 5): Retention time=1.62 min
Example 658
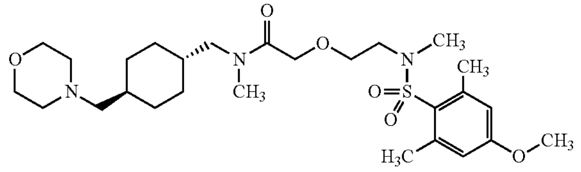 [SMILES: COc1cc(C)c(S(=O)(=O)N(C)CCOCC(=O)N(C)C[C@H]2CC[C@H](CN3CCOCC3)CC2)c(C)c1]
$C_{27}H_{45}N_3O_6S$ (539.73)
[M+H]+=540
HPLC (Method 5): Retention time=1.67 min
Example 659
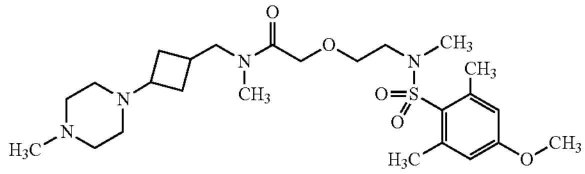
$C_{25}H_{42}N_4O_5S$ (510.70)
[M+H]+=511
HPLC (Method 5): Retention time=1.33 min
Example 660
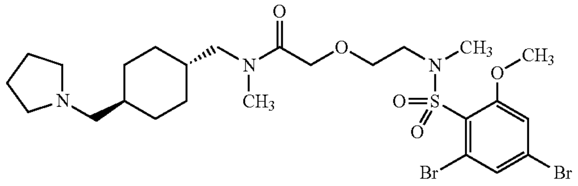 [SMILES: COc1cc(Br)cc(Br)c1S(=O)(=O)N(C)CCOCC(=O)N(C)C[C@H]1CC[C@H](CN2CCCC2)CC1]
$C_{25}H_{39}Br_2N_3O_5S$ (653.47)
[M+H]+=652/54/56
HPLC (Method 5): Retention time=1.82 min
Example 661
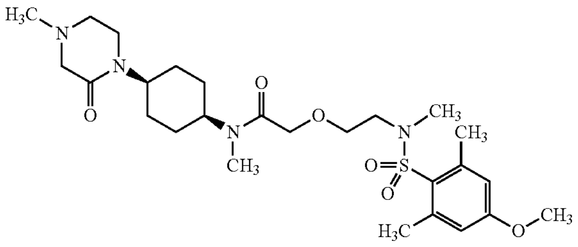
$C_{26}H_{42}N_4O_6S$ (538.71)
[M+H]+=539
HPLC (Method 5): Retention time=1.49 min
Example 662
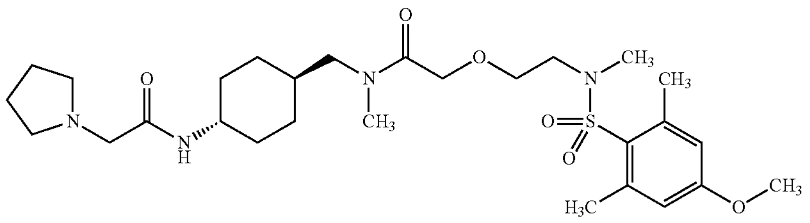 [SMILES: COc1cc(C)c(S(=O)(=O)N(C)CCOCC(=O)N(C)C[C@H]2CC[C@H](NC(=O)CN3CCCC3)CC2)c(C)c1]

$C_{28}H_{46}N_4O_6S$ (566.76)
[M+H]+=567
HPLC (Method 5): Retention time=1.62 min
Example 663
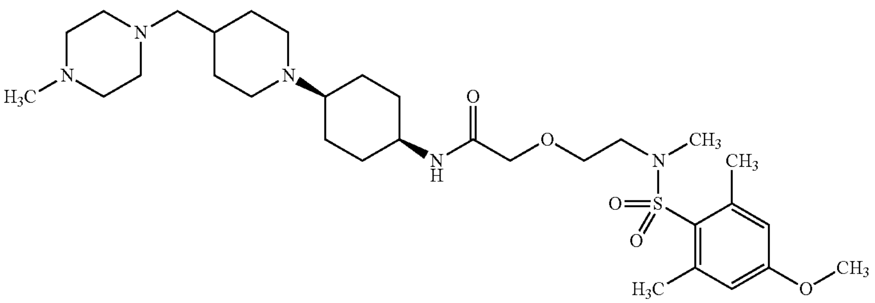
$C_{31}H_{53}N_5O_5S$ (607.86)
[M+H]+=608
HPLC (Method 7): Retention time=1.21 min
Example 664
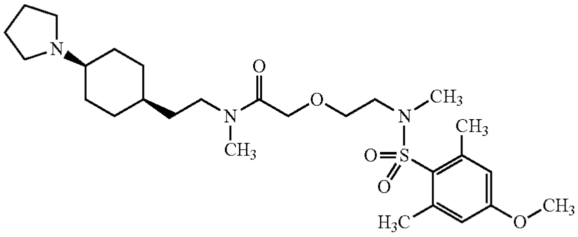 [SMILES: COc1cc(C)c(S(=O)(=O)N(C)CCOCC(=O)N(C)CC[C@H]2CC[C@@H](N3CCCC3)CC2)c(C)c1]
$C_{27}H_{45}N_3O_5S$ (523.73)
[M+H]+=524
HPLC (Method 5): Retention time=1.74 min
Example 665
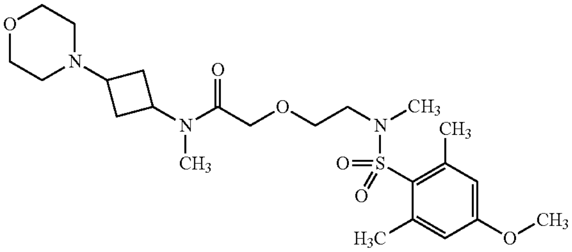 [SMILES: COc1cc(C)c(S(=O)(=O)N(C)CCOCC(=O)N(C)C2CC(N3CCOCC3)C2)c(C)c1]
$C_{23}H_{37}N_3O_6S$ (483.63)
[M+H]+=484
HPLC (Method 5): Retention time=1.46 min
Example 666
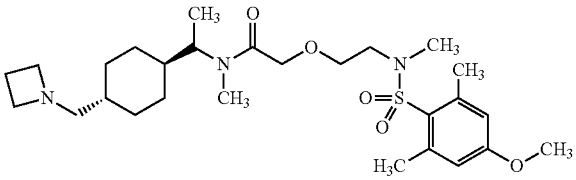 [SMILES: COc1cc(C)c(S(=O)(=O)N(C)CCOCC(=O)N(C)C(C)[C@H]2CC[C@H](CN3CCC3)CC2)c(C)c1]
$C_{27}H_{45}N_3O_5S$ (523.73)
[M+H]+=524
HPLC (Method 12): Retention time=3.09 min
Example 667
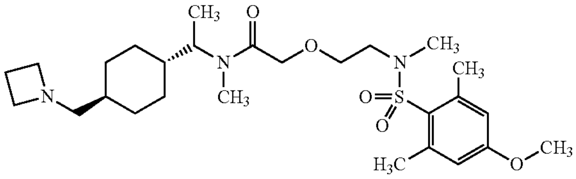 [SMILES: COc1cc(C)c(S(=O)(=O)N(C)CCOCC(=O)N(C)C(C)[C@H]2CC[C@H](CN3CCC3)CC2)c(C)c1]
$C_{27}H_{45}N_3O_5S$ (523.73)
[M+H]+=524
HPLC (Method 12): Retention time=3.04 min Example 668
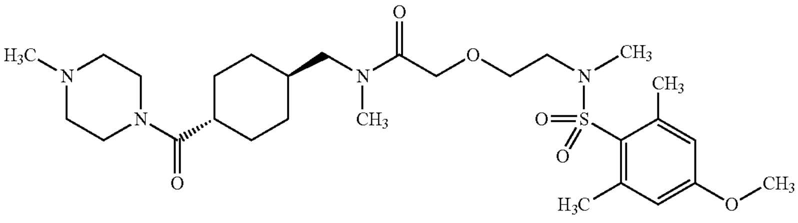
$C_{28}H_{46}N_4O_6S$ (566.76)
[M+H]+=567
HPLC (Method 5): Retention time=1.62 min
Example 669
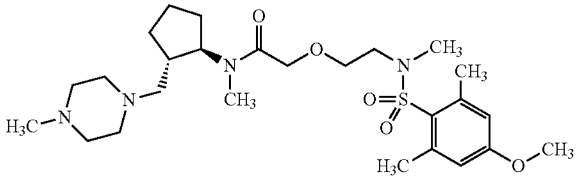
$C_{26}H_{44}N_4O_5S$ (524.72)
[M+H]+=525
HPLC (Method 4): Retention time=3.63 min
Example 670
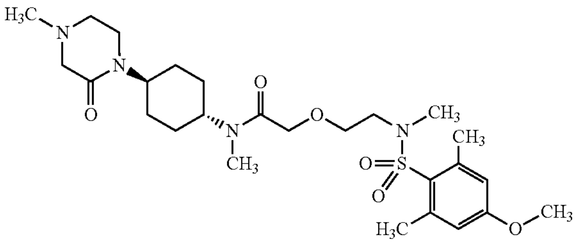
$C_{26}H_{42}N_4O_6S$ (538.71)
[M+H]+=539
HPLC (Method 5): Retention time=1.53 min
Example 671
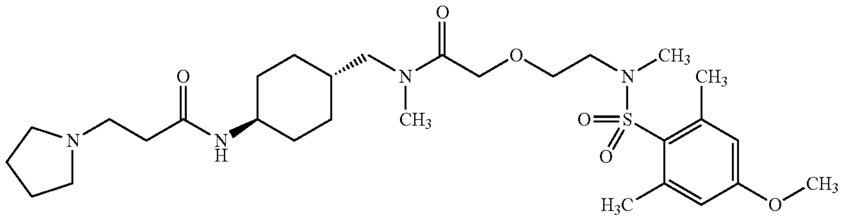 [SMILES: COc1cc(C)c(S(=O)(=O)N(C)CCOCC(=O)N(C)C[C@H]2CC[C@H](NC(=O)CCN3CCCC3)CC2)c(C)c1]
$C_{29}H_{48}N_4O_6S$ (580.79)
[M+H]+=581
HPLC (Method 5): Retention time=1.61 min
Example 672
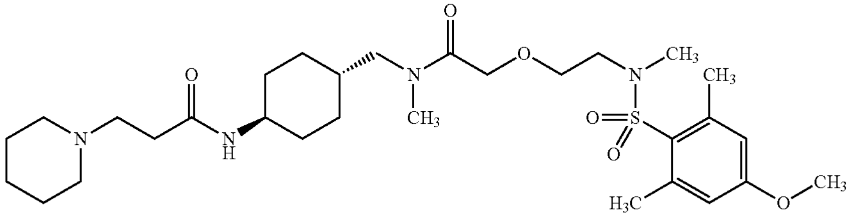 [SMILES: COc1cc(C)c(S(=O)(=O)N(C)CCOCC(=O)N(C)C[C@H]2CC[C@H](NC(=O)CCN3CCCCC3)CC2)c(C)c1]
$C_{30}H_{50}N_4O_6S$ (594.81)
[M+H]+=595
HPLC (Method 5): Retention time=1.64 min Example 673
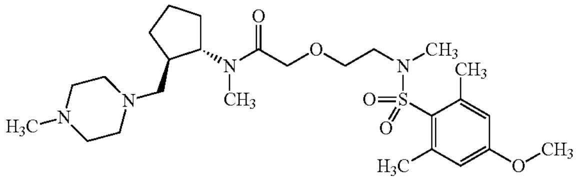
$C_{26}H_{44}N_4O_5S$ (524.72)
[M+H]+=525
HPLC (Method 4): Retention time=3.67 min
Example 674
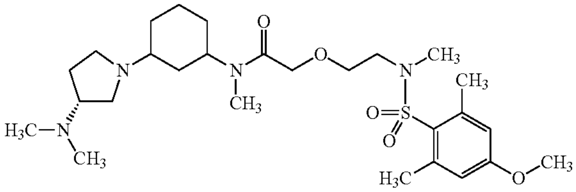
$C_{27}H_{46}N_4O_5S$ (538.75)
[M+H]+=539
HPLC (Method 5): Retention time=1.40 min
Example 675
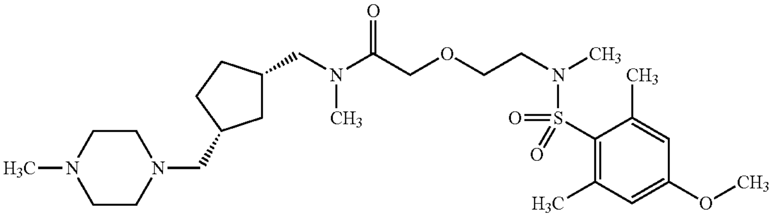
$C_{27}H_{46}N_4O_5S$ (538.75)
[M+H]+=539
HPLC (Method 5): Retention time=1.46 min
Example 676
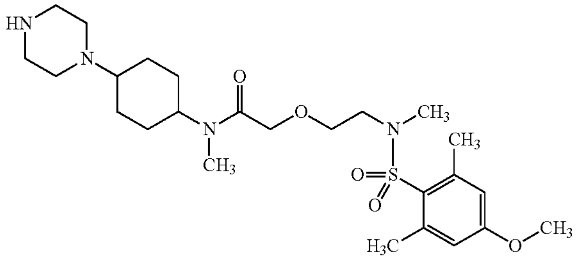 [SMILES: COc1cc(C)c(S(=O)(=O)N(C)CCOCC(=O)N(C)C2CCC(N3CCNCC3)CC2)c(C)c1]
$C_{25}H_{42}N_4O_5S$ (510.70)
[M+H]+=511
HPLC (Method 8): Retention time=1.45 min
Example 677
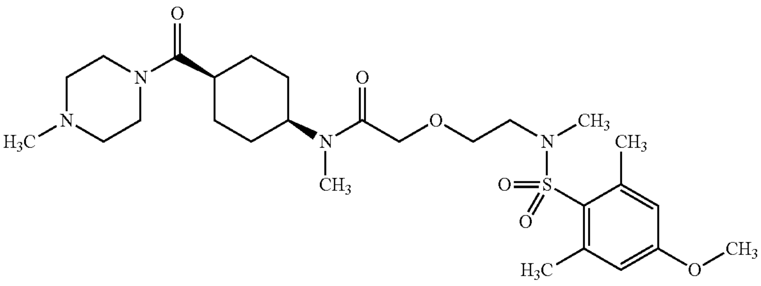
$C_{27}H_{44}N_4O_6S$ (552.73)
[M+H]+=553
HPLC (Method 5): Retention time=1.57 min Example 678
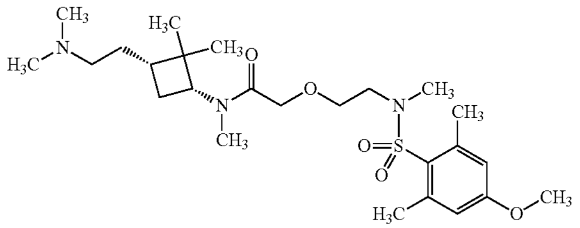
$C_{25}H_{43}N_3O_5S$ (497.70)
[M+H]+=498
HPLC (Method 5): Retention time=1.65 min
Example 679
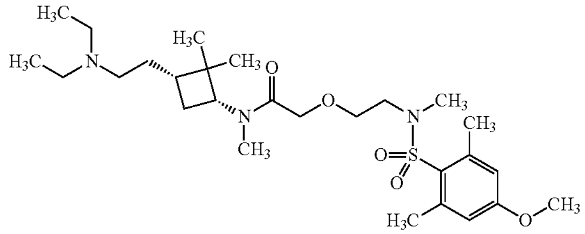 [SMILES: CCN(CC)CC[C@H]1C[C@@H](N(C)C(=O)COCCN(C)S(=O)(=O)c2c(C)cc(OC)cc2C)C1(C)C]
$C_{27}H_{47}N_3O_5S$ (525.75)
[M+H]+=526
HPLC (Method 5): Retention time=1.72 min
Example 680
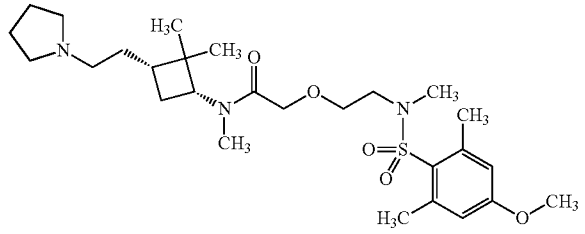 [SMILES: COc1cc(C)c(S(=O)(=O)N(C)CCOCC(=O)N(C)[C@@H]2C[C@H](CCN3CCCC3)C2(C)C)c(C)c1]
$C_{27}H_{45}N_3O_5S$ (523.73)
[M+H]+=524
HPLC (Method 5): Retention time=1.71 min
Example 681
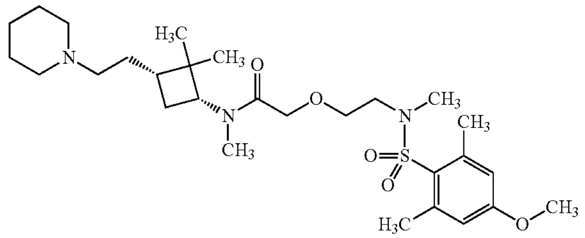 [SMILES: COc1cc(C)c(S(=O)(=O)N(C)CCOCC(=O)N(C)[C@@H]2C[C@H](CCN3CCCCC3)C2(C)C)c(C)c1]
$C_{28}H_{47}N_3O_5S$ (537.76)
[M+H]+=538
HPLC (Method 5): Retention time=1.73 min
Example 682
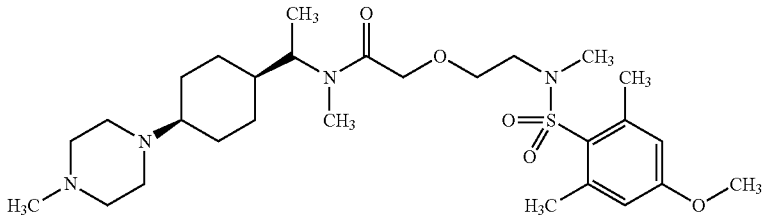
$C_{28}H_{48}N_4O_5S$ (552.78)
[M+H]+=553
HPLC (Method 8): Retention time=1.53 min
Example 683
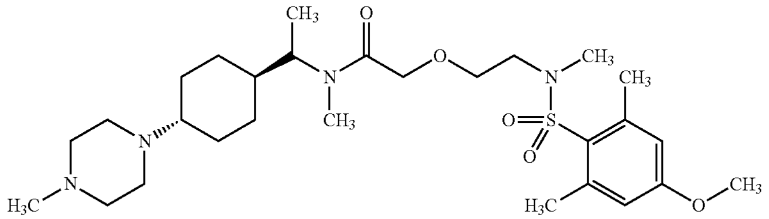
$C_{28}H_{48}N_4O_5S$ (552.78)
[M+H]+=553
HPLC (Method 8): Retention time=1.46 min Example 684

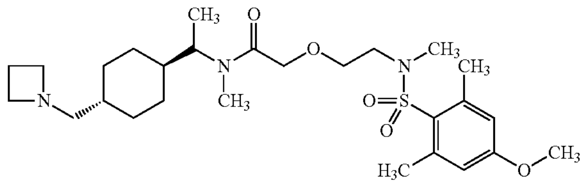 [SMILES: COc1cc(C)c(S(=O)(=O)N(C)CCOCC(=O)N(C)C(C)[C@H]2CC[C@H](CN3CCC3)CC2)c(C)c1]

$C_{27}H_{45}N_3O_5S$ (523.73)
[M+H]+=511
HPLC (Method 12): Retention time=3.09 min Example 685

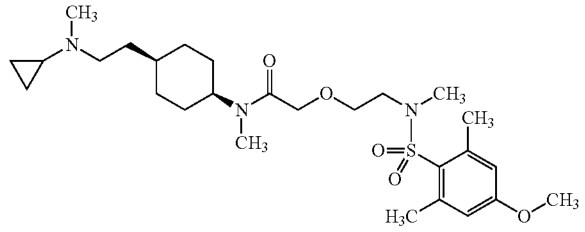 [SMILES: COc1cc(C)c(S(=O)(=O)N(C)CCOCC(=O)N(C)[C@H]2CC[C@@H](CCN(C)C3CC3)CC2)c(C)c1]

$C_{27}H_{45}N_3O_5S$ (523.73)
[M+H]+=524
HPLC (Method 5): Retention time=1.86 min Example 686

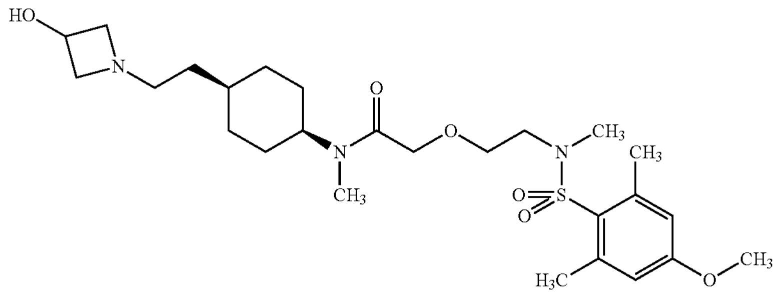 [SMILES: COc1cc(C)c(S(=O)(=O)N(C)CCOCC(=O)N(C)[C@H]2CC[C@@H](CCN3CC(O)C3)CC2)c(C)c1]

$C_{26}H_{43}N_3O_6S$ (525.71)
[M+H]+=526
HPLC (Method 5): Retention time=1.16 min Example 687

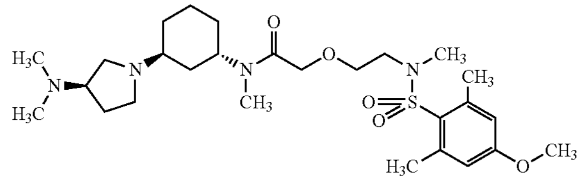

$C_{27}H_{46}N_4O_5S$ (538.75)
[M+H]+=539
HPLC (Method 14): Retention time=1.82 min Example 688

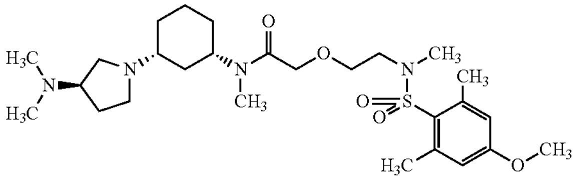

$C_{27}H_{46}N_4O_5S$ (538.75)
[M+H]+=539
HPLC (Method 5): Retention time=1.61 min Example 689

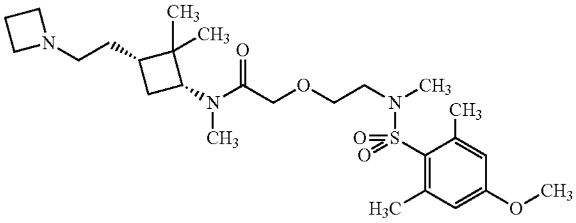 [SMILES: COc1cc(C)c(S(=O)(=O)N(C)CCOCC(=O)N(C)[C@@H]2C[C@H](CCN3CCC3)C2(C)C)c(C)c1]

$C_{26}H_{43}N_3O_5S$ (509.71)
[M+H]+=510
HPLC (Method 5): Retention time=1.68 min Example 690

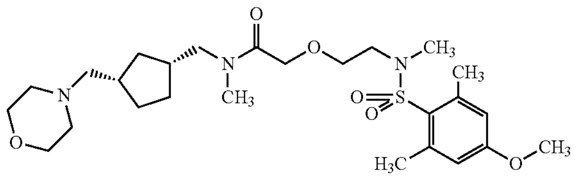 [SMILES: COc1cc(C)c(S(=O)(=O)N(C)CCOCC(=O)N(C)C[C@@H]2CC[C@H](CN3CCOCC3)C2)c(C)c1]

$C_{26}H_{43}N_3O_6S$ (525.71)
[M++]+=526
HPLC (Method 5): Retention time=1.69 min Example 691
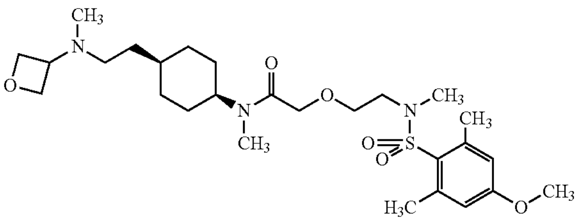 [SMILES: COc1cc(C)c(S(=O)(=O)N(C)CCOCC(=O)N(C)[C@H]2CC[C@@H](CCN(C)C3COC3)CC2)c(C)c1]
$C_{27}H_{145}N_3O_6S$ (539.73)
[M+H]+=540
HPLC (Method 5): Retention time=1.65 min
Example 692
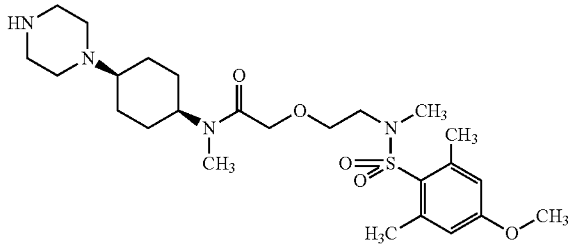 [SMILES: COc1cc(C)c(S(=O)(=O)N(C)CCOCC(=O)N(C)[C@H]2CC[C@@H](N3CCNCC3)CC2)c(C)c1]
$C_{25}H_{42}N_4O_5S$ (510.70)
[M+H]+=511
HPLC (Method 14): Retention time=1.68 min
Example 693
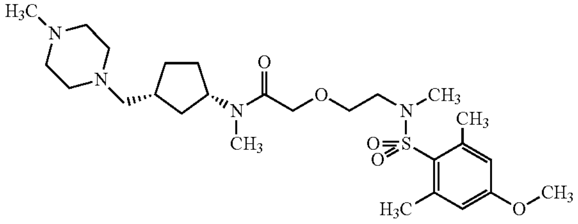
$C_{26}H_{44}N_4O_5S$ (524.72)
[M+H]+=525
HPLC (Method 5): Retention time=1.77 min
Example 694
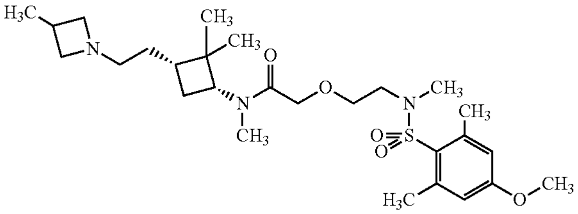
$C_{27}H_{45}N_3O_5S$ (523.73)
[M+H]+=524
HPLC (Method 5): Retention time=1.76 min
Example 695
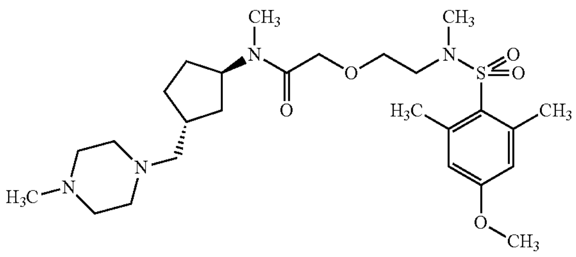
$C_{26}H_{44}N_4O_5S$ (524.72)
[M+H]+=525
HPLC (Method 5): Retention time=1.47 min
Example 696
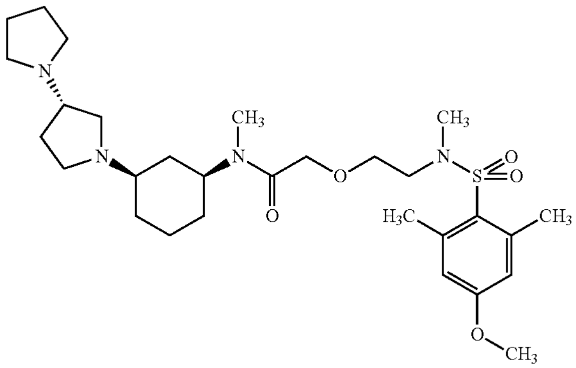 [SMILES: COc1cc(C)c(S(=O)(=O)N(C)CCOCC(=O)N(C)[C@H]2CCC[C@@H](N3CC[C@H](N4CCCC4)C3)C2)c(C)c1]
$C_{29}H_{48}N_4O_5S$ (564.79)
[M+H]+=565
HPLC (Method 14): Retention time=1.58 min Example 697
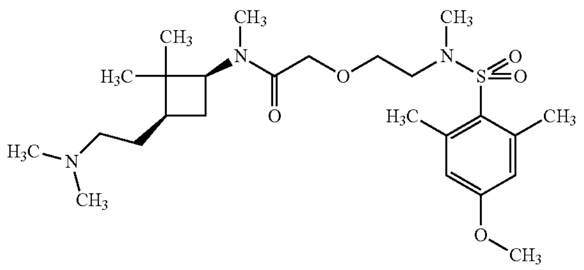
$C_{25}H_{43}N_3O_5S$ (497.70)
[M+H]+=498
HPLC (Method 5): Retention time=1.81 min
Example 698
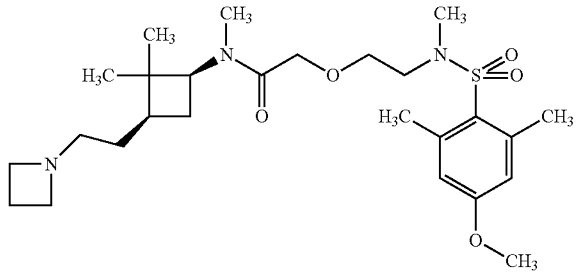 [SMILES: COc1cc(C)c(S(=O)(=O)N(C)CCOCC(=O)N(C)[C@H]2C[C@@H](CCN3CCC3)C2(C)C)c(C)c1]
$C_{26}H_{43}N_3O_5S$ (509.71)
[M+H]+=510
HPLC (Method 5): Retention time=1.83 min
Example 699
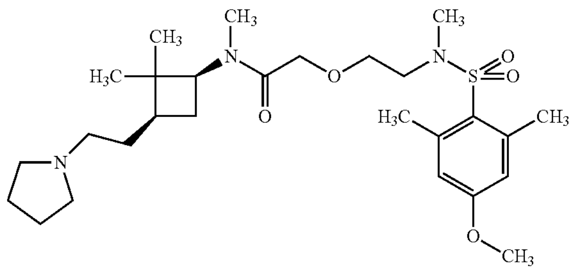 [SMILES: COc1cc(C)c(S(=O)(=O)N(C)CCOCC(=O)N(C)[C@H]2C[C@@H](CCN3CCCC3)C2(C)C)c(C)c1]
$C_{27}H_{45}N_3O_5S$ (523.73)
[M+H]+=524
HPLC (Method 5): Retention time=1.87 min
Example 700
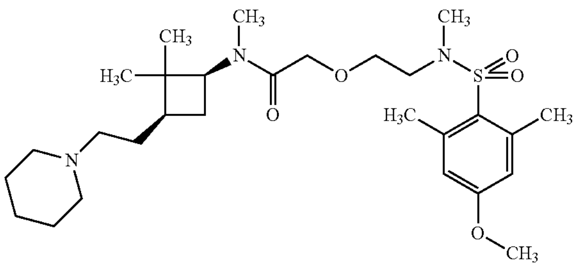 [SMILES: COc1cc(C)c(S(=O)(=O)N(C)CCOCC(=O)N(C)[C@H]2C[C@@H](CCN3CCCCC3)C2(C)C)c(C)c1]
$C_{28}H_{47}N_3O_5S$ (537.76)
[M+H]+=538
HPLC (Method 5): Retention time=1.91 min
Example 701
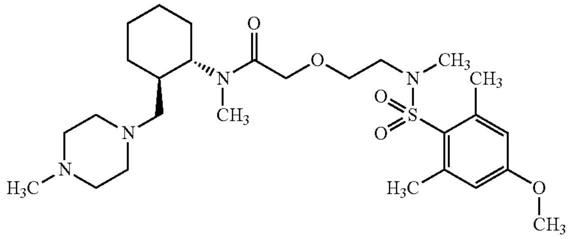
$C_{27}H_{46}N_4O_5S$ (538.75)
[M+H]+=539
HPLC (Method 5): Retention time=1.36 min
Example 702
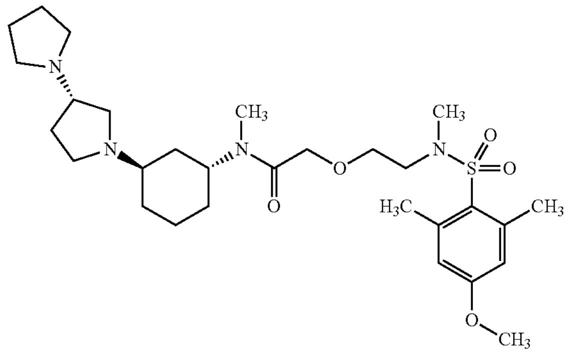 [SMILES: COc1cc(C)c(S(=O)(=O)N(C)CCOCC(=O)N(C)[C@@H]2CCC[C@@H](N3CC[C@H](N4CCCC4)C3)C2)c(C)c1]
$C_{29}H_{48}N_4O_5S$ (564.79)
[M+H]+=565
HPLC (Method 14): Retention time=1.95 min Example 703

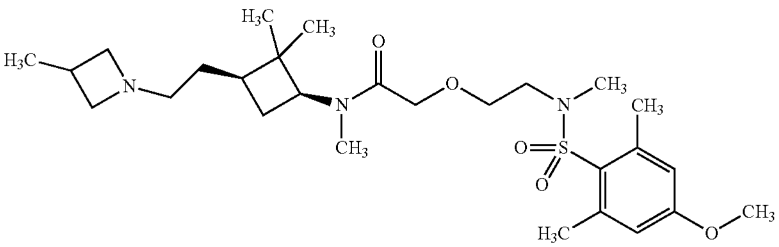

$C_{27}H_{45}N_3O_5S$ (523.73)
[M+H]+=524
HPLC (Method 5): Retention time=1.90 min Example 704

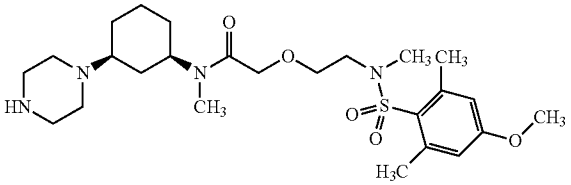 [SMILES: COc1cc(C)c(S(=O)(=O)N(C)CCOCC(=O)N(C)[C@@H]2CCC[C@H](N3CCNCC3)C2)c(C)c1]

$C_{25}H_{42}N_4O_5S$ (510.70)
[M+H]+=511
HPLC (Method 5): Retention time=1.63 min Example 705

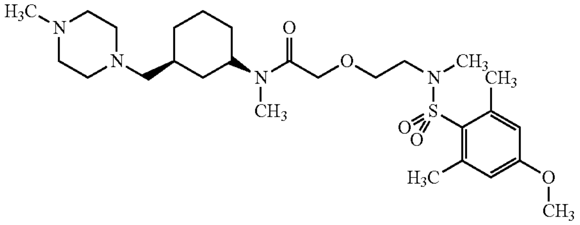

$C_{27}H_{46}N_4O_5S$ (538.75)
[M+H]+=539
HPLC (Method 5): Retention time=1.69 min Example 706

706a)

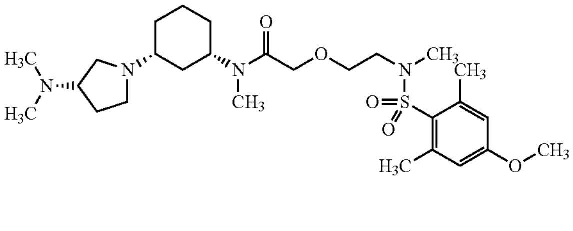

-continued

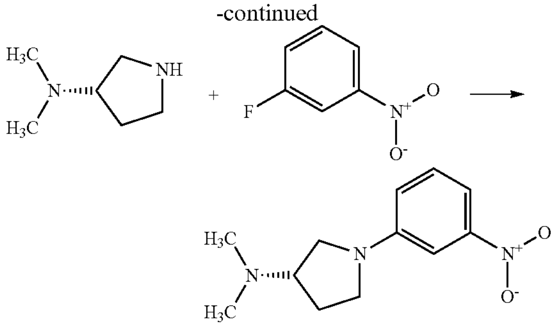

A solution of 800 mg (5.67 mmol) of 3-fluoronitrobenzene, 647.4 mg (5.67 mmol) of (3S)-(−)-(dimethylamino)-pyrrolidine and 1.27 ml diisopropylethylamine in 2 ml N-methyl-pyrrolidinone was stirred for 14 hours at 100° C. The crude product thus obtained was isolated and purified by chromatography.

$C_{12}H_{17}N_3O_2$ (235.3)

Yield: 630 mg (47% of theory)

$[M+H]^+$=236

706b)

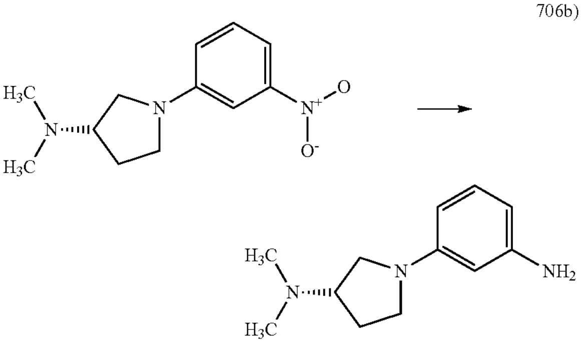

The product of Example 706a) was dissolved in 15 ml ethyl acetate, combined with 200 mg Raney nickel and hydrogenated at ambient temperature and under 3 bar of $H_2$ pressure.

$C_{12}H_{19}N_3$ (205.3)

Yield: 104 mg (18% of theory)

$[M+H]^+$=206

706c)

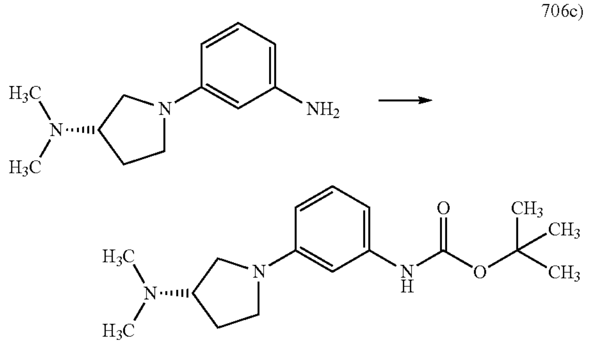

The product of Example 706b) (100 mg, 0.49 mmol) was dissolved in 2 ml ethyl acetate and combined with 159 mg (0.73 mmol) of di-tert-butyl-dicarbonate and stirred for two hours at ambient temperature. Then the solution was evaporated down and the crude product thus obtained was purified by chromatography.

$C_{17}H_{27}N_3O_2$ (305.4)

Yield: 134 mg (90% of theory)

$[M+H]^+=306$

706d)

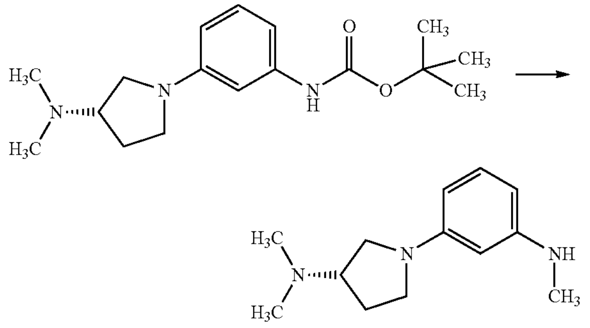

A solution of lithium aluminium hydride (2N in THF), which had previously been diluted with 2 ml of anhydrous THF, was carefully added dropwise to a solution of the product of Example 706c) (132 mg, 0.44 mmol) in 3 ml of anhydrous THF, while cooling. Then the mixture was slowly heated and then the reaction mixture was refluxed for 4 hours. It was then cooled to −5° C. and 1 ml of a 1N sodium hydroxide solution was added dropwise. The precipitate formed was filtered off and washed with approx. 5 ml THF and then with methanol. The combined organic solutions were dried on sodium sulphate and then evaporated down. The product thus obtained was reacted further without purification.

$C_{13}H_{21}N_3$ (219.3)

Yield: 80 mg (83% of theory)

$[M+H]^+=220$

Analytical HPLC (method 10): retention time: 0.31 min.

706e)

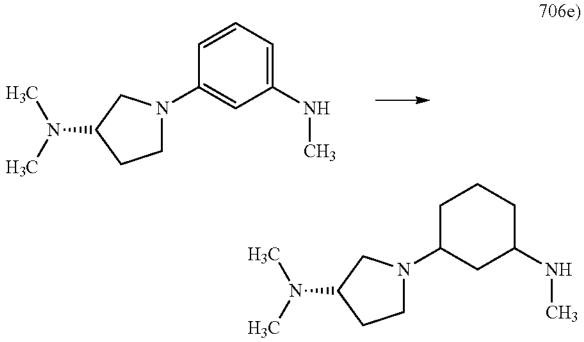

The product of Example 706d) was dissolved in 5 ml of methanol and after the addition of 10 mg of a Nishimura catalyst it was hydrogenated at ambient temperature and under 3 bar $H_2$ pressure. The crude product thus obtained was reacted further without purification.

$C_{13}H_{27}N_3$ (225.4)

Yield: 80 mg (97% of theory)

$[M+H]^+=226$

Analytical HPLC (method 10): retention time: 0.28 min.

706f)

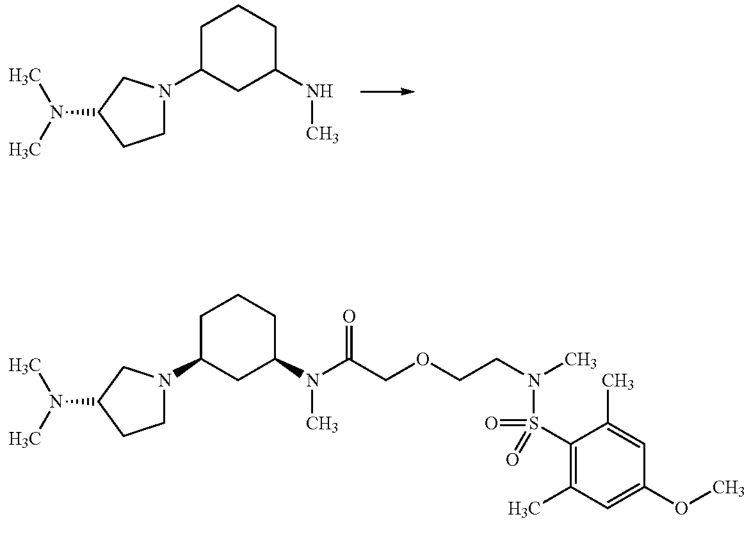

+

-continued

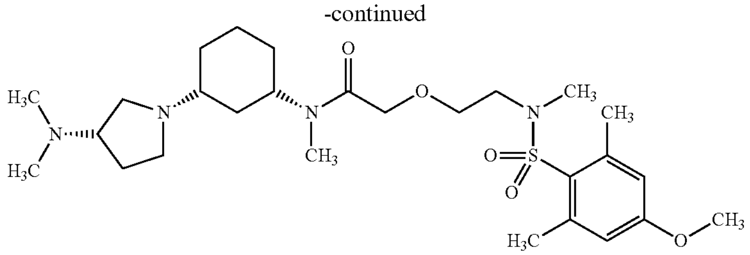

The product of Example 706e) was further reacted analogously to Example 53. The crude mixture of diastereomers thus obtained was separated by chromatography into two pairs of diastereomers (HPLC method 13). In this way, the pair of diastereomers was obtained with substituents in the cis position on the cyclohexane ring.

$C_{27}H_{46}N_4O_5S$ (538.7)

Yield: 14 mg (7.2% of theory)

$[M+H]^+=539$

HPLC (method 13): retention time: 1.79 min.

Example 707

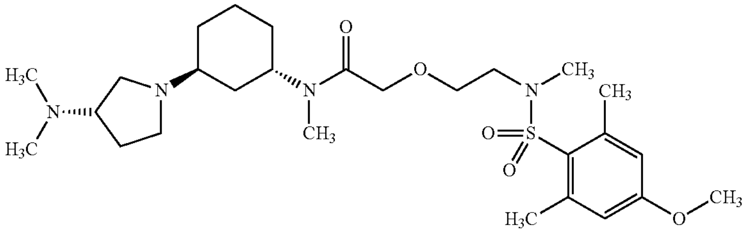

+

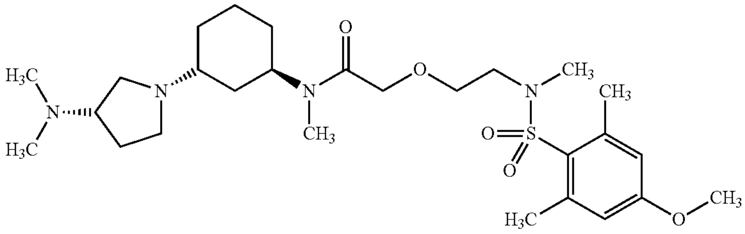

The product of Example 706e) was further reacted analogously to Example 53. The crude mixture of diastereomers thus obtained was separated by chromatography into two pairs of diastereomers (HPLC method 13). In this way, the pair of diastereomers was obtained with substituents in the trans position on the cyclohexane ring.

$C_{27}H_{46}N_4O_5S$ (538.7)

Yield: 3 mg (1.5% of theory)

$[M+H]^+=539$

HPLC (method 13): retention time: 1.91 min

Example 708

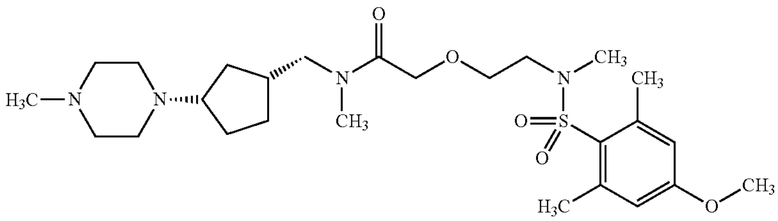

-continued

708a)

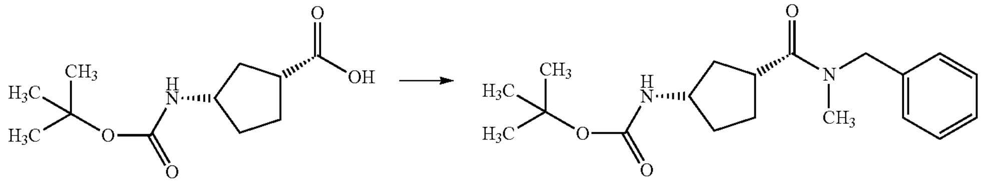

Analogously to Example (55f) (1R,3S)-3-tert-butyloxycarbonylamino-cyclopentanecarboxylic acid was reacted with N-methyl-benzylamine.

Yield: 82% of theory $C_{19}H_{28}N_2O_3$ (332.44)

$[M+H]^+$=333

HPLC (method 5): retention time: 2.41 min

708b)

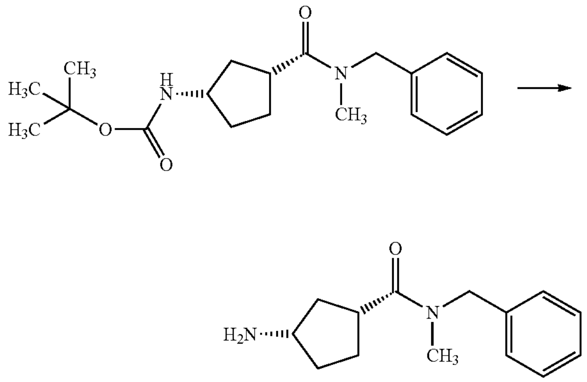

The tert-butoxycarbonyl protective group was cleaved under standard conditions with trifluoroacetic acid in dichloromethane.

Yield: 92% of theory $C_{14}H_{20}N_2O_3$ (232.32)

708c)

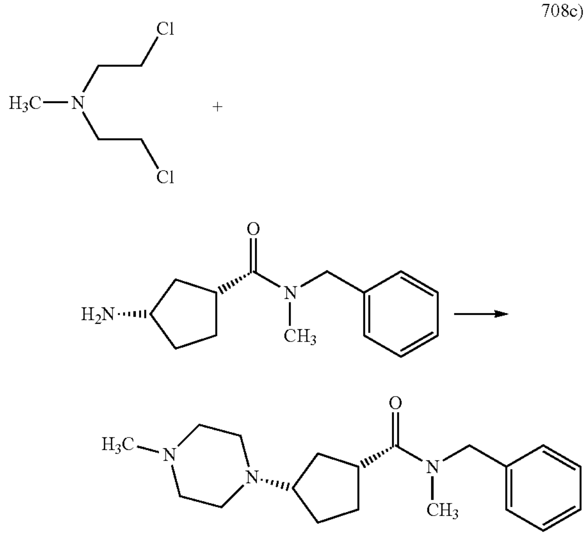

A solution of the product of Example (708b) (3.0 g, 12.91 mmol) in 45 ml acetonitrile was combined with 8.92 g (65 mmol) of potassium carbonate, 0.10 g (0.6 mmol) of potassium iodide and 2.49 g (12.91 mmol) of bis-chloroethyl-methylamine hydrochloride and refluxed for four hours. After cooling the reaction mixture was diluted with approx. 50 ml dichloromethane and extracted with 50 ml of water. The organic phase was dried on sodium sulphate and evaporated down. The crude product thus obtained was reacted further without purification.

Yield: 65% of theory $C_{19}H_{29}N_3O$ (315.45)

708d)

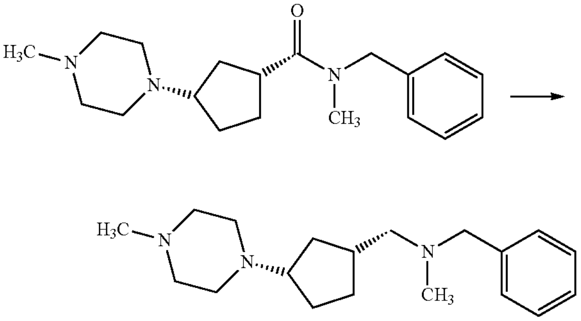

1.0 g (3.17 mmol) of the product of Example 708c) was reduced under standard conditions with lithium aluminium hydride in THF.

Yield: 880 mg (91% of theory)

$C_{19}H_{31}N_3$ (301.47)

708e)

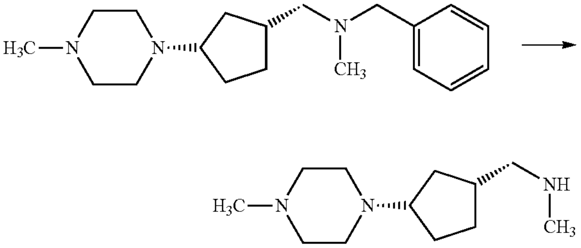

The product of Example 708d) (880 mg, 2.92 mmol) was hydrogenated in methanol with the addition of Pd/charcoal (10%) at ambient temperature and 3 bar of $H_2$ pressure.

Yield: (94% of theory)

$C_{12}H_{25}N_3$ (211.35)

708f)

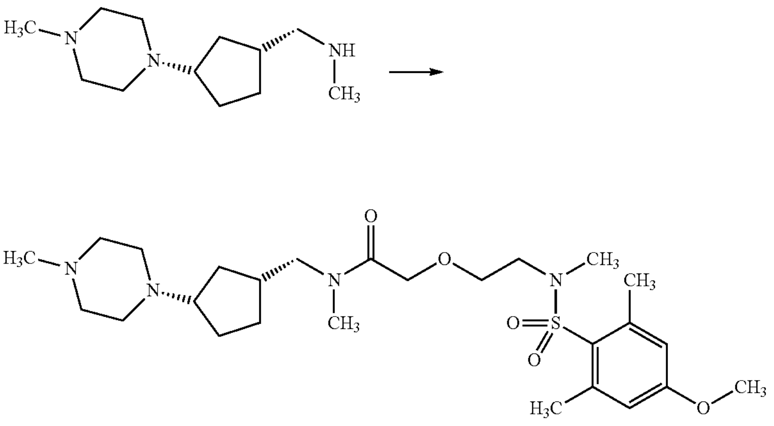

The product of Example 708e) was further reacted analogously to Example (53).

Yield: 67% of theory $C_{26}H_{44}N_4O_5S$ (524.72)

[M+H]+=525

HPLC (method 5): Retention time=1.44 min

Example 70

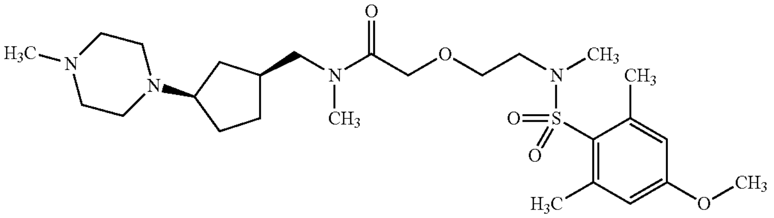

$C_{26}H_{44}N_4O_5S$ (524.72)

[M+H]+=525

HPLC (method 5): Retention time=1.43 min

The following Examples describe pharmaceutical formulations which contain as active substance any desired compound of general formula I:

Example I

Dry Ampoule with 75 mg of Active Compound Per 10 ml

Composition:

| | |
|---|---|
| Active compound | 75.0 mg |
| Mannitol | 50.0 mg |
| Water for injection | ad 10.0 ml |

Production:

Active compound and mannitol are dissolved in water. The charged ampoules are freeze dried. Water for injection is used to dissolve to give the solution ready for use.

Example II

Tablet with 50 mg of Active Compound

Composition:

| | |
|---|---|
| (1) Active compound | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Production:

(1), (2) and (3) are mixed and granulated with an aqueous solution of (4). (5) is admixed to the dry granules. Tablets are compressed from this mixture, biplanar with a bevel on both sides and dividing groove on one side.

Diameter of the tablets: 9 mm.

Example III

Tablet with 350 mg of Active Compound

Composition:

| | |
|---|---|
| (1) Active compound | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Production:

(1), (2) and (3) are mixed and granulated with an aqueous solution of (4). (5) is admixed to the dry granules. Tablets are compressed from this mixture, biplanar with a bevel on both sides and dividing groove on one side.

Diameter of the tablets: 12 mm.

Example IV

Capsule with 50 mg of Active Compound

Composition:

| | |
|---|---|
| (1) Active compound | 50.0 mg |
| (2) Maize starch dried | 58.0 mg |
| (3) Lactose powdered | 50.0 mg |
| (4) Magnesium stearate | 2.0 mg |
| | 160.0 mg |

Production:

(1) is triturated with (3). This trituration is added to the mixture of (2) and (4) with vigorous mixing.

This powder mixture is packed into hard gelatine two-piece capsules of size 3 in a capsule-filling machine.

Example V

Capsules with 350 mg of Active Compound

Composition:

| | |
|---|---|
| (1) Active compound | 350.0 mg |
| (2) Maize starch dried | 46.0 mg |
| (3) Lactose powdered | 30.0 mg |
| (4) Magnesium stearate | 4.0 mg |
| | 430.0 mg |

Production:

(1) is triturated with (3). This trituration is added to the mixture of (2) and (4) with vigorous stirring.

This powder mixture is packed into hard gelatine two-piece capsules of size 0 in a capsule-filling machine.

Example VI

Suppositories with 100 mg of Active Compound

1 Suppository Comprises:

| | |
|---|---|
| Active compound | 100.0 mg |
| Polyethylene glycol (M.W. 1500) | 600.0 mg |
| Polyethylene glycol (M.W. 6000) | 460.0 mg |
| Polyethylene sorbitan monostearate | 840.0 mg |
| | 2000.0 mg |

The invention claimed is:

1. A compound selected from the group consisting of:

| Example | Structure |
|---|---|
| (651) | 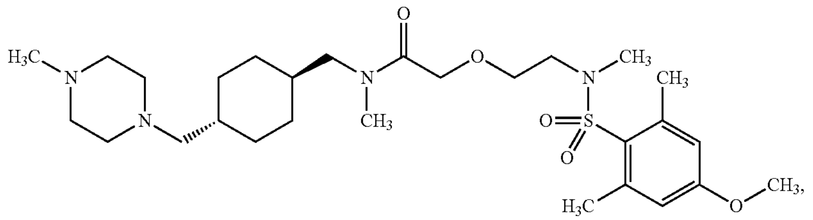 |
| (652) | 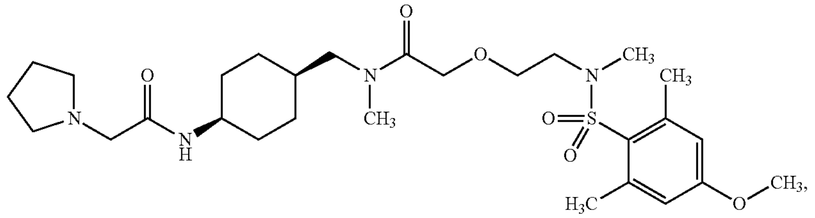 |

-continued
| Example | Structure |
|---|---|
| (655) | 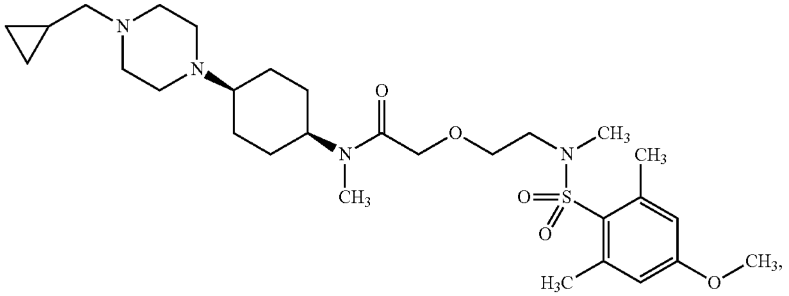 |
| (656) | 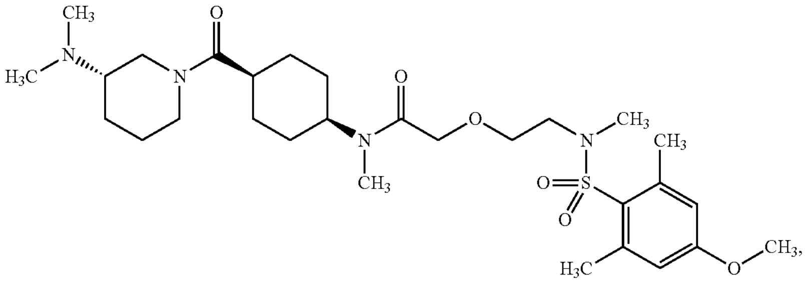 |
| (657) | 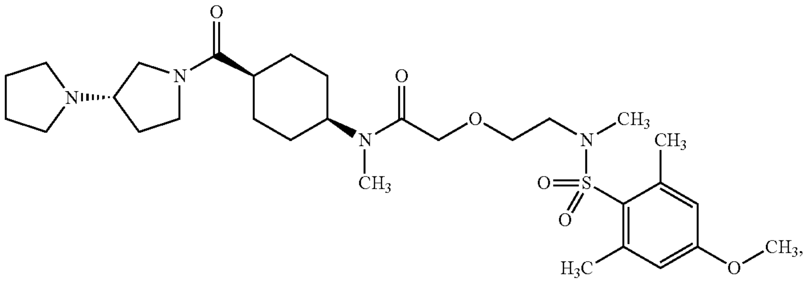 |
| (658) | 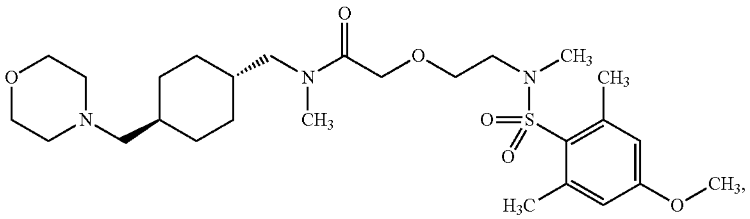 |
| (659) | 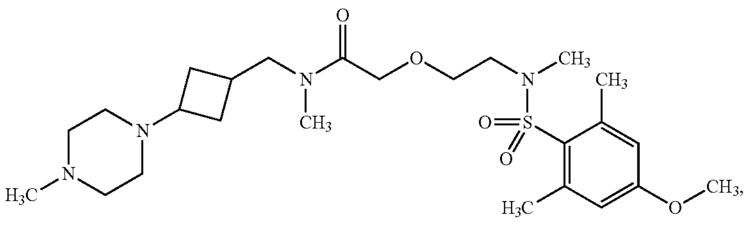 |
| (660) | 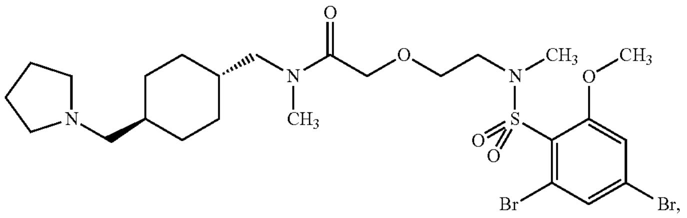 |

-continued
| Example | Structure |
| --- | --- |
| (661) | 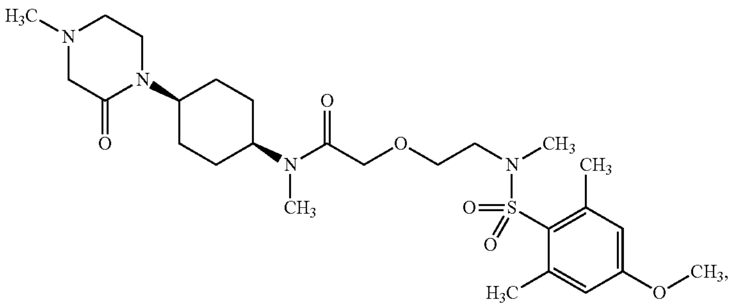 |
| (662) | 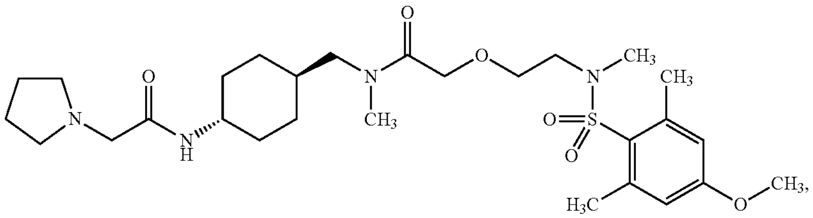 |
| (663) | 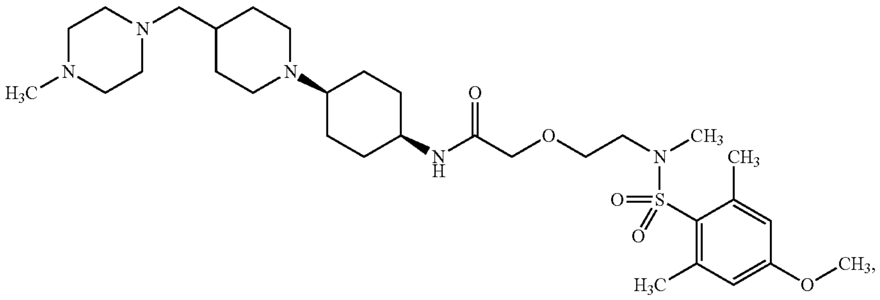 |
| (664) | 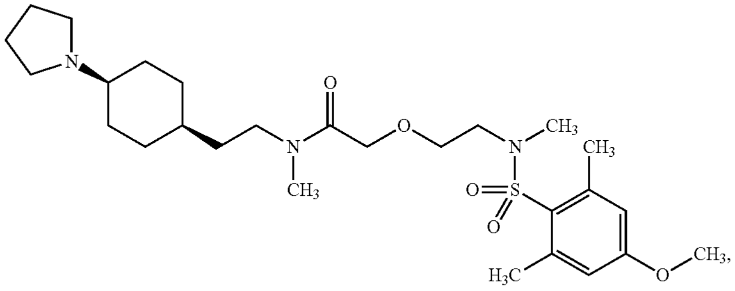 |
| (665) | 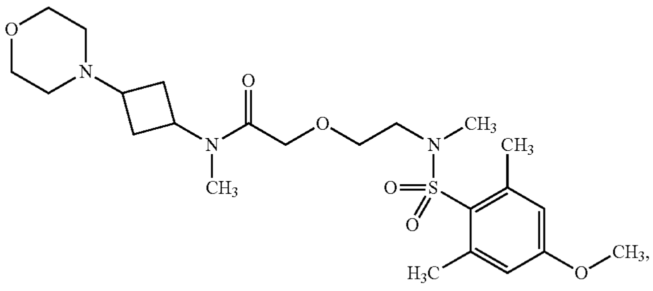 |

-continued
| Example | Structure |
| --- | --- |
| (666) | 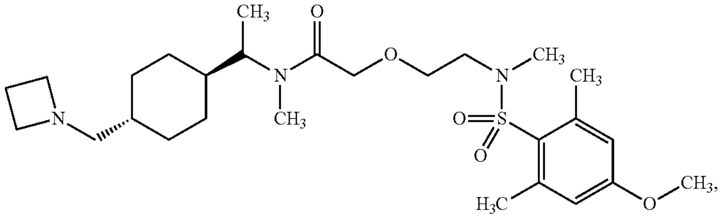 |
| (667) | 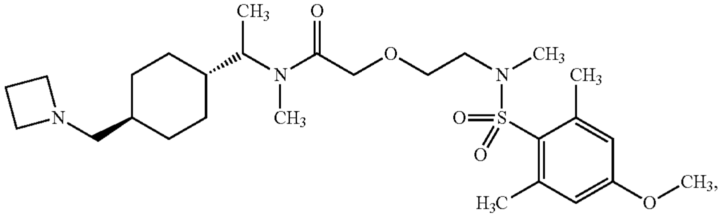 |
| (668) | 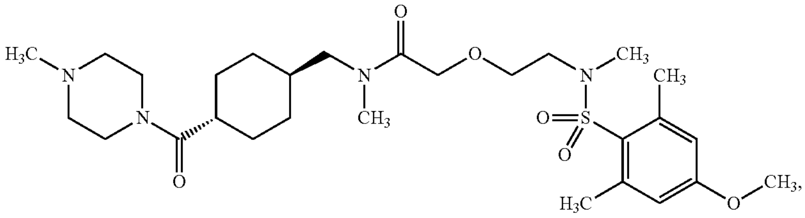 |
| (669) | 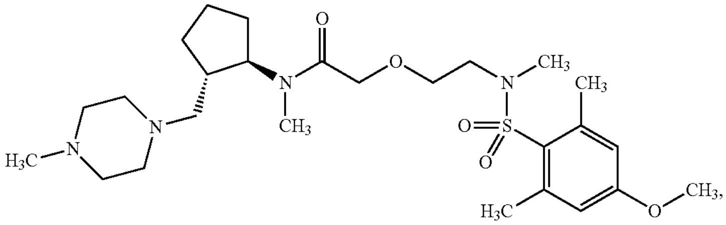 |
| (670) | 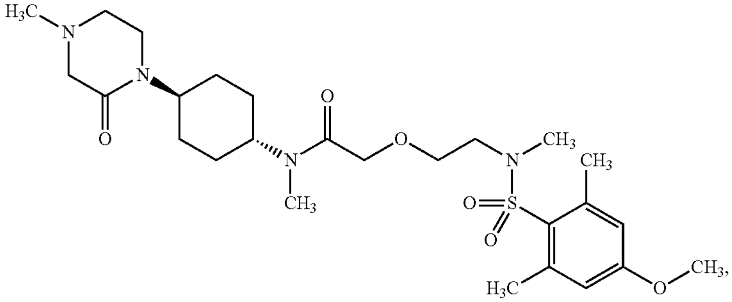 |
| (671) | 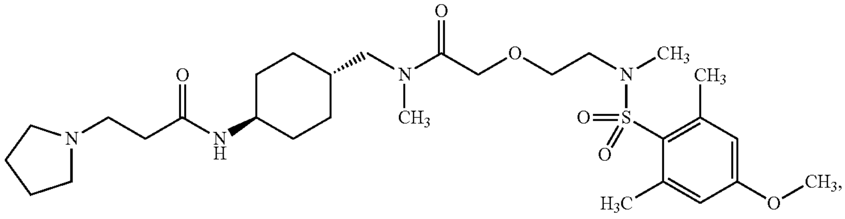 |

-continued
| Example | Structure |
| --- | --- |
| (672) | 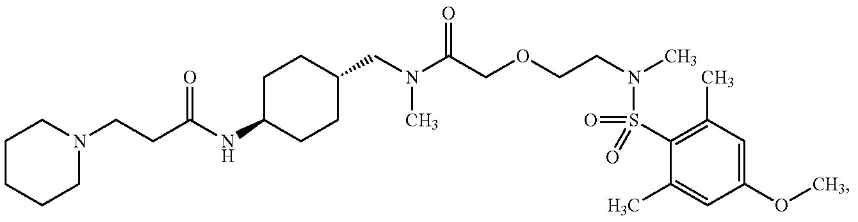 |
| (673) | 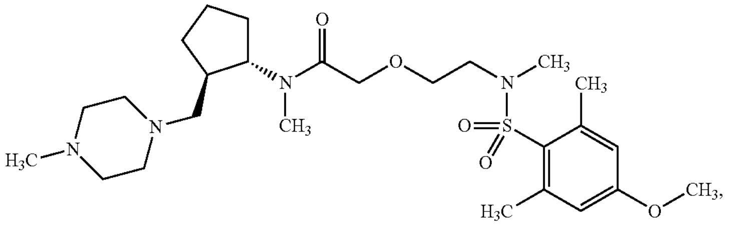 |
| (674) | 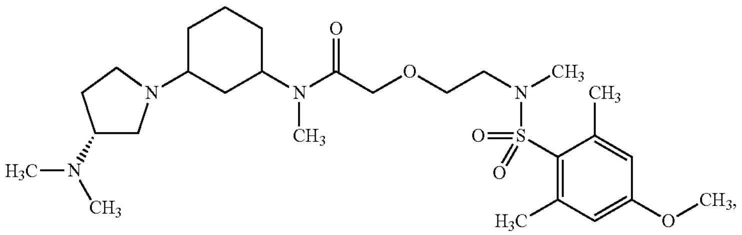 |
| (675) | 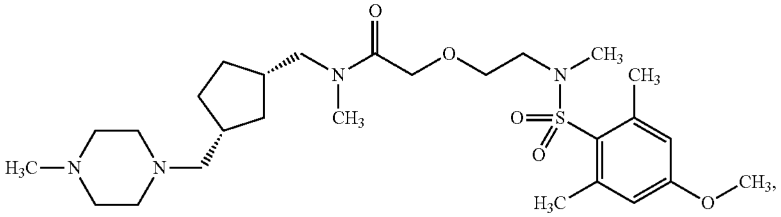 |
| (677) | 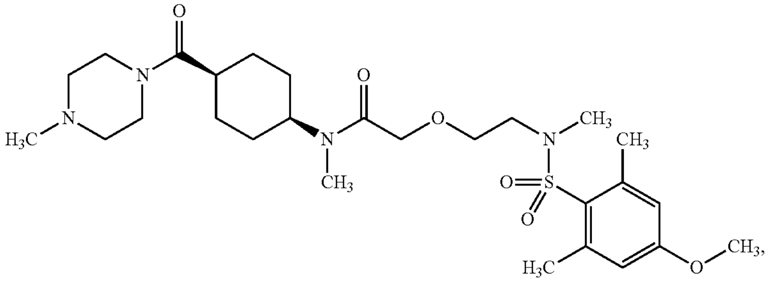 |
| (678) | 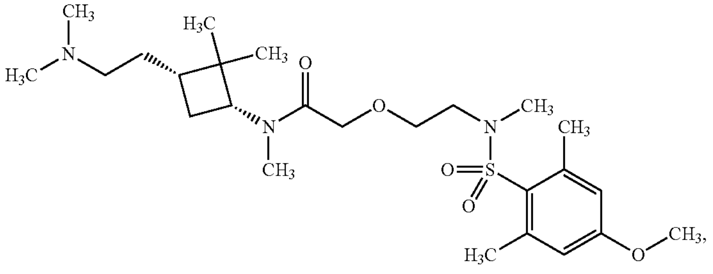 |

-continued
| Example | Structure |
| --- | --- |
| (679) | 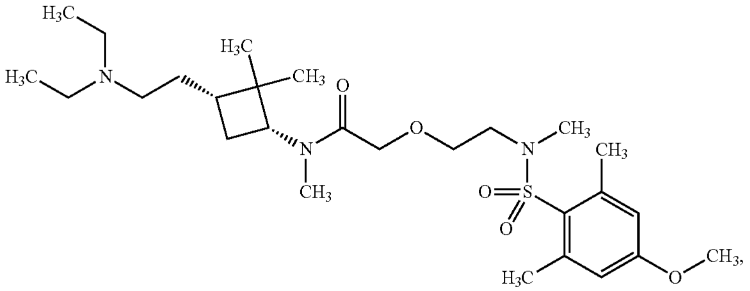 |
| (680) | 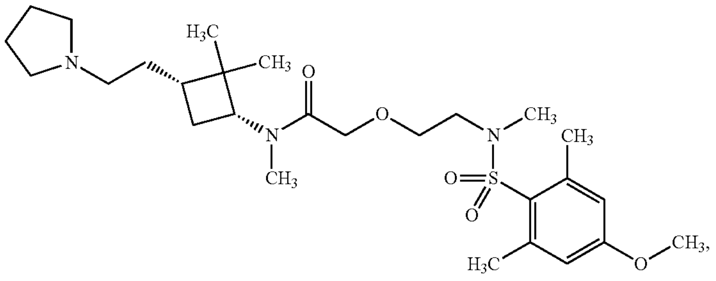 |
| (681) | 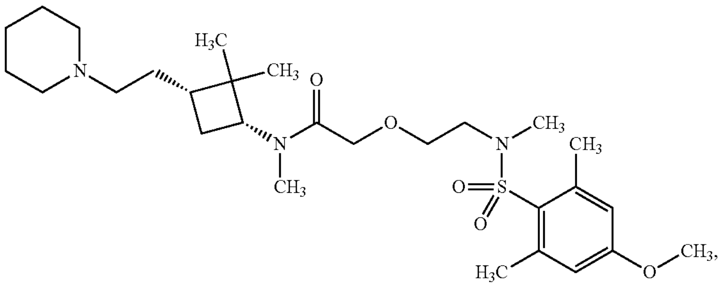 |
| (682) | 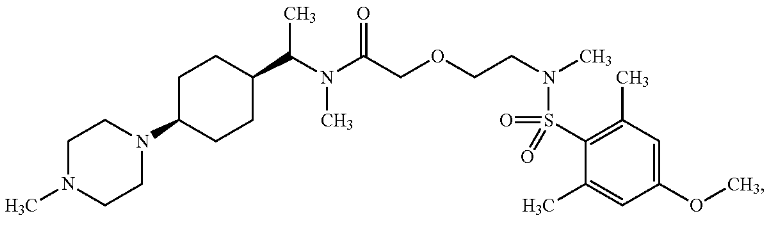 |
| (683) | 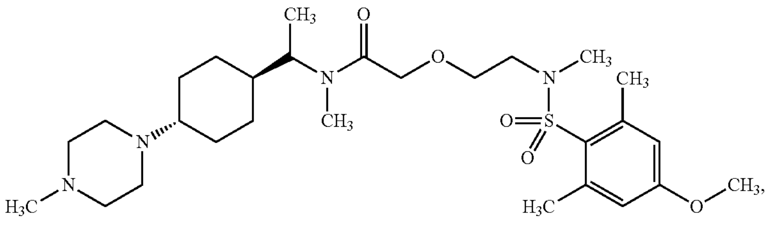 |

-continued
| Example | Structure |
|---|---|
| (685) | 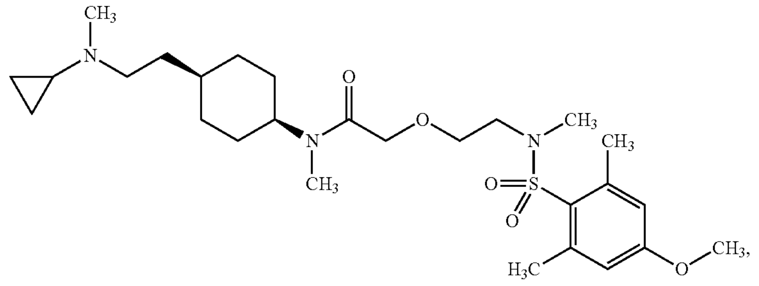 |
| (686) | 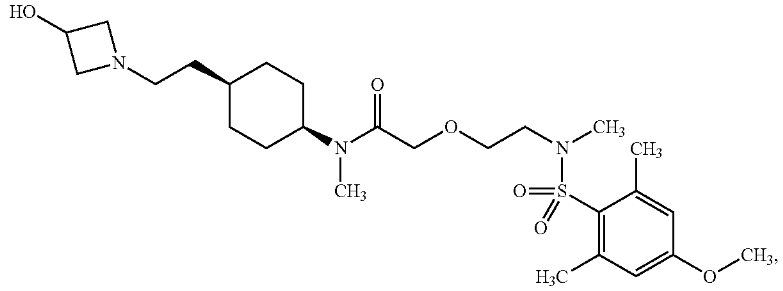 |
| (687) | 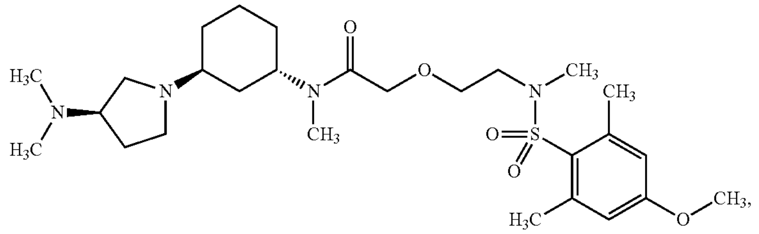 |
| (688) | 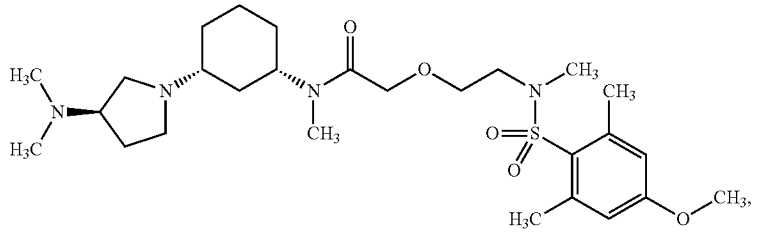 |
| (689) | 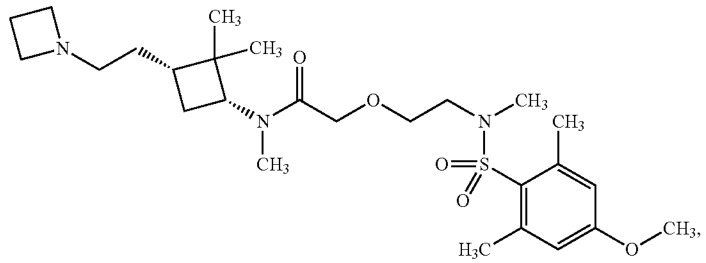 |
| (690) | 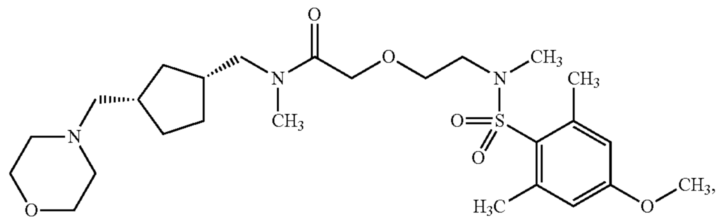 |

-continued
| Example | Structure |
| --- | --- |
| (691) | 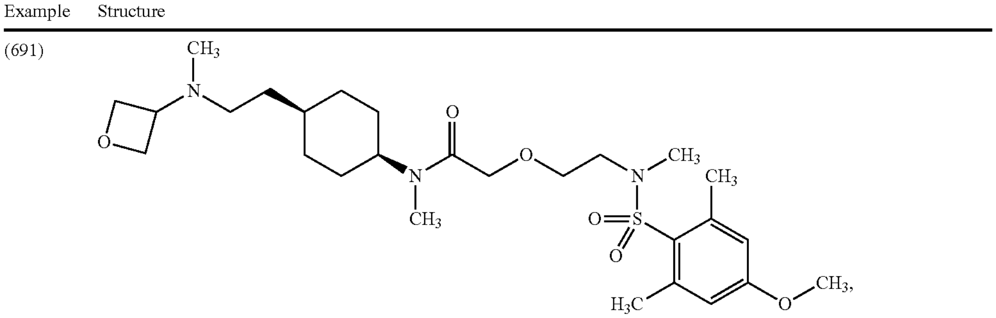 |
| (693) | 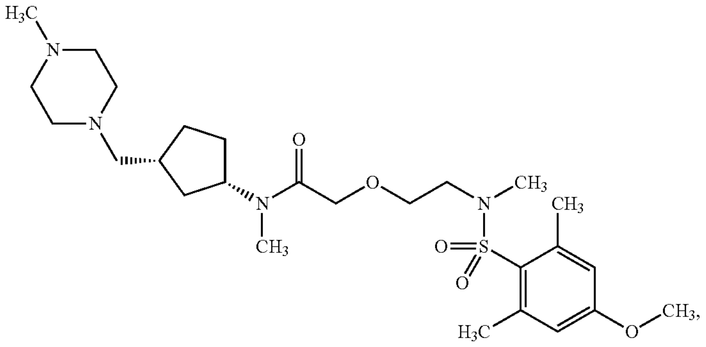 |
| (694) | 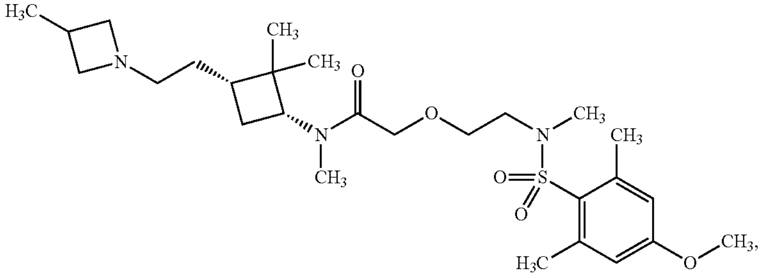 |
| (695) | 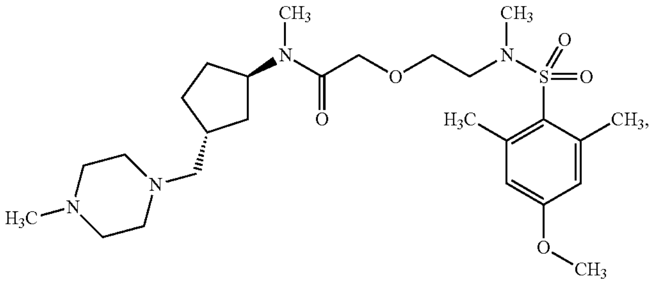 |
| (696) | 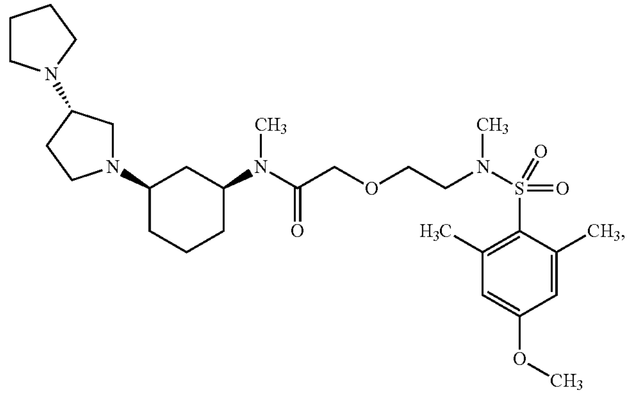 |

-continued
| Example | Structure |
|---|---|
| (697) | 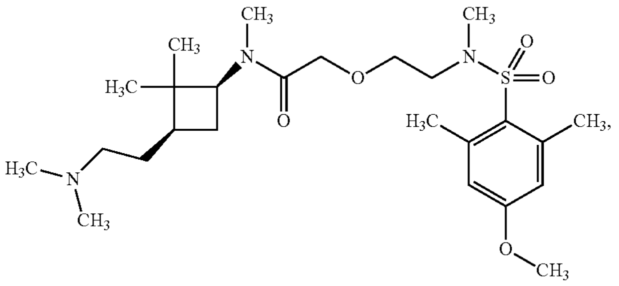 |
| (698) | 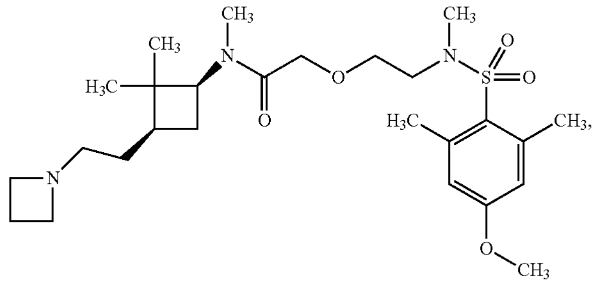 |
| (699) | 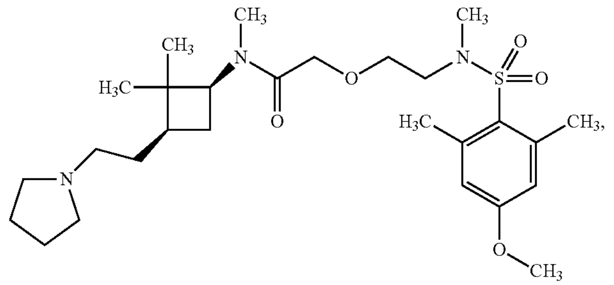 |
| (700) | 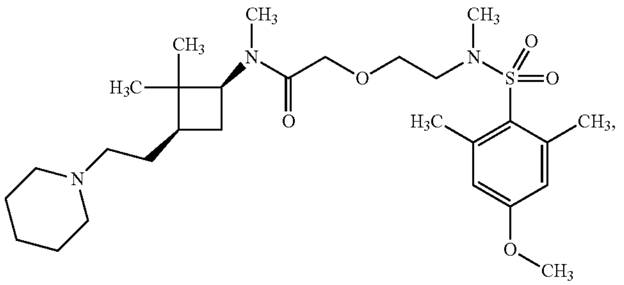 |
| (701) | 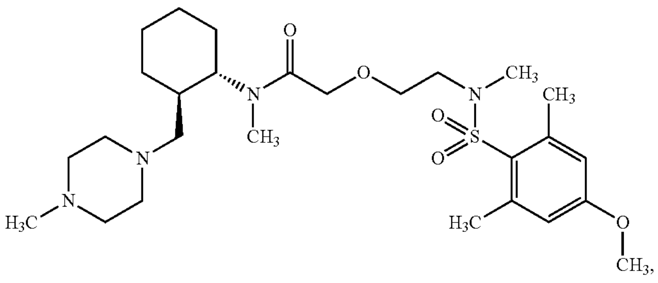 |

-continued

| Example | Structure |
|---|---|
| (702) | 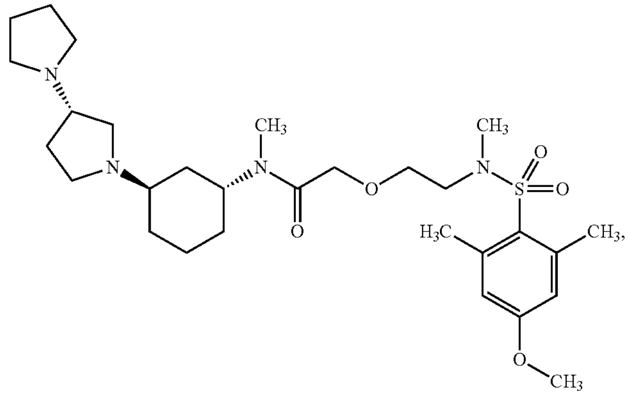 |
| (703) | 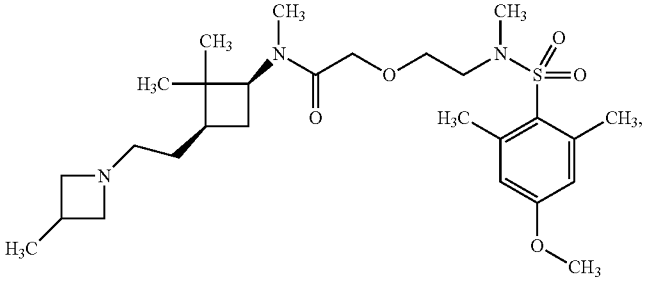 and |
| (707b) | 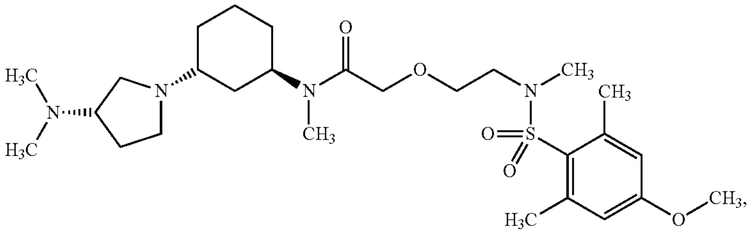 |

or a salt thereof.

2. A physiologically acceptable salt of a compound according to claim 1.

3. A pharmaceutical composition comprising a compound according to claim 1 or a physiologically acceptable salt thereof and a carrier or diluent.

4. A method for treating acute pain, visceral pain, neuropathic pain, inflammatory/pain receptor-mediated pain, tumour pain or headache diseases which comprises administering to a host suffering from the same acute pain, visceral pain, neuropathic pain, inflammatory/pain receptor-mediated pain, tumour pain or headache diseases a therapeutically effective amount of a a compound according to claim 1 or a physiologically acceptable salt thereof.

* * * * *

UNITED STATES PATENT AND TRADEMARK OFFICE

CERTIFICATE OF CORRECTION

PATENT NO. : 8,450,306 B2
APPLICATION NO. : 12/672650
DATED : May 28, 2013
INVENTOR(S) : Hauel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 499 days.

Signed and Sealed this
Fourth Day of November, 2014

Michelle K. Lee

Michelle K. Lee
*Deputy Director of the United States Patent and Trademark Office*